(12) United States Patent
Poolman et al.

(10) Patent No.: US 9,365,624 B2
(45) Date of Patent: Jun. 14, 2016

(54) VACCINE

(75) Inventors: Jan Poolman, Rixensart (BE); Michiel Stork, Utrecht (NL); Johannes Petrus Maria Tommassen, Utrecht (NL); Nathalie Isabelle Devos, Rixensart (BE); Vincent Weynants, Rixensart (BE)

(73) Assignees: GlaxoSmithKline Biologicals, S.A., Rixensart (BE); Utrecht University, Utrecht (NL)

( * ) Notice: Subject to any disclaimer, the term of this patent is extended or adjusted under 35 U.S.C. 154(b) by 127 days.

(21) Appl. No.: 13/583,419

(22) PCT Filed: Mar. 11, 2011

(86) PCT No.: PCT/EP2011/053665
§ 371 (c)(1),
(2), (4) Date: Sep. 7, 2012

(87) PCT Pub. No.: WO2011/110655
PCT Pub. Date: Sep. 15, 2011

(65) Prior Publication Data
US 2013/0004510 A1    Jan. 3, 2013

Related U.S. Application Data

(60) Provisional application No. 61/312,959, filed on Mar. 11, 2010.

(51) Int. Cl.
| | | |
|---|---|---|
| *A61K 39/095* | (2006.01) | |
| *C07K 14/195* | (2006.01) | |
| *C07K 14/21* | (2006.01) | |
| *C07K 14/22* | (2006.01) | |
| *A61K 39/00* | (2006.01) | |

(52) U.S. Cl.
CPC .............. *C07K 14/22* (2013.01); *A61K 39/095* (2013.01); *C07K 14/195* (2013.01); *A61K 39/00* (2013.01)

(58) Field of Classification Search
None
See application file for complete search history.

(56) References Cited

U.S. PATENT DOCUMENTS

| | | | | |
|---|---|---|---|---|
| 7,862,827 | B2 * | 1/2011 | Giuliani et al. | ............ 424/250.1 |
| 2007/0031449 | A1 | 2/2007 | Bos et al. | |

FOREIGN PATENT DOCUMENTS

| | | |
|---|---|---|
| WO | 99/57280 | 11/1999 |
| WO | 00/11182 | 3/2000 |
| WO | 00/55327 | 9/2000 |
| WO | 00/71725 | 11/2000 |
| WO | 01/85772 | 11/2001 |
| WO | 2007/148363 | 12/2007 |
| WO | 2010/025964 | 3/2010 |

OTHER PUBLICATIONS

Li et al (Proc. Natl. Acad. Sci. USA 77:3211-3214, 1980).*
Houghten et al. (Vaccines, 1986, Edited by Fred Brown: Cold Spring Harbor Laboratory).*
Lederman et al (Molecular Immunology 28:1171-1181, 1991).*
Chen, et al., (2001), FEMS Microbiology Letters, vol. 202, No. 1, pp. 67-71.
Silke, et al., (1998), Molecular Microbiology, vol. 28 No. 6, pp. 1199-1210.
Campoy, et al., (2002), Infection and Immunity, vol. 70, No. 8, pp. 4721-4725.
Turner, et al., (2001), Microbiology, vol. 147, No. 5 pp. 1277-1290.
Vipond, et al. (2005), Human Vaccines, vol. 1, No. 2, pp. 80-84.
Stork, et al., (2010), PLOS Pathogens, vol. 6, No. 7, pp. E1000969-1.

* cited by examiner

*Primary Examiner* — Padma V Baskar
(74) *Attorney, Agent, or Firm* — Eric J. Kron

(57) ABSTRACT

Compositions and methods for the treatment or prevention of Gram-negative bacterial strain infection are provided herein. Methods for the manufacture of said compositions are also provided herein.

4 Claims, 33 Drawing Sheets

FIG.5

Expression of TdfI in 32 different Neisseria meningitidis strains

| Strain | Serogroup | Clonal lineage[a] | Zinc<br>− + | Strain | Serogroup | Clonal lineage[a] | Zinc<br>− + |
|---|---|---|---|---|---|---|---|
| Z2491 | A | IV | | MC51 | C | | |
| FAM18 | C | ET-37 | | MC50 | C | | |
| MC58 | B | ET-5 | | 126E | C | - | |
| B40 | A | I | | 2208 | A | | |
| Z6835 | A | VI | | BNCV | B | ET-37 | |
| Z3524 | A | III | | 6940 | B | - | |
| Z6466 | A | | | M981 | B | ET-2 | |
| ROU | W135 | ET-37 | | M992 | B | - | |
| BZ10 | B | A4 cluster | | 881710 | B | | |
| BZ198 | B | Lineage 3 | | 881607 | B | | |
| NG G40 | B | ET-57 | | 2996 | B | ST-8 | |
| NG4/88 | B | ET-67 | | S3446 | B | ET-8 | |
| BZ147 | B | ET-164 | | 13077 | A | IV | |
| 297-0 | B | ET-69 | | B16B6 | B | ET-37 | |
| M990 | B | - | | H44/76 | B | ET-5 | |
| 35E | C | - | | 8013 | C | ST-18 | |

FIG.8

```
            <    Signal sequence    >        <Tb > <    plug domain
MC58    1  MAQTTLKPIVLSILLINTPLLAQAHETEQSVDLETVSVVGKSRPRATSGLLHTSTASDKI  60
O53322     ...............................G....T.....................
Z2491      ................S...G.....G.................................
FAM18      ............................................................
α14        ............................................................
α153       ................................DR..........................
α275       ............................................................

Plug domain
MC58   61  ISGDTLRQKAVNLGDALDGVPGIHASQYGGGASAPVIRGQTGRRIKVLNHHGETGDMADF 120
O53422     ............................................................
Z2491      ............................................................
FAM18      L...........................................................
α14        ............................................................
α153       ............................................................
α275       ............................................................

plug domain                 >< Tm1    >
MC58  121  SPDHAIMVDTALSQQVEILRGPVTLLYSSGNVAGLVDVADGKIPEKMPENGVSGELGLRL 180
O53422     ............................................................
Z2491      ........S...................................................
FAM18      ............................................................
α14        ............................................................
α153       ............................................................
α275       ........S...................................................

<loop1>< Tm2    >  <    Tm3   ><    loop2     ><    Tm4
MC58  181  SSGNLEKLTSGGINIGLGKNFVLHTEGLYRKSGDYAVPRYRNLKRLPDSHADSQTGSIGL 240
O53422     ...........................................................K......
Z2491      ............................................................
FAM18      ............................................................
α14        ............................................................
α153       ............................................................
α275       ............................................................

>  <   Tm5    ><            loop3
MC58  241  SWVGEKGFIGVAYSDRRDQYGLPAHSHEYDDCHADIIWQKSLINKRYLQLYPHLLTEEDI 300
O53422     ..........A................................................V
Z2491      ..........A.................................................
FAM18      ............................................................
α14        ...........................................................V
α153       ..........A.................................................
α275       ..........A.................................................

>< Tm6    >  <  Tm7    >
MC58  301  DYDNPGLSCGFHDDDNAHAHTHSGRPWIDLRNKRYELRAEWKQPFPGFEALRVHLNRNDY 360
O53422     ................N.K.......................L.................
Z2491      ...............D....A.N.K....................................
FAM18      ...............D.............................................
α14        ...............D....A.N.K....................................
α153       ...............D....A.N.K....................................
α275       ...............D....A.N.K....................................
```

FIG.8(Cont.)

```
                    <   loop4    >< Tm8    > <   Tm9   ><   loop5
MC58    361 RHDEKAGDAVENFFNNQTQNARIELRHQPIGRLKGSWGVQYLQQKSSALSAISEAVKQPM 420
O53422      H............K..............................................
Z2491       ...............................................G........T........
FAM18       ....................................................................
α14         ..........................................................T........
α153        ..........................................................T........
α275        H................................................G........T........

><   Tm10   > <   Tm11  ><   loop6
MC58    421 LLDNKVQHYSFFGVEQANWDNFTLEGGVRVEKQKASIQYDKALIDRENYYNHPLPDLGAH 480
O53422      ..............E..................................KQ........
Z2491       .........................................R..................
FAM18       .........................................R..................
α14         .........................................R..................
α153        .........................................R..................
α275        .........................................R..................

><   Tm12   > <   Tm13  ><      loop7           >
MC58    481 RQTARSFALSGNWYFTPQHKLSLTASHQERLPSTQELYAHGKHVATNTFEVGNKHLNKER 540
O53422      ............................................................
Z2491       ............................................................
FAM18       ............................................................
α14         ............................................................
α153        ............................................................
α275        ............................................................

<   Tm14   > <   Tm15  ><         loop 8
MC58    541 SNNIELALGYEGDRWQYNLALYRNRFGNYIYAQTLNDGRGPKSIEDDSEMKLVRYNQSGA 600
O53422      ............................................................
Z2491       ............................................................
FAM18       ............................................................
α14         ............................................................
α153        ............................................................
α275        ............................................................

><   Tm16   > <   Tm17  ><         loop9
MC58    601 DFYGAEGEIYFKPTPRYRIGVSGDYVRGRLKNLPSLPGREDAYGNRPFIAQDDQNAPRVP 660
O53422      ............................................................
Z2491       ...........................................L...A..........
FAM18       ............................................................
α14         ............................................................
α153        ............................................................
α275        ............................................................

><   Tm18   > <   Tm19  ><   loop10 ><   Tm20    > <
MC58    661 AARLGFHLKASLTDRIDANLDYYRVFAQNKLARYETRTPGHHMLNLGANYRRNTRYGEWN 720
O53422      .....V......................................................
Z2491       .....V......................................................
FAM18       .....V......................................................
α14         .....V......................................................
α153        .....V......................................................
α275        .....V......................................................

Tm21   ><   loop 11  ><   Tm22   >
MC58    721 WYVKADNLLNQSVYAHSSFLSDTPQMGRSFTGGVNVKF 758
O53422      ......................................
Z2491       ......................................
FAM18       ......................................
α14         ......................................
α153        ......................................
α275        ......................................
```

FIG.9

```
CLUSTAL FORMAT for T-COFFEE Version_6.07 [http://www.tcoffee.org]

A. baumannii        MLNKSK--------------------LFLAL-ITLGASK-ILL--AA---EGPVTTLNTI
A. pleuropneumoniae MFNKKL--------------------LAVL-ISAQFSP-LVW--AN---NNDVAVLDEV H. parasuis         MINNRTTE---------------QQNNRTTA-FSLAFSL-LLCCLGI---NAEQLELDEI
B. pertussis        MICYIVSFNENGTSFYREGNMRFERHPLSAAL-ALALAWQGAHAQASADGTSEAATLAPI
M. catarrhalis      MKVTMI------------------KKPLACAI-LATFSM-PMLAEANLKD-KPTVILDGV
M. haemolytica      ML----------------------KKNYLTVSI-LLAISG-VGYA--------NEISLETI
P. multocida        MPLLTLKINM-----F-----F-MRKISYLSLCVISALYSQ-LAVAQSPLKNTSEHIELEPI
N. meningitidis     MAQTTL------------------KPIVLSI-LLINT--PLLAQAHE--TEQSVDLETV
                        *                            :                 *    :

A. baumannii        VLTAQSDELGSELLGKSLNVSNQFIDTSK-LKQRSTTLGDALGTELGIHSNQYGGGASAP
A. pleuropneumoniae SVVGSTPSISQGSEVTLLKVSDKIIAGKE-FKKRSATLGNALAAELGVHSNPFGGGASKP H. parasuis         SVMGKVPE---GNSISFLKVSDAIIDGEK-FKNRSATLGNALSSELGVHSTPFGGGASAP
B. pertussis        TVSA--SPL-AG-DLDSMTAPAAVLEGDQLLLRRQGTLGDTLDGLPGVHADTFGGGASRP
M. catarrhalis      SITSLADQNTEFGVNHSKTVSGITVSKEQ-LQQRATTLGDALAGELGVHSNHFGGGASAP
M. haemolytica      TVDGNTPSTKGKLLGGELNSNESVVDEKN-LKQGSITLGNALSGELGIHSSQFGGGASTP
P. multocida        FVNTLIESREGAPLGGRLMASEKIIPAYS-LKQRGSNLGDALSSELGIHASQFGGGASAP
N. meningitidis     SVVGKSRPRATSGLLHTSTASDKIISGDT-LRQKAVNLGDALDGVPGIHASQYGGGASAP
                        :                 :     : .   .**::*    *:*: :***** *

A. baumannii        IIRGQEGKRIKVLQNNADVLDMSNMSPDHAVTVEPSLAKSIEIIRGASTLLYSSNSAAGV
A. pleuropneumoniae IIRGQEGARIRILQNGSDVIDMSNLSPDHAVVADSLLAKQVEILRGSSTLLYASSSPAGI H. parasuis         IIRGQEGVRVKILQNNADVVDMSNISPDHAITADTLLANQVEILRGASTLLYASSSPAGI
B. pertussis        VIRGQTAPRVKVLSDGSELMDASAISPDHAVTTEPLLADKIEVLRGPATLLYGGGAIGGV
M. catarrhalis      IIRGQEGKRLKILQNGSEVVDMSGLSPDHAIAVDTTLAKQVEIVRGSGALLYASGNSAGV
M. haemolytica      IIRGQESKRAKILQNNGENLDMSGMSPDHAVTVDALLAKRIEILRGPTTLLYSAGNTAGV
P. multocida        VIRGQEGKRIKVLSSGNETLDMSAMSPDHAVAVDSLLAKKVEILRGANTLLYSSGNAAGV
N. meningitidis     VIRGQTGRRIKVLNHHGETGDMADFSPDHAIMVDTALSQQVEILRGPVTLLYSSGNVAGL
                    :**** . * ::*.      :  * : :*****:  .:. *:. :*::**. :***... .*:

A. baumannii        VNVIDYKIPTQMPQDGLEGNTTLRFNTGSNEKLTTAGVTVGLSPRVALRAEGLYRNAGNY
A. pleuropneumoniae VNVVDKRIPTEIPEKGYEVELNSRFDTAAKEKVGALGATFGIGKHIAVRAEGLTRHSDNY H. parasuis         VNIVDQRIPNKMPKKGYEVTLSSRFDTASKEKVYALGTTIGIGKHLALRLEGLDRQSQNY
B. pertussis        VNVLDRKIPTAVPQQGIEAEAELRGATGTKERAGAIGITAGSG-NFAVRVEGLKRRSSDY
M. catarrhalis      VNVVDDKIPSKLPSK-LQGDVTVRLSSANREKLITASAEAPLGEHVAVRVAGLSKQAADY
M. haemolytica      INVVDNKIPTAIPEKGYEGQFGVRFGSASKERLTYAGSTFALGNHLALRVQGMYNKASEY
P. multocida        VNVVDNKIPTAE-VVGVEGEVGLRTGSADNERLVNVALDVGLSKHFALHLEGLHKKAGDY
N. meningitidis     VDVADGKIPEKMPENGVSGELGLRLSSGNLEKLTSGGINIGLGKNFVLHTEGLYRKSGDY
                    ::: * :**         .    * :. *:   .    . ...:*  *:  ..: :*

A. baumannii        KTPHYQSSSYNSLEDLEN---QNIVYKNLKYLPESWAESRLGTLGLSWIDDNTYLGVSYT
A. pleuropneumoniae RVPGINL------------------GERLNYVPDTYNKSKVGTLGLSFVGEQGYIGASYS H. parasuis         KVPQIKL------------------GETLNYVPDTYHQSKVGTIGLSFIGEKGYLGASYN
B. pertussis        RVPDWPD-----------------------GKLAGSYSESGQGTVGMSWITPRGYVGVAFT
M. catarrhalis      KTPRFDRHVFNKKHEDDNTQPEFIYKDTLKHLPDSHAKSNAGTLGVSWVGNQGFLGASVS
M. haemolytica      YAPHFTI------------------EGKPYHRVPDSDVQSQTGTVSLSWIGERGHLGIAYT
P. multocida        RTPSYQY------------------QGSTHHKLANSFVDNRSGSVGLSWVGDKGYLGVAYS
N. meningitidis     AVPRYR-------------------NLKRLPDSHADSQTGSIGLSWVGEKGFIGVAYS
                       .*                       :.. : ..  *::..:*::  . ..:* : .

A. baumannii        HRHEDEYGLPA[HSHLYEGCGAS]AISINTRISGLKNYLLYYPQLMEEQDINYVNPRPDC[H]--
A. pleuropneumoniae KRRDNYGLPG[HNHKFDFCIGH]IYGN---KQGKYAYTYLYPHLIGEENIG-SNPHFHCGT[D]

H. parasuis         QRKDRYGLPG[HNHKFDTCIAH]IYDM--RLQGKHSYTNLYPHLMSDEMVT-ENPHFHCGT[D]
B. pertussis        HLESKYGLPG[HNHEYEGCHPH]G------------------------SHLHCGG[H]
M. catarrhalis      LRRDKYGLPN[HSHEYEECSVH]GISQ--SALQYKPYLRLYPFLMENDDLEFDNAGLECHT[H]
M. haemolytica      DRRDKYGLIG[HTHKYDHYTIS]IIRQ--AVMFAKGYLRFYPHLAEEGDIDYNNPGIRLL--
P. multocida        QRKDKYGLPA[HSHLYDEYYMH]VLLS--DAHWRKPYLKHYPFLMEETDIDYNNPGIDCIKK
N. meningitidis     DRRDQYGLPA[HSHEYDDCHAD]IIWQ--KSLINKRYLQLYPHLLTEEDIDYDNPGLSCGF-
                       ...*** *.*  ::
```

FIG.9(Cont.i)

```
A. baumannii       --------------QH----NHIHET-TFSH---NAPYIDLNTRRYDMRGEFTQPFTGIDK
A. pleuropneumoniae ------HAEDGTHSHDN--PFGHDH-DHTH---PGPWVDLESKRFDVKAELRQPFKGIDK H. parasuis        ------YDLDPSHSHDH--PYGHDH-DHTH---IGPWVDLHSKRIDIKGEIKQPLPMLDK
B. pertussis       DDHG------HGHDEHEEGEAEHDH-GHEHGAGDVPYVKLRSNRTDLRAEYTDPFAGFEK
M. catarrhalis     DDHD------HEHDHAH--DHEHDH-EHDH---GKPWIDLKMKRYDVQGQINAPFAGIDK
M. haemolytica     ----HTHIPGGSH---------YG-QDTHEH---GKPWIDMHSKRYDIDGSLQNPLPGFEE
P. multocida       EWHSHGHLCNHGHAHHG--NGQHSHDHHAH---ADPHIALNTQRWDLRGEWKNPVKGLDK
N. meningitidis    ------H--------DD--DNAHA---HTHS--GRPWIDLRNKRYELRAEWKQPFPGFEA
                                . *       *  : :.  .*   ::    ..    *.   ::

A. baumannii       IRTSLSYIDYFHNELEGDKI----------------TNFFKNTGKVGRIELSHQ----
A. pleuropneumoniae IKVSYADADYYHDEKDAGVLATRYH-KQLKKDQDYGKPVNIFKNRGKNARLEIYHA----

H. parasuis        IQLSYAQTDYYHDEKDAGKSGDTINPNRVDKSKDFGKPVNIFKNQGKNARLEFFHT----
B. pertussis       IRFRGGLTDYRHDEIEGGQL---------------GTRFQNRGYDARLELTHR----
M. catarrhalis     IRASMGKVDYHHDEIDGGEK---------------TSFFDNQANVWRLEASHTPIHT
M. haemolytica     AKISANYVDYYHDEKDGKRV---------------ENYFKNKGKNLRFELVHK----
P. multocida       VRFSIAKVGYRHDEKSGAIS---------------DNSFKNKGYSARVEFLHQ----
N. meningitidis    LRVHLNRNDYRHDEKAGDAV---------------ENFFNNQTQNARIELRHQ----
                           : .* *:*  .            . *.*   .*.*   *

A. baumannii       PLGELTGILGLQYLEQDNSALSPVHSQEGHTTYLDTQQLLNRNVTKNFSVFGLEKYNW-N
A. pleuropneumoniae PLGGLTGVWGVQYQTQKSSMHAPKD--------REVKFPLVENTNKQMSLFGIEQYMW-D H. parasuis        PIGGLTGMFGVQYQTLQSSANTPNN--------REVQWPLVDNRNKQISLFALEQYAW-D
B. pertussis       PLYGWHGVVGVQTSYSDFRA------------TGEEAFLPRSKTRAHGLFLLEEYRW-A
M. catarrhalis     PMGKFSGVFGVGYLTSKNSGLVPPRYEDG--NKQDTQNILHNNKTKTGSVFWFEEYKPND
M. haemolytica     EWKGLKGAIGVQYTNQSTSALALEASRAA--KVFNKQPLLNNPKTKLWSLFAIERLNL-G
P. multocida       PIAGVSGLIGLSHVYQDSYALDNHTL------EYRKQNLLSDHTTAQQSLFLMEHVEL-G
N. meningitidis    PIGRLKGSWGVQYLQQKSSALSAIS-------EAVKQPMLLDNKVQHYSFFGVEQANW-D
                        *  *:          .                :  *            ..*  .*.

A. baumannii       DFTFELGARIEKQKVSMDYDIEKIKDSMKPWPNKYNSPYVEKNNKIRAQNLK-SILEAVQ
A. pleuropneumoniae NFALEFAGRVEKQKIEIEYDRNEIKRLQDHYRIS---------------GGK-QVEPDLS H. parasuis        NFAIELGLRTEKQNIHIDYDLAKIQKQQKFNERT--------------YGK-QVDPDLS
B. pertussis       DWRFELGARQDWQRVSPQ-----------------------------------SGAP
M. catarrhalis     KLTVDAAARIEKQTITMDYDKDAIYQSLNLGLATAHEPDI--------RFKRLLDSGTLN
M. haemolytica     DFTFELSGRAERQKIAMDYDVKLIDRWLGFNT---------------------PMPNLD
P. multocida       KWQFDIGGRVEKQRIAMKYHFNVPKDEQP------------------------PEELTR
N. meningitidis    NFTLEGGVRVEKQKASIQYDKALIDRENYYNH-----------------------PLPDLG
                       .  .: . *  : *    .

A. baumannii       PNKETAFSYAGTVHWRFAPNYILSLTGTHQERLPNAQEMYTHGMHLATNSFEIGNRFLRK
A. pleuropneumoniae PYNQNAYAYSSTLNWFFHPDYQLSFTASHNERFPTPMELYYHGQHIATNSFEYGNKDLKK H. parasuis        DYDEKAISYTGAFNWFFHPDYQLSFTASHNERLPTPMELYYHGQHLATNSFEYGNKDLKK
B. pertussis       ASRTAGTSLSAAAIWDFAPQYSLALVSRSQRLPSAQELYADGVHLATNTYEIGDPGLDR
M. catarrhalis     PKKQTARSYAVGTHLQLTPKHKLSLNLSHQERLPNAQEMYAHGMHLATNSFEIGNRFLNK
M. haemolytica     PHKDKGYSYSFATHWYFAPNHKLTLNAAHQERLPNAQELYAHGKHIALNAFEAGNKNLKK
P. multocida       PHKSKAYSYALSANYQLNEQHQFNMIVSHQERLPNAQELYAHGKHLATNSFEAGNKNLTK
N. meningitidis    AHRQTARSFALSGNWYFTPQHKLSLTASHQERLPSTQELYAHGKHVATNTFEVGNKHLNK
                          . : :    :    .: : :    ::.:*:*.. *:*  .*  *:*  *:::*  *:    *  :

A. baumannii       EKSNNLEISLAYKDDLLDYQISTYYYDFDNYIYLQTLNEVL---------GTTKVRDQHT
A. pleuropneumoniae EQSNNVELGLGYQTERVGYKVNVYYNHFKNYIYNENLFR-----------------ENQ H. parasuis        EISNNFELGLGYHTEKLDYKLSTYYNNFDNYIYNETLYR-----------------SNN
B. pertussis       ETSRNVDLTLRKHSGDTTFSVSAFHNRVKNYIYANTLDR-----------------YED
M. catarrhalis     EKSNNIDLGLTFQGDKWDYRLGGYHYDFDNYVFLQTLSQYK---------QGLRGMRHDKD
M. haemolytica     ERSNQIELSLAYVGDKWDYKLNLYHTRYGNYIYPLTLNDNR---------GPKSFTDEYN
P. multocida       ERSNNVELGWGYTGEKLGIKLSGYYQQFSNYIYAAILNNKTSCPWRPNSRCLRSLSDDYP
N. meningitidis    ERSNNIELALGYEGDRWQYNLALYRNRFGNYIYAQTLNDGR---------GPKSIEDDSE
                   * *.:.::               :   :      **::      *
```

FIG.9(Cont.ii)

```
A. baumannii       LRINHYSQSAANFYGLEGNIGYQFNSVYHGSLFGDYVKGRLTNLPDAVIAYDIWNRE---
A. pleuropneumoniae LFMRRYNQAKARFYGIEAEASYRFNDKYQATIFGDMVRGWLTNLPPLTVNSDYSVFK---

H. parasuis        LFMRRYNQAKATFYGLEGIINYRFTPDYQFSVFGDMVKGKLKQLPDIKGLNDVYGEPILN
B. pertussis       FRLIEYTQRDAEFTGVEGEVRHRFGKVFSAAVFGDYVRGRLTG-----------------
M. catarrhalis     LKTARYEQAAAKFYGFDVNIGYQINDVYHVALFGDYIRGKLTNLPDKKGRTDAYGN----
M. haemolytica     LKVNRYYQGEARFSGAEGEIGYLFTPNYRLAVFGDYVRGKLVNLPNIAMSYNIWTGE---
P. multocida       LRLYRYNQAKAKIYGLEAEVSYQISSTHSVSIFGDYVRGKLKDLPSLPIGYKYIYNE---
N. meningitidis    MKLVRYNQSGADFYGAEGEIYFKFTPRYRIGVSGDYVRGRLKNLPSLPGREDAYGN----
                    : .* *  *:*:          .      :** ::* *

A. baumannii       --------------------PTLAPQKDRYTPRLPPARLGTRLKADFDESLKGEIEYYRV
A. pleuropneumoniae -DYLPKDAKPG--------EDYLIYRADQNTPRTPPVRLGFRFNAEFTPNWSGDLELIRT H. parasuis        PDYDPEYDEPEDQYYRPYLGKEMIKQADRVSPRLPPIRLGARFNAQLTENLSGSVEWMKV
B. pertussis       -------------------------GGGNLPRIPAARLGVRADAQWQ-NWAGGVEYFHV
M. catarrhalis     --------RP-------------LIKQPDSHTPRLPPKRLGMKLTANVNANWSGFLEYRHT
M. haemolytica     ---------V----------DKWASQPDISAPRIPPLRLGARFNADFNLNWSGMLEYYRV
P. multocida       -NYDMVGVQP----------TGWEKQPDGNAPRMSPMRLGIKWNAYFDNGISFNTQLYRV
N. meningitidis    --------RP-------------FIAQDDQNAPRVPAARLGFHLKASLTDRIDANLDYYRV
                                      ** .. *** : *           : :.

A. baumannii       FKQDNISKFEQVTSGYNMLNMTLAYKNKLSHT--EYDLFFKANNLLDQKVYAHETFLPYI
A. pleuropneumoniae FTQRRTSQLEYITEGNTMLNIGVAYSNKWKDL--DYKISLNGTNLLNQPVYIHTSYHQFV H. parasuis        FTQNKVSKLESSTKGYQLLNASLNYRRQIKGV--EYTVSLTGNNLLNQAVYIHNSYHPYV
B. pertussis       YRQDDIAAYESSTPGYDMVNATIRYRGKLDRT--AYEIYLRGNNLLNKLAFNHASFISTV
M. catarrhalis     FKQDKLANFERPTPAHNLVNLGLNYQHKPSHQAGSVQVFFNANNLLNDKVFAHETFFPDM
M. haemolytica     FAQKKVSKYEQVTPGHHQVNLGVTYSNHFNQT--EYQVFLKVDNLLNQKMYQHASYLPHI
P. multocida       FAQNKVARLETPTKGHTMLNLGMSYDGKMGNN--EYTLFANVNNVLNSRVYNHTSFLSYI
N. meningitidis    FAQNKLARYETRTPGHHEMLNLGANYRRNTRYG--EWNWYVKADNLLNQSVYAHSSFLSDT
                   : *   :   * *   .  :*   *  :         *:*:.  : * ::

A. baumannii       -PQIGRNFSLGLNLNF
A. pleuropneumoniae -PQTGRNFILVVNVKF

H. parasuis        -PQMGRNFILGLDLSF
B. pertussis       APLPGRSVLLGVRLTY
M. catarrhalis     -PQMGRNFMLGANFKF
M. haemolytica     -PQMGRNAMLGMNISF
P. multocida       -PQSGLGLNVGMNFKF
N. meningitidis    -PQMGRSFTGGVNVKF
                     *  *  .      ..:
```

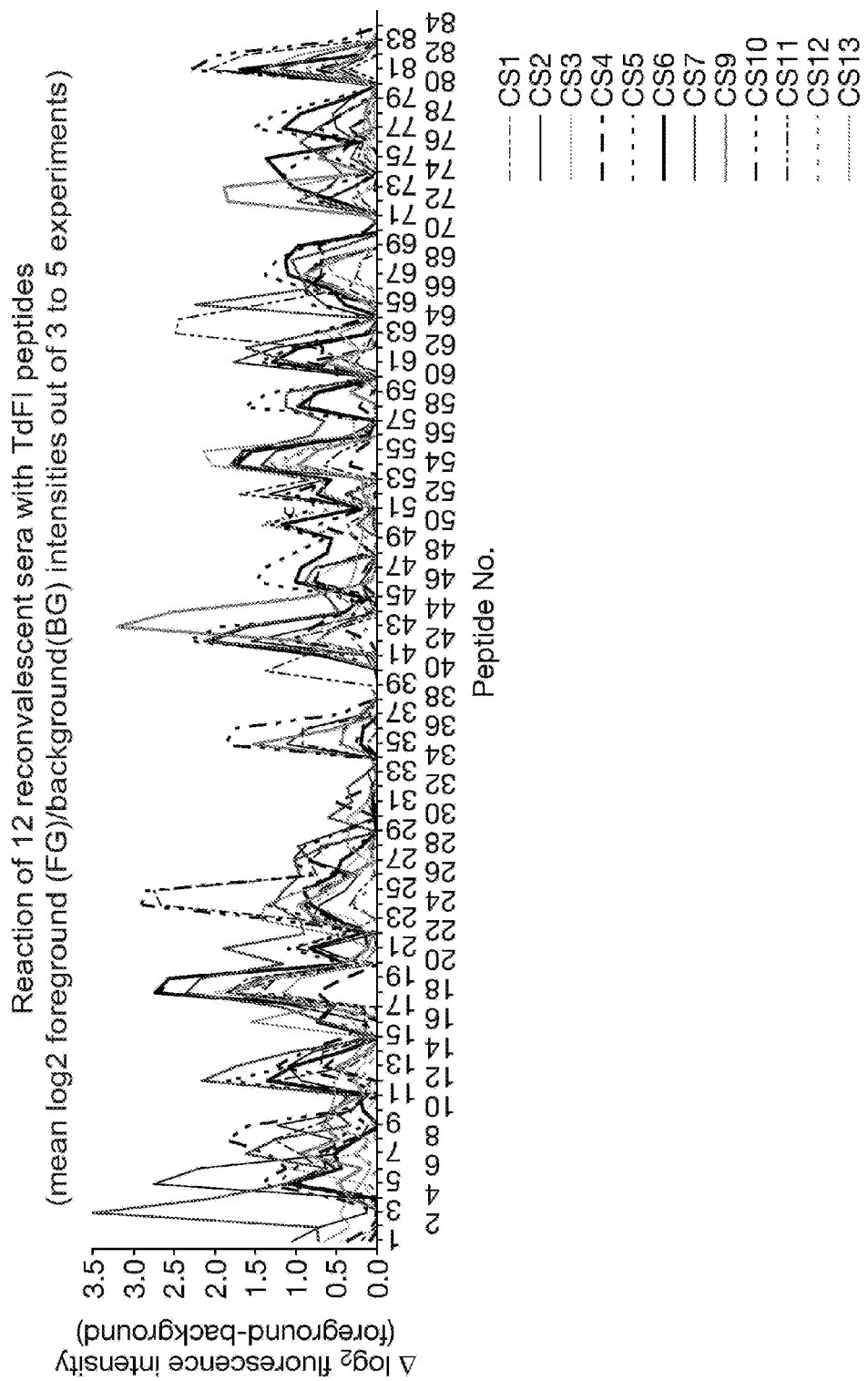
FIG. 10  ZnuD (TdfI) peptide array: Individual response of human sera obtained for convalescent patients or healthy carriers.

OMVs used for immunization

Prescence of fHbp in OMVs preparation (ELISA)

FIG.13(Cont.iii)

FIG.13(Cont.vii)

FIG.13(Cont.viii)

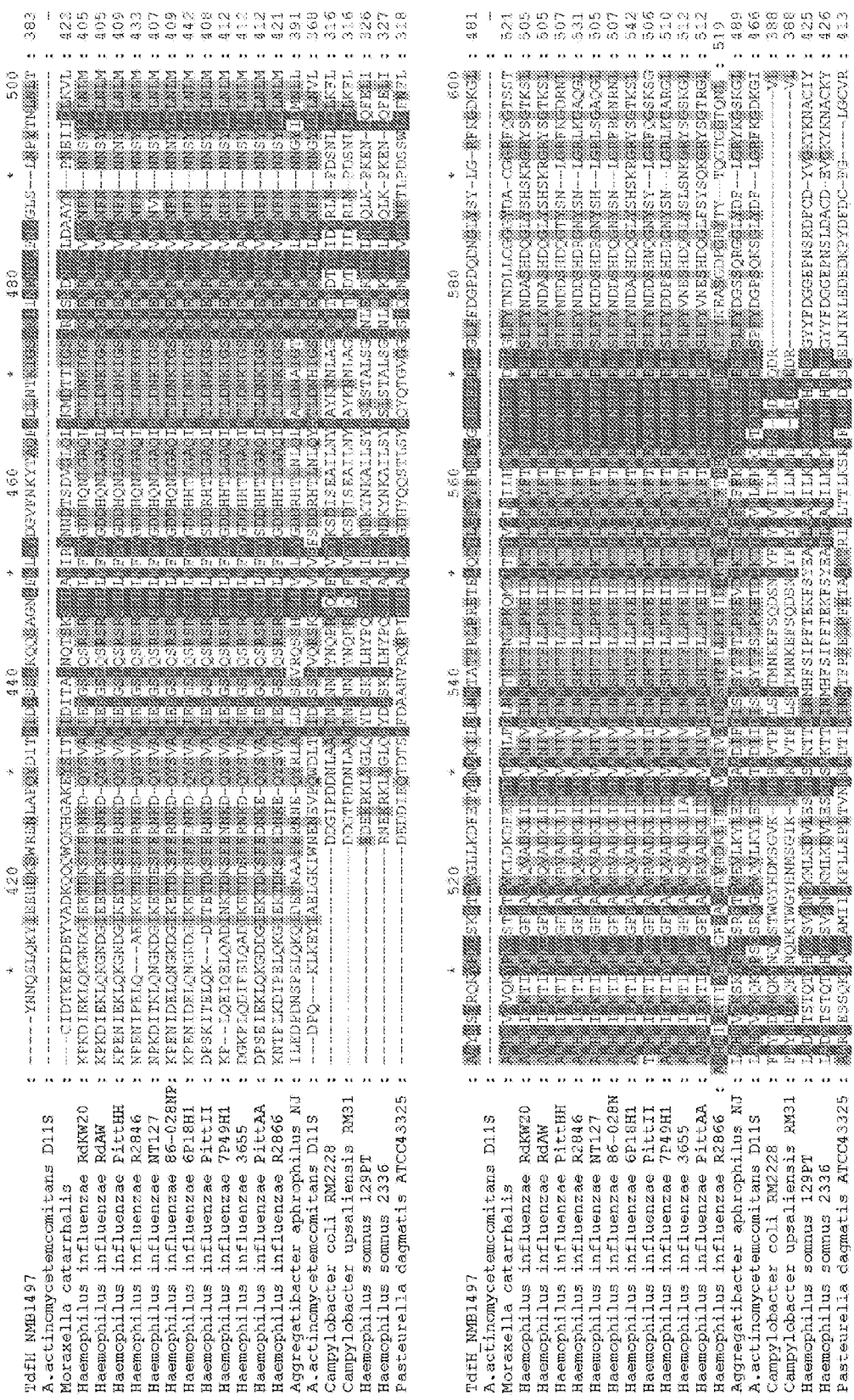
FIG.14(Cont.ii)

FIG.14(Cont.iii)

VACCINE

This application is filed pursuant to 35 U.S.C. §371 as a United States National Phase Application of International Patent Application Serial No. PCT/EP/2011/053665 filed Mar. 10, 2011, which claims priority from Provisional Application No. 61/312,959 filed Mar. 11, 2010.

TECHNICAL FIELD

The present invention relates to the field of Gram-negative bacterial immunogenic compositions and vaccines, their manufacture and the use of such compositions in medicine. More particularly, it relates to immunogenic compositions comprising outer membrane proteins of Gram-negative bacteria which are involved in uptake of extracellular zinc. Such proteins are promising antigens as they show high conservation between strains belonging to many different Gram-negative bacterial species.

BACKGROUND

Gram negative bacteria are the causative agents for a number of human pathologies and there is a need for effective vaccines to be developed against many of these bacteria. There is accordingly a need to identify further antigens, such as outer membrane proteins, which are well conserved within, and possibly between, Gram-negative species in order that such antigens may be useful as vaccine components.

In the case of serogroup B of N. meningitidis, the development of a vaccine has been impeded due to the fact that the polysaccharide capsule is poorly immunogenic owing to its immunologic similarity to human polysialylated glycoproteins such as neural cell adhesion molecule. Strategies for vaccine production have therefore concentrated on the surface exposed structures of the meningococcal outer membrane such as PorA, but have been hampered by the high antigenic variability of the major outer membrane proteins among strains.

However, N. meningitidis has recently been found to express an outer membrane protein, "TdfI" or "ZnuD" (BASB082 of WO 00/55327; locus tag NMB0964 in the sequenced genome of N. meningitidis serogroup B; herein SEQ ID NO. 1) involved in the uptake of extracellular zinc. This is surprising as it was previously believed that zinc crosses the outer membrane by passive diffusion through porins, and this finding is the first discovery of a protein involved in zinc uptake across the outer membrane of a Gram-negative bacterium.

SUMMARY OF THE INVENTION

The present inventors have identified homologues of TdfI in many strains from numerous Gram-negative bacterial species. The conservation of the amino acid sequence between these species may reflect the importance of TdfI in the active uptake of zinc in environments having low levels of free zinc. TdfI and its identified homologues, as well as homologues yet to be identified, represent a promising source of antigens for the development of vaccines against Gram-negative infection. Due to the amino acid sequence conservation of secondary structure amongst TdfI and its identified homologues, such vaccines may confer protection not only to individual serotypes, sub-species and strains, but across all members of a bacterial species, or other taxonomic level. Indeed, as shown in the Examples, TdfI can induce cross-bactericidal antibodies against almost all Neisserial strains tested regardless of serogroup, supporting the potential of this outer membrane protein to be used as a universal N. meningitidis antigen. A further surprising discovery on which the present invention is predicated is the identification of another N. meningitidis outer membrane protein involved in uptake of extracellular zinc, "TdfH" (BASB024 of WO 00/11182; herein SEQ ID NO. 50). Whilst TdfI is believed to be involved in the acquisition of free zinc from the extracellular environment, it appears that TdfH binds to non-free, complexed zinc, such as zinc bound to calprotectin as shown in the Examples. Homologues of TdfH have been identified in several strains from different Gram-negative bacterial species, and a high degree of amino acid sequence conservation is observed. Hence, analogous to TdfI, TdfH and homologues thereof are expected to be useful as a source of antigens for vaccination against Gram-negative infection and disease.

Following the work underpinning this present invention, it is now believed that N. meningitidis, and many other Gram-negative species, have active mechanisms for uptake of zinc across the outer membrane. Such mechanisms, which involve at least TdfI and TdfH, may be necessary due to the low levels of free zinc in the host (for example in the human body), especially in certain compartments such as the respiratory tract. As shown in the Examples, the viability of cells lacking TdfI or H is impaired in conditions of low free zinc, or where the zinc is complexed to e.g. calprotectin, respectively. Vaccination with the aim of targeting the host immune system to Gram-negative bacteria expressing TdfI or TdfH promises to provide effective prevention or treatment against infection by such bacteria, and such vaccines may have significant cross-protectivity within, and possibly between, Gram-negative species as a result of the conserved nature of the proteins. The protection conferred by a vaccine comprising an antigen based on one of these proteins could result from a bactericidal immune response towards the bacterium in question, or simply from a prevention of the zinc uptake activity the protein. It is envisaged that a vaccine comprising both TdfI- and TdfH-derived antigens, thereby targeting both identified zinc uptake mechanisms, may be particularly effective.

The present invention accordingly provides immunogenic compositions or vaccines, and methods, for eliciting an immune response against Gram-negative bacteria expressing outer membrane proteins involved in uptake of extracellular zinc, such as TdfI and/or TdfH and homologues thereof. Methods for preparing such compositions or vaccines are also provided.

BRIEF DESCRIPTION OF DRAWINGS

FIG. 1. Detection of TdfI on Western blot.

(FIG. 2) The presence of TdfI in cell lysates of HB-1 and the zur mutant grown in RPMI, RPMI with 600 nM zinc or TSB was assessed by Western blot analysis.

FIG. 3. Topology model of TdfI.

FIG. 5. Zinc regulation of TdfI is highly conserved in meningococci. (FIG. 5) Western blot of cell lysates of the indicated strains grown in RPMI with or without added zinc. [a] Clonal group designations taken from (36); – indicates that the strain was typed by Multi-Locus Enzyme Electrophoresis but could not be assigned to a specific clone.

(FIG. 6) Outer membrane vesicles used to immunize mice for antiserum production were separated by SDS-PAGE and stained with Coomassie brilliant blue.

(FIG. 7) See Example 1.

FIG. 8. (FIG. 8 & FIG. 8(Cont.)) Amino acid sequence alignment of TdfI of N. meningitidis strains MC58 with those of 053422, FAM18 and Z2491, the carrier strains α14, α153 and α275 The TonB box (Tb), the plug domain, the loops and the transmembrane domains (Tm) are marked above the sequence and the His- and Asp-rich stretches are underlined.

FIG. 9 (FIG. 9-FIG. 9(Cont. ii)) Amino acid sequence alignment of the TdfI homologues. The histidine aspartic acid rich stretches are highlighted in grey.

(FIG. 10-FIG. 10(Cont. i)) See Example 3. This Figure corresponds to FIG. 8 in U.S. 61/312,959. The samples listed top-to-bottom in the legends to FIG. 10 correspond to the samples listed from top-left to bottom-right (reading by rows) in the legends to FIG. 8 in U.S. 61/312,959.

(FIG. 11) FACs analysis using anti-ZnuD monoclonal antibody of H44/76 WT strain grown on either MH agar (gray shaded profile) or MH+20μM TPEN agar (thick line) and on Δzur H44/76 strain cultivated on MH agar (thin line).

TABLE 2

Figure 1A:
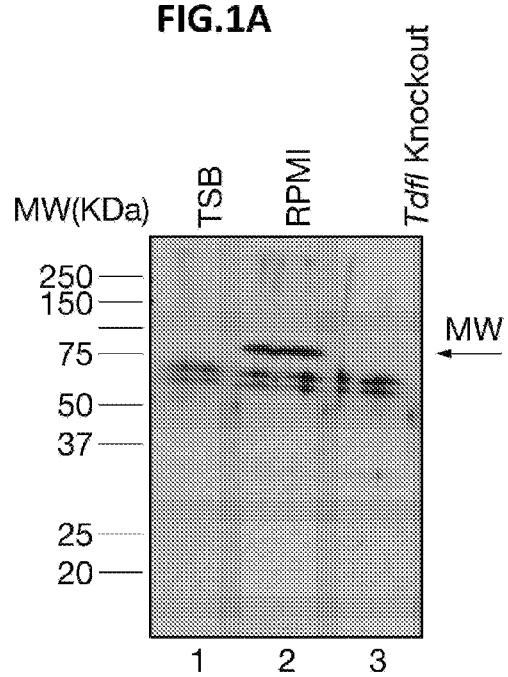
(FIG. 1A) HB-1 grown in TSB (lane 1), RPMI (lane 2) and the tdfI knockout strain grown in RPMI (lane 3).

Level of anti-fHbp and anti-ZnuD antibodies produced in mice and guinea-pigs after immunization with control OMVs and ZnuD OMVs

|  | Mice | | GP | |
| --- | --- | --- | --- | --- |
|  | TdfI | fHbp | TdfI | fHbp |
| Ctrl OMVs | 73[a] | 1342 | 10 | 335 |
| ZnuD OMVs | 15096 | 59314 | 5893 | 2733 |

[a]Geometric mean titers (expressed in EU/ml) from three pools of sera per group.

TABLE 3

Serum bactericidal titers (GMT for 50% killing) performed in presence of baby rabbit complement on a panel of 14 serogroup B strains cultivated with or without TPEN.

| Strains | H44/76 | NZ98/254 | M01-240101 | M01-240355 | M01-240013 | M01-240149 | MC-58 | 180-25 | DE10690-06 | M05-0240-471 | 175-40 | M05-0240-072* | 760-676 | M98-250-771 |
| --- | --- | --- | --- | --- | --- | --- | --- | --- | --- | --- | --- | --- | --- | --- |
| fHbp family | B | B | B | A | A | B | B | B | B | B | B | B | A | A |
| fHbp expression | ++ | + | + | + | + | + | ++ | +/- | +/- | +/- | - | - | - | +/- |
| TdfI expression | + | + | + | + | + | + | + | + | + | + | + | + | + | + |

| Animal species | Treatment | Culture condition | | | | | | Serum bactericidal titers | | | | | | | |
| --- | --- | --- | --- | --- | --- | --- | --- | --- | --- | --- | --- | --- | --- | --- | --- |
| Mouse | fHbp B | MH agar | 3383 | 110 | 494 | 50 | 50 | 2293 | 3993 | 3804 | 50 | 50 | 50 | 50 | 50 | 50 |
|  |  | MH-TPEN agar | 3539 | 388 | 509 | 50 | 50 | 2104 | 5786 | 4373 | 169 | 50 | 50 | 50 | 50 | 50 |
| Mouse | Control OMVs | MH agar | 103 | 50 | 50 | 50 | 50 | 71 | 88 | 50 | 50 | 50 | 50 | 50 | 50 | 50 |
|  |  | MH-TPEN agar | 265 | 112 | 50 | 50 | 50 | 50 | 304 | 182 | 50 | 50 | 50 | 50 | 50 | 50 |
|  | ZnuD OMVs | MH agar | 3605 | 69 | 519 | 50 | 50 | 3116 | 1734 | 50 | 50 | 50 | 50 | 50 | 50 | 50 |
|  |  | MH-TPEN agar | 7903 | 1854 | 1733 | 3310 | 852 | 3374 | 17486 | 4872 | 937 | 197 | 286 | 50 | 50 | 143 |
| GP | Control OMVs | MH agar | 55 | 50 | 50 | 50 | 50 | 50 | 67 | 67 | 50 | 50 | 50 | 50 | 50 | 50 |
|  |  | MH-TPEN agar | 115 | 50 | 50 | 50 | 50 | 50 | 50 | 50 | 50 | 50 | 50 | 50 | 50 | 50 |
|  | ZnuD OMVs | MH agar | 331 | 50 | 50 | 50 | 50 | 94 | 240 | 234 | 50 | 50 | 50 | 94 | 122 | 50 |
|  |  | MH-TPEN agar | 1751 | 2592 | 2153 | 2497 | 3706 | 2961 | 1846 | 752 | 1781 | 2005 | 667 | 50 | 50 | 2021 |

[a]Geometric mean titers (expressed in EU/ml) from three pools of sera per group. GMT above the threshold for a positive result (titer ≥ 128) are shown in bold

TABLE 4

Impact of culture conditions (ZnuD expression or not) on the bactericidal activity of sera on H44/76 WT strain and and delta fHbp or delta znuD H44/76 strains

| Species | SBA condition | Treatment | H44/76 strains | | |
|---|---|---|---|---|---|
| | | | WT | delta fHbp | delta Tdfl |
| Mouse | MH agar | CTRL OMVs | 97[a] | 50 | 50 |
| | | ZnuD OMVs | 5332 | 50 | 3925 |
| | MH-TPEN agar | CTRL OMVs | 304 | 50 | 216 |
| | | ZnuD OMVs | 13397 | 1581 | 9603 |
| Guinea-pig | MH agar | CTRL OMVs | 58 | 50 | 138 |
| | | ZnuD OMVs | 310 | 50 | 409 |
| | MH-TPEN agar | CTRL OMVs | 118 | 50 | 129 |
| | | ZnuD OMVs | 2402 | 3678 | 765 |

[a]Geometric mean titers (expressed in EU/ml) from three pools of sera per group.

See Example 3.

Figure 12A:
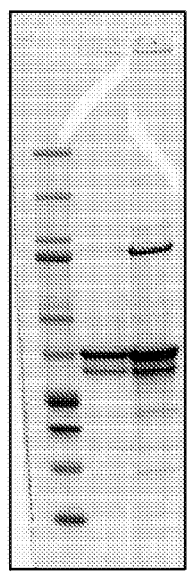
Figure 12B:
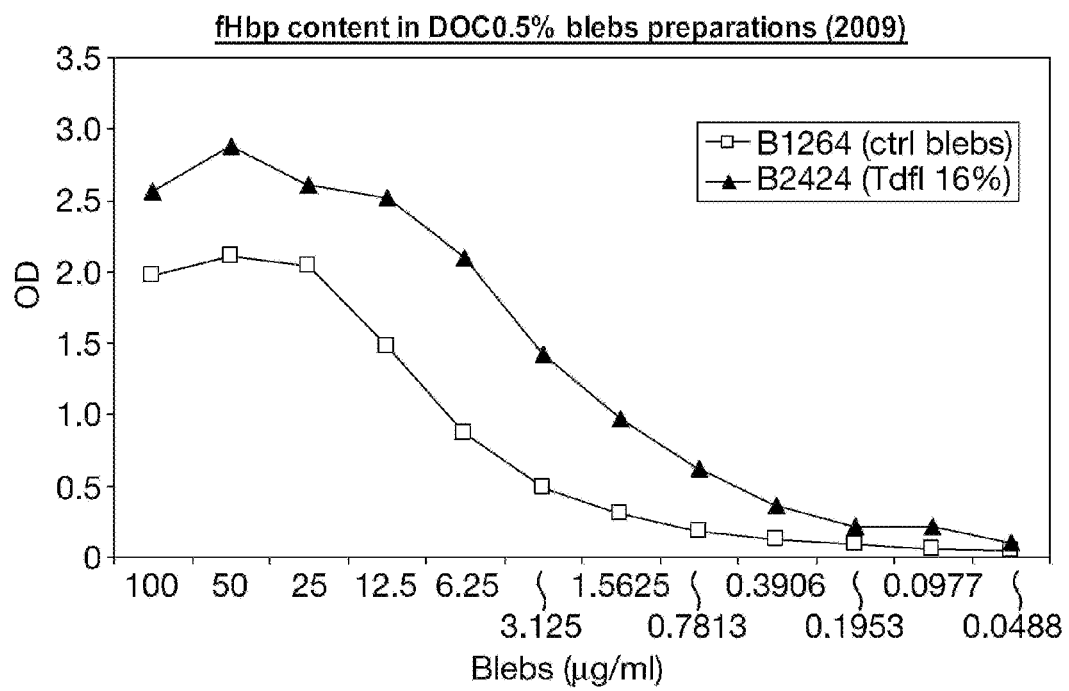

FIG. 12: OMVs used for immunization. SDS-PAGE (FIG. 12A). Presence of fHbp in OMVs preparation (ELISA) (FIG. 12B).

TABLE 5

Tdfl homologues

| Accession No. | Bacteria name | No. amino acids | No. amino acids identical to SEQ ID No. 1 | % identity over length of SEQ ID No. 1 | SEQ ID No. |
|---|---|---|---|---|---|
| AAF62323 | Neisseria meningitidis MC58 | 758 | 758 | 100 | 1 |
| YP_986285 | Acidovorax sp. JS42 | 695 | 252 | 33 | 2 |
| YP_002967458 | Acinetobacter baumannii | 803 | 325 | 43 | 3 |
| YP_003208315 | Acinetobacter baumannii | 803 | 328 | 43 | 4 |
| YP_001708692 | Acinetobacter baumannii | 803 | 325 | 43 | 5 |
| ZP_04661004 | Acinetobacter baumannii AB900 | 685 | 306 | 40 | 6 |
| YP_001847801 | Acinetobacter baumannii ACICU | 685 | 306 | 40 | 7 |
| YP_001083098 | Acinetobacter baumannii ATCC 17978 | 803 | 327 | 43 | 8 |
| YP_001706181 | Acinetobacter baumannii SDF | 685 | 306 | 40 | 9 |
| ZP_06058868 | Acinetobacter calcoaceticus RUH2202 | 691 | 309 | 41 | 10 |
| ZP_06064377 | Acinetobacter johnsonii SH046 | 680 | 302 | 40 | 11 |
| ZP_06064957 | Acinetobacter junii SH205 | 685 | 304 | 40 | 12 |
| ZP_06068135 | Acinetobacter lwoffii SH145 | 684 | 288 | 38 | 13 |
| ZP_05362119 | Acinetobacter radioresistens SK82 | 699 | 309 | 41 | 14 |
| YP_045356 | Acinetobacter sp. ADP1 | 693 | 296 | 39 | 15 |
| ZP_03824903 | Acinetobacter sp. ATCC27244 | 696 | 303 | 40 | 16 |
| ZP_05823027 | Acinetobacter sp. RUH2624 | 670 | 277 | 37 | 17 |
| ZP_03612144 | Actinobacillus minor 202 | 823 | 339 | 45 | 18 |
| ZP_04754640 | Actinobacillus minor NM305 | 823 | 340 | 45 | 19 |
| YP_001053620 | Actinobacillus pleuropneumoniae L20 | 782 | 317 | 42 | 20 |
| ZP_00133885 | Actinobacillus pleuropneumoniae serovar 1 str. 4074 | 782 | 317 | 42 | 21 |
| YP_001651932 | Actinobacillus pleuropneumoniae serovar 3 str. JL03 | 790 | 317 | 42 | 22 |
| YP_693858 | Alcanivorax borkumensis SK2 | 689 | 265 | 35 | 23 |
| YP_931882 | Azoarcus sp. BH72 | 691 | 271 | 36 | 24 |
| YP_002798586 | Azotobacter vinelanii DJ | 682 | 256 | 34 | 25 |
| NP_886739 | Bordetella bronchispetica RB50 | 713 | 264 | 35 | 26 |
| NP_882547 | Bordetella parapertussis | 711 | 264 | 35 | 27 |
| NP_881648 | Bordetella pertussis Tohama I | 713 | 263 | 35 | 28 |
| YP_001633406 | Bordetella petrii | 684 | 274 | 36 | 29 |
| YP_003278330 | Comamonas testosteroni CNB-2 | 711 | 248 | 33 | 30 |
| ZP_03543249 | Comamonas testosteroni KF-1 | 711 | 250 | 33 | 31 |
| YP_001564964 | Delftia acidovorans SPH-1 | 730 | 257 | 34 | 32 |
| YP_002553299 | Diaphorobacter sp. TPSY | 693 | 251 | 33 | 33 |
| ZP_02478325 | Haemophilus parasuis 29755 | 809 | 327 | 43 | 34 |
| YP_002474986 | Haemophilus parasuis SH0165 | 797 | 321 | 42 | 35 |
| YP_718275 | Haemophilus somnus 129PT | 868 | 294 | 39 | 36 |
| YP_001785276 | Haemophilus somnus 2336 | 868 | 304 | 40 | 37 |
| AAK29743 | Mannheimia haemolytica | 766 | 346 | 46 | 38 |
| ZP_04977416 | Mannheimia haemolytica PHL213 | 790 | 310 | 41 | 39 |
| ZP_05988256 | Mannheimia haemolytica serotype A2 str. BOVINE | 654 | 311 | 41 | 40 |
| ZP_05990414 | Mannheimia haemolytica serotype A2 str. BOVINE | 793 | 313 | 41 | 41 |
| AAU94646 | Moraxella catarrhalis | 818 | 343 | 45 | 42 |
| ZP_05920958 | Pasteurella dagmatis ATCC 43325 | 796 | 340 | 45 | 43 |
| NP_246018 | Pasteurella multocida subsp. multocida str. Pm70 | 809 | 339 | 45 | 44 |
| NP_246367 | Pasteurella multocida subsp. multocida str. Pm70 | 805 | 301 | 40 | 45 |

TABLE 5-continued

TdfI homologues

| Accession No. | Bacteria name | No. amino acids | No. amino acids identical to SEQ ID No. 1 | % identity over length of SEQ ID No. 1 | SEQ ID No. |
|---|---|---|---|---|---|
| NP_245682 | *Pasteurella multocida* subsp. *multocida* str. Pm70 | 925 | 270 | 36 | 46 |
| ZP_03841874 | *Proteus mirabilis* ATCC 29906 | 697 | 224 | 30 | 47 |
| YP_001171782 | *Pseudomonas stutzeri* A1501 | 672 | 251 | 33 | 48 |
| ZP_01302207 | *Sphingomonas* sp. SKA58 | 686 | 255 | 34 | 49 |

TdfH homologues

| Accession No. | bacteria name | No. amino acids | No. amino acids identical to SEQ ID No. 1 | % identity over length of SEQ ID No. 1 | SEQ ID No. |
|---|---|---|---|---|---|
| AAF41853.1 | *Neisseria meningitidis* MC58 | 921 | 921 | 100 | 50 |
| YP_003254871 | *Aggregatibacter actinomycetemcomitans* | 530 | 296 | 32 | 51 |
| YP_003254872 | *Aggregatibacter actinomycetemcomitans* D11S-1 | 365 | 245 | 27 | 52 |
| YP_003008699 | *Aggregatibacter aphrophilus* NJ8700 | 924 | 520 | 56 | 53 |
| ZP_00367782 | *Campylobacter coli* RM2228 | 758 | 286 | 31 | 54 |
| ZP_00371680 | *Campylobacter upsaliensis* RM3195 | 758 | 290 | 31 | 55 |
| ZP_01788784 | *Haemophilus influenzae* 3655 | 921 | 478 | 52 | 56 |
| ZP_04464966 | *Haemophilus influenzae* 6P18H1 | 950 | 487 | 53 | 57 |
| ZP_04466359 | *Haemophilus influenzae* 7P49H1 | 915 | 486 | 54 | 58 |
| YP_248875 | *Haemophilus influenzae* 86-028NP | 915 | 486 | 53 | 59 |
| ZP_05849940 | *Haemophilus influenzae* NT127 | 910 | 486 | 53 | 60 |
| ZP_01790772 | *Haemophilus influenzae* PittAA | 921 | 482 | 52 | 61 |
| ZP_01792691 | *Haemophilus influenzae* PittHH | 915 | 489 | 53 | 62 |
| ZP_01794868 | *Haemophilus influenzae* PittII | 915 | 491 | 53 | 63 |
| ZP_00154314 | *Haemophilus influenzae* R2846 | 934 | 488 | 53 | 64 |
| ZP_00157057 | *Haemophilus influenzae* R2866 | 929 | 476 | 52 | 65 |
| NP_439373 | *Haemophilus influenzae* Rd KW20 | 913 | 486 | 53 | 66 |
| ZP_05848904 | *Haemophilus influenzae* RdAW | 913 | 486 | 53 | 67 |
| YP_718388 | *Haemophilus somnus* 128PT | 915 | 350 | 38 | 68 |
| YP_001783402 | *Haemophilus somnus* 2336 | 917 | 356 | 39 | 69 |
| AAT76666 | *Moraxella catarrhalis* | 902 | 467 | 51 | 70 |
| ZP_05921174 | *Pasteurella dagmatis* ATCC 43325 | 860 | 326 | 35 | 71 |

Figure 13:
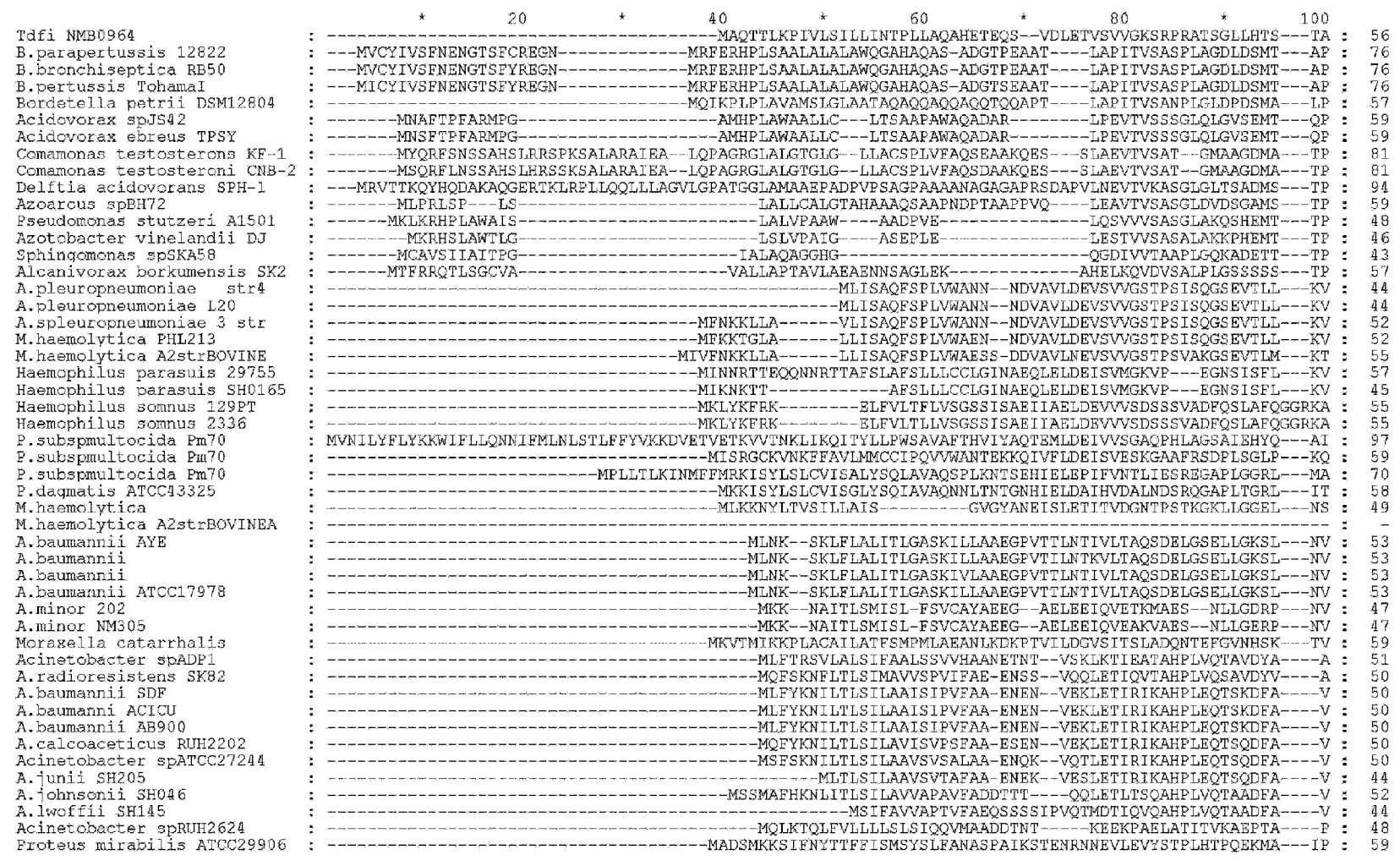
Figure 13:
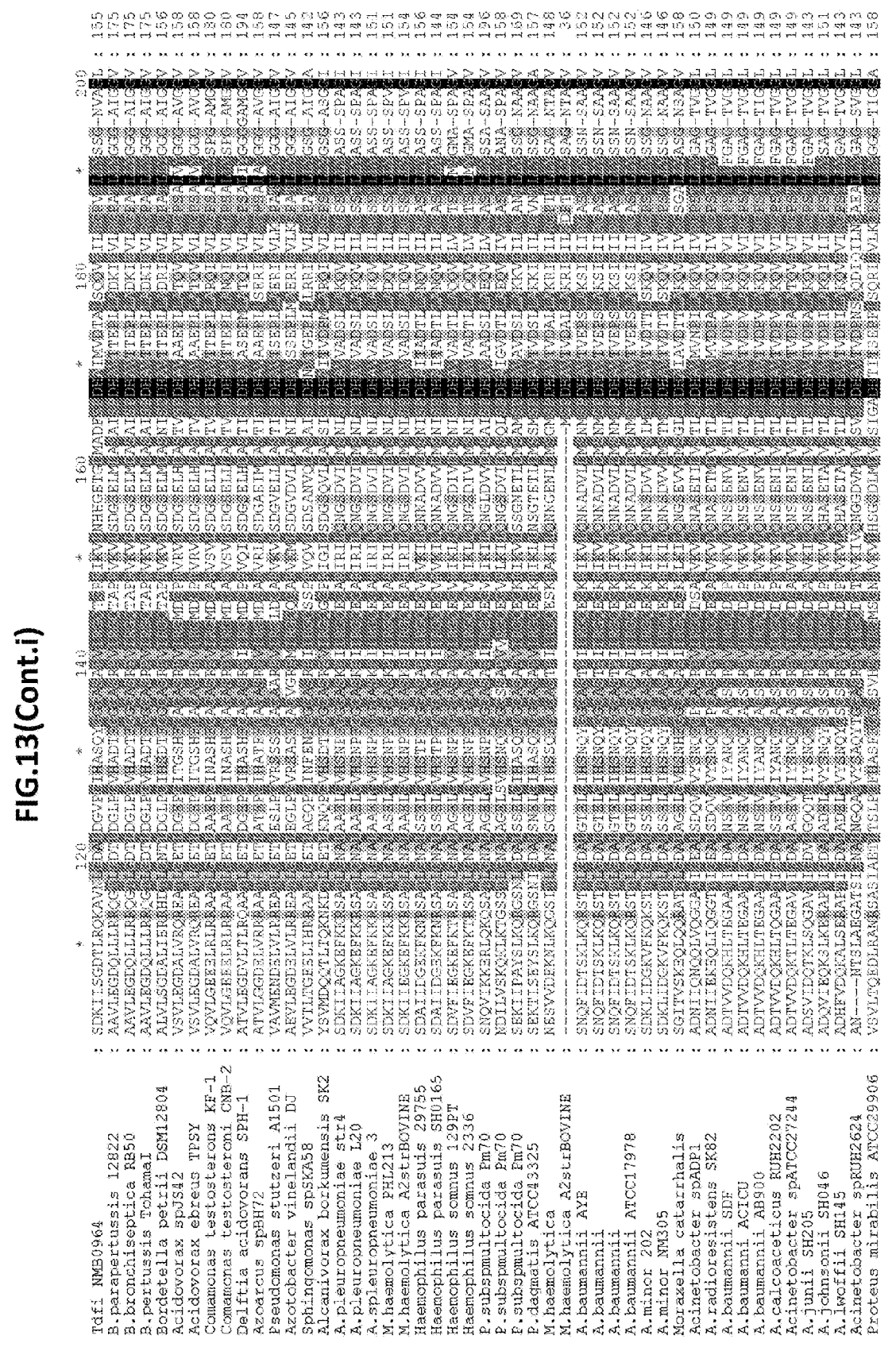
Figure 13:
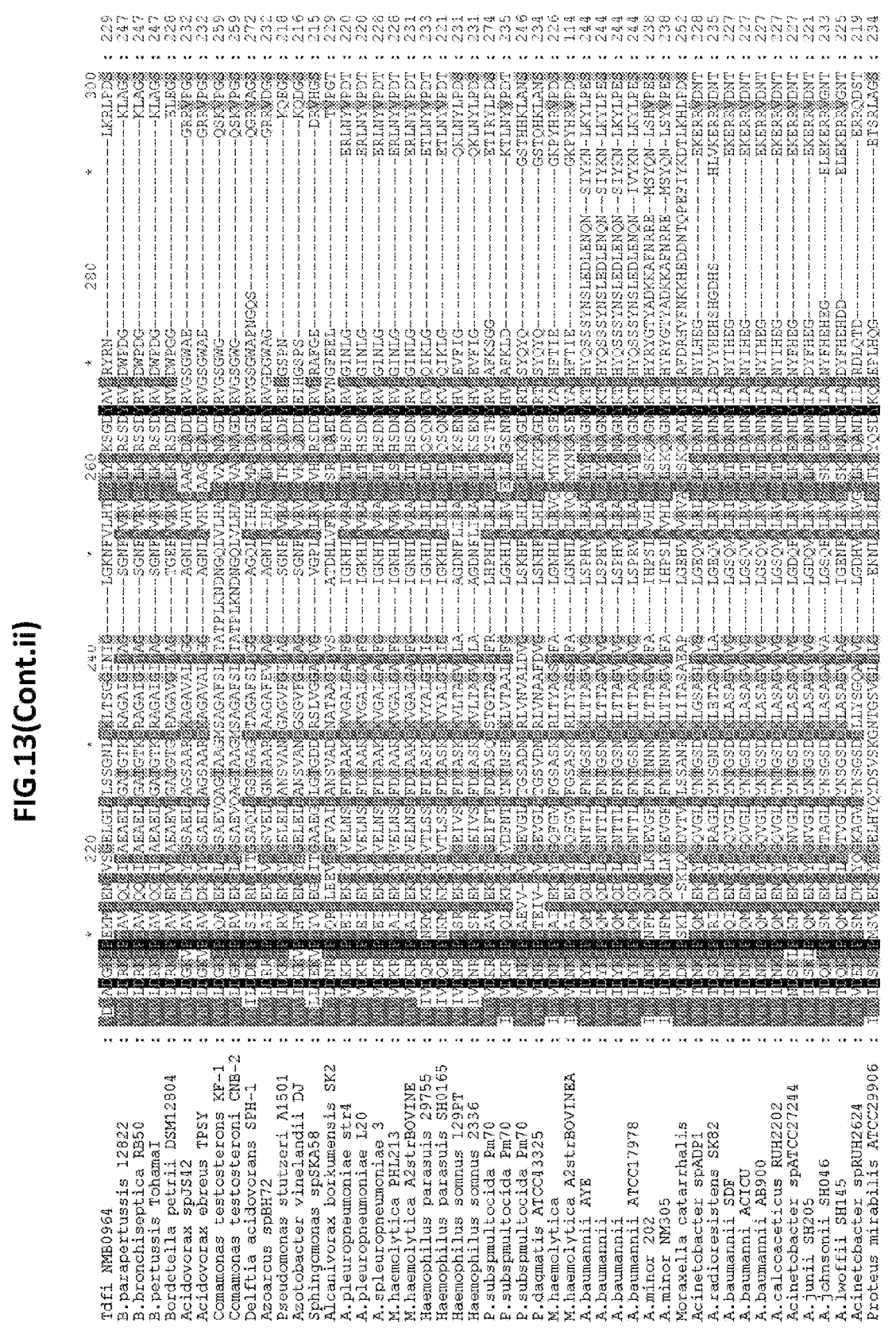
Figure 13:
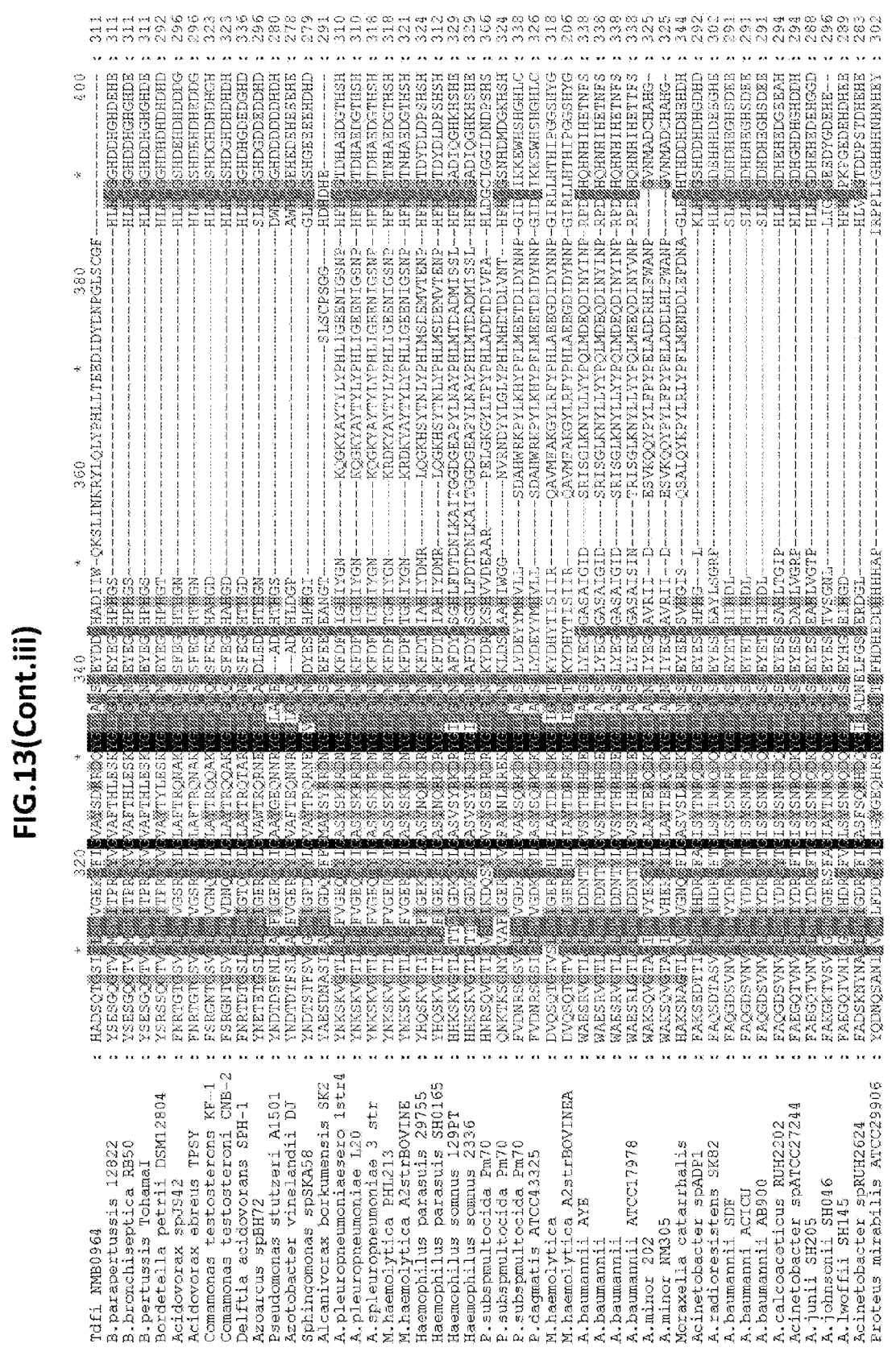
Figure 13:
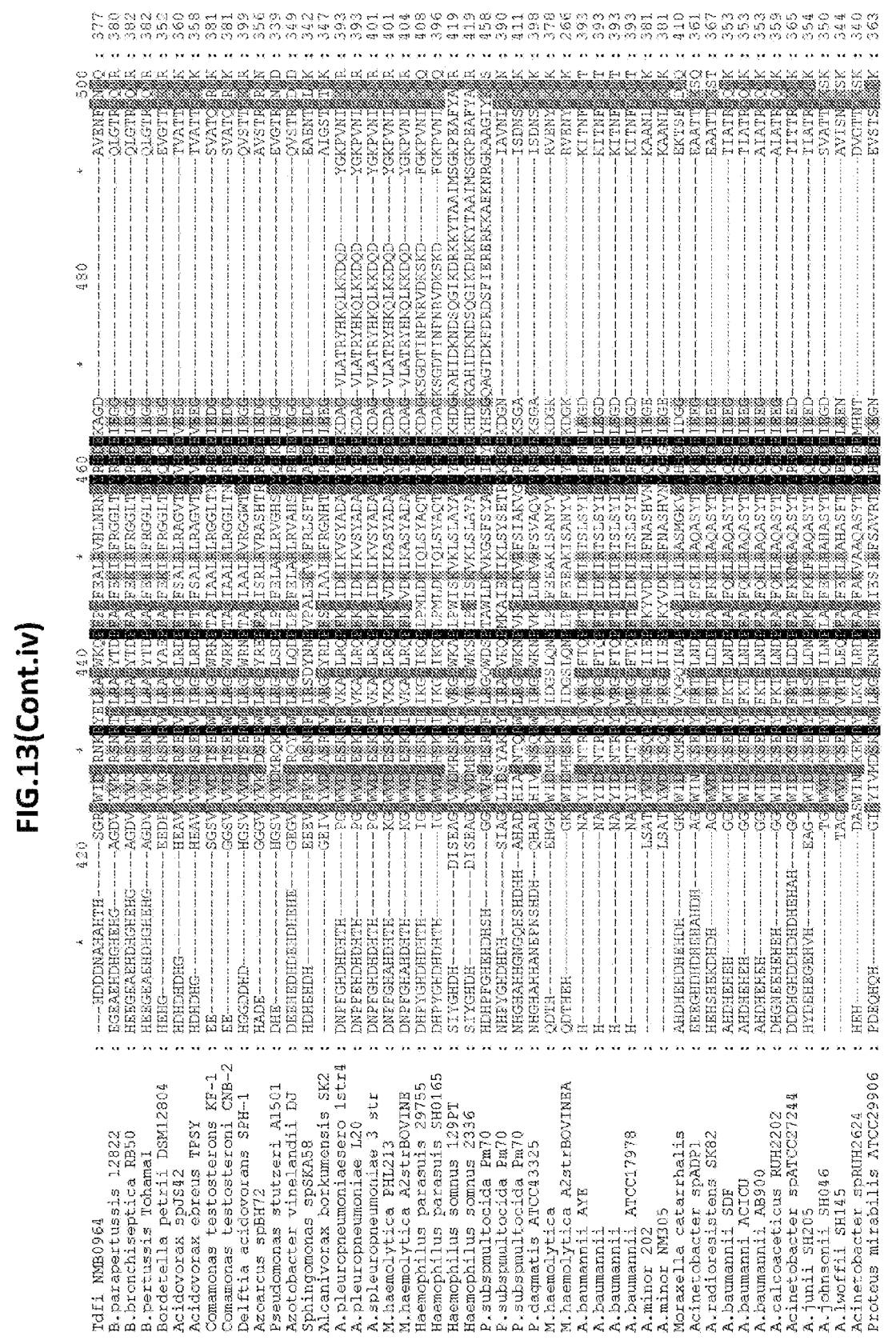
Figure 13:
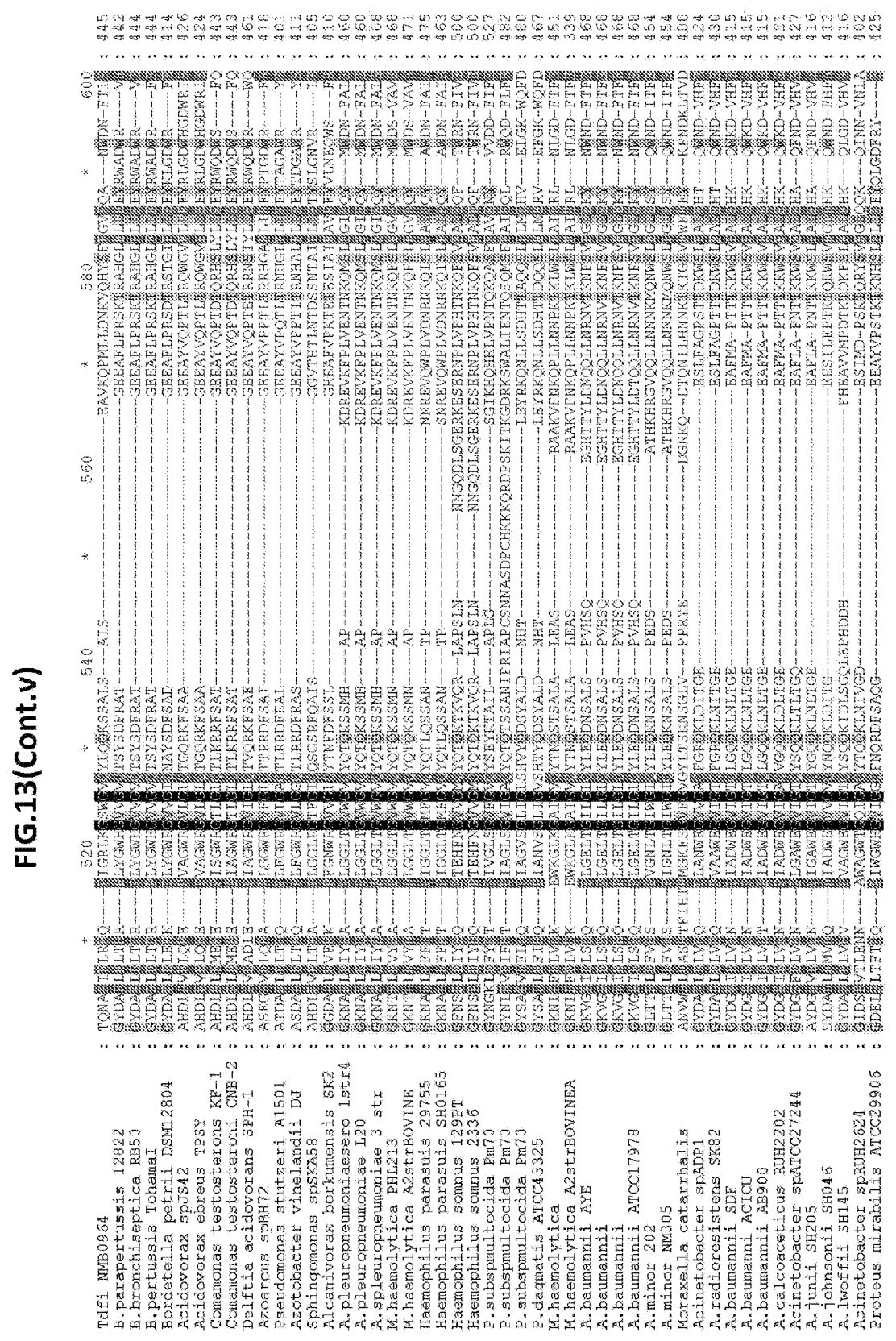
Figure 13:
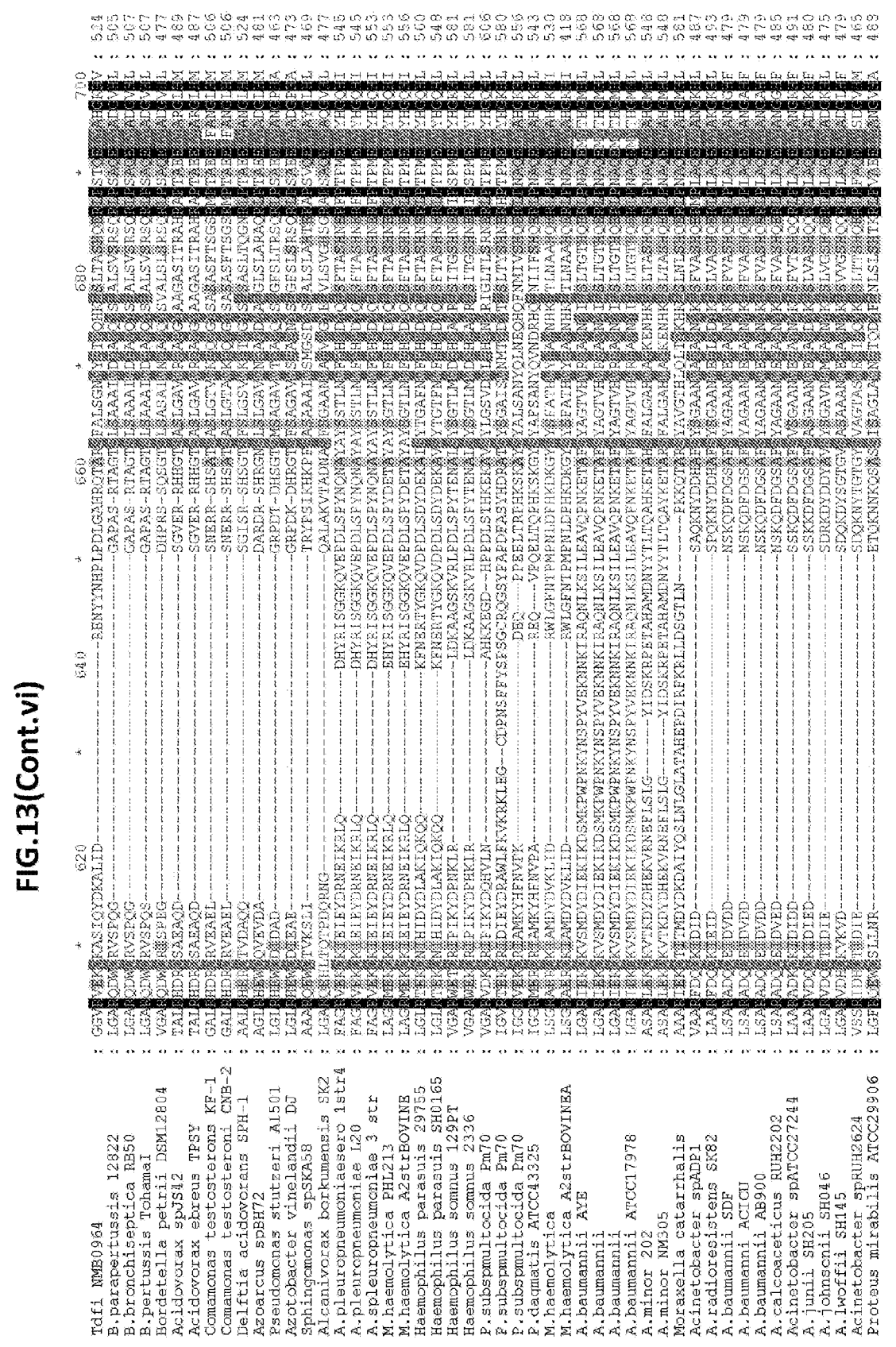
Figure 13:
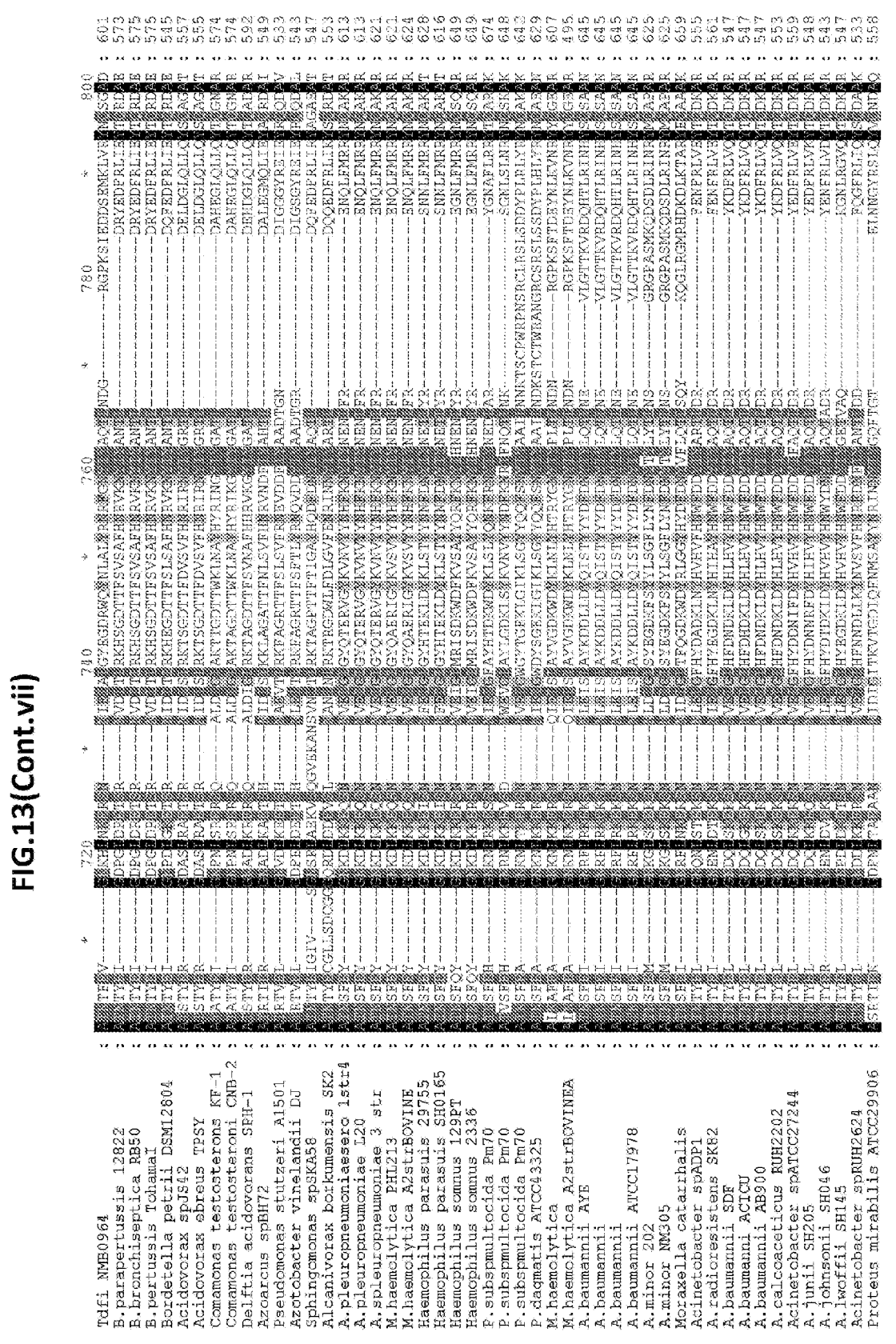
Figure 13:
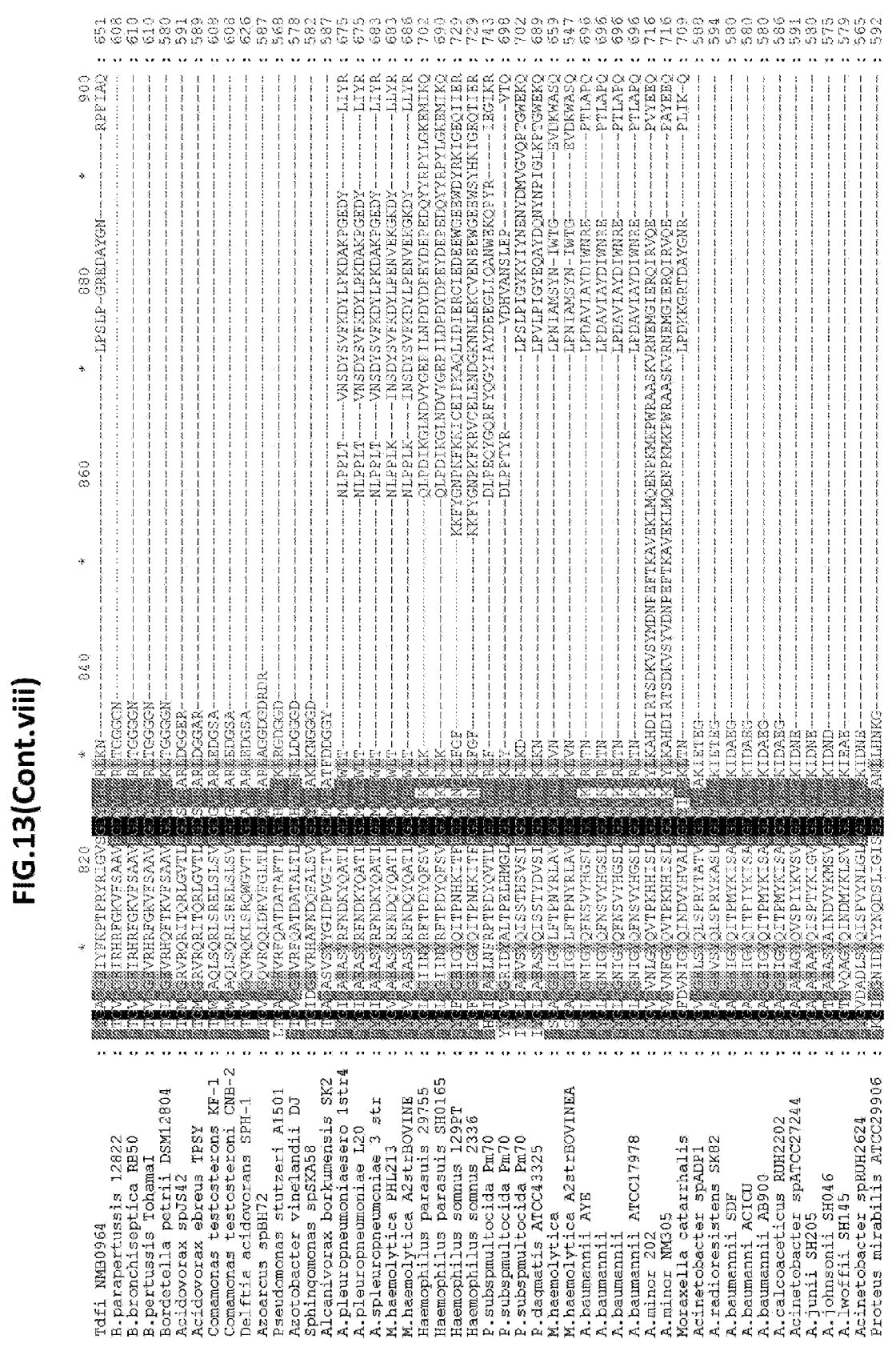
Figure 13:
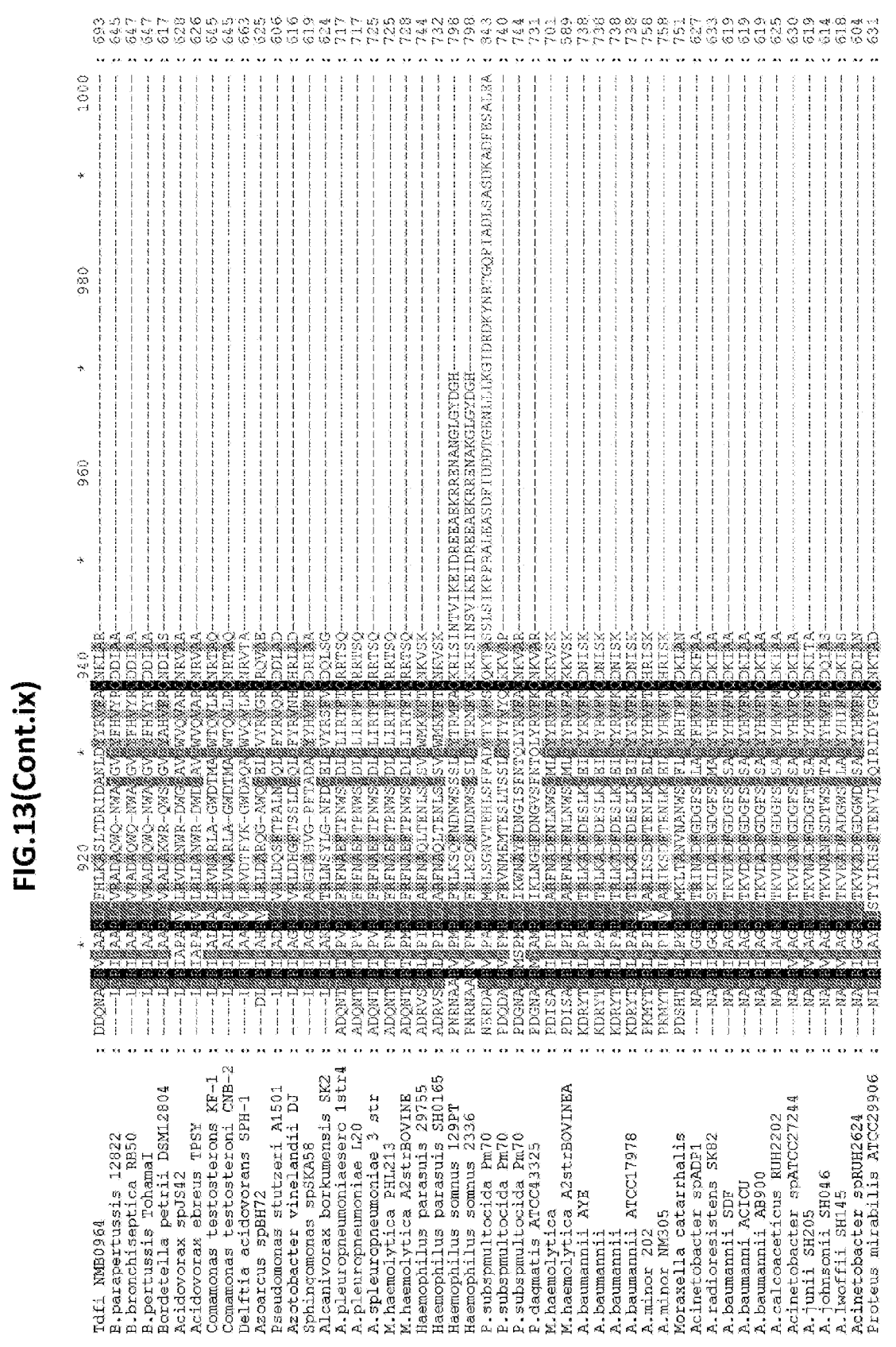
Figure 13:
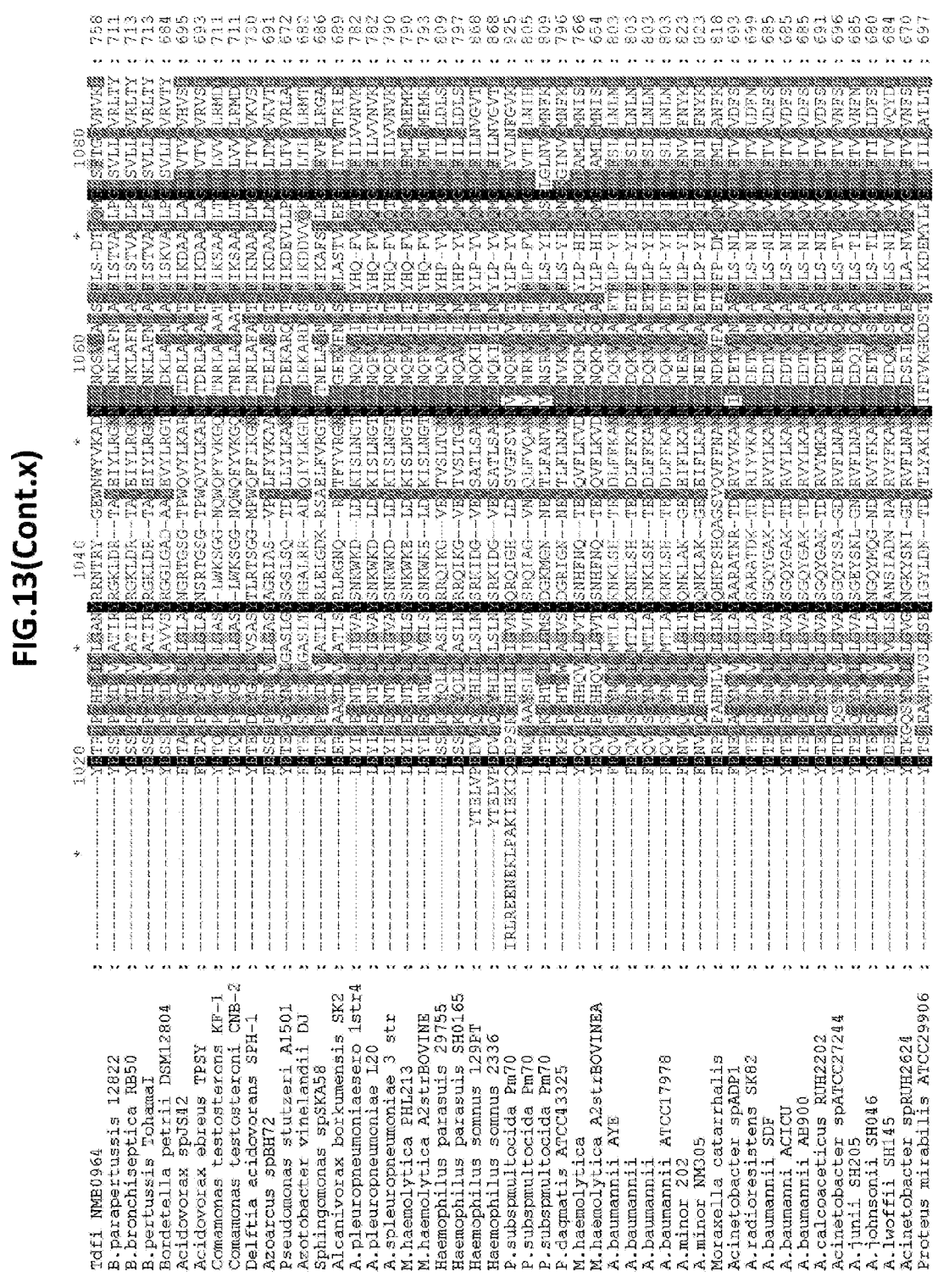

FIG. 13: multiple alignment of TdfI homologues. (FIG. 13-FIG. 13(Cont. x)).

Figure 14:
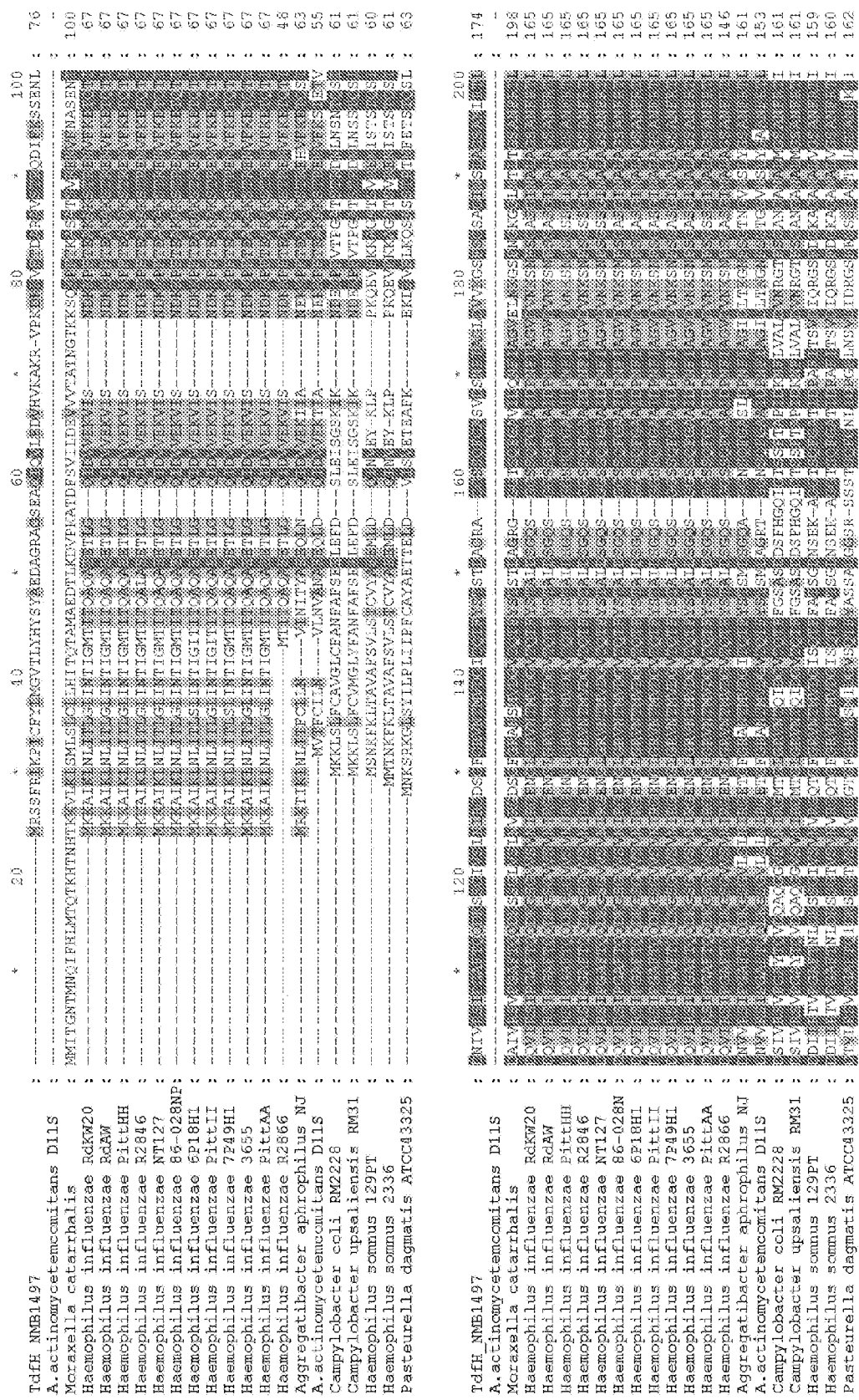

FIG. 14: multiple alignment of TdfH homologues. (FIG. 14-FIG. 14(Cont. v)).

Figure 15:
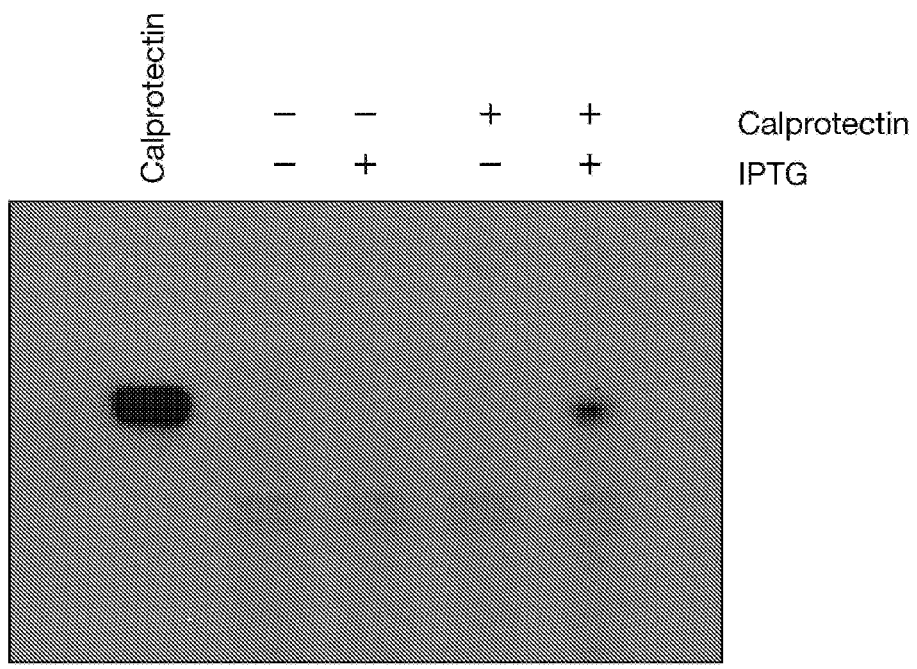

FIG. 15: calprotectin binding to TdfH (FIG. 15).

Figure 16:
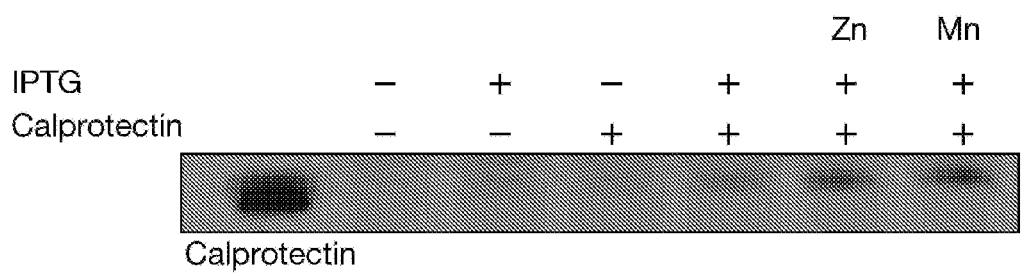

FIG. 16: calprotectin binding to TdfH in presence of Zn or Mn. (FIG. 16).

DETAILED DESCRIPTION OF THE INVENTION

The present invention is based on the discovery that *N. meningitidis* expresses outer membrane proteins involved in zinc uptake, at least one of which (TdfI) is found in most tested *N. meningitidis* strains as well as in numerous other Gram-negative bacterial species. TdfI from *N. meningitidis* serogroup B has been found to induce cross-bactericidal antibodies to *N. meningitidis* strains of all serogroups, and hence these proteins and their homologues in other Gram-negative species represent promising antigens for protecting against Gram-negative infection.

As used herein, the terms "TdfI protein" and "TdfH protein" are used to refer to the respective proteins as identified in *N. meningitidis* as well as to homologues thereof.

Hence, in one aspect the invention provides an immunogenic composition or vaccine comprising an antigen which is capable of raising an immune response, if necessary when coupled to a carrier protein, which recognises an outer membrane protein of at least a first gram-negative bacterial strain, wherein said protein is involved in uptake of extracellular zinc.

As used herein, by "immunogenic composition" or "vaccine" is meant a composition comprising at least one antigen which is capable of generating an immune response when administered to a host. "Immune response" as used herein means a B-cell antibody response.

An "antigen", according to the context of the present invention, is any substance which stimulates an immune response in the body. In one embodiment, the antigen is a polypeptide derived from the outer membrane protein of the first Gram-negative strain that is recognised by the immune response raised by said antigen. By "derived" in this sense is meant that the antigen is generated using said outer membrane protein as a starting point physically (e.g. by target mutation, truncation etc.) or intellectually (e.g. using the known sequence of said protein to design a synthesised polypeptide). As used herein, "polypeptide" means any chain of two or more amino acid residues linked by peptide bonds. The immunogenic composition or vaccine may comprise, in addition to said antigen, one or more additional antigens.

By "carrier protein" is meant any protein to which the antigen is coupled or attached or conjugated, typically for the purpose of enhancing or facilitating detection of the antigen by the immune system. The term is intended to cover both small peptides and large polypeptides (>10 kDa). The carrier may be any peptide or protein. It may comprise one or more T-helper epitopes. The carrier protein may be, for example, tetanus toxoid (TT), tetanus toxoid fragment C, non-toxic mutants of tetanus toxin, diphtheria toxoid (DT), CRM197, Pneumolysin (Ply), protein D, PhtD or PhtDE.

The immune response raised by the antigen may recognise an outer membrane protein of a first (i.e. of a single) bacterial strain, or it may recognise an outer membrane protein present on two or more strains, in which case said proteins need not be identical between the strains but must share similar epitopes such that each of the respective proteins is recognised by the immune response raised by the antigen. Of particular interest is the raising of an immune response which recognises multiple, or all, strains of a given Gram-negative species, wherein said strains differ by at least one of serogroup, serotype, serosubtype or the precise amino acid sequence of the outer membrane protein from which the antigen is derived. Cross-protection may also extend beyond individual species.

The term "outer membrane protein" as used herein means a polypeptide or protein integral to or attached to or expressed on the outer membrane of Gram-negative bacteria. The protein may be an integral membrane protein, i.e. "embedded" within the membrane, optionally having portions exposed periplasmically and/or extracellularly. Alternatively, the protein may be attached to the extracellular surface of the outer membrane, either directly to the lipid bilayer or to an integral protein. Suitably, the outer membrane protein is between 600-1000 amino acids in length.

Involvement of the protein in zinc uptake means that the protein binds free or complexed extracellular zinc, and optionally transports the bound zinc across the outer membrane. Whether or not a Gram-negative outer membrane protein is involved in zinc binding, and optionally transport, would be readily ascertainable to one skilled in the art, and the Examples provide several ways in which this may be accomplished, including modelling of protein structure, a zinc sequestration competition assay and an assay of the regulation of expression of the protein in response to external zinc concentration. More particularly, the involvement of said outer membrane protein in zinc uptake is such that zinc binding is reduced for outer membrane vesicles lacking said protein and accumulation of zinc is reduced in cells lacking said protein, and/or is such that cells lacking said protein have a reduced ability to grow in the presence of calprotectin as sole zinc source.

It is to be noted that the outer membrane protein recognised by said immune response may, in certain embodiments, not consist of the amino acid sequence of an NMB0964 polypeptide according to PCT/EP2009/052689 or a fragment thereof as disclosed therein, SEQ ID NO. 2 of WO 00/55327 or a fragment thereof as disclosed therein, SEQ ID NO. 606 of WO 99/57280 or a fragment thereof as disclosed therein, or SEQ ID Nos. 2, 4 and 6 of WO 00/11182 or a fragment thereof as disclosed therein. Additionally or alternatively, said first Gram-negative bacterial strain which expresses said outer membrane protein is not a Neisserial strain.

In one embodiment, the expression of said outer membrane protein is upregulated in response to low zinc availability. Said upregulation of expression relative to the level of expression of the protein during growth on a complex, zinc-containing medium such as tryptic soy broth (TSB) may be 1.5, 2, 2.5, 3, 3.5, 4, 4.5, 5, 5.5, 6, 6.5, 7, 7.5, 8, 8.5, 9, 9.5, 10-fold or greater. Such upregulation of expression may be achieved using a zinc chelator, suitably TPEN (N,N,N',N'-Tetrakis(2-pyridylmethyl)ethylenediamine) at for example 1-25 μm, or a chemically-defined medium low in zinc such as Catlin medium.

In one embodiment, said first Gram-negative bacterial strain which expresses the outer membrane protein recognised by said immune response is a strain which infects body compartments of humans and/or animals having low levels of free zinc. Such compartments include, for example, the respiratory tract and the blood as well as the urinary tract and intestine. Suitably, said first Gram-negative bacterial strain belongs to a species which infects the respiratory tract such as *Brucella* sp., *Coxiella* sp., *Pseudomonas* sp., *Acinetobacter* sp., *Moraxella* sp., *Chlamydia psittaci*, *Chlamydia trachomatis*, *Haemophilus influenzae*, *Haemophilus parasuis*, *Haemophilus somnus*, *Legionella pneumophila*, *Actinobacillus pleuropneumoniae*, *Bordetella pertussis*, *Bordetella parapertussis*, *Bordetella bronchoseptica*, *Mannheimia haemolytica*, *Pasteurella dagmatis* and *Pasteurella multocida*. In one embodiment, said low level of free zinc is a result of binding of zinc to molecules such as calprotectin.

By a low level of free zinc is meant under 5, 4, 3, 2, 1, 0.9, 0.8, 0.7, 0.6, 0.5, 0.4, 0.3, 0.2, 0.1, 0.05 or 0.01 μM free zinc, such as is present in Roswell Park Memorial Institute medium 1640 (RPMI) which has around 1.69 μM zinc by inductively coupled plasma mass spectroscopy. As used herein, "zinc" refers to $Zn^{2+}$.

In a particular embodiment, said first Gram-negative strain belongs to a species or genus selected from the group consisting of *Bordetella*; *Bordetella pertussis*; *Borrelia*; *Borrelia burgdorferi*; *Brucella*; *Brucella melitensis*; *Brucella ovis*; *Chlamydia*; *Chlamydia psittaci*; *Chlamydia trachomatis*; *Escherichia*; *Escherichia coli*; *Haemophilus*; *Haemophilus influenzae*; *Legionella*; *Legionella pneumophila*; *Neisseria*; *Neisseria gonorrhoeae*; *Neisseria meningitidis*; *Pseudomonas*; *Pseudomonas aeruginosa*; *Yersinia*; *Yersinia enterocolitica*; *Moraxella*; *Moraxella catarrhalis*; *Shigella*; *Shigella flexneri*; *Shigella dysenteriae*; *Shigella boydii*; *Coxiella*; and *Coxiella burnetii*.

In another embodiment, said first Gram-negative strain belongs to a species or genus selected from the group consisting of *Acidovorax*; *Acinetobacter*; *Acinetobacter baumannii*; *Acinetobacter baumannii*; *Acinetobacter calcoaceticus*; *Acinetobacter johnsonii*; *Acinetobacter junii*; *Acinetobacter lwoffii*; *Acinetobacter radioresistens*; *Actinobacillus*; *Actinobacillus minor*; *Actinobacillus pleuropneumoniae*; *Aggregatibacter*; *Aggregatibacter actinomycetemcomitans*; *Aggregatibacter aphrophilus*; *Alcanivorax*; *Alcanivorax borkumensis*; *Azoarcus*; *Azotobacter*; *Azotobacter vinelandii*; *Bordetella*; *Bordetella bronchiseptica*; *Bordetella parapertussis*; *Bordetella pertussis*; *Bordetella petrii*; *Campylobacter*; *Campylobacter coli*; *Campylobacter upsoliensis*; *Comamonas*; *Comamonas testosteroni*; *Delftia*; *Delftia acidovorans*; *Diaphorobacter*; *Haemophilus*; *Haemophilus influenzae*; *Haemophilus parasuis*; *Haemophilus somnus*; *Mannheimia*; *Mannheimia haemolytica*; *Moraxella*; *Moraxella catarrhalis*; *Neisseria*; *Neisseria gonorrhoeae*; *Neisseria meningitidis*; *Pasteurella*; *Pasteurella dagmatis*; *Pasteurella multocida*; *Proteus*; *Proteus mirabilis*; *Pseudomonas*; *Pseudomonas stutzeri*; and *Sphingomonas*.

More particularly, the outer membrane protein of said first Gram-negative strain comprises an amino acid sequence selected from the group consisting of SEQ ID No. 1; SEQ ID No. 2; SEQ ID No. 3; SEQ ID No. 4; SEQ ID No. 5; SEQ ID No. 6; SEQ ID No. 7; SEQ ID No. 8; SEQ ID No. 9; SEQ ID No. 10; SEQ ID No. 11; SEQ ID No. 12; SEQ ID No. 13; SEQ ID No. 14; SEQ ID No. 15; SEQ ID No. 16; SEQ ID No. 17; SEQ ID No. 18; SEQ ID No. 19; SEQ ID No. 20; SEQ ID No. 21; SEQ ID No. 22; SEQ ID No. 23; SEQ ID No. 24; SEQ ID No. 25; SEQ ID No. 26; SEQ ID No. 27; SEQ ID No. 28; SEQ ID No. 29; SEQ ID No. 30; SEQ ID No. 31; SEQ ID No. 32; SEQ ID No. 33; SEQ ID No. 34; SEQ ID No. 35; SEQ ID No. 36; SEQ ID No. 37; SEQ ID No. 38; SEQ ID No. 39; SEQ ID No. 40; SEQ ID No. 41; SEQ ID No. 42; SEQ ID No. 43; SEQ ID No. 44; SEQ ID No. 45; SEQ ID No. 46; SEQ ID No. 47; SEQ ID No. 48; SEQ ID No. 49; SEQ ID No. 50; SEQ ID No. 51; SEQ ID No. 52; SEQ ID No. 53; SEQ ID No. 54; SEQ ID No. 55; SEQ ID No. 56; SEQ ID No. 57; SEQ ID No. 58; SEQ ID No. 59; SEQ ID No. 60; SEQ ID No. 61; SEQ ID No. 62; SEQ ID No. 63; SEQ ID No. 64; SEQ ID No. 65; SEQ ID No. 66; SEQ ID No. 67; SEQ ID No. 68; SEQ ID No. 69; SEQ ID No. 70; and SEQ ID No. 71, wherein SEQ ID No. 1 is TdfI from *N. meningitidis* strain MC58 and SEQ ID Nos. 2 to 49 are homologues thereof and SEQ ID No. 50 is TdfH from *N. meningitidis* strain MC58 and SEQ ID Nos. 51 to 71 are homologues thereof.

In another aspect, the present invention provides an immunogenic composition or vaccine comprising an antigen, which antigen comprises a polypeptide having at least 30%, at least 40%, at least 50%, at least 60%, at least 70%, at least 80%, at least 90%, at least 95%, at least 99% or at least 100% identity to an amino acid sequence selected from the group consisting of SEQ ID No. 1; SEQ ID No. 2; SEQ ID No. 3; SEQ ID No. 4; SEQ ID No. 5; SEQ ID No. 6; SEQ ID No. 7; SEQ ID No. 8; SEQ ID No. 9; SEQ ID No. 10; SEQ ID No. 11; SEQ ID No. 12; SEQ ID No. 13; SEQ ID No. 14; SEQ ID No. 15; SEQ ID No. 16; SEQ ID No. 17; SEQ ID No. 18; SEQ ID No. 19; SEQ ID No. 20; SEQ ID No. 21; SEQ ID No. 22; SEQ ID No. 23; SEQ ID No. 24; SEQ ID No. 25; SEQ ID No. 26; SEQ ID No. 27; SEQ ID No. 28; SEQ ID No. 29; SEQ ID No. 30; SEQ ID No. 31; SEQ ID No. 32; SEQ ID No. 33; SEQ ID No. 34; SEQ ID No. 35; SEQ ID No. 36; SEQ ID No. 37; SEQ ID No. 38; SEQ ID No. 39; SEQ ID No. 40; SEQ ID No. 41; SEQ ID No. 42; SEQ ID No. 43; SEQ ID No. 44; SEQ ID No. 45; SEQ ID No. 46; SEQ ID No. 47; SEQ ID No. 48; SEQ ID No. 49; SEQ ID No. 50; SEQ ID No. 51; SEQ ID No. 52; SEQ ID No. 53; SEQ ID No. 54; SEQ ID No. 55; SEQ ID No. 56; SEQ ID No. 57; SEQ ID No. 58; SEQ ID No. 59; SEQ ID No. 60; SEQ ID No. 61; SEQ ID No. 62; SEQ ID No. 63; SEQ ID No. 64; SEQ ID No. 65; SEQ ID No. 66; SEQ ID No. 67; SEQ ID No. 68; SEQ ID No. 69; SEQ ID No. 70; and SEQ ID No. 71, optionally wherein said antigen is capable of raising an immune response, if necessary when coupled to a carrier protein, which recognises the amino acid sequence.

In this aspect, the polypeptide of which the antigen is (at least in part) comprised is capable of raising an immune response which recognises at least the amino acid sequence with which said polypeptide shares a degree of amino acid sequence identity. The degree of identity may be 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%. In one embodiment, the polypeptide has the same or substantially the same immunogenic activity as the amino acid sequence with which said polypeptide shares such amino acid sequence identity.

"Identity," as known in the art, is a relationship between two or more polypeptide sequences or two or more polynucleotide sequences, as the case may be, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heine, G., Academic Press, 1987; and *Sequence Analysis Primer*, Gribskov, M. and Devereux, J., eds., M Stockton Press, New York, 1991; and Carillo, H., and Lipman, D., SIAM *J Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GAP program in the GCG program package (Devereux, J., et al., *Nucleic Acids Research* 12(1): 387 (1984)), BLASTP, BLASTN (Altschul, S. F. et al., *J Mol. Biol.* 215: 403-410 (1990), and FASTA (Pearson and Lipman Proc. Natl. Acad. Sci. USA 85; 2444-2448 (1988). The BLAST family of programs is publicly available from NCBI and other sources (*BLAST Manual*, Altschul, S., et al., NCBI NLM NIH Bethesda, Md. 20894; Altschul, S., et al., *J Mol. Biol.* 215: 403-410 (1990). The well known Smith Waterman algorithm may also be used to determine identity.

Parameters for polypeptide sequence comparison can include the following:
Algorithm: Needleman and Wunsch, J. Mol Biol. 48: 443-453 (1970)
Comparison matrix: BLOSSUM62 from Henikoff and Henikoff,
Proc. Natl. Acad. Sci. USA. 89:10915-10919 (1992)
Gap Penalty: 8
Gap Length Penalty: 2

A program useful with these parameters is publicly available as the "gap" program from Genetics Computer Group, Madison Wis. The aforementioned parameters are the default parameters for peptide comparisons (along with no penalty for end gaps).

Parameters for pairwise alignment using the ClustalW program can include:
Gap Open Penalty: 10.00
Gap Extension Penalty: 0.10
Protein weight matrix: Gonnet series
DNA weight matrix: IUB Parameters for multiple alignment using the ClustalW program can include:
Gap Opening Penalty: 10.00
Gap Extension Penalty: 0.20
Delay divergent sequences: 30%
DNA Transitions Weight: 0.50
Protein weight matrix: Gonnet series
DNA weight matrix: IUB
Use negative matrix: OFF Unless otherwise stated, herein "identity" is expressed over the entire length of the reference, rather than the test, sequence. Multiple alignments of SEQ ID Nos. 1 and 50 with their respective identified homologues are shown FIGS. 10 and 11, and the identity values are shown in Tables 5 and 6.

In certain embodiments of this aspect, said antigen or polypeptide may optionally not have the amino acid sequence of an NMB0964 polypeptide according to PCT/EP2009/

052689 or a fragment thereof as disclosed therein, SEQ ID NO. 2 of WO 00/55327 or a fragment thereof as disclosed therein, SEQ ID NO. 606 of WO 99/57280 or a fragment thereof as disclosed therein, or SEQ ID Nos. 2, 4 and 6 of WO 00/11182 or a fragment thereof as disclosed therein.

In a further aspect, the present invention provides an immunogenic composition or vaccine comprising an antigen, which antigen comprises a polypeptide comprising an immunogenic fragment of a sequence selected from the group consisting of SEQ ID No. 1; SEQ ID No. 2; SEQ ID No. 3; SEQ ID No. 4; SEQ ID No. 5; SEQ ID No. 6; SEQ ID No. 7; SEQ ID No. 8; SEQ ID No. 9; SEQ ID No. 10; SEQ ID No. 11; SEQ ID No. 12; SEQ ID No. 13; SEQ ID No. 14; SEQ ID No. 15; SEQ ID No. 16; SEQ ID No. 17; SEQ ID No. 18; SEQ ID No. 19; SEQ ID No. 20; SEQ ID No. 21; SEQ ID No. 22; SEQ ID No. 23; SEQ ID No. 24; SEQ ID No. 25; SEQ ID No. 26; SEQ ID No. 27; SEQ ID No. 28; SEQ ID No. 29; SEQ ID No. 30; SEQ ID No. 31; SEQ ID No. 32; SEQ ID No. 33; SEQ ID No. 34; SEQ ID No. 35; SEQ ID No. 36; SEQ ID No. 37; SEQ ID No. 38; SEQ ID No. 39; SEQ ID No. 40; SEQ ID No. 41; SEQ ID No. 42; SEQ ID No. 43; SEQ ID No. 44; SEQ ID No. 45; SEQ ID No. 46; SEQ ID No. 47; SEQ ID No. 48; SEQ ID No. 49; SEQ ID No. 50; SEQ ID No. 51; SEQ ID No. 52; SEQ ID No. 53; SEQ ID No. 54; SEQ ID No. 55; SEQ ID No. 56; SEQ ID No. 57; SEQ ID No. 58; SEQ ID No. 59; SEQ ID No. 60; SEQ ID No. 61; SEQ ID No. 62; SEQ ID No. 63; SEQ ID No. 64; SEQ ID No. 65; SEQ ID No. 66; SEQ ID No. 67; SEQ ID No. 68; SEQ ID No. 69; SEQ ID No. 70; and SEQ ID No. 71, wherein said immunogenic fragment consists of an amino acid sequence having 7, 8, 9, 10, 11, 12, 13, 14, 15, 20, 30, 40, 50 or more contiguous amino acids of said selected sequence, and wherein said immunogenic fragment is capable of raising an immune response, if necessary when coupled to a carrier protein, which recognises said selected sequence.

An "immunogenic fragment" as used herein is a polypeptide having an amino acid sequence that is entirely the same over its length as part, but not all, of an amino acid sequence of the invention (i.e. of one of SEQ ID Nos. 1 to 71), and which is capable of raising an immune response which recognises at least the amino acid sequence of which it is a fragment. In one embodiment, the immunogenic fragment has the same or substantially the same immunogenic activity as the amino acid sequence of which said fragment is a fragment. Suitably said immunogenic fragment is, at least in part, from an extracellular portion of the amino acid sequence of which it is a fragment. Said fragments may otherwise be, for example, truncated derivatives of the amino acids sequences of the invention, such as a continuous series of residues that includes an amino- or carboxyl-terminal amino acid sequence. Degradation forms of the amino acids sequences of the invention may also be used.

In certain embodiments of this aspect, said antigen or polypeptide or immunogenic fragment may optionally not have the amino acid sequence of an NMB0964 polypeptide according to PCT/EP2009/052689 or a fragment thereof as disclosed therein, SEQ ID NO. 2 of WO 00/55327 or a fragment thereof as disclosed therein, SEQ ID NO. 606 of WO 99/57280 or a fragment thereof as disclosed therein, or SEQ ID Nos. 2, 4 and 6 of WO 00/11182 or a fragment thereof as disclosed therein.

Said antigen or said polypeptide or said immunogenic fragment may in particular be derived from a TdfI protein, in which case the amino acid sequences with which said polypeptide has amino acid sequence identity, or of which said immunogenic fragment is a fragment, are selected from the group consisting of SEQ ID No. 1; SEQ ID No. 2; SEQ ID No. 3; SEQ ID No. 4; SEQ ID No. 5; SEQ ID No. 6; SEQ ID No. 7; SEQ ID No. 8; SEQ ID No. 9; SEQ ID No. 10; SEQ ID No. 11; SEQ ID No. 12; SEQ ID No. 13; SEQ ID No. 14; SEQ ID No. 15; SEQ ID No. 16; SEQ ID No. 17; SEQ ID No. 18; SEQ ID No. 19; SEQ ID No. 20; SEQ ID No. 21; SEQ ID No. 22; SEQ ID No. 23; SEQ ID No. 24; SEQ ID No. 25; SEQ ID No. 26; SEQ ID No. 27; SEQ ID No. 28; SEQ ID No. 29; SEQ ID No. 30; SEQ ID No. 31; SEQ ID No. 32; SEQ ID No. 33; SEQ ID No. 34; SEQ ID No. 35; SEQ ID No. 36; SEQ ID No. 37; SEQ ID No. 38; SEQ ID No. 39; SEQ ID No. 40; SEQ ID No. 41; SEQ ID No. 42; SEQ ID No. 43; SEQ ID No. 44; SEQ ID No. 45; SEQ ID No. 46; SEQ ID No. 47; SEQ ID No. 48; and SEQ ID No. 49.

In a further embodiment, said polypeptide or immunogenic fragment of the immunogenic composition or vaccine of the invention comprises at least one of the following amino acid motifs:

91-G-S/A/V-S/A/V/G-X-P-V/I/M-V/I-R-G-Q/M/L-X-G/S/A-X-R;
116-D-V/A/M-S/A-2(X)-S/G-P/A-D-H-T/A/N-V/I;
154-G-L/V/A/I-V/I-N/D-V/I/L-X-D-X-K/R-I/L/V-P;
250-G-X-G/S/A-Y/F/W/V-G/S/T/N-X-Q/R/L-3(X)-Y-G-L/I/V-L/I/P-G/A-H/D;
334-R-X-D/E-X-R/K/Q/D-G/T/S/A-E/Q/S/D-3(X)-P-3(X)-I/F/V/L-3(X)-R/A/K/Q-5(X)-D/N/R/G-Y-X-H-X-E;
510-R-X-P-X-A/P/V/T-Q/E/M-E-L/M-Y/F-A/S/Y/T-X-G-X-H-X-A-T/L/S-X-T/S/A-F/Y/I/V-E/Q-(1-9)X-G-D/N/Q-X-X-L;
595-Y-X-Q/G-2(X)-A-X-F/L/Y/I-X-G-X-E/D-G/A/V-3(X)-Y/F/H/Q-8(X)-G/S/A/T-X-F/S-G-D-X-V/I-R/K/N-A/G; and

657-P/A-R-X-P/S/A-A/P/G-X-R-L/V/A-S/G.

The number preceding each motif indicates, in a still further embodiment, the position in the sequence of SEQ ID No. 1 of the first amino acid of the sequence of SEQ ID No. 1 that corresponds to that motif when SEQ ID No. 1 and said polypeptide comprising said motif are aligned. In one embodiment, said polypeptide or immunogenic fragment comprises 1, 2, 3, 4, 5, 10, 15, 20, 25, 30, 35, 40, 45, 50, 60, 70, 80, 90, 100 or more further amino acids at the N- and/or C-terminus of said motif from the sequence contiguous to said motif beginning at the position of said first amino acid of SEQ ID No. 1 or at the equivalent positions of SEQ ID No. 2 to 49.

The motifs are depicted using the standard single-letter amino acid code, expressed in N- to C-terminal direction from left to right. For example, "-G-" at a particular position relative to the other amino acids of the motif indicates a requirement for a glycine residue at that position, whilst for example "-S/A/V-" specifies that a serine or an alanine or a valine residue (in no order of preference) must occupy that position. An unspecified position, i.e. which may be any amino acid residue, is represented by "X", and multiple contiguous such residues are indicted by, for example, 3(X) meaning "-X-X-X-".

As mentioned above, said antigen or said polypeptide or said immunogenic fragment may in particular be derived from a TdfI protein. Alternatively, said antigen or said polypeptide or said immunogenic fragment may be derived from a TdfH protein, in which case the amino acid sequences with which said polypeptide has amino acid sequence identity, or of which said immunogenic fragment is a fragment, are selected from the group consisting of SEQ ID No. 50; SEQ ID No. 51; SEQ ID No. 52; SEQ ID No. 53; SEQ ID No. 54; SEQ ID No. 55; SEQ ID No. 56; SEQ ID No. 57; SEQ ID No. 58; SEQ ID No. 59; SEQ ID No. 60; SEQ ID No. 61; SEQ ID No. 62; SEQ ID No. 63; SEQ ID No. 64; SEQ ID No. 65;

SEQ ID No. 66; SEQ ID No. 67; SEQ ID No. 68; SEQ ID No. 69; SEQ ID No. 70; and SEQ ID No. 71.

In a further embodiment, said polypeptide or immunogenic fragment of the immunogenic composition or vaccine of the invention comprises at least one of the following amino acid motifs:
81-R-S/T-V/I-P-G-A-F/Y-T-Q/N-Q/V/L/I-D-K/Q-G/A/S-S/Q-G-X-V/L-S-V/L-N-V/I-R-G-X-S/N/T-G-F/L-G-R-V/A-N-S/T-M/Q-V/I-D-G-V/I-S/T-Q-T-F;
156-F-S/N/D/E-G-S/T/A/K-A/G/S/N-G-I/L/V/A-N-S/T/A-L-X-G-S-A-N-L/F-R/K-T-L/I-G/N/S-V/A-D/N-D;
226-S-X-R/K/Q-X-V/I/S/L-S/A-Q-N/D-Y/F-R/K-V/I-G-G-G;
333-L-F/A/L/V-K-L/I/F/V-E/R-Y-X-G/N/D/S-V/D/K/H-4(X)-T/G/N/I-A/L-Q/N/S-F/L/I/Y-R-X-L/M/Y-X-T/N-X-I/L/V-G/A/S-S/T/G-R-K/R/N/S-I/L-X-N-R/D/K/N-N/T-Y-Q;
491-P-X-G-S/K/E-Q-X-F/I-N/H/K/I-T/S-F/I/V/L-Y-F/L/I-D;
574-N-H/Y-S-V/A/L/M-S/T/I/M-I/L/F-S-A-X-F/Y/L/I-G/D/S/H-D/T/P-Y/G/L-F-M/N/S/T-P-F-X-S/T/G-Y/F-S/A-R/H/K-T/S-H-R-M/I/V/A-P-N-I/V-Q/K/R-E-M/Y/V-Y/F-F-S/T; and

846-E/D-V/I-K/Q-N-L/A/V-F/L-D-R/K-R/L/K/N-Y-I/V/M-D/N-P/A-L-D/Y.

The number preceding each motif indicates, in a still further embodiment, the position in the sequence of SEQ ID No. 50 of the first amino acid of the sequence of SEQ ID No. 50 that corresponds to that motif when SEQ ID No. 50 and said polypeptide comprising said motif are aligned. In one embodiment, said polypeptide or immunogenic fragment comprises 1, 2, 3, 4, 5, 10, 15, 20, 25, 30, 35, 40, 45, 50, 60, 70, 80, 90, 100 or more further amino acids at the N- and/or C-terminus of said motif from the sequence contiguous to said motif beginning at the position of said first amino acid of SEQ ID No. 50 or at the equivalent positions of SEQ ID No. 51 to 71. The motifs are depicted as described above in connection with TdfI motifs.

As mentioned above, the immunogenic composition or vaccine of the invention may comprise one or more antigens additional to that defined supra. In an embodiment in which said immunogenic composition or vaccine comprises an antigen which is capable of raising an immune response which recognises a TdfI protein, said at least one additional antigen may be one which is capable of raising an immune response which recognises a TdfH protein as defined herein. Conversely, in an embodiment in which said immunogenic composition or vaccine comprises an antigen which is capable of raising an immune response which recognises a TdfH protein, said at least one additional antigen may be one which is capable of raising an immune response which recognises a TdfI protein as defined herein. Alternatively or additionally, such additional antigens may include any antigen, which antigen may or may not raise an immune response to the same Gram-negative strain or species as the "first" antigen, or even to a Gram-negative bacterium or taxonomic group thereof. Suitably, said at least one additional antigen is a fHbp polypeptide or a Hsf polypeptide or a Hap polypeptide or a NadA polypeptide or a lipo28 polypeptide, for instance from *N. meningitidis*.

fHbp can mean the GNA1870 protein from *Neisseria*, Hsf the NMB0992 (WO99/31132; SEQ ID NO: 2 and 4 [BASB029] in WO99/58683) protein from *Neisseria*, Hap the NMB1985 (WO99/55873-BASB006) protein from *Neisseria*, NadA the NMB1994 protein from *Neisseria*, lipo28 the GNA2132 or NMB2132 protein from *Neisseria*. GNA and NMB numbers referred to herein refer to polypeptides encoded by *Neisseria meningitidis* group A and B, respectively, genome sequences available from www.neisseria.org.

Additionally, where a protein is specifically mentioned herein, it is suitably a reference to a native, full-length protein, and to its natural variants, but it may also encompass antigenic fragments thereof. These are fragments (often specifically described herein) containing or comprising at least 15 amino acids, suitably at least 20 amino acids, at least 30 amino acids, at least 40 amino acids or at least 50 amino acids, taken contiguously from the amino acid sequence of the protein. Antigenic fragments may also be immunogenic fragments. It is further envisaged that reference to proteins and protein sequences herein includes a polypeptide comprising an immunogenic fragment of 7, 10, 12, 15, 20, 30, 40 or 50 (or more) contiguous amino acids from said protein sequence or from the amino acid sequence of said protein (optionally wherein said immunogenic fragment is capable of eliciting—if necessary when coupled to a protein carrier—an immune response which can recognise said protein or said protein sequence).

Hsf:

Hsf has a structure that is common to autotransporter proteins. For example, Hsf from *N. meningitidis* strain H44/76 consists of a signal sequence made up of amino acids 1-51, a head region at the amino terminus of the mature protein (amino acids 52-479) that is surface exposed and contains variable regions (amino acids 52-106, 121-124, 191-210 and 230-234), a neck region (amino acids 480-509), a hydrophobic alpha-helix region (amino acids 518-529) and an anchoring domain in which four transmembrane strands span the outer membrane (amino acids 539-591).

Although full length Hsf may be used in immunogenic compositions of the disclosure, various Hsf truncates and deletions may also be used depending on the type of immunogenic composition or vaccine.

Where Hsf is used in a subunit composition or vaccine, a portion of the soluble passenger domain may be used; for instance the complete domain of amino acids 52 to 479, most suitably a conserved portion thereof, for instance the sequence of amino acids 134 to 479. Suitable forms of Hsf may be truncated so as to delete variable regions of the protein disclosed in WO01/55182.

Suitable variants would include the deletion of one, two, three, four, or five variable regions as defined in WO01/55182. The above sequences and those described below, can be extended or truncated by up to 1, 3, 5, 7, 10 or 15 amino acids at either or both N or C termini.

Suitable fragments of Hsf therefore include the entire head region of Hsf, suitably containing amino acids 52-473. Additional suitable fragments of Hsf include surface exposed regions of the head including one or more of the following amino acid sequences; 52-62, 76-93, 116-134, 147-157, 157-175, 199-211, 230-252, 252-270, 284-306, 328-338, 362-391, 408-418, 430-440 and 469-479.

Where Hsf is present in an outer membrane vesicle preparation, it may be expressed as the full-length protein or as a variant made up of a fusion of amino acids 1-51 and 134-591 (yielding a mature outer membrane protein of amino acid sequence 134 to the C-terminus). Suitable forms of Hsf may be truncated so as to delete variable regions of the protein disclosed in WO01/55182. Suitable variants would include the deletion of one, two, three, four, or five variable regions as defined in WO01/55182. In one aspect the first and second variable regions are deleted.

Suitable variants would delete residues from between amino acid sequence 52 through to 237 or 54 through to 237, more suitably deleting residues between amino acid 52 through to 133 or 55 through to 133. The mature protein would lack the signal peptide.

Hap:

Computer analysis of the Hap-like protein from *Neisseria meningitidis* reveals at least three structural domains. Considering the Hap-like sequence from strain H44/76 as a reference, Domain 1, comprising amino-acid 1 to 42, encodes a sec-dependant signal peptide characteristic of the auto-transporter family, Domain 2, comprising amino-acids 43 to 950, encode the passenger domain likely to be surface exposed and accessible to the immune system, Domain 3, comprising residues 951 to the C-terminus (1457), is predicted to encode beta-strands likely to assemble into a barrel-like structure and to be anchored into the outer-membrane. Since domains 2 and 3 are likely to be surface-exposed, well conserved (more than 80% in all strains tested) and could be produced as subunit antigens in *E. coli*, it represents an interesting vaccine candidate (see also Pizza et al. (2000), Science 287: 1816-1820).

Immunogenic compositions of the disclosure may comprise the full-length Hap protein, suitably incorporated into an OMV preparation. Immunogenic compositions of the disclosure may also comprise the passenger domain of Hap which in strain H44/76 is composed of amino acid residues 43-950. This fragment of Hap would be particularly advantageously used in a subunit composition of the disclosure. The above sequence for the passenger domain of Hap can be extended or truncated by up to 1, 3, 5, 7, 10, 15, 20, 25, or 30 amino acids at either or both N or C termini.

The immunogenic composition or vaccine of the invention, in one embodiment, comprises a bacterial outer membrane vesicle preparation, which preparation comprises the antigen of the composition or vaccine. Such a composition or vaccine may be produced by a method provided as another aspect of the invention, which method comprises culturing at least a first gram-negative bacterial strain which produces said antigen, wherein said antigen is produced at a level sufficient to provide for production of outer membrane vesicles that, when administered to a subject, raise a protective response against infection by at least said first gram-negative bacterial strain; preparing outer membrane vesicles from the cultured strain; and combining said outer membrane vesicles with a pharmaceutically acceptable carrier or excipient to produce an immunogenic composition suitable for administration to a subject.

By "a level sufficient to provide for production of outer membrane vesicles that, when administered to a subject, raise a protective response against infection by at least said first gram-negative bacterial strain" is meant that sufficient antigen is produced such that upon administration of outer membrane vesicles comprising said antigen an immune response is induced that prevents, retards the development of, or reduces the severity of a disease that is caused by said first Gram-negative strain, or diminishes or completely eliminates the symptoms of the disease.

As is shown in the Examples, the expression of TdfI is regulated in response to the free zinc concentration, such that decreasing levels of free zinc correlate with an upregulation of TdfI expression. (The expression of TdfH is believed also to be influenced by free zinc levels, although to a lesser extent.) Hence, in said method, the culturing of said bacterial strain may be in a medium comprising a zinc chelator, suitably at a concentration of 0.01-100, 0.1-10, 0.3-5, or 0.5-1 µM, in order to upregulate expression of said antigen. Said zinc chelator may, for example, be TPEN. As an alternative to the use of a zinc chelator, said culturing according to the method may take place in Catlin medium.

In one embodiment of the method, the antigen is expressed in said first gram-negative bacterial strain from an expression vector comprising a polynucleotide encoding said antigen. Additionally or alternatively, said antigen is produced by expression from a heterologous and/or strong promoter, i.e. in one embodiment such a promoter is engineered into the chromosome of said bacterial strain such that it is operably linked with the polynucleotide sequence encoding said antigen. As is well known to one skilled in the art, the term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. A "strong" promoter is a promoter which drives expression of a polynucleotide sequence operably linked thereto at a high level. What constitutes a high level, in the context of a bacterial strain belonging to a particular species, would be well known to one skilled in the art, as would be the identity of strong promoters in such a strain.

Further as regards said method, the step of preparing the outer membrane vesicles from the cultured strain may be performed using detergent extraction, or may be achieved by alternative means. In the former case, said extraction may involve the use of 0-0.5%, 0.02-0.4%, 0.04-0.3%, 0.06-0.2%, 0.08-0.15% or 0.1% detergent. Preferably, the detergent is deoxycholate.

As mentioned above, the expression of said antigen may be upregulated in the outer membrane vesicles produced from said first gram-negative bacterial strain, for example as a result of culturing in conditions of low free zinc. Hence, the expression of said antigen may be upregulated in outer membrane vesicle preparations in immunogenic compositions or vaccines of the invention which comprise such preparations. Such upregulation may be relative to the expression of said antigen in an outer membrane vesicle preparation from a wild-type bacterium of the same strain. In particular, expression of said antigen may be upregulated 1.5, 2, 2.5, 3, 3.5, 4, 4.5, 5, 5.5, 6, 6.5, 7, 7.5, 8, 8.5, 9, 9.5, 10-fold or greater.

Alternatively or additionally to culturing in conditions of low free zinc, in order to achieve such upregulation of expression of said antigen a host cell from which said outer membrane vesicle preparation is derived may be genetically modified in production of said antigen. Such modification may involve disruption of functional expression of an endogenous protein, which protein in a non-genetically-modified host cell represses expression of said antigen. Hence, following such targeted disruption of the endogenous repressor protein the expression of said antigen is no longer repressed, i.e. is upregulated relatively. In one embodiment, the endogenous repressor protein is the Neisserial or Gram-negative bacterial Zur repressor. Alternatively or additionally to disruption of repressor protein expression, the host cell may be modified by the introduction of a heterologous and/or strong promoter operably linked to the polynucleotide encoding the antigen. Such promoters are discussed supra. Said introduced promoter may be inducible, i.e. the promoter may be "switched on" or upregulated in response to a chemical or environmental stimulus, such as for example IPTG or heat, respectively.

The present invention further provides, in another aspect, a genetically engineered Gram-negative bacterial strain from which the outer membrane vesicle preparations, of immunogenic compositions or vaccines of the invention which comprise such preparations, can be derived.

In one embodiment, the immunogenic composition or vaccine comprises outer membrane vesicle preparations isolated from two or more Gram-negative bacterial strains. In a further embodiment, at least one of said strains belongs to a bacterial species or genus selected from the group consisting of *Borrelia; Borrelia burgdorferi; Brucella; Brucella melitensis; Brucella ovis; Chlamydia; Chlamydia psittaci; Chlamydia trachomatis; Escherichia; Escherichia coli; Legionella; Legionella pneumophila; Yersinia; Yersinia enterocolitica; Shigella; Shigella flexneri; Shigella dysenteriae; Shigella boydii; Coxiella; Coxiella burnetii; Acidovorax; Acinetobacter; Acinetobacter baumannii; Acinetobacter calcoaceticus; Acinetobacter johnsonii; Acinetobacter junii; Acinetobacter lwoffii; Acinetobacter radioresistens; Actinobacillus; Actinobacillus minor; Actinobacillus pleuropneumoniae; Aggregatibacter; Aggregatibacter actinomycetemcomitans; Aggregatibacter aphrophilus; Alcanivorax; Alcanivorax borkumensis; Azoarcus; Azotobacter; Azotobacter vinelandii; Bordetella; Bordetella bronchiseptica; Bordetella parapertussis; Bordetella pertussis; Bordetella petrii; Campylobacter; Campylobacter coli; Campylobacter upsaliensis; Comamonas; Comamonas testosteroni; Delftia; Delftia acidovorans; Diaphorobacter; Haemophilus; Haemophilus influenzae; Haemophilus parasuis; Haemophilus somnus; Mannheimia; Mannheimia haemolytica; Moraxella; Moraxella catarrhalis; Neisseria; Neisseria gonorrhoeae; Neisseria meningitidis; Pasteurella; Pasteurella dagmatis; Pasteurella multocida; Proteus; Proteus mirabilis; Pseudomonas; Pseudomonas aeruginosa; Pseudomonas stutzeri*; and *Sphingomonas*.

In another aspect of the invention is provided a method for producing an immunogenic composition or vaccine comprising: culturing a host cell comprising an expression vector comprising a polynucleotide encoding said antigen under conditions and for a time sufficient for the production of said antigen and recovering the antigen from the culture medium; optionally purifying said antigen by a method selected from the group consisting of ammonium sulphate precipitation, ethanol precipitation, acid extraction, phosphocellulose chromatography, hydrophobic interaction chromatography, hydroxylapatite chromatography and lectin chromatography; and formulating said antigen with a pharmaceutically acceptable carrier or excipient. In the context of such a method the antigen may be endogenous to the host cell, or the host cell may be genetically modified by the introduction of an exogenous antigen. Genetic modification of the host cell for the purposes of producing said antigen include disruption of an endogenous repressor protein, and use of a heterologous and/or strong promoter, as discussed supra.

The present invention extends to an immunogenic composition or vaccine produced by the provided methods.

In addition to said antigen, and optionally one or more further antigens, the immunogenic composition or vaccine of the invention may comprise one or more of a pharmaceutically acceptable excipient, an adjuvant and a zinc salt.

In a further aspect of the invention is provided an immunogenic composition or vaccine comprising at least one polynucleotide encoding an antigen, and optionally an additional antigen, as defined supra, wherein said polynucleotide is operably linked to a eukaryotic promoter. In such an aspect, the antigen itself is not administered, but is produced in vivo following administration of the encoding polynucleotide. Such techniques are known in the art, see for example Wolff et al., Science, (1990) 247: 1465-8. The expression of the antigen in such a polynucleotide would be under the control of a eukaryotic promoter, capable of driving expression within a mammalian cell. The polynucleotide may additionally comprise sequence encoding other antigens. Examples of such eukaryotic promoters include promoters from viruses using mammalian cells as host including adenovirus promoters and retroviral promoters. Alternatively, mammalian promoters could be used.

The immunogenic composition or vaccine defined supra is, in one embodiment, capable of generating a protective response against infection by a Gram-negative bacterial strain. By a "protective response" as used herein is meant an immune response that prevents, retards the development of, or reduces the severity of a disease that is caused by a Gram-negative bacterial strain, or diminishes or altogether eliminates the symptoms of the disease. In a further embodiment, said composition or vaccine is capable of generating a protective response against infection by two or more different bacterial strains. Suitably, one or more of said different Gram-negative bacterial strains belong to a bacterial genus or species selected from the group consisting of *Borrelia; Borrelia burgdorferi; Brucella; Brucella melitensis; Brucella ovis; Chlamydia; Chlamydia psittaci; Chlamydia trachomatis; Escherichia; Escherichia coli; Legionella; Legionella pneumophila; Yersinia; Yersinia enterocolitica; Shigella; Shigella flexneri; Shigella dysenteriae; Shigella boydii; Coxiella; Coxiella burnetii; Acidovorax; Acinetobacter; Acinetobacter baumannii; Acinetobacter calcoaceticus; Acinetobacter johnsonii; Acinetobacter junii; Acinetobacter lwoffii; Acinetobacter radioresistens; Actinobacillus; Actinobacillus minor; Actinobacillus pleuropneumoniae; Aggregatibacter; Aggregatibacter actinomycetemcomitans; Aggregatibacter aphrophilus; Alcanivorax; Alcanivorax borkumensis; Azoarcus; Azotobacter; Azotobacter vinelandii; Bordetella; Bordetella bronchiseptica; Bordetella parapertussis; Bordetella pertussis; Bordetella petrii; Campylobacter; Campylobacter coli; Campylobacter upsaliensis; Comamonas; Comamonas testosteroni; Delftia; Delftia acidovorans; Diaphorobacter; Haemophilus; Haemophilus influenzae; Haemophilus parasuis; Haemophilus somnus; Mannheimia; Mannheimia haemolytica; Moraxella; Moraxella catarrhalis; Neisseria; Neisseria gonorrhoeae; Neisseria meningitidis; Pasteurella; Pasteurella dagmatis; Pasteurella multocida; Proteus; Proteus mirabilis; Pseudomonas; Pseudomonas aeruginosa; Pseudomonas stutzeri*; and *Sphingomonas*.

In one aspect, the present invention provides a method for the treatment or prevention of Gram-negative bacterial disease or infection comprising administering a protective dose or an effective amount of an immunogenic composition or vaccine of the invention as defined supra.

In another aspect is provided an immunogenic composition or vaccine as defined supra for use in the treatment or prevention of Gram-negative bacterial disease or infection.

By "disease" as used herein means infection by a bacteria or any disease caused by or related to infection by a bacteria including, for example, upper respiratory tract infection and invasive bacterial diseases such as bacteraemia and meningitis.

Whilst said Gram-negative bacterial disease may be infection, or disease caused, by any Gram-negative bacterial strain, suitably said strain belongs to a bacterial genus or species selected from the group consisting of *Borrelia; Borrelia burgdorferi; Brucella; Brucella melitensis; Brucella ovis; Chlamydia; Chlamydia psittaci; Chlamydia trachomatis; Escherichia; Escherichia coli; Legionella; Legionella pneumophila; Yersinia; Yersinia enterocolitica; Shigella; Shigella flexneri; Shigella dysenteriae; Shigella boydii; Coxiella; Coxiella burnetii; Acidovorax; Acinetobacter; Acinetobacter baumannii; Acinetobacter calcoaceticus; Acinetobacter johnsonii; Acinetobacter junii; Acinetobacter lwoffii; Acinetobacter radioresistens; Actinobacillus; Actinobacillus* minor; *Actinobacillus pleuropneumoniae*; *Aggregatibacter*; *Aggregatibacter actinomycetemcomitans*; *Aggregatibacter aphrophilus*; *Alcanivorax*; *Alcanivorax borkumensis*; *Azoarcus*; *Azotobacter*; *Azotobacter vinelandii*; *Bordetella*; *Bordetella bronchiseptica*; *Bordetella parapertussis*; *Bordetella pertussis*; *Bordetella pertussis*; *Bordetella petrii*; *Campylobacter*; *Campylobacter coli*; *Campylobacter upsaliensis*; *Comamonas*; *Comamonas testosteroni*; *Delftia*; *Delftia acidovorans*; *Diaphorobacter*; *Haemophilus*; *Haemophilus influenzae*; *Haemophilus parasuis*; *Haemophilus somnus*; *Mannheimia*; *Mannheimia haemolytica*; *Moraxella*; *Moraxella catarrhalis*; *Neisseria*; *Neisseria gonorrhoeae*; *Neisseria meningitidis*; *Pasteurella*; *Pasteurella dagmatis*; *Pasteurella multocida*; *Proteus*; *Proteus mirabilis*; *Pseudomonas*; *Pseudomonas aeruginosa*; *Pseudomonas stutzeri*; and *Sphingomonas*. In a particular embodiment, optionally said strain is not a Neisserial strain.

The immunogenic compositions or vaccines of the invention can be administered orally, nasally, nasopharyngeally, parenterally, enterically, gastrically, topically, transdermally, subcutaneously, intramuscularly, in tablet, solid, powdered, liquid, aerosol form, locally or systemically, with or without added excipients. Actual methods for preparing parenterally administrable compositions will be known or apparent to those skilled in the art and are described in more detail in such publications as Remingtons Pharmaceutical Science, 15th ed., Mack Publishing Company, Easton, Pa. (1980).

It is recognized that oral administration can require protection of the compositions from digestion. This is typically accomplished either by association of the composition with an agent that renders it resistant to acidic and enzymatic hydrolysis or by packaging the composition in an appropriately resistant carrier. Means of protecting from digestion are well known in the art.

The compositions are administered to an animal that is at risk from acquiring a Gram-negative disease to prevent or at least partially arrest the development of disease and its complications. An amount adequate to accomplish this is defined as a "therapeutically effective dose". Amounts effective for therapeutic use will depend on, for example, the immunogenic composition or vaccine, the manner of administration, the weight and general state of health of the patient, and the judgment of the prescribing physician. Single or multiple doses of the immunogenic compositions or vaccines may be administered depending on the dosage and frequency required and tolerated by the patient, and route of administration.

The immunogenic compositions or vaccines are administered in an amount effective to elicit an immune response, particularly a humoral immune response, in the host. Amounts for the immunization generally range from about 0.001 mg to about 1.0 mg per 70 kilogram patient, more commonly from about 0.001 mg to about 0.2 mg per 70 kilogram patient. Dosages from 0.001 up to about 10 mg per patient per day may be used, particularly when the antigen is administered to a secluded site and not into the blood stream, such as into a body cavity or into a lumen of an organ. Substantially higher dosages (e.g. 10 to 100 mg or more) are possible in oral, nasal, or topical administration. The initial administration can be followed by booster immunization of the same of different composition, with at least one booster, more usually two boosters, being preferred. The immunogenic compositions or vaccines are typically administered to a mammal that is immunologically naïve with respect to a given Gram-negative strain or species. In a particular embodiment, the mammal is a human child about five years or younger, and preferably about two years old or younger, and the antigen compositions are administered at any one or more of the following times: two weeks, one month, 2, 3, 4, 5, 6, 7, 8, 9, 10, or 11 months, or one year or 15, 18, or 21 months after birth, or at 2, 3, 4, or 5 years of age. In general, administration to any mammal is preferably initiated prior to the first sign of disease symptoms, or at the first sign of possible or actual exposure to a given Gram-negative strain or species.

In a further aspect, the present invention provides a method of preparing an immune globulin (for instance for use in prevention or treatment of Gram-negative bacterial disease), comprising the steps of immunising a recipient with an immunogenic composition or vaccine of the invention and isolating immune globulin from the recipient. An immune globulin preparation so obtained, optionally in the form of a pharmaceutical preparation additionally comprising a pharmaceutically acceptable excipient, is also provided.

Inocula for polyclonal antibody production are typically prepared by dispersing the immunogenic composition or vaccine in a physiologically tolerable diluent such as saline or other adjuvants suitable for human use to form an aqueous composition. An immunostimulatory amount of inoculum is administered to a mammal and the inoculated mammal is then maintained for a time sufficient for the immunogenic composition or vaccine to induce protective antibodies. The antibodies can be isolated to the extent desired by well known techniques such as affinity chromatography. Antibodies can include antiserum preparations from a variety of commonly used animals e.g. goats, primates, donkeys, swine, horses, guinea pigs, rats or man. The animals are bled and serum recovered.

An immune globulin produced in accordance with the present invention can include whole antibodies, antibody fragments or subfragments. Antibodies can be whole immunoglobulins of any class e.g. IgG, IgM, IgA, IgD or IgE, chimeric antibodies, or hybrid antibodies having dual specificity to a TdfI protein and a TdfH protein. They may also be fragments e.g. F(ab')2, Fab', Fab, Fv and the like including hybrid fragments. An immune globulin also includes natural, synthetic or genetically engineered proteins that act like an antibody by binding to specific antigens to form a complex.

An immunogenic composition or vaccine of the present invention can be administered to a recipient who then acts as a source of immune globulin, produced in response to challenge from the specific immunogenic composition or vaccine. A subject thus treated would donate plasma from which hyperimmune globulin would be obtained via conventional plasma fractionation methodology. The hyperimmune globulin would be administered to another subject in order to impart resistance against or treat infection by a given Gram-negative bacterial species or strain. Hyperimmune globulins of the invention are particularly useful for treatment or prevention of Gram-negative bacterial disease in infants, immune compromised individuals or where treatment is required and there is no time for the individual to produce antibodies in response to vaccination.

An additional aspect of the invention is a pharmaceutical preparation comprising monoclonal antibodies reactive against a TdfI protein and/or a TdfH protein, and a pharmaceutically acceptable excipient, which could be used to treat or prevent infection by Gram-negative bacteria. Such pharmaceutical preparations comprise monoclonal antibodies that can be whole immunoglobulins of any class e.g. IgG, IgM, IgA, IgD or IgE, chimeric antibodies, or hybrid antibodies having dual specificity to a TdfI protein and a TdfH protein. They may also be fragments e.g. F(ab')2, Fab', Fab, Fv and the like including hybrid fragments. Methods of making monoclonal antibodies are well known in the art and can include the fusion of splenocytes with myeloma cells (Kohler and Milstein, 1975, Nature 256; 495; Antibodies—a laboratory manual Harlow and Lane 1988). Alternatively, monoclonal Fv fragments can be obtained by screening a suitable phage display library (Vaughan T J et al, 1998, Nature Biotechnology 16; 535). Monoclonal antibodies may also be humanised or part-humanised using techniques that are well-known in the art.

The present invention extends to a method for treatment or prevention of Gram-negative bacterial disease comprising a step of administering to a patient an effective amount of such a pharmaceutical preparation comprising immune globulin or monoclonal antibodies, and to such preparations for use in the treatment or prevention of such a disease.

All references or patent applications cited within this patent specification are incorporated by reference herein.

EXAMPLES

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 1

Immunogenicity of OMVs with Up-Regulation of TdfI

TdfI is a gene which is thought to be expressed when *N. meningitidis* is within the blood. It is therefore not normally expressed when strains are grown in conventional culture media, but wild-type strain H44/76, for example, can be made to express the protein in special culture conditions (RPMI culture media supplemented with hemin). The following experiment details the use of an H44/76 strain where TdfI expression has been recombinantly made inducible (through the use of IPTG). This allows the over-expression of TdfI on the surface of OMV vaccines made from the strain, and provides an easy way of culturing a strain expressing the antigen to establish whether antibodies generated against TdfI are capable of killing such a modified strain which expresses TdfI under normal culture conditions (+IPTG). The impact of IPTG on expression of TdfI on cells used in the SBA is shown in FIG. 7.

Groups of 10 mice were immunized three times with OMV by the intramuscular route on day 0, 21 and 28. Each inoculation was made up of 5 μg (protein content) of OMVs formulated on AlPO4 with MPL. The OMVs were derived from *Neisseria meningitidis* strain H44/76, engineered so that capsular polysaccharides and PorA were down regulated and LOS immunotype was galE type. A comparison was made of OMVs in which TdfI was or was not up-regulated (up-regulation under the control of IPTG inducible promoter). On day 42, blood samples were taken for analysis by serum bactericidal assay using either the homologous strain H44/76 (B:15:P1.7,16) expressing or not TdfI (after addition or not of IPTG in the culture media).

*N. meningitidis* strains were cultivated overnight on GC-agar with 10 μg/ml chloramphenicol Petri Dishes at 37° C.+5% $CO_2$. They were sub-cultured for 3 hours in a liquid TSB medium supplemented or not with IPTG 1000 μM. Individual sera were inactivated for 30 min at 56° C. Serum samples were diluted in HBSS-BSA 0.5% and then twofold diluted (8 dilutions) in a volume of 25 μl in flat bottom microplates. Bacteria were diluted in HBSS-BSA 0.5% to yield $8\cdot10^3$ CFU/ml and 12.5 μl of this dilution was added to the serum dilution. Rabbit complement (12.5 μl) was also added to each well. After 75 min of incubation at 37° C. under shaking, 15 μl of the mixture was spread onto pre-warmed GC-agar plates incubated overnight at 37° C.+$CO_2$. The CFU's were counted and the percentage of killing was calculated. The SBA titer is the dilution giving 50% of killing.

SBA Titers

Impact of Expression of TdfI by Target Cells

| | SBA titers |
|---|---|
| H44/76 without IPTG | <50 |
| H44/76 with IPTG | 400; 400; 800 |

Without IPTG, TdfI is not expressed on target cells which are not killed by sera from mice immunized with up-regulated TdfI OMVs. When the expression of TdfI is specifically induced by IPTG the target cells express TdfI and are killed by anti-TdfI-OMVs mice sera.

Example 2

A Novel Zinc-Regulated Outer Membrane Protein in *Neisseria meningitidis* with Vaccine Potential Abstract Since the concentration of free iron in the human host is low, efficient iron-acquisition mechanisms constitute important virulence factors for pathogenic bacteria. In the Gram-negative bacteria, TonB-dependent outer membrane receptors are implicated in iron acquisition. However, transport across the bacterial outer membrane of other metals that are also scarce in the human host is far less clear. In this study we characterized a novel TonB-dependent receptor in *Neisseria meningitidis*. We show that the bacteria produce this protein under zinc limitation and that it is involved in zinc uptake. Furthermore, since the protein is highly conserved among isolates and is capable of inducing bactericidal antibodies, it constitutes a novel candidate for the development of a vaccine against *N. meningitidis* for which no effective universal vaccine is available so far. Homologues of the protein, designated TfdI, are found in many other pathogens residing in the respiratory tract, suggesting that receptor-mediated zinc uptake is particularly important for survival in this niche.

Introduction

The cell envelope of Gram-negative bacteria consists of two membranes, the inner and the outer membrane, which are separated by the periplasm containing the peptidoglycan layer. The outer membrane forms a barrier for harmful compounds from the environment. Most nutrients can pass the outer membrane by passive diffusion via abundant channel-forming outer membrane proteins, collectively called porins. However, diffusion is not an option when the extracellular concentration of a nutrient is low. This is the case, for example, for iron. Pathogens are confronted with low concentrations of free iron within the human host, where iron is bound by iron-transport and -storage proteins, such as lactoferrin and transferrin. Hence, efficient iron acquisition mechanisms constitute important virulence factors and have been studied extensively in many pathogens (1, 2).

When grown under iron-limiting conditions, Gram-negative bacteria induce the synthesis of outer membrane proteins that function as receptors for the iron-binding proteins of the host, for heme, or for siderophores, which are small iron-chelating compounds produced and secreted by the bacteria under iron limitation. The resolved crystal structures of such receptors revealed 22-stranded β-barrels, which do not form open channels but are closed by an N-terminal plug domain (3). After binding of the ligand to the receptor, the subsequent uptake is an active process that requires the energy of the proton gradient across the inner membrane, which is coupled to the receptors in the outer membrane via a complex of three proteins, the TonB complex (4, 5).

While iron-acquisition mechanisms have been studied extensively in many Gram-negative bacteria, little is known yet about the transport of other essential heavy metals, such as zinc and manganese, across the bacterial outer membrane. The concentration of these trace elements also is low in the human host, which, for example, responds to infections by the production of metallothioneins and calprotectin thereby reducing the availability of metals to the invading pathogens (6, 7). Therefore, Gram-negative pathogens likely possess effective acquisition mechanisms for these metals, which may or may not resemble the iron-acquisition systems.

*Neisseria meningitidis* is an obligate human pathogen that can colonize the nasopharyngeal mucosa asymptomatically. Occasionally the bacterium enters the bloodstream and can cause meningitis and sepsis with a high mortality rate (8). While vaccines are available for most pathogenic serogroups of *N. meningitidis* based on the capsular polysaccharides, a vaccine against serogroup B meningococci is lacking. The polysaccharide capsule of the serogroup B strains is poorly immunogenic due to its resemblance to human glycoproteins (9). Thus, subcapsular antigens are being studied as alternative vaccine components; however, these studies are frustrated by the high antigenic variability of the major outer membrane proteins. Therefore, attention has shifted to minor antigens, including the TonB-dependent receptors.

When grown under iron limitation, *N. meningitidis* produces TonB-dependent receptors for lactoferrin (10), transferrin (11), hemoglobin (12, 13) and enterobactin (14), all involved in the uptake of iron. Based on homology searches, Turner et al (15) identified seven additional genes for putative TonB-dependent family (Tdf) members in the available genome sequences of three Neisserial strains. Interestingly, the expression of some of these tdf genes appeared unaffected by iron availability in various microarray studies (16, 17), indicating that their products might be implicated in the transport of metals other than iron. Here we studied the regulation of the synthesis, the function and the vaccine potential of one of these receptors and show that this receptor is involved in the uptake of zinc.

Results
TdfJ is not a Heme Receptor

TdfJ (locus tags NMA1161 and NMB0964 in the sequenced genomes of *N. meningitidis* serogroup A strain Z2491 and serogroup B strain MC58, respectively) was previously identified as one of seven novel putative TonB-dependent receptors present in the Neisserial genomes (15) and was found to be up-regulated in the presence of naïve human serum (18). Since almost all TonB-dependent receptors studied to date are involved in iron acquisition we assumed that TdfJ transports an iron complex. This idea was strengthened by the fact that blast searches (19) with the amino-acid sequence of NMA1161 revealed high sequence similarity to outer membrane receptors for the uptake of heme, such as HumA of *Moraxella catarrhalis* (20) with 41% identity and 58% similarity.

To assess the function of TdfJ, we constructed a tdfJ deletion mutant of a non-encapsulated derivative of serogroup B strain H44/76 called HB-1. We found similar binding of heme to HB-1 and the tdfJ mutant as assessed by dot blot analysis and the tdfJ mutant strain could still grow on plates with heme as the sole iron source. We could also not find increased heme binding by *Escherichia coli* cells expressing TdfJ. Also we were unable to complement an *E. coli* heme auxotroph (data not shown). Therefore, we hypothesized that TdfJ, although homologous to heme receptors, does not function as a heme receptor.

Regulation of tdfJ by Zinc

Figure 1B:
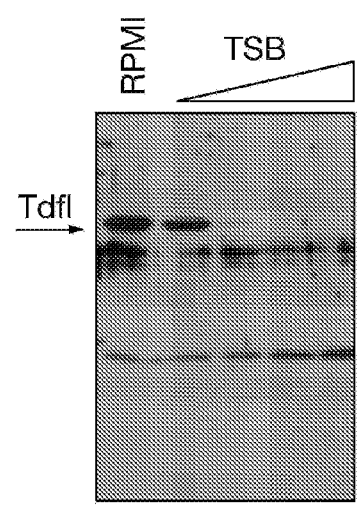
(FIG. 1B) HB-1 grown in RPMI with increasing amounts of TSB added.
Figure 1C:
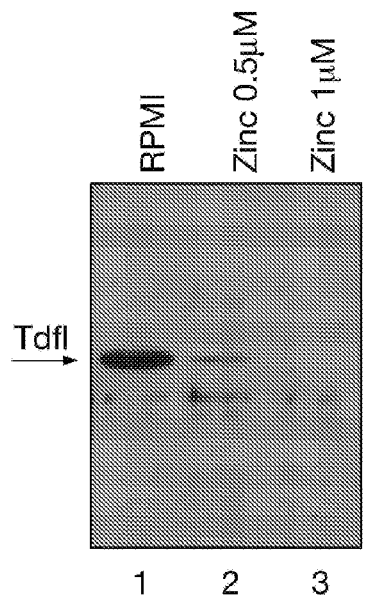
(FIG. 1C) HB-1 grown in RPMI (lane 1), supplemented with 0.5 µM zinc (lane 2) or 1 µM zinc (lane 4).

Since TdfJ is not a heme receptor and is not found to be regulated by iron, we sought conditions where we could detect tdfJ is expression in the capsule deficient H44/76 *Neisseria meningitidis* HB-1. We could never detect TdfJ on Western blots when the bacteria were grown in tryptic soy broth (TSB), a complex rich medium (FIG. 1A, lane 1). However, when the bacteria were grown in the chemically defined RPMI medium, TdfJ was detectable in bacterial lysates (FIG. 1A, lane 2). The specificity of the signal detected was demonstrated by its absence in the tdfJ knockout strain grown in RPMI (FIG. 1A, lane 3). We noted that the presence of even small amounts of TSB added to RPMI negatively affected TdfJ synthesis (FIG. 1B); apparently TSB contains a compound that represses the transcription of tdfJ. Since we noticed that RPMI does not contain a source of trace metals, we decided to test whether addition of a cocktail of trace metals, containing cobalt, molybdenum, manganese, copper and zinc, would repress tdfJ expression, which indeed appeared to be the case. We then tested all these metals separately and found that specifically zinc, even at sub-µM concentrations, caused repression of tdfJ expression (FIG. 1C). Since standard RPMI is not supplemented with a specific zinc source, the available zinc required for bacterial growth presumably comes from the water and/or traces in the salts used to make the medium. We measured the zinc concentration in RPMI medium by inductively coupled plasma mass spectrometry (ICP-MS) and found it to be ~110 parts per billion (~1.69 µM).

Figure 1D:
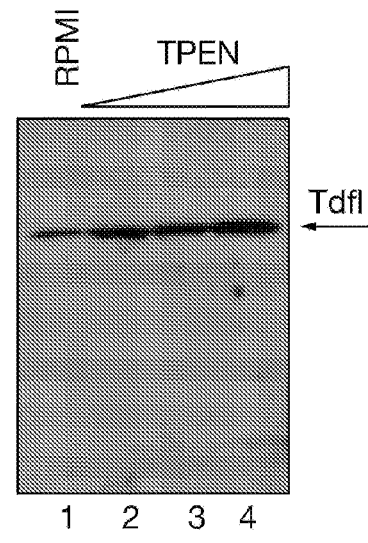
(FIG. 1D) HB-1 grown in RPMI (lane 1), with increasing concentrations of TPEN (0.1, 0.5 and 1 µM in lanes 2-4, respectively)

The zinc regulation of tdfJ became even more evident when we supplemented the RPMI medium with the specific zinc chelator N,N,N',N'-Tetrakis-(2-pyridylmethyl)-Ethylenediamine (TPEN). Addition of TPEN to the medium resulted in a dose-dependent increase in TdfJ synthesis (FIG. 1D). However, concentrations above 1 µM TPEN totally inhibited cell growth presumably due to total zinc depletion from the medium. Growth could be restored by the addition of zinc (data not shown). The zinc regulation of tdfJ was confirmed by real-time quantitative PCR (RT-qPCR) using total RNA obtained from cultures grown in RPMI supplemented or not with 500 nM zinc or 0.5 µM TPEN. The data showed a 13.8-fold repression in the presence of zinc and a 3.8-fold up regulation in the presence of TPEN. The fold difference between added TPEN and zinc was 52.6-fold.

Role of the Transcriptional Regulator Zur in tdfJ Expression

In *E. coli*, the zinc uptake regulator (Zur) has been shown to regulate the expression of the znuACB genes, which encode the periplasmic binding protein, the ATPase and the integral inner membrane component required for zinc transport from the periplasm to the cytoplasm (23). In the presence of zinc, Zur binds a Zur-binding element (consensus GAAATGTTA-TANTATAACATTTC) in the promoter of the znuACB operon and thereby blocks transcription.

Figure 2:
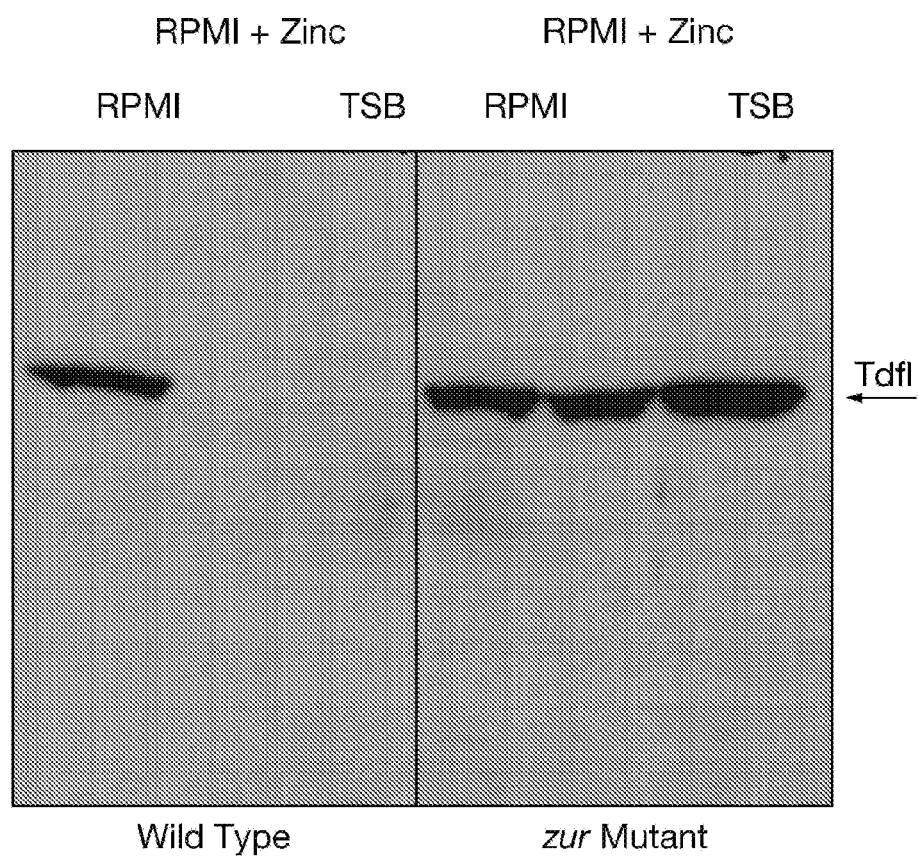
FIG. 2. TdfI expression in wild type and zur mutant strains.

In the genome sequence of *N. meningitidis* strain MC58, we identified homologues of the *E. coli* zur gene, i.e. NMB1266, and of znuCBA, i.e. NMB0588, NMB0587, and NMB0586. In addition, we found sequences resembling the *E. coli* Zur binding consensus in the regions upstream of the neisserial tdfI (GtAATGTTATATaATAACAaact) and znuC (cAAAcGTTATACagTAtCATaTC) (identical nucleotides to the *E. coli* consensus are in capital case). To confirm the involvement of Zur in the regulation of tdfI expression, we generated a zur mutant of strain HB-1, which, indeed, produced TdfI constitutively (FIG. 2). Also, RT-qPCR demonstrated the involvement of Zur in the expression of znuA and tdfI as znuA and tdfI expression levels increased 5- and 34-fold, respectively, in the zur mutant compared to its parent strain both grown in the presence of zinc.

TdfI Facilitates Zinc Acquisition

Figure 3A:
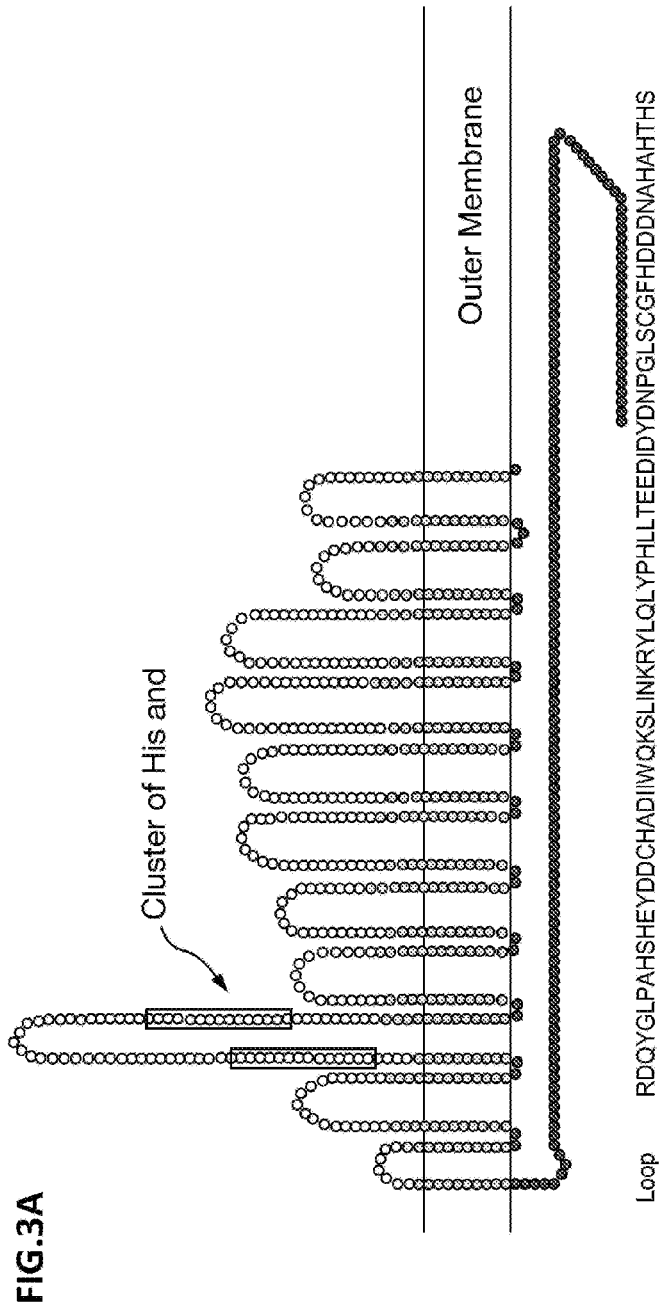
(FIG. 3A & FIG. 3B) The plug domain is colored dark grey, the beta strands light gray and the extracellular loops white. The histidine/aspartic acid stretches are boxed.
Figure 3B:
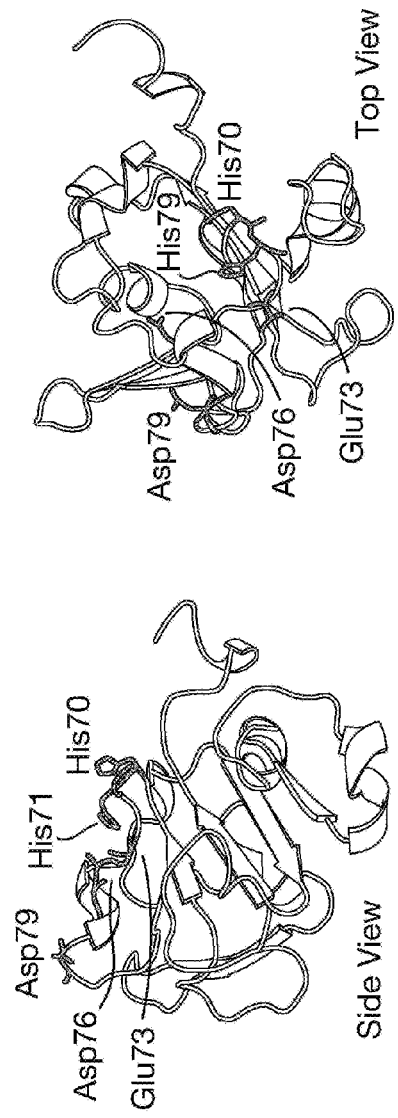
Figure 4A:
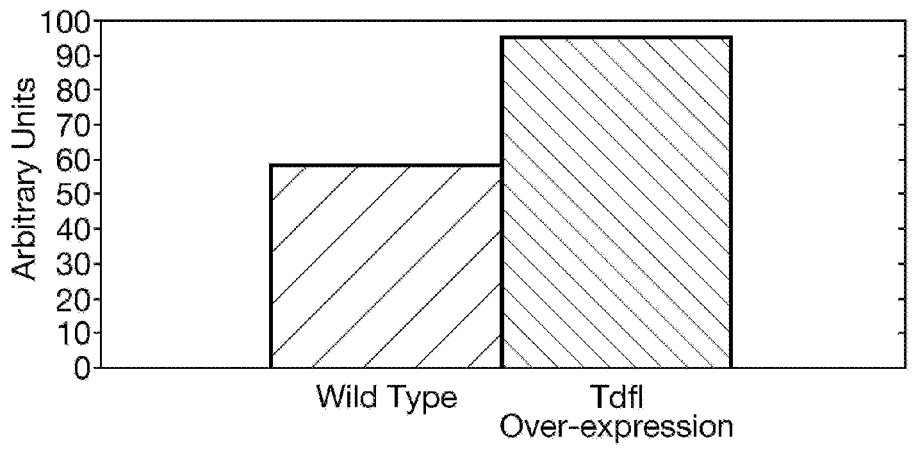
(FIG. 4A) Zinc binding to outer membrane vesicles either containing or not TdfI was measured by a PAR competition assay (FIG. 4B) Intracellular zinc concentrations as measured by ICP-MS of the wild-type strain, the tdfI mutant and the tonB mutant.
Figure 4B:
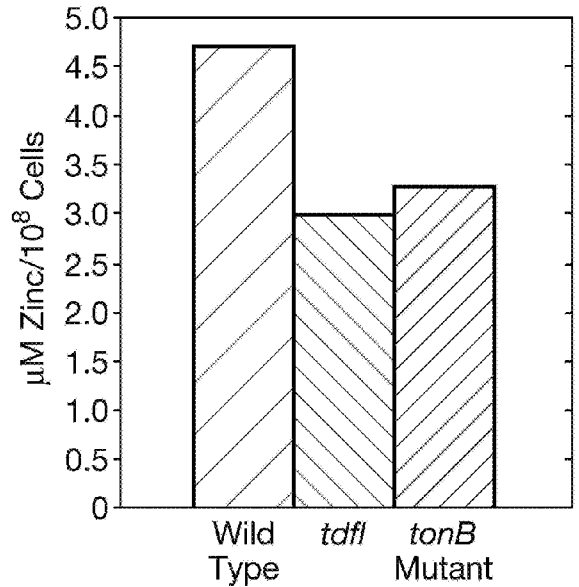
FIG. 4. Zinc binding and transport by TdfI.
(FIG. 4C) RPMI +Zinc in wild type and znuA knockout.

Since the expression of tdfI is regulated by the availability of zinc, it is likely that TdfI acts as a receptor for zinc or a zinc-containing complex. We first analyzed the amino acid sequence and constructed a topology model of TdfI using the PROFtmb program at www.rostlab.org, (FIG. 3). TdfI contains two cysteine residues in the putative extracellular loop L3. If these cysteines form a disulfide bond (supported by our analysis of the membrane fraction of bacteria by SDS-PAGE with and without DTT where incubation of the sample with the reducing agent resulted in a shift in electrophoretic mobility, presumably due to the disruption of the disulfide bond), they bring two stretches of amino acid residues, both rich in histidine and aspartic acid residues, in close proximity (FIG. 3), which could be of functional importance, since also in the periplasmic ZnuA protein of *E. coli*, a stretch of His and Asp residues is involved in binding zinc (25). Thus, we considered the possibility that TdfI binds free zinc and transports it to the periplasm. To test this hypothesis we first determined whether TdfI could bind zinc. We compared outer membrane vesicles with and without TdfI for their ability to compete with 4-(2-pyridylazo)resorcinol (PAR) for zinc. The outer membrane vesicles containing TdfI showed ~40% increased binding of zinc compared to the vesicles without TdfI (FIG. 4A). To test transport of zinc we compared the tdfI knockout, a tonB knockout and their parent strain for the accumulation of intracellular zinc using ICP-MS. HB-1 accumulated ~33% more zinc than the tdfI mutant or the tonB mutant, indicating that TdfI transports free zinc and that this transport needs the TonB system (FIG. 4B).

Figure 4C:
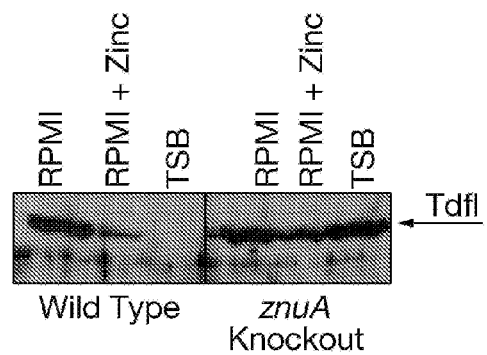

If indeed TdfI is involved in the uptake of free zinc, than one would expect derepression of znu gene expression to occur at higher external zinc concentrations in the tdfI mutant as compared with the wild-type strain. To test this idea, we grew the tdfI mutant and the parent strain in RPMI medium with 500 nM additional zinc, which largely, but not completely represses tdfI expression in the wild-type strain (FIG. 1C). We subsequently measured the relative levels of tdfI and znuA mRNA by RT-qPCR. The tdfI mutant still contains the first 437 nucleotides of the tdfI gene that were used for the detection of gene expression. In the tdfI mutant, there was 18.6-fold more tdfI and 7.4-fold more znuA expressed, showing that indeed the intracellular zinc concentration in the tdfI mutant is lower than that in the parent strain under the applied growth conditions. Also a znuA knockout strain expressed high levels of TdfI in the presence of zinc, confirming that ZnuA is required to sustain sufficient zinc levels in the cell (FIG. 4C). Thus, both TdfI and ZnuA are involved in the transport of zinc.

Conservation of TdfI

Besides the function of TdfI we also want to investigate whether TdfI is a vaccine candidate for a universal *N. meningitidis* vaccine. One of the criteria is that the antigen has to be conserved. We first looked at the available *N. meningitidis* genomes and found that TdfI has a striking 97-99% amino acid identity of the mature protein (FIG. 8). The sequence differences are scattered throughout the protein and are not clustered in predicted extracellular loop regions, which are often antigenically variable in *Neisseria* outer membrane proteins (FIG. 8). We subsequently analyzed the presence of TdfI in a panel of 32 different *N. meningitidis* isolates from different serogroups and different clonal lineages. Each strain was grown in RPMI medium supplemented or not with 500 nM zinc and analyzed by Western blotting with the antiserum raised against TdfI of H44/76. All strains showed a repression of TdfI in the presence of zinc (FIG. 5).

We then wanted to know the homology of TdfI to other pathogenic bacteria. We first compared TdfI with *N. gonorrhea* and found a 96% identity and a 97% similarity between these two *Neisseria* strains. Next, we used the blast program at NCBI with a cutoff of 40% identity at the amino acid level to search for homologs of TdfI in other pathogenic bacteria. We identified homologs in other pathogenic bacteria, including *M. catarrhalis, Haemophilus parasuis, Mannheimia haemolytica, Acinetobacter baumannii, Pasteurella multocida, Bordetella pertussis* and *Actinobacillus pleuropneumoniae*, averaging a 41% identity and 59% similarity at the amino acid level and all TdfI homologs have the His/Asp region (FIG. 9). Interestingly, in *B. pertussis* the tdfI homologue is located adjacent to homologues of the znuABC and zur genes, again indicating a functional relationship between these genes. Furthermore, all these TdfI homologs contain His- and Asp-rich stretches (FIG. 9).

TdfI Induces Bactericidal Antibodies

Figure 6:
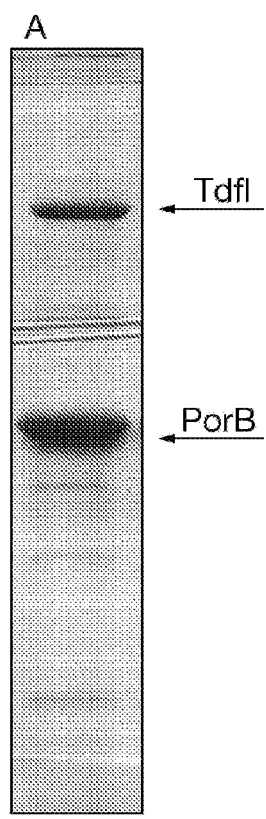
FIG. 6. Protein profile of the TdfI vaccine.
Figure 7:
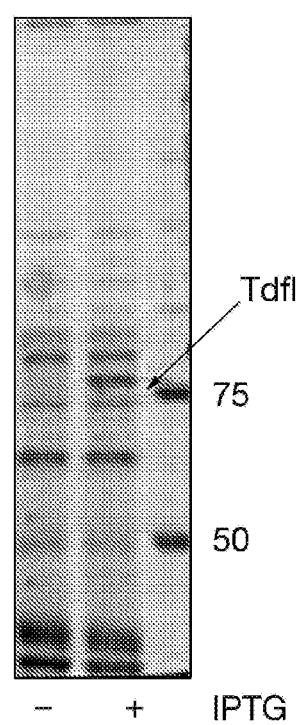
FIG. 7. Impact of IPTG on expression of TdfI on cells used in SBA.

To investigate the vaccine potential of TdfI, we immunized mice with Neisserial outer membrane vesicles containing overexpression levels of this protein (FIG. 6A) and tested the resultant sera for the presence of bactericidal antibodies. Routinely, we perform serum bactericidal assays on bacteria grown in TSB medium; however, under these conditions tdfI is not expressed. Therefore, we tested the sera for bactericidal activity on a strain that expressed TdfI from an isopropyl β-D-1-thiogalactopyranoside (IPTG)-inducible promoter and compared cultures grown with and without IPTG. The bactericidal titers of the sera were <1:100 when IPTG was absent, but 1:1042 when IPTG was present during growth of the bacteria. Titers in pre-immune sera were also <1:100. These data clearly show that TdfI is able to elicit bactericidal antibodies. We also wanted to investigate whether normal chromosome-encoded tdfI expression levels are sufficient to mediate complement-mediated killing. For this we employed the zur knockout strain that produces TdfI constitutively in the TSB medium and grows comparable to the wild-type strain in this medium.

Discussion

The high-affinity ZnuABC uptake system for zinc has previously been identified in *N. gonorrhoeae* (30). Homologues can be found in the meningococcal genome, as described above, and in the genomes of many other bacteria. In *Salmonella enterica* this ABC transporter has been associated with virulence (31). In no case, an outer membrane receptor involved in zinc acquisition has been identified and it is thought that zinc diffuses through the porins.

In the human host, however, the free zinc levels are most likely too low to sustain bacterial growth by passive diffusion. The total amount of zinc in human serum is approximately 19 µM, but the vast majority is bound by serum proteins such as albumin (32). Here we have identified an outer membrane receptor, TdfI that is regulated by zinc. The addition of 700 nM zinc to the growth medium completely repressed TdfI expression. The function of TdfI is to bind and transport of unbound (free) zinc. We predict that the zinc is bound initially by the His/Asp stretch in the external loop and then internalized via two histidines that are on top of the plug domain (FIG. 3b). A possible role for the TonB system in zinc uptake is that it pulls the plug out of the barrel and with this movement the zinc bound to the two His residues is transported into the periplasm where it is picked up by the periplasmic binding protein ZnuA.

Interestingly, similar regulation of tdfI and znuA expression was reported in a microarray study using N. gonorrhoeae (33). The tdfI homolog NGO1205 and the znuA homolog NGO0168 were upregulated in a mutant lacking the NGO0542 gene. This gene was annotated in that study as perR because of its homology to a manganese-dependent peroxide-responsive regulator found in gram-positive organisms (34). However, this is the same gene we have annotated as zur. The zur annotation is clearly more accurate, because we show an identical regulation by the absence of zur or the absence of zinc. More evidence for the annotation zur rather than perR comes from the same study in N. gonorrhoeae. Microarrays performed with the gonococcal perR mutant showed upregulation also of the ribosomal proteins L31 and L36. The Neisserial genomes contain two copies for each of the genes encoding these proteins with one form of each protein containing a zinc ribbon motif. Zinc availability was found to be the key factor controlling the type of L31/L36 protein expressed in B. subtilis (34). In the gonococcal perR mutant, expression specifically of L31 and L36 paralogs lacking the zinc ribbons is induced, highly indicative of a disturbed zinc regulation in a perR mutant. Moreover in another study (17) a microarray was performed to identify the response to oxidative stress and neither perR nor any of the genes identified in the PerR study (33) were de-repressed and we do not see any regulatory effect of manganese on the expression of tdfI and znuA.

Previously, tdfI expression was reported to be induced in the presence of active complement (18). In this microarray study expression profiles were compared of N. meningitidis grown in the presence of serum and heat-inactivated serum, and TdfI was found 23-fold de-repressed in the presence of the untreated serum. The relationship between zinc and complement regulation may not be obvious at first sight. A possible explanation for finding similar regulatory circuits may be that the bacteria in the array study were pre-grown in RMPI with BSA. Albumin is known to chelate zinc, and therefore, pre-growth conditions may have been severely zinc-limited. Heat-treatment of human serum will release zinc from albumin, thereby repressing tdfI expression. This explanation is strengthened by the fact that TdfI expression is induced when BSA is added to TSB medium during bacterial growth (data not shown).

A study by Hagen and Cornelissen (35) investigated whether any of the Tdf proteins is essential for intracellular survival of N. gonorrhoeae in human epithelial cells. The authors also tested a TdfI homologue knockout (NG1205), but this mutant was not affected in the intracellular survival.

The conservation of TdfI is striking; with an identity of 98.6% among the sequenced N. meningitidis strains and a 99.2% similarity at the amino acid level of the mature protein. The TdfI protein was found in all meningococci tested and all strains showed zinc-regulated expression of tdfI. Between the TdfI proteins of the sequenced meningococcal and gonococcal strains there is 96.1% identity and 97.3% similarity at the amino acid level. The differences between the sequences of TdfI are scattered throughout the protein and do not cluster in a specific loop. We find an average 41% amino acid identity of TdfI with homologs in other bacteria and in all cases the His/Asp stretch is conserved. Intriguingly, TdfI homologs were particularly found in bacterial species residing in the respiratory tract of humans and animals. Possibly in the mucosal layers of the respiratory tract the unbound zinc concentration is too low to allow sufficient passive diffusion through the porins and therefore TdfI becomes essential for bacterial growth and survival. While TdfI is not essential for intracellular survival (35) it could be essential in the bodily fluids like serum and liquor where the free zinc concentration could also be very low. Also, we cannot rule out that TdfI additionally recognizes a complexed form of zinc which may available in the respiratory tract, serum and or cerebral fluid.

We have further shown that TdfI can induce bactericidal antibodies in mice and that these antibodies are specifically directed at TdfI. Also when we used bacteria expressing TdfI from the chromosomal locus we could detect bactericidal activity, showing that during infection the antigen concentration is high enough to allow clearing of N. meningitidis.

The high level of conservation and the possibility to raise TdfI-specific bactericidal antibodies make TdfI an excellent vaccine candidate.

Materials and Methods

Abbreviations used: IPTG, isopropyl β-D-1-thiogalactopyranoside; PAR, 4-(2-pyridylazo)resorcinol; RPMI, Roswell Park Memorial Institute medium 1640; Tdf, TonB-dependent family; TPEN, N,N,N',N'-Tetrakis(2-pyridylmethyl)ethylenediamine; TSB, tryptic soy broth; ICP-MS, Inductively coupled plasma mass spectrometry.

Bacterial Strains and Growth Conditions.

Neisserial strains, listed in FIG. 5 are from the laboratory collection. Except when indicated otherwise, experiments were performed with strain HB-1 and mutants thereof. HB-1 is a non-encapsulated derivative of serogroup B strain H44/76 (Bos & Tommassen, 2005). N. meningitidis was grown on GC agar (Oxoid) plates containing Vitox (Oxoid) and antibiotics when appropriate (kanamycin, 100 μg/ml; chloramphenicol, 10 μg/ml) in candle jars at 37° C. Liquid cultures were grown in TSB (Difco) or in RPMI (Sigma) in plastic flasks at 37° C. with shaking. IPTG, zinc, and TPEN were added in the concentrations indicated s. Metals were added as a cocktail (340 nM $ZnSO_4$, 160 nM $Na_2MoO_4$, 800 nM $MnCl_2$, 80 nM $CoCl_2$ and 80 nM $CuSO_4$ final concentrations) or as single compounds in the same concentrations as in the cocktail unless indicated otherwise. Ferric chloride was added as a final concentration of 8 μM. E. coli strains DH5α and TOP10F' (Invitrogen) were used for routine cloning and BL21(DE3) (Invitrogen) for expression. An E. coli hemA mutant was used to assess the heme transport of TdfI ((22). E. coli was propagated on Luria-Bertani medium supplemented when appropriate with 100 μg/ml ampicillin, 50 μg/ml kanamycin, or 25 μg/ml chloramphenicol. For the E. coli heme-auxotroph C600 hemA::kan (22) the medium was supplemented with 5-aminolevulinic acid.

Construction of Plasmids and Mutants.

All primers were designed on the MC58 genome sequence, using NMB0964 (tdfI), NMB1730 (tong), NMN0586 (znuA), NMB1266 (zur).

For high-level protein production in E. coli the tdfI gene without the signal sequence-encoding part was amplified from chromosomal DNA of strain H44/76 by PCR using the primers 0964-F-GATCATATGCATGAAACTGAG-CAATCGGTG- and 0964-R-GATGGATCCTTAAATCT-TCACGTTCACGCCGCC- that carry the restriction sites NdeI and BamHI, respectively (bold). The resulting product was cloned into pCRII-TOPO according to the manufacturer's recommendation (Invitrogen), yielding pCRII-tdfI, and subcloned into pET11a (Novagen) using NdeI/BamHI restriction, resulting in plasmid pET11a-tdfI.

To obtain a tdfI deletion construct, a kanamycin-resistance gene cassette (36) was amplified by PCR with the primers Kan-R-TGACGCGTCTCGACGCTGAGGTCTGC- and Kan-F-TGTGTACAGTCGACTTCAGACGGCCACG- and cloned after MluI and BsrGI digestion into pCRII-tdfI digested with the same enzymes. In the resulting construct, pCRII-tdfI::kan, the kanamycin-resistance cassette substitutes for the region between by 437 and 1344 of tdfI. pCRII-tdfI::kan was used in a PCR with the 0964-R and 0964-F primers and the resulting product was used to transform HB-1 (37). Kanamycin-resistant colonies were tested for correct gene replacement by PCR.

The entire tdfI gene from H44/76 was amplified with primers TdfI-F-GCATCATATGGCACAAACTACACT-CAAACCC- and TdfI-R-ATGACGTCTTAAAACT-TCACGTTCACGCCGCC- that contain recognition sites for NdeI and AatII (bold), respectively. The resulting PCR product was cloned into pCRII-TOPO and subcloned into pEN11-pldA (36) using NdeI and AatII restriction sites. The resulting plasmid, pEN11-tdfI, constitutes a Neisserial replicative plasmid, containing a lacI$^Q$ gene and a tandem lac/tac promoter for controlled expression of tdfI.

The construct to generate a tonB knockout was made by amplifying DNA fragments upstream and downstream of the tonB gene using primers tonB-1 (GTACGATGATTGTGC-CGACC), tonB-2 (ACTTTAAACTCCGTCGACG-CAAGTCGACTGCGGGGGTTAA) with AccI restriction sites (bold) for one fragment, and, tonB-3 (TTAACCCCCG-CAGTCGACTTGCGTCGACGGAGTTTAAAGT) with restriction site AccI (bold) and tonB-4 (GCCATACTGT-TGCGGATTTGA) for the other fragment. The two fragments were each cloned into pCRII-TOPO and then ligated to each other using the introduced restriction site AccI and the SpeI site in the pCRII-TOPO vector. The AccI site was subsequently used to clone the chloramphenicol transacetylase gene from pKD3 (38) previously cloned into pCRII-TOPO by PCR amplification with primers containing an AccI site. The resulting construct was amplified by PCR using primers tonB-1 and tonB-4 and this linear fragment was used to transform N. meningitidis HB-1.

The zur gene was knocked out following the same strategy. Upstream and downstream fragments were amplified in this case with primers: zur-1 (TTCGCCGATGGCGGAATACA), zur-2 (CTTTCAGCGCAAAGTCGACTCCGTC-GACGCGTGCCTGTTC) with the restriction site AccI in bold, zur-3 (GAACAGGCACGCGTCGACGGAGTC-GACTTTGCGCTGAAAG) with the restriction site AccI in bold and zur-4 (TCCTATTGCGCAATACCCCC)

A porA derivative of N. meningiditis strain H44/76, called CE2001 (39) was transformed with pMF121, resulting in deletion of the entire capsule locus and production of lipopolysaccharide with a truncated outer core (36). A pLAFR-derived plasmid containing the tonB, exbB and exbD genes of N. meningitidis ((13) was described previously.

SDS-PAGE and Western Blot Analysis.

Cell lysates were prepared from bacteria grown for 6 hours. The cells were diluted to $OD_{600nm}$ 1, pelleted, and boiled in 100 μl SDS-PAGE sample buffer containing 2% SDS and 5% 2-mercaptoethanol. Proteins were separated by standard SDS-PAGE. Gels were either stained with Coomassie brilliant blue or the proteins were transferred to nitrocellulose membranes (Protran) using a wet transfer system (Biorad) in 25 mM Tris-HCl, 192 mM glycine, 20% methanol. Membranes were blocked for 1 h in PBS containing 0.1% Tween 20 and 0.5% Protifar (Nutricia). Blots were incubated with antibodies in blocking buffer. Antibody binding was detected by using goat anti-rabbit IgG peroxidase-conjugated secondary antibodies (Biosource) and enhanced chemiluminescence detection (Pierce).

Immunizations.

BL21(DE3) cells containing pET11a-tdfI were grown in LB to an OD $A_{600}$ of 0.6 after which 1 mM IPTG was added and growth was continued for 2 h. The TdfI protein accumulated in inclusion bodies, which were isolated as described (40), and the purified protein was used to immunize rabbits at Eurogentec. The resulting antiserum, SN1042, was used in a 1/5000 dilution.

Outer membrane vesicles of strain CE1523/pEN11-tdfI grown in the presence or absence of 1 mM IPTG, were prepared by deoxycholate extraction (41) and used to immunize mice as described (32). Sera from ten mice per group were collected after 42 days and pooled. The experiments complied with the relevant national guidelines of Belgium and institutional policies of GlaxoSmithKline Biologicals.

RT-qPCR.

RT-qPCR was performed using an Applied Biosystems 7900HT Fast Real-Time PCR System and SYBR green master mix (Applied Biosystems) according to the manufacturer's recommendations. Total RNA was isolated by resuspending approximately $4 \times 10^9$ Neisseria cells in 3 ml Trizol (Invitrogen). After the addition of 600 μl chloroform and centrifugation, the upper phase was mixed 1:1 with 75% ethanol. This was loaded on a nucleospin RNA II column (Macherey-Nagel), which was subsequently washed with buffer R3 from the nucleospin RNA II kit and eluted with 100 μl water. The RNA was then treated with Turbo DNA Free (Ambion) to yield DNA-free RNA. To generate the cDNA, 1 μg of total RNA was reverse transcribed from random hexamers using transcriptor High fidelity cDNA synthesis kit (Roche) according to the manufacturer's recommendations. As a control, parallel samples were prepared in which the reverse transcriptase was omitted from the reaction mixture. PCRs were performed in triplicate in a 25-μl volume in a 96-well plate (Applied Biosystems) with the following cycle parameters: 95° C. for 10 min for enzyme activation followed by 40 cycles of 95° C. for 15 s and 60° C. for 1 min. A melting plot was performed to ensure that the signal originated from the specific amplicon. Data analysis was performed using the comparative cycle threshold method (Applied Biosystems) to determine relative expression levels. The rmpM transcript was used to normalize all data.

ICP-MS.

Total zinc concentrations were measured by ICP-MS at the integrated laboratory of the department of Geochemistry at the Utrecht University. N. meningitidis strains were grown in RPMI medium from a 0.1 starting $OD_{A550}$ for 6 h; at this time point a sample was taken and the remaining culture was grown for an additional hour in the presence of 1 μM zinc. After this hour, a second sample was taken. Both samples (7 ml) were washed in phosphate-buffered saline and resuspended in water, killed for 1 h at 56° C. and frozen at −80° C. The samples were then thawed, sonicated and filtered through 0.22-μm filters (Millipore).

PAR Competition Assay.

The PAR competition assay is a colorimetric reaction where the orange color of the PAR-zinc complex changes towards yellow in the presence of a protein or chemical that is able to release zinc from PAR. The assay was performed as described (42) with the following modifications: Instead of 50 μM we added 30 μM zinc and we first measured the PAR-zinc solution and then added the outer membrane vesicles to the cuvette and re-measured the solution. In this way we avoided the potential color change induced in time by UV. The data was then first normalized to the PAR-zinc measurement and then to the PAR alone sample to obtain the binding values for the outer membrane vesicles. The results shown are the normalized data of the absorption at 500 nm.

Serum Bactericidal Assay.

Wild-type H44/76 was transformed with pEN11-tdfI and inoculated from overnight grown plates in TSB with 125 µM $FeCl_3$ with or without 1 mM IPTG in shaking flasks for 3 h at 37° C. until an $OD_{550}$ of 0.5 was reached. Serum to be tested was diluted 1:100 in Hank's balanced salt solution (HBSS) (GIBCO), 0.3% BSA and then serially diluted (two-fold dilution steps, eight dilutions) in a 50-µl volume in sterile U-bottom 96-well microtiter plates (NUNC). Bacteria were diluted in HBSS, 0.3% BSA to yield ~13,000 CFU per ml and 37.5 µl samples of the suspension were added to the serum dilutions. The microtiter plates were incubated at 37° C. for 15 min while shaking. Subsequently, 12.5 µl of baby-rabbit complement (Pelfreez) or, as control for toxicity of the sera, heat-inactivated (56° C. for 45 min) complement was added to the wells. After 1 h incubation at 37° C. while shaking, the microtiter plates were placed on ice to stop the killing. Of each well, 20 µl was spotted on GC plates while plates were tilted to allow the drop to "run" down the plate. After overnight incubation, colonies were counted and the percentage of killing was calculated. The bactericidal titer was defined as the highest serum dilution yielding >50% killing.

REFERENCES

1. Ratledge, C. 2007. Iron metabolism and infection. *Food. Nutr. Bull.* 28:5515-523.
2. Wandersman, C., and P. Delepelaire. 2004. Bacterial iron sources: from siderophores to hemophores. *Annu. Rev. Microbiol.* 58:611-647.
3. Wiener, M. C. 2005. TonB-dependent outer membrane transport: going for Baroque? *Curr. Opin. Struct. Biol.* 15:394-400.
4. Postle, K. 1993. TonB protein and energy transduction between membranes. *J. Bioenerg. Biomembr.* 25:591-601.
5. Braun, V. 2006. Energy transfer between biological membranes. *ACS Chem. Biol.* 1:352-354.
6. De, S. K., M. T. McMaster, and G. K. Andrews. 1990. Endotoxin induction of murine metallothionein gene expression. *J. Biol. Chem.* 265:15267-15274.
7. Corbin, B. D., E. H. Seeley, A. Raab, J. Feldmann, M. R. Miller, V. J. Torres, K. L. Anderson, B. M. Dattilo, P. M. Dunman, R. Gerads, R. M. Caprioli, W. Nacken, W. J. Chazin, and E. P. Skaar. 2008. Metal chelation and inhibition of bacterial growth in tissue abscesses. *Science.* 319: 962-965.
8. Stephens, D. S., and S. M. Zimmer. 2002. Pathogenesis, therapy, and prevention of meningococcal sepsis. *Curr. Infect. Dis. Rep.* 4:377-386.
9. Finne, J., M. Leinonen, and P. H. Makela. 1983. Antigenic similarities between brain components and bacteria causing meningitis. Implications for vaccine development and pathogenesis. *Lancet.* 2:355-357.
10. Pettersson, A., A. Maas, and J. Tommassen. 1994. Identification of the iroA gene product of *Neisseria meningitidis* as a lactoferrin receptor. *J. Bacteriol.* 176:1764-1766.
11. Legrain, M., V. Mazarin, S. W. Irwin, B. Bouchon, M. J. Quentin-Millet, E. Jacobs, and A. B. Schryvers. 1993. Cloning and characterization of *Neisseria meningitidis* genes encoding the transferrin-binding proteins Tbp1 and Tbp2. *Gene.* 130:73-80.
12. Lewis, L. A., E. Gray, Y. P. Wang, B. A. Roe, and D. W. Dyer. 1997. Molecular characterization of hpuAB, the haemoglobin-haptoglobin-utilization operon of *Neisseria meningitidis*. *Mol. Microbiol.* 23:737-749.
13. Stojiljkovic, I., V. Hwa, L. de Saint Martin, P. O'Gaora, X. Nassif, F. Heffron, and M. So. 1995. The *Neisseria meningitidis* haemoglobin receptor: its role in iron utilization and virulence. *Mol. Microbiol.* 15:531-541.
14. Carson, S. D., P. E. Klebba, S. M. Newton, and P. F. Sparling. 1999. Ferric enterobactin binding and utilization by *Neisseria gonorrhoeae*. *J. Bacteriol.* 181:2895-2901.
15. Turner, P. C., C. E. Thomas, I. Stojiljkovic, C. Elkins, G. Kizel, D. A. Ala'Aldeen, and P. F. Sparling. 2001. Neisserial TonB-dependent outer-membrane proteins: detection, regulation and distribution of three putative candidates identified from the genome sequences. *Microbiology.* 147:1277-1290.
16. Ducey, T. F., M. B. Carson, J. Orvis, A. P. Stintzi, and D. W. Dyer. 2005. Identification of the iron-responsive genes of *Neisseria gonorrhoeae* by microarray analysis in defined medium. *J. Bacteriol.* 187:4865-4874.
17. Grifantini, R., E. Frigimelica, I. Delany, E. Bartolini, S. Giovinazzi, S. Balloni, S. Agarwal, G. Galli, C. Genco, and G. Grandi. 2004. Characterization of a novel *Neisseria meningitidis* Fur and iron-regulated operon required for protection from oxidative stress: utility of DNA microarray in the assignment of the biological role of hypothetical genes. *Mol. Microbiol.* 54:962-979.
18. Dove, J. E., K. Yasukawa, C. R. Tinsley, and X. Nassif. 2003. Production of the signalling molecule, autoinducer-2, by *Neisseria meningitidis*: lack of evidence for a concerted transcriptional response. *Microbiology.* 149:1859-1869.
19. Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. *Nucleic Acids Res.* 25:3389-3402.
20. Furano, K., and A. A. Campagnari. 2004. Identification of a hemin utilization protein of *Moraxella catarrhalis* (HumA). *Infect. Immun.* 72:6426-6432.
21. Mazoy, R., and M. L. Lemos. 1996. Identification of heme-binding proteins in the cell membranes of *Vibrio anguillarum*. *FEMS Microbiol. Lett.* 135:265-270.
22. Ghigo, J. M., S. Létoffé, and C. Wandersman. 1997. A new type of hemophore-dependent heme acquisition system of *Serratia marcescens* reconstituted in *Escherichia coli*. *J. Bacteriol.* 179:3572-3579.
23. Patzer, S. I., and K. Hantke. 1998. The ZnuABC high-affinity zinc uptake system and its regulator Zur in *Escherichia coli*. *Mol. Microbiol.* 28:1199-1210.
24. Ferguson, A. D., E. Hofmann, J. W. Coulton, K. Diederichs, and W. Welte. 1998. Siderophore-mediated iron transport: crystal structure of FhuA with bound lipopolysaccharide. *Science.* 282:2215-2220.
25. Yatsunyk, L. A., J. A. Easton, L. R. Kim, S. A. Sugarbaker, B. Bennett, R. M. Breece, Vorontsov, II, D. L. Tierney, M. W. Crowder, and A. C. Rosenzweig. 2008. Structure and metal binding properties of ZnuA, a periplasmic zinc transporter from *Escherichia coli*. *J. Biol. Inorg. Chem.* 13:271-288.
26. Bentley, S. D., G. S. Vernikos, L. A. Snyder, C. Churcher, C. Arrowsmith, T. Chillingworth, A. Cronin, P. H. Davis, N. E. Holroyd, K. Jagels, M. Maddison, S. Moule, E. Rabbinowitsch, S. Sharp, L. Unwin, S. Whitehead, M. A. Quail, M. Achtman, B. Barrell, N. J. Saunders, and J. Parkhill. 2007. Meningococcal genetic variation mechanisms viewed through comparative analysis of serogroup C strain FAM18. *PLoS Genet.* 3:e23.
27. Dempsey, J. A., W. Litaker, A. Madhure, T. L. Snodgrass, and J. G. Cannon. 1991. Physical map of the chromosome of *Neisseria gonorrhoeae* FA1090 with locations of genetic markers, including opa and pil genes. *J. Bacteriol.* 173:5476-5486.
28. Parkhill, J., M. Achtman, K. D. James, S. D. Bentley, C. Churcher, S. R. Klee, G. Morelli, D. Basham, D. Brown, T. Chillingworth, R. M. Davies, P. Davis, K. Devlin, T. Feltwell, N. Hamlin, S. Holroyd, K. Jagels, S. Leather, S. Moule, K. Mungall, M. A. Quail, M. A. Rajandream, K. M. Rutherford, M. Simmonds, J. Skelton, S. Whitehead, B. G. Spratt, and B. G. Barrell. 2000. Complete DNA sequence of a serogroup A strain of *Neisseria meningitidis* Z2491. *Nature.* 404:502-506.
29. Tettelin, H., N. J. Saunders, J. Heidelberg, A. C. Jeffries, K. E. Nelson, J. A. Eisen, K. A. Ketchum, D. W. Hood, J. F. Peden, R. J. Dodson, W. C. Nelson, M. L. Gwinn, R. DeBoy, J. D. Peterson, E. K. Hickey, D. H. Haft, S. L. Salzberg, O. White, R. D. Fleischmann, B. A. Dougherty, T. Mason, A. Ciecko, D. S. Parksey, E. Blair, H. Cittone, E. B. Clark, M. D. Cotton, T. R. Utterback, H. Khouri, H. Qin, J. Vamathevan, J. Gill, V. Scarlato, V. Masignani, M. Pizza, G. Grandi, L. Sun, H. O. Smith, C. M. Fraser, E. R. Moxon, R. Rappuoli, and J. C. Venter. 2000. Complete genome sequence of *Neisseria meningitidis* serogroup B strain MC58. *Science.* 287:1809-1815.
30. Chen, C. Y., and S. A. Morse. 2001. Identification and characterization of a high-affinity zinc uptake system in *Neisseria gonorrhoeae. FEMS Microbiol. Lett.* 202:67-71.
31. Ammendola, S., P. Pasquali, C. Pistoia, P. Petrucci, P. Petrarca, G. Rotilio, and A. Battistoni. 2007. The high affinity $Zn^{2+}$ uptake system ZnuABC is required for bacterial zinc homeostasis in intracellular environments and contributes to virulence of *Salmonella enterica. Infect. Immun.* 75:5867-5876.
32. Stewart, A. J., C. A. Blindauer, S. Berezenko, D. Sleep, and P. J. Sadler. 2003. Interdomain zinc site on human albumin. *Proc. Natl. Acad. Sci. USA.* 100:3701-3706.
33. Wu, H. J., K. L. Seib, Y. N. Srikhanta, S. P. Kidd, J. L. Edwards, T. L. Maguire, S. M. Grimmond, M. A. Apicella, A. G. McEwan, and M. P. Jennings. 2006. PerR controls Mn-dependent resistance to oxidative stress in *Neisseria gonorrhoeae. Mol. Microbiol.* 60:401-416.
34. Nanamiya, H., G. Akanuma, Y. Natori, R. Murayama, S. Kosono, T. Kudo, K. Kobayashi, N. Ogasawara, S. M. Park, K. Ochi, and F. Kawamura. 2004. Zinc is a key factor in controlling alternation of two types of L31 protein in the *Bacillus subtilis* ribosome. *Mol. Microbiol.* 52:273-283.
35. Hagen, T. A., and C. N. Cornelissen. 2006. *Neisseria gonorrhoeae* requires expression of TonB and the putative transporter TdfF to replicate within cervical epithelial cells. *Mol. Microbiol.* 62:1144-1157.
36. Bos, M. P., B. Tefsen, P. Voet, V. Weynants, J. P. M. van Putten, and J. Tommassen. 2005. Function of neisserial outer membrane phospholipase A in autolysis and assessment of its vaccine potential. *Infect. Immun.* 73:2222-2231.
37. Voulhoux, R., M. P. Bos, J. Geurtsen, M. Mols, and J. Tommassen. 2003. Role of a highly conserved bacterial protein in outer membrane protein assembly. *Science.* 299:262-265.
38. Datsenko, K. A., and B. L. Wanner. 2000. One-step inactivation of chromosomal genes in *Escherichia coli* K-12 using PCR products. *Proc. Natl. Acad. Sci. USA.* 97:6640-6645.
39. Tommassen, J., P. Vermeij, M. Struyvé, R. Benz, and J. T. Poolman. 1990. Isolation of *Neisseria meningitidis* mutants deficient in class 1 (PorA) and class 3 (PorB) outer membrane proteins. *Infect. Immun.* 58:1355-1359.
40. Dekker, N., K. Merck, J. Tommassen, and H. M. Verheij. 1995. In vitro folding of *Escherichia coli* outer-membrane phospholipase A. *Eur. J. Biochem.* 232:214-219.
41. Weynants, V. E., C. M. Feron, K. K. Goraj, M. P. Bos, P. A. Denoel, V. G. Verlant, J. Tommassen, I. R. Peak, R. C. Judd, M. P. Jennings, and J. T. Poolman. 2007. Additive and synergistic bactericidal activity of antibodies directed against minor outer membrane proteins of *Neisseria meningitidis. Infect. Immun.* 75:5434-5442.
42. Lim, K. H., C. E. Jones, R. N. vanden Hoven, J. L. Edwards, M. L. Falsetta, M. A. Apicella, M. P. Jennings, and A. G. McEwan. 2008. Metal binding specificity of the MntABC permease of *Neisseria gonorrhoeae* and its influence on bacterial growth and interaction with cervical epithelial cells. *Infect. Immun.* 76:3569-3576.

TABLE 1

Conservation of the mature TdfI protein sequence in the sequenced *Neisseria* strains.

| | | Identity (%) | | | | | | |
|---|---|---|---|---|---|---|---|---|
| | | Strain | | | | | | |
| | | MC58 | Fam18 | Z2491 | 053442 | FA1090 | NCCP 11945 | ST-640 |
| Similarity (%) | *N. meningitidis* MC58 | | 730/734 (99.5) | 720/734 (98.1) | 720/734 (98.1) | 706/734 (96.2) | 707/734 (96.3) | 712/734 (97.0) |
| | *N. meningitidis* Fam18 | 733/734 (99.9) | | 722/734 (98.4) | 718/734 (97.8) | 705/734 (96.0) | 706/734 (96.2) | 712/734 (97.0) |
| | *N. meningitidis* Z2491 | 725/734 (98.8) | 726/734 (98.9) | | 716/734 (97.5) | 707/734 (96.3) | 706/734 (96.2) | 710/734 (96.7) |
| | *N. meningitidis* 053442 | 726/734 (98.9) | 727/734 (99.0) | 723/734 (98.5) | | 706/734 (96.2) | 707/734 (96.3) | 707/734 (96.3) |
| | *N. gonorrhoeae* FA1090 | 715/734 (97.4) | 714/734 (97.3) | 714/734 (97.3) | 715/734 (97.4) | | 733/734 (99.9) | 702/734 (95.6) |
| | *N. gonorrhoeae* NCCP11945 | 716/734 (97.5) | 715/734 (97.4) | 713/734 (97.1) | 716/734 (97.5) | 733/734 (99.9) | | 701/734 (95.5) |
| | *N. lactamica* ST-640 | 717/734 (97.7) | 718/734 (97.8) | 718/734 (97.8) | 715/734 (97.4) | 711/734 (96.9) | 710/734 (96.7) | |

Example 3

ZnuD: a Potential Vaccine Candidate for a Simple and Universal *Neisseria meningitidis* Vaccine

Abstract

*Neisseria meningitidis* serogroup B is a major cause of bacterial sepsis and meningitis in younger populations. Available vaccines are based on outer membrane vesicles obtained from wild type strains. However, in toddlers and infants, they confer protection only against strains expressing homologous PorA, a major and variable outer membrane protein. In the quest to identify vaccine antigens allowing the development of vaccines able to prevent meningococcal infection in the younger populations, ZnuD (TdfI) has been identified as a potential candidate. Here, we have extended the analysis of the potential value of ZnuD showing that it is a very well conserved antigen expressed by all the *N. meningitidis* serogroup B strains tested when growing under Zinc limitation, induces cross-bactericidal antibodies against most of the strains tested, whatever the serogroup, and is also expressed during infection and most probably during carriage. In addition, anti-ZnuD antibodies are able to mediate the complement killing of strains not killed by anti-human factor H binding protein (fHbp).

Introduction

*Neisseria meningitidis* is a gram negative, encapsulated bacterium. It is an obligate human pathogen that asymptomatically colonizes the upper respiratory tract of around 10% of the adult population. Occasionally, it translocates to the bloodstream resulting in bacteremia with possible progression to meningitis and death. *N. meningitidis* is one of the most feared bacterial infections due to its rapid progression and tendency to cause epidemics. This bacterium is classified into 13 serogroups on the basis of the chemical composition of the capsular polysaccharides. However, only serogroups A, B, C, Y, and W-135, and to a minor extent X, have been associated with disease. Conjugate polysaccharide vaccines that provide effective immunity in humans are becoming available for serogroups A, C, Y and W135. Unfortunately, the conjugate approach cannot be easily applied to serogroup B (MenB) because its capsular polysaccharide shares structural similarity with polysialylated host glycoproteins, such as the neural cell adhesion molecule.

First generation of MenB vaccines were based on outer membrane vesicles (OMVs) purified after detergent extraction to reduce the lipooligosaccharide (LOS) content. PorA is one of the most abundant outer membrane proteins (OMPs) and an immunodominant component in these OMVs. However, PorA displays high antigenic variability limiting the efficacy of OMV-based vaccines, especially below 2-4 years of age; an age group which totalized around 50% of MenB cases in Europe with an incidence of around 16/100,000 babies below 1 year old. To overcome this limitation, the use of conserved minor OMPs has been explored Recently, the potential of an integral OMPs has vaccine candidate was recognised. This protein, named ZnuD for zinc uptake component D, is expressed under zinc limitation and is involved in zinc uptake. Based on the potential of this protein as vaccine candidates, we have extended its study, looking for the presence of anti-ZnuD antibodies in human, its potential to induce cross-bactericidal antibodies and confirming that this protein is very well conserved and expressed all the *N. meningitidis* strains tested, whatever the serogroup, with the exception of few serogroup Y strains from ST-23 clonal complex.

Results

ZnuD is Immunogenic and Expressed in Humans.

ZnuD is not expressed by *N. meningitidis* growing on classical agar culture media except after addition of zinc chelator such as TPEN, questioning its expression in the host. An indirect way to demonstrate that ZnuD is expressed in human is to evaluate the presence of anti-ZnuD antibodies in sera from convalescent patients and/or healthy carriers. For this purpose, a peptide array approach was used covering 77% of the non-mature protein.

Figure 10:
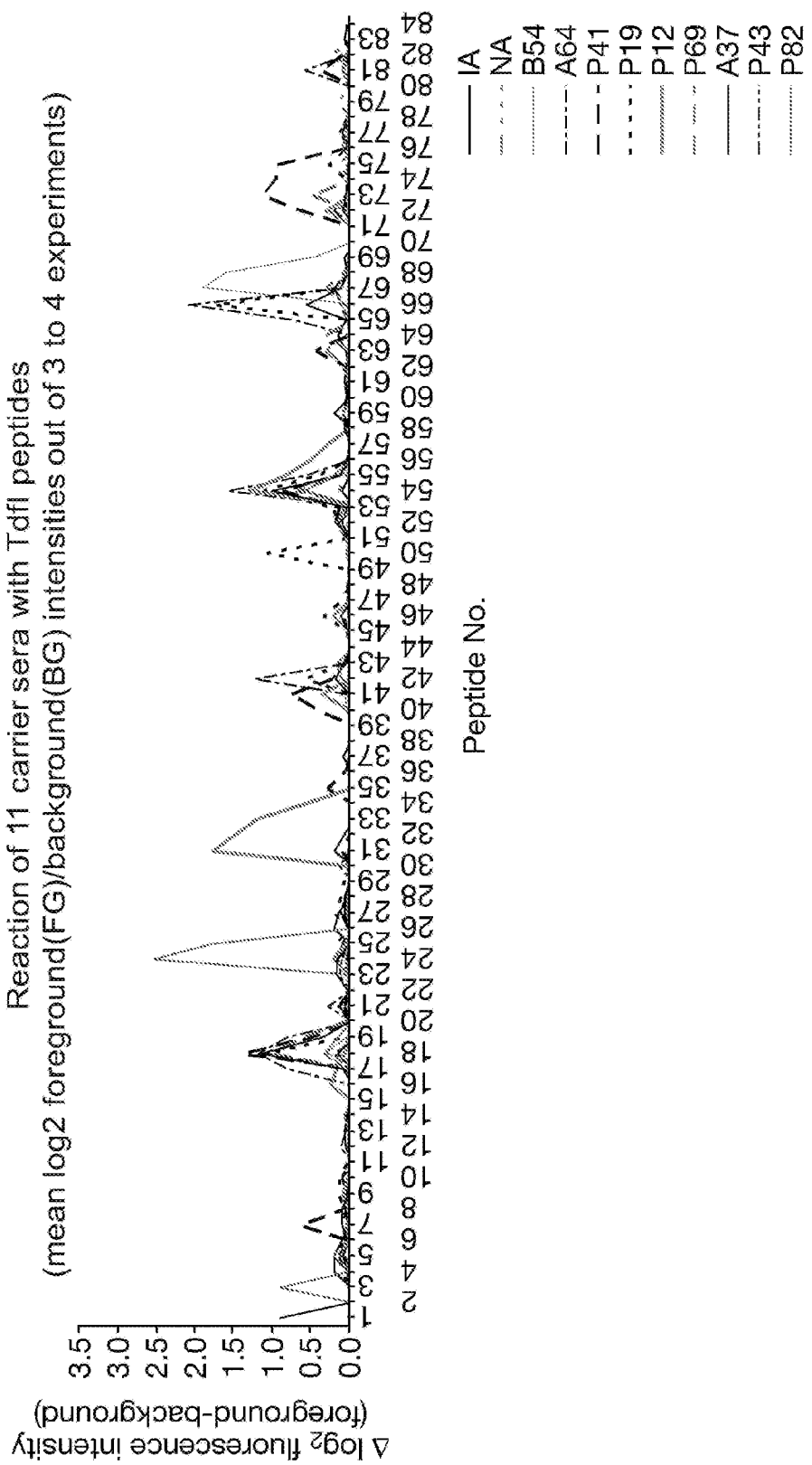
FIG. 10. ZnuD peptide array: Individual response of human sera obtained for convalescent patients or healthy carriers.

Sera from 12 convalescent subjects and from 11 carriers were tested 3 to 5 times in this peptide array. The FIG. 10 shows the intensity of the individual responses between the two groups of subjects. Both the intensity of the response against the peptides and the number of peptides recognized by the sera were greater in the convalescent group than in the carrier group. All the convalescent sera reacted at least against the same 5 non-consecutive peptides indicating that ZnuD is clearly expressed during infection. Presence of antibodies in carrier sera reacting against some peptides also suggests that ZnuD is expressed during colonization of the upper-respiratory tract.

Figure 11:
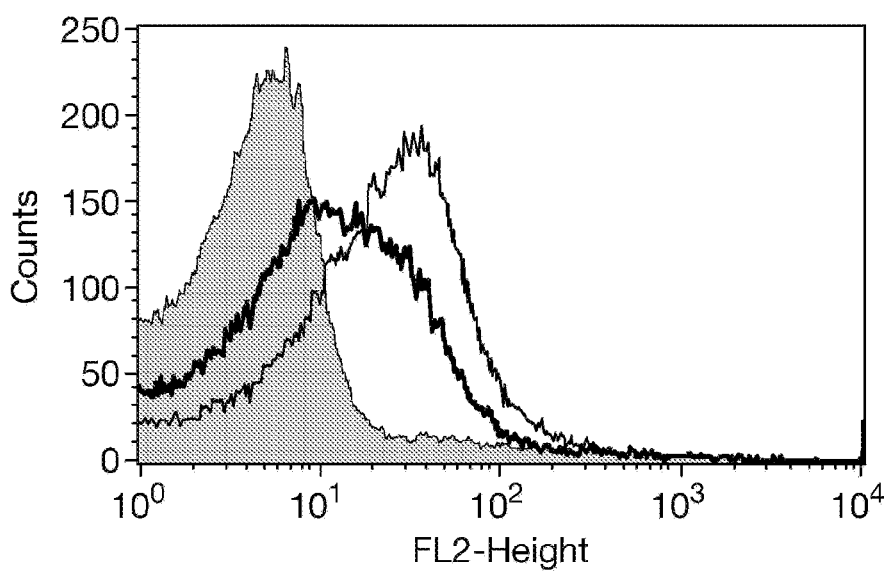
FIG. 11. Expression level of ZnuD in function of culture media.

Development of Relevant Culture Conditions to Assess the Vaccine Potential of ZnuD As has previously been demonstrated, anti-ZnuD antibodies are able to mediate the complement killing of its homologous strain genetically modified to over-express ZnuD. The evaluation of the cross-bactericidal potential of ZnuD antibodies by using a large panel of strains does not allow to modify genetically all these strains. Because, the expression of ZnuD is regulated by Zur, we have defined the amount of zinc chelator needed to achieve the same level of ZnuD expression by a wild type strain than a delta zur strain. This was achieved by using 20 µM of TPEN in MH agar plates (FIG. 11).

ZnuD is a Very Well Conserved Antigen and Expressed by all *Neisseria meningitidis* Strains Except Some German Serogroup Y Strains from ST23 Clonal Complex.

It has already been demonstrated that ZnuD is expressed by all strains but one on a panel of 132 strains from serogroups A, B, C, W-135 and Y. This was extended and confirmed for 43 additional strains, including 2 strains of each serogroup A, C, W-135 and Y and 30 serogroup B strains isolated since 2005 from convalescent subjects located in United Kingdom, Spain and Germany. Globally, of the 175 strains tested, only one did not express ZnuD. This strain is a serogroup Y from ST-23 clonal complex isolated in a German patient.

Particular attention was paid to serogroup Y strains from this ST-23 clonal complex. Seven strains, isolated in Germany were tested and all did not express ZnuD. Sequence analysis has revealed for 4 strains a stop mutation due to single nucleotide deletion. Three of them had the deletion at the same position.

Znu D Induces Cross-Bactericidal Antibodies Against Serogroups A, B, C, W-135 and Y The demonstration of the expression and immunogenicity of ZnuD in humans prompted us to more deeply evaluate the potential of ZnuD as a universal *N. meningitidis* vaccine antigen. For this purpose, OMVs were produced from two strains over-expressing ZnuD or not. These two strains have a similar background since both are derived from H44/76 strain which express an fHbp family B. To avoid the presence of residual capsular polysaccharide in OMV preparations and the induction of anti-LOS and PorA-specific bactericidal antibodies, galE and porA deletion mutations were performed in both strains.

SDS-PAGE analysis suggested that ZnuD represents around 15% of the protein content of OMVs produced from the over-expressing strains while ZnuD is not observed in the control OMVs preparations (FIG. 12a). Because fHbp was described to be very immunogenic when presented in OMVs, its content was checked by ELISA. It was estimated that the amount of fHbp in ZnuD OMVs was 4 fold higher than in the control OMVs (FIG. 12b). Mice and guinea-pigs were immunized three times with OMVs adsorbed on AlPO4. Serum samples were obtained 2 weeks after the third immunization and they were pooled in order to get 3 pools of sera per groups.

ELISA was used to assess the response against both ZnuD and fHbp (Table 3). Immunisation with control OMVs induced few or no anti-ZnuD antibodies in both mice and guinea-pigs (GMT=73 and 10 EU/ml, respectively). As expected, high level of anti-ZnuD antibodies were measured in the sera from animals immunized with ZnuD OMVs (GMT=15096 and 5893 EU/ml, respectively). Surprisingly, the immunogenicity of fHbp appears to be different between mice and guinea-pigs. The level of anti-fHbp antibodies in sera from guinea-pig immunized with either control or ZnuD OMVs are clearly lower (335 and 2733 EU/ml, respectively) compared to mice sera (1342 and 59314 EU/ml, respectively). The different level of anti-fHbp antibodies between anti-control OMV and anti-ZnuD OMV sera is in line with the different amount of fHbp in control and ZnuD OMVs.

Pooled sera were tested in SBA against a panel of 14 serogroup B N. meningitidis strains cultivated with or without TPEN. Six of these strains are regularly used by the HPA for the evaluation of MenB vaccine. This panel include two epidemic strains (H44/76 and NZ98/254) as well as 4 strains of the 4 most prevalent United Kingdom serosubtypes which were accountable for 59.3% of the MenB disease in 2000 and 2001 (M01-240013, M01-240101, M01-240149 and M01-240355). The expression of ZnuD, in presence of TPEN, was confirmed by Western-blot analysis for all these 14 strains. In addition, and due to the presence of anti-fHbp antibodies in sera from animals immunized with OMVs, a pool of sera from mice immunized with a recombinant fHbp B was also tested in bactericidal assay (Table 3).

The bactericidal activity of anti-fHbp antibodies is related to the level of expression of fHbp by the bacteria and is family specific. Using classical culture conditions, only 5 strains, expressing medium (+/−) to high level (++) of the fHbp B, were killed by anti-fHbp B sera (cut-off of positivity fixed at 128), while none of strains expressing either fHbp A or low level of fHbp B were killed. In presence of TPEN, the same 5 strains plus two (NZ124 and DE10690-06) are killed by anti-fHbp B antibodies. SBA titers, obtained in presence or absence of TPEN, are globally similar with a trend to measure slightly higher titers in presence of TPEN. This suggests that the sensitivity of strains to the complement killing mediated by antibodies is not dramatically increased in presence of the chelator.

Sera from mice immunized with control OMVs were not able to mediate the complement killing of strains when cultivated in absence of TPEN. In presence of the chelator, only three strains displayed SBA titers just above the cut-off. As these 3 strains were killed by anti-fHbp B antibodies, the killing observed with anti-control OMVs sera is most probably due to the presence of anti-fHbp antibodies and a slightly increased sensitivity of the strains to complement killing when cultivated with TPEN. The role of these anti-fHbp antibodies was clearly demonstrated for one of these 3 strains by performing bactericidal assay with a ΔfHbp H44/76 strain (Table 4). Absence of killing by sera from guinea-pig immunized with control OMVs is expected and attributed to the lower immunogenicity of fHbp in this species as suggested by the ELISA results.

In absence of zinc chelator, sera from mice immunized with ZnuD OMVs did not mediate the complement killing of the tested strains except four. These four strains are also killed by anti-fHbp antibodies. The role of these anti-fHbp antibodies was clearly demonstrated for the strain H44/76 by performing bactericidal assay with a ΔfHbp H44/76 strain (Table 4). The same anti-ZnuD OMVs sera tested in a bactericidal assay allowing the expression of ZnuD allow to mediate the killing of 12 of the 14 strains tested. Similar results were observed with sera from guinea-pigs. In absence of TPEN in the culture media, strains were not killed in presence of active complement except three. Again, for one of these three strains, H44/76, the role of anti-fHbp antibodies was demonstrated by using a ΔfHbp strain. In presence of TPEN, all the strains except two were killed with SBA titers clearly above the cut-off. The two strains that were not killed are the same strains not killed by the mouse sera. The expression of ZnuD by these two strains (760676 and M05-024072) was demonstrated by Western-blot analysis.

A third group of mice and guinea-pigs were immunized with OMVs purified from a H44/76 strain over-expressing an irrelevant antigen. In absence or presence of TPEN in the serum bactericidal assay, the results are similar to the results observed with the control sera (data not shown). In addition, bactericidal assay were also performed on one strain of each serogroup, A, C, W-135 and Y, confirming the cross-bactericidal activity of anti-ZnuD antibodies against these four serogroups (data not shown).

Confirmation of ZnuD and fHbp as Target of Bactericidal Antibodies

To confirm that ZnuD is a major target of bactericidal antibodies and because there was a trend to observe higher bactericidal titers in presence of TPEN, a delta znuD H44/76 strain was used in bactericidal assays with or without of TPEN (Table 4).

In absence of TPEN, the SBA titers were similar between the H44/76 WT and the delta znuD strains, whatever the origin of the sera (animal species and OMVs used for immunization). In this bactericidal condition, no killing was observed with the delta fHbp strain. These results demonstrate that fHbp is a major target of bactericidal antibodies in absence of ZnuD expression.

In presence of TPEN, the delta fHbp strain was not killed by sera from control animals while similar titers were measured for both the delta znuD strain and the WT H44/76 strain. As expected, when using anti-ZnuD OMVs sera, the bactericidal titers were lower for the delta znuD strain compared to H44/76.

These results demonstrate that ZnuD OMVs have induced both anti-fHbp and anti-ZnuD bactericidal antibodies, while the control OMVs have only elicited the production of anti-fHbp antibodies. The results also demonstrate that the co-expression of fHbp and ZnuD is not required to induce the complement killing mediated by bactericidal antibodies.

Discussion

ZnuD is not expressed on classical culture media such as Mueller Hinton medium or Tryptic Soy Broth medium. These media were developed for the culture of fastidious microorganisms and so are rich in oligo-elements. In MH agar, the total amount of zinc ranges from 200 µg to 450 µg/L depending on the manufacturer. In such media, free Zinc is probably available in such concentration that *N. meningitidis* does not require to specifically express an outer membrane receptor dedicated in zinc acquisition because passive diffusion of zinc via non-specific porins is probably sufficient to allow the growth of the bacterium. In bovine serum, the amount of free zinc is estimated to approximately 0.01 µg/L (0.15 nM) corresponding to around 0.0008% of the total amount of zinc in the serum (800 µg/L). In children, the total zinc concentration is estimated around 750 µg/L and, by extrapolation, free zinc should be also around 0.01 µg/L. In cerebrospinal fluids, the total concentration of zinc is around 111 µg/L. The expression of ZnuD in human was indirectly demonstrated by the detection of antibodies in sera from convalescent patients. The peptide array results, also suggest an expression in carriers. Based on the intensity of the signal measured in the peptide array, it should be wrong to conclude that ZnuD expression in the upper respiratory tract is lower than that in the blood. Indeed, the experiment was designed to detect serum IgG which poorly reflects a mucosal immune response induced by micro-organism colonisation. Ongoing experiments aim to demonstrate the in-vivo expression of ZnuD by performing staining of *N. meningitidis* directly in the cerebrospinal fluids of acute patients.

To allow the expression of ZnuD on classical media, the use of zinc chelator is required. This does not set a precedent because the use of metal chelator was already described to demonstrate the potential of iron binding proteins such as TbpA/B. However, the impact of the concentration of TPEN on the level of ZnuD expression was investigated (data not shown) with the aim to select a concentration that should correspond to the in-vivo ZnuD expression level. For this purpose, the expression of ZnuD in a delta zur strain was used as benchmark. From dose-range experiments, the concentration of 20 µM of TPEN was selected. It is to be noted that in the attempt to avoid the use of chelator, other media are under evaluation. Promising results were obtained with the Catlin medium which is a chemically defined medium developed previously for the growth of *Neisseria*. Flow cytometry analysis suggests that ZnuD expression in this medium is similar to the expression of ZnuD by a delta zur strain growing on MH agar (data not shown).

Using the culture condition selected to potentially mimic the in-vivo expression of ZnuD (MH agar+20 µM TPEN), a panel of 43 strains was assessed for the expression of this OMP. ZnuD was detected in all these strains. Globally, 182 *N. meningitidis* strains have been analysed for their expression of ZnuD. ZnuD expression was demonstrated in all strains except 7 serogroup Y strains all recently isolated in Germany and from the ST-23 clonal complex. For 4 of them, absence of expression was linked to a stop mutation, for the remaining 3 strains, there is no explanation based on nucleotide sequence analysis. A more careful attention will be put to assess the expression of ZnuD in serogroup Y strains, because its expression was demonstrated in older MenY strains.

Because ZnuD is an integral OMP, we have selected OMVs for its presentation to the immune system. These OMVs were extracted from a ΔgalE and ΔporA H44/76 strain by 0.5% DOC to reduce the LOS content. In such conditions, we have previously demonstrated that this kind of OMVs did not induce the production of bactericidal antibodies directed against the LOS. Mice and guinea-pigs immunized with control OMVs have induced a limited bactericidal response against few strains. This protective response is most probably related to the production of some anti-fHbp antibodies as demonstrated by their presence in ELISA and by the use of ΔfHbp strain in bactericidal assay. The results also suggested that fHbp is a highly immunogenic protein, especially in mice, when presented in its natural conformation in OMVs even if present in low amount in these OMVs due to the use of detergent for the extraction of the vesicles. Both mice and guinea-pigs immunized with ZnuD OMVs have elicited the production of anti-ZnuD antibodies. Based on the ELISA data, the immunogenicity of ZnuD in the two species appears to be quite similar by contrast to fHbp. The anti-ZnuD OMVs sera were able to mediate the complement killing of all the strains tested whatever the serogroup but only in culture condition allowing the expression of ZnuD. The exception is two serogroup B strains for which absence of killing is not due to absence of ZnuD expression. Further investigations are ongoing to explain this absence of killing. Among the strains killed two are of interest because they have been used recently in an infant clinical trial assessing the cross-protection induced by a multivalent vaccine based on 5 proteins and OMVs derived from the NZ98/254 strain. Sera from subjects immunized with this complex vaccine failed to mediate the killing of the strain M01-240355 and only 50% of the infants have shown a cross-protection against the strain M01-240101 at the age of 1 year. These two strains were isolated in United Kingdom and are from ST-213 and ST-269 clonal complexes, respectively. These two clonal complexes represent 39% of MenB strains isolated from UK cases in 2008. In the present preclinical experiments, both mice and guinea-pigs immunized with ZnuD OMVs have elicited a high bactericidal response against these two strains (rabbit SBA titers >1700). For the strain M01-240355, this killing is not due to the co-presence of anti-ZnuD and anti-fHbp B antibodies because this strain expresses fHbp A. In addition, we have confirmed that the strain M01-240101 is also killed by anti-ZnuD antibodies in presence of human complement (data not shown).

In conclusion, ZnuD is a protein very well conserved, expressed by all serogroup B strains and able to mediate a cross-bactericidal response against most of the serogroup B strains tested and also against serogroup A, C, W and Y strains. An advantage of ZnuD is that ZnuD is very well conserved and up to now only one family is described. A more comprehensive vaccine could combine both fHbp and ZnuD.

Example 4

Calprotectin Binding to TdfH

Calprotectin is produced by neutrophils, macrophages and squamous epithelia. It is used as a diagnostic tool in faeces for Inflammatory bowel disease. Furthermore it is upregulated upon contact with LPS and it can be found in cerebrospinal fluid when the patient has meningitis. Calprotectin is a heterotetramer of human proteins S100A8 and S100A9 and can bind two zinc or manganese atoms. When calprotectin is spotted on a plate where *Neisseria* is plated in a confluent layer there is an initial inhibition of growth, due to the sequestering of zinc and/or manganese. We believe that *Neisseria* can take the zinc and/or manganese from only one of the binding sites (the low affinity site). The initial clearing comes from the sequestering of zinc and/or manganese to the high affinity site, causing growth inhibition. When also the low affinity site becomes loaded with zinc and/or manganese *Neisseria* can use these metals by taking up though TdfH. Therefore, after the initial clearing, growth is observed in the clearing zone. Furthermore, the uptake process needs energy from the proton motive force in the inner membrane that is shuttled to the outer membrane by TonB, as shown by the lack of growth of the TonB mutant in the clearing zone.

| Strain | Growth in clearing zone |
|---|---|
| H44/76 cps- | Yes |
| TdfH K.O. | No |
| TdfI K.O. | Yes |
| TdfH/TdfI K.O. | No |
| TonB K.O. | No |

A pEN11 derivative that expressed TdfH in high amounts was used to test whether TdfH can bind to calprotectin. B2540 with pEN11-TdfH-terminator was grown in TSB medium with and without 1 mM IPTG. 1 $OD_{550nm}$ of bacteria were taken after 6 hours of growth and washed once in HBSS. The bacteria were resuspended in 1 ml HBSS and 4 ug of calprotectin was added. Calprotectin was allowed to bind for 1 hour after which the cells were washed twice in HBSS. The pellet was then resuspended in sample buffer and boiled for 10 minutes. The lysates where then analyzed by SDS-PAGE and western blots with anti-calprotectin (FIG. 15.)

As shown in FIG. 15, a signal was detectable but was weaker than expected for the amount of TdfH present in the samples. It was then investigated if the binding is better when zinc or manganese is added to the binding step (FIG. 16). Significantly more calprotectin was bound to TdfH when zinc or manganese was present.

The invention claimed is:

1. An immunogenic composition comprising:
 (a) a bacterial outer membrane vesicle preparation comprising an antigen comprising a polypeptide having the amino acid sequence of SEQ ID NO: 50, an antigen comprising a polypeptide having the amino acid sequence of SEQ ID NO: 1, and a pharmaceutically acceptable excipient;
 wherein said immunogenic composition is suitable for administration to a human and induces anti-TdfI bactericidal antibodies that are cross-bactericidal against multiple strains of Neisseria meningitidis.

2. The immunogenic composition of claim 1, wherein expression of SEQ ID NO:1 is up-regulated in said outer membrane vesicle preparation.

3. The immunogenic composition of claim 1, further comprising a zinc salt.

4. The immunogenic composition of claim 1, wherein around 15% of the protein content of said bacterial outer membrane vesicle preparation comprises a polypeptide having the amino acid sequence of is SEQ ID NO:1.

* * * * *

SEQUENCE LISTING

<160> NUMBER OF SEQ ID NOS: 119

<210> SEQ ID NO 1
<211> LENGTH: 758
<212> TYPE: PRT
<213> ORGANISM: Neisseria meningitidis MC58

<400> SEQUENCE: 1

```
Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255

Arg Asp Gln Tyr Gly Leu Pro Ala His Ser His Glu Tyr Asp Asp Cys
            260                 265                 270
```

```
His Ala Asp Ile Ile Trp Gln Lys Ser Leu Ile Asn Lys Arg Tyr Leu
            275                 280                 285

Gln Leu Tyr Pro His Leu Leu Thr Glu Glu Asp Ile Asp Tyr Asp Asn
        290                 295                 300

Pro Gly Leu Ser Cys Gly Phe His Asp Asp Asn Ala His Ala His
305                 310                 315                 320

Thr His Ser Gly Arg Pro Trp Ile Asp Leu Arg Asn Lys Arg Tyr Glu
                325                 330                 335

Leu Arg Ala Glu Trp Lys Gln Pro Pro Gly Phe Glu Ala Leu Arg
            340                 345                 350

Val His Leu Asn Arg Asn Asp Tyr Arg His Asp Glu Lys Ala Gly Asp
        355                 360                 365

Ala Val Glu Asn Phe Phe Asn Asn Gln Thr Gln Asn Ala Arg Ile Glu
    370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
        435                 440                 445

Arg Val Glu Lys Gln Lys Ala Ser Ile Gln Tyr Asp Lys Ala Leu Ile
    450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Asp Ser Glu Met Lys Leu
            580                 585                 590

Val Arg Tyr Asn Gln Ser Gly Ala Asp Phe Tyr Gly Ala Glu Gly Glu
        595                 600                 605

Ile Tyr Phe Lys Pro Thr Pro Arg Tyr Arg Ile Gly Val Ser Gly Asp
    610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Phe His Leu Lys Ala Ser Leu
            660                 665                 670

Thr Asp Arg Ile Asp Ala Asn Leu Asp Tyr Tyr Arg Val Phe Ala Gln
        675                 680                 685

Asn Lys Leu Ala Arg Tyr Glu Thr Arg Thr Pro Gly His His Met Leu
```

```
                690                 695                 700
Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
                740                 745                 750

Gly Val Asn Val Lys Phe
            755

<210> SEQ ID NO 2
<211> LENGTH: 695
<212> TYPE: PRT
<213> ORGANISM: Acidovorax sp JS42

<400> SEQUENCE: 2

Met Asn Ala Phe Thr Pro Phe Ala Arg Met Pro Gly Ala Met His Pro
1               5                   10                  15

Leu Ala Trp Ala Ala Leu Leu Cys Leu Thr Ser Ala Ala Pro Ala Trp
            20                  25                  30

Ala Gln Ala Asp Ala Arg Leu Pro Glu Val Thr Val Ser Ser Ser Gly
        35                  40                  45

Leu Gln Leu Gly Val Ser Glu Met Thr Gln Pro Val Ser Val Leu Glu
50                  55                  60

Gly Asp Ala Leu Val Arg Gln Arg Glu Ala Thr Leu Gly Glu Thr Leu
65                  70                  75                  80

Asp Gly Glu Pro Gly Ile Thr Gly Ser His Phe Gly Ala Gly Ala Ser
                85                  90                  95

Arg Pro Val Ile Arg Gly Met Asp Gly Pro Arg Val Arg Val Leu Ser
            100                 105                 110

Asp Gly Ser Glu Leu His Asp Ala Ser Thr Val Ser Pro Asp His Ala
        115                 120                 125

Val Ala Ala Glu Pro Leu Leu Ala Thr Gln Val Glu Val Leu Arg Gly
130                 135                 140

Pro Ser Ala Leu Val Tyr Gly Gly Ala Val Gly Gly Val Val Asn
145                 150                 155                 160

Val Leu Asp Gly Lys Val Pro Thr Ala Val Pro Asp Lys Gly Tyr Glu
                165                 170                 175

Gly Ser Ala Glu Leu Arg Ala Gly Ser Ala Ala Arg Glu Lys Ala Gly
            180                 185                 190

Ala Val Ala Leu Thr Gly Gly Ala Gly Asn Leu Ala Val His Val Glu
        195                 200                 205

Ala Ala Gly Arg Asp Ala Asp Tyr Arg Val Gly Ser Gly Trp Ala
210                 215                 220

Glu Gly Arg Arg Val Pro Gly Ser Phe Asn Arg Thr Gly Thr Gly Ser
225                 230                 235                 240

Val Gly Leu Ser Trp Val Gly Ser Arg Gly Tyr Leu Gly Leu Ala Phe
                245                 250                 255

Thr Arg Gln Asn Ala Lys Tyr Gly Leu Pro Gly His Ser His Ser Phe
            260                 265                 270

Glu Gly Cys His Thr His Gly Asn His Leu His Cys Gly Ser His Asp
        275                 280                 285

Glu His Asp His Asp Asp Gly His Asp His Asp His Gly
290                 295                 300
```

-continued

His Glu Ala Val Pro Val Asp Leu Arg Ser Glu Arg Val Asp Ile
305                 310                 315                 320

Arg Gly Glu Leu Arg Asp Pro Phe Thr Gly Phe Ser Ala Leu Arg Leu
            325                 330                 335

Arg Ala Gly Val Thr Asp Tyr Val His Asp Glu Val Glu Glu Gly Thr
        340                 345                 350

Val Ala Thr Thr Phe Lys Asn Lys Ala His Asp Leu Arg Val Glu Leu
        355                 360                 365

Gln His Glu Pro Val Ala Gly Trp Arg Gly Val Leu Gly Leu Gln Thr
    370                 375                 380

Gly Gln Arg Lys Phe Ser Ala Ala Gly Glu Glu Ala Tyr Val Gln Pro
385                 390                 395                 400

Thr Leu Thr Arg Gln Trp Gly Val Phe Leu Leu Glu Glu Tyr Arg Leu
            405                 410                 415

Gly Asp Trp His Gly Asp Trp Arg Ile Glu Thr Ala Leu Arg His Asp
        420                 425                 430

Arg Gln Ser Ala Glu Ala Gln Asp Ser Gly Val Glu Arg His His
    435                 440                 445

Gly Thr Ser Ala Ser Leu Gly Ala Val Trp Arg Phe Ala Pro Gly Tyr
450                 455                 460

Ala Ala Gly Ala Ser Ile Thr Arg Ala His Arg Ala Pro Thr Ala Glu
465                 470                 475                 480

Glu Leu Tyr Ala Arg Gly Leu His Met Ala Thr Ser Tyr Glu Arg
            485                 490                 495

Gly Asp Ala Ser Leu Arg Ala Glu Thr Ser Arg Asn Ile Asp Leu Ser
        500                 505                 510

Leu Arg Lys Thr Ser Gly Asp Thr Thr Phe Asp Val Ser Val Phe His
    515                 520                 525

Asn Arg Ile Arg Asn Tyr Ile Tyr Gly Arg Thr Leu Asp Glu Leu Asp
530                 535                 540

Gly Leu Gln Leu Leu Gln Tyr Ser Gln Ala Gly Ala Thr Phe Thr Gly
545                 550                 555                 560

Met Glu Gly Arg Val Arg Gln Arg Ile Thr Gln Arg Leu Gly Val Thr
            565                 570                 575

Leu Phe Gly Asp Ser Val Arg Ala Arg Leu Asp Gly Gly Glu Arg Leu
        580                 585                 590

Pro Arg Ile Ala Pro Ala Arg Val Gly Leu Arg Val Asp Ala Asn Trp
    595                 600                 605

Arg Asp Trp Gly Gly Ala Val Glu Trp Val Gln Val Ala Arg Gln Asn
610                 615                 620

Arg Val Ala Ala Phe Glu Thr Ala Thr Pro Gly Tyr Gly Met Leu Asn
625                 630                 635                 640

Leu Gly Leu Ala Tyr Asn Gly Arg Thr Gly Ser Gly Thr Pro Trp Gln
            645                 650                 655

Val Tyr Leu Lys Ala Arg Asn Leu Thr Asp Arg Leu Ala Tyr Ala His
        660                 665                 670

Thr Ser Phe Ile Lys Asp Ala Ala Pro Leu Ala Gly Arg Asn Val Thr
    675                 680                 685

Val Gly Val His Val Ser Phe
690                 695

<210> SEQ ID NO 3
<211> LENGTH: 803
<212> TYPE: PRT

<213> ORGANISM: Acinetobacter baumannii

<400> SEQUENCE: 3

```
Met Leu Asn Lys Ser Lys Leu Phe Leu Ala Leu Ile Thr Leu Gly Ala
1               5                   10                  15

Ser Lys Ile Val Leu Ala Ala Glu Gly Pro Val Thr Thr Leu Asn Thr
            20                  25                  30

Ile Val Leu Thr Ala Gln Ser Asp Glu Leu Gly Ser Glu Leu Leu Gly
        35                  40                  45

Lys Ser Leu Asn Val Ser Asn Gln Phe Ile Asp Thr Ser Lys Leu Lys
    50                  55                  60

Gln Arg Ser Thr Thr Leu Gly Asp Ala Leu Gly Thr Glu Leu Gly Ile
65                  70                  75                  80

His Ser Asn Gln Tyr Gly Gly Gly Ala Ser Thr Pro Ile Ile Arg Gly
                85                  90                  95

Gln Glu Gly Lys Arg Ile Lys Val Leu Gln Asn Asn Ala Asp Val Leu
            100                 105                 110

Asp Met Ser Asn Met Ser Pro Asp His Ala Val Thr Val Glu Pro Ser
        115                 120                 125

Leu Ala Lys Ser Ile Glu Ile Ile Arg Gly Ala Ser Thr Leu Leu Tyr
    130                 135                 140

Ser Ser Asn Ser Ala Ala Gly Val Val Asn Val Ile Asp Tyr Lys Ile
145                 150                 155                 160

Pro Thr Gln Met Pro Gln Asp Gly Leu Glu Gly Asn Thr Thr Leu Arg
                165                 170                 175

Phe Asn Thr Gly Ser Asn Glu Lys Leu Thr Thr Ala Gly Val Thr Val
            180                 185                 190

Gly Leu Ser Pro His Val Ala Leu Arg Ala Glu Gly Leu Tyr Arg Asn
        195                 200                 205

Ala Gly Asn Tyr Lys Thr Pro His Tyr Gln Ser Ser Ser Tyr Asn Ser
    210                 215                 220

Leu Glu Asp Leu Glu Asn Gln Asn Ser Ile Tyr Lys Asn Leu Lys Tyr
225                 230                 235                 240

Leu Pro Glu Ser Trp Ala Glu Ser Arg Val Gly Thr Leu Gly Leu Ser
                245                 250                 255

Trp Ile Asp Asp Asn Thr Tyr Leu Gly Val Ser Tyr Thr His Arg His
            260                 265                 270

Asp Glu Tyr Gly Leu Pro Ala His Ser His Leu Tyr Glu Gly Cys Gly
        275                 280                 285

Ala Ser Ala Ile Gly Ile Asp Ser Arg Ile Ser Gly Leu Lys Asn Tyr
    290                 295                 300

Leu Leu Tyr Tyr Pro Gln Leu Met Asp Glu Gln Asp Ile Asn Tyr Ile
305                 310                 315                 320

Asn Pro Arg Pro Asp Cys His Gln His Asn His Ile His Glu Thr Asn
                325                 330                 335

Phe Ser His Asn Ala Pro Tyr Ile Asp Leu Asn Thr Arg Arg Tyr Asp
            340                 345                 350

Val Arg Gly Glu Phe Thr Gln Pro Phe Thr Gly Ile Asp Lys Ile Arg
        355                 360                 365

Thr Ser Leu Ser Tyr Ile Asp Tyr Phe His Asn Glu Leu Glu Gly Asp
    370                 375                 380

Lys Ile Thr Asn Phe Phe Lys Asn Thr Gly Lys Val Gly Arg Ile Glu
385                 390                 395                 400
```

Leu Ser His Gln Pro Leu Gly Glu Leu Thr Gly Ile Leu Gly Leu Gln
                405                 410                 415

Tyr Leu Glu Gln Asp Asn Ser Ala Leu Ser Pro Val His Ser Gln Glu
            420                 425                 430

Gly His Thr Thr Tyr Leu Asp Asn Gln Gln Leu Leu Asn Arg Asn Val
        435                 440                 445

Thr Lys Asn Phe Ser Val Phe Gly Leu Glu Lys Tyr Asn Trp Asn Asp
450                 455                 460

Phe Thr Phe Glu Leu Gly Ala Arg Ile Glu Lys Gln Lys Val Ser Met
465                 470                 475                 480

Asp Tyr Asp Ile Glu Lys Ile Lys Asp Ser Met Lys Pro Trp Pro Asn
                485                 490                 495

Lys Tyr Asn Ser Pro Tyr Val Glu Lys Asn Asn Lys Ile Arg Ala Gln
            500                 505                 510

Asn Leu Lys Ser Ile Leu Glu Ala Val Gln Pro Asn Lys Glu Thr Ala
        515                 520                 525

Phe Ser Tyr Ala Gly Thr Val His Trp Arg Phe Ala Pro Asn Tyr Ile
    530                 535                 540

Leu Ser Leu Thr Gly Thr His Gln Glu Arg Leu Pro Asn Ala Gln Glu
545                 550                 555                 560

Met Tyr Thr His Gly Met His Leu Ala Thr Asn Ser Phe Glu Ile Gly
                565                 570                 575

Asn Arg Phe Leu Arg Lys Glu Lys Ser Asn Asn Leu Glu Ile Ser Leu
            580                 585                 590

Ala Tyr Lys Asp Asp Leu Leu Asp Tyr Gln Ile Ser Thr Tyr Tyr Tyr
        595                 600                 605

Asp Phe Asp Asn Tyr Ile Tyr Leu Gln Thr Leu Asn Glu Val Leu Gly
    610                 615                 620

Thr Thr Lys Val Arg Asp Gln His Thr Leu Arg Ile Asn His Tyr Ser
625                 630                 635                 640

Gln Ser Ala Ala Asn Phe Tyr Gly Leu Glu Gly Asn Ile Gly Tyr Gln
                645                 650                 655

Phe Asn Ser Val Tyr His Gly Ser Leu Phe Gly Asp Tyr Val Lys Gly
            660                 665                 670

Arg Leu Thr Asn Leu Pro Asp Ala Val Ile Ala Tyr Asp Ile Trp Asn
        675                 680                 685

Arg Glu Pro Thr Leu Ala Pro Gln Lys Asp Arg Tyr Thr Pro Arg Leu
    690                 695                 700

Pro Pro Ala Arg Leu Gly Thr Arg Leu Lys Ala Asp Phe Asp Glu Ser
705                 710                 715                 720

Leu Lys Gly Glu Ile Glu Tyr Arg Val Phe Lys Gln Asp Asn Ile
                725                 730                 735

Ser Lys Phe Glu Gln Val Thr Ser Gly Tyr Asn Met Leu Asn Met Thr
            740                 745                 750

Leu Ala Tyr Lys Asn Lys Leu Ser His Thr Glu Tyr Asp Leu Phe Phe
        755                 760                 765

Lys Ala Asn Asn Leu Leu Asp Gln Lys Val Tyr Ala His Glu Thr Phe
    770                 775                 780

Leu Pro Tyr Ile Pro Gln Ile Gly Arg Asn Phe Ser Leu Gly Leu Asn
785                 790                 795                 800

Leu Asn Phe

<210> SEQ ID NO 4

```
<211> LENGTH: 803
<212> TYPE: PRT
<213> ORGANISM: Acinetobacter baumannii

<400> SEQUENCE: 4
```

| | | | | | | | | | | | | | | |
|---|---|---|---|---|---|---|---|---|---|---|---|---|---|---|
| Met | Leu | Asn | Lys | Ser | Lys | Leu | Phe | Leu | Ala | Leu | Ile | Thr | Leu | Gly | Ala |
| 1 | | | | 5 | | | | | 10 | | | | | 15 | |

| Ser | Lys | Ile | Leu | Leu | Ala | Ala | Glu | Gly | Pro | Val | Thr | Ile | Leu | Asn | Thr |
|---|---|---|---|---|---|---|---|---|---|---|---|---|---|---|---|
| | | | 20 | | | | | 25 | | | | | 30 | | |

| Lys | Val | Leu | Thr | Ala | Gln | Ser | Asp | Glu | Leu | Gly | Ser | Glu | Leu | Leu | Gly |
|---|---|---|---|---|---|---|---|---|---|---|---|---|---|---|---|
| | | | 35 | | | | | 40 | | | | | 45 | | |

| Lys | Ser | Leu | Asn | Val | Ser | Asn | Gln | Phe | Ile | Asp | Thr | Ser | Lys | Leu | Lys |
|---|---|---|---|---|---|---|---|---|---|---|---|---|---|---|---|
| | 50 | | | | | 55 | | | | | 60 | | | | |

| Gln | Arg | Ser | Thr | Thr | Leu | Gly | Asp | Ala | Leu | Gly | Thr | Glu | Leu | Gly | Ile |
|---|---|---|---|---|---|---|---|---|---|---|---|---|---|---|---|
| 65 | | | | | 70 | | | | | 75 | | | | | 80 |

| His | Ser | Asn | Gln | Tyr | Gly | Gly | Ala | Ser | Thr | Pro | Ile | Ile | Arg | Gly |
|---|---|---|---|---|---|---|---|---|---|---|---|---|---|---|
| | | | | 85 | | | | | 90 | | | | | 95 |

| Gln | Glu | Gly | Lys | Arg | Ile | Lys | Val | Leu | Gln | Asn | Asn | Ala | Asp | Val | Leu |
|---|---|---|---|---|---|---|---|---|---|---|---|---|---|---|---|
| | | | 100 | | | | | 105 | | | | | 110 | | |

| Asp | Met | Ser | Asn | Met | Ser | Pro | Asp | His | Ala | Val | Thr | Val | Glu | Pro | Ser |
|---|---|---|---|---|---|---|---|---|---|---|---|---|---|---|---|
| | | 115 | | | | | 120 | | | | | 125 | | | |

| Leu | Ala | Lys | Ser | Ile | Glu | Ile | Ile | Arg | Gly | Ala | Ser | Thr | Leu | Leu | Tyr |
|---|---|---|---|---|---|---|---|---|---|---|---|---|---|---|---|
| | 130 | | | | | 135 | | | | | 140 | | | | |

| Ser | Ser | Asn | Ser | Ala | Ala | Gly | Val | Val | Asn | Val | Ile | Asp | Tyr | Lys | Ile |
|---|---|---|---|---|---|---|---|---|---|---|---|---|---|---|---|
| 145 | | | | | 150 | | | | | 155 | | | | | 160 |

| Pro | Thr | Gln | Met | Pro | Gln | Asp | Gly | Leu | Glu | Gly | Asn | Thr | Thr | Leu | Arg |
|---|---|---|---|---|---|---|---|---|---|---|---|---|---|---|---|
| | | | | 165 | | | | | 170 | | | | | 175 | |

| Phe | Asn | Thr | Gly | Ser | Asn | Glu | Lys | Leu | Thr | Thr | Ala | Gly | Val | Thr | Val |
|---|---|---|---|---|---|---|---|---|---|---|---|---|---|---|---|
| | | | 180 | | | | | 185 | | | | | 190 | | |

| Gly | Leu | Ser | Pro | His | Val | Ala | Leu | Arg | Ala | Glu | Gly | Leu | Tyr | Arg | Asn |
|---|---|---|---|---|---|---|---|---|---|---|---|---|---|---|---|
| | | | 195 | | | | | 200 | | | | | 205 | | |

| Ala | Gly | Asn | Tyr | Lys | Thr | Pro | His | Tyr | Gln | Ser | Ser | Tyr | Asn | Ser |
|---|---|---|---|---|---|---|---|---|---|---|---|---|---|---|
| | 210 | | | | | 215 | | | | | 220 | | | |

| Leu | Glu | Asp | Leu | Glu | Asn | Gln | Asn | Ser | Ile | Tyr | Lys | Asn | Leu | Lys | Tyr |
|---|---|---|---|---|---|---|---|---|---|---|---|---|---|---|---|
| 225 | | | | | 230 | | | | | 235 | | | | | 240 |

| Leu | Pro | Glu | Ser | Trp | Ala | Glu | Ser | Arg | Val | Gly | Thr | Leu | Gly | Leu | Ser |
|---|---|---|---|---|---|---|---|---|---|---|---|---|---|---|---|
| | | | | 245 | | | | | 250 | | | | | 255 | |

| Trp | Ile | Asp | Asp | Asn | Thr | Tyr | Leu | Gly | Val | Ser | Tyr | Thr | His | Arg | His |
|---|---|---|---|---|---|---|---|---|---|---|---|---|---|---|---|
| | | | 260 | | | | | 265 | | | | | 270 | | |

| Asp | Glu | Tyr | Gly | Leu | Pro | Ala | His | Ser | His | Leu | Tyr | Glu | Gly | Cys | Gly |
|---|---|---|---|---|---|---|---|---|---|---|---|---|---|---|---|
| | | 275 | | | | | 280 | | | | | 285 | | | |

| Ala | Ser | Ala | Ile | Gly | Ile | Asp | Ser | Arg | Ile | Ser | Gly | Leu | Lys | Asn | Tyr |
|---|---|---|---|---|---|---|---|---|---|---|---|---|---|---|---|
| | 290 | | | | | 295 | | | | | 300 | | | | |

| Leu | Leu | Tyr | Tyr | Pro | Gln | Leu | Met | Asp | Glu | Gln | Asp | Ile | Asn | Tyr | Ile |
|---|---|---|---|---|---|---|---|---|---|---|---|---|---|---|---|
| 305 | | | | | 310 | | | | | 315 | | | | | 320 |

| Asn | Pro | Arg | Pro | Asp | Cys | His | Gln | His | Asn | His | Ile | His | Glu | Thr | Asn |
|---|---|---|---|---|---|---|---|---|---|---|---|---|---|---|---|
| | | | | 325 | | | | | 330 | | | | | 335 | |

| Phe | Ser | His | Asn | Ala | Pro | Tyr | Ile | Asp | Leu | Asn | Thr | Arg | Arg | Tyr | Asp |
|---|---|---|---|---|---|---|---|---|---|---|---|---|---|---|---|
| | | | 340 | | | | | 345 | | | | | 350 | | |

| Val | Arg | Gly | Glu | Phe | Thr | Gln | Pro | Phe | Thr | Gly | Ile | Asp | Lys | Ile | Arg |
|---|---|---|---|---|---|---|---|---|---|---|---|---|---|---|---|
| | | | 355 | | | | | 360 | | | | | 365 | | |

| Thr | Ser | Leu | Ser | Tyr | Ile | Asp | Tyr | Phe | His | Asn | Glu | Leu | Glu | Gly | Asp |
|---|---|---|---|---|---|---|---|---|---|---|---|---|---|---|---|
| | 370 | | | | | 375 | | | | | 380 | | | | |

| Lys | Ile | Thr | Asn | Phe | Phe | Lys | Asn | Thr | Gly | Lys | Val | Gly | Arg | Ile | Glu |
|---|---|---|---|---|---|---|---|---|---|---|---|---|---|---|---|

```
            385                 390                 395                 400
Leu Ser His Gln Pro Leu Gly Glu Leu Thr Gly Ile Leu Gly Leu Gln
                405                 410                 415
Tyr Leu Glu Gln Asp Asn Ser Ala Leu Ser Pro Val His Ser Gln Glu
                420                 425                 430
Gly His Thr Thr Tyr Leu Asp Asn Gln Gln Leu Leu Asn Arg Asn Val
                435                 440                 445
Thr Lys Asn Phe Ser Val Phe Gly Leu Glu Lys Tyr Asn Trp Asn Asp
            450                 455                 460
Phe Thr Phe Glu Leu Gly Ala Arg Ile Glu Lys Gln Lys Val Ser Met
465                 470                 475                 480
Asp Tyr Asp Ile Glu Lys Ile Lys Asp Ser Met Lys Pro Trp Pro Asn
                485                 490                 495
Lys Tyr Asn Ser Pro Tyr Val Glu Lys Asn Asn Lys Ile Arg Ala Gln
                500                 505                 510
Asn Leu Lys Ser Ile Leu Glu Ala Val Gln Pro Asn Lys Glu Thr Ala
                515                 520                 525
Phe Ser Tyr Ala Gly Thr Val His Trp Arg Phe Ala Pro Asn Tyr Ile
            530                 535                 540
Leu Ser Leu Thr Gly Thr His Gln Glu Arg Leu Pro Asn Ala Gln Glu
545                 550                 555                 560
Met Tyr Thr His Gly Met His Leu Ala Thr Asn Ser Phe Glu Ile Gly
                565                 570                 575
Asn Arg Phe Leu Arg Lys Glu Lys Ser Asn Asn Leu Glu Ile Ser Leu
                580                 585                 590
Ala Tyr Lys Asp Asp Leu Leu Asp Tyr Gln Ile Ser Thr Tyr Tyr Tyr
                595                 600                 605
Asp Phe Asp Asn Tyr Ile Tyr Leu Gln Thr Leu Asn Glu Val Leu Gly
            610                 615                 620
Thr Thr Lys Val Arg Asp Gln His Thr Leu Arg Ile Asn His Tyr Ser
625                 630                 635                 640
Gln Ser Ala Ala Asn Phe Tyr Gly Leu Glu Gly Asn Ile Gly Tyr Gln
                645                 650                 655
Phe Asn Ser Val Tyr His Gly Ser Leu Phe Gly Asp Tyr Val Lys Gly
                660                 665                 670
Arg Leu Thr Asn Leu Pro Asp Ala Val Ile Ala Tyr Asp Ile Trp Asn
                675                 680                 685
Arg Glu Pro Thr Leu Ala Pro Gln Lys Asp Arg Tyr Thr Pro Arg Leu
            690                 695                 700
Pro Pro Ala Arg Leu Gly Thr Arg Leu Lys Ala Asp Phe Asp Glu Ser
705                 710                 715                 720
Leu Lys Gly Glu Ile Glu Tyr Tyr Arg Val Phe Lys Gln Asp Asn Ile
                725                 730                 735
Ser Lys Phe Glu Gln Val Thr Ser Gly Tyr Asn Met Leu Asn Met Thr
                740                 745                 750
Leu Ala Tyr Lys Asn Lys Leu Ser His Thr Glu Tyr Asp Leu Phe Phe
            755                 760                 765
Lys Ala Asn Asn Leu Leu Asp Gln Lys Val Tyr Ala His Glu Thr Phe
            770                 775                 780
Leu Pro Tyr Ile Pro Gln Ile Gly Arg Asn Phe Ser Leu Gly Leu Asn
785                 790                 795                 800
Leu Asn Phe
```

<210> SEQ ID NO 5
<211> LENGTH: 803
<212> TYPE: PRT
<213> ORGANISM: Acinetobacter baumannii

<400> SEQUENCE: 5

```
Met Leu Asn Lys Ser Lys Leu Phe Leu Ala Leu Ile Thr Leu Gly Ala
1               5                   10                  15

Ser Lys Ile Leu Leu Ala Ala Glu Gly Pro Val Thr Thr Leu Asn Thr
            20                  25                  30

Ile Val Leu Thr Ala Gln Ser Asp Glu Leu Gly Ser Glu Leu Leu Gly
        35                  40                  45

Lys Ser Leu Asn Val Ser Asn Gln Phe Ile Asp Thr Ser Lys Leu Lys
    50                  55                  60

Gln Arg Ser Thr Thr Leu Gly Asp Ala Leu Gly Thr Glu Leu Gly Ile
65                  70                  75                  80

His Ser Asn Gln Tyr Gly Gly Gly Ala Ser Thr Pro Ile Ile Arg Gly
                85                  90                  95

Gln Glu Gly Lys Arg Ile Lys Val Leu Gln Asn Asn Ala Asp Val Leu
            100                 105                 110

Asp Met Ser Asn Met Ser Pro Asp His Ala Val Thr Val Glu Pro Ser
        115                 120                 125

Leu Ala Lys Ser Ile Glu Ile Ile Arg Gly Ala Ser Thr Leu Leu Tyr
    130                 135                 140

Ser Ser Asn Ser Ala Ala Gly Val Val Asn Val Ile Asp Tyr Lys Ile
145                 150                 155                 160

Pro Thr Gln Met Pro Gln Asp Gly Leu Glu Gly Asn Thr Thr Leu Arg
                165                 170                 175

Phe Asn Thr Gly Ser Asn Glu Lys Leu Thr Thr Ala Gly Val Thr Val
            180                 185                 190

Gly Leu Ser Pro His Val Ala Leu Arg Ala Glu Gly Leu Tyr Arg Asn
        195                 200                 205

Ala Gly Asn Tyr Lys Thr Pro His Tyr Gln Ser Ser Ser Tyr Asn Ser
    210                 215                 220

Leu Glu Asp Leu Glu Asn Gln Asn Ser Ile Tyr Lys Asn Leu Lys Tyr
225                 230                 235                 240

Leu Pro Glu Ser Trp Ala Glu Ser Arg Val Gly Thr Leu Gly Leu Ser
                245                 250                 255

Trp Ile Asp Asp Asn Thr Tyr Leu Gly Val Ser Tyr Thr His Arg His
            260                 265                 270

Asp Glu Tyr Gly Leu Pro Ala His Ser His Leu Tyr Glu Gly Cys Gly
        275                 280                 285

Ala Ser Ala Ile Gly Ile Asp Ser Arg Ile Ser Gly Leu Lys Asn Tyr
    290                 295                 300

Leu Leu Tyr Tyr Pro Gln Leu Met Asp Glu Gln Asp Ile Asn Tyr Ile
305                 310                 315                 320

Asn Pro Arg Pro Asp Cys His Gln His Asn His Ile His Glu Thr Asn
                325                 330                 335

Phe Ser His Asn Ala Pro Tyr Ile Asp Leu Asn Thr Arg Arg Tyr Asp
            340                 345                 350

Val Arg Gly Glu Phe Thr Gln Pro Phe Thr Gly Ile Asp Lys Ile Arg
        355                 360                 365

Thr Ser Leu Ser Tyr Ile Asp Tyr Phe His Asn Glu Leu Glu Gly Asp
    370                 375                 380
```

-continued

```
Lys Ile Thr Asn Phe Phe Lys Asn Thr Gly Lys Val Gly Arg Ile Glu
385                 390                 395                 400

Leu Ser His Gln Pro Leu Gly Glu Leu Thr Gly Ile Leu Gly Leu Gln
            405                 410                 415

Tyr Leu Glu Gln Asp Asn Ser Ala Leu Ser Pro Val His Ser Gln Glu
        420                 425                 430

Gly His Thr Thr Tyr Leu Asp Asn Gln Gln Leu Leu Asn Arg Asn Val
            435                 440                 445

Thr Lys Asn Phe Ser Val Phe Gly Leu Glu Lys Tyr Asn Trp Asn Asp
450                 455                 460

Phe Thr Phe Glu Leu Gly Ala Arg Ile Glu Lys Gln Lys Val Ser Met
465                 470                 475                 480

Asp Tyr Asp Ile Glu Lys Ile Lys Asp Ser Met Lys Pro Trp Pro Asn
                485                 490                 495

Lys Tyr Asn Ser Pro Tyr Val Glu Lys Asn Asn Lys Ile Arg Ala Gln
            500                 505                 510

Asn Leu Lys Ser Ile Leu Glu Ala Val Gln Pro Asn Lys Glu Thr Ala
        515                 520                 525

Phe Ser Tyr Ala Gly Thr Val His Trp Arg Phe Ala Pro Asn Tyr Ile
530                 535                 540

Leu Ser Leu Thr Gly Thr His Gln Glu Arg Leu Pro Asn Ala Gln Glu
545                 550                 555                 560

Met Tyr Thr His Gly Met His Leu Ala Thr Asn Ser Phe Glu Ile Gly
                565                 570                 575

Asn Arg Phe Leu Arg Lys Glu Lys Ser Asn Asn Leu Glu Ile Ser Leu
            580                 585                 590

Ala Tyr Lys Asp Asp Leu Leu Asp Tyr Gln Ile Ser Thr Tyr Tyr Tyr
        595                 600                 605

Asp Phe Asp Asn Tyr Ile Tyr Leu Gln Thr Leu Asn Glu Val Leu Gly
    610                 615                 620

Thr Thr Lys Val Arg Asp Gln His Thr Leu Arg Ile Asn His Tyr Ser
625                 630                 635                 640

Gln Ser Ala Ala Asn Phe Tyr Gly Leu Glu Gly Asn Ile Gly Tyr Gln
                645                 650                 655

Phe Asn Ser Val Tyr His Gly Ser Leu Phe Gly Asp Tyr Val Lys Gly
            660                 665                 670

Arg Leu Thr Asn Leu Pro Asp Ala Val Ile Ala Tyr Asp Ile Trp Asn
        675                 680                 685

Arg Glu Pro Thr Leu Ala Pro Gln Lys Asp Arg Tyr Thr Pro Arg Leu
    690                 695                 700

Pro Pro Ala Arg Leu Gly Thr Arg Leu Lys Ala Asp Phe Asp Glu Ser
705                 710                 715                 720

Leu Lys Gly Glu Ile Glu Tyr Tyr Arg Val Phe Lys Gln Asp Asn Ile
                725                 730                 735

Ser Lys Phe Glu Gln Val Thr Ser Gly Tyr Asn Met Leu Asn Met Thr
            740                 745                 750

Leu Ala Tyr Lys Asn Lys Leu Ser His Thr Glu Tyr Asp Leu Phe Phe
        755                 760                 765

Lys Ala Asn Asn Leu Leu Asp Gln Lys Val Tyr Ala His Glu Thr Phe
    770                 775                 780

Leu Pro Tyr Ile Pro Gln Ile Gly Arg Asn Phe Ser Leu Gly Leu Asn
785                 790                 795                 800
```

Leu Asn Phe

<210> SEQ ID NO 6
<211> LENGTH: 685
<212> TYPE: PRT
<213> ORGANISM: Acinetobacter baumannii AB900

<400> SEQUENCE: 6

Met Leu Phe Tyr Lys Asn Ile Leu Thr Leu Ser Ile Leu Ala Ala Ile
1               5                   10                  15

Ser Ile Pro Val Phe Ala Ala Glu Asn Glu Asn Val Glu Lys Leu Glu
            20                  25                  30

Thr Ile Arg Ile Lys Ala His Pro Leu Glu Gln Thr Ser Lys Asp Phe
        35                  40                  45

Ala Val Ala Asp Thr Val Val Asp Gln Lys His Leu Thr Glu Gly Ala
    50                  55                  60

Ala Thr Ile Gly Asp Ala Leu Asn Ser Glu Val Gly Ile Tyr Ala Asn
65                  70                  75                  80

Gln Phe Gly Ala Gly Ser Ser Arg Pro Val Ile Arg Gly Gln Asp Gly
                85                  90                  95

Pro Arg Val Lys Val Leu Gln Asn Ser Ser Glu Asn Val Asp Val Ser
            100                 105                 110

Thr Leu Ser Pro Asp His Ala Val Thr Val Asp Pro Val Leu Ala Lys
        115                 120                 125

Gln Val Glu Val Ile Arg Gly Pro Ser Thr Leu Leu Phe Gly Ala Gly
    130                 135                 140

Thr Ile Gly Gly Leu Val Asn Val Ile Asp Asn Lys Ile Pro Thr Gln
145                 150                 155                 160

Met Pro Glu Asn Gly Tyr Glu Gly Gln Val Gly Leu Arg Tyr Asn Thr
                165                 170                 175

Gly Ser Asp Glu Lys Leu Ala Ser Ala Gly Val Thr Val Gly Leu Gly
            180                 185                 190

Ser Gln Val Ala Leu Arg Val Glu Gly Leu Thr Arg Asp Ala Asn Asn
        195                 200                 205

Tyr Ile Ala Pro Asn Tyr Ile His Glu Gly Lys Glu Arg Arg Val
    210                 215                 220

Asp Asn Thr Phe Ala Gln Gly Asp Ser Val Asn Val Gly Leu Ser Trp
225                 230                 235                 240

Ile Tyr Asp Arg Gly Tyr Thr Gly Ile Ser Tyr Ser Asn Arg Asp
                245                 250                 255

Gln Tyr Gly Leu Pro Gly His Ser His Glu Tyr Glu Thr Cys His Ile
            260                 265                 270

His Asp Leu Ser Leu His Cys Gly Asp His Asp His Glu Gly His Ser
        275                 280                 285

Asp Glu Glu Ala His Asp His Glu His Gly Gly Pro Trp Ile
    290                 295                 300

Asp Leu Lys Ser Glu Arg Tyr Asp Phe Lys Thr Glu Leu Asn Asp Pro
305                 310                 315                 320

Phe Ala Gly Phe Gln Lys Leu Arg Ala Gln Ala Ser Tyr Thr Asp Tyr
                325                 330                 335

Gln His Asp Glu Ile Glu Gly Ala Ile Ala Thr Arg Phe Gln Asn
            340                 345                 350

Lys Gly Tyr Asp Gly Arg Ile Glu Leu Val His Thr Pro Ile Ala Asp
        355                 360                 365

```
Trp Glu Gly Val Ile Gly Thr Gln Leu Gly Gln Gln Lys Leu Asn Leu
370                 375                 380

Thr Gly Glu Glu Ala Phe Met Ala Pro Thr Thr Thr Lys Lys Trp Ser
385                 390                 395                 400

Val Phe Ala Leu Glu His Lys Gln Trp Lys Asp Val His Phe Glu Leu
                405                 410                 415

Ser Ala Arg Ala Asp Gln Gln Glu Ile Asp Val Asp Asn Ser Lys
            420                 425                 430

Gln Asp Phe Asp Gly Ser Ala Phe Ser Tyr Ala Gly Ala Ala Asn Trp
            435                 440                 445

Glu Phe Ala Pro Asn Tyr Lys Leu Ser Phe Val Ala Ser His Gln Glu
450                 455                 460

Arg Leu Pro Leu Ala Gln Glu Leu Tyr Ala Asn Gly Ala His Phe Ala
465                 470                 475                 480

Thr Asn Thr Tyr Glu Leu Gly Asn Asp Gln Leu Ser Lys Glu Lys Ser
                485                 490                 495

Asn Asn Val Glu Leu Gly Leu His Phe Asp Asn Asp Lys Leu Asp Tyr
            500                 505                 510

His Leu His Val Tyr His Asn Trp Phe Asp Asp Tyr Ile Tyr Ala Gln
            515                 520                 525

Thr Leu Asp Arg Tyr Lys Asp Phe Arg Leu Val Gln Tyr Thr Gln Asp
530                 535                 540

Lys Ala Arg Phe Tyr Gly Ala Glu Gly Glu Ile Gly Tyr Gln Ile Thr
545                 550                 555                 560

Pro Met Tyr Lys Ile Ser Ala Phe Gly Asp Tyr Val Arg Gly Lys Ile
                565                 570                 575

Asp Ala Glu Gly Asn Ala Pro Arg Ile Pro Ala Gly Arg Leu Gly Thr
            580                 585                 590

Lys Val Asp Ala Asp Phe Gly Asp Gly Phe Ser Gly Ser Ala Glu Tyr
            595                 600                 605

Tyr His Val Phe Asn Gln Asp Lys Ile Ala Ala Tyr Glu Thr Glu Thr
610                 615                 620

Glu Gly Tyr Asn Met Leu Asn Leu Gly Val Ala Tyr Ser Gly Gln Tyr
625                 630                 635                 640

Gly Ala Lys Thr Asp Tyr Arg Val Tyr Leu Lys Ala Asn Asn Leu Leu
                645                 650                 655

Asp Asp Thr Val Tyr Gln His Ala Ser Phe Leu Ser Asn Ile Pro Gln
            660                 665                 670

Val Gly Arg Asn Phe Thr Val Gly Val Asp Phe Ser Phe
            675                 680                 685

<210> SEQ ID NO 7
<211> LENGTH: 685
<212> TYPE: PRT
<213> ORGANISM: Acinetobacter baumannii ACICU

<400> SEQUENCE: 7

Met Leu Phe Tyr Lys Asn Ile Leu Thr Leu Ser Ile Leu Ala Ala Ile
1               5                   10                  15

Ser Ile Pro Val Phe Ala Ala Glu Asn Glu Asn Val Glu Lys Leu Glu
                20                  25                  30

Thr Ile Arg Ile Lys Ala His Pro Leu Glu Gln Thr Ser Lys Asp Phe
            35                  40                  45

Ala Val Ala Asp Thr Val Val Asp Gln Lys His Leu Thr Glu Gly Ala
50                  55                  60
```

```
Ala Thr Ile Gly Asp Ala Leu Asn Ser Glu Val Gly Ile Tyr Ala Asn
 65                  70                  75                  80

Gln Phe Gly Ala Gly Ser Ser Arg Pro Val Ile Arg Gly Gln Asp Gly
                 85                  90                  95

Pro Arg Val Lys Val Leu Gln Asn Ser Ser Glu Asn Val Asp Val Ser
            100                 105                 110

Thr Leu Ser Pro Asp His Ala Val Thr Val Asp Pro Val Leu Ala Lys
        115                 120                 125

Gln Val Glu Val Ile Arg Gly Pro Ser Thr Leu Leu Phe Gly Ala Gly
    130                 135                 140

Thr Val Gly Gly Leu Val Asn Val Ile Asp Asn Lys Ile Pro Thr Gln
145                 150                 155                 160

Met Pro Glu Asn Gly Tyr Glu Gly Gln Val Gly Leu Arg Tyr Asn Thr
                165                 170                 175

Gly Ser Asp Glu Lys Leu Ala Ser Ala Gly Val Thr Val Gly Leu Gly
            180                 185                 190

Ser Gln Val Ala Leu Arg Val Glu Gly Leu Thr Arg Asp Ala Asn Asn
        195                 200                 205

Tyr Ile Ala Pro Asn Tyr Ile His Glu Gly Lys Glu Arg Arg Val
    210                 215                 220

Asp Asn Thr Phe Ala Gln Gly Asp Ser Val Asn Val Gly Leu Ser Trp
225                 230                 235                 240

Ile Tyr Asp Arg Gly Tyr Thr Gly Ile Ser Tyr Ser Asn Arg Arg Asp
                245                 250                 255

Gln Tyr Gly Leu Pro Gly His Ser His Glu Tyr Glu Thr Cys His Ile
            260                 265                 270

His Asp Leu Ser Leu His Cys Gly Asp His Asp His Glu Gly His Ser
        275                 280                 285

Asp Glu Glu Ala His Asp His Glu His Glu His Gly Gly Pro Trp Ile
    290                 295                 300

Asp Leu Lys Ser Glu Arg Tyr Asp Phe Lys Thr Glu Leu Asn Asp Pro
305                 310                 315                 320

Phe Ala Gly Phe Gln Lys Leu Arg Ala Gln Ala Ser Tyr Thr Asp Tyr
                325                 330                 335

Gln His Asp Glu Ile Glu Glu Gly Thr Ile Ala Thr Arg Phe Gln Asn
            340                 345                 350

Lys Gly Tyr Asp Gly Arg Ile Glu Leu Val His Asn Pro Ile Ala Asp
        355                 360                 365

Trp Glu Gly Val Ile Gly Thr Gln Leu Gly Gln Gln Lys Leu Asn Leu
    370                 375                 380

Thr Gly Glu Glu Ala Phe Met Ala Pro Thr Thr Lys Lys Trp Ser
385                 390                 395                 400

Val Phe Ala Leu Glu His Lys Gln Trp Lys Asp Val His Phe Glu Leu
                405                 410                 415

Ser Ala Arg Ala Asp Gln Gln Glu Ile Asp Val Asp Asn Ser Lys
            420                 425                 430

Gln Asp Phe Asp Gly Ser Ala Phe Ser Tyr Ala Gly Ala Asn Trp
        435                 440                 445

Glu Phe Ala Pro Asn Tyr Lys Leu Ser Phe Val Ala Ser His Gln Glu
    450                 455                 460

Arg Leu Pro Leu Ala Gln Glu Leu Tyr Ala Asn Gly Ala His Phe Ala
465                 470                 475                 480
```

-continued

```
Thr Asn Thr Tyr Glu Leu Gly Asn Asp Gln Leu Gly Lys Glu Lys Ser
            485                 490                 495

Asn Asn Val Glu Leu Gly Leu His Phe Asp His Asp Lys Leu Asp Tyr
            500                 505                 510

His Leu His Val Tyr His Asn Trp Phe Asp Asp Tyr Ile Tyr Ala Gln
            515                 520                 525

Thr Leu Asp Arg Tyr Lys Asp Phe Arg Leu Val Gln Tyr Thr Gln Asp
            530                 535                 540

Lys Ala Arg Phe Tyr Gly Ala Glu Gly Glu Ile Gly Tyr Gln Ile Thr
545                 550                 555                 560

Pro Ile Tyr Lys Ile Ser Ala Phe Gly Asp Tyr Val Arg Gly Lys Ile
                565                 570                 575

Asp Ala Glu Gly Asn Ala Pro Arg Ile Pro Ala Gly Arg Leu Gly Thr
            580                 585                 590

Lys Val Asp Ala Asp Phe Gly Asp Gly Phe Ser Gly Ser Ala Glu Tyr
            595                 600                 605

Tyr His Val Phe Asn Gln Asp Lys Ile Ala Ala Tyr Glu Thr Glu Thr
            610                 615                 620

Glu Gly Tyr Asn Met Leu Asn Leu Gly Val Ala Tyr Ser Gly Gln Tyr
625                 630                 635                 640

Gly Ala Lys Thr Asp Tyr Arg Val Tyr Leu Lys Ala Asn Asn Leu Leu
                645                 650                 655

Asp Asp Thr Val Tyr Gln His Ala Ser Phe Leu Ser Asn Ile Pro Gln
            660                 665                 670

Val Gly Arg Asn Phe Thr Val Gly Val Asp Phe Ser Phe
            675                 680                 685

<210> SEQ ID NO 8
<211> LENGTH: 803
<212> TYPE: PRT
<213> ORGANISM: Acinetobacter baumannii ATCC 17978

<400> SEQUENCE: 8

Met Leu Asn Lys Ser Lys Leu Phe Leu Ala Leu Ile Thr Leu Gly Ala
1               5                   10                  15

Ser Lys Ile Leu Leu Ala Ala Glu Gly Pro Val Thr Thr Leu Asn Thr
            20                  25                  30

Ile Val Leu Thr Ala Gln Ser Asp Glu Leu Gly Ser Glu Leu Leu Gly
            35                  40                  45

Lys Ser Leu Asn Val Ser Asn Gln Phe Ile Asp Thr Ser Lys Leu Lys
50                  55                  60

Gln Arg Ser Thr Thr Leu Gly Asp Ala Leu Gly Thr Glu Leu Gly Ile
65                  70                  75                  80

His Ser Asn Gln Tyr Gly Gly Gly Ala Ser Ala Pro Ile Ile Arg Gly
                85                  90                  95

Gln Glu Gly Lys Arg Ile Lys Val Leu Gln Asn Asn Ala Asp Val Leu
            100                 105                 110

Asp Met Ser Asn Met Ser Pro Asp His Ala Val Thr Val Glu Pro Ser
            115                 120                 125

Leu Ala Lys Ser Ile Glu Ile Ile Arg Gly Ala Ser Thr Leu Leu Tyr
            130                 135                 140

Ser Ser Asn Ser Ala Ala Gly Val Val Asn Val Ile Asp Tyr Lys Ile
145                 150                 155                 160

Pro Thr Gln Met Pro Gln Asp Gly Leu Glu Gly Asn Thr Thr Leu Arg
                165                 170                 175
```

```
Phe Asn Thr Gly Ser Asn Glu Lys Leu Thr Thr Ala Gly Val Thr Val
            180                 185                 190

Gly Leu Ser Pro Arg Val Ala Leu Arg Ala Glu Gly Leu Tyr Arg Asn
        195                 200                 205

Ala Gly Asn Tyr Lys Thr Pro His Tyr Gln Ser Ser Tyr Asn Ser
210                 215                 220

Leu Glu Asp Leu Glu Asn Gln Asn Ile Val Tyr Lys Asn Leu Lys Tyr
225                 230                 235                 240

Leu Pro Glu Ser Trp Ala Glu Ser Arg Leu Gly Thr Leu Gly Leu Ser
                245                 250                 255

Trp Ile Asp Asp Asn Thr Tyr Leu Gly Val Ser Tyr Thr His Arg His
                260                 265                 270

Asp Glu Tyr Gly Leu Pro Ala His Ser His Leu Tyr Glu Gly Cys Gly
            275                 280                 285

Ala Ser Ala Ile Ser Ile Asn Thr Arg Ile Ser Gly Leu Lys Asn Tyr
290                 295                 300

Leu Leu Tyr Tyr Pro Gln Leu Met Glu Glu Gln Asp Ile Asn Tyr Val
305                 310                 315                 320

Asn Pro Arg Pro Asp Cys His Gln His Asn His Ile His Glu Thr Thr
                325                 330                 335

Phe Ser His Asn Ala Pro Tyr Ile Asp Leu Asn Thr Arg Arg Tyr Asp
            340                 345                 350

Met Arg Gly Glu Phe Thr Gln Pro Phe Thr Gly Ile Asp Lys Ile Arg
        355                 360                 365

Thr Ser Leu Ser Tyr Ile Asp Tyr Phe His Asn Glu Leu Glu Gly Asp
    370                 375                 380

Lys Ile Thr Asn Phe Phe Lys Asn Thr Gly Lys Val Gly Arg Ile Glu
385                 390                 395                 400

Leu Ser His Gln Pro Leu Gly Glu Leu Thr Gly Ile Leu Gly Leu Gln
                405                 410                 415

Tyr Leu Glu Gln Asp Asn Ser Ala Leu Ser Pro Val His Ser Gln Glu
                420                 425                 430

Gly His Thr Thr Tyr Leu Asp Thr Gln Gln Leu Leu Asn Arg Asn Val
        435                 440                 445

Thr Lys Asn Phe Ser Val Phe Gly Leu Glu Lys Tyr Asn Trp Asn Asp
    450                 455                 460

Phe Thr Phe Glu Leu Gly Ala Arg Ile Glu Lys Gln Lys Val Ser Met
465                 470                 475                 480

Asp Tyr Asp Ile Glu Lys Ile Lys Asp Ser Met Lys Pro Trp Pro Asn
                485                 490                 495

Lys Tyr Asn Ser Pro Tyr Val Glu Lys Asn Asn Lys Ile Arg Ala Gln
                500                 505                 510

Asn Leu Lys Ser Ile Leu Glu Ala Val Gln Pro Asn Lys Glu Thr Ala
            515                 520                 525

Phe Ser Tyr Ala Gly Thr Val His Trp Arg Phe Ala Pro Asn Tyr Ile
        530                 535                 540

Leu Ser Leu Thr Gly Thr His Gln Glu Arg Leu Pro Asn Ala Gln Glu
545                 550                 555                 560

Met Tyr Thr His Gly Met His Leu Ala Thr Asn Ser Phe Glu Ile Gly
                565                 570                 575

Asn Arg Phe Leu Arg Lys Glu Lys Ser Asn Asn Leu Glu Ile Ser Leu
            580                 585                 590
```

-continued

Ala Tyr Lys Asp Asp Leu Leu Asp Tyr Gln Ile Ser Thr Tyr Tyr Tyr
            595                 600                 605

Asp Phe Asp Asn Tyr Ile Tyr Leu Gln Thr Leu Asn Glu Val Leu Gly
610                 615                 620

Thr Thr Lys Val Arg Asp Gln His Thr Leu Arg Ile Asn His Tyr Ser
625                 630                 635                 640

Gln Ser Ala Ala Asn Phe Tyr Gly Leu Glu Gly Asn Ile Gly Tyr Gln
            645                 650                 655

Phe Asn Ser Val Tyr His Gly Ser Leu Phe Gly Asp Tyr Val Lys Gly
            660                 665                 670

Arg Leu Thr Asn Leu Pro Asp Ala Val Ile Ala Tyr Asp Ile Trp Asn
            675                 680                 685

Arg Glu Pro Thr Leu Ala Pro Gln Lys Asp Arg Tyr Thr Pro Arg Leu
            690                 695                 700

Pro Pro Ala Arg Leu Gly Thr Arg Leu Lys Ala Asp Phe Asp Glu Ser
705                 710                 715                 720

Leu Lys Gly Glu Ile Glu Tyr Tyr Arg Val Phe Lys Gln Asp Asn Ile
            725                 730                 735

Ser Lys Phe Glu Gln Val Thr Ser Gly Tyr Asn Met Leu Asn Met Thr
            740                 745                 750

Leu Ala Tyr Lys Asn Lys Leu Ser His Thr Glu Tyr Asp Leu Phe Phe
            755                 760                 765

Lys Ala Asn Asn Leu Leu Asp Gln Lys Val Tyr Ala His Glu Thr Phe
            770                 775                 780

Leu Pro Tyr Ile Pro Gln Ile Gly Arg Asn Phe Ser Leu Gly Leu Asn
785                 790                 795                 800

Leu Asn Phe

<210> SEQ ID NO 9
<211> LENGTH: 685
<212> TYPE: PRT
<213> ORGANISM: Acinetobacter baumannii SDF

<400> SEQUENCE: 9

Met Leu Phe Tyr Lys Asn Ile Leu Thr Leu Ser Ile Leu Ala Ala Ile
1               5                   10                  15

Ser Ile Pro Val Phe Ala Ala Glu Asn Glu Asn Val Glu Lys Leu Glu
            20                  25                  30

Thr Ile Arg Ile Lys Ala His Pro Leu Glu Gln Thr Ser Lys Asp Phe
            35                  40                  45

Ala Val Ala Asp Thr Val Val Asp Gln Lys His Leu Thr Glu Gly Ala
        50                  55                  60

Ala Thr Ile Gly Asp Ala Leu Asn Ser Glu Val Gly Ile Tyr Ala Asn
65                  70                  75                  80

Gln Phe Gly Ala Gly Ser Ser Arg Pro Val Ile Arg Gly Gln Asp Gly
            85                  90                  95

Pro Arg Val Lys Val Leu Gln Asn Ser Ser Glu Asn Val Asp Val Ser
            100                 105                 110

Thr Leu Ser Pro Asp His Ala Val Thr Val Asp Pro Val Leu Ala Lys
            115                 120                 125

Gln Val Glu Val Ile Arg Gly Pro Ser Thr Leu Leu Phe Gly Ala Gly
        130                 135                 140

Thr Val Gly Gly Leu Val Asn Val Ile Asp Asn Lys Ile Pro Thr Gln
145                 150                 155                 160

```
Ile Pro Glu Asn Gly Tyr Glu Gly Gln Val Gly Leu Arg Tyr Asn Thr
            165                 170                 175
Gly Ser Asp Glu Lys Leu Ala Ser Ala Gly Val Thr Val Gly Leu Gly
        180                 185                 190
Ser Gln Val Ala Leu Arg Ile Glu Gly Leu Thr Arg Asp Ala Asn Asn
    195                 200                 205
Tyr Ile Ala Pro Asn Tyr Ile His Glu Gly Lys Glu Arg Arg Val
210                 215                 220
Asp Asn Thr Phe Ala Gln Gly Asp Ser Val Asn Val Gly Leu Ser Trp
225                 230                 235                 240
Val Tyr Asp Arg Gly Tyr Thr Gly Ile Ser Tyr Ser Asn Arg Arg Asp
                245                 250                 255
Gln Tyr Gly Leu Pro Gly His Ser His Glu Tyr Glu Thr Cys His Ile
            260                 265                 270
His Asp Leu Ser Leu His Cys Gly Asp His Asp His Glu Gly His Ser
        275                 280                 285
Asp Glu Glu Ala His Asp His Glu His Glu His Gly Gly Pro Trp Ile
    290                 295                 300
Asp Leu Lys Ser Glu Arg Tyr Asp Phe Lys Thr Glu Leu Asn Asp Pro
305                 310                 315                 320
Phe Ala Gly Phe Gln Lys Leu Arg Ala Gln Ala Ser Tyr Thr Asp Tyr
                325                 330                 335
Gln His Asp Glu Ile Glu Gly Thr Ile Ala Thr Arg Phe Gln Asn
            340                 345                 350
Lys Gly Tyr Asp Gly Arg Ile Glu Leu Val His Asn Pro Ile Ala Asp
        355                 360                 365
Trp Glu Gly Val Ile Gly Thr Gln Leu Gly Gln Gln Lys Leu Asn Leu
    370                 375                 380
Thr Gly Glu Glu Ala Phe Met Ala Pro Thr Thr Lys Lys Trp Ser
385                 390                 395                 400
Val Phe Ala Leu Glu His Lys Gln Trp Lys Asp Val His Phe Glu Leu
                405                 410                 415
Ser Ala Arg Ala Asp Gln Gln Glu Ile Asp Val Asp Asp Asn Ser Lys
            420                 425                 430
Gln Asp Phe Asp Gly Ser Ala Phe Ser Tyr Ala Gly Ala Ala Asn Trp
        435                 440                 445
Glu Phe Ala Pro Asn Tyr Lys Leu Ser Phe Val Ala Ser His Gln Glu
    450                 455                 460
Arg Leu Pro Leu Ala Gln Glu Leu Tyr Ala Asn Gly Gly His Phe Ala
465                 470                 475                 480
Thr Asn Thr Tyr Glu Leu Gly Asn Asp Gln Leu Ser Lys Glu Lys Ser
                485                 490                 495
Asn Asn Val Glu Leu Gly Leu His Phe Asp Asn Asp Lys Leu Asp Tyr
            500                 505                 510
His Leu His Val Tyr His Asn Trp Phe Asp Asp Tyr Ile Tyr Ala Gln
        515                 520                 525
Thr Leu Asp Arg Tyr Lys Asp Phe Arg Leu Val Gln Tyr Thr Gln Asp
    530                 535                 540
Lys Ala Arg Phe Tyr Gly Ala Glu Gly Glu Ile Gly Tyr Gln Ile Thr
545                 550                 555                 560
Pro Met Tyr Lys Ile Ser Ala Phe Gly Asp Tyr Val Arg Gly Lys Ile
                565                 570                 575
Asp Ala Glu Gly Asn Ala Pro Arg Ile Pro Ala Gly Arg Leu Gly Thr
```

```
                580                  585                  590
Lys Val Asp Ala Asp Phe Gly Asp Gly Phe Ser Gly Ser Ala Glu Tyr
            595                  600                  605

Tyr His Val Phe Asn Gln Asp Lys Ile Ala Ala Tyr Glu Thr Glu Thr
            610                  615                  620

Glu Gly Tyr Asn Met Leu Asn Leu Gly Val Ala Tyr Ser Gly Gln Tyr
625                  630                  635                  640

Gly Ala Lys Thr Asp Tyr Arg Val Tyr Leu Lys Ala Asn Asn Leu Leu
            645                  650                  655

Asp Asp Thr Val Tyr Gln His Ala Ser Phe Leu Ser Asn Ile Pro Gln
            660                  665                  670

Val Gly Arg Asn Phe Thr Val Gly Val Asp Phe Ser Phe
            675                  680                  685

<210> SEQ ID NO 10
<211> LENGTH: 691
<212> TYPE: PRT
<213> ORGANISM: Acinetobacter calcoaceticus RUH2202

<400> SEQUENCE: 10

Met Gln Phe Tyr Lys Asn Ile Leu Thr Leu Ser Ile Leu Ala Val Ile
1               5                   10                  15

Ser Val Pro Ser Phe Ala Ala Glu Ser Glu Asn Val Glu Lys Leu Glu
            20                  25                  30

Thr Ile Arg Ile Lys Ala His Pro Leu Glu Gln Thr Ser Gln Asp Phe
        35                  40                  45

Ala Val Ala Asp Thr Val Val Asp Gln Lys His Leu Thr Gln Gly Ala
    50                  55                  60

Ala Thr Ile Gly Asp Ala Leu Ser Ser Glu Val Gly Ile Tyr Ala Asn
65                  70                  75                  80

Gln Phe Gly Ala Gly Ser Ser Arg Pro Val Ile Arg Gly Gln Asp Gly
                85                  90                  95

Pro Arg Val Lys Val Leu Gln Asn Ser Ser Glu Asn Ile Asp Val Ser
            100                 105                 110

Thr Leu Ser Pro Asp His Ala Val Thr Val Asp Pro Val Leu Ala Lys
        115                 120                 125

Gln Val Glu Val Ile Arg Gly Pro Ser Thr Leu Leu Phe Gly Ala Gly
    130                 135                 140

Thr Val Gly Gly Leu Val Asn Val Ile Asp Asn Lys Ile Pro Thr Gln
145                 150                 155                 160

Met Pro Glu Asn Gly Tyr Glu Gly Gln Val Gly Leu Arg Tyr Asn Thr
                165                 170                 175

Gly Ser Asp Glu Lys Leu Ala Ser Ala Gly Val Thr Val Gly Leu Gly
            180                 185                 190

Ser Gln Val Ala Leu Arg Val Glu Gly Leu Thr Arg Asp Ala Asn Asn
        195                 200                 205

Tyr Ile Ala Pro Asn Tyr Ile His Glu Gly Glu Lys Glu Arg Arg Val
    210                 215                 220

Asp Asn Thr Phe Ala Gln Gly Asp Ser Val Asn Val Gly Leu Ser Trp
225                 230                 235                 240

Ile Tyr Asp Arg Gly Tyr Thr Gly Ile Ser Tyr Ser Asn Arg Arg Asp
                245                 250                 255

Gln Tyr Gly Leu Pro Gly His Ser His Glu Tyr Glu Ser Cys Ser Ala
            260                 265                 270
```

-continued

```
His Leu Thr Gly Ile Pro His Leu His Cys Gly Asp His Glu His Glu
        275                 280                 285
Asp Gly Glu Glu Ala His Asp His Gly Asn Glu Glu His Glu His Glu
290                 295                 300
His Gly Gly Pro Trp Ile Asp Leu Lys Ser Glu Arg Tyr Asp Phe Lys
305                 310                 315                 320
Thr Glu Leu Asn Asp Pro Phe Ala Gly Phe Gln Lys Leu Arg Ala Gln
                325                 330                 335
Ala Ser Tyr Thr Asp Tyr Gln His Asp Glu Ile Glu Gly Ala Ile
            340                 345                 350
Ala Thr Arg Phe Gln Asn Lys Gly Tyr Asp Gly Arg Ile Glu Leu Val
        355                 360                 365
His Asn Pro Ile Ala Asp Trp Glu Gly Val Ile Gly Ala Gln Val Gly
    370                 375                 380
Gln Gln Lys Leu Asp Leu Thr Gly Glu Glu Ala Phe Met Ala Pro Thr
385                 390                 395                 400
Thr Thr Lys Lys Trp Ser Val Phe Ala Leu Glu His Lys Gln Trp Lys
                405                 410                 415
Asp Val His Phe Glu Leu Ser Ala Arg Ala Asp Gln Gln Glu Ile Asp
            420                 425                 430
Val Glu Asp Asn Ser Lys Gln Asp Phe Asp Gly Ser Ala Phe Ser Tyr
        435                 440                 445
Ala Gly Ala Ala Asn Trp Glu Phe Ala Pro Asn Tyr Lys Leu Ser Phe
    450                 455                 460
Val Ala Ser His Gln Glu Arg Leu Pro Leu Ala Gln Glu Leu Tyr Ala
465                 470                 475                 480
Asn Gly Gly His Phe Ala Thr Asn Thr Tyr Glu Leu Gly Asn Asp Gln
                485                 490                 495
Leu Ser Lys Glu Lys Ser Asn Asn Val Glu Leu Gly Leu His Phe Asp
            500                 505                 510
Asn Asp Lys Leu Asp Tyr His Leu His Val Tyr His Asn Trp Phe Asp
        515                 520                 525
Asp Tyr Ile Tyr Ala Gln Thr Leu Asp Arg Tyr Lys Asp Phe Arg Leu
    530                 535                 540
Val Gln Tyr Thr Gln Asp Lys Ala Arg Phe Tyr Gly Ala Glu Gly Glu
545                 550                 555                 560
Ile Gly Tyr Gln Ile Thr Pro Met Tyr Lys Ile Ser Ala Phe Gly Asp
                565                 570                 575
Tyr Val Arg Gly Lys Ile Asp Ala Glu Gly Asn Ala Pro Arg Ile Pro
            580                 585                 590
Ala Gly Arg Leu Gly Thr Lys Val Asp Ala Asp Phe Gly Asp Gly Phe
        595                 600                 605
Ser Gly Ser Ala Glu Tyr Tyr His Val Phe Asn Gln Asp Lys Ile Ala
    610                 615                 620
Ala Tyr Glu Thr Glu Thr Glu Gly Tyr Asn Met Leu Asn Leu Gly Val
625                 630                 635                 640
Ala Tyr Ser Gly Gln Tyr Gly Ala Lys Thr Asp Tyr Arg Val Tyr Met
                645                 650                 655
Lys Ala Asn Asn Leu Leu Asp Asp Thr Val Tyr Gln His Ala Ser Phe
            660                 665                 670
Leu Ser Asn Ile Pro Gln Val Gly Arg Asn Phe Thr Val Gly Val Asp
        675                 680                 685
Phe Ser Phe
```

-continued

690

<210> SEQ ID NO 11
<211> LENGTH: 680
<212> TYPE: PRT
<213> ORGANISM: Acinetobacter johnsonii SH046

<400> SEQUENCE: 11

Met Ser Ser Met Ala Phe His Lys Asn Leu Ile Thr Leu Ser Ile Leu
1               5                   10                  15

Ala Val Val Ala Pro Ala Val Phe Ala Asp Asp Thr Thr Gln Gln
            20                  25                  30

Leu Glu Thr Leu Thr Ser Gln Ala His Pro Leu Val Gln Thr Ala Ala
        35                  40                  45

Asp Phe Ala Val Ala Asp Gln Val Ile Glu Gln Lys Ser Leu Lys Glu
    50                  55                  60

Arg Ala Pro Thr Ile Gly Asp Ala Leu Ala Asp Glu Leu Gly Val Tyr
65                  70                  75                  80

Ser Asn Gln Tyr Gly Ser Gly Ser Arg Pro Val Ile Arg Gly Gln
                85                  90                  95

Asp Gly Pro Arg Val Lys Val Leu Gln His Ala Ser Glu Thr Ala Asp
            100                 105                 110

Val Ser Thr Leu Ser Pro Asp His Ala Val Thr Val Asp Pro Ile Leu
        115                 120                 125

Ala Lys Gln Ile Glu Ile Ile Arg Gly Pro Ser Thr Leu Leu Tyr Ser
    130                 135                 140

Ala Gly Thr Val Gly Gly Leu Val Asn Val Thr Asp Gln Lys Ile Pro
145                 150                 155                 160

Thr Ser Met Pro Glu Lys Gly Leu Glu Gly Thr Ala Gly Leu Arg Tyr
                165                 170                 175

Asn Ser Gly Ser Asp Glu Lys Leu Ala Ser Ala Gly Ala Thr Val Ala
            180                 185                 190

Leu Gly Ser Gln Phe Ala Leu Arg Val Glu Gly Ser Lys Arg Glu Ala
        195                 200                 205

Asn Asp Tyr Ile Ala Pro Asn Tyr Phe His Glu His Glu Gly Glu Leu
    210                 215                 220

Glu Lys Glu Arg Arg Val Gly Asn Thr Phe Ala Lys Gly Lys Thr Val
225                 230                 235                 240

Ser Val Gly Gly Ser Trp Ile Gly Glu Arg Ser Phe Ala Gly Ile Ala
                245                 250                 255

Tyr Thr Asn Arg Gln Asp Gln Tyr Gly Leu Pro Gly His Ser His Glu
            260                 265                 270

Tyr Glu Ser Cys Thr Val Ser Gly Asn Leu Leu Ile Gly Cys Gly Glu
        275                 280                 285

Glu Asp Tyr Gly Asp Glu His Glu Thr Gly Pro Trp Val Asp Leu Lys
    290                 295                 300

Ser Glu Arg Tyr Asp Phe Arg Thr Glu Ile Leu Asn Pro Leu Ala Gly
305                 310                 315                 320

Phe Glu Lys Leu Arg Ala His Ala Ser Tyr Thr Asp Tyr Gln His Asp
                325                 330                 335

Glu Ile Glu Gly Asp Ser Val Ala Thr Thr Phe Lys Ser Lys Ser Tyr
            340                 345                 350

Asp Ala Arg Leu Glu Met Val His Gln Pro Ile Ala Asp Trp Glu Gly
        355                 360                 365

Val Val Gly Val Gln Tyr Asn Gln Gln Lys Leu Asp Ile Thr Gly Glu
            370                 375                 380

Glu Ser Ile Leu Glu Pro Thr Lys Thr Gln Lys Trp Ser Val Phe Gly
385                 390                 395                 400

Leu Glu His Lys Gln Trp Asn Asp Phe His Phe Glu Leu Gly Ala Arg
                405                 410                 415

Val Asp Gln Gln Thr Ile Asp Ile Glu Ser Asp Arg Lys Asp Tyr Asp
            420                 425                 430

Asp Tyr Ala Val Ser Tyr Ser Gly Ala Val Asn Trp Met Phe Ala Pro
                435                 440                 445

Asn Tyr Lys Leu Ser Leu Val Gly Ser His Gln Glu Arg Leu Pro Leu
450                 455                 460

Ala Gln Glu Leu Tyr Ala Asp Gly Lys His Leu Ala Thr Asn Thr Tyr
465                 470                 475                 480

Glu Arg Gly Asn Glu Asn Leu Asp Val Glu Lys Ser Asn Asn Leu Glu
                485                 490                 495

Leu Gly Phe His Tyr Asp Thr Asp Lys Ile Asp Tyr His Val His Val
                500                 505                 510

Tyr His Asn Trp Tyr Asp Asn Tyr Ile Tyr Ala Gln Thr Ala Asp Arg
            515                 520                 525

Tyr Glu Asn Phe Arg Leu Val Asp Tyr Thr Gln Asp Lys Ala Arg Phe
530                 535                 540

Tyr Gly Thr Glu Ala Glu Ala Ser Tyr Ala Ile Asn Asp Val Tyr Lys
545                 550                 555                 560

Met Ser Val Phe Gly Asp Tyr Val Arg Gly Lys Ile Asp Asn Asp Asn
                565                 570                 575

Ala Pro Arg Val Pro Ala Gly Arg Leu Gly Thr Lys Val Asn Ala Asn
            580                 585                 590

Phe Ser Asp Thr Trp Ser Gly Thr Ala Glu Tyr Tyr His Val Phe Glu
                595                 600                 605

Gln Asp Gln Ile Ala Ser Tyr Glu Thr Glu Thr Glu Gly Tyr Asn Met
            610                 615                 620

Val Asn Leu Gly Leu Ala Tyr Asn Gly Gln Tyr Met Gln Gly Asn Asp
625                 630                 635                 640

Tyr Arg Val Tyr Phe Lys Ala Asn Asn Leu Leu Asp Glu Thr Val Tyr
                645                 650                 655

Ser His Thr Ser Phe Leu Ser Thr Leu Pro Gln Val Gly Arg Asn Phe
                660                 665                 670

Thr Ile Gly Leu Asp Phe Ser Phe
            675                 680

<210> SEQ ID NO 12
<211> LENGTH: 685
<212> TYPE: PRT
<213> ORGANISM: Acinetobacter junii SH205

<400> SEQUENCE: 12

Met Leu Thr Leu Ser Ile Leu Ala Ala Val Ser Val Thr Ala Phe Ala
1               5                   10                  15

Ala Glu Asn Glu Lys Val Glu Ser Leu Glu Thr Ile Arg Ile Lys Ala
                20                  25                  30

His Pro Leu Glu Gln Thr Ser Gln Asp Phe Ala Val Ala Asp Ser Val
            35                  40                  45

Ile Asp Gln Thr Lys Leu Ser Gln Gly Ala Val Thr Ile Gly Asp Val
50                  55                  60

```
Leu Gly Gln Gln Thr Gly Ile Tyr Ser Asn Gln Phe Gly Ala Gly Ser
 65                  70                  75                  80

Ser Arg Pro Val Ile Arg Gly Gln Asp Gly Ala Arg Val Lys Ile Leu
                 85                  90                  95

Gln Asn Ser Ser Glu Asn Ile Asp Val Ser Thr Leu Ser Pro Asp His
                100                 105                 110

Ala Val Thr Val Asp Pro Ala Leu Ala Lys Gln Val Glu Val Ile Arg
                115                 120                 125

Gly Pro Ser Thr Leu Leu Phe Gly Ala Gly Thr Val Gly Gly Leu Val
                130                 135                 140

Asn Val Ile Asp Ser Lys Leu Pro Thr Gln Met Pro Glu Lys Gly Tyr
145                 150                 155                 160

Glu Gly Asn Val Gly Leu Arg Tyr Asn Thr Gly Ser Asp Glu Lys Leu
                165                 170                 175

Ala Ser Ala Gly Val Thr Val Gly Leu Gly Asp Gln Val Ala Leu Arg
                180                 185                 190

Val Glu Gly Leu Lys Arg Asp Ala Asn Asn Tyr Ile Ala Pro Asp Tyr
                195                 200                 205

Phe His Glu Gly Glu Lys Glu Arg Arg Val Asp Asn Thr Phe Ala Glu
210                 215                 220

Gly Gln Thr Val Asn Val Gly Leu Ser Trp Ile Tyr Asp Arg Gly Phe
225                 230                 235                 240

Thr Gly Ile Ser Tyr Ser Asn Arg Gln Asp Lys Tyr Gly Leu Pro Gly
                245                 250                 255

His Ser His Glu Tyr Glu Ser Cys Glu Ala His Leu Val Gly Thr Pro
                260                 265                 270

His Leu His Cys Gly Asp His Glu His Glu Asp Glu His Gly Gly Asp
                275                 280                 285

His Tyr Asp Glu His Glu Gly Glu His Val His Glu Ala Gly Pro Trp
                290                 295                 300

Ile Asp Leu Lys Ser Glu Arg Tyr Asp Ile Arg Ser Glu Leu Asp Asn
305                 310                 315                 320

Pro Phe Lys Gly Phe Lys Lys Phe Arg Ala Gln Ala Ser Tyr Thr Asp
                325                 330                 335

Tyr Gln His Asp Glu Ile Glu Leu Asp Thr Ile Ala Thr Arg Phe Lys
                340                 345                 350

Asn Lys Ala Tyr Asp Gly Arg Val Glu Leu Val His Asn Pro Ile Gly
                355                 360                 365

Ala Trp Glu Gly Val Ile Gly Thr Gln Tyr Gly Gln Gln Lys Leu Asn
                370                 375                 380

Leu Thr Gly Glu Glu Ala Phe Leu Ala Pro Asn Thr Thr Lys Lys Trp
385                 390                 395                 400

Ser Leu Phe Ala Leu Glu His Ala Gln Phe Asn Asp Val His Val Glu
                405                 410                 415

Leu Ala Ala Arg Val Asp Gln Gln Lys Ile Asp Ile Glu Asp Ser Ser
                420                 425                 430

Lys Lys Asp Phe Asp Gly Ser Ala Phe Ser Ala Ser Gly Ala Ala Asn
                435                 440                 445

Trp Glu Phe Ala Pro Asp Tyr Lys Leu Ser Leu Val Ala Ser His Gln
                450                 455                 460

Gln Arg Leu Pro Leu Ala Gln Glu Leu Tyr Ala Asp Gly Lys His Phe
465                 470                 475                 480
```

```
Ala Thr Asn Thr Tyr Glu Leu Gly Asn Asp Gln Leu Lys Lys Glu Gln
                485                 490                 495

Ser Asn Asn Val Glu Leu Gly Phe His Tyr Asp Asn Arg Phe Asp
            500                 505                 510

Tyr His Ile His Val Tyr His Asn Trp Phe Asp Asp Tyr Ile Tyr Ala
                515                 520                 525

Gln Thr Leu Asp Arg Tyr Glu Asp Phe Arg Leu Val Lys Tyr Thr Gln
                530                 535                 540

Asp Lys Ala Arg Phe Tyr Gly Ala Glu Ala Ala Ala Tyr Gln Ile
545                 550                 555                 560

Ser Pro Thr Tyr Lys Ile Gly Val Phe Gly Asp Tyr Val Arg Gly Lys
                565                 570                 575

Ile Asp Asn Glu Asn Ala Pro Arg Val Pro Ala Gly Arg Leu Gly Thr
                580                 585                 590

Lys Val Asn Ala Asp Phe Gly Asp Phe Thr Gly Ser Ala Glu Tyr
            595                 600                 605

Tyr His Val Phe Asn Gln Asp Lys Ile Thr Ala Tyr Glu Thr Glu Thr
                610                 615                 620

Gln Gly Tyr Asn Met Leu Asn Leu Gly Val Ala Tyr Ser Gly Glu Tyr
625                 630                 635                 640

Ser Asn Leu Gly Asn Tyr Arg Val Phe Leu Asn Ala Asn Asn Leu Leu
                645                 650                 655

Asp Asp Gln Ile Tyr Gln His Ala Ser Phe Leu Ser Thr Ile Pro Gln
                660                 665                 670

Val Gly Arg Asn Phe Thr Val Gly Val Asn Phe Asn Phe
                675                 680                 685

<210> SEQ ID NO 13
<211> LENGTH: 684
<212> TYPE: PRT
<213> ORGANISM: Acinetobacter lwoffii SH145

<400> SEQUENCE: 13

Met Ser Ile Phe Ala Val Val Ala Pro Thr Val Phe Ala Glu Gln Ser
1               5                   10                  15

Ser Ser Ser Ile Pro Val Gln Thr Met Asp Thr Ile Gln Val Gln Ala
                20                  25                  30

His Pro Leu Val Gln Thr Ala Ala Asp Phe Ala Val Ala Asp His Phe
            35                  40                  45

Val Asp Gln Lys Ala Leu Ser Glu Arg Ala Pro Thr Ile Gly Asp Ala
    50                  55                  60

Leu Ala Asp Glu Leu Gly Val Tyr Ser Asn Gln Tyr Gly Ser Gly Ser
65                  70                  75                  80

Ser Arg Pro Val Ile Arg Gly Gln Asp Gly Pro Arg Val Lys Val Leu
                85                  90                  95

Gln His Ala Ser Glu Thr Ala Asp Val Ser Thr Leu Ser Pro Asp His
            100                 105                 110

Ala Val Thr Val Asp Pro Ile Leu Ala Lys Gln Val Glu Val Ile Arg
        115                 120                 125

Gly Pro Ser Thr Leu Leu Tyr Gly Ala Gly Thr Val Gly Gly Leu Val
    130                 135                 140

Asn Val Thr Asp Gln Lys Ile Pro Thr Gln Met Pro Glu Asp Gly Leu
145                 150                 155                 160

Glu Gly Thr Val Gly Leu Arg Tyr Asn Ser Gly Ser Asp Glu Lys Leu
                165                 170                 175
```

```
Ala Ser Ala Gly Val Thr Ala Gly Ile Gly Glu Asn Phe Ala Leu Arg
            180                 185                 190

Val Glu Gly Ser Lys Arg Asn Ala Asn Asp Tyr Ile Ala Pro Asp Tyr
            195                 200                 205

Phe His Glu His Asp Asp Glu Leu Glu Lys Glu Arg Arg Val Gly Asn
    210                 215                 220

Thr Phe Ala Glu Gly Gln Thr Val Asn Ile Gly Gly Ser Trp Ile His
225                 230                 235                 240

Asp Arg Gly Phe Val Gly Leu Ser Tyr Ser Asn Arg Gln Asp Gln Tyr
                245                 250                 255

Gly Leu Pro Gly His Ser His Glu Tyr His Gly Cys Glu Ile His Gly
            260                 265                 270

Asp His Phe His Cys Pro Lys Pro Gly Glu Asp Glu His Asp His Glu
            275                 280                 285

Glu Thr Ala Gly Pro Trp Val Asp Leu Lys Ser Glu Arg Tyr Asp Val
            290                 295                 300

Arg Thr Glu Leu Glu Gln Pro Phe Ala Gly Phe Glu Lys Leu Arg Ala
305                 310                 315                 320

His Ala Ser Phe Thr Asp Tyr Glu His Asp Glu Leu Glu Glu Asn Ala
                325                 330                 335

Val Ile Ser Asn Phe Lys Ser Lys Gly Tyr Asp Ala Arg Leu Glu Leu
            340                 345                 350

Val His Val Pro Val Ala Gly Trp Glu Gly Val Ile Gly Thr Gln Tyr
            355                 360                 365

Ser Gln Gln Lys Ile Asp Leu Ser Gly Gln Leu Glu Pro His Asp Asp
            370                 375                 380

His Phe His Glu Ala Val Val Met Pro Asp Thr Lys Thr Asp Lys Phe
385                 390                 395                 400

Ser Leu Phe Ala Leu Glu His Lys Gln Leu Gly Asp Val His Val Glu
                405                 410                 415

Leu Gly Ala Arg Val Asp His Gln Lys Val Lys Val Asp Ser Asp Gln
            420                 425                 430

Lys Asp Tyr Ser Gly Thr Gly Val Ser Ala Ser Ala Ala Asn Trp
            435                 440                 445

Glu Phe Ala Pro Asn Tyr Lys Leu Ser Val Val Gly Ser His Gln Gln
    450                 455                 460

Arg Leu Pro Leu Ala Gln Glu Leu Tyr Ala Asp Gly Leu His Phe Ala
465                 470                 475                 480

Thr Asn Thr Tyr Glu Leu Gly Asn Pro Asp Leu Asp Lys Glu Thr Ser
                485                 490                 495

Asn Asn Leu Glu Leu Gly Leu His Tyr Glu Gly Asp Lys Leu Asp Tyr
            500                 505                 510

His Val His Val Tyr His Asn Trp Phe Asp Asp Tyr Ile Tyr Gly Glu
            515                 520                 525

Thr Val Ala Gln Lys Gly Asn Leu Arg Gly Val Gln Tyr Thr Gln Asp
            530                 535                 540

Lys Ala Arg Phe Tyr Gly Thr Glu Val Gln Ala Gly Tyr Gln Ile Asn
545                 550                 555                 560

Asp Met Tyr Lys Leu Ser Val Phe Gly Asp Tyr Val Arg Gly Lys Ile
                565                 570                 575

Glu Ala Glu Asn Ala Pro Arg Val Pro Ala Gly Arg Leu Gly Thr Lys
            580                 585                 590
```

Val Glu Ala Asp Phe Ala Asp Gly Trp Ser Gly Leu Ala Glu Tyr Tyr
            595                 600                 605

His Ile Phe Asn Gln Asp Lys Ile Ala Ser Tyr Glu Asp Glu Thr Gln
            610                 615                 620

Gly Tyr Asn Met Val Asn Val Gly Leu Ser Tyr Ala Asn Ser Ile Ala
625                 630                 635                 640

Asp Asn Asn Ala Tyr Arg Val Tyr Phe Lys Ala Asn Asn Leu Leu Asp
            645                 650                 655

Asp Gln Val Tyr Ser His Thr Ser Phe Leu Ser Asn Ile Pro Gln Val
            660                 665                 670

Gly Arg Asn Phe Thr Val Gly Val Gln Tyr Asp Phe
            675                 680

<210> SEQ ID NO 14
<211> LENGTH: 699
<212> TYPE: PRT
<213> ORGANISM: Acinetobacter radioresistens SK82

<400> SEQUENCE: 14

Met Gln Phe Ser Lys Asn Phe Leu Thr Leu Ser Ile Met Ala Val Val
1               5                   10                  15

Ser Pro Val Ile Phe Ala Glu Glu Asn Ser Ser Val Gln Gln Leu Glu
            20                  25                  30

Thr Ile Gln Val Thr Ala His Pro Leu Val Gln Ser Ala Val Asp Tyr
        35                  40                  45

Val Ala Ala Asp Asn Ile Ile Glu Lys Glu Gln Leu Ile Gln Gly Gly
    50                  55                  60

Thr Thr Ile Gly Glu Ala Leu Ser Asp Gln Val Gly Val Tyr Ser Asn
65                  70                  75                  80

Gln Phe Gly Pro Gly Ala Ser Arg Pro Val Ile Arg Gly Gln Glu Gly
                85                  90                  95

Ala Arg Val Lys Val Leu Gln Asn Ala Ser Glu Thr Met Asp Val Ser
            100                 105                 110

Thr Leu Ser Pro Asp His Ala Val Met Val Asp Pro Ala Leu Ala Lys
        115                 120                 125

Gln Val Glu Ile Val Arg Gly Pro Ser Thr Leu Leu Tyr Gly Ala Gly
    130                 135                 140

Thr Val Gly Gly Leu Val Asn Val Thr Asp Ser Lys Ile Pro Thr Arg
145                 150                 155                 160

Ile Pro Asp Asn Gly Tyr Glu Gly Arg Ala Gly Leu Arg Tyr Asn Ser
                165                 170                 175

Gly Asn Asp Glu Lys Leu Glu Thr Ala Gly Val Thr Leu Ala Leu Gly
            180                 185                 190

Glu Gln Val Ala Leu Arg Val Glu Gly Leu Lys Arg Asp Ala Asn Asn
        195                 200                 205

Tyr Ile Ala Pro Asp Tyr Tyr His Glu His Ser His Gly Asp His Ser
    210                 215                 220

His Leu Val Lys Glu Arg Arg Val Asp Asn Thr Phe Ala Gln Ser Asp
225                 230                 235                 240

Thr Ala Ser Val Gly Leu Ser Trp Ile His Asp Arg Gly Phe Thr Gly
                245                 250                 255

Leu Ser Tyr Thr Asn Arg Gln Asp Gln Tyr Gly Leu Pro Gly His Ser
            260                 265                 270

His Glu Tyr Glu Ser Cys Glu Ala Tyr Leu Ser Gly Arg Pro His Leu
        275                 280                 285

```
His Cys Gly Asp Glu His His Asp Glu Gly His Glu His Glu
    290                 295             300
His Ser His Glu Lys Asp His Asp His Ala Gly Pro Trp Val Asp Leu
305             310             315                 320
Lys Ser Glu Arg Tyr Asp Phe Arg Thr Glu Leu Asp Asp Pro Phe Ala
                325             330                 335
Gly Phe Lys Lys Leu Arg Ala Gln Ala Ser Tyr Thr Asp Tyr Lys His
            340             345             350
Asp Glu Ile Glu Glu Gly Glu Ala Ala Thr Thr Phe Lys Ser Thr Gly
            355             360             365
Tyr Asp Ala Arg Leu Glu Leu Val His Gln Pro Val Ala Ala Trp Glu
370             375             380
Gly Val Ile Gly Thr Gln Phe Gly Arg Gln Lys Leu Asn Ile Thr Gly
385             390             395                 400
Glu Glu Ser Leu Phe Ala Gly Pro Thr Thr Thr Asp Lys Trp Ser Leu
                405             410             415
Phe Ala Leu Glu His Thr Gln Trp Asn Asp Val His Phe Glu Leu Ala
            420             425             430
Ala Arg Phe Asp Gln Gln Lys Ile Glu Ile Asp Ser Pro Gln Lys Asn
            435             440             445
Tyr Asp Asp His Ala Phe Ser Tyr Ser Gly Ala Ala Asn Trp Glu Phe
450             455             460
Leu Pro Asp Tyr Lys Leu Ser Leu Val Ala Ser His Gln Glu Arg Leu
465             470             475             480
Pro Leu Ala Gln Glu Leu Tyr Ala Lys Gly Lys His Leu Ala Thr Asn
                485             490             495
Thr Tyr Glu Ile Gly Asn Glu Asn Leu Asp Thr Glu Lys Ser Asn Asn
            500             505             510
Ile Glu Leu Gly Phe His Tyr Glu Gly Asp Lys Leu Asn Tyr His Ile
            515             520             525
His Ala Tyr His Asn Trp Phe Asp Asp Tyr Ile Tyr Ala Gln Thr Leu
            530             535             540
Asp Arg Phe Glu Asn Phe Arg Leu Val Glu Tyr Thr Gln Asp Lys Ala
545             550             555             560
Arg Phe Tyr Gly Ala Glu Gly Glu Val Ser Tyr Gln Leu Ser Pro Arg
            565             570             575
Tyr Lys Ala Ser Leu Phe Gly Asp Tyr Val Arg Gly Lys Ile Glu Thr
            580             585             590
Glu Gly Asn Ala Pro Arg Ile Pro Gly Gly Arg Leu Gly Ser Lys Ile
            595             600             605
Asp Ala Asp Phe Gly Asp Gly Phe Ser Gly Met Ala Glu Tyr Tyr His
610             615             620
Val Phe Thr Gln Asp Lys Ile Ala Ala Tyr Glu Thr Glu Thr Glu Gly
625             630             635             640
Tyr Asn Met Val Asn Leu Gly Leu Ala Tyr Ser Ala Arg Ala Thr Asp
                645             650             655
Lys Thr Asp Tyr Arg Ile Tyr Val Lys Ala Asn Asn Leu Leu Asp Glu
            660             665             670
Thr Val Tyr Asn His Ala Ser Phe Leu Ser Asn Ile Pro Gln Val Gly
            675             680             685
Arg Asn Phe Thr Val Gly Leu Asp Phe Asn Phe
            690             695
```

<210> SEQ ID NO 15
<211> LENGTH: 693
<212> TYPE: PRT
<213> ORGANISM: Acinetobacter sp. ADP1

<400> SEQUENCE: 15

```
Met Leu Phe Thr Arg Ser Val Leu Ala Leu Ser Ile Phe Ala Ala Leu
1               5                   10                  15

Ser Ser Val Val His Ala Ala Asn Glu Thr Asn Thr Val Ser Lys Leu
            20                  25                  30

Lys Thr Ile Glu Ala Thr Ala His Pro Leu Val Gln Thr Ala Val Asp
        35                  40                  45

Tyr Ala Ala Asp Asn Ile Ile Gln Asn Gln Gln Leu Val Gln Gly
    50                  55                  60

Gly Ala Thr Ile Gly Glu Ala Leu Ser Asp Gln Val Gly Val Tyr Ser
65              70                  75                  80

Asn Gln Phe Gly Pro Gly Ala Ser Arg Pro Val Ile Arg Gly Gln Asp
                85                  90                  95

Ser Ala Arg Val Lys Val Leu Gln Asn Ala Ser Glu Thr Ile Asp Val
            100                 105                 110

Ser Thr Leu Ser Pro Asp His Ala Val Met Val Asn Pro Ile Leu Ala
        115                 120                 125

Lys Gln Val Glu Ile Val Arg Gly Pro Ser Thr Leu Leu Tyr Gly Ala
    130                 135                 140

Gly Thr Val Gly Gly Leu Val Asn Val Thr Asp Asn Lys Ile Pro Thr
145                 150                 155                 160

Gln Met Pro Glu Lys Gly Tyr Glu Gly Gln Val Gly Leu Arg Tyr Asn
                165                 170                 175

Thr Gly Ser Asp Glu Lys Leu Gly Ser Ala Gly Leu Thr Val Gly Leu
            180                 185                 190

Gly Glu Gln Val Ala Leu Arg Leu Gly Gly Leu Lys Arg Asp Ala Asn
        195                 200                 205

Asn Tyr Ile Ala Pro Asn Tyr Leu His Glu Gly Glu Lys Glu Arg Arg
    210                 215                 220

Val Asp Asn Thr Phe Ala Lys Ser Glu Asp Thr Thr Ile Gly Leu Ser
225                 230                 235                 240

Trp Ile His Asp Arg Gly Phe Ala Gly Ile Ser Tyr Thr Asn Arg Gln
                245                 250                 255

Asp Lys Tyr Gly Leu Pro Gly His Ser His Glu Tyr Glu Ser Cys His
            260                 265                 270

Pro His Gly Leu Lys Leu His Cys Gly Ser His Asp His Asp His
        275                 280                 285

Gly Asp His Asp Glu Glu Gly His Asp His Asp His Glu His Ala
    290                 295                 300

His Asp His Ala Gly Pro Trp Ile Asn Leu Lys Ser Glu Arg Tyr Asp
305                 310                 315                 320

Phe Arg Thr Glu Leu Asn Asp Pro Phe Ser Gly Phe Ser Lys Leu Arg
                325                 330                 335

Ala Gln Ala Ser Tyr Thr Asp Tyr Lys His Asp Glu Ile Glu Glu Gly
            340                 345                 350

Glu Ala Ala Thr Thr Phe Lys Ser Gln Gly Tyr Asp Ala Arg Leu Glu
        355                 360                 365

Leu Val His Gln Pro Leu Ala Asn Trp Glu Gly Val Val Gly Ala Gln
    370                 375                 380
```

Phe Gly Arg Gln Lys Leu Asp Ile Thr Gly Glu Ser Leu Phe Ala
385                 390                 395                 400

Gly Pro Ser Thr Thr Asp Lys Trp Ser Leu Phe Ala Leu Glu His Thr
            405                 410                 415

Gln Trp Asn Asp Val His Phe Glu Val Ala Ala Arg Phe Asp Gln Gln
        420                 425                 430

Lys Ile Asp Ile Asp Ser Ala Gln Lys Asn Tyr Asp Asp His Ala Phe
    435                 440                 445

Ser Tyr Ser Gly Ala Ala Asn Trp Ala Phe Ala Pro Asn Tyr Lys Leu
450                 455                 460

Ser Phe Val Ala Ser His Gln Glu Arg Met Pro Leu Ala Gln Glu Leu
465                 470                 475                 480

Tyr Ala Asn Gly Lys His Leu Ala Thr Asn Thr Tyr Glu Leu Gly Asn
            485                 490                 495

Gln Asn Leu Ser Thr Glu Lys Ser Asn Asn Leu Glu Leu Gly Phe His
        500                 505                 510

Tyr Asp Ala Asp Lys Leu Asn Tyr His Val His Val Phe His Asn Trp
    515                 520                 525

Phe Asp Asp Tyr Ile Tyr Ala Arg Thr Leu Asp Arg Phe Glu Asn Phe
530                 535                 540

Arg Leu Val Glu Tyr Thr Gln Asp Lys Ala Arg Phe Tyr Gly Val Glu
545                 550                 555                 560

Gly Glu Leu Ser Tyr Gln Leu Ser Pro Arg Tyr Thr Ala Thr Val Phe
            565                 570                 575

Gly Asp Tyr Val Arg Ala Lys Ile Glu Thr Gly Asn Ala Pro Arg
    580                 585                 590

Ile Pro Gly Gly Arg Leu Gly Thr Arg Ile Asn Ala Asp Phe Gly Asp
    595                 600                 605

Gly Phe Ser Gly Leu Ala Glu Tyr Phe His Val Phe Lys Gln Asp Lys
610                 615                 620

Phe Ala Ala Phe Glu Asn Glu Thr Ala Gly Tyr Asn Met Val Asn Leu
625                 630                 635                 640

Gly Leu Ala Tyr Ala Ala Arg Ala Thr Asn Arg Thr Asp Tyr Arg Val
            645                 650                 655

Tyr Val Lys Ala Asn Asn Ile Leu Asp Glu Thr Val Tyr Asn His Ala
        660                 665                 670

Ser Phe Leu Ser Asn Leu Pro Gln Val Gly Arg Asn Phe Thr Val Gly
    675                 680                 685

Val Asp Phe Ser Phe
        690

<210> SEQ ID NO 16
<211> LENGTH: 696
<212> TYPE: PRT
<213> ORGANISM: Acinetobacter sp. ATCC 27244

<400> SEQUENCE: 16

Met Ser Phe Ser Lys Asn Ile Leu Thr Leu Ser Ile Leu Ala Ala Val
1               5                   10                  15

Ser Val Ser Ala Leu Ala Ala Glu Asn Gln Lys Val Gln Thr Leu Glu
            20                  25                  30

Thr Ile Arg Ile Lys Ala His Pro Leu Glu Gln Thr Ser Gln Asp Phe
        35                  40                  45

Ala Val Ala Asp Thr Val Val Asp Gln Lys Thr Leu Thr Glu Gly Ala

```
                50                  55                  60
Val Thr Ile Gly Asp Ala Leu Ala Ser Glu Val Gly Ile Tyr Ser Asn
65                  70                  75                  80

Gln Phe Gly Ala Gly Ser Ser Arg Pro Val Ile Arg Gly Gln Asp Gly
                85                  90                  95

Ala Arg Val Lys Val Leu Gln Asn Ser Ser Glu Asn Ile Asp Val Ser
            100                 105                 110

Thr Leu Ser Pro Asp His Ala Val Thr Val Asp Pro Ala Leu Ala Thr
            115                 120                 125

Gln Val Glu Val Ile Arg Gly Pro Ser Thr Leu Leu Phe Gly Ala Gly
            130                 135                 140

Thr Val Gly Gly Leu Val Asn Val Asn Asp Ser Lys Leu Pro Thr Lys
145                 150                 155                 160

Met Pro Glu Lys Gly Tyr Glu Gly Asn Val Gly Leu Arg Tyr Asn Thr
                165                 170                 175

Gly Ser Asp Glu Lys Leu Ala Ser Ala Gly Val Thr Val Gly Leu Gly
            180                 185                 190

Asp Gln Phe Ala Leu Arg Val Glu Gly Leu Lys Arg Glu Ala Asn Asp
            195                 200                 205

Tyr Ile Ala Pro Asn Tyr Phe His Glu Gly Lys Glu Arg Arg Val
            210                 215                 220

Asp Asn Thr Phe Ala Glu Gly Gln Thr Val Asn Val Gly Leu Ser Trp
225                 230                 235                 240

Ile Tyr Asp Arg Gly Phe Thr Gly Ile Ser Tyr Ser Asn Arg Gln Asp
                245                 250                 255

Lys Tyr Gly Leu Pro Gly His Ser His Glu Tyr Glu Ser Cys Asp Ala
            260                 265                 270

His Leu Val Gly Arg Pro His Leu His Cys Gly Asp His Gly His Asp
            275                 280                 285

His Gly His Asp Asp His Asp Asp His Gly His Asp Asp His Asp
            290                 295                 300

His Asp His Glu His Ala His Gly Gly Pro Trp Ile Asp Leu Lys Ser
305                 310                 315                 320

Glu Arg Tyr Asp Phe Arg Thr Glu Leu Asp Asp Pro Phe Ala Gly Phe
                325                 330                 335

Lys Lys Met Arg Ala Gln Ala Ser Tyr Thr Asp Tyr Arg His Asp Glu
            340                 345                 350

Ile Glu Glu Asp Thr Ile Thr Thr Arg Phe Lys Asn Lys Gly Tyr Asp
            355                 360                 365

Gly Arg Phe Glu Leu Val His Asn Pro Leu Gly Ala Trp Glu Gly Val
            370                 375                 380

Ile Gly Thr Gln Tyr Ser Gln Gln Lys Leu Thr Leu Thr Gly Gln Glu
385                 390                 395                 400

Ala Phe Leu Ala Pro Asn Thr Thr Lys Lys Trp Ser Val Phe Ala Leu
                405                 410                 415

Glu His Ala Gln Phe Asn Asp Val His Val Glu Leu Ala Ala Arg Ala
            420                 425                 430

Asp Lys Gln Lys Ile Asp Ile Asp Asp Ser Ser Lys Gln Asp Phe Asp
            435                 440                 445

Gly Ser Ala Phe Ser Val Ser Gly Ala Ala Asn Trp Glu Phe Ala Pro
            450                 455                 460

Asn Tyr Lys Leu Ser Phe Val Thr Ser His Gln Gln Arg Leu Pro Leu
465                 470                 475                 480
```

```
Ala Gln Glu Leu Tyr Ala Asn Gly Lys His Phe Ala Thr Asn Thr Tyr
                485                 490                 495

Glu Leu Gly Asn Asp Gln Leu Lys Lys Glu Lys Ser Asn Asn Val Glu
            500                 505                 510

Leu Gly Phe His Tyr Asp Asp Asn Ile Phe Asp Tyr His Val His Val
        515                 520                 525

Tyr His Asn Trp Phe Asp Asp Tyr Ile Phe Ala Gln Thr Leu Asp Arg
    530                 535                 540

Tyr Glu Asp Phe Arg Leu Val Glu Tyr Thr Gln Asp Lys Ala Arg Phe
545                 550                 555                 560

Tyr Gly Ala Glu Ala Glu Ala Gly Tyr Gln Val Ser Pro Ile Tyr Lys
                565                 570                 575

Val Ser Val Phe Gly Asp Tyr Val Arg Gly Lys Ile Asp Asn Glu Asn
            580                 585                 590

Ala Pro Arg Val Pro Ala Gly Arg Leu Gly Thr Lys Val Lys Ala Asn
        595                 600                 605

Phe Gly Asp Gly Phe Ser Gly Ser Ala Glu Tyr Tyr His Val Phe Gln
610                 615                 620

Gln Asp Lys Ile Ala Ala Tyr Glu Thr Asp Thr Gln Ser Tyr Asn Met
625                 630                 635                 640

Val Asn Leu Gly Val Ala Tyr Ser Gly Gln Tyr Ser Ser Ala Gly Asp
                645                 650                 655

Tyr Arg Val Phe Leu Asn Ala Asn Asn Leu Leu Asp Glu Lys Val Tyr
            660                 665                 670

Gln His Ala Ser Phe Leu Ser Thr Val Pro Gln Val Gly Arg Asn Phe
        675                 680                 685

Thr Val Gly Val Asn Phe Ser Phe
    690                 695

<210> SEQ ID NO 17
<211> LENGTH: 670
<212> TYPE: PRT
<213> ORGANISM: Acinetobacter sp. RUH2624

<400> SEQUENCE: 17

Met Gln Leu Lys Thr Gln Leu Phe Val Leu Leu Leu Ser Leu Ser
1               5                   10                  15

Ile Gln Gln Val Met Ala Ala Asp Asp Thr Asn Thr Lys Glu Glu Lys
            20                  25                  30

Pro Ala Glu Leu Ala Thr Ile Thr Val Lys Ala Glu Pro Thr Ala Pro
        35                  40                  45

Ala Asn Asn Thr Ser Leu Ala Glu Gly Ala Thr Ser Ile Gly Asn Ala
    50                  55                  60

Leu Asn Gly Gln Ala Gly Val Tyr Ser Ala Gln Tyr Thr Gly Gly Ala
65                  70                  75                  80

Ser Arg Pro Val Ile Arg Gly Gln Asp Gly Thr Arg Val Lys Ile Val
                85                  90                  95

Gln Asn Gly Gly Asp Val Met Asp Val Ser Ser Val Ser Pro Asp His
            100                 105                 110

Ala Val Thr Val Asp Pro Asn Ser Ala Gln Asp Ile Gln Ile Leu Asn
        115                 120                 125

Gly Ala Glu Ala Leu Leu Tyr Gly Ala Gly Ser Val Gly Gly Leu Val
    130                 135                 140

Asn Val Val Asp Glu Lys Ile Pro Thr Ser Met Pro Asp Lys Gly Tyr
```

```
            145                 150                 155                 160
        Gln Gly Lys Ala Gly Val Arg Tyr Asn Ser Gly Ser Asp Glu Leu Leu
                        165                 170                 175

Tyr Ser Gly Gln Ala Thr Val Gly Leu Gly Asp His Val Ala Leu Arg
                        180                 185                 190

Val Gly Leu Lys Arg Asp Ala Asn Asp Tyr Ile Leu Pro Arg Asp
                        195                 200                 205

Leu Gln Thr Asp Glu Arg Arg Gln Asp Ser Thr Phe Ala Asp Ser Lys
        210                 215                 220

Asn Tyr Asn Ala Gly Leu Ser Trp Ile Gly Asp Arg Gly Phe Ile Gly
        225                 230                 235                 240

Ala Ser Phe Ser Gln Arg His Asp Gln Tyr Gly Ile Pro Ala Asp Asn
                        245                 250                 255

Glu Leu Phe Gly Ser Cys Glu Arg Asp Gly Leu His Leu Val Cys Gly
                        260                 265                 270

Thr Asp Asp Pro Ser Thr Asp His Glu His Glu His Glu His Asp Ala
                        275                 280                 285

Ser Trp Ile Asn Leu Lys Glu Lys Arg Tyr Asp Leu Lys Gly Glu Leu
                        290                 295                 300

Arg Asp Pro Phe Ala Gly Phe Ala Lys Val Ala Ala Gln Ala Ser Tyr
        305                 310                 315                 320

Thr Asp Tyr Gln His Glu Glu Met His Asn Thr Asp Val Gly Thr Thr
                        325                 330                 335

Phe Lys Ser Lys Gly Ile Asp Ser Arg Val Thr Leu Glu Asn Asn Ala
                        340                 345                 350

Trp Ala Gly Trp Thr Gly Gln Ile Gly Ala Gln Tyr Thr Gln Gln Lys
                        355                 360                 365

Leu Asn Ile Val Gly Asp Glu Ser Ile Met Asp Pro Ser Lys Thr Gln
                        370                 375                 380

Arg Tyr Ser Val Phe Gly Leu Gln Gln Lys Gln Ile Asn Asn Val Asn
        385                 390                 395                 400

Leu Ala Val Ser Ser Arg Ile Asp His Gln Thr Ile Asp Ile Glu Ser
                        405                 410                 415

Asp Gln Lys Asn Tyr Thr Gly Thr Gly Tyr Ser Val Ala Gly Thr Ala
                        420                 425                 430

Ser Trp Glu Phe Ile Pro Gln Tyr Lys Leu Ser Leu Thr Thr Ser His
                        435                 440                 445

Gln Glu Arg Leu Pro Phe Ala Gln Glu Leu Tyr Ser Asp Gly Val His
        450                 455                 460

Met Ala Thr Asn Thr Tyr Glu Leu Gly Asn Asp Asp Leu Lys Lys Glu
        465                 470                 475                 480

Arg Ser Asn Asn Val Glu Leu Gly Leu His Phe Asn Asn Asp Leu Leu
                        485                 490                 495

Lys Tyr Asn Val Ser Val Phe His Asn Arg Phe Asp Asn Phe Ile Tyr
                        500                 505                 510

Ala Asn Thr Leu Asp Asp Phe Gln Gly Phe Arg Leu Ile Gln Tyr Ser
                        515                 520                 525

Gln Asp Ala Ala Lys Phe Tyr Gly Val Asp Ala Asp Leu Ser Tyr Gln
        530                 535                 540

Ile Ser Pro Val Tyr Asn Leu Gly Leu Phe Gly Asp Tyr Val Arg Gly
        545                 550                 555                 560

Lys Ile Asp Asn Glu Asn Ala Pro Arg Ile Pro Gly Gly Arg Leu Gly
                        565                 570                 575
```

```
Thr Lys Val Lys Ala Asp Phe Gly Asp Gly Trp Asp Gly Ser Ala Glu
            580                 585                 590

Tyr Tyr His Val Phe Lys Gln Asp Asp Ile Ala Asn Tyr Glu Thr Lys
            595                 600                 605

Gly Gln Ser Tyr Asn Met Leu Asn Leu Gly Val Gly Tyr Asn Gly Lys
            610                 615                 620

Tyr Ser Asn Ile Gly Asp Tyr Arg Val Phe Leu Asn Ala Asn Asn Leu
625                 630                 635                 640

Leu Asp Ser Arg Ile Tyr Gln His Glu Ser Phe Leu Ala Asn Val Pro
                645                 650                 655

Gln Val Gly Arg Asn Phe Thr Val Gly Val Asn Phe Ser Phe
            660                 665                 670

<210> SEQ ID NO 18
<211> LENGTH: 823
<212> TYPE: PRT
<213> ORGANISM: Actinobacillus minor 202

<400> SEQUENCE: 18

Met Lys Lys Asn Ala Ile Thr Leu Ser Met Ile Ser Leu Phe Ser Val
1               5                   10                  15

Cys Ala Tyr Ala Glu Glu Gly Ala Glu Leu Glu Glu Ile Gln Val Glu
            20                  25                  30

Thr Lys Met Ala Glu Ser Asn Leu Leu Gly Asp Arg Pro Asn Val Ser
            35                  40                  45

Asp Lys Leu Ile Asp Gly Lys Val Phe Lys Gln Lys Ser Thr Thr Leu
50                  55                  60

Gly Asp Ala Leu Ser Ser Glu Leu Gly Ile His Ser Asn Gln Tyr Gly
65                  70                  75                  80

Gly Gly Ala Ser Ala Pro Ile Ile Arg Gly Gln Glu Gly Lys Arg Ile
            85                  90                  95

Lys Ile Leu Gln Asn Asn Ser Asp Val Val Asp Met Ser Ile Met Ser
            100                 105                 110

Pro Asp His Ala Val Thr Val Asp Thr Thr Leu Ser Lys Gln Val Glu
            115                 120                 125

Ile Val Arg Gly Pro Ser Thr Leu Leu Tyr Ser Ser Gly Asn Ala Ala
            130                 135                 140

Gly Val Ile Asn Val Leu Asp Asn Lys Ile Pro Asn Phe Met Pro Gln
145                 150                 155                 160

Asn Gly Leu Lys Gly Glu Val Gly Phe Arg Phe Asn Thr Asn Asn Asn
            165                 170                 175

Glu Lys Leu Thr Thr Ala Gly Val Thr Phe Ala Ile His Pro Ser Ile
            180                 185                 190

Ala Val His Leu Glu Gly Leu Ser Lys Gln Ala Gly Asn Tyr Lys Thr
            195                 200                 205

Pro His Tyr Arg Tyr Gly Thr Tyr Ala Asp Lys Ala Phe Asn Arg
            210                 215                 220

Arg Glu Met Ser Tyr Gln Asn Leu Ser His Val Pro Glu Ser Trp Ala
225                 230                 235                 240

Lys Ser Gln Val Gly Thr Ala Gly Ile Ser Trp Val Tyr Glu Lys Gly
            245                 250                 255

Tyr Leu Gly Leu Ala Tyr Thr Glu Arg Gln Asp Lys Tyr Gly Leu Pro
            260                 265                 270

Ala His Asn His Ile Tyr Glu Gly Cys Ala Val Arg Ile Ile Asp Glu
```

```
            275                 280                 285
Ser Val Lys Gln Gln Tyr Pro Tyr Leu Phe Pro Tyr Pro Glu Leu Ala
290                 295                 300

Asp Asp Arg His Leu Phe Trp Ala Asn Pro Gly Val Asn Met Ala Asp
305                 310                 315                 320

Cys His Ala His Gly Leu Ser Ala Thr Pro Tyr Val Asp Leu Lys Ser
            325                 330                 335

Gln Arg Tyr Asp Phe Arg Gly Glu Ile Ile Glu Pro Phe Lys Tyr Val
            340                 345                 350

Asp Lys Leu Arg Phe Asn Ala Ser His Val Asn Tyr Gln His Gly Glu
            355                 360                 365

Ile Glu Gly Glu Lys Ala Ala Asn Leu Phe Lys Asn Lys Gly Leu Thr
            370                 375                 380

Thr Arg Leu Glu Phe Val His Ser Pro Val Gly Asn Leu Thr Gly Ile
385                 390                 395                 400

Trp Gly Ile Gln Tyr Leu Glu Gln Lys Asn Ser Ala Leu Ser Pro Glu
            405                 410                 415

Asp Ser Ala Thr His Lys His Arg Gly Val Gln Gln Leu Leu Asn Asn
            420                 425                 430

Asn Lys Met Gln Asn Trp Ser Leu Phe Gly Leu Glu Ser Tyr Gln Trp
            435                 440                 445

Asn Asp Ile Thr Phe Glu Ala Ser Ala Arg Leu Glu Lys Gln Lys Val
            450                 455                 460

Thr Lys Asp Tyr Asp His Glu Lys Val Arg Asn Glu Phe Leu Ser Leu
465                 470                 475                 480

Gly Tyr Ile Asp Ser Lys Arg Pro Glu Thr Ala His Ala Met Asp Asn
            485                 490                 495

Tyr Tyr Thr Leu Thr Gln Ala His Lys Glu Thr Ala His Ser Phe Ala
            500                 505                 510

Leu Gly Ala His Trp Ala Phe Lys Glu Asn His Lys Leu Ser Leu Thr
            515                 520                 525

Ala Ser His Gln Glu Arg Leu Pro Asn Ala Gln Glu Leu Tyr Ala His
            530                 535                 540

Gly Met His Leu Ala Thr Asn Ser Phe Glu Met Gly Asn Lys Gly Leu
545                 550                 555                 560

Ser Lys Glu Lys Ser Asn Asn Leu Asp Leu Gly Leu Ser Tyr Glu Gly
            565                 570                 575

Asp Lys Phe Ser Tyr Tyr Leu Ser Gly Phe Leu Tyr Asn Phe Asp Asn
            580                 585                 590

Tyr Thr Tyr Leu Tyr Thr Leu Asn Ser Gly Arg Gly Pro Ala Ser Met
            595                 600                 605

Lys Gln Asp Ser Asp Leu Arg Ile Asn Arg Tyr Met Gln Ala Pro Ala
            610                 615                 620

Arg Phe Tyr Gly Val Glu Val Asn Leu Gly Tyr Gln Val Thr Pro Lys
625                 630                 635                 640

His His Ile Ser Leu Phe Gly Asp Tyr Val Lys Gly Tyr Leu Lys Ala
            645                 650                 655

His Asp Ile Arg Thr Ser Asp Lys Val Ser Tyr Met Asp Asn Pro Glu
            660                 665                 670

Phe Thr Lys Ala Val Glu Lys Leu Met Gln Glu Asn Pro Lys Met Lys
            675                 680                 685

Pro Trp Arg Ala Ala Ser Lys Val Arg Asn Glu Met Gly Ile Glu Arg
690                 695                 700
```

```
Gln Ile Arg Val Gln Glu Pro Val Tyr Glu Gln Pro Lys Met Tyr
705                 710                 715                 720

Thr Pro Arg Leu Pro Pro Ile Arg Val Gly Ala Arg Ile Lys Ser Asp
                725                 730                 735

Phe Thr Glu Asn Leu Lys Gly Glu Leu Glu Tyr Tyr His Val Phe Thr
            740                 745                 750

Gln His Arg Ile Ser Lys Phe Glu Asn Val Thr Gln Gly His Asn Met
        755                 760                 765

Leu Asn Leu Gly Leu Thr Tyr Gln Asn Lys Leu Ala Lys Gly Glu Tyr
    770                 775                 780

Glu Ile Phe Leu Lys Ala Asn Asn Leu Leu Asn Glu Glu Val Tyr Ala
785                 790                 795                 800

His Glu Thr Phe Leu Pro Tyr Ile Pro Gln Ile Gly Arg Asn Phe Asn
                805                 810                 815

Val Gly Phe Asn Tyr Lys Phe
                820

<210> SEQ ID NO 19
<211> LENGTH: 823
<212> TYPE: PRT
<213> ORGANISM: Actinobacillus minor NM305

<400> SEQUENCE: 19

Met Lys Lys Asn Ala Ile Thr Leu Ser Met Ile Ser Leu Phe Ser Val
1               5                   10                  15

Cys Ala Tyr Ala Glu Glu Gly Ala Glu Leu Glu Glu Ile Gln Val Glu
            20                  25                  30

Ala Lys Val Ala Glu Ser Asn Leu Leu Gly Glu Arg Pro Asn Val Ser
        35                  40                  45

Asp Lys Leu Ile Asp Gly Lys Val Phe Lys Gln Lys Ser Thr Thr Leu
    50                  55                  60

Gly Asp Ala Leu Ser Ser Glu Leu Gly Ile His Ser Asn Gln Tyr Gly
65                  70                  75                  80

Gly Gly Ala Ser Ala Pro Ile Ile Arg Gly Gln Glu Gly Lys Arg Ile
                85                  90                  95

Lys Ile Leu Gln Asn Asn Ser Asp Val Val Asp Met Ser Thr Met Ser
            100                 105                 110

Pro Asp His Ala Val Thr Val Asp Thr Thr Leu Ser Lys Gln Val Glu
        115                 120                 125

Ile Val Arg Gly Pro Ser Thr Leu Leu Tyr Ser Ser Gly Asn Ala Ala
    130                 135                 140

Gly Val Ile Asn Val Leu Asp Asn Lys Ile Pro Asn Phe Met Pro Gln
145                 150                 155                 160

Asn Gly Leu Lys Gly Glu Val Gly Phe Arg Phe Asn Thr Asn Asn Asn
                165                 170                 175

Glu Lys Leu Thr Thr Ala Gly Val Thr Phe Ala Ile His Pro Ser Ile
            180                 185                 190

Ala Val His Leu Glu Gly Leu Ser Lys Gln Ala Gly Asn Tyr Lys Thr
        195                 200                 205

Pro His Tyr Arg Tyr Gly Thr Tyr Ala Asp Lys Ala Phe Asn Arg
    210                 215                 220

Arg Glu Met Ser Tyr Gln Asn Leu Ser Tyr Val Pro Glu Ser Trp Ala
225                 230                 235                 240

Lys Ser Gln Val Gly Thr Ala Gly Ile Ser Trp Val His Glu Lys Gly
```

-continued

```
                245                 250                 255
Tyr Leu Gly Leu Ala Tyr Thr Glu Arg Gln Asp Lys Tyr Gly Leu Pro
            260                 265                 270

Ala His Asn His Ile Tyr Glu Gly Cys Ala Val Arg Ile Ile Asp Glu
        275                 280                 285

Ser Val Lys Gln Gln Tyr Pro Tyr Leu Phe Pro Tyr Pro Glu Leu Ala
    290                 295                 300

Asp Asp Leu His Leu Phe Trp Ala Asn Pro Gly Val Asn Met Ala Asp
305                 310                 315                 320

Cys His Ala His Gly Leu Ser Ala Thr Pro Tyr Val Asp Leu Lys Ser
                325                 330                 335

Gln Arg Tyr Asp Phe Arg Gly Glu Ile Ile Glu Pro Phe Lys Tyr Val
            340                 345                 350

Asp Lys Leu Arg Phe Asn Ala Ser His Val Asn Tyr Gln His Gly Glu
        355                 360                 365

Ile Glu Gly Glu Lys Ala Ala Asn Leu Phe Lys Asn Lys Gly Leu Thr
    370                 375                 380

Thr Arg Leu Glu Phe Val His Ser Pro Ile Gly Asn Leu Thr Gly Ile
385                 390                 395                 400

Trp Gly Ile Gln Tyr Leu Glu Gln Lys Asn Ser Ala Leu Ser Pro Glu
                405                 410                 415

Asp Ser Ala Thr His Lys His Arg Gly Val Gln Gln Leu Leu Asn Asn
            420                 425                 430

Asn Lys Met Gln Asn Trp Ser Leu Phe Gly Leu Glu Ser Tyr Gln Trp
        435                 440                 445

Asn Asp Ile Thr Phe Glu Ala Ser Ala Arg Leu Glu Lys Gln Lys Val
    450                 455                 460

Thr Lys Asp Tyr Asp His Glu Lys Val Arg Asn Glu Phe Leu Ser Leu
465                 470                 475                 480

Gly Tyr Ile Asp Ser Lys Arg Pro Glu Thr Ala His Ala Met Asp Asn
                485                 490                 495

Tyr Tyr Thr Leu Thr Gln Ala Tyr Lys Glu Thr Ala Arg Ser Phe Ala
            500                 505                 510

Leu Gly Ala His Trp Ala Phe Lys Glu Asn His Lys Leu Ser Leu Thr
        515                 520                 525

Ala Ser His Gln Glu Arg Leu Pro Asn Ala Gln Glu Leu Tyr Ala His
    530                 535                 540

Gly Met His Leu Ala Thr Asn Ser Phe Glu Met Gly Asn Lys Gly Leu
545                 550                 555                 560

Ser Lys Glu Lys Ser Asn Asn Leu Asp Leu Gly Leu Ser Tyr Glu Gly
                565                 570                 575

Asp Lys Phe Ser Tyr Tyr Leu Ser Gly Phe Leu Tyr Asn Phe Asp Asn
            580                 585                 590

Tyr Thr Tyr Leu Tyr Thr Leu Asn Ser Gly Arg Gly Pro Ala Ser Met
        595                 600                 605

Lys Gln Asp Ser Asp Leu Arg Ile Asn Arg Tyr Met Gln Ala Pro Ala
    610                 615                 620

Arg Phe Tyr Gly Val Glu Val Asn Phe Gly Tyr Gln Val Thr Pro Lys
625                 630                 635                 640

His His Ile Ser Leu Phe Gly Asp Tyr Val Lys Gly Tyr Leu Lys Ala
                645                 650                 655

His Asp Ile Arg Thr Ser Asp Lys Val Ser Tyr Val Asp Asn Pro Glu
            660                 665                 670
```

```
Phe Thr Lys Ala Val Glu Lys Leu Met Gln Glu Asn Pro Lys Met Lys
            675                 680                 685

Pro Trp Arg Ala Ala Ser Lys Val Arg Asn Glu Met Gly Ile Glu Arg
    690                 695                 700

Gln Ile Arg Val Gln Glu Pro Ala Tyr Glu Gln Pro Lys Met Tyr
705                 710                 715                 720

Thr Pro Arg Leu Pro Pro Ile Arg Val Gly Ala Arg Ile Lys Ser Asp
                725                 730                 735

Phe Thr Glu Asn Leu Lys Gly Glu Leu Glu Tyr Tyr His Val Phe Thr
                740                 745                 750

Gln His Arg Ile Ser Lys Phe Glu Asn Val Thr Gln Gly His Asn Met
            755                 760                 765

Leu Asn Leu Gly Leu Thr Tyr Gln Asn Lys Leu Ala Lys Gly Glu Tyr
770                 775                 780

Glu Ile Phe Leu Lys Ala Asn Asn Leu Leu Asn Glu Glu Val Tyr Ala
785                 790                 795                 800

His Glu Thr Phe Leu Pro Tyr Ile Pro Gln Ile Gly Arg Asn Phe Asn
                805                 810                 815

Ile Gly Phe Asn Tyr Lys Phe
            820

<210> SEQ ID NO 20
<211> LENGTH: 782
<212> TYPE: PRT
<213> ORGANISM: Actinobacillus pleuropneumoniae L20

<400> SEQUENCE: 20

Met Leu Ile Ser Ala Gln Phe Ser Pro Leu Val Trp Ala Asn Asn Asn
1               5                   10                  15

Asp Val Ala Val Leu Asp Glu Val Ser Val Val Gly Ser Thr Pro Ser
                20                  25                  30

Ile Ser Gln Gly Ser Glu Val Thr Leu Leu Lys Val Ser Asp Lys Ile
            35                  40                  45

Ile Ala Gly Lys Glu Phe Lys Lys Arg Ser Ala Thr Leu Gly Asn Ala
        50                  55                  60

Leu Ala Ala Glu Leu Gly Val His Ser Asn Pro Phe Gly Gly Ala
65              70                  75                  80

Ser Lys Pro Ile Ile Arg Gly Gln Gly Ala Arg Ile Arg Ile Leu
                85                  90                  95

Gln Asn Gly Ser Asp Val Ile Asp Met Ser Asn Leu Ser Pro Asp His
            100                 105                 110

Ala Val Val Ala Asp Ser Leu Leu Ala Lys Gln Val Glu Ile Leu Arg
            115                 120                 125

Gly Ser Ser Thr Leu Leu Tyr Ala Ser Ser Pro Ala Gly Ile Val
130                 135                 140

Asn Val Val Asp Lys Arg Ile Pro Thr Glu Ile Pro Lys Gly Tyr
145                 150                 155                 160

Glu Val Glu Leu Asn Ser Arg Phe Asp Thr Ala Ala Lys Glu Lys Val
                165                 170                 175

Gly Ala Leu Gly Ala Thr Phe Gly Ile Gly Lys His Ile Ala Val Arg
            180                 185                 190

Ala Glu Gly Leu Thr Arg His Ser Asp Asn Tyr Arg Val Pro Gly Ile
        195                 200                 205

Asn Leu Gly Glu Arg Leu Asn Tyr Val Pro Asp Thr Tyr Asn Lys Ser
```

```
                210                 215                 220
Lys Val Gly Thr Leu Gly Leu Ser Phe Val Gly Glu Gln Gly Tyr Ile
225                 230                 235                 240

Gly Ala Ser Tyr Ser Lys Arg Arg Asp Asn Tyr Gly Leu Pro Gly His
                245                 250                 255

Asn His Lys Phe Asp Phe Cys Ile Gly His Ile Tyr Gly Asn Lys Gln
                260                 265                 270

Gly Lys Tyr Ala Tyr Thr Tyr Leu Tyr Pro His Leu Ile Gly Glu Glu
            275                 280                 285

Asn Ile Gly Ser Asn Pro His Phe His Cys Gly Thr Asp His Ala Glu
            290                 295                 300

Asp Gly Thr His Ser His Asp Asn Pro Phe Glu His Asp His Asp His
305                 310                 315                 320

Thr His Pro Gly Pro Trp Val Asp Leu Glu Ser Lys Arg Phe Asp Val
                325                 330                 335

Lys Ala Glu Leu Arg Gln Pro Phe Lys Gly Ile Asp Lys Ile Lys Val
                340                 345                 350

Ser Tyr Ala Asp Ala Asp Tyr Tyr His Asp Glu Lys Asp Ala Gly Val
            355                 360                 365

Leu Ala Thr Arg Tyr His Lys Gln Leu Lys Lys Asp Gln Asp Tyr Gly
            370                 375                 380

Lys Pro Val Asn Ile Phe Lys Asn Arg Gly Lys Asn Ala Arg Leu Glu
385                 390                 395                 400

Ile Tyr His Ala Pro Leu Gly Gly Leu Thr Gly Val Trp Gly Val Gln
                405                 410                 415

Tyr Gln Thr Gln Lys Ser Ser Met His Ala Pro Lys Asp Arg Glu Val
                420                 425                 430

Lys Phe Pro Leu Val Glu Asn Thr Asn Lys Gln Met Ser Leu Phe Gly
            435                 440                 445

Ile Glu Gln Tyr Met Trp Asp Asn Phe Ala Leu Glu Phe Ala Gly Arg
            450                 455                 460

Val Glu Lys Gln Lys Ile Glu Ile Glu Tyr Asp Arg Asn Glu Ile Lys
465                 470                 475                 480

Arg Leu Gln Asp His Tyr Arg Ile Ser Gly Gly Lys Gln Val Glu Pro
                485                 490                 495

Asp Leu Ser Pro Tyr Asn Gln Asn Ala Tyr Ala Tyr Ser Ser Thr Leu
            500                 505                 510

Asn Trp Phe Phe His Pro Asp Tyr Gln Leu Ser Phe Thr Ala Ser His
            515                 520                 525

Asn Glu Arg Phe Pro Thr Pro Met Glu Leu Tyr Tyr His Gly Gln His
            530                 535                 540

Ile Ala Thr Asn Ser Phe Glu Tyr Gly Asn Lys Asp Leu Lys Lys Glu
545                 550                 555                 560

Gln Ser Asn Asn Val Glu Leu Gly Leu Gly Tyr Gln Thr Glu Arg Val
                565                 570                 575

Gly Tyr Lys Val Asn Val Tyr Tyr Asn His Phe Lys Asn Tyr Ile Tyr
                580                 585                 590

Asn Glu Asn Leu Phe Arg Glu Asn Gln Leu Phe Met Arg Arg Tyr Asn
            595                 600                 605

Gln Ala Lys Ala Arg Phe Tyr Gly Ile Glu Ala Glu Ala Ser Tyr Arg
            610                 615                 620

Phe Asn Asp Lys Tyr Gln Ala Thr Ile Phe Gly Asp Met Val Arg Gly
625                 630                 635                 640
```

```
Trp Leu Thr Asn Leu Pro Pro Leu Thr Val Asn Ser Asp Tyr Ser Val
            645                 650                 655

Phe Lys Asp Tyr Leu Pro Lys Asp Ala Lys Pro Gly Glu Asp Tyr Leu
            660                 665                 670

Ile Tyr Arg Ala Asp Gln Asn Thr Pro Arg Thr Pro Val Arg Leu
            675                 680                 685

Gly Phe Arg Phe Asn Ala Glu Phe Thr Pro Asn Trp Ser Gly Asp Leu
            690                 695                 700

Glu Leu Ile Arg Thr Phe Thr Gln Arg Arg Thr Ser Gln Leu Glu Tyr
705                 710                 715                 720

Ile Thr Glu Gly Asn Thr Met Leu Asn Ile Gly Val Ala Tyr Ser Asn
            725                 730                 735

Lys Trp Lys Asp Leu Asp Tyr Lys Ile Ser Leu Asn Gly Thr Asn Leu
            740                 745                 750

Leu Asn Gln Pro Val Tyr Ile His Thr Ser Tyr His Gln Phe Val Pro
            755                 760                 765

Gln Thr Gly Arg Asn Phe Ile Leu Val Val Asn Val Lys Phe
            770                 775                 780

<210> SEQ ID NO 21
<211> LENGTH: 782
<212> TYPE: PRT
<213> ORGANISM: Actinobacillus pleuropneumoniae serovar 1 str. 4074

<400> SEQUENCE: 21

Met Leu Ile Ser Ala Gln Phe Ser Pro Leu Val Trp Ala Asn Asn Asn
1               5                   10                  15

Asp Val Ala Val Leu Asp Glu Val Ser Val Val Gly Ser Thr Pro Ser
            20                  25                  30

Ile Ser Gln Gly Ser Glu Val Thr Leu Leu Lys Val Ser Asp Lys Ile
            35                  40                  45

Ile Ala Gly Lys Glu Phe Lys Lys Arg Ser Ala Thr Leu Gly Asn Ala
        50                  55                  60

Leu Ala Ala Glu Leu Gly Val His Ser Asn Pro Phe Gly Gly Gly Ala
65                  70                  75                  80

Ser Lys Pro Ile Ile Arg Gly Gln Glu Gly Ala Arg Ile Arg Ile Leu
            85                  90                  95

Gln Asn Gly Ser Asp Val Ile Asp Met Ser Asn Leu Ser Pro Asp His
            100                 105                 110

Ala Val Val Ala Asp Ser Leu Leu Ala Lys Gln Val Glu Ile Leu Arg
            115                 120                 125

Gly Ser Ser Thr Leu Leu Tyr Ala Ser Ser Pro Ala Gly Ile Val
130                 135                 140

Asn Val Val Asp Lys Arg Ile Pro Thr Glu Ile Pro Glu Lys Gly Tyr
145                 150                 155                 160

Glu Val Glu Leu Asn Ser Arg Phe Asp Thr Ala Ala Lys Glu Lys Val
            165                 170                 175

Gly Ala Leu Gly Ala Thr Phe Gly Ile Gly Lys His Ile Ala Val Arg
            180                 185                 190

Ala Glu Gly Leu Thr Arg His Ser Asp Asn Tyr Arg Val Pro Gly Ile
            195                 200                 205

Asn Leu Gly Glu Arg Leu Asn Tyr Val Pro Asp Thr Tyr Asn Lys Ser
210                 215                 220

Lys Val Gly Thr Leu Gly Leu Ser Phe Val Gly Glu Gln Gly Tyr Ile
```

-continued

```
            225                 230                 235                 240
Gly Ala Ser Tyr Ser Lys Arg Arg Asp Asn Tyr Gly Leu Pro Gly His
                245                 250                 255
Asn His Lys Phe Asp Phe Cys Ile Gly His Ile Tyr Gly Asn Lys Gln
                260                 265                 270
Gly Lys Tyr Ala Tyr Thr Tyr Leu Tyr Pro His Leu Ile Gly Glu Glu
                275                 280                 285
Asn Ile Gly Ser Asn Pro His Phe His Cys Gly Thr Asp His Ala Glu
            290                 295                 300
Asp Gly Thr His Ser His Asp Asn Pro Phe Gly His Asp His Asp His
305                 310                 315                 320
Thr His Pro Gly Pro Trp Val Asp Leu Glu Ser Lys Arg Phe Asp Val
                325                 330                 335
Lys Ala Glu Leu Arg Gln Pro Phe Lys Gly Ile Asp Lys Ile Lys Val
                340                 345                 350
Ser Tyr Ala Asp Ala Asp Tyr Tyr His Asp Glu Lys Asp Ala Gly Val
                355                 360                 365
Leu Ala Thr Arg Tyr His Lys Gln Leu Lys Lys Asp Gln Asp Tyr Gly
            370                 375                 380
Lys Pro Val Asn Ile Phe Lys Asn Arg Gly Lys Asn Ala Arg Leu Glu
385                 390                 395                 400
Ile Tyr His Ala Pro Leu Gly Gly Leu Thr Gly Val Trp Gly Val Gln
                405                 410                 415
Tyr Gln Thr Gln Lys Ser Ser Met His Ala Pro Lys Asp Arg Glu Val
                420                 425                 430
Lys Phe Pro Leu Val Glu Asn Thr Asn Lys Gln Met Ser Leu Phe Gly
                435                 440                 445
Ile Glu Gln Tyr Met Trp Asp Asn Phe Ala Leu Glu Phe Ala Gly Arg
            450                 455                 460
Val Glu Lys Gln Lys Ile Glu Ile Glu Tyr Asp Arg Asn Glu Ile Lys
465                 470                 475                 480
Arg Leu Gln Asp His Tyr Arg Ile Ser Gly Gly Lys Gln Val Glu Pro
                485                 490                 495
Asp Leu Ser Pro Tyr Asn Gln Asn Ala Tyr Ala Tyr Ser Ser Thr Leu
                500                 505                 510
Asn Trp Phe Phe His Pro Asp Tyr Gln Leu Ser Phe Thr Ala Ser His
            515                 520                 525
Asn Glu Arg Phe Pro Thr Pro Met Glu Leu Tyr Tyr His Gly Gln His
            530                 535                 540
Ile Ala Thr Asn Ser Phe Glu Tyr Gly Asn Lys Asp Leu Lys Lys Glu
545                 550                 555                 560
Gln Ser Asn Asn Val Glu Leu Gly Leu Gly Tyr Gln Thr Glu Arg Val
                565                 570                 575
Gly Tyr Lys Val Asn Val Tyr Asn His Phe Lys Asn Tyr Ile Tyr
                580                 585                 590
Asn Glu Asn Leu Phe Arg Glu Asn Gln Leu Phe Met Arg Arg Tyr Asn
            595                 600                 605
Gln Ala Lys Ala Arg Phe Tyr Gly Ile Glu Ala Glu Ala Ser Tyr Arg
            610                 615                 620
Phe Asn Asp Lys Tyr Gln Ala Thr Ile Phe Gly Asp Met Val Arg Gly
625                 630                 635                 640
Trp Leu Thr Asn Leu Pro Pro Leu Thr Val Asn Ser Asp Tyr Ser Val
                645                 650                 655
```

```
Phe Lys Asp Tyr Leu Pro Lys Asp Ala Lys Pro Gly Glu Asp Tyr Leu
                660                 665                 670

Ile Tyr Arg Ala Asp Gln Asn Thr Pro Arg Thr Pro Val Arg Leu
            675                 680                 685

Gly Phe Arg Phe Asn Ala Glu Phe Thr Pro Asn Trp Ser Gly Asp Leu
    690                 695                 700

Glu Leu Ile Arg Thr Phe Thr Gln Arg Arg Thr Ser Gln Leu Glu Tyr
705                 710                 715                 720

Ile Thr Glu Gly Asn Thr Met Leu Asn Ile Gly Val Ala Tyr Ser Asn
                725                 730                 735

Lys Trp Lys Asp Leu Asp Tyr Lys Ile Ser Leu Asn Gly Thr Asn Leu
            740                 745                 750

Leu Asn Gln Pro Val Tyr Ile His Thr Ser Tyr His Gln Phe Val Pro
        755                 760                 765

Gln Thr Gly Arg Asn Phe Ile Leu Val Val Asn Val Lys Phe
    770                 775                 780

<210> SEQ ID NO 22
<211> LENGTH: 790
<212> TYPE: PRT
<213> ORGANISM: Actinobacillus pleuropneumoniae serovar 3 str. JL03

<400> SEQUENCE: 22

Met Phe Asn Lys Lys Leu Leu Ala Val Leu Ile Ser Ala Gln Phe Ser
1               5                   10                  15

Pro Leu Val Trp Ala Asn Asn Asn Asp Val Ala Val Leu Asp Glu Val
                20                  25                  30

Ser Val Val Gly Ser Thr Pro Ser Ile Ser Gln Gly Ser Glu Val Thr
            35                  40                  45

Leu Leu Lys Val Ser Asp Lys Ile Ile Ala Gly Lys Glu Phe Lys Lys
        50                  55                  60

Arg Ser Ala Thr Leu Gly Asn Ala Leu Ala Glu Leu Gly Val His
65                  70                  75                  80

Ser Asn Pro Phe Gly Gly Ala Ser Lys Pro Ile Ile Arg Gly Gln
                85                  90                  95

Glu Gly Ala Arg Ile Arg Ile Leu Gln Asn Gly Ser Asp Val Ile Asp
            100                 105                 110

Met Ser Asn Leu Ser Pro Asp His Ala Val Val Ala Asp Ser Leu Leu
        115                 120                 125

Ala Lys Gln Val Glu Ile Leu Arg Gly Ser Ser Thr Leu Leu Tyr Ala
    130                 135                 140

Ser Ser Ser Pro Ala Gly Ile Val Asn Val Val Asp Lys Arg Ile Pro
145                 150                 155                 160

Thr Glu Ile Pro Glu Lys Gly Tyr Glu Val Glu Leu Asn Ser Arg Phe
                165                 170                 175

Asp Thr Ala Ala Lys Glu Lys Val Gly Ala Leu Gly Ala Thr Phe Gly
            180                 185                 190

Ile Gly Lys His Ile Ala Val Arg Ala Glu Gly Leu Thr Arg His Ser
        195                 200                 205

Asp Asn Tyr Arg Val Pro Gly Ile Asn Leu Gly Glu Arg Leu Asn Tyr
    210                 215                 220

Val Pro Asp Thr Tyr Asn Lys Ser Lys Val Gly Thr Leu Gly Leu Ser
225                 230                 235                 240

Phe Val Gly Glu Gln Gly Tyr Ile Gly Ala Ser Tyr Ser Lys Arg Arg
```

```
                    245                 250                 255
Asp Asn Tyr Gly Leu Pro Gly His Asn His Lys Phe Asp Phe Cys Ile
            260                 265                 270

Gly His Ile Tyr Gly Asn Lys Gln Gly Lys Tyr Ala Tyr Thr Tyr Leu
            275                 280                 285

Tyr Pro His Leu Ile Gly Glu Asn Ile Gly Ser Asn Pro His Phe
            290                 295                 300

His Cys Gly Thr Asp His Ala Glu Asp Gly Thr His Ser His Asp Asn
305                 310                 315                 320

Pro Phe Gly His Asp His Thr His Pro Gly Pro Trp Val Asp
                325                 330                 335

Leu Glu Ser Lys Arg Phe Asp Val Lys Ala Glu Leu Arg Gln Pro Phe
                340                 345                 350

Lys Gly Ile Asp Lys Ile Lys Val Ser Tyr Ala Asp Ala Asp Tyr Tyr
                355                 360                 365

His Asp Glu Lys Asp Ala Gly Val Leu Ala Thr Arg Tyr His Lys Gln
370                 375                 380

Leu Lys Lys Asp Gln Asp Tyr Gly Lys Pro Val Asn Ile Phe Lys Asn
385                 390                 395                 400

Arg Gly Lys Asn Ala Arg Leu Glu Ile Tyr His Ala Pro Leu Gly Gly
                405                 410                 415

Leu Thr Gly Val Trp Gly Val Gln Tyr Gln Thr Gln Lys Ser Ser Met
                420                 425                 430

His Ala Pro Lys Asp Arg Glu Val Lys Phe Pro Leu Val Glu Asn Thr
                435                 440                 445

Asn Lys Gln Met Ser Leu Phe Gly Ile Glu Gln Tyr Met Trp Asp Asn
450                 455                 460

Phe Ala Leu Glu Phe Ala Gly Arg Val Glu Lys Gln Lys Ile Glu Ile
465                 470                 475                 480

Glu Tyr Asp Arg Asn Glu Ile Lys Arg Leu Gln Asp His Tyr Arg Ile
                485                 490                 495

Ser Gly Gly Lys Gln Val Glu Pro Asp Leu Ser Pro Tyr Asn Gln Asn
                500                 505                 510

Ala Tyr Ala Tyr Ser Ser Thr Leu Asn Trp Phe Phe His Pro Asp Tyr
            515                 520                 525

Gln Leu Ser Phe Thr Ala Ser His Asn Glu Arg Phe Pro Thr Pro Met
            530                 535                 540

Glu Leu Tyr Tyr His Gly Gln His Ile Ala Thr Asn Ser Phe Glu Tyr
545                 550                 555                 560

Gly Asn Lys Asp Leu Lys Lys Glu Gln Ser Asn Asn Val Glu Leu Gly
                565                 570                 575

Leu Gly Tyr Gln Thr Glu Arg Val Gly Tyr Lys Val Asn Val Tyr Tyr
            580                 585                 590

Asn His Phe Lys Asn Tyr Ile Tyr Asn Glu Asn Leu Phe Arg Glu Asn
            595                 600                 605

Gln Leu Phe Met Arg Arg Tyr Asn Gln Ala Lys Ala Arg Phe Tyr Gly
    610                 615                 620

Ile Glu Ala Glu Ala Ser Tyr Arg Phe Asn Asp Lys Tyr Gln Ala Thr
625                 630                 635                 640

Ile Phe Gly Asp Met Val Arg Gly Trp Leu Thr Asn Leu Pro Pro Leu
                645                 650                 655

Thr Val Asn Ser Asp Tyr Ser Val Phe Lys Asp Tyr Leu Pro Lys Asp
                660                 665                 670
```

```
Ala Lys Pro Gly Glu Asp Tyr Leu Ile Tyr Arg Ala Asp Gln Asn Thr
        675                 680                 685

Pro Arg Thr Pro Pro Val Arg Leu Gly Phe Arg Phe Asn Ala Glu Phe
690                 695                 700

Thr Pro Asn Trp Ser Gly Asp Leu Glu Leu Ile Arg Thr Phe Thr Gln
705                 710                 715                 720

Arg Arg Thr Ser Gln Leu Glu Tyr Ile Thr Glu Gly Asn Thr Met Leu
                725                 730                 735

Asn Ile Gly Val Ala Tyr Ser Asn Lys Trp Lys Asp Leu Asp Tyr Lys
            740                 745                 750

Ile Ser Leu Asn Gly Thr Asn Leu Leu Asn Gln Pro Val Tyr Ile His
        755                 760                 765

Thr Ser Tyr His Gln Phe Val Pro Gln Thr Gly Arg Asn Phe Ile Leu
770                 775                 780

Val Val Asn Val Lys Phe
785                 790

<210> SEQ ID NO 23
<211> LENGTH: 689
<212> TYPE: PRT
<213> ORGANISM: Alcanivorax borkumensis SK2

<400> SEQUENCE: 23

Met Thr Phe Arg Arg Gln Thr Leu Ser Gly Cys Val Ala Val Ala Leu
1               5                   10                  15

Leu Ala Pro Thr Ala Val Leu Ala Glu Ala Glu Asn Asn Ser Ala Gly
            20                  25                  30

Leu Glu Lys Ala His Glu Leu Lys Gln Val Asp Val Ser Ala Leu Pro
        35                  40                  45

Leu Gly Ser Ser Ser Ser Thr Pro Tyr Ser Val Met Asp Gln Gln
    50                  55                  60

Thr Leu Thr Gln Lys Asn Lys Asp Thr Leu Gly Glu Thr Leu Lys Asn
65                  70                  75                  80

Gln Pro Gly Val His Ser Asp Thr Phe Gly Gly Gly Ala Ser Arg Pro
                85                  90                  95

Val Ile Arg Gly Gln Gly Gly Pro Arg Ile Gly Ile Leu Ser Asp Gly
            100                 105                 110

Ser Gln Val Leu Asp Ala Ser Ile Ser Pro Asp His Ala Ile Thr
        115                 120                 125

Val Asp Pro Met Leu Ala Arg Gln Ile Glu Val Leu Arg Gly Pro Ser
    130                 135                 140

Thr Leu Leu Tyr Gly Ser Gly Ala Ser Gly Gly Ile Val Asn Val Leu
145                 150                 155                 160

Asp Asn Arg Ile Pro Thr Gln Arg Pro Leu Glu Val Glu Gly Phe
                165                 170                 175

Val Ala Ile Arg Ala Asn Ser Val Ala Asp Glu Asn Ala Thr Ala Ala
            180                 185                 190

Gly Ile Thr Val Ser Ala Thr Asp His Leu Val Phe Arg Val Glu Gly
        195                 200                 205

Ser Arg Arg Asp Ala Glu Asp Tyr Glu Val Asn Gly Phe Glu Glu Leu
    210                 215                 220

Thr Val Pro Gly Thr Tyr Ala Glu Ser Asp Asn Ala Ser Ile Gly Ala
225                 230                 235                 240

Ser Trp Ile Gly Asp Gln Gly Phe Phe Gly Met Ala Tyr Ser Tyr Arg
```

```
            245                 250                 255
Arg Asp Asn Tyr Gly Leu Pro Gly His Ser His Glu Phe Glu Glu Cys
            260                 265                 270

Glu Ala Asn Gly Thr Ser Leu Ser Cys Pro Ser Gly His Asp His
        275                 280                 285

Asp His Glu Gly Glu Ile Val Pro Tyr Val Asp Leu Ala Ser Arg Arg
290                 295                 300

Val Asp Ala Arg Gly Glu Tyr Arg Asp Pro Phe Ser Gly Ile Ala Ala
305                 310                 315                 320

Ile Arg Phe Arg Gly Asn His Thr Asp Tyr Arg His His Glu Ile Glu
                325                 330                 335

Glu Gly Ala Ile Gly Ser Thr Phe Thr Asn Lys Gly Gly Asp Ala Arg
            340                 345                 350

Leu Glu Val Glu His Lys Pro Phe Gly Asn Trp Arg Gly Val Val Gly
            355                 360                 365

Leu Gln Tyr Thr Asn Phe Asp Phe Ser Ser Leu Gly His Glu Ala Phe
        370                 375                 380

Val Pro Lys Thr Glu Thr Glu Ser Ile Ala Ile Phe Ala Val Glu Glu
385                 390                 395                 400

Tyr Val Leu Asn Glu Gln Trp Ser Phe Glu Leu Gly Ala Arg Gln Glu
                405                 410                 415

His Leu Thr Gln Thr Pro Asp Gln Arg Asn Gly Gln Ala Leu Ala Lys
            420                 425                 430

Val Thr Ala Asp Asn Ala Ser Phe Ser Gly Ala Ala Asn Trp Ala Phe
        435                 440                 445

Val Pro Gly Tyr Glu Leu Val Leu Ser Val Gly His Ser Gly Arg Ala
450                 455                 460

Pro Ser Ala Gln Glu Leu Tyr Ala Gln Gly Val His Leu Ala Thr Asn
465                 470                 475                 480

Thr Tyr Glu Cys Gly Leu Leu Ser Asp Cys Gly Gly Gly Gln Arg Asp
                485                 490                 495

Leu Asp Asp Glu Val Ser Leu Asn Ala Asn Leu Asn Leu Arg Lys Thr
            500                 505                 510

Arg Gly Asp Trp Leu Phe Asp Leu Gly Val Phe Glu Asn Arg Ile Asn
        515                 520                 525

Asn Tyr Ile Tyr Ala Arg Thr Leu Asp Gln Gln Glu Asp Phe Arg Leu
        530                 535                 540

Ile Lys Tyr Ser Gln Arg Asp Ala Thr Phe Thr Gly Ala Glu Ala Ser
545                 550                 555                 560

Val Ser Tyr Tyr Gly Ile Asp Pro Val Gly Ile Thr Val Phe Gly Asp
                565                 570                 575

Met Val Arg Ala Thr Phe Asp Asp Gly Gly Tyr Leu Pro Arg Ile Pro
            580                 585                 590

Ala Lys Arg Leu Gly Thr Arg Leu Asn Ser Tyr Leu Gly Asn Phe Asp
        595                 600                 605

Gly Glu Leu Glu Val Tyr Arg Ser Phe Val Gln Asp Gln Leu Ser Gly
        610                 615                 620

Phe Glu Glu Arg Thr Ala Ala Tyr Asp Met Val Asn Ala Thr Leu Ser
625                 630                 635                 640

Tyr Arg Leu Arg Gly Asn Gln Arg Tyr Thr Phe Tyr Val Arg Gly Asn
                645                 650                 655

Asn Leu Leu Gly Glu Glu Val Phe Asn His Ser Ser Phe Leu Ala Ser
            660                 665                 670
```

```
Thr Val Pro Glu Pro Gly Arg Asn Ile Thr Val Gly Thr Arg Ile Glu
        675                 680                 685
Phe

<210> SEQ ID NO 24
<211> LENGTH: 691
<212> TYPE: PRT
<213> ORGANISM: Azoarcus sp. BH72

<400> SEQUENCE: 24

Met Leu Pro Arg Leu Ser Pro Leu Ser Leu Ala Leu Leu Cys Ala Leu
1               5                   10                  15

Gly Thr Ala His Ala Ala Ala Gln Ser Ala Ala Pro Asn Asp Pro Thr
            20                  25                  30

Ala Ala Pro Pro Val Gln Leu Glu Ala Val Thr Val Ser Ala Ser Gly
        35                  40                  45

Leu Asp Val Asp Ser Gly Ala Met Ser Thr Pro Ala Thr Val Leu Gly
    50                  55                  60

Gly Asp Glu Leu Val Arg Arg Ala Ala Thr Leu Gly Glu Thr Leu
65              70                  75                  80

Ala Thr Glu Pro Gly Ile His Ala Thr Glu Phe Gly Ala Gly Ala Ser
                85                  90                  95

Arg Pro Val Ile Arg Gly Met Asp Gly Ala Arg Val Arg Leu Leu Ser
            100                 105                 110

Asp Gly Ala Glu Ile Met Asp Ala Ser Thr Ile Ser Pro Asp His Ala
        115                 120                 125

Val Ala Ala Glu Pro Leu Leu Ser Glu Arg Ile Glu Val Leu Arg Gly
    130                 135                 140

Pro Ser Ala Leu Ala Tyr Gly Gly Gly Ala Val Gly Gly Val Val Asn
145             150                 155                 160

Val Leu Asp Arg Arg Ile Pro Thr Ala Ile Pro Glu Arg Gly Val Glu
                165                 170                 175

Gly Ser Val Glu Leu Arg Gly Asn Thr Ala Ala Arg Glu Ala Ala Gly
            180                 185                 190

Ala Phe Glu Val Thr Ala Gly Ala Gly Asn Ile Ala Ile His Ala Glu
        195                 200                 205

Gly Leu Lys Arg Asp Ala Arg Asp Tyr Arg Val Gly Asp Gly Trp Ala
    210                 215                 220

Gly Gly Arg Arg Val Asp Gly Ser Tyr Asn Glu Thr Glu Thr Gly Ser
225             230                 235                 240

Leu Gly Leu Ser Trp Ile Gly Glu Arg Gly Tyr Leu Gly Val Ala Trp
                245                 250                 255

Thr Arg Gln Arg Asn Glu Tyr Gly Leu Pro Gly His Ala His Asp Leu
            260                 265                 270

Glu Asp Cys His Thr His Gly Asn Ser Leu His Cys Gly Gly His Asp
        275                 280                 285

Gly Asp Asp Glu Asp Asp His Asp His Ala Asp Glu Gly Gly Gly Val
    290                 295                 300

Pro Tyr Val Lys Leu Asp Ser Glu Arg Trp Asp Leu Arg Gly Glu Tyr
305             310                 315                 320

Arg Glu Pro Phe Ala Gly Ile Ser Arg Leu Arg Val Arg Ala Ser His
                325                 330                 335

Thr Arg Tyr Arg His Asp Glu Ile Glu Asp Gly Ala Val Ser Thr Arg
            340                 345                 350
```

```
Phe Arg Asn Asn Ala Ser Glu Gly Arg Val Glu Leu Gln His Ala Pro
            355                 360                 365

Leu Gly Gly Trp Arg Gly Val Phe Gly Leu Gln Thr Thr Arg Arg Asp
    370                 375                 380

Phe Ser Ala Ile Gly Glu Ala Tyr Val Pro Pro Thr Leu Thr Arg
385                 390                 395                 400

Arg His Gly Ala Phe Leu Ile Glu Glu Tyr Pro Thr Gly Asp Trp Arg
                405                 410                 415

Phe Glu Ala Gly Leu Arg His Glu Trp Gln Gln Val Glu Val Asp Ala
                420                 425                 430

Asp Ala Arg Asp Arg Ser His Arg Gly Asn Ser Leu Ser Leu Gly Ala
                435                 440                 445

Val Trp Asn Phe Ala Pro Asp Tyr Ala Leu Gly Leu Ser Leu Ala Arg
            450                 455                 460

Ala Gln Arg Leu Pro Thr Ala Glu Glu Leu Tyr Ala Asp Gly Leu His
465                 470                 475                 480

Met Ala Thr Arg Thr Ile Glu Arg Gly Asn Ala Asp Leu Lys Ala Glu
                485                 490                 495

Thr Ser His Asn Ile Asp Leu Ser Leu Lys Lys Leu Ala Gly Ala Thr
            500                 505                 510

Thr Phe Asn Leu Ser Val Phe His Asn Arg Val Asn Asp Phe Ile Tyr
            515                 520                 525

Ala His Thr Leu Asp Ala Leu Glu Gly Met Gln Leu Ile Glu Tyr Ala
            530                 535                 540

Gln Arg Asp Ala Ile Phe Thr Gly Val Glu Gly Val Arg Gln Gln
545                 550                 555                 560

Leu Asp Arg Val Phe Gly Leu Thr Leu Phe Gly Asp Tyr Val Arg Ala
                565                 570                 575

Arg Leu Ala Gly Gly Asp Gly Asp Arg Asp Arg Asp Leu Pro Arg Ile
                580                 585                 590

Pro Ala His Arg Val Gly Leu Arg Leu Asp Ala Arg Gln Gly Ala Trp
            595                 600                 605

Gln Gly Glu Leu Glu Val Tyr Arg Val Gly Arg Gln Arg Gln Val Ala
            610                 615                 620

Glu Phe Glu Ser Ser Thr Pro Gly Tyr Asn Met Val Asn Leu Gly Ala
625                 630                 635                 640

Ser Tyr Ala Gly Arg Ile Ala Ser Val Pro Tyr Leu Phe Tyr Val Lys
                645                 650                 655

Ala Ala Asn Leu Thr Asp Glu Leu Ala Tyr Ser His Thr Ser Phe Ile
                660                 665                 670

Lys Asp Ala Ala Pro Leu Met Gly Arg Asn Leu Thr Met Gly Val Lys
                675                 680                 685

Val Thr Phe
    690

<210> SEQ ID NO 25
<211> LENGTH: 682
<212> TYPE: PRT
<213> ORGANISM: Azotobacter vinelandii DJ

<400> SEQUENCE: 25

Met Lys Arg His Ser Leu Ala Trp Thr Leu Gly Leu Ser Leu Val Pro
1               5                   10                  15

Ala Ile Gly Ala Ser Glu Pro Leu Glu Leu Glu Ser Thr Val Val Ser
```

```
                  20                  25                  30
Ala Ser Ala Leu Ala Lys Lys Pro His Glu Met Thr Thr Pro Ala Glu
             35                  40                  45
Val Leu Glu Gly Asp Glu Leu Val Leu Arg Arg Glu Ala Thr Leu Gly
         50                  55                  60
Glu Thr Leu Glu Gly Leu Pro Gly Val Arg Ser Ala Ser Phe Gly Ala
 65                  70                  75                  80
Gly Val Gly Arg Pro Met Ile Arg Gly Gln Gln Gly Ala Arg Val Lys
                 85                  90                  95
Met Leu Ser Asp Gly Val Asp Val Leu Asp Ala Ser Asn Ile Ser Pro
             100                 105                 110
Asp His Ala Val Ser Ser Glu Pro Leu Met Ala Glu Arg Ile Glu Val
         115                 120                 125
Leu Lys Gly Pro Ala Thr Leu Leu Tyr Gly Gly Ala Ile Gly Gly
     130                 135                 140
Val Val Asn Val Ile Asp Lys Lys Val Pro Thr His Val Pro Glu Asn
145                 150                 155                 160
Gly Tyr Glu Gly Glu Leu Glu Leu Arg Ala Asn Ser Val Ala Asn Glu
                 165                 170                 175
Gly Ser Gly Val Phe Gly Ile Thr Ala Gly Ser Gly Asn Phe Ala Val
             180                 185                 190
Arg Val Glu Gly Val Lys Arg Gln Ala Asp Tyr Glu Ile His Gly
         195                 200                 205
Ser Pro Ser Lys Gln Asp Gly Ser Tyr Asn Asp Thr Asp Thr Phe Ser
     210                 215                 220
Leu Gly Ala Ser Phe Val Gly Glu Arg Gly Tyr Leu Gly Val Ala Phe
225                 230                 235                 240
Thr Glu Gln Asn Asn Arg Tyr Gly Leu Leu Gly His Gln His Ala Asp
                 245                 250                 255
Cys His Leu Asp Gly Pro Ala Trp His Cys Gly Glu His Glu Asp Glu
             260                 265                 270
His Glu Glu Glu His Glu Asp Glu His Glu Asp His Asp Glu His
         275                 280                 285
Asp His Glu His Glu Gly Glu Gly Val Pro Tyr Val Asp Leu Arg Gln
     290                 295                 300
Tyr Arg Trp Asp Leu Arg Gly Glu Leu Gln Asp Pro Leu Pro Gly Phe
305                 310                 315                 320
Glu Leu Ala Arg Leu Arg Val Ala His Ser Asp Tyr Arg His Glu Glu
                 325                 330                 335
Val Glu Gly Gly Gln Val Ser Thr Arg Phe Asp Asn Asp Ala Ser Asp
             340                 345                 350
Ala Arg Leu Glu Leu Thr His Gln Pro Leu Phe Gly Trp Arg Gly Val
         355                 360                 365
Leu Gly Gly Gln Thr Leu Arg Arg Asp Phe Arg Ala Ser Gly Glu Glu
     370                 375                 380
Ala Tyr Val Pro Pro Thr Ile Thr Arg Asn His Ala Leu Phe Leu Leu
385                 390                 395                 400
Glu Glu Tyr Thr Asp Gly Ala Trp Arg Tyr Glu Leu Gly Leu Arg His
                 405                 410                 415
Glu Trp Gln Asp Ile Glu Ala Glu Gly Arg Pro Asp Lys Asp His Arg
             420                 425                 430
Gly Thr Ser Phe Ser Ala Gly Ala Val Trp Ser Phe Ala Pro Asn Tyr
         435                 440                 445
```

Ser Leu Gly Phe Ser Leu Ser Arg Ser Gln Arg Leu Pro Ser Ala Glu
                450                 455                 460

Glu Leu Tyr Ala Asp Gly Pro His Ala Ala Thr Arg Thr Val Glu Leu
465                 470                 475                 480

Gly Asp Pro Glu Leu Asp Glu Glu Thr Ser His Asn Leu Glu Leu Thr
                485                 490                 495

Leu Arg Lys Phe Ala Gly Arg Thr Thr Phe Ser Phe Thr Leu Tyr Arg
                500                 505                 510

Asn Gln Val Asp Asp Tyr Ile Tyr Ala Ala Asp Thr Gly Arg Asp Ile
                515                 520                 525

Gly Ser Gly Tyr Arg Glu Ile Glu Tyr Arg Gln Gln Asp Ala Leu Phe
                530                 535                 540

Thr Gly Val Glu Gly Glu Val Arg Phe Gln Ala Thr Asp Ala Thr Ala
545                 550                 555                 560

Leu Thr Leu Phe Gly Asp His Val Arg Gly Lys Leu Leu Asp Gly Gly
                565                 570                 575

Gly Asp Leu Pro Arg Ile Pro Ala Gly Arg Leu Gly Val Arg Leu Asp
                580                 585                 590

His Gly Phe Thr Ser Ser Leu Asp Gly Gln Leu Glu Phe Tyr Arg Val
                595                 600                 605

Asn His Gln His Arg Leu Ala Asp Phe Glu Thr Glu Thr Ser Gly Tyr
                610                 615                 620

Ser Met Leu Gly Ala Ser Leu Thr Tyr His Gly Ala Leu Arg Arg Ala
625                 630                 635                 640

Asp Tyr Gln Ile Tyr Leu Lys Gly Asp Asn Leu Leu Asp Glu Lys Ala
                645                 650                 655

Arg Asp His Ser Ser Phe Ile Lys Asp Asp Val Val Gln Pro Gly Arg
                660                 665                 670

Asn Leu Thr Leu Gly Leu Arg Met Thr Phe
                675                 680

<210> SEQ ID NO 26
<211> LENGTH: 713
<212> TYPE: PRT
<213> ORGANISM: Bordetella bronchiseptica RB50

<400> SEQUENCE: 26

Met Val Cys Tyr Ile Val Ser Phe Asn Glu Asn Gly Thr Ser Phe Tyr
1               5                   10                  15

Arg Glu Gly Asn Met Arg Phe Glu Arg His Pro Leu Ser Ala Ala Leu
                20                  25                  30

Ala Leu Ala Leu Ala Trp Gln Gly Ala His Ala Gln Ala Ser Ala Asp
                35                  40                  45

Gly Thr Pro Glu Ala Ala Thr Leu Ala Pro Ile Thr Val Ser Ala Ser
50                  55                  60

Pro Leu Ala Gly Asp Leu Asp Ser Met Thr Ala Pro Ala Ala Val Leu
65                  70                  75                  80

Glu Gly Asp Gln Leu Leu Leu Arg Arg Gln Gly Thr Leu Gly Asp Thr
                85                  90                  95

Leu Asp Gly Leu Pro Gly Val His Ala Asp Thr Phe Gly Gly Gly Ala
                100                 105                 110

Ser Arg Pro Val Ile Arg Gly Gln Thr Ala Pro Arg Val Lys Val Leu
                115                 120                 125

Ser Asp Gly Ser Glu Leu Met Asp Ala Ser Ala Ile Ser Pro Asp His

```
            130                 135                 140
Ala Val Thr Thr Glu Pro Leu Leu Ala Asp Lys Ile Glu Val Leu Arg
145                 150                 155                 160

Gly Pro Ala Thr Leu Leu Tyr Gly Gly Ala Ile Gly Gly Val Val
                165                 170                 175

Asn Val Leu Asp Arg Lys Ile Pro Thr Ala Val Pro Gln Gln Gly Ile
            180                 185                 190

Glu Ala Glu Ala Glu Leu Arg Gly Ala Thr Gly Thr Lys Glu Arg Ala
        195                 200                 205

Gly Ala Ile Gly Ile Thr Ala Gly Ser Gly Asn Phe Ala Val Arg Val
        210                 215                 220

Glu Gly Leu Lys Arg Arg Ser Ser Asp Tyr Arg Val Pro Asp Trp Pro
225                 230                 235                 240

Asp Gly Lys Leu Ala Gly Ser Tyr Ser Glu Ser Gly Gln Gly Thr Val
                245                 250                 255

Gly Met Ser Trp Ile Thr Pro Arg Gly Tyr Val Gly Val Ala Phe Thr
                260                 265                 270

His Leu Glu Ser Lys Tyr Gly Leu Pro Gly His Asn His Glu Tyr Glu
            275                 280                 285

Gly Cys His Pro His Gly Ser His Leu His Cys Gly Gly His Asp Asp
        290                 295                 300

His Gly His Gly His Asp Glu His Glu Glu Gly Glu Ala Glu His Asp
305                 310                 315                 320

His Gly His Glu His Gly Ala Gly Asp Val Pro Tyr Val Lys Leu Arg
                325                 330                 335

Ser Asn Arg Thr Asp Leu Arg Ala Glu Tyr Thr Asp Pro Phe Ala Gly
            340                 345                 350

Phe Glu Lys Ile Arg Phe Arg Gly Gly Leu Thr Asp Tyr Arg His Asp
        355                 360                 365

Glu Ile Glu Gly Gly Gln Leu Gly Thr Arg Phe Gln Asn Arg Gly Tyr
        370                 375                 380

Asp Ala Arg Leu Glu Leu Thr His Arg Pro Leu Tyr Gly Trp His Gly
385                 390                 395                 400

Val Val Gly Val Gln Thr Ser Tyr Ser Asp Phe Arg Ala Thr Gly Glu
                405                 410                 415

Glu Ala Phe Leu Pro Arg Ser Lys Thr Arg Ala His Gly Leu Phe Leu
                420                 425                 430

Leu Glu Glu Tyr Arg Trp Ala Asp Trp Arg Val Glu Leu Gly Ala Arg
            435                 440                 445

Gln Asp Trp Gln Arg Val Ser Pro Gln Gly Gly Ala Pro Ala Ser Arg
        450                 455                 460

Thr Ala Gly Thr Ser Leu Ser Ala Ala Ile Trp Asp Phe Ala Pro
465                 470                 475                 480

Gln Tyr Ser Leu Ala Leu Ser Val Ser Arg Ser Gln Arg Leu Pro Ser
                485                 490                 495

Ala Gln Glu Leu Tyr Ala Asp Gly Val His Leu Ala Thr Asn Thr Tyr
            500                 505                 510

Glu Ile Gly Asp Pro Gly Leu Asp Arg Glu Thr Ser Arg Asn Val Asp
        515                 520                 525

Leu Thr Leu Arg Lys His Ser Gly Asp Thr Thr Phe Ser Val Ser Ala
        530                 535                 540

Phe His Asn Arg Val Lys Asn Tyr Ile Tyr Ala Asn Thr Leu Asp Arg
545                 550                 555                 560
```

```
Tyr Glu Asp Phe Arg Leu Ile Glu Tyr Thr Gln Arg Asp Ala Glu Phe
                565                 570                 575

Thr Gly Val Glu Gly Glu Ile Arg His Arg Phe Gly Lys Val Phe Ser
            580                 585                 590

Ala Ala Val Phe Gly Asp Tyr Val Arg Gly Arg Leu Thr Gly Gly Gly
        595                 600                 605

Gly Asn Leu Pro Arg Ile Pro Ala Ala Arg Leu Gly Val Arg Ala Asp
    610                 615                 620

Ala Gln Trp Gln Asn Trp Ala Gly Gly Val Glu Tyr Phe His Val Tyr
625                 630                 635                 640

Arg Gln Asp Asp Ile Ala Ala Tyr Glu Ser Ser Thr Pro Gly Tyr Asp
                645                 650                 655

Met Val Asn Ala Thr Ile Arg Tyr Arg Gly Lys Leu Asp Arg Thr Ala
            660                 665                 670

Tyr Glu Ile Tyr Leu Arg Gly Asn Asn Leu Leu Asn Lys Leu Ala Phe
        675                 680                 685

Asn His Ala Ser Phe Ile Ser Thr Val Ala Pro Leu Pro Gly Arg Ser
    690                 695                 700

Val Leu Leu Gly Val Arg Leu Thr Tyr
705                 710

<210> SEQ ID NO 27
<211> LENGTH: 711
<212> TYPE: PRT
<213> ORGANISM: Bordetella parapertussis

<400> SEQUENCE: 27

Met Val Cys Tyr Ile Val Ser Phe Asn Glu Asn Gly Thr Ser Phe Cys
1               5                   10                  15

Arg Glu Gly Asn Met Arg Phe Glu Arg His Pro Leu Ser Ala Ala Leu
            20                  25                  30

Ala Leu Ala Leu Ala Trp Gln Gly Ala His Ala Gln Ala Ser Ala Asp
        35                  40                  45

Gly Thr Pro Glu Ala Ala Thr Leu Ala Pro Ile Thr Val Ser Ala Ser
    50                  55                  60

Pro Leu Ala Gly Asp Leu Asp Ser Met Thr Ala Pro Ala Ala Val Leu
65                  70                  75                  80

Glu Gly Asp Gln Leu Leu Arg Arg Gln Gly Thr Leu Gly Asp Thr
            85                  90                  95

Leu Asp Gly Leu Pro Gly Val His Ala Asp Thr Phe Gly Gly Gly Ala
            100                 105                 110

Ser Arg Pro Val Ile Arg Gly Gln Thr Ala Pro Arg Val Lys Val Leu
        115                 120                 125

Ser Asp Gly Ser Glu Leu Met Asp Ala Ser Ala Ile Ser Pro Asp His
    130                 135                 140

Ala Val Thr Thr Glu Pro Leu Leu Ala Asp Lys Ile Glu Val Leu Arg
145                 150                 155                 160

Gly Pro Ala Thr Leu Leu Tyr Gly Gly Ala Ile Gly Gly Val Val
            165                 170                 175

Asn Val Leu Asp Arg Lys Ile Pro Thr Ala Val Pro Gln Gln Gly Ile
            180                 185                 190

Glu Ala Glu Ala Glu Leu Arg Gly Ala Thr Gly Thr Lys Glu Arg Ala
        195                 200                 205

Gly Ala Ile Gly Ile Thr Ala Gly Ser Gly Asn Phe Ala Val Arg Val
```

-continued

```
            210                 215                 220
Glu Gly Leu Lys Arg Arg Ser Ser Asp Tyr Arg Val Pro Asp Trp Pro
225                 230                 235                 240

Asp Gly Lys Leu Ala Gly Ser Tyr Ser Glu Ser Gly Gln Gly Thr Val
                    245                 250                 255

Gly Met Ser Trp Ile Thr Pro Arg Gly Tyr Val Gly Val Ala Phe Thr
                260                 265                 270

His Leu Glu Ser Lys Tyr Gly Leu Pro Gly His Asn His Glu Tyr Glu
            275                 280                 285

Gly Cys His Pro His Gly Ser His Leu His Cys Gly Gly His Asp Asp
        290                 295                 300

His Gly His Asp Glu His Glu Gly Glu Ala Glu His Asp His Gly
305                 310                 315                 320

His Glu His Gly Ala Gly Asp Val Pro Tyr Val Lys Leu Arg Ser Asn
                325                 330                 335

Arg Thr Asp Leu Arg Ala Glu Tyr Thr Asp Pro Phe Ala Gly Phe Glu
                340                 345                 350

Lys Ile Arg Phe Arg Gly Gly Leu Thr Asp Tyr Arg His Asp Glu Ile
            355                 360                 365

Glu Gly Gly Gln Leu Gly Thr Arg Phe Gln Asn Arg Gly Tyr Asp Ala
370                 375                 380

Arg Leu Glu Leu Thr His Arg Pro Leu Tyr Gly Trp His Gly Val Val
385                 390                 395                 400

Gly Val Gln Thr Ser Tyr Ser Asp Phe Arg Ala Thr Gly Glu Glu Ala
                405                 410                 415

Phe Leu Pro Arg Ser Lys Thr Arg Ala His Gly Leu Phe Leu Leu Glu
                420                 425                 430

Glu Tyr Arg Trp Ala Asp Trp Arg Val Glu Leu Gly Ala Arg Gln Asp
            435                 440                 445

Trp Gln Arg Val Ser Pro Gln Gly Gly Ala Pro Ala Ser Arg Thr Ala
450                 455                 460

Gly Thr Ser Leu Ser Ala Ala Ile Trp Asp Phe Ala Pro Gln Tyr
465                 470                 475                 480

Ser Leu Ala Leu Ser Val Ser Arg Ser Gln Arg Leu Pro Ser Ala Gln
                485                 490                 495

Glu Leu Tyr Ala Asp Gly Val His Leu Ala Thr Asn Thr Tyr Glu Ile
            500                 505                 510

Gly Asp Pro Gly Leu Asp Arg Glu Thr Ser Arg Asn Val Asp Leu Thr
        515                 520                 525

Leu Arg Lys His Ser Gly Asp Thr Thr Phe Ser Val Ser Ala Phe His
530                 535                 540

Asn Arg Val Lys Asn Tyr Ile Tyr Ala Asn Thr Leu Asp Arg Tyr Glu
545                 550                 555                 560

Asp Phe Arg Leu Ile Glu Tyr Thr Gln Arg Asp Ala Glu Phe Thr Gly
                565                 570                 575

Val Glu Gly Glu Ile Arg His Arg Phe Gly Lys Val Phe Ser Ala Ala
                580                 585                 590

Val Phe Gly Asp Tyr Val Arg Gly Arg Leu Thr Gly Gly Gly Asn
            595                 600                 605

Leu Pro Arg Ile Pro Ala Ala Arg Leu Gly Val Arg Ala Asp Ala Gln
        610                 615                 620

Trp Gln Asn Trp Ala Gly Gly Val Glu Tyr Phe His Val Tyr Arg Gln
625                 630                 635                 640
```

```
Asp Asp Ile Ala Ala Tyr Glu Ser Ser Thr Pro Gly Tyr Asp Met Val
                645                 650                 655

Asn Ala Thr Ile Arg Tyr Arg Gly Lys Leu Asp Arg Thr Ala Tyr Glu
            660                 665                 670

Ile Tyr Leu Arg Gly Asn Asn Leu Leu Asn Lys Leu Ala Phe Asn His
        675                 680                 685

Ala Ser Phe Ile Ser Thr Val Ala Pro Leu Pro Gly Arg Ser Val Leu
690                 695                 700

Leu Gly Val Arg Leu Thr Tyr
705                 710

<210> SEQ ID NO 28
<211> LENGTH: 713
<212> TYPE: PRT
<213> ORGANISM: Bordetella pertussis Tohama I

<400> SEQUENCE: 28

Met Ile Cys Tyr Ile Val Ser Phe Asn Glu Asn Gly Thr Ser Phe Tyr
1               5                   10                  15

Arg Glu Gly Asn Met Arg Phe Glu Arg His Pro Leu Ser Ala Ala Leu
            20                  25                  30

Ala Leu Ala Leu Ala Trp Gln Gly Ala His Ala Gln Ala Ser Ala Asp
        35                  40                  45

Gly Thr Ser Glu Ala Ala Thr Leu Ala Pro Ile Thr Val Ser Ala Ser
    50                  55                  60

Pro Leu Ala Gly Asp Leu Asp Ser Met Thr Ala Pro Ala Ala Val Leu
65                  70                  75                  80

Glu Gly Asp Gln Leu Leu Leu Arg Arg Gln Gly Thr Leu Gly Asp Thr
                85                  90                  95

Leu Asp Gly Leu Pro Gly Val His Ala Asp Thr Phe Gly Gly Gly Ala
            100                 105                 110

Ser Arg Pro Val Ile Arg Gly Gln Thr Ala Pro Arg Val Lys Val Leu
        115                 120                 125

Ser Asp Gly Ser Glu Leu Met Asp Ala Ser Ala Ile Ser Pro Asp His
    130                 135                 140

Ala Val Thr Thr Glu Pro Leu Leu Ala Asp Lys Ile Glu Val Leu Arg
145                 150                 155                 160

Gly Pro Ala Thr Leu Leu Tyr Gly Gly Gly Ala Ile Gly Gly Val Val
                165                 170                 175

Asn Val Leu Asp Arg Lys Ile Pro Thr Ala Val Pro Gln Gln Gly Ile
            180                 185                 190

Glu Ala Glu Ala Glu Leu Arg Gly Ala Thr Gly Thr Lys Glu Arg Ala
        195                 200                 205

Gly Ala Ile Gly Ile Thr Ala Gly Ser Gly Asn Phe Ala Val Arg Val
    210                 215                 220

Glu Gly Leu Lys Arg Arg Ser Ser Asp Tyr Arg Val Pro Asp Trp Pro
225                 230                 235                 240

Asp Gly Lys Leu Ala Gly Ser Tyr Ser Glu Ser Gly Gln Gly Thr Val
                245                 250                 255

Gly Met Ser Trp Ile Thr Pro Arg Gly Tyr Val Gly Val Ala Phe Thr
            260                 265                 270

His Leu Glu Ser Lys Tyr Gly Leu Pro Gly His Asn His Glu Tyr Glu
        275                 280                 285

Gly Cys His Pro His Gly Ser His Leu His Cys Gly Gly His Asp Asp
```

```
                290                 295                 300
His Gly His Gly His Asp Glu His Glu Glu Gly Ala Glu His Asp
305                 310                 315                 320

His Gly His Glu His Gly Ala Gly Asp Val Pro Tyr Val Lys Leu Arg
                325                 330                 335

Ser Asn Arg Thr Asp Leu Arg Ala Glu Tyr Thr Asp Pro Phe Ala Gly
                340                 345                 350

Phe Glu Lys Ile Arg Phe Arg Gly Gly Leu Thr Asp Tyr Arg His Asp
                355                 360                 365

Glu Ile Glu Gly Gly Gln Leu Gly Thr Arg Phe Gln Asn Arg Gly Tyr
370                 375                 380

Asp Ala Arg Leu Glu Leu Thr His Arg Pro Leu Tyr Gly Trp His Gly
385                 390                 395                 400

Val Val Gly Val Gln Thr Ser Tyr Ser Asp Phe Arg Ala Thr Gly Glu
                405                 410                 415

Glu Ala Phe Leu Pro Arg Ser Lys Thr Arg Ala His Gly Leu Phe Leu
                420                 425                 430

Leu Glu Glu Tyr Arg Trp Ala Asp Trp Arg Phe Glu Leu Gly Ala Arg
                435                 440                 445

Gln Asp Trp Gln Arg Val Ser Pro Gln Ser Gly Ala Pro Ala Ser Arg
                450                 455                 460

Thr Ala Gly Thr Ser Leu Ser Ala Ala Ile Trp Asp Phe Ala Pro
465                 470                 475                 480

Gln Tyr Ser Leu Ala Leu Ser Val Ser Arg Ser Gln Arg Leu Pro Ser
                485                 490                 495

Ala Gln Glu Leu Tyr Ala Asp Gly Val His Leu Ala Thr Asn Thr Tyr
                500                 505                 510

Glu Ile Gly Asp Pro Gly Leu Asp Arg Glu Thr Ser Arg Asn Val Asp
                515                 520                 525

Leu Thr Leu Arg Lys His Ser Gly Asp Thr Thr Phe Ser Val Ser Ala
530                 535                 540

Phe His Asn Arg Val Lys Asn Tyr Ile Tyr Ala Asn Thr Leu Asp Arg
545                 550                 555                 560

Tyr Glu Asp Phe Arg Leu Ile Glu Tyr Thr Gln Arg Asp Ala Glu Phe
                565                 570                 575

Thr Gly Val Glu Gly Glu Val Arg His Arg Phe Gly Lys Val Phe Ser
                580                 585                 590

Ala Ala Val Phe Gly Asp Tyr Val Arg Gly Arg Leu Thr Gly Gly Gly
                595                 600                 605

Gly Asn Leu Pro Arg Ile Pro Ala Ala Arg Leu Gly Val Arg Ala Asp
610                 615                 620

Ala Gln Trp Gln Asn Trp Ala Gly Gly Val Glu Tyr Phe His Val Tyr
625                 630                 635                 640

Arg Gln Asp Asp Ile Ala Ala Tyr Glu Ser Ser Thr Pro Gly Tyr Asp
                645                 650                 655

Met Val Asn Ala Thr Ile Arg Tyr Arg Gly Lys Leu Asp Arg Thr Ala
                660                 665                 670

Tyr Glu Ile Tyr Leu Arg Gly Asn Asn Leu Leu Asn Lys Leu Ala Phe
                675                 680                 685

Asn His Ala Ser Phe Ile Ser Thr Val Ala Pro Leu Pro Gly Arg Ser
                690                 695                 700

Val Leu Leu Gly Val Arg Leu Thr Tyr
705                 710
```

<210> SEQ ID NO 29
<211> LENGTH: 684
<212> TYPE: PRT
<213> ORGANISM: Bordetella petrii

<400> SEQUENCE: 29

```
Met Gln Ile Lys Pro Leu Pro Leu Ala Val Ala Met Ser Leu Gly Leu
1               5                   10                  15

Ala Ala Thr Ala Gln Ala Gln Gln Ala Gln Gln Thr Gln
            20                  25                  30

Gln Ala Pro Thr Leu Ala Pro Ile Thr Val Ser Ala Asn Pro Leu Gly
            35                  40                  45

Leu Asp Pro Asp Ser Met Ala Leu Pro Ala Leu Val Leu Ser Gly Asp
        50                  55                  60

Ala Leu Ile Glu Arg Arg His Asp Thr Leu Gly Asn Thr Leu Asp Gly
65                  70                  75                  80

Leu Pro Gly Ile His Ser Asp Thr Phe Gly Gly Ala Ser Arg Pro
                85                  90                  95

Val Ile Arg Gly Gln Thr Ala Pro Arg Val Lys Val Leu Ser Asp Gly
                100                 105                 110

Ser Glu Leu Met Asp Ala Ser Asn Ile Ser Pro Asp His Ala Val Thr
            115                 120                 125

Thr Glu Pro Leu Leu Ala Asp Arg Ile Glu Val Leu Arg Gly Pro Ala
        130                 135                 140

Thr Leu Leu Tyr Gly Gly Gly Ala Ile Gly Gly Val Val Asn Val Leu
145                 150                 155                 160

Asp Arg Lys Ile Pro Thr Ala Val Pro Glu Lys Gly Val Glu Ala Glu
                165                 170                 175

Ala Glu Val Arg Gly Ala Thr Gly Thr Gly Glu Arg Ala Gly Ala Val
            180                 185                 190

Gly Ile Thr Ala Gly Thr Gly Glu Phe Ala Val Arg Val Glu Gly Leu
        195                 200                 205

Lys Arg Arg Ser Asp Asp Tyr Asn Val Pro Asp Trp Pro Gly Gly Glu
    210                 215                 220

Leu Glu Gly Ser Tyr Ser Arg Ser Ser Gln Gly Thr Val Gly Leu Ser
225                 230                 235                 240

Trp Ile Thr Pro Arg Gly Tyr Val Gly Val Ala Tyr Thr Tyr Leu Glu
                245                 250                 255

Ser Lys Tyr Gly Leu Pro Gly His Asn His Glu Tyr Glu Gly Cys His
            260                 265                 270

Pro His Gly Thr His Leu His Cys Gly Gly His Asp His Asp
        275                 280                 285

His Asp His Asp His Glu His Gly Glu Glu Asp Pro Pro Tyr Val Lys
    290                 295                 300

Leu Arg Ser Asn Arg Val Asp Leu Arg Ala Glu Tyr Ala Glu Pro Phe
305                 310                 315                 320

Ala Gly Phe Glu Lys Ile Arg Phe Arg Gly Leu Thr Asp Tyr Gln
                325                 330                 335

His Gln Glu Ile Glu Gly Gly Glu Val Gly Thr Thr Phe Lys Asn Arg
            340                 345                 350

Gly Tyr Asp Ala Arg Leu Glu Leu Glu His Lys Pro Leu Tyr Gly Trp
        355                 360                 365

Arg Gly Val Val Gly Ile Gln Asn Ala Tyr Ser Asp Phe Ser Ala Asp
```

```
            370                 375                 380
Gly Glu Glu Ala Phe Leu Pro Arg Ser Asp Thr Arg Ser Thr Gly Ile
385                 390                 395                 400

Phe Leu Leu Glu Glu Tyr Lys Leu Gly Asp Trp Arg Phe Glu Val Gly
                405                 410                 415

Ala Arg Gln Asp Trp Gln Arg Ile Ser Pro Glu Gly Asp His Pro Arg
            420                 425                 430

Ser Ser Gln Ser Gly Thr Ser Leu Ser Ala Ser Ala Ile Trp Asn Phe
            435                 440                 445

Ala Pro Gln Tyr Ser Val Ala Leu Ser Leu Ser Arg Ser Gln Arg Leu
        450                 455                 460

Pro Ser Ala Gln Glu Leu Tyr Ala Asp Gly Val His Leu Ala Thr Asn
465                 470                 475                 480

Thr Tyr Glu Ile Gly Asn Pro Asp Leu Gly Lys Glu Thr Ser Arg Asn
                485                 490                 495

Ile Asp Leu Thr Leu Arg Lys His Glu Gly Asp Thr Thr Phe Ser Leu
            500                 505                 510

Ser Ala Phe His Asn Arg Val Lys Asn Tyr Ile Tyr Ala Asn Thr Leu
        515                 520                 525

Asp Gln Phe Glu Asp Phe Arg Leu Ile Glu Tyr Thr Gln Arg Asp Ala
530                 535                 540

Glu Phe Thr Gly Leu Glu Gly Glu Val Arg His Gln Phe Thr Lys Val
545                 550                 555                 560

Phe Ser Ala Ala Val Phe Gly Asp Tyr Val Arg Gly Lys Leu Thr Gly
                565                 570                 575

Gly Gly Gly Asn Leu Pro Arg Ile Pro Ala Ala Arg Leu Gly Val Arg
            580                 585                 590

Ala Asp Ala Lys Trp Arg Gln Trp Ser Gly Val Glu Tyr Ala His
        595                 600                 605

Val Phe Arg Gln Asn Asp Ile Ala Ser Tyr Glu Ser Ser Thr Pro Gly
610                 615                 620

Tyr Asp Met Val Asn Ala Val Val Ser Tyr Arg Gly Leu Gly Ala
625                 630                 635                 640

Asp Ala Ala Tyr Glu Val Tyr Leu Arg Gly Thr Asn Leu Leu Asp Lys
                645                 650                 655

Leu Ala Tyr Asn His Ala Ser Phe Ile Ser Lys Val Ala Pro Leu Pro
            660                 665                 670

Gly Arg Ser Val Leu Leu Gly Val Arg Val Thr Tyr
            675                 680

<210> SEQ ID NO 30
<211> LENGTH: 711
<212> TYPE: PRT
<213> ORGANISM: Comamonas testosteroni CNB-2

<400> SEQUENCE: 30

Met Ser Gln Arg Phe Leu Asn Ser Ser Ala His Ser Leu His Arg Ser
1               5                   10                  15

Ser Lys Ser Ala Leu Ala Arg Ala Ile Glu Ala Leu Gln Pro Ala Gly
            20                  25                  30

Arg Gly Leu Ala Leu Gly Thr Gly Leu Gly Leu Leu Ala Cys Ser Pro
        35                  40                  45

Leu Val Phe Ala Gln Ser Asp Ala Ala Lys Gln Glu Ser Ser Leu Ala
    50                  55                  60
```

```
Glu Val Thr Val Ser Ala Thr Gly Met Ala Ala Gly Asp Met Ala Thr
 65                  70                  75                  80

Pro Val Gln Val Leu Gly Glu Glu Leu Arg Leu Arg Arg Ala Ala
                 85                  90                  95

Thr Leu Gly Glu Thr Leu Ala Ala Glu Pro Gly Ile Asn Ala Ser His
                100                 105                 110

Phe Gly Ala Gly Ala Ser Arg Pro Val Ile Arg Gly Met Asp Gly Ala
            115                 120                 125

Arg Val Ser Val Leu Ser Asp Gly Ser Glu Leu Leu Asp Ala Ser Thr
    130                 135                 140

Val Ser Pro Asp His Ala Val Thr Thr Glu Pro Leu Leu Ala Asn Gln
145                 150                 155                 160

Ile Glu Val Leu Arg Gly Pro Ser Ala Leu Leu Tyr Ser Pro Gly Ala
                165                 170                 175

Met Gly Gly Val Val Asn Val Leu Asp Gly Lys Ile Pro Thr Arg Val
            180                 185                 190

Pro Glu Lys Gly Leu Glu Gly Ser Ala Glu Val Gln Ala Gly Thr Ala
        195                 200                 205

Ala Gly Met Ser Ala Gly Ala Phe Ser Leu Thr Thr Ala Thr Pro Leu
210                 215                 220

Lys Asn Asp Asn Gly Gln Leu Val Leu His Ala Glu Gly Val Ala Arg
225                 230                 235                 240

Asn Ala Gly Asp Tyr Arg Val Gly Ser Gly Trp Gly Gln Ser Lys Val
                245                 250                 255

Pro Gly Ser Phe Ser Arg Gly Asn Thr Gly Ser Val Gly Leu Ser Trp
            260                 265                 270

Val Asp Asn Gln Gly Tyr Leu Gly Leu Ala Tyr Thr Arg Gln Gln Ala
    275                 280                 285

Lys Tyr Gly Leu Pro Gly His Gln Ser Phe Glu Gly Cys His Ala
290                 295                 300

His Gly Asp His Leu His Cys Gly Ser His Asp Gly His Asp His Asp
305                 310                 315                 320

His Asp His Glu Glu Gly Gly Ser Val Pro Val Val Asp Leu Thr Ser
                325                 330                 335

Glu Arg Trp Asp Leu Arg Gly Glu Trp Arg Lys Pro Thr Ala Gly Ile
            340                 345                 350

Ala Ala Leu Arg Leu Arg Gly Leu Thr Asn Tyr Arg His Asp Glu
    355                 360                 365

Ile Glu Asp Gly Ser Val Ala Thr Gln Phe Arg Asn Lys Ala His Asp
370                 375                 380

Leu Arg Leu Glu Met Glu His Glu Pro Ile Ala Gly Trp Arg Gly Thr
385                 390                 395                 400

Leu Gly Leu Gln Thr Leu Lys Arg Arg Phe Ser Ala Thr Gly Glu Glu
                405                 410                 415

Ala Tyr Val Gln Pro Thr Asp Thr Gln Arg His Ser Leu Tyr Leu Leu
            420                 425                 430

Glu Glu Tyr Arg Trp Gln Asp Trp Ser Phe Gln Gly Ala Leu Arg His
    435                 440                 445

Asp Arg Gln Arg Val Glu Ala Glu Leu Ser Asn Glu Arg Ser His
450                 455                 460

Ser Ala Thr Ser Ala Ser Leu Gly Thr Ala Trp Lys Phe Gln Pro Gly
465                 470                 475                 480

Tyr Ser Ala Ser Ala Ser Phe Thr Ser Gly Ser Arg Met Pro Thr Ala
```

```
                485                 490                 495
Glu Glu Leu Phe Ala Asn Gly Leu His Met Ala Thr Ala Thr Tyr Glu
            500                 505                 510
Ile Gly Asn Pro Asn Leu Ser Arg Glu Arg Ser Gln Ala Leu Asp Leu
        515                 520                 525
Gly Leu Ala Lys Thr Ala Gly Asp Thr Thr Trp Lys Leu Asn Ala Tyr
    530                 535                 540
His Tyr Arg Ile Lys Gly Tyr Ile Tyr Gly Ala Thr Leu Asp Ala His
545                 550                 555                 560
Glu Gly Leu Gln Leu Leu Gln Tyr Thr Gln Gly Asn Ala Arg Phe Thr
            565                 570                 575
Gly Trp Glu Ala Gln Leu Ser Gln Arg Leu Ser Arg Glu Leu Ser Leu
        580                 585                 590
Ser Val Phe Gly Asp Gly Val Arg Ala Arg Leu Glu Asp Gly Ser Ala
    595                 600                 605
Leu Pro Arg Ile Pro Ala Leu Arg Ala Gly Leu Arg Val Asn Ala Arg
610                 615                 620
Leu Ala Gly Trp Asp Thr Met Ala Glu Trp Thr Gln Val Leu Arg Gln
625                 630                 635                 640
Asn Arg Thr Ala Gln Tyr Glu Thr Gln Thr Pro Gly Tyr Gly Met Leu
            645                 650                 655
Asn Leu Gly Ala Ser Tyr Leu Trp Lys Ser Gly Gly Asn Gln Trp Gln
        660                 665                 670
Phe Tyr Val Lys Gly Gln Asn Leu Thr Asn Arg Leu Ala Tyr Ala Ala
    675                 680                 685
Thr Ser Phe Ile Lys Ser Ala Ala Pro Leu Thr Gly Arg Asn Leu Val
690                 695                 700
Val Gly Leu Arg Met Asp Phe
705                 710

<210> SEQ ID NO 31
<211> LENGTH: 711
<212> TYPE: PRT
<213> ORGANISM: Comamonas testosteroni KF-1

<400> SEQUENCE: 31

Met Tyr Gln Arg Phe Ser Asn Ser Ser Ala His Ser Leu Arg Arg Ser
1               5                   10                  15
Pro Lys Ser Ala Leu Ala Arg Ala Ile Glu Ala Leu Gln Pro Ala Gly
            20                  25                  30
Arg Gly Leu Ala Leu Gly Thr Gly Leu Gly Leu Leu Ala Cys Ser Pro
        35                  40                  45
Leu Val Phe Ala Gln Ser Glu Ala Ala Lys Gln Glu Ser Ser Leu Ala
    50                  55                  60
Glu Val Thr Val Ser Ala Thr Gly Met Ala Ala Gly Asp Met Ala Thr
65                  70                  75                  80
Pro Val Gln Val Leu Gly Glu Glu Glu Leu Arg Leu Arg Arg Ala Ala
            85                  90                  95
Thr Leu Gly Glu Thr Leu Ala Ala Glu Pro Gly Ile Asn Ala Ser His
        100                 105                 110
Phe Gly Ala Gly Ala Ser Arg Pro Val Ile Arg Gly Met Asp Gly Ala
    115                 120                 125
Arg Val Ser Val Leu Ser Asp Gly Ser Glu Leu Leu Asp Ala Ser Thr
    130                 135                 140
```

```
Val Ser Pro Asp His Ala Val Thr Thr Glu Pro Leu Leu Ala Arg Gln
145                 150                 155                 160

Ile Glu Val Leu Arg Gly Pro Ser Ala Leu Leu Tyr Ser Pro Gly Ala
                165                 170                 175

Met Gly Val Val Asn Val Leu Asp Gly Lys Ile Pro Thr Gln Ala
            180                 185                 190

Pro Glu Lys Gly Leu Glu Gly Ser Ala Glu Val Gln Ala Gly Thr Ala
                195                 200                 205

Ala Gly Met Ser Ala Gly Ala Phe Ser Leu Thr Thr Ala Thr Pro Leu
        210                 215                 220

Lys Asn Asp Asn Gly Gln Leu Val Leu His Ala Glu Gly Val Ala Arg
225                 230                 235                 240

Asn Ala Gly Asp Tyr Arg Val Gly Ser Gly Trp Gly Gln Ser Lys Val
                245                 250                 255

Pro Gly Ser Phe Ser Arg Gly Asn Thr Gly Ser Val Gly Leu Ser Trp
                260                 265                 270

Val Gly Asn Gln Gly Tyr Leu Gly Leu Ala Tyr Thr Arg Gln Gln Ala
                275                 280                 285

Lys Tyr Gly Leu Pro Gly His Gln His Ser Phe Glu Gly Cys His Ala
        290                 295                 300

His Gly Asp His Leu His Cys Gly Ser His Asp Gly His Asp His Asp
305                 310                 315                 320

His Gly His Glu Glu Ser Gly Ser Val Pro Val Val Asp Leu Thr Ser
                325                 330                 335

Glu Arg Trp Asp Leu Arg Gly Glu Trp Arg Lys Pro Thr Ala Gly Ile
                340                 345                 350

Ala Ala Leu Arg Leu Arg Gly Gly Leu Thr Asn Tyr Arg His Asp Glu
                355                 360                 365

Ile Glu Asp Gly Ser Val Ala Thr Gln Phe Arg Asn Lys Ala His Asp
        370                 375                 380

Leu Arg Leu Glu Met Glu His Glu Pro Ile Ser Gly Trp Arg Gly Thr
385                 390                 395                 400

Leu Gly Leu Gln Thr Leu Lys Arg Arg Phe Ser Ala Thr Gly Glu Glu
                405                 410                 415

Ala Tyr Val Gln Pro Thr Asp Thr Gln Arg His Ser Leu Tyr Leu Leu
                420                 425                 430

Glu Glu Tyr Arg Trp Gln Asp Trp Ser Phe Gln Gly Ala Leu Arg His
            435                 440                 445

Asp Arg Gln Arg Val Glu Ala Glu Leu Ser Asn Glu Arg Arg Ser His
450                 455                 460

Ser Ala Thr Ser Ala Ser Leu Gly Thr Val Trp Lys Phe Gln Pro Gly
465                 470                 475                 480

Tyr Ser Ala Ser Ala Ser Phe Thr Ser Gly Ser Arg Met Pro Thr Ala
            485                 490                 495

Glu Glu Leu Phe Ala Asn Gly Leu His Met Ala Thr Ala Thr Tyr Glu
                500                 505                 510

Ile Gly Asn Pro Asn Leu Ser Arg Glu Arg Ser Gln Ala Leu Asp Leu
            515                 520                 525

Gly Leu Ala Lys Thr Thr Gly Asp Thr Thr Trp Lys Leu Asn Ala Tyr
            530                 535                 540

His Tyr Arg Ile Asn Gly Tyr Ile Tyr Gly Ala Thr Leu Asp Ala His
545                 550                 555                 560

Glu Gly Leu Gln Leu Leu Gln Tyr Thr Gln Gly Asn Ala Arg Phe Thr
```

```
                      565                 570                 575
Gly Trp Glu Ala Gln Leu Ser Gln Arg Leu Ser Arg Glu Leu Ser Leu
                580                 585                 590

Ser Val Phe Gly Asp Gly Val Arg Ala Arg Leu Glu Asp Gly Ser Ala
                595                 600                 605

Leu Pro Arg Ile Pro Ala Leu Arg Ala Gly Leu Arg Val Asn Ala Arg
                610                 615                 620

Leu Ala Gly Trp Asp Thr Met Ala Glu Trp Thr Gln Val Leu Arg Gln
625                 630                 635                 640

Asn Arg Thr Ala Gln Tyr Glu Thr Gln Thr Pro Gly Tyr Gly Met Leu
                645                 650                 655

Asn Leu Gly Ala Ser Tyr Leu Trp Lys Ser Gly Asn Gln Trp Gln
                660                 665                 670

Phe Tyr Val Lys Gly Gln Asn Leu Thr Asn Arg Leu Ala Tyr Ala Ala
                675                 680                 685

Thr Ser Phe Ile Lys Ser Ala Ala Pro Leu Thr Gly Arg Asn Leu Val
                690                 695                 700

Val Gly Leu Arg Met Asp Phe
705                 710

<210> SEQ ID NO 32
<211> LENGTH: 730
<212> TYPE: PRT
<213> ORGANISM: Delftia acidovorans SPH-1

<400> SEQUENCE: 32

Met Arg Val Thr Thr Lys Gln Tyr His Gln Asp Ala Lys Ala Gln Gly
1               5                   10                  15

Glu Arg Thr Lys Leu Arg Pro Leu Leu Gln Gln Leu Leu Leu Ala Gly
                20                  25                  30

Val Leu Gly Pro Ala Thr Gly Gly Leu Ala Met Ala Ala Glu Pro Ala
                35                  40                  45

Asp Pro Val Pro Ser Ala Gly Pro Ala Ala Ala Asn Ala Gly Ala
50                  55                  60

Gly Ala Pro Arg Ser Asp Ala Pro Val Leu Asn Glu Val Thr Val Lys
65                  70                  75                  80

Ala Ser Gly Leu Gly Leu Thr Ser Ala Asp Met Ser Thr Pro Ala Thr
                85                  90                  95

Val Leu Glu Gly Asp Val Leu Thr Leu Arg Gln Ala Ala Thr Leu Gly
                100                 105                 110

Glu Thr Leu Asp Gly Glu Pro Gly Ile His Ala Ser His Phe Gly Ala
                115                 120                 125

Gly Ala Ser Arg Pro Ile Ile Arg Gly Met Asp Gly Pro Arg Val Gln
                130                 135                 140

Ile Leu Ser Asp Gly Ser Glu Leu His Asp Ala Ser Thr Ile Ser Pro
145                 150                 155                 160

Asp His Ala Val Ala Ser Glu Pro Met Leu Ala Thr Gln Ile Glu Val
                165                 170                 175

Leu Arg Gly Pro Ser Ala Leu Ile Tyr Gly Gly Gly Ala Met Gly
                180                 185                 190

Gly Val Val Asn Ile Leu Asp Asp Lys Ile Pro Thr Ser Ile Pro Arg
                195                 200                 205

Asn Gly Ile Thr Gly Ser Ala Gln Leu Arg Gly Ser Thr Gly Ala Gly
                210                 215                 220
```

```
Glu Thr Ala Gly Ala Phe Ser Leu Thr Gly Gly Ala Gly Gln Leu Ala
225                 230                 235                 240

Ile His Ala Glu Gly Met Ala Arg Asp Ala Gly Asp Tyr Arg Val Gly
                245                 250                 255

Ser Gly Trp Ala Pro Asn Gly Gln Ser Gln Gly Arg Val Ala Gly Ser
                260                 265                 270

Phe Asn Arg Thr Asp Thr Gly Ser Leu Gly Leu Ser Trp Ile Gly Thr
                275                 280                 285

Gln Gly Tyr Leu Gly Leu Ala Tyr Thr Arg Gln Thr Ala Arg Tyr Gly
290                 295                 300

Leu Pro Gly His Asn His Ser Phe Glu Gly Cys His Thr His Gly Asp
305                 310                 315                 320

His Leu His Cys Gly His Asp His Gly Asp Glu Asp Gly His Asp
                325                 330                 335

His Gly Gly Asp Asp His Asp His Gly Ser Val Pro Val Val Asp Leu
                340                 345                 350

Thr Ser Glu Arg Trp Asp Leu Arg Gly Glu Trp Arg Asn Pro Thr Ala
                355                 360                 365

Gly Ile Ala Ala Leu Arg Val Arg Gly Gly Trp Thr Asp Tyr Arg His
370                 375                 380

Asp Glu Ile Glu Gly Gly Gln Val Ser Thr Thr Phe Lys Asn Arg Ala
385                 390                 395                 400

His Asp Leu Arg Val Glu Ala Asp Leu Glu Pro Ile Ala Gly Trp Arg
                405                 410                 415

Gly Val Ile Gly Leu Gln Thr Val Gln Arg Lys Phe Ser Ala Glu Gly
                420                 425                 430

Glu Glu Ala Tyr Val Gln Pro Thr Glu Thr Arg Arg Asn Ser Ile Tyr
                435                 440                 445

Leu Leu Glu Glu Tyr Arg Trp Gln Asp Trp Arg Trp Gln Ala Ala Leu
450                 455                 460

Arg His Glu Arg Gln Thr Val Asp Ala Gln Ser Gly Ile Ser Arg
465                 470                 475                 480

Ser His Ser Gly Thr Ser Phe Ser Leu Gly Ser Val Trp Lys Phe Thr
                485                 490                 495

Pro Gly Tyr Ser Leu Ser Ala Ser Leu Thr Gln Gly Asn Arg Leu Pro
                500                 505                 510

Thr Ala Glu Glu Leu Tyr Ala Asn Gly Leu His Met Ala Thr Ser Thr
                515                 520                 525

Tyr Glu Arg Gly Asn Ala Asp Leu Lys Arg Glu Arg Ser Gln Ala Leu
                530                 535                 540

Asp Ile Gly Leu Arg Lys Thr Ala Gly Asp Thr Thr Phe Ser Val Asn
545                 550                 555                 560

Ala Phe His His Arg Val Lys Gly Tyr Ile Tyr Gly Ala Thr Leu Asp
                565                 570                 575

Glu His Asp Gly Leu Gln Leu Leu Gln Tyr Thr Gln Ala Asp Ala Arg
                580                 585                 590

Phe Thr Gly Val Glu Gly Gln Val Arg Gln Lys Leu Ser Arg Gln Trp
                595                 600                 605

Gly Val Thr Leu Phe Gly Asp Ala Val Arg Ala Arg Leu Glu Asp Gly
                610                 615                 620

Ser Ala Leu Pro Arg Ile Pro Ala Ala Arg Val Gly Leu Arg Val Asp
625                 630                 635                 640

Thr Phe Tyr Lys Gly Trp Asp Ala Gln Ala Glu Trp Val Gln Val Leu
```

```
                    645                 650                 655
Arg Gln Asn Arg Val Thr Ala Tyr Glu Thr Glu Thr Asp Gly Tyr Gly
                660                 665                 670

Met Leu Asn Val Ser Ala Ser Tyr Thr Leu Arg Thr Ser Gly Gly Met
                675                 680                 685

Pro Trp Gln Phe Phe Ile Lys Gly Asn Asn Leu Thr Asn Arg Leu Ala
            690                 695                 700

Phe Ala His Thr Ser Phe Ile Lys Asn Ala Ala Pro Leu Met Gly Arg
705                 710                 715                 720

Asn Ile Thr Val Gly Val Lys Val Ser Phe
                725                 730

<210> SEQ ID NO 33
<211> LENGTH: 693
<212> TYPE: PRT
<213> ORGANISM: Diaphorobacter sp. TPSY

<400> SEQUENCE: 33

Met Asn Ser Phe Thr Pro Phe Ala Arg Met Pro Gly Ala Met His Pro
1               5                   10                  15

Leu Ala Trp Ala Ala Leu Leu Cys Leu Thr Ser Ala Ala Pro Ala Trp
                20                  25                  30

Ala Gln Ala Asp Ala Arg Leu Pro Glu Val Thr Val Ser Ser Ser Gly
            35                  40                  45

Leu Gln Leu Gly Val Ser Glu Met Thr Gln Pro Val Ser Val Leu Glu
        50                  55                  60

Gly Asp Ala Leu Val Arg Gln Arg Glu Ala Thr Leu Gly Glu Thr Leu
65                  70                  75                  80

Asp Gly Glu Pro Gly Ile Thr Gly Ser His Phe Gly Ala Gly Ala Ser
                85                  90                  95

Arg Pro Val Ile Arg Gly Met Asp Gly Pro Arg Val Arg Val Leu Ser
                100                 105                 110

Asp Gly Ser Glu Leu His Asp Ala Ser Thr Val Ser Pro Asp His Ala
            115                 120                 125

Val Ala Ala Glu Pro Leu Leu Ala Thr Gln Val Glu Val Leu Arg Gly
        130                 135                 140

Pro Ser Ala Leu Val Tyr Gly Gly Ala Val Gly Gly Val Val Asn
145                 150                 155                 160

Val Leu Asp Gly Lys Val Pro Thr Ala Val Pro Asp Lys Gly Tyr Glu
                165                 170                 175

Gly Ser Ala Glu Leu Arg Ala Gly Ser Ala Ala Arg Glu Lys Ala Gly
                180                 185                 190

Ala Val Ala Leu Thr Gly Gly Ala Gly Asn Leu Ala Val His Val Glu
            195                 200                 205

Ala Ala Gly Arg Asp Ala Asp Asp Tyr Arg Val Gly Ser Gly Trp Ala
        210                 215                 220

Glu Gly Arg Arg Val Pro Gly Ser Phe Asn Arg Thr Gly Thr Gly Ser
225                 230                 235                 240

Val Gly Leu Ser Trp Val Gly Ser Arg Gly Tyr Leu Gly Leu Ala Phe
                245                 250                 255

Thr Arg Gln Asn Ala Lys Tyr Gly Leu Pro Gly His Ser His Ser Phe
                260                 265                 270

Glu Gly Cys His Thr His Gly Asn His Leu His Cys Gly Ser His Asp
            275                 280                 285
```

```
Glu His Asp His Glu Asp Asp Gly His Asp His Asp His Gly His Glu
290                 295                 300
Ala Val Pro Val Val Asp Leu Arg Ser Glu Arg Val Asp Ile Arg Gly
305                 310                 315                 320
Glu Leu Arg Asp Pro Phe Thr Gly Phe Ser Ala Leu Arg Leu Arg Ala
                    325                 330                 335
Gly Val Thr Asp Tyr Val His Asp Glu Val Glu Gly Thr Val Ala
                340                 345                 350
Thr Thr Phe Lys Asn Lys Ala His Asp Leu Arg Val Glu Leu Gln His
            355                 360                 365
Glu Pro Val Ala Gly Trp Arg Gly Val Leu Gly Leu Gln Thr Gly Gln
370                 375                 380
Arg Lys Phe Ser Ala Ala Gly Glu Glu Ala Tyr Val Gln Pro Thr Leu
385                 390                 395                 400
Thr Arg Gln Trp Gly Val Phe Leu Leu Glu Glu Tyr Arg Leu Gly Asp
                405                 410                 415
Trp His Gly Asp Trp Arg Ile Glu Thr Ala Leu Arg His Asp Arg Gln
                420                 425                 430
Ser Ala Glu Ala Gln Asp Ser Gly Val Glu Arg Arg His His Gly Thr
            435                 440                 445
Ser Ala Ser Leu Gly Ala Val Trp Arg Phe Ala Pro Gly Tyr Ala Ala
450                 455                 460
Gly Ala Ser Ile Thr Arg Ala His Arg Ala Pro Thr Ala Glu Glu Leu
465                 470                 475                 480
Tyr Ala Arg Gly Leu His Met Ala Thr Ser Thr Tyr Glu Arg Gly Asp
                485                 490                 495
Ala Ser Leu Arg Ala Glu Thr Ser Arg Asn Ile Asp Leu Ser Leu Arg
            500                 505                 510
Lys Thr Ser Gly Asp Thr Thr Phe Asp Val Ser Val Phe His Asn Arg
            515                 520                 525
Ile Arg Asn Tyr Ile Tyr Gly Arg Thr Leu Asp Glu Leu Asp Gly Leu
            530                 535                 540
Gln Leu Leu Gln Tyr Ser Gln Ala Gly Ala Thr Phe Thr Gly Met Glu
545                 550                 555                 560
Gly Arg Val Arg Gln Arg Ile Thr Gln Arg Leu Gly Val Thr Leu Phe
                565                 570                 575
Gly Asp Ser Val Arg Ala Arg Leu Asp Gly Gly Ala Arg Leu Pro Arg
                580                 585                 590
Ile Ala Pro Ala Arg Val Gly Leu Arg Leu Asp Ala Asn Trp Arg Asp
            595                 600                 605
Trp Asp Gly Ala Val Glu Trp Val Gln Val Ala Arg Gln Asn Arg Val
610                 615                 620
Ala Ala Phe Glu Thr Ala Thr Pro Gly Tyr Gly Met Leu Asn Leu Gly
625                 630                 635                 640
Leu Ala Tyr Asn Ser Arg Thr Gly Ser Gly Thr Pro Trp Gln Val Tyr
                645                 650                 655
Leu Lys Ala Arg Asn Leu Thr Asp Arg Leu Ala Tyr Ala His Thr Ser
                660                 665                 670
Phe Ile Lys Asp Ala Ala Pro Leu Ala Gly Arg Asn Val Thr Val Gly
            675                 680                 685

Val Arg Val Ser Phe
690
```

```
<210> SEQ ID NO 34
<211> LENGTH: 809
<212> TYPE: PRT
<213> ORGANISM: Haemophilus parasuis 29755

<400> SEQUENCE: 34
```

| | | | | | | | | | | | | | | | |
|---|---|---|---|---|---|---|---|---|---|---|---|---|---|---|---|
| Met | Ile | Asn | Asn | Arg | Thr | Thr | Glu | Gln | Gln | Asn | Asn | Arg | Thr | Thr | Ala |
| 1 | | | | 5 | | | | | 10 | | | | | 15 | |
| Phe | Ser | Leu | Ala | Phe | Ser | Leu | Leu | Cys | Cys | Leu | Gly | Ile | Asn | Ala | |
| | | | 20 | | | | | 25 | | | | | 30 | | |
| Glu | Gln | Leu | Glu | Leu | Asp | Glu | Ile | Ser | Val | Met | Gly | Lys | Val | Pro | Glu |
| | | | 35 | | | | | 40 | | | | | 45 | | |
| Gly | Asn | Ser | Ile | Ser | Phe | Leu | Lys | Val | Ser | Asp | Ala | Ile | Ile | Asp | Gly |
| | 50 | | | | | 55 | | | | | 60 | | | | |
| Glu | Lys | Phe | Lys | Asn | Arg | Ser | Ala | Thr | Leu | Gly | Asn | Ala | Leu | Ser | Ser |
| 65 | | | | | 70 | | | | | 75 | | | | | 80 |
| Glu | Leu | Gly | Val | His | Ser | Thr | Pro | Phe | Gly | Gly | Ala | Ser | Ala | Pro | |
| | | | | 85 | | | | | 90 | | | | | 95 | |
| Ile | Ile | Arg | Gly | Gln | Glu | Gly | Val | Arg | Val | Lys | Ile | Leu | Gln | Asn | Asn |
| | | | 100 | | | | | 105 | | | | | 110 | | |
| Ala | Asp | Val | Val | Asp | Met | Ser | Asn | Ile | Ser | Pro | Asp | His | Ala | Ile | Thr |
| | | | 115 | | | | | 120 | | | | | 125 | | |
| Ala | Asp | Thr | Leu | Leu | Ala | Asn | Gln | Val | Glu | Ile | Leu | Arg | Gly | Ala | Ser |
| | 130 | | | | | 135 | | | | | 140 | | | | |
| Thr | Leu | Leu | Tyr | Ala | Ser | Ser | Pro | Ala | Gly | Ile | Val | Asn | Ile | Val | |
| 145 | | | | | 150 | | | | | 155 | | | | | 160 |
| Asp | Gln | Arg | Ile | Pro | Asn | Lys | Met | Pro | Lys | Lys | Gly | Tyr | Glu | Val | Thr |
| | | | | 165 | | | | | 170 | | | | | 175 | |
| Leu | Ser | Ser | Arg | Phe | Asp | Thr | Ala | Ser | Lys | Glu | Lys | Val | Tyr | Ala | Leu |
| | | | 180 | | | | | 185 | | | | | 190 | | |
| Gly | Thr | Thr | Ile | Gly | Ile | Gly | Lys | His | Leu | Ala | Leu | Arg | Leu | Glu | Gly |
| | | | | 195 | | | | | 200 | | | | | 205 | |
| Leu | Asp | Arg | Gln | Ser | Gln | Asn | Tyr | Lys | Val | Pro | Gln | Ile | Lys | Leu | Gly |
| | 210 | | | | | 215 | | | | | 220 | | | | |
| Glu | Thr | Leu | Asn | Tyr | Val | Pro | Asp | Thr | Tyr | His | Gln | Ser | Lys | Val | Gly |
| 225 | | | | | 230 | | | | | 235 | | | | | 240 |
| Thr | Ile | Gly | Leu | Ser | Phe | Ile | Gly | Glu | Lys | Gly | Tyr | Leu | Gly | Ala | Ser |
| | | | | 245 | | | | | 250 | | | | | 255 | |
| Tyr | Asn | Gln | Arg | Lys | Asp | Arg | Tyr | Gly | Leu | Pro | Gly | His | Asn | His | Lys |
| | | | 260 | | | | | 265 | | | | | 270 | | |
| Phe | Asp | Thr | Cys | Ile | Ala | His | Ile | Tyr | Asp | Met | Arg | Leu | Gln | Gly | Lys |
| | | | | 275 | | | | | 280 | | | | | 285 | |
| His | Ser | Tyr | Thr | Asn | Leu | Tyr | Pro | His | Leu | Met | Ser | Asp | Glu | Met | Val |
| | 290 | | | | | 295 | | | | | 300 | | | | |
| Thr | Glu | Asn | Pro | His | Phe | His | Cys | Gly | Thr | Asp | Tyr | Asp | Leu | Asp | Pro |
| 305 | | | | | 310 | | | | | 315 | | | | | 320 |
| Ser | His | Ser | His | Asp | His | Pro | Tyr | Gly | His | Asp | His | Asp | His | Thr | His |
| | | | | 325 | | | | | 330 | | | | | 335 | |
| Ile | Gly | Pro | Trp | Val | Asp | Leu | His | Ser | Lys | Arg | Ile | Asp | Ile | Lys | Gly |
| | | | 340 | | | | | 345 | | | | | 350 | | |
| Glu | Ile | Lys | Gln | Pro | Leu | Pro | Met | Leu | Asp | Lys | Ile | Gln | Leu | Ser | Tyr |
| | | | | 355 | | | | | 360 | | | | | 365 | |
| Ala | Gln | Thr | Asp | Tyr | Tyr | His | Asp | Glu | Lys | Asp | Ala | Gly | Lys | Ser | Gly |
| | 370 | | | | | 375 | | | | | 380 | | | | |

```
Asp Thr Ile Asn Pro Asn Arg Val Asp Lys Ser Lys Asp Phe Gly Lys
385                 390                 395                 400

Pro Val Asn Ile Phe Lys Asn Gln Gly Lys Asn Ala Arg Leu Glu Phe
                405                 410                 415

Phe His Thr Pro Ile Gly Gly Leu Thr Gly Met Phe Gly Val Gln Tyr
            420                 425                 430

Gln Thr Leu Gln Ser Ser Ala Asn Thr Pro Asn Asn Arg Glu Val Gln
        435                 440                 445

Trp Pro Leu Val Asp Asn Arg Asn Lys Gln Ile Ser Leu Phe Ala Leu
    450                 455                 460

Glu Gln Tyr Ala Trp Asp Asn Phe Ala Ile Glu Leu Gly Leu Arg Thr
465                 470                 475                 480

Glu Lys Gln Asn Ile His Ile Asp Tyr Asp Leu Ala Lys Ile Gln Lys
                485                 490                 495

Gln Gln Lys Phe Asn Glu Arg Thr Tyr Gly Lys Gln Val Asp Pro Asp
            500                 505                 510

Leu Ser Asp Tyr Asp Glu Lys Ala Ile Ser Tyr Thr Gly Ala Phe Asn
    515                 520                 525

Trp Phe Phe His Pro Asp Tyr Gln Leu Ser Phe Thr Ala Ser His Asn
530                 535                 540

Glu Arg Leu Pro Thr Pro Met Glu Leu Tyr Tyr His Gly Gln His Leu
545                 550                 555                 560

Ala Thr Asn Ser Phe Glu Tyr Gly Asn Lys Asp Leu Lys Lys Glu Ile
                565                 570                 575

Ser Asn Asn Phe Glu Leu Gly Leu Gly Tyr His Thr Glu Lys Leu Asp
            580                 585                 590

Tyr Lys Leu Ser Thr Tyr Tyr Asn Asn Phe Asp Asn Tyr Ile Tyr Asn
    595                 600                 605

Glu Thr Leu Tyr Arg Ser Asn Asn Leu Phe Met Arg Arg Tyr Asn Gln
610                 615                 620

Ala Lys Ala Thr Phe Tyr Gly Leu Glu Gly Ile Ile Asn Tyr Arg Phe
625                 630                 635                 640

Thr Pro Asp Tyr Gln Phe Ser Val Phe Gly Asp Met Val Lys Gly Lys
                645                 650                 655

Leu Lys Gln Leu Pro Asp Ile Lys Gly Leu Asn Asp Val Tyr Gly Glu
            660                 665                 670

Pro Ile Leu Asn Pro Asp Tyr Asp Pro Glu Tyr Asp Glu Pro Glu Asp
    675                 680                 685

Gln Tyr Tyr Arg Pro Tyr Leu Gly Lys Glu Met Ile Lys Gln Ala Asp
690                 695                 700

Arg Val Ser Pro Arg Leu Pro Pro Ile Arg Leu Gly Ala Arg Phe Asn
705                 710                 715                 720

Ala Gln Leu Thr Glu Asn Leu Ser Gly Ser Val Glu Trp Met Lys Val
                725                 730                 735

Phe Thr Gln Asn Lys Val Ser Lys Leu Glu Ser Ser Thr Lys Gly Tyr
            740                 745                 750

Gln Leu Leu Asn Ala Ser Leu Asn Tyr Arg Arg Gln Ile Lys Gly Val
        755                 760                 765

Glu Tyr Thr Val Ser Leu Thr Gly Asn Asn Leu Leu Asn Gln Ala Val
    770                 775                 780

Tyr Ile His Asn Ser Tyr His Pro Tyr Val Pro Gln Met Gly Arg Asn
785                 790                 795                 800

Phe Ile Leu Gly Leu Asp Leu Ser Phe
```

<210> SEQ ID NO 35
<211> LENGTH: 797
<212> TYPE: PRT
<213> ORGANISM: Haemophilus parasuis SH0165

<400> SEQUENCE: 35

```
Met Ile Lys Asn Lys Thr Thr Ala Phe Ser Leu Leu Cys Cys Leu
1               5                   10                  15

Gly Ile Asn Ala Glu Gln Leu Glu Leu Asp Glu Ile Ser Val Met Gly
            20                  25                  30

Lys Val Pro Glu Gly Asn Ser Ile Ser Phe Leu Lys Val Ser Asp Ala
        35                  40                  45

Ile Ile Asp Gly Glu Lys Phe Lys Asn Arg Ser Ala Thr Leu Gly Asn
    50                  55                  60

Ala Leu Ser Ser Glu Leu Gly Val His Ser Thr Pro Phe Gly Gly Gly
65              70                  75                  80

Ala Ser Ala Pro Ile Ile Arg Gly Gln Glu Gly Val Arg Val Lys Ile
                85                  90                  95

Leu Gln Asn Asn Ala Asp Val Val Asp Met Ser Asn Ile Ser Pro Asp
            100                 105                 110

His Ala Ile Thr Ala Asp Thr Leu Leu Ala Asn Gln Val Glu Ile Leu
        115                 120                 125

Arg Gly Ala Ser Thr Leu Leu Tyr Ala Ser Ser Pro Ala Gly Ile
    130                 135                 140

Val Asn Ile Val Asp Gln Arg Ile Pro Asn Lys Met Pro Lys Lys Gly
145                 150                 155                 160

Tyr Glu Val Thr Leu Ser Ser Arg Phe Asp Thr Ala Ser Lys Glu Lys
                165                 170                 175

Val Tyr Ala Leu Gly Thr Thr Ile Gly Ile Gly Lys His Leu Ala Leu
            180                 185                 190

Arg Leu Glu Gly Leu Asp Arg Gln Ser Gln Asn Tyr Lys Val Pro Gln
        195                 200                 205

Ile Lys Leu Gly Glu Thr Leu Asn Tyr Val Pro Asp Thr Tyr His Gln
    210                 215                 220

Ser Lys Val Gly Thr Ile Gly Leu Ser Phe Ile Gly Glu Lys Gly Tyr
225                 230                 235                 240

Leu Gly Ala Ser Tyr Asn Gln Arg Lys Asp Arg Tyr Gly Leu Pro Gly
                245                 250                 255

His Asn His Lys Phe Asp Thr Cys Ile Ala His Ile Tyr Asp Met Arg
            260                 265                 270

Leu Gln Gly Lys His Ser Tyr Thr Asn Leu Tyr Pro His Leu Met Ser
        275                 280                 285

Asp Glu Met Val Thr Glu Asn Pro His Phe His Cys Gly Thr Asp Tyr
    290                 295                 300

Asp Leu Asp Pro Ser His Ser His Asp His Pro Tyr Gly His Asp His
305                 310                 315                 320

Asp His Thr His Ile Gly Pro Trp Val Asp Leu His Ser Lys Arg Ile
                325                 330                 335

Asp Ile Lys Gly Glu Ile Lys Gln Pro Leu Pro Met Leu Asp Lys Ile
            340                 345                 350

Gln Leu Ser Tyr Ala Gln Thr Asp Tyr Tyr His Asp Glu Lys Asp Ala
        355                 360                 365
```

-continued

```
Gly Lys Ser Gly Asp Thr Ile Asn Pro Asn Arg Val Asp Lys Ser Lys
    370                 375                 380
Asp Phe Gly Lys Pro Val Asn Ile Phe Lys Asn Gln Gly Lys Asn Ala
385                 390                 395                 400
Arg Leu Glu Phe Phe His Thr Pro Ile Gly Gly Leu Thr Gly Met Phe
                    405                 410                 415
Gly Val Gln Tyr Gln Thr Leu Gln Ser Ser Ala Asn Thr Pro Ser Asn
                420                 425                 430
Arg Glu Val Gln Trp Pro Leu Val Asp Asn Arg Asn Lys Gln Ile Ser
            435                 440                 445
Leu Phe Ala Leu Glu Gln Tyr Ala Trp Asp Asn Phe Ala Ile Glu Leu
450                 455                 460
Gly Leu Arg Thr Glu Lys Gln Asn Ile His Ile Asp Tyr Asp Leu Ala
465                 470                 475                 480
Lys Ile Gln Lys Gln Gln Lys Phe Asn Glu Arg Thr Tyr Gly Lys Gln
                    485                 490                 495
Val Asp Pro Asp Leu Ser Asp Tyr Asp Glu Lys Ala Val Ser Tyr Thr
                500                 505                 510
Gly Thr Phe Asn Trp Phe Phe His Pro Asp Tyr Gln Leu Ser Phe Thr
            515                 520                 525
Ala Ser His Asn Glu Arg Leu Pro Thr Pro Met Glu Leu Tyr Tyr His
530                 535                 540
Gly Gln His Leu Ala Thr Asn Ser Phe Glu Tyr Gly Asn Lys Asp Leu
545                 550                 555                 560
Lys Lys Glu Ile Ser Asn Asn Phe Glu Leu Gly Leu Gly Tyr His Thr
                    565                 570                 575
Glu Lys Leu Asp Tyr Lys Leu Ser Thr Tyr Tyr Asn Asn Phe Asp Asn
                580                 585                 590
Tyr Ile Tyr Asn Glu Thr Leu Tyr Arg Ser Asn Asn Leu Phe Met Arg
            595                 600                 605
Arg Tyr Asn Gln Ala Lys Ala Thr Phe Tyr Gly Leu Glu Gly Ile Ile
610                 615                 620
Asn Tyr Arg Phe Thr Pro Asp Tyr Gln Phe Ser Val Phe Gly Asp Met
625                 630                 635                 640
Val Lys Gly Lys Leu Lys Gln Leu Pro Asp Ile Lys Gly Leu Asn Asp
                    645                 650                 655
Val Tyr Gly Glu Pro Ile Leu Asp Pro Asp Tyr Asp Pro Glu Tyr Asp
                660                 665                 670
Glu Pro Glu Asp Gln Tyr Tyr Arg Pro Tyr Leu Gly Lys Glu Met Ile
            675                 680                 685
Lys Gln Ala Asp Arg Val Ser Pro Arg Leu Pro Pro Ile Arg Leu Gly
690                 695                 700
Ala Arg Phe Asn Ala Gln Leu Thr Glu Asn Leu Ser Gly Ser Val Glu
705                 710                 715                 720
Trp Met Lys Val Phe Thr Gln Asn Lys Val Ser Lys Leu Glu Ser Ser
                    725                 730                 735
Thr Lys Gly Tyr Gln Leu Leu Asn Ala Ser Leu Asn Tyr Arg Arg Gln
                740                 745                 750
Ile Lys Gly Val Glu Tyr Thr Val Ser Leu Thr Gly Asn Asn Leu Leu
            755                 760                 765
Asn Gln Ala Val Tyr Ile His Asn Ser Tyr His Pro Tyr Val Pro Gln
770                 775                 780
Met Gly Arg Asn Phe Ile Leu Gly Leu Asp Leu Ser Phe
```

785                 790                 795

<210> SEQ ID NO 36
<211> LENGTH: 868
<212> TYPE: PRT
<213> ORGANISM: Haemophilus somnus 129PT

<400> SEQUENCE: 36

Met Lys Leu Tyr Lys Phe Arg Lys Glu Leu Phe Val Leu Thr Phe Leu
1               5                   10                  15

Val Ser Gly Ser Ser Ile Ser Ala Glu Ile Ile Ala Glu Leu Asp Glu
            20                  25                  30

Val Val Val Ser Asp Ser Ser Val Ala Asp Phe Gln Ser Leu Ala
        35                  40                  45

Phe Gln Gly Gly Arg Lys Ala Ser Asp Val Phe Ile Glu Gly Lys Glu
    50                  55                  60

Phe Lys Thr Arg Ser Ala Thr Leu Gly Asn Ala Leu Ala Gly Glu Leu
65                  70                  75                  80

Gly Val His Ser Asn Pro Phe Gly Gly Ala Ser Ala Pro Val Ile
                85                  90                  95

Arg Gly Gln Glu Gly Val Arg Ile Lys Leu Leu Gln Asn Gly Ser Asp
            100                 105                 110

Ile Val Asp Met Ser Asn Ile Ser Pro Asp His Ala Val Val Ala Asp
        115                 120                 125

Thr Leu Leu Ala Gln Gln Val Glu Leu Val Arg Gly Thr Ser Thr Leu
130                 135                 140

Met Tyr Gly Met Ala Ser Pro Ala Gly Val Val Asn Ile Val Asp Asn
145                 150                 155                 160

Arg Ile Pro Thr Ser Arg Pro Glu Lys Gly Tyr Glu Gly Glu Ile Val
                165                 170                 175

Ser Arg Phe Asp Thr Ala Ser Lys Glu Lys Val Leu Thr Ala Gly Val
            180                 185                 190

Thr Leu Ala Ala Gly Asp Asn Phe Leu Ile Arg Ala Glu Gly Leu Thr
        195                 200                 205

Arg Lys Ser Glu Asn Tyr His Val Pro Glu Val Phe Ile Gly Gln Lys
    210                 215                 220

Leu Asn Tyr Leu Pro Asp Ser His His Lys Ser Lys Val Gly Thr Leu
225                 230                 235                 240

Gly Thr Thr Trp Ile Gly Asp Lys Gly Tyr Leu Gly Ala Ser Val Ser
                245                 250                 255

Tyr Arg Lys Asp Arg Tyr Gly Ile Pro Gly His Asn His Ala Phe Asp
            260                 265                 270

Tyr Cys Ser Gly His Leu Phe Asp Thr Asp Asn Leu Lys Ala Ile Thr
        275                 280                 285

Gly Gly Asp Gly Glu Ala Pro Tyr Leu Asn Ala Tyr Pro His Leu Met
    290                 295                 300

Thr Asp Ala Asp Met Ile Ser Ser Leu His Phe His Cys Gly Ala Asp
305                 310                 315                 320

Ile Gln Gly His Lys His Ser His Glu Ser Ile Tyr Gly His Asp His
                325                 330                 335

Asp Ile Ser Glu Ala Gly Pro Val Val Asp Met Arg Ser Lys Arg Tyr
            340                 345                 350

Asp Val Arg Gly Glu Trp Lys Ala Pro Leu Pro Trp Ile Ser Lys Val
        355                 360                 365

-continued

```
Lys Leu Ser Leu Ala Tyr Ala Asp Tyr Tyr His Asp Glu Lys His Asp
    370                 375                 380
Gly Lys Ala His Ile Asp Lys Asn Asp Ser Gln Gly Ile Lys Asp Arg
385                 390                 395                 400
Lys Lys Tyr Thr Ala Ala Ile Met Ser Gly Lys Pro Glu Ala Phe Tyr
                405                 410                 415
Ala Asn Arg Gly Phe Asn Ser Arg Leu Glu Ile Tyr His Gln Pro Thr
                420                 425                 430
Glu His Phe Asn Gly Val Val Gly Met Gln Tyr Gln Thr Gln Lys Thr
            435                 440                 445
Lys Val Gln Arg Leu Ala Pro Ser Leu Asn Asn Asn Gly Gln Asp Leu
450                 455                 460
Ser Gly Glu Arg Lys Glu Ser Glu Arg Asn Pro Leu Val Pro His Thr
465                 470                 475                 480
Asn Lys Gln Phe Ser Val Phe Ala Leu Glu Gln Phe Thr Trp Arg Asn
                485                 490                 495
Phe Ile Val Glu Val Gly Ala Arg Trp Glu Thr Gln Arg Ile Pro Ile
                500                 505                 510
Lys Tyr Asp Pro Asn Lys Leu Arg Leu Asp Lys Ala Ala Gly Ser Lys
                515                 520                 525
Val Arg Leu Pro Asp Leu Ser Pro Tyr Thr Glu Asn Ala Leu Ser Tyr
            530                 535                 540
Ser Gly Thr Leu Met Trp Asp Phe His Pro Ala Tyr Arg Leu Ser Ile
545                 550                 555                 560
Thr Gly Ser His Asn Glu Arg Ile Pro Ser Pro Met Glu Leu Tyr Tyr
                565                 570                 575
His Gly Lys His Leu Ala Thr Asn Ser Phe Gln Tyr Gly Asn Lys Asp
            580                 585                 590
Leu Lys Lys Glu Arg Ser Asn Val Glu Ile Gly Leu Met Arg Ile
            595                 600                 605
Ser Asp Lys Trp Asp Phe Lys Val Ser Ala Tyr Tyr Gln Arg Phe Lys
    610                 615                 620
Asn Tyr Ile His Asn Glu Asn Leu Tyr Arg Glu Gly Asn Leu Phe Met
625                 630                 635                 640
Arg Arg Tyr Asn Gln Ser Gln Ala Arg Phe Tyr Gly Phe Glu Gly Glu
                645                 650                 655
Ile Gly Tyr Gln Ile Thr Pro Asn His Lys Ile Thr Phe Phe Gly Asp
                660                 665                 670
Tyr Val Asn Gly Lys Leu Phe Gly Phe Lys Lys Phe Tyr Gly Asn Pro
            675                 680                 685
Lys Phe Lys Lys Ile Cys Glu Ile Pro Lys Ala Gln Leu Ile Asp Ile
    690                 695                 700
Glu Arg Cys Ile Glu Asp Glu Trp Gly Glu Trp Asp Tyr Arg
705                 710                 715                 720
Lys Ile Gly Glu Gln Ile Ile Glu Arg Pro Asn Arg Asn Ala Ala Arg
                725                 730                 735
Val Pro Pro Met Arg Leu Gly Phe Arg Leu Lys Ser Gln Phe Asn Asp
            740                 745                 750
Asn Trp Ser Ser Ser Leu Glu Tyr Thr Arg Met Phe Ala Gln Lys Arg
    755                 760                 765
Ile Ser Ile Asn Thr Val Ile Lys Glu Ile Asp Arg Glu Glu Ala Glu
770                 775                 780
Lys Arg Arg Glu Asn Ala Asn Gly Leu Gly Tyr Asp Gly His Tyr Thr
```

```
                 785                 790                 795                 800

Glu Leu Val Pro Glu Asp Val Thr Gln Gly Tyr His Leu Leu Asn Leu
                805                 810                 815

Ser Leu Asn Tyr Ser Arg Lys Ile Asp Gly Val Glu Tyr Ser Ala Thr
                820                 825                 830

Leu Ser Ala Asn Asn Leu Leu Asn Gln Lys Ile Tyr Ile His Asn Ser
                835                 840                 845

Tyr Leu Pro Tyr Val Pro Gln Met Gly Arg Asn Phe Ile Leu Asn Val
                850                 855                 860

Gly Val Thr Phe
865

<210> SEQ ID NO 37
<211> LENGTH: 868
<212> TYPE: PRT
<213> ORGANISM: Haemophilus somnus 2336

<400> SEQUENCE: 37

Met Lys Leu Tyr Lys Phe Arg Lys Glu Leu Phe Val Leu Thr Leu Leu
1               5                   10                  15

Val Ser Gly Ser Ile Ser Ala Glu Ile Ala Glu Leu Asp Glu
                20                  25                  30

Val Val Val Ser Asp Ser Ser Val Ala Asp Phe Gln Ser Leu Ala
                35                  40                  45

Phe Gln Gly Gly Arg Lys Ala Ser Asp Val Phe Ile Glu Gly Lys Glu
    50                  55                  60

Phe Lys Thr Arg Ser Ala Thr Leu Gly Asn Ala Leu Ala Gly Glu Leu
65                  70                  75                  80

Gly Val His Ser Asn Pro Phe Gly Gly Ala Ser Ala Pro Val Ile
                85                  90                  95

Arg Gly Gln Glu Gly Val Arg Ile Lys Leu Leu Gln Asn Gly Ser Asp
                100                 105                 110

Ile Val Asp Met Ser Asn Ile Ser Pro Asp His Ala Val Val Ala Asp
                115                 120                 125

Thr Leu Leu Ala Gln Gln Val Glu Leu Val Arg Gly Thr Ser Thr Leu
    130                 135                 140

Met Tyr Gly Met Ala Ser Pro Ala Gly Val Val Asn Ile Val Asp Asn
145                 150                 155                 160

Arg Ile Pro Thr Ser Arg Pro Glu Lys Gly Tyr Glu Gly Glu Ile Val
                165                 170                 175

Ser Arg Phe Asp Thr Ala Ser Lys Glu Lys Val Leu Thr Ala Gly Val
                180                 185                 190

Thr Leu Ala Ala Gly Asp Asn Phe Leu Ile Arg Ala Glu Gly Leu Thr
                195                 200                 205

Arg Lys Ser Glu Asn Tyr His Val Pro Glu Val Phe Ile Gly Gln Lys
    210                 215                 220

Leu Asn Tyr Leu Pro Asp Ser His His Lys Ser Lys Val Gly Thr Leu
225                 230                 235                 240

Gly Thr Thr Trp Ile Gly Asp Lys Gly Tyr Leu Gly Ala Ser Val Ser
                245                 250                 255

Tyr Arg Lys Asp His Tyr Gly Ile Pro Gly His Asn His Ala Phe Asp
                260                 265                 270

Tyr Cys Ser Gly His Leu Phe Asp Thr Asp Asn Leu Lys Ala Ile Thr
                275                 280                 285
```

```
Gly Gly Asp Gly Glu Ala Pro Tyr Leu Asn Ala Tyr Pro His Leu Met
290                 295                 300
Thr Asp Ala Asp Met Ile Ser Ser Leu His Phe His Cys Gly Ala Asp
305                 310                 315                 320
Ile Gln Gly His Lys His Ser His Glu Ser Ile Tyr Gly His Asp His
                325                 330                 335
Asp Ile Ser Glu Ala Gly Pro Val Val Asp Met Arg Ser Lys Arg Tyr
            340                 345                 350
Asp Val Arg Gly Glu Trp Lys Ser Pro Ile Pro Gly Ile Ser Lys Val
        355                 360                 365
Lys Leu Ser Leu Ala Tyr Ala Asp Tyr Tyr His Asp Glu Lys His Asp
370                 375                 380
Gly Lys Ala His Ile Asp Lys Asn Asp Ser Gln Gly Ile Lys Asp Arg
385                 390                 395                 400
Lys Lys Tyr Thr Ala Ala Ile Met Ser Gly Lys Pro Glu Ala Phe Tyr
                405                 410                 415
Ala Asn Arg Gly Phe Asn Ser Arg Leu Glu Ile Tyr His Gln Pro Thr
            420                 425                 430
Glu His Phe Asn Gly Val Val Gly Met Gln Tyr Gln Thr Gln Lys Thr
        435                 440                 445
Lys Val Gln Arg Leu Ala Pro Ser Leu Asn Asn Asn Gly Gln Asp Leu
450                 455                 460
Ser Gly Glu Arg Lys Glu Ser Glu Arg Asn Pro Leu Val Pro His Thr
465                 470                 475                 480
Asn Lys Gln Phe Ser Val Phe Ala Leu Glu Gln Phe Thr Trp Arg Asn
                485                 490                 495
Phe Ile Val Glu Val Gly Ala Arg Trp Glu Lys Gln Arg Ile Pro Ile
            500                 505                 510
Lys Tyr Asp Pro His Lys Leu Arg Leu Asp Lys Ala Ala Gly Ser Lys
        515                 520                 525
Val Arg Leu Pro Asp Leu Ser Pro Tyr Thr Glu Asn Ala Leu Ser Tyr
530                 535                 540
Ser Gly Thr Leu Met Trp Asp Phe His Pro Ala Tyr Arg Leu Ser Ile
545                 550                 555                 560
Thr Gly Ser His Asn Glu Arg Ile Pro Ser Pro Met Glu Leu Tyr Tyr
                565                 570                 575
His Gly Lys His Leu Ala Thr Asn Ser Phe Gln Tyr Gly Asn Lys Asp
            580                 585                 590
Leu Lys Lys Glu Arg Ser Asn Asn Val Glu Ile Gly Leu Met Arg Ile
        595                 600                 605
Ser Asp Lys Trp Asp Phe Lys Val Ser Ala Tyr Tyr Gln Arg Phe Lys
610                 615                 620
Asn Tyr Ile His Asn Glu Asn Leu Tyr Arg Glu Gly Asn Leu Phe Met
625                 630                 635                 640
Arg Arg Tyr Asn Gln Ser Gln Ala Arg Phe Tyr Gly Phe Glu Gly Glu
                645                 650                 655
Ile Gly Tyr Gln Ile Thr Pro Asn His Lys Ile Thr Phe Phe Gly Asp
            660                 665                 670
Tyr Val Asn Gly Lys Leu Phe Gly Phe Lys Lys Phe Tyr Gly Asn Pro
        675                 680                 685
Lys Phe Lys Arg Val Cys Glu Leu Glu Asn Asp Gly Lys Asn Asn Leu
690                 695                 700
Glu Lys Cys Val Glu Asn Glu Glu Trp Gly Glu Glu Trp Ser Tyr His
```

```
            705                 710                 715                 720
Lys Ile Gly Glu Gln Thr Ile Glu Arg Pro Asn Arg Asn Ala Ala Arg
                    725                 730                 735

Val Pro Pro Met Arg Leu Gly Phe Arg Leu Lys Ser Gln Phe Asn Asp
                740                 745                 750

Asn Trp Ser Gly Ser Leu Glu Tyr Thr Arg Met Phe Val Gln Lys Arg
                755                 760                 765

Ile Ser Ile Asn Ser Val Ile Lys Glu Ile Asp Arg Glu Glu Ala Glu
            770                 775                 780

Lys Arg Arg Glu Asn Ala Lys Gly Leu Gly Tyr Asp Gly His Tyr Thr
785                 790                 795                 800

Glu Leu Val Pro Glu Asp Val Thr Gln Gly Tyr His Leu Leu Asn Leu
                805                 810                 815

Ser Leu Asn Tyr Ser Arg Lys Ile Asp Gly Val Glu Tyr Ser Ala Thr
                820                 825                 830

Leu Ser Ala Asn Asn Leu Leu Asn Gln Lys Ile Tyr Ile His Asn Ser
            835                 840                 845

Tyr Leu Pro Tyr Val Pro Gln Met Gly Arg Asn Phe Ile Leu Asn Val
    850                 855                 860

Gly Val Thr Phe
865

<210> SEQ ID NO 38
<211> LENGTH: 766
<212> TYPE: PRT
<213> ORGANISM: Mannheimia haemolytica

<400> SEQUENCE: 38

Met Leu Lys Lys Asn Tyr Leu Thr Val Ser Ile Leu Ala Ile Ser
1               5                   10                  15

Gly Val Gly Tyr Ala Asn Glu Ile Ser Leu Glu Thr Ile Thr Val Asp
                20                  25                  30

Gly Asn Thr Pro Ser Thr Lys Gly Lys Leu Leu Gly Gly Glu Leu Asn
            35                  40                  45

Ser Asn Glu Ser Val Val Asp Glu Lys Asn Leu Lys Gln Gly Ser Ile
    50                  55                  60

Thr Leu Gly Asn Ala Leu Ser Gly Glu Leu Gly Ile His Ser Ser Gln
65                  70                  75                  80

Phe Gly Gly Gly Ala Ser Thr Pro Ile Ile Arg Gly Gln Glu Ser Lys
                85                  90                  95

Arg Ala Lys Ile Leu Gln Asn Asn Gly Glu Asn Leu Asp Met Ser Gly
                100                 105                 110

Met Ser Pro Asp His Ala Val Thr Val Asp Ala Leu Leu Ala Lys Arg
            115                 120                 125

Ile Glu Ile Leu Arg Gly Pro Thr Thr Leu Leu Tyr Ser Ala Gly Asn
130                 135                 140

Thr Ala Gly Val Ile Asn Val Val Asp Asn Lys Ile Pro Thr Ala Ile
145                 150                 155                 160

Pro Glu Lys Gly Tyr Glu Gly Gln Phe Gly Val Arg Phe Gly Ser Ala
                165                 170                 175

Ser Lys Glu Arg Leu Thr Tyr Ala Gly Ser Thr Phe Ala Leu Gly Asn
                180                 185                 190

His Leu Ala Leu Arg Val Gln Gly Met Tyr Asn Lys Ala Ser Glu Tyr
            195                 200                 205
```

-continued

```
Tyr Ala Pro His Phe Thr Ile Glu Gly Lys Pro Tyr His Arg Val Pro
    210                 215                 220
Asp Ser Asp Val Gln Ser Gln Thr Gly Thr Val Ser Leu Ser Trp Ile
225                 230                 235                 240
Gly Glu Arg Gly His Leu Gly Ile Ala Tyr Thr Asp Arg Arg Asp Lys
                245                 250                 255
Tyr Gly Leu Ile Gly His Thr His Lys Tyr Asp His Tyr Thr Ile Ser
            260                 265                 270
Ile Ile Arg Gln Ala Val Met Phe Ala Lys Gly Tyr Leu Arg Phe Tyr
        275                 280                 285
Pro His Leu Ala Glu Glu Gly Asp Ile Asp Tyr Asn Asn Pro Gly Ile
    290                 295                 300
Arg Leu Leu His Thr His Ile Pro Gly Gly Ser His Tyr Gly Gln Asp
305                 310                 315                 320
Thr His Glu His Gly Lys Pro Trp Ile Asp Met His Ser Lys Arg Tyr
                325                 330                 335
Asp Ile Asp Gly Ser Leu Gln Asn Pro Leu Pro Gly Phe Glu Glu Ala
            340                 345                 350
Lys Ile Ser Ala Asn Tyr Val Asp Tyr His Asp Glu Lys Asp Gly
        355                 360                 365
Lys Arg Val Glu Asn Tyr Phe Lys Asn Lys Gly Asn Leu Arg Phe
    370                 375                 380
Glu Leu Val His Lys Glu Trp Lys Gly Leu Lys Gly Ala Ile Gly Val
385                 390                 395                 400
Gln Tyr Thr Asn Gln Ser Thr Ser Ala Leu Ala Leu Glu Ala Ser Arg
                405                 410                 415
Ala Ala Lys Val Phe Asn Lys Gln Pro Leu Leu Asn Asn Pro Lys Thr
            420                 425                 430
Lys Leu Trp Ser Leu Phe Ala Ile Glu Arg Leu Asn Leu Gly Asp Phe
        435                 440                 445
Thr Phe Glu Leu Ser Gly Arg Ala Glu Arg Gln Lys Ile Ala Met Asp
    450                 455                 460
Tyr Asp Val Lys Leu Ile Asp Arg Trp Leu Gly Phe Asn Thr Pro Met
465                 470                 475                 480
Pro Asn Leu Asp Pro His Lys Asp Lys Gly Tyr Ser Tyr Ser Phe Ala
                485                 490                 495
Thr His Trp Tyr Phe Ala Pro Asn His Lys Leu Thr Leu Asn Ala Ala
            500                 505                 510
His Gln Glu Arg Leu Pro Asn Ala Gln Glu Leu Tyr Ala His Gly Lys
        515                 520                 525
His Ile Ala Leu Asn Ala Phe Glu Ala Gly Asn Lys Asn Leu Lys Lys
    530                 535                 540
Glu Arg Ser Asn Gln Ile Glu Leu Ser Leu Ala Tyr Val Gly Asp Lys
545                 550                 555                 560
Trp Asp Tyr Lys Leu Asn Leu Tyr His Thr Arg Tyr Gly Asn Tyr Ile
                565                 570                 575
Tyr Pro Leu Thr Leu Asn Asp Asn Arg Gly Pro Lys Ser Phe Thr Asp
            580                 585                 590
Glu Tyr Asn Leu Lys Val Asn Arg Tyr Tyr Gln Gly Glu Ala Arg Phe
        595                 600                 605
Ser Gly Ala Glu Gly Glu Ile Gly Tyr Leu Phe Thr Pro Asn Tyr Arg
    610                 615                 620
Leu Ala Val Phe Gly Asp Tyr Val Arg Gly Lys Leu Val Asn Leu Pro
```

```
                625                 630                 635                 640
Asn Ile Ala Met Ser Tyr Asn Ile Trp Thr Gly Glu Val Asp Lys Trp
                    645                 650                 655
Ala Ser Gln Pro Asp Ile Ser Ala Pro Arg Ile Pro Pro Leu Arg Leu
                    660                 665                 670
Gly Ala Arg Phe Asn Ala Asp Phe Asn Leu Asn Trp Ser Gly Met Leu
                    675                 680                 685
Glu Tyr Tyr Arg Val Phe Ala Gln Lys Lys Val Ser Lys Tyr Glu Gln
                    690                 695                 700
Val Thr Pro Gly His His Gln Val Asn Leu Gly Val Thr Tyr Ser Asn
705                 710                 715                 720
His Phe Asn Gln Thr Glu Tyr Gln Val Phe Leu Lys Val Asp Asn Leu
                    725                 730                 735
Leu Asn Gln Lys Met Tyr Gln His Ala Ser Tyr Leu Pro His Ile Pro
                    740                 745                 750
Gln Met Gly Arg Asn Ala Met Leu Gly Met Asn Ile Ser Phe
                    755                 760                 765

<210> SEQ ID NO 39
<211> LENGTH: 790
<212> TYPE: PRT
<213> ORGANISM: Mannheimia haemolytica PHL213

<400> SEQUENCE: 39

Met Phe Lys Lys Thr Gly Leu Ala Leu Leu Ile Ser Ala Gln Phe Ser
1               5                   10                  15
Pro Leu Val Trp Ala Glu Asn Asn Asp Val Ala Val Leu Asp Glu Val
                    20                  25                  30
Ser Val Val Gly Ser Thr Pro Ser Ile Ser Gln Gly Ser Glu Val Thr
            35                  40                  45
Leu Leu Lys Val Ser Asp Lys Ile Ile Ala Gly Lys Glu Phe Lys Lys
        50                  55                  60
Arg Ser Ala Thr Leu Gly Asn Ala Leu Ala Ser Glu Leu Gly Val His
65                  70                  75                  80
Ser Asn Pro Phe Gly Gly Ala Ser Lys Pro Ile Ile Arg Gly Gln
                85                  90                  95
Glu Gly Ala Arg Ile Arg Ile Leu Gln Asn Gly Ser Asp Val Ile Asp
                100                 105                 110
Met Ser Asn Leu Ser Pro Asp His Ala Val Val Ala Asp Ser Leu Leu
            115                 120                 125
Ala Asp Gln Val Glu Ile Leu Arg Gly Ser Ser Thr Leu Leu Tyr Ala
        130                 135                 140
Ser Ser Ser Pro Val Gly Ile Val Asn Val Val Asp Lys Arg Ile Pro
145                 150                 155                 160
Thr Ala Ile Pro Glu Lys Gly Tyr Glu Val Glu Leu Asn Ser Arg Phe
                165                 170                 175
Asp Thr Ala Ala Lys Glu Lys Val Gly Ala Leu Gly Ala Thr Phe Gly
                180                 185                 190
Ile Gly Asn His Ile Ala Val Arg Val Glu Gly Leu Ser Arg His Ser
            195                 200                 205
Asp Asn Tyr Arg Val Pro Gly Ile Asn Leu Gly Glu Arg Leu Asn Tyr
        210                 215                 220
Val Pro Asp Thr Tyr Asn Lys Ser Lys Val Gly Thr Leu Gly Leu Ser
225                 230                 235                 240
```

Phe Val Gly Glu Arg Gly Tyr Ile Gly Ala Ser Tyr Ser Lys Arg Arg
                245                 250                 255

Asp Asn Tyr Gly Leu Pro Gly His Asn His Lys Phe Asp Phe Cys Thr
            260                 265                 270

Gly His Ile Tyr Gly Asn Lys Arg Asp Lys Tyr Ala Tyr Thr Tyr Leu
        275                 280                 285

Tyr Pro His Leu Ile Gly Glu Asn Ile Gly Ser Asn Pro His Phe
    290                 295                 300

His Cys Gly Thr Asn His Ala Glu Asp Gly Thr His Ser His Asp Asn
305                 310                 315                 320

Pro Phe Gly His Ala His Asp His Thr His Lys Gly Pro Trp Val Asp
                325                 330                 335

Leu Glu Ser Lys Arg Ile Asp Val Lys Ala Glu Leu Arg Gln Pro Phe
            340                 345                 350

Lys Gly Val Asp Lys Ile Lys Ala Ser Tyr Ala Asp Ala Asp Tyr Tyr
        355                 360                 365

His Asp Glu Lys Asp Ala Gly Val Leu Ala Thr Arg Tyr His Lys Gln
    370                 375                 380

Leu Lys Lys Asp Gln Asp Tyr Gly Lys Pro Val Asn Ile Phe Lys Asn
385                 390                 395                 400

Arg Gly Lys Asn Thr Arg Leu Glu Val Tyr His Ala Pro Leu Gly Gly
                405                 410                 415

Leu Thr Gly Val Trp Gly Val Gln Tyr Gln Thr Gln Lys Ser Ser Met
            420                 425                 430

Asn Ala Pro Lys Asp Arg Glu Val Lys Phe Pro Leu Val Glu Asn Thr
        435                 440                 445

Asn Lys Gln Phe Ser Leu Phe Gly Val Glu Gln Tyr Met Trp Asp Ser
    450                 455                 460

Val Ala Val Glu Leu Ala Gly Arg Met Glu Lys Gln Lys Ile Glu Ile
465                 470                 475                 480

Glu Tyr Asp Arg Asn Glu Ile Lys Arg Leu Gln Glu His Tyr Arg Ile
                485                 490                 495

Ser Gly Gly Lys Gln Val Glu Pro Asp Leu Ser Pro Tyr Asp Glu Thr
            500                 505                 510

Ala Tyr Ala Tyr Ser Gly Thr Leu Asn Trp Phe Phe His Pro Asp Tyr
        515                 520                 525

Gln Leu Ser Phe Thr Ala Ser His Asn Glu Arg Leu Pro Thr Pro Met
    530                 535                 540

Glu Leu Tyr Tyr His Gly Gln His Ile Ala Thr Asn Ser Phe Glu Tyr
545                 550                 555                 560

Gly Asn Lys Asp Leu Lys Lys Glu Gln Ser Asn Asn Val Glu Leu Gly
                565                 570                 575

Leu Gly Tyr Gln Ala Glu Arg Ile Gly Tyr Lys Val Ser Val Tyr Tyr
            580                 585                 590

Asn His Phe Lys Asn Tyr Ile Tyr Asn Glu Asn Leu Phe Arg Glu Asn
        595                 600                 605

Gln Leu Phe Met Arg Arg Tyr Asn Gln Ala Lys Ala Arg Phe Tyr Gly
    610                 615                 620

Val Glu Ala Glu Ala Ser Tyr Arg Phe Asn Asp Gln Tyr Gln Ala Thr
625                 630                 635                 640

Ile Phe Gly Asp Met Val Arg Gly Trp Leu Thr Asn Leu Pro Pro Leu
                645                 650                 655

Lys Ile Asn Ser Asp Tyr Ser Val Phe Lys Asp Tyr Leu Pro Glu Asn

```
                660               665               670
Val Glu Lys Gly Lys Asp Tyr Leu Leu Tyr Arg Ala Asp Gln Asn Thr
            675               680               685

Pro Arg Thr Pro Pro Met Arg Leu Gly Phe Arg Phe Asn Ala Glu Phe
        690               695               700

Thr Pro Asn Trp Ser Gly Asp Leu Glu Leu Ile Arg Thr Phe Thr Gln
705               710               715               720

Arg Arg Thr Ser Gln Leu Glu Tyr Ile Thr Glu Gly Asn Thr Met Leu
                725               730               735

Asn Val Gly Leu Ser Tyr Ser Asn Lys Trp Lys Glu Leu Asp Tyr Lys
            740               745               750

Ile Ser Leu Asn Gly Thr Asn Leu Leu Asn Gln Pro Val Tyr Ile His
            755               760               765

Thr Ser Tyr His Gln Phe Val Pro Gln Met Gly Arg Asn Phe Met Leu
            770               775               780

Gly Met Glu Met Lys Phe
785               790

<210> SEQ ID NO 40
<211> LENGTH: 654
<212> TYPE: PRT
<213> ORGANISM: Mannheimia haemolytica serotype A2 str. BOVINE

<400> SEQUENCE: 40

Met Ser Pro Asp His Ala Val Thr Val Asp Ala Leu Leu Ala Lys Arg
1               5                   10                  15

Ile Glu Ile Leu Arg Asp Pro Thr Thr Leu Leu Tyr Ser Ala Gly Asn
            20                  25                  30

Thr Ala Gly Val Ile Asn Val Val Asp Asn Lys Ile Pro Thr Ala Ile
        35                  40                  45

Pro Glu Lys Gly Tyr Glu Gly Gln Phe Gly Val Arg Phe Gly Ser Ala
    50                  55                  60

Ser Lys Glu Arg Leu Thr Tyr Ala Gly Ser Thr Phe Ala Leu Gly Asn
65                  70                  75                  80

His Leu Ala Leu Arg Val Gln Gly Met Tyr Asn Lys Ala Ser Glu Tyr
                85                  90                  95

Tyr Ala Pro His Phe Thr Ile Gly Lys Pro Tyr His Arg Val Pro
            100                 105                 110

Asp Ser Asp Val Gln Ser Gln Thr Gly Thr Val Gly Leu Ser Trp Ile
        115                 120                 125

Gly Glu Arg Gly His Leu Gly Ile Ala Tyr Thr Asp Arg Arg Asp Lys
    130                 135                 140

Tyr Gly Leu Ile Gly His Thr Lys Tyr Asp His Tyr Thr Ile Ser
145                 150                 155                 160

Ile Ile Arg Gln Ala Val Met Phe Ala Lys Gly Tyr Leu Arg Phe Tyr
                165                 170                 175

Pro His Leu Ala Glu Glu Gly Asp Ile Asp Tyr Asn Asn Pro Gly Ile
            180                 185                 190

Arg Leu Leu His Thr His Ile Pro Gly Gly Ser His Tyr Gly Gln Asp
        195                 200                 205

Thr His Glu His Gly Lys Pro Trp Ile Asp Met His Ser Lys Arg Tyr
    210                 215                 220

Asp Ile Asp Gly Ser Leu Gln Asn Pro Leu Pro Gly Phe Glu Glu Ala
225                 230                 235                 240
```

-continued

Lys Ile Ser Ala Asn Tyr Val Asp Tyr Tyr His Asp Glu Lys Asp Gly
            245                 250                 255

Lys Arg Val Glu Asn Tyr Phe Lys Asn Lys Gly Lys Asn Leu Arg Phe
        260                 265                 270

Glu Leu Val His Lys Glu Trp Lys Gly Leu Lys Gly Ala Ile Gly Val
            275                 280                 285

Gln Tyr Thr Asn Gln Ser Thr Ser Ala Leu Ala Leu Glu Ala Ser Arg
    290                 295                 300

Ala Ala Lys Val Phe Asn Lys Gln Pro Leu Leu Asn Asn Pro Lys Thr
305                 310                 315                 320

Lys Leu Trp Ser Leu Phe Ala Ile Glu Arg Leu Asn Leu Gly Asp Phe
                325                 330                 335

Thr Phe Glu Leu Ser Gly Arg Ala Glu Arg Gln Lys Ile Ala Met Asp
            340                 345                 350

Tyr Asp Val Lys Leu Ile Asp Arg Trp Leu Gly Phe Asn Thr Pro Met
        355                 360                 365

Pro Asn Leu Asp Pro His Lys Asp Lys Gly Tyr Ser Tyr Ser Phe Ala
    370                 375                 380

Thr His Trp Tyr Phe Ala Pro Asn His Lys Leu Thr Leu Asn Ala Ala
385                 390                 395                 400

His Gln Glu Arg Leu Pro Asn Ala Gln Glu Leu Tyr Ala His Gly Lys
                405                 410                 415

His Ile Ala Leu Asn Ala Phe Glu Ala Gly Asn Lys Asn Leu Lys Lys
            420                 425                 430

Glu Arg Ser Asn Gln Ile Glu Leu Ser Leu Ala Tyr Val Gly Asp Lys
        435                 440                 445

Trp Asp Tyr Lys Leu Asn Leu Tyr His Thr Arg Tyr Gly Asn Tyr Ile
    450                 455                 460

Tyr Pro Leu Thr Leu Asn Asp Asn Arg Gly Pro Lys Ser Phe Thr Asp
465                 470                 475                 480

Glu Tyr Asn Leu Lys Val Asn Arg Tyr Tyr Gln Gly Glu Ala Arg Phe
                485                 490                 495

Ser Gly Ala Glu Gly Glu Ile Gly Tyr Leu Phe Thr Pro Asn Tyr Arg
            500                 505                 510

Leu Ala Val Phe Gly Asp Tyr Val Arg Gly Lys Leu Val Asn Leu Pro
        515                 520                 525

Asn Ile Ala Met Ser Tyr Asn Ile Trp Thr Gly Glu Val Asp Lys Trp
    530                 535                 540

Ala Ser Gln Pro Asp Ile Ser Ala Pro Arg Ile Pro Pro Leu Arg Leu
545                 550                 555                 560

Gly Ala Arg Phe Asn Ala Asp Phe Asn Leu Asn Trp Ser Gly Met Leu
                565                 570                 575

Glu Tyr Tyr Arg Val Phe Ala Gln Lys Lys Val Ser Lys Tyr Glu Gln
            580                 585                 590

Val Thr Pro Gly His His Gln Val Asn Leu Gly Val Thr Tyr Ser Asn
        595                 600                 605

His Phe Asn Gln Thr Glu Tyr Gln Val Phe Leu Lys Val Asp Asn Leu
    610                 615                 620

Leu Asn Gln Lys Met Tyr Gln His Ala Ser Tyr Leu Pro His Ile Pro
625                 630                 635                 640

Gln Met Gly Arg Asn Ala Met Leu Gly Met Asn Ile Ser Phe
                645                 650

```
<210> SEQ ID NO 41
<211> LENGTH: 793
<212> TYPE: PRT
<213> ORGANISM: Mannheimia haemolytica serotype A2 str. BOVINE

<400> SEQUENCE: 41

Met Ile Val Phe Asn Lys Lys Leu Leu Ala Leu Leu Ile Ser Ala Gln
1               5                   10                  15

Phe Ser Pro Leu Val Trp Ala Glu Ser Ser Asp Asp Val Ala Val Leu
            20                  25                  30

Asn Glu Val Ser Val Val Gly Ser Thr Pro Ser Val Ala Lys Gly Ser
        35                  40                  45

Glu Val Thr Leu Met Lys Thr Ser Asp Lys Ile Ile Glu Gly Lys Glu
    50                  55                  60

Phe Lys Lys Arg Ser Ala Thr Leu Gly Asn Ala Leu Ala Ala Glu Leu
65                  70                  75                  80

Gly Val His Ser Asn Pro Phe Gly Gly Ala Ser Lys Pro Ile Ile
                85                  90                  95

Arg Gly Gln Glu Gly Ala Arg Ile Arg Ile Leu Gln Asn Gly Ser Asp
            100                 105                 110

Val Ile Asp Met Ser Asn Leu Ser Pro Asp His Ala Val Val Ala Asp
        115                 120                 125

Ser Leu Leu Ala Asp Gln Val Glu Ile Leu Arg Gly Ser Ser Thr Leu
    130                 135                 140

Leu Tyr Ala Ser Ser Ser Pro Val Gly Ile Val Asn Val Val Asp Lys
145                 150                 155                 160

Arg Ile Pro Thr Ala Ile Pro Glu Lys Gly Tyr Glu Val Glu Leu Asn
                165                 170                 175

Ser Arg Phe Asp Thr Ala Ala Lys Glu Lys Val Gly Ala Leu Gly Ala
            180                 185                 190

Thr Phe Gly Ile Gly Asn His Ile Ala Val Arg Ala Glu Gly Leu Thr
        195                 200                 205

Arg His Ser Asp Asn Tyr Arg Val Pro Gly Ile Asn Leu Gly Glu Arg
    210                 215                 220

Leu Asn Tyr Val Pro Asp Thr Tyr Asn Lys Ser Lys Val Gly Thr Leu
225                 230                 235                 240

Gly Leu Ser Phe Val Gly Glu Arg Gly Tyr Ile Gly Ala Ser Tyr Ser
                245                 250                 255

Lys Arg Arg Asp Asn Tyr Gly Leu Pro Gly His Asn His Lys Phe Asp
            260                 265                 270

Phe Cys Thr Gly His Ile Tyr Gly Asn Lys Arg Asp Lys Tyr Ala Tyr
        275                 280                 285

Thr Tyr Leu Tyr Pro His Leu Ile Gly Glu Glu Asn Ile Gly Ser Asn
    290                 295                 300

Pro His Phe His Cys Gly Thr Asn His Ala Glu Asp Gly Thr His Ser
305                 310                 315                 320

His Asp Asn Pro Phe Gly His Ala His Asp His Thr His Lys Gly Pro
                325                 330                 335

Trp Val Asp Leu Glu Ser Lys Arg Ile Asp Val Lys Ala Glu Leu Arg
            340                 345                 350

Gln Pro Phe Lys Gly Val Asp Lys Ile Lys Ala Ser Tyr Ala Asp Ala
        355                 360                 365

Asp Tyr Tyr His Asp Glu Lys Asp Ala Gly Val Leu Ala Thr Arg Tyr
    370                 375                 380
```

```
His Lys Gln Leu Lys Lys Asp Gln Asp Tyr Gly Lys Pro Val Asn Ile
385                 390                 395                 400

Phe Lys Asn Arg Gly Lys Asn Thr Arg Leu Glu Val Tyr His Ala Pro
            405                 410                 415

Leu Gly Gly Leu Thr Gly Val Trp Gly Val Gln Tyr Gln Thr Gln Lys
        420                 425                 430

Ser Ser Met Asn Ala Pro Lys Asp Arg Glu Val Lys Phe Pro Leu Val
    435                 440                 445

Glu Asn Thr Asn Lys Gln Phe Ser Leu Phe Gly Val Glu Gln Tyr Met
450                 455                 460

Trp Asp Ser Val Ala Val Glu Leu Ala Gly Arg Met Glu Lys Gln Lys
465                 470                 475                 480

Ile Glu Ile Glu Tyr Asp Arg Asn Glu Ile Lys Arg Leu Gln Glu His
            485                 490                 495

Tyr Arg Ile Ser Gly Gly Lys Gln Val Glu Pro Asp Leu Ser Pro Tyr
        500                 505                 510

Asp Glu Thr Ala Tyr Ala Tyr Ser Gly Thr Leu Asn Trp Phe Phe His
        515                 520                 525

Pro Asp Tyr Gln Leu Ser Phe Thr Ala Ser His Asn Glu Arg Leu Pro
    530                 535                 540

Thr Pro Met Glu Leu Tyr Tyr His Gly Gln His Ile Ala Thr Asn Ser
545                 550                 555                 560

Phe Glu Tyr Gly Asn Lys Asp Leu Lys Lys Glu Gln Ser Asn Asn Val
            565                 570                 575

Glu Leu Gly Leu Gly Tyr Gln Ala Glu Arg Ile Gly Tyr Lys Val Ser
        580                 585                 590

Val Tyr Tyr Asn His Phe Lys Asn Tyr Ile Tyr Asn Glu Asn Leu Phe
    595                 600                 605

Arg Glu Asn Gln Leu Phe Met Arg Arg Tyr Asn Gln Ala Lys Ala Arg
610                 615                 620

Phe Tyr Gly Val Glu Ala Glu Ala Ser Tyr Arg Phe Asn Asp Gln Tyr
625                 630                 635                 640

Gln Ala Thr Ile Phe Gly Asp Met Val Arg Gly Trp Leu Thr Asn Leu
            645                 650                 655

Pro Pro Leu Lys Ile Asn Ser Asp Tyr Ser Val Phe Lys Asp Tyr Leu
        660                 665                 670

Pro Glu Asn Val Glu Lys Gly Lys Asp Tyr Leu Leu Tyr Arg Ala Asp
    675                 680                 685

Gln Asn Thr Pro Arg Thr Pro Pro Met Arg Leu Gly Phe Arg Phe Asn
690                 695                 700

Ala Glu Phe Thr Pro Asn Trp Ser Gly Asp Leu Glu Leu Ile Arg Thr
705                 710                 715                 720

Phe Thr Gln Arg Arg Thr Ser Gln Leu Glu Tyr Ile Thr Glu Gly Asn
            725                 730                 735

Thr Met Leu Asn Val Gly Leu Ser Tyr Ser Asn Lys Trp Lys Glu Leu
        740                 745                 750

Asp Tyr Lys Ile Ser Leu Asn Gly Thr Asn Leu Leu Asn Gln Pro Val
    755                 760                 765

Tyr Ile His Thr Ser Tyr His Gln Phe Val Pro Gln Met Gly Arg Asn
770                 775                 780

Phe Met Leu Gly Met Glu Met Lys Phe
785                 790
```

<210> SEQ ID NO 42
<211> LENGTH: 818
<212> TYPE: PRT
<213> ORGANISM: Moraxella catarrhalis

<400> SEQUENCE: 42

| | | | | | | | | | | | | | | |
|---|---|---|---|---|---|---|---|---|---|---|---|---|---|---|
| Met | Lys | Val | Thr | Met | Ile | Lys | Lys | Pro | Leu | Ala | Cys | Ala | Ile | Leu | Ala |
| 1 | | | | 5 | | | | | 10 | | | | | 15 | |
| Thr | Phe | Ser | Met | Pro | Met | Leu | Ala | Glu | Ala | Asn | Leu | Lys | Asp | Lys | Pro |
| | | | 20 | | | | | 25 | | | | | 30 | | |
| Thr | Val | Ile | Leu | Asp | Gly | Val | Ser | Ile | Thr | Ser | Leu | Ala | Asp | Gln | Asn |
| | | 35 | | | | | 40 | | | | | 45 | | | |
| Thr | Glu | Phe | Gly | Val | Asn | His | Ser | Lys | Thr | Val | Ser | Gly | Ile | Thr | Val |
| | 50 | | | | | 55 | | | | | 60 | | | | |
| Ser | Lys | Glu | Gln | Leu | Gln | Gln | Arg | Ala | Thr | Thr | Leu | Gly | Asp | Ala | Leu |
| 65 | | | | | 70 | | | | | 75 | | | | | 80 |
| Ala | Gly | Glu | Leu | Gly | Val | His | Ser | Asn | His | Phe | Gly | Gly | Ala | Ser |
| | | | | 85 | | | | | 90 | | | | | 95 |
| Ala | Pro | Ile | Ile | Arg | Gly | Gln | Glu | Gly | Lys | Arg | Leu | Lys | Ile | Leu | Gln |
| | | | 100 | | | | | 105 | | | | | 110 | | |
| Asn | Gly | Ser | Glu | Val | Val | Asp | Met | Ser | Gly | Leu | Ser | Pro | Asp | His | Ala |
| | | 115 | | | | | 120 | | | | | 125 | | | |
| Ile | Ala | Val | Asp | Thr | Thr | Leu | Ala | Lys | Gln | Val | Glu | Ile | Val | Arg | Gly |
| | 130 | | | | | 135 | | | | | 140 | | | | |
| Ser | Gly | Ala | Leu | Leu | Tyr | Ala | Ser | Gly | Asn | Ser | Ala | Gly | Val | Val | Asn |
| 145 | | | | | 150 | | | | | 155 | | | | | 160 |
| Val | Val | Asp | Asp | Lys | Ile | Pro | Ser | Lys | Leu | Pro | Ser | Lys | Leu | Gln | Gly |
| | | | | 165 | | | | | 170 | | | | | 175 | |
| Asp | Val | Thr | Val | Arg | Leu | Ser | Ser | Ala | Asn | Arg | Glu | Lys | Leu | Ile | Thr |
| | | | 180 | | | | | 185 | | | | | 190 | | |
| Ala | Ser | Ala | Glu | Ala | Pro | Leu | Gly | Glu | His | Val | Ala | Val | Arg | Val | Ala |
| | | 195 | | | | | 200 | | | | | 205 | | | |
| Gly | Leu | Ser | Lys | Gln | Ala | Ala | Asp | Tyr | Lys | Thr | Pro | Arg | Phe | Asp | Arg |
| | 210 | | | | | 215 | | | | | 220 | | | | |
| His | Val | Phe | Asn | Lys | Lys | His | Glu | Asp | Asp | Asn | Thr | Gln | Pro | Glu | Phe |
| 225 | | | | | 230 | | | | | 235 | | | | | 240 |
| Ile | Tyr | Lys | Asp | Thr | Leu | Lys | His | Leu | Pro | Asp | Ser | His | Ala | Lys | Ser |
| | | | | 245 | | | | | 250 | | | | | 255 | |
| Asn | Ala | Gly | Thr | Leu | Gly | Val | Ser | Trp | Val | Gly | Asn | Gln | Gly | Phe | Leu |
| | | | 260 | | | | | 265 | | | | | 270 | | |
| Gly | Ala | Ser | Val | Ser | Leu | Arg | Arg | Asp | Lys | Tyr | Gly | Leu | Pro | Asn | His |
| | | 275 | | | | | 280 | | | | | 285 | | | |
| Ser | His | Glu | Tyr | Glu | Gln | Cys | Ser | Val | His | Gly | Ile | Ser | Gln | Ser | Ala |
| | 290 | | | | | 295 | | | | | 300 | | | | |
| Leu | Gln | Tyr | Lys | Pro | Tyr | Leu | Arg | Leu | Tyr | Pro | Phe | Leu | Met | Glu | Asn |
| 305 | | | | | 310 | | | | | 315 | | | | | 320 |
| Asp | Asp | Leu | Glu | Phe | Asp | Asn | Ala | Gly | Leu | Glu | Cys | His | Thr | His | Asp |
| | | | | 325 | | | | | 330 | | | | | 335 | |
| Asp | His | Asp | His | Glu | His | Asp | His | Ala | His | Asp | His | Glu | His | Asp | His |
| | | | 340 | | | | | 345 | | | | | 350 | | |
| Glu | His | Asp | His | Gly | Lys | Pro | Trp | Ile | Asp | Leu | Lys | Met | Lys | Arg | Tyr |
| | | 355 | | | | | 360 | | | | | 365 | | | |
| Asp | Val | Gln | Gly | Gln | Ile | Asn | Ala | Pro | Phe | Ala | Gly | Ile | Asp | Lys | Ile |
| | 370 | | | | | 375 | | | | | 380 | | | | |

-continued

```
Arg Ala Ser Met Gly Lys Val Asp Tyr His His Asp Glu Ile Asp Gly
385                 390                 395                 400

Gly Glu Lys Thr Ser Phe Phe Asp Asn Gln Ala Asn Val Trp Arg Leu
            405                 410                 415

Glu Ala Ser His Thr Pro Ile His Thr Pro Met Gly Lys Phe Ser Gly
        420                 425                 430

Val Phe Gly Val Gly Tyr Leu Thr Ser Lys Asn Ser Gly Leu Val Pro
    435                 440                 445

Pro Arg Tyr Glu Asp Gly Asn Lys Gln Asp Thr Gln Asn Ile Leu His
450                 455                 460

Asn Asn Lys Thr Lys Thr Gly Ser Val Phe Trp Phe Glu Glu Tyr Lys
465                 470                 475                 480

Pro Asn Asp Lys Leu Thr Val Asp Ala Ala Arg Ile Glu Lys Gln
            485                 490                 495

Thr Ile Thr Met Asp Tyr Asp Lys Asp Ala Ile Tyr Gln Ser Leu Asn
                500                 505                 510

Leu Gly Leu Ala Thr Ala His Glu Pro Asp Ile Arg Phe Lys Arg Leu
            515                 520                 525

Leu Asp Ser Gly Thr Leu Asn Pro Lys Lys Gln Thr Ala Arg Ser Tyr
    530                 535                 540

Ala Val Gly Thr His Leu Gln Leu Thr Pro Lys His Lys Leu Ser Leu
545                 550                 555                 560

Asn Leu Ser His Gln Glu Arg Leu Pro Asn Ala Gln Glu Leu Tyr Ala
                565                 570                 575

His Gly Met His Leu Ala Thr Asn Ser Phe Glu Ile Gly Asn Arg Phe
            580                 585                 590

Leu Asn Lys Glu Lys Ser Asn Asn Ile Asp Leu Gly Leu Thr Phe Gln
    595                 600                 605

Gly Asp Lys Trp Asp Tyr Arg Leu Gly Gly Tyr His Tyr Asp Phe Asp
610                 615                 620

Asn Tyr Val Phe Leu Gln Thr Leu Ser Gln Tyr Lys Gln Gly Leu Arg
625                 630                 635                 640

Gly Met Arg His Asp Lys Asp Leu Lys Thr Ala Arg Tyr Glu Gln Ala
                645                 650                 655

Ala Ala Lys Phe Tyr Gly Phe Asp Val Asn Ile Gly Tyr Gln Ile Asn
            660                 665                 670

Asp Val Tyr His Val Ala Leu Phe Gly Asp Tyr Ile Arg Gly Lys Leu
    675                 680                 685

Thr Asn Leu Pro Asp Lys Lys Gly Arg Thr Asp Ala Tyr Gly Asn Arg
690                 695                 700

Pro Leu Ile Lys Gln Pro Asp Ser His Thr Pro Arg Leu Pro Pro Lys
705                 710                 715                 720

Arg Leu Gly Met Lys Leu Thr Ala Asn Val Asn Ala Asn Trp Ser Gly
                725                 730                 735

Phe Leu Glu Tyr Arg His Thr Phe Lys Gln Asp Lys Leu Ala Asn Phe
            740                 745                 750

Glu Arg Pro Thr Pro Ala His Asn Leu Val Asn Leu Gly Leu Asn Tyr
    755                 760                 765

Gln His Lys Pro Ser His Gln Ala Gly Ser Val Gln Val Phe Phe Asn
770                 775                 780

Ala Asn Asn Leu Leu Asn Asp Lys Val Phe Ala His Glu Thr Phe Phe
785                 790                 795                 800

Pro Asp Met Pro Gln Met Gly Arg Asn Phe Met Leu Gly Ala Asn Phe
```

-continued 805             810             815
Lys Phe

<210> SEQ ID NO 43
<211> LENGTH: 796
<212> TYPE: PRT
<213> ORGANISM: Pasteurella dagmatis ATCC 43325

<400> SEQUENCE: 43

Met Lys Lys Ile Ser Tyr Leu Ser Leu Cys Val Ile Ser Gly Leu Tyr
1               5                   10                  15

Ser Gln Ile Ala Val Ala Gln Asn Asn Leu Thr Asn Thr Gly Asn His
            20                  25                  30

Ile Glu Leu Asp Ala Ile His Val Asp Ala Leu Asn Asp Ser Arg Gln
        35                  40                  45

Gly Ala Pro Leu Thr Gly Arg Leu Ile Thr Ser Glu Lys Thr Ile Ser
    50                  55                  60

Glu Tyr Ser Leu Lys Gln Arg Gly Ser Asn Ile Gly Asp Ala Leu Ser
65                  70                  75                  80

Asn Glu Leu Gly Ile His Ala Ser Gln Phe Gly Gly Ala Ser Ala
                85                  90                  95

Pro Val Ile Arg Gly Gln Glu Gly Lys Arg Ile Lys Leu Leu Asn Ser
            100                 105                 110

Gly Thr Glu Thr Leu Asp Met Ser Ser Met Ser Pro Asp His Ala Val
        115                 120                 125

Thr Val Asp Ser Leu Leu Ala Lys Lys Ile Glu Ile Leu Arg Gly Val
    130                 135                 140

Asn Thr Leu Leu Tyr Ser Ser Gly Asn Ala Ala Gly Ala Val Asn Val
145                 150                 155                 160

Val Asp Asn Lys Ile Pro Thr Thr Glu Ile Val Gly Val Glu Gly Glu
                165                 170                 175

Val Gly Leu Arg Thr Gly Ser Val Asp Asn Glu Arg Leu Val Asn Ala
            180                 185                 190

Ala Phe Asp Val Gly Leu Ser Lys His Phe Ala Leu His Leu Glu Gly
        195                 200                 205

Leu Tyr Lys Lys Ala Gly Asp Tyr Arg Thr Pro Ser Tyr Gln Tyr Gln
    210                 215                 220

Gly Ser Thr Gln His Lys Leu Ala Asn Ser Phe Val Asp Asn Arg Ser
225                 230                 235                 240

Gly Ser Ile Gly Leu Ser Trp Val Gly Asp Lys Gly Tyr Leu Gly Ala
                245                 250                 255

Ser Tyr Ser Gln Arg Lys Asp Lys Tyr Gly Leu Pro Ala His Ser His
            260                 265                 270

Leu Tyr Asp Glu Tyr Tyr Met His Val Leu Leu Ser Asp Ala His Trp
        275                 280                 285

Arg Lys Pro Tyr Leu Lys His Tyr Pro Phe Leu Met Glu Glu Thr Asp
    290                 295                 300

Ile Asp Tyr Asn Asn Pro Gly Ile Asp Cys Ile Lys Lys Ser Trp His
305                 310                 315                 320

Ser His Gly His Leu Cys Asn His Gly His Ala His His Ala Asn Glu
                325                 330                 335

Pro Asn Ser His Asp His Gln His Ala Asp Pro His Ile Val Leu Asn
            340                 345                 350

Ser Gln Arg Trp Asp Ile Arg Gly Glu Trp Lys Asn Pro Val Lys Gly

-continued

```
                355                 360                 365
Leu Asp Lys Val Arg Phe Ser Val Ala Gln Val Asp Tyr Arg His Asp
    370                 375                 380
Glu Lys Ser Gly Ala Ile Ser Asp Asn Ser Phe Lys Asn Lys Gly Tyr
385                 390                 395                 400
Ser Ala Arg Leu Glu Phe Ile His Gln Pro Ile Ala Asn Val Ser Gly
                405                 410                 415
Leu Ile Gly Val Ser His Thr Tyr Gln Asp Ser Tyr Ala Leu Asp Asn
                420                 425                 430
His Thr Leu Glu Tyr Arg Lys Gln Asn Leu Leu Ser Asp His Thr Thr
                435                 440                 445
Asp Gln Gln Ser Leu Phe Leu Met Glu Arg Val Glu Phe Gly Lys Trp
            450                 455                 460
Gln Phe Asp Ile Gly Gly Arg Met Glu Arg Gln Arg Ile Ala Met Lys
465                 470                 475                 480
Tyr His Phe Asn Val Pro Ala Arg Glu Gln Val Pro Gln Glu Leu Thr
                485                 490                 495
Gln Pro His Lys Ser Lys Gly Tyr Ser Tyr Ala Phe Ser Ala Asn Tyr
            500                 505                 510
Gln Val Asn Asp Arg His Gln Leu Asn Ile Ile Phe Ser His Gln Glu
        515                 520                 525
Arg Leu Pro Asn Ala Gln Glu Leu Tyr Ala His Gly Lys His Leu Ala
    530                 535                 540
Thr Asn Ser Phe Glu Ala Gly Asn Lys Asn Leu Lys Lys Glu Arg Ser
545                 550                 555                 560
Asn Asn Ile Glu Leu Gly Trp Asp Tyr Ser Gly Lys Leu Gly Ile
                565                 570                 575
Lys Leu Ser Gly Tyr Tyr Gln Gln Phe Ser Asn Tyr Ile Tyr Ala Ala
                580                 585                 590
Ile Leu Asn Asp Lys Ser Thr Cys Thr Trp Arg Ala Asn Gly Arg Cys
                595                 600                 605
Ser Arg Ser Leu Ser Ser Asp Tyr Pro Leu His Leu Tyr Arg Tyr Asn
    610                 615                 620
Gln Ala Glu Ala Asn Ile Tyr Gly Leu Glu Ala Gly Ala Ser Tyr Gln
625                 630                 635                 640
Ile Ser Ser Thr Tyr Asp Val Ser Ile Phe Gly Asp Tyr Val Arg Gly
                645                 650                 655
Lys Leu Lys Asn Leu Pro Val Leu Pro Ile Gly Tyr Glu Gln Ala Tyr
                660                 665                 670
Asp Gln Asn Tyr Asn Pro Ile Gly Leu Lys Pro Thr Gly Trp Glu Lys
            675                 680                 685
Gln Pro Asp Gly Asn Ala Pro Arg Met Pro Ala Met Arg Leu Gly Ile
    690                 695                 700
Lys Leu Asn Gly His Phe Asp Asn Gly Val Ser Phe Asn Thr Gln Leu
705                 710                 715                 720
Tyr Arg Val Phe Lys Gln Asn Lys Val Ala Arg Leu Glu Lys Pro Thr
                725                 730                 735
Pro Gly His Thr Met Trp Asn Ala Gly Val Ser Tyr Asp Gly Arg Ile
                740                 745                 750
Gly Asn Asn Glu Tyr Thr Leu Phe Leu Asn Ala Asn Asn Leu Leu Asn
            755                 760                 765
Val Lys Val Tyr Asn His Ala Ser Phe Leu Ser Tyr Ile Pro Gln Asn
    770                 775                 780
```

```
Gly Arg Gly Ile Asn Val Gly Met Asn Phe Lys Phe
785                 790                 795

<210> SEQ ID NO 44
<211> LENGTH: 809
<212> TYPE: PRT
<213> ORGANISM: Pasteurella multocida subsp. multocida str. Pm70

<400> SEQUENCE: 44

Met Pro Leu Leu Thr Leu Lys Ile Asn Met Phe Phe Met Arg Lys Ile
1               5                   10                  15

Ser Tyr Leu Ser Leu Cys Val Ile Ser Ala Leu Tyr Ser Gln Leu Ala
            20                  25                  30

Val Ala Gln Ser Pro Leu Lys Asn Thr Ser Glu His Ile Glu Leu Glu
        35                  40                  45

Pro Ile Phe Val Asn Thr Leu Ile Glu Ser Arg Glu Gly Ala Pro Leu
    50                  55                  60

Gly Gly Arg Leu Met Ala Ser Glu Lys Ile Ile Pro Ala Tyr Ser Leu
65                  70                  75                  80

Lys Gln Arg Gly Ser Asn Leu Gly Asp Ala Leu Ser Ser Glu Leu Gly
                85                  90                  95

Ile His Ala Ser Gln Phe Gly Gly Ala Ser Ala Pro Val Ile Arg
            100                 105                 110

Gly Gln Glu Gly Lys Arg Ile Lys Val Leu Ser Ser Gly Asn Glu Thr
        115                 120                 125

Leu Asp Met Ser Ala Met Ser Pro Asp His Ala Val Ala Val Asp Ser
130                 135                 140

Leu Leu Ala Lys Lys Val Glu Ile Leu Arg Gly Ala Asn Thr Leu Leu
145                 150                 155                 160

Tyr Ser Ser Gly Asn Ala Ala Gly Val Val Asn Val Asp Asn Lys
                165                 170                 175

Ile Pro Thr Ala Glu Val Val Gly Val Glu Gly Glu Val Gly Leu Arg
            180                 185                 190

Thr Gly Ser Ala Asp Asn Glu Arg Leu Val Asn Val Ala Leu Asp Val
        195                 200                 205

Gly Leu Ser Lys His Phe Ala Leu His Leu Glu Gly Leu His Lys Lys
210                 215                 220

Ala Gly Asp Tyr Arg Thr Pro Ser Tyr Gln Tyr Gln Gly Ser Thr His
225                 230                 235                 240

His Lys Leu Ala Asn Ser Phe Val Asp Asn Arg Ser Gly Ser Val Gly
                245                 250                 255

Leu Ser Trp Val Gly Asp Lys Gly Tyr Leu Gly Val Ala Tyr Ser Gln
            260                 265                 270

Arg Lys Asp Lys Tyr Gly Leu Pro Ala His Ser His Leu Tyr Asp Glu
        275                 280                 285

Tyr Tyr Met His Val Leu Leu Ser Asp Ala His Trp Arg Lys Pro Tyr
290                 295                 300

Leu Lys His Tyr Pro Phe Leu Met Glu Glu Thr Asp Ile Asp Tyr Asn
305                 310                 315                 320

Asn Pro Gly Ile Asp Cys Ile Lys Lys Glu Trp His Ser His Gly His
                325                 330                 335

Leu Cys Asn His Gly His Ala His His Gly Asn Gly Gln His Ser His
            340                 345                 350

Asp His His Ala His Ala Asp Pro His Ile Ala Leu Asn Thr Gln Arg
```

```
                355                 360                 365
Trp Asp Leu Arg Gly Glu Trp Lys Asn Pro Val Lys Gly Leu Asp Lys
    370                 375                 380

Val Arg Phe Ser Ile Ala Lys Val Gly Tyr Arg His Asp Glu Lys Ser
385                 390                 395                 400

Gly Ala Ile Ser Asp Asn Ser Phe Lys Asn Lys Gly Tyr Ser Ala Arg
                405                 410                 415

Val Glu Phe Leu His Gln Pro Ile Ala Gly Val Ser Gly Leu Ile Gly
            420                 425                 430

Leu Ser His Val Tyr Gln Asp Ser Tyr Ala Leu Asp Asn His Thr Leu
        435                 440                 445

Glu Tyr Arg Lys Gln Asn Leu Leu Ser Asp His Thr Thr Ala Gln Gln
    450                 455                 460

Ser Leu Phe Leu Met Glu His Val Glu Leu Gly Lys Trp Gln Phe Asp
465                 470                 475                 480

Ile Gly Gly Arg Val Glu Lys Gln Arg Ile Ala Met Lys Tyr His Phe
                485                 490                 495

Asn Val Pro Lys Asp Glu Gln Pro Glu Glu Leu Thr Arg Pro His
            500                 505                 510

Lys Ser Lys Ala Tyr Ser Tyr Ala Leu Ser Ala Asn Tyr Gln Leu Asn
        515                 520                 525

Glu Gln His Gln Phe Asn Met Ile Val Ser His Gln Glu Arg Leu Pro
    530                 535                 540

Asn Ala Gln Glu Leu Tyr Ala His Gly Lys His Leu Ala Thr Asn Ser
545                 550                 555                 560

Phe Glu Ala Gly Asn Lys Asn Leu Thr Lys Glu Arg Ser Asn Asn Val
                565                 570                 575

Glu Leu Gly Trp Gly Tyr Thr Gly Glu Lys Leu Gly Ile Lys Leu Ser
            580                 585                 590

Gly Tyr Tyr Gln Gln Phe Ser Asn Tyr Ile Tyr Ala Ala Ile Leu Asn
        595                 600                 605

Asn Lys Thr Ser Cys Pro Trp Arg Pro Asn Ser Arg Cys Leu Arg Ser
    610                 615                 620

Leu Ser Asp Asp Tyr Pro Leu Arg Leu Tyr Arg Tyr Asn Gln Ala Lys
625                 630                 635                 640

Ala Lys Ile Tyr Gly Leu Glu Ala Glu Val Ser Tyr Gln Ile Ser Ser
                645                 650                 655

Thr His Ser Val Ser Ile Phe Gly Asp Tyr Val Arg Gly Lys Leu Lys
            660                 665                 670

Asp Leu Pro Ser Leu Pro Ile Gly Tyr Lys Tyr Ile Tyr Asn Glu Asn
        675                 680                 685

Tyr Asp Met Val Gly Val Gln Pro Thr Gly Trp Glu Lys Gln Pro Asp
    690                 695                 700

Gly Asn Ala Pro Arg Met Ser Pro Met Arg Leu Gly Ile Lys Trp Asn
705                 710                 715                 720

Ala Tyr Phe Asp Asn Gly Ile Ser Phe Asn Thr Gln Leu Tyr Arg Val
                725                 730                 735

Phe Ala Gln Asn Lys Val Ala Arg Leu Glu Thr Pro Thr Lys Gly His
            740                 745                 750

Thr Met Leu Asn Leu Gly Met Ser Tyr Asp Gly Lys Met Gly Asn Asn
        755                 760                 765

Glu Tyr Thr Leu Phe Ala Asn Val Asn Asn Val Leu Asn Ser Arg Val
    770                 775                 780
```

```
Tyr Asn His Thr Ser Phe Leu Ser Tyr Ile Pro Gln Ser Gly Leu Gly
785                 790                 795                 800

Leu Asn Val Gly Met Asn Phe Lys Phe
                805

<210> SEQ ID NO 45
<211> LENGTH: 805
<212> TYPE: PRT
<213> ORGANISM: Pasteurella multocida subsp. multocida str. Pm70

<400> SEQUENCE: 45

Met Ile Ser Arg Gly Cys Lys Val Asn Lys Phe Phe Ala Val Leu Met
1               5                   10                  15

Met Cys Cys Ile Pro Gln Val Val Trp Ala Asn Thr Glu Lys Lys Gln
                20                  25                  30

Ile Val Phe Leu Asp Glu Ile Ser Val Glu Ser Lys Gly Ala Ala Phe
            35                  40                  45

Arg Ser Asp Pro Leu Ser Gly Leu Pro Lys Gln Asn Asp Ile Leu Val
50                  55                  60

Ser Lys Gln Lys Leu Lys Thr Gly Ser Ser Thr Leu Gly Asn Ala Leu
65                  70                  75                  80

Ala Gly Glu Leu Ser Val His Ser Asn Gln Phe Gly Gly Gly Ser Ser
                85                  90                  95

Ala Pro Val Val Arg Gly Gln Glu Gly Val Arg Leu Lys Ile Leu Gln
            100                 105                 110

Asn Gly Ser Asp Val Ile Asp Met Ser Gln Leu Ser Pro Asp His Ala
        115                 120                 125

Ile Gly Val Asp Thr Leu Leu Ala Glu Gln Val Glu Ile Val Arg Gly
130                 135                 140

Ala Ser Thr Leu Leu Tyr Ala Asn Ala Ser Pro Ala Gly Val Ile Asn
145                 150                 155                 160

Val Val Asp Lys Arg Ile Pro Thr Gln Leu Pro Lys Lys Gly Tyr Glu
                165                 170                 175

Val Asp Phe Asn Thr Arg Tyr Asn Thr Asn Ser His Glu Lys Leu Val
            180                 185                 190

Thr Ala Ala Leu Thr Phe Gly Leu Gly Lys His Ile Ala Leu Arg Val
        195                 200                 205

Glu Glu Leu Leu Arg Gly Ser Asn Asn Tyr His Val Pro Ala Phe Lys
210                 215                 220

Leu Asp Lys Thr Leu Asn Tyr Val Pro Asp Thr Gln Asn Lys Thr Lys
225                 230                 235                 240

Ser Gly Asn Tyr Gly Val Ala Phe Ile Gly Glu Arg Gly Tyr Val Gly
                245                 250                 255

Phe Ala Tyr Asn Leu Arg Arg Glu Lys Tyr Gly Leu Pro Gly His Asn
            260                 265                 270

His Lys Leu Asp Ser Cys Ala His Ile Trp Gly Gly Asn Val Arg
        275                 280                 285

Asn Asp Tyr Tyr Leu Gly Leu Tyr Pro His Leu Met His Asp Thr Asp
290                 295                 300

Leu Val Asn Thr His Phe His Cys Gly Ser Asn His Asp Met Asp Gly
305                 310                 315                 320

Lys His Ser His Asn His Pro Tyr Gly His Asp His Asp His Ser Ile
                325                 330                 335

Ala Gly Pro Leu Ile Asp Ser Tyr Ala Lys Arg Tyr Asp Ile Arg Ala
```

-continued

```
                340                 345                 350
Glu Val Lys Gln Pro Met Lys Ala Ile Glu Lys Ile Lys Leu Ser Tyr
            355                 360                 365
Ser Glu Thr Arg Tyr Lys His Asp Glu Lys Asp Gly Asn Ile Ala Val
        370                 375                 380
Asn Leu Phe Lys Asn Asn Gly Tyr Asn Leu Arg Val Glu Ile Phe His
385                 390                 395                 400
Thr Pro Ile Ala Gly Leu Ser Gly Val Ile Gly Ala Gln Tyr Gln Thr
                405                 410                 415
Gln Thr Ser Ser Ala Asn Ile Pro Arg Ile Ala Pro Cys Ser Asn Asn
            420                 425                 430
Ala Ser Asp Pro Cys His Lys Lys Gln Arg Asp Pro Ser Lys Ile
        435                 440                 445
Thr Lys Gly Asp Arg Lys Ser Trp Ala Leu Ile Glu Asn Thr Gln Ser
    450                 455                 460
Gln Met Ser Phe Phe Ala Ile Glu Gln Leu Arg Trp Gln Asp Phe Leu
465                 470                 475                 480
Phe Glu Ile Gly Val Arg Thr Glu Lys Gln Arg Ile Asp Ile Glu Tyr
                485                 490                 495
Asp Arg Ala Trp Leu Phe Lys Val Lys Arg Lys Leu Glu Gly Cys Asp
            500                 505                 510
Pro Asn Ser Phe Phe Tyr Ser Pro Ser Gly Cys Arg Gln Gly Ser Tyr
        515                 520                 525
Pro Ala Pro Asp Phe Ala Ser Tyr His Asp Arg Ala Thr Ser Tyr Ser
    530                 535                 540
Gly Ala Ile Ser Trp Asn Met Thr Pro Asp Tyr Thr Leu Ser Leu Thr
545                 550                 555                 560
Tyr Ser His Asn Glu Arg His Pro Thr Pro Met Glu Leu Tyr Tyr His
                565                 570                 575
Gly Lys His Leu Ala Thr Val Ser Phe Glu His Gly Asn Arg Asn Leu
            580                 585                 590
Lys Lys Glu Val Ser Asp Asn Trp Glu Val Gly Leu Ala Tyr Leu Gly
        595                 600                 605
Asp Lys Leu Ser Tyr Lys Val Asn Val Tyr Asn Asp Phe Lys Asn
    610                 615                 620
Arg Ile Phe Asn Gln Thr Leu Asn Lys Ser Gly Asn Leu Ser Leu Asn
625                 630                 635                 640
Arg Tyr Asn Gln Ser Lys Ala Lys Tyr Tyr Gly Val Glu Gly Arg Ile
                645                 650                 655
Asp Tyr Ala Leu Thr Pro Glu Leu His Met Gly Leu Phe Gly Asp Tyr
            660                 665                 670
Val Arg Gly Lys Leu Tyr Asp Leu Pro Pro Thr Tyr Arg Val Asp His
        675                 680                 685
Val Ala Asn Ser Leu Glu Pro Val Thr Gln Pro Asp Gln Asp Ala Pro
    690                 695                 700
Arg Val Pro Pro Met Arg Leu Gly Phe Arg Val Asn Met Glu Met Thr
705                 710                 715                 720
Glu Ser Leu Thr Ser Ser Leu Glu Tyr Thr Tyr Val Tyr Gln Gln Lys
                725                 730                 735
Lys Val Ala Pro Leu Glu Asn Gln Thr Ala Ala Tyr Ser Leu Leu Asn
            740                 745                 750
Ile Gly Val Asp Tyr Ser Arg Gln Ile Ala Gly Val Asn Tyr Gln Leu
        755                 760                 765
```

```
Phe Val Gln Ala Asn Asn Val Leu Asn Arg Lys Val Tyr Ser His Thr
        770                 775                 780

Ser Phe Leu Pro Phe Val Pro Gln Met Gly Arg Asn Val Thr Leu Gly
785                 790                 795                 800

Leu Asn Ile His Phe
            805

<210> SEQ ID NO 46
<211> LENGTH: 925
<212> TYPE: PRT
<213> ORGANISM: Pasteurella multocida subsp. multocida str. Pm70

<400> SEQUENCE: 46

Met Val Asn Ile Leu Tyr Phe Leu Tyr Lys Lys Trp Ile Phe Leu Leu
1               5                   10                  15

Gln Asn Asn Ile Phe Met Leu Asn Leu Ser Thr Leu Phe Phe Tyr Val
            20                  25                  30

Lys Lys Asp Val Glu Thr Val Glu Thr Lys Val Val Thr Asn Lys Leu
        35                  40                  45

Ile Lys Gln Ile Thr Tyr Leu Leu Pro Trp Ser Ala Val Ala Phe Thr
50                  55                  60

His Val Ile Tyr Ala Gln Thr Glu Met Leu Asp Glu Ile Val Val Ser
65                  70                  75                  80

Gly Ala Gln Pro His Leu Ala Gly Ser Ala Ile Glu His Tyr Gln Ala
                85                  90                  95

Ile Ser Asn Gln Val Ile Lys Lys Glu Arg Leu Gln Lys Gln Ser Ala
            100                 105                 110

Thr Leu Gly Asn Ala Leu Ala Gly Glu Leu Gly Val His Ser Asn Pro
        115                 120                 125

Phe Gly Gly Gly Ala Ser Ala Pro Ile Ile Arg Gly Gln Glu Gly Val
130                 135                 140

Arg Ile Lys Ile Leu Gln Asn Gly Leu Asp Val Val Asp Met Ser Ala
145                 150                 155                 160

Ile Ser Pro Asp His Ala Val Ala Ala Asp Ser Leu Leu Ala Glu Gln
                165                 170                 175

Val Glu Leu Val Arg Gly Ala Ser Thr Leu Leu Tyr Ser Ser Ala Ser
            180                 185                 190

Ala Ala Gly Val Val Asn Val Asp Lys Arg Ile Pro Thr Ala Val
        195                 200                 205

Pro Glu Lys Gly Tyr Glu Gly Glu Ile Phe Thr Arg Phe Asp Thr Ala
210                 215                 220

Ser Gln Glu Ser Thr Gly Thr Ala Gly Ile Thr Phe Arg Leu His Pro
225                 230                 235                 240

His Leu Ala Leu Arg Leu Glu Gly Leu Lys Arg Tyr Ser Thr His Tyr
                245                 250                 255

Arg Val Pro Ala Phe Lys Ser Gly Gly Glu Thr Ile Tyr Leu Pro
            260                 265                 270

Asp Ser His Asn Arg Ser Gln Val Gly Thr Ile Gly Val Ser Trp Ile
        275                 280                 285

Lys Asp Gln Ser Tyr Leu Gly Val Ser Tyr Ser Glu Arg Arg Asp Arg
290                 295                 300

Tyr Gly Leu Pro Gly His Asn His Lys Tyr Asp Arg Cys Lys Ser His
305                 310                 315                 320

Val Val Asp Glu Ala Ala Arg Pro Glu Leu Gly Lys Gly Tyr Leu Thr
```

```
                    325                 330                 335
Pro Tyr Pro His Leu Ala Asp Asp Thr Asp Ile Val Phe Ala His Leu
                340                 345                 350

Asp Gly Cys Ile Gly Gly Ile Asp Asn Asp Pro Ser His Ser His Asp
            355                 360                 365

His Pro Phe Gly His Glu His Asp His Ser His Gly Gly Pro Trp Val
        370                 375                 380

Arg Leu His Ser Arg Arg Phe Asp Leu Arg Gly Gln Trp Asp Ser Pro
385                 390                 395                 400

Thr Ala Trp Leu Asp Lys Val Lys Gly Ser Phe Ser Tyr Ala Asp Tyr
                405                 410                 415

Ile His Tyr Glu Tyr His Ser Gly Gln Ala Gly Thr Asp Lys Phe Asp
            420                 425                 430

Arg Asp Ser Phe Ile Glu Arg Glu Arg Lys Ala Glu Lys Asn Arg
        435                 440                 445

Gly Lys Ala Ala Gly Ile Tyr Lys Asn Ser Gly Tyr Asn Gly Lys Leu
450                 455                 460

Glu Phe Tyr His Thr Pro Ile Val Gly Leu Ser Gly Val Phe Gly Val
465                 470                 475                 480

Gln Tyr Ser Glu Tyr Lys Thr Ala Ile Leu Ala Pro Leu Gly Ser Gly
                485                 490                 495

Ile Lys His Gln His His Leu Val Pro Asn Thr Gln Lys Gln Ala Ser
            500                 505                 510

Phe Phe Ala Val Glu Asn Tyr Val Val Asp Asp Phe Ile Phe Glu Val
        515                 520                 525

Gly Ala Arg Val Asp Lys Gln Arg Ile Pro Ile Lys Tyr Asp Gln His
530                 535                 540

Val Leu Asn Ala His Lys Lys Glu Gly Asp His Pro Pro Asp Leu Ser
545                 550                 555                 560

Thr His Lys Glu Lys Ala Val Ser Tyr Leu Gly Ser Val Asp Trp Leu
                565                 570                 575

Phe His Pro Asn Tyr Arg Ile Gly Leu Thr Leu Ser Arg Asn Glu Arg
            580                 585                 590

Leu Pro Thr Pro Met Glu Leu Tyr Tyr His Gly Gln His Leu Ala Thr
        595                 600                 605

Asn Ser Phe Glu His Gly Asn Lys Asn Leu Arg Lys Glu Ser Ser Asn
610                 615                 620

Asn Ile Glu Leu Gly Phe Ala Tyr His Thr Asp Lys Trp Asp Tyr Lys
625                 630                 635                 640

Leu Ser Leu Tyr Gln Asn Lys Phe Arg Asn Tyr Ile Tyr Asn Glu Asp
                645                 650                 655

Leu Ala Arg Tyr Gly Asn Ala Phe Leu Arg Arg Tyr Thr Gln Ala Arg
            660                 665                 670

Ala Lys Phe His Gly Ile Glu Ala Glu Leu Asn Phe Arg Pro Thr Pro
        675                 680                 685

Asp Tyr Gln Val Thr Leu Phe Gly Asp Tyr Val Arg Gly Arg Leu Phe
690                 695                 700

Asp Leu Pro Glu Gln Tyr Gly Gln Arg Phe Tyr Gln Gly Tyr Ile Ala
705                 710                 715                 720

Tyr Asp Glu Glu Gly Leu Ile Gln Ala Asn Trp Glu Lys Gln Pro Tyr
                725                 730                 735

Arg Ile Glu Gly Ile Lys Arg Asn Glu Arg Asp Ala Pro Arg Val Pro
            740                 745                 750
```

```
Pro Ala Arg Leu Gly Met Arg Leu Ser Gly Asn Val Thr Glu His Leu
            755                 760                 765

Ser Phe Phe Ala Asp Tyr Thr Tyr Val Phe Ser Gln Gln Lys Thr Ala
770                 775                 780

Ser Ser Leu Ser Ile Lys Pro Pro Arg Ala Leu Glu Ala Ser Asp Phe
785                 790                 795                 800

Ile Asp Asp Asp Thr Gly Glu Asn Leu Leu Leu Lys Gly Ile Asp Arg
                805                 810                 815

Asp Lys Tyr Asn Arg Thr Gly Gln Pro Ile Ala Asp Leu Ser Ala Ser
                820                 825                 830

Asp Lys Ala Asp Phe Glu Ser Ala Leu Glu Ala Ile Arg Leu Arg Glu
                835                 840                 845

Glu Asn Glu Lys Leu Pro Ala Lys Ile Glu Lys Ile Gln Glu Asp Pro
            850                 855                 860

Ser Lys Gly His His Leu Leu Asn Ile Gly Val Asn Tyr Gln Arg Gln
865                 870                 875                 880

Ile Gly His Leu Asp Tyr Ser Val Gly Phe Ser Val Asn Asn Val Leu
                885                 890                 895

Asn Gln Arg Val Tyr Val His Thr Ser Tyr Leu Pro Tyr Val Pro Gln
            900                 905                 910

Met Gly Arg Asn Tyr Val Leu Asn Phe Gly Val Lys Phe
            915                 920                 925

<210> SEQ ID NO 47
<211> LENGTH: 697
<212> TYPE: PRT
<213> ORGANISM: Proteus mirabilis ATCC 29906

<400> SEQUENCE: 47

Met Ala Asp Ser Met Lys Lys Ser Ile Phe Asn Tyr Thr Thr Phe Phe
1               5                   10                  15

Ile Ser Met Ser Tyr Ser Leu Phe Ala Asn Ala Ser Pro Ala Ile Lys
                20                  25                  30

Ser Thr Glu Asn Arg Asn Asn Glu Val Leu Glu Val Tyr Ser Thr Pro
            35                  40                  45

Leu His Thr Pro Gln Glu Lys Met Ala Ile Pro Val Ser Val Leu Thr
        50                  55                  60

Gln Glu Asp Leu Arg Ala Asn Arg Ser Ala Ser Ile Ala Glu Thr Leu
65                  70                  75                  80

Thr Ser Leu Pro Gly Phe His Ala Ser Phe Phe Gly Gly Gly Ser Val
                85                  90                  95

His Pro Val Ile Arg Gly Met Ser Gly Asn Arg Val Lys Val Leu His
                100                 105                 110

Ser Gly Ser Asp Leu Met Asp Val Ser Ser Ile Gly Ala Asp His Thr
            115                 120                 125

Ile Thr Ser Glu Pro Phe Leu Ser Gln Arg Ile Glu Val Leu Lys Gly
        130                 135                 140

Pro Ser Thr Leu Leu Tyr Gly Gly Thr Ile Gly Gly Ala Ile Asn
145                 150                 155                 160

Val Ile Asp Ser Lys Ile Pro Met Ser Val Pro Glu Lys Gly Tyr Glu
                165                 170                 175

Gly Glu Leu His Tyr Gln Tyr Asp Ser Val Ser Lys Gly Asn Thr Gly
            180                 185                 190

Ser Val Gly Leu Thr Leu Gly Glu Asn Asn Leu Ala Leu Arg Leu Glu
```

```
            195                 200                 205
Gly Thr Lys Arg Tyr Gln Ser Asp Tyr Lys Gln Pro Glu Pro Leu His
210                 215                 220

Gln Gly Glu Thr Ser Arg Leu Ala Gly Ser Tyr Gln Asp Asn Gln Ser
225                 230                 235                 240

Ala Asn Ile Gly Val Ser Trp Leu Phe Asp Asp Gly Tyr Ile Gly Ile
                    245                 250                 255

Gly Tyr Gly Glu Gln His Arg Arg Tyr Gly Leu Pro Gly His Thr His
                260                 265                 270

Phe His Asp His Glu Asp Asp His His His Ala Pro Ile Arg Pro
            275                 280                 285

Pro Leu Ile Gly His His His Asn His Asn His Glu Tyr Pro Asp
290                 295                 300

Glu Gln His Gln His Gly Ile Pro Tyr Ile Val Met Asp Ser Lys Arg
305                 310                 315                 320

Trp Asp Leu Arg Gly Glu Lys Asn Asn Pro Phe Thr Gly Ile Glu Ser
                325                 330                 335

Ile Arg Phe Ser Ala Val Arg Thr Asp Tyr His His Asp Glu Lys Glu
                340                 345                 350

Gly Asn Glu Val Ser Thr Ser Phe Lys Asn Lys Gly Asp Glu Leu Arg
            355                 360                 365

Leu Thr Phe Thr His Gln Pro Ile Trp Gly Trp His Gly Val Ile Gly
370                 375                 380

Gly Gln Phe Asn Gln Arg Asp Phe Ser Ala Gln Gly Glu Glu Ala Tyr
385                 390                 395                 400

Val Pro Ser Thr Lys Thr Lys Asn His Ser Leu Phe Leu Leu Glu Glu
                    405                 410                 415

Tyr Gln Leu Gly Asp Phe Arg Tyr Glu Leu Gly Phe Arg Gln Glu Trp
                420                 425                 430

Gln Ser Leu Leu Asn Arg Glu Thr Gln Lys Asn Asn Lys Gln Ser Ala
            435                 440                 445

Ser Ser Ile Ser Ala Gly Leu Ala Trp Asn Phe Thr Gln Asp Tyr Phe
450                 455                 460

Leu Asn Leu Ser Leu Ser His Thr Lys Arg Leu Pro Val Ala Glu Glu
465                 470                 475                 480

Leu Tyr Ala Asn Gly Val His Ala Ala Ser Arg Thr Ile Glu Lys Gly
                    485                 490                 495

Asp Pro Asn Leu Thr Ala Glu Ala Asn Asn Ile Asp Ile Gly Ile
                500                 505                 510

Thr Lys Val Thr Gly Asp Ile Gln Phe Asn Met Ser Ala Tyr Tyr Asn
            515                 520                 525

Arg Ile Asn Asn Tyr Ile Tyr Gly Gln Phe Thr Gly Thr Glu Leu Asn
        530                 535                 540

Asn Gly Tyr Arg Ser Leu Gln Tyr Val Gln Asn Asp Ala Gln Phe Lys
545                 550                 555                 560

Gly Ile Glu Gly Asn Ile Asp Tyr Tyr Asn Gln Asp Ser Leu Ile
                    565                 570                 575

Gly Ile Ser Gly Asp Tyr Val Arg Ala Asn Leu Leu His Asn Lys Gly
                580                 585                 590

Asn Ile Pro Arg Ile Pro Ala Tyr Arg Leu Ser Thr Tyr Ile Lys His
            595                 600                 605

Ser Phe Thr Glu Asn Val Ile Gly Gln Ile Arg Ile Asp Tyr Phe Gly
610                 615                 620
```

Lys Gln Asn Lys Thr Ala Asp Tyr Glu Thr Ser Thr Glu Ala Tyr Asn
625                 630                 635                 640

Thr Val Ser Leu Gly Ser Glu Tyr Ile Gly Tyr Leu Asp Asn Thr Asp
            645                 650                 655

Tyr Thr Leu Tyr Ala Lys Ile Asn Asn Ile Phe Asp Val Lys Gly Lys
            660                 665                 670

Asp Ser Thr Ser Tyr Ile Lys Asp Glu Met Tyr Leu Pro Gly Arg Asn
            675                 680                 685

Ile Ile Leu Gly Ala Thr Leu Thr Phe
690                 695

<210> SEQ ID NO 48
<211> LENGTH: 672
<212> TYPE: PRT
<213> ORGANISM: Pseudomonas stutzeri A1501

<400> SEQUENCE: 48

Met Lys Leu Lys Arg His Pro Leu Ala Trp Ala Ile Ser Leu Ala Leu
1               5                   10                  15

Val Pro Ala Ala Trp Ala Ala Asp Pro Val Glu Leu Gln Ser Val Val
            20                  25                  30

Val Ser Ala Ser Gly Leu Ala Lys Gln Ser His Glu Met Thr Thr Pro
        35                  40                  45

Val Ala Val Met Glu Asn Asp Glu Leu Val Leu Arg Arg Glu Ala Thr
    50                  55                  60

Leu Gly Glu Thr Leu Glu Ser Leu Pro Gly Val Arg Ser Ser Ser Phe
65                  70                  75                  80

Gly Ala Gly Ala Ala Arg Pro Val Ile Arg Gly Leu Asp Gly Ala Arg
                85                  90                  95

Val Lys Val Leu Ser Asp Gly Val Glu Leu Leu Asp Ala Ser Thr Ile
            100                 105                 110

Ser Pro Asp His Ala Val Thr Ser Glu Pro Leu Leu Ala Glu Arg Ile
            115                 120                 125

Glu Val Leu Lys Gly Pro Ala Thr Leu Leu Tyr Gly Gly Gly Ala Ile
        130                 135                 140

Gly Gly Val Val Asn Val Ile Asp Lys Lys Ile Pro Thr Arg Val Pro
145                 150                 155                 160

Glu Lys Gly Tyr Glu Gly Glu Leu Glu Leu Arg Ala Asn Ser Val Ala
                165                 170                 175

Asn Glu Gly Ala Gly Val Phe Gly Ile Thr Ala Gly Ser Gly Asn Phe
            180                 185                 190

Ala Val Arg Ala Glu Gly Thr Lys Arg Gln Ala Asp Pro Tyr Glu Ile
        195                 200                 205

Pro Gly Ser Pro Asn Lys Gln Glu Gly Ser Tyr Asn Asp Thr Asp Ser
    210                 215                 220

Phe Asn Leu Gly Ala Ser Phe Ile Gly Glu Arg Gly Tyr Ile Gly Ala
225                 230                 235                 240

Ala Tyr Gly Glu Gln Asn Asn Arg Tyr Gly Leu Leu Ala His Glu His
                245                 250                 255

Ala Asp Cys His Thr His Gly Ser Asp Trp Cys Gly Gly His Asp
            260                 265                 270

Asp Asp Asp Asp His Asp His Asp His Glu His Gly Ser Val Pro
        275                 280                 285

Tyr Val Asp Met Arg Gln Lys Arg Trp Asp Leu Arg Gly Glu Leu Ser 290                 295                 300

Asp Pro Leu Pro Gly Phe Glu Leu Ala Arg Leu Arg Val Gly His Ser
305                 310                 315                 320

Asp Tyr Gln His Lys Glu Ile Glu Gly Gly Glu Val Gly Thr Arg Phe
                325                 330                 335

Asn Asn Asp Ala Thr Asp Ala Arg Leu Glu Leu Thr His Gln Pro Leu
            340                 345                 350

Phe Gly Trp Arg Gly Val Leu Gly Ala Gln Thr Leu Arg Arg Asp Phe
        355                 360                 365

Glu Ala Leu Gly Glu Glu Ala Tyr Val Pro Gln Thr Leu Thr Arg Asn
370                 375                 380

His Gly Leu Phe Leu Leu Glu Glu Tyr Thr Ala Gly Ala Trp Arg Tyr
385                 390                 395                 400

Glu Leu Gly Leu Arg His Glu Trp Gln Asp Ile Asp Ala Asp Gly Arg
                405                 410                 415

Pro Asp Thr Asp His Ser Gly Thr Ser Met Ser Ala Gly Ala Val Trp
            420                 425                 430

Thr Phe Ala Pro Gln Tyr Ser Leu Gly Phe Ser Leu Thr Arg Ser Gln
        435                 440                 445

Arg Leu Pro Ser Ala Glu Glu Leu Tyr Ala Asn Gly Pro His Ala Ala
450                 455                 460

Thr Arg Thr Val Glu Leu Gly Asn Val Asp Leu Lys Glu Glu Thr Ser
465                 470                 475                 480

His Asn Ala Glu Val Thr Leu Arg Lys Phe Ala Gly Arg Thr Thr Phe
                485                 490                 495

Ser Leu Ser Val Phe Arg Asn Glu Val Asp Asp Phe Ile Tyr Ala Ala
            500                 505                 510

Asp Thr Gly Asn Asp Ile Gly Gly Gly Tyr Arg Glu Ile Glu Tyr Arg
        515                 520                 525

Gln Gln Asp Ala Val Leu Thr Gly Ala Glu Gly Glu Val Arg Phe Gln
530                 535                 540

Ala Thr Asp Ala Thr Ala Phe Thr Leu Phe Gly Asp His Val Arg Gly
545                 550                 555                 560

Lys Leu Arg Gly Asp Gly Asp Leu Pro Arg Ile Pro Ala Asp Arg
                565                 570                 575

Leu Gly Val Arg Leu Asp Gln Ser Phe Thr Pro Ala Leu Asn Gly Gln
            580                 585                 590

Leu Glu Phe Tyr Arg Val Gln Arg Gln Asp Leu Ala Asp Tyr Glu
        595                 600                 605

Thr Glu Thr Gly Gly Tyr Asn Met Leu Gly Ala Ser Leu Gly Tyr Ser
610                 615                 620

Gly Ser Leu Ser Gln Thr Asp Tyr Leu Leu Tyr Leu Lys Ala Asn Asn
625                 630                 635                 640

Leu Leu Asp Glu Lys Ala Arg Gln His Thr Ser Phe Ile Lys Asp Glu
                645                 650                 655

Val Leu Leu Pro Gly Arg Asn Leu Thr Val Gly Val Arg Leu Ala Phe
            660                 665                 670

<210> SEQ ID NO 49
<211> LENGTH: 686
<212> TYPE: PRT
<213> ORGANISM: Sphingomonas sp. SKA58

<400> SEQUENCE: 49

```
Met Cys Ala Val Ser Ile Ile Ala Ile Thr Pro Gly Ile Ala Leu Ala
1               5                   10                  15

Gln Ala Gly Gly His Gly Gln Gly Asp Ile Val Val Thr Ala Ala Pro
            20                  25                  30

Leu Gly Gln Lys Ala Asp Glu Thr Thr Thr Pro Val Val Thr Leu Thr
            35                  40                  45

Gly Glu Glu Leu Ile His Arg Arg Ala Ala Thr Leu Gly Glu Thr Leu
        50                  55                  60

Ala Gly Gln Pro Gly Ile Asn Phe Glu Asn Phe Gly Gly Ala Ser
65                  70                  75                  80

Arg Pro Ile Ile Arg Gly Gln Ser Ser Pro Arg Val Gln Val Leu Ser
                85                  90                  95

Asp Ser Ala Asn Val Gln Asp Ala Ser Ala Ile Ser Pro Asp His Asn
            100                 105                 110

Val Thr Gly Glu Pro Leu Leu Leu Arg Arg Ile Glu Val Leu Arg Gly
            115                 120                 125

Pro Ala Thr Leu Leu Tyr Gly Ser Gly Ala Ile Gly Gly Ala Val Asn
            130                 135                 140

Leu Leu Asp Glu Lys Val Pro Thr Tyr Val Pro Glu Gly Gly Ile Thr
145                 150                 155                 160

Gly Ala Ala Glu Gly Arg Leu Gly Thr Gly Asp Asp Glu Arg Ser Leu
                165                 170                 175

Val Gly Gly Ala Thr Val Gly Val Gly Pro Leu Ala Leu Arg Val Glu
            180                 185                 190

Gly Val His Arg Ser Asp Asp Tyr Arg Val Pro Arg Ala Phe Gly
            195                 200                 205

Glu Asp Arg Val His Gly Ser Tyr Asn Asp Thr Ser Thr Phe Ser Val
210                 215                 220

Gly Gly Ser Trp Ile Gly Pro Asp Gly Tyr Leu Gly Val Ala Tyr Thr
225                 230                 235                 240

Arg Gln Arg Asn Glu Tyr Gly Val Pro Gly His Asn His Asp Tyr Glu
                245                 250                 255

Ser Cys His Pro His Gly Ile Gly Leu His Cys Gly Ser His Gly Glu
            260                 265                 270

Glu Glu Glu His Asp His Asp His Asp His Glu His Asp His Glu Glu
            275                 280                 285

Glu Val Pro Phe Val Lys Leu Arg Ser Asn Arg Phe Asp Ile Arg Ser
            290                 295                 300

Asp Tyr Asn Asn Pro Val Pro Ala Leu Glu Lys Val Arg Phe Arg Leu
305                 310                 315                 320

Ser Phe Thr Asp Tyr Ala His Asp Glu Ile Glu Asp Gly Glu Ala Glu
                325                 330                 335

Asn Thr Phe Leu Asn Lys Ala His Asp Leu Arg Val Glu Leu Thr His
            340                 345                 350

Ala Pro Leu Gly Gly Leu Arg Gly Thr Phe Gly Ile Gln Gln Ser Gly
            355                 360                 365

Ser Arg Phe Gln Ala Ile Ser Gly Gly Val Thr His Thr Leu Asn Thr
    370                 375                 380

Asp Ser Ser Asn Thr Ala Ile Phe Leu Leu Glu Thr Tyr Ser Leu Gly
385                 390                 395                 400

Asn Val Arg Leu Glu Ala Ala Ala Arg Gln Glu Trp Gln Thr Val Lys
            405                 410                 415

Ser Leu Ile Thr Arg Tyr Pro Ser Ile Lys His Lys Pro Phe Ser Ala
```

```
            420                 425                 430
Ser Ala Ala Ile Trp Ser Met Gly Ser Asp Tyr Ser Leu Ala Leu
        435                 440                 445

Ser Leu Ala His Thr Glu Arg Ala Pro Ser Val Gln Glu Leu Tyr Ala
        450                 455                 460

Tyr Gly Leu His Leu Ala Thr Asn Thr Tyr Glu Ile Gly Ile Val Ser
465                 470                 475                 480

Gly Asn Ser Arg Leu Ala Glu Lys Val Ser Gln Gly Val Glu Lys Ala
                485                 490                 495

Asn Ser Val Asn Leu Thr Leu Arg Lys Thr Ala Gly Pro Thr Thr Phe
            500                 505                 510

Thr Ile Gly Ala Tyr His Gln Asp Phe Asp Asn Tyr Ile Tyr Ala Gln
        515                 520                 525

Thr Leu Asp Gln Phe Glu Asp Phe Arg Leu Ile Arg Tyr Ala Gly Ala
        530                 535                 540

Glu Ala Thr Phe Thr Gly Ile Asp Gly Glu Val Arg His Ala Phe Asn
545                 550                 555                 560

Asp Gln Phe Ala Leu Ser Val Phe Gly Asp Tyr Val Arg Ala Lys Leu
                565                 570                 575

Lys Asn Gly Gly Gly Asp Leu Pro Arg Ile Pro Ala Gly Arg Leu Gly
                580                 585                 590

Ala Arg Gly Asp Ala His Val Gly Pro Phe Thr Ala Asp Ala Glu Tyr
            595                 600                 605

Tyr His Val Phe Glu Gln Asp Arg Ile Ala Ala Phe Glu Thr Arg Thr
        610                 615                 620

Pro Gly Tyr Asp Met Val Asn Ala Thr Leu Ala Tyr Arg Leu Glu Leu
625                 630                 635                 640

Gly Asp Lys Arg Ser Ala Glu Leu Phe Val Arg Gly Thr Asn Leu Thr
                645                 650                 655

Asn Glu Leu Ala Tyr Asn His Ser Ser Phe Ile Lys Ala Phe Ser Pro
                660                 665                 670

Leu Arg Gly Arg Asn Phe Val Phe Gly Leu Arg Gly Ala Phe
        675                 680                 685

<210> SEQ ID NO 50
<211> LENGTH: 921
<212> TYPE: PRT
<213> ORGANISM: Neisseria meningitidis MC58

<400> SEQUENCE: 50

Met Arg Ser Ser Phe Arg Leu Lys Pro Ile Cys Phe Tyr Leu Met Gly
1               5                   10                  15

Val Thr Leu Tyr His Tyr Ser Tyr Ala Glu Asp Ala Gly Arg Ala Gly
            20                  25                  30

Ser Glu Ala Gln Ile Gln Val Leu Glu Asp Val His Val Lys Ala Lys
        35                  40                  45

Arg Val Pro Lys Asp Lys Lys Val Phe Thr Asp Ala Arg Ala Val Ser
    50                  55                  60

Thr Arg Gln Asp Ile Phe Lys Ser Ser Glu Asn Leu Asp Asn Ile Val
65                  70                  75                  80

Arg Ser Ile Pro Gly Ala Phe Thr Gln Gln Asp Lys Ser Ser Gly Ile
                85                  90                  95

Val Ser Leu Asn Ile Arg Gly Asp Ser Gly Phe Gly Arg Val Asn Thr
            100                 105                 110
```

```
Met Val Asp Gly Ile Thr Gln Thr Phe Tyr Ser Thr Ser Thr Asp Ala
            115                 120                 125

Gly Arg Ala Gly Gly Ser Ser Gln Phe Gly Ala Ser Val Asp Ser Asn
        130                 135                 140

Phe Ile Ala Gly Leu Asp Val Val Lys Gly Ser Phe Ser Gly Ser Ala
145                 150                 155                 160

Gly Ile Asn Ser Leu Ala Gly Ser Ala Asn Leu Arg Thr Leu Gly Val
                165                 170                 175

Asp Asp Val Val Gln Gly Asn Asn Thr Tyr Gly Leu Leu Lys Gly
            180                 185                 190

Leu Thr Gly Thr Asn Ser Thr Lys Gly Asn Ala Met Ala Ala Ile Gly
        195                 200                 205

Ala Arg Lys Trp Leu Glu Ser Gly Ala Ser Val Gly Val Leu Tyr Gly
        210                 215                 220

His Ser Arg Arg Ser Val Ala Gln Asn Tyr Arg Val Gly Gly Gly
225                 230                 235                 240

Gln His Ile Gly Asn Phe Gly Ala Glu Tyr Leu Glu Arg Arg Lys Gln
                245                 250                 255

Arg Tyr Phe Val Gln Glu Gly Ala Leu Lys Phe Asn Ser Asp Ser Gly
            260                 265                 270

Lys Trp Glu Arg Asp Leu Gln Arg Gln Trp Lys Tyr Lys Pro Tyr
        275                 280                 285

Lys Asn Tyr Asn Asn Gln Glu Leu Gln Lys Tyr Ile Glu Glu His Asp
        290                 295                 300

Lys Ser Trp Arg Glu Asn Leu Ala Pro Gln Tyr Asp Ile Thr Pro Ile
305                 310                 315                 320

Asp Pro Ser Ser Leu Lys Gln Gln Ser Ala Gly Asn Leu Phe Lys Leu
                325                 330                 335

Glu Tyr Asp Gly Val Phe Asn Lys Tyr Thr Ala Gln Phe Arg Asp Leu
            340                 345                 350

Asn Thr Lys Ile Gly Ser Arg Lys Ile Ile Asn Arg Asn Tyr Gln Phe
        355                 360                 365

Asn Tyr Gly Leu Ser Leu Asn Pro Tyr Thr Asn Leu Asn Leu Thr Ala
        370                 375                 380

Ala Tyr Asn Ser Gly Arg Gln Lys Tyr Pro Lys Gly Ser Lys Phe Thr
385                 390                 395                 400

Gly Trp Gly Leu Leu Lys Asp Phe Glu Thr Tyr Asn Asn Ala Lys Ile
                405                 410                 415

Leu Asp Leu Asn Asn Thr Ala Thr Phe Arg Leu Pro Arg Glu Thr Glu
            420                 425                 430

Leu Gln Thr Thr Leu Gly Phe Asn Tyr Phe His Asn Glu Tyr Gly Lys
        435                 440                 445

Asn Arg Phe Pro Glu Glu Leu Gly Leu Phe Phe Asp Gly Pro Asp Gln
        450                 455                 460

Asp Asn Gly Leu Tyr Ser Tyr Leu Gly Arg Phe Lys Gly Asp Lys Gly
465                 470                 475                 480

Leu Leu Pro Gln Lys Ser Thr Ile Val Gln Pro Ala Gly Ser Gln Tyr
                485                 490                 495

Phe Asn Thr Phe Tyr Phe Asp Ala Ala Leu Lys Lys Asp Ile Tyr Arg
            500                 505                 510

Leu Asn Tyr Ser Thr Asn Thr Val Gly Tyr Arg Phe Gly Gly Glu Tyr
        515                 520                 525

Thr Gly Tyr Tyr Gly Ser Asp Asp Glu Phe Lys Arg Ala Phe Gly Glu
```

```
                530               535               540
Asn Ser Pro Thr Tyr Lys Lys His Cys Asn Arg Ser Cys Gly Ile Tyr
545                 550                 555                 560

Glu Pro Val Leu Lys Lys Tyr Gly Lys Lys Arg Ala Asn Asn His Ser
                565                 570                 575

Val Ser Ile Ser Ala Asp Phe Gly Asp Tyr Phe Met Pro Phe Ala Ser
            580                 585                 590

Tyr Ser Arg Thr His Arg Met Pro Asn Ile Gln Glu Met Tyr Phe Ser
        595                 600                 605

Gln Ile Gly Asp Ser Gly Val His Thr Ala Leu Lys Pro Glu Arg Ala
    610                 615                 620

Asn Thr Trp Gln Phe Gly Phe Asn Thr Tyr Lys Lys Gly Leu Leu Lys
625                 630                 635                 640

Gln Asp Asp Thr Leu Gly Leu Lys Leu Val Gly Tyr Arg Ser Arg Ile
                645                 650                 655

Asp Asn Tyr Ile His Asn Val Tyr Gly Lys Trp Trp Asp Leu Asn Gly
            660                 665                 670

Asp Ile Pro Ser Trp Val Ser Ser Thr Gly Leu Ala Tyr Thr Ile Gln
        675                 680                 685

His Arg Asn Phe Lys Asp Lys Val His Lys His Gly Phe Glu Leu Glu
    690                 695                 700

Leu Asn Tyr Asp Tyr Gly Arg Phe Phe Thr Asn Leu Ser Tyr Ala Tyr
705                 710                 715                 720

Gln Lys Ser Thr Gln Pro Thr Asn Phe Ser Asp Ala Ser Glu Ser Pro
                725                 730                 735

Asn Asn Ala Ser Lys Glu Asp Gln Leu Lys Gln Gly Tyr Gly Leu Ser
            740                 745                 750

Arg Val Ser Ala Leu Pro Arg Asp Tyr Gly Arg Leu Glu Val Gly Thr
        755                 760                 765

Arg Trp Leu Gly Asn Lys Leu Thr Leu Gly Gly Ala Met Arg Tyr Phe
    770                 775                 780

Gly Lys Ser Ile Arg Ala Thr Ala Glu Glu Arg Tyr Ile Asp Gly Thr
785                 790                 795                 800

Asn Gly Gly Asn Thr Ser Asn Phe Arg Gln Leu Gly Lys Arg Ser Ile
                805                 810                 815

Lys Gln Thr Glu Thr Leu Ala Arg Gln Pro Leu Ile Phe Asp Phe Tyr
            820                 825                 830

Ala Ala Tyr Glu Pro Lys Lys Asn Leu Ile Phe Arg Ala Glu Val Lys
        835                 840                 845

Asn Leu Phe Asp Arg Arg Tyr Ile Asp Pro Leu Asp Ala Gly Asn Asp
850                 855                 860

Ala Ala Thr Gln Arg Tyr Tyr Ser Ser Phe Asp Pro Lys Asp Lys Asp
865                 870                 875                 880

Glu Asp Val Thr Cys Asn Ala Asp Lys Thr Leu Cys Asn Gly Lys Tyr
                885                 890                 895

Gly Gly Thr Ser Lys Ser Val Leu Thr Asn Phe Ala Arg Gly Arg Thr
            900                 905                 910

Phe Leu Met Thr Met Ser Tyr Lys Phe
        915                 920

<210> SEQ ID NO 51
<211> LENGTH: 530
<212> TYPE: PRT
<213> ORGANISM: Aggregatibacter actinomycetemcomitans
```

<400> SEQUENCE: 51

```
Met Val Thr Phe Cys Ile Leu Asn Val Leu Asn Val Ala Asn Ala Glu
1               5                   10                  15

Glu Gln Leu Asp Gln Ile Asp Val Val Glu Lys Thr Ile Ala Asn Glu
            20                  25                  30

Lys Lys Pro Phe Thr Glu Ala Lys Ala Lys Ser Thr Arg Glu Asn Val
        35                  40                  45

Phe Lys Ser Thr Glu Thr Val Asp Asn Val Val Arg Ser Ile Pro Gly
    50                  55                  60

Ala Phe Thr Gln Gln Asp Lys Gly Ser Gly Val Leu Ser Leu Asn Ile
65                  70                  75                  80

Arg Gly Glu Thr Gly Phe Gly Arg Ala Asn Thr Met Val Asp Gly Val
                85                  90                  95

Thr Gln Thr Phe Tyr Ser Thr Ser Met Asp Ala Gly Arg Thr Gly Gly
            100                 105                 110

Asn Ser Gln Phe Gly Ala Ala Ile Asp Pro Asn Phe Ile Ala Gly Ile
        115                 120                 125

Asp Leu Thr Lys Gly Asn Phe Ser Gly Thr Gly Val Asn Ser Leu
    130                 135                 140

Tyr Gly Ala Ala Asn Phe Arg Thr Leu Gly Val Asn Asp Val Ile Gln
145                 150                 155                 160

Gly Asp Lys Asn Tyr Gly Phe Leu Thr Lys Gly Leu Ser Gly Asp Asn
                165                 170                 175

Glu Thr Lys Tyr Asn Tyr Met Ala Met Gly Ala Ala Arg Lys Trp Leu
            180                 185                 190

Asp Asn Gly Gly Tyr Ile Gly Val Leu Tyr Gly Tyr Ser Gln Arg Glu
        195                 200                 205

Val Ser Gln Asn Tyr Lys Val Gly Gly Gly Glu Arg Ile Ser Asp
    210                 215                 220

Val Gly Lys Gly Phe Leu Glu Arg Lys Asn Glu Phe Phe Arg Ser
225                 230                 235                 240

His Gln Leu Lys Phe Asn Ser Glu Lys Asn Glu Trp Glu Arg Asp Phe
                245                 250                 255

Ser Ile Lys Asn Ser Ala Gly Lys Ser Thr Trp Glu Tyr Pro Trp Asn
            260                 265                 270

Lys Lys Tyr Asn Asp Pro Gln Lys Leu Lys Glu Tyr Ile Ala Glu Leu
        275                 280                 285

Gly Lys Ile Trp Asn Glu Asn Glu Val Pro Gln Trp Asp Leu Thr Pro
    290                 295                 300

Ile Asp Pro Ser Ser Leu Val Gln Arg Ser Lys Ser His Leu Val Lys
305                 310                 315                 320

Val Glu Phe Ser Asp Asp Arg His Thr Leu Asn Leu Gln Tyr Arg Thr
                325                 330                 335

Leu Asp Asn His Ile Gly Ser Arg Lys Ile Glu Asn Arg Asn Tyr Gln
            340                 345                 350

Leu Asn Tyr Asn Phe Asn Asn Asn Gly Tyr Leu Asp Leu Asn Val Leu
        355                 360                 365

Leu Ala His Asn Val Gly Lys Gln Lys Tyr Pro Ser Gly Ser Arg Phe
    370                 375                 380

Gly Gly Trp Gln Val Leu Lys Tyr Leu Glu Thr Lys Asn Thr Ala Asp
385                 390                 395                 400

Ile Ile Asp Ile Ser Asn Ser Tyr Thr Phe Ser Leu Pro Lys Glu Thr
```

405                 410                 415
Asp Leu Lys Thr Thr Leu Gly Val Asn Leu Phe Lys Asn Gln Tyr Thr
                    420                 425                 430

Lys Asn Arg Phe Pro Glu Glu Leu Ser Pro Phe Tyr Asp Gly Pro Ser
                435                 440                 445

Gln Lys Ser Gly Leu Tyr Asp Phe Leu Gly Arg Phe Lys Gly Asp Lys
            450                 455                 460

Gly Ile Leu Pro Gln Lys Ser Thr Ile Leu Gln Pro Ser Gly Glu Gln
465                 470                 475                 480

Arg Phe Asn Thr Val Tyr Leu Asp Thr Ser Leu Thr Arg Asp Ile Phe
                485                 490                 495

Lys Leu Asp Tyr Ser Val Asn Phe Val Lys Tyr Lys Phe Asn Gly Glu
                500                 505                 510

Tyr Thr Ala Tyr Tyr Asn Ser Pro Ser Asp Phe Lys Lys Ala Phe Gly
            515                 520                 525

Glu Asp
    530

<210> SEQ ID NO 52
<211> LENGTH: 365
<212> TYPE: PRT
<213> ORGANISM: Aggregatibacter actinomycetemcomitans D11S-1

<400> SEQUENCE: 52

Met Tyr Glu Pro Val Tyr Lys Lys Gly Gly Lys Lys Ser Ala Val Asn
1               5                   10                  15

His Ser Val Val Leu Ser Ala Ala Pro Ser Asp Tyr Phe Met Pro Phe
                20                  25                  30

Ile Ser Tyr Ala Arg Thr His Arg Met Pro Asn Ile Gln Glu Met Tyr
            35                  40                  45

Phe Ser Gln Ile Gly Asp Ser Gly Val Asn Thr Asn Leu Lys Pro Glu
        50                  55                  60

Arg Ala Asp Thr Tyr Gln Ile Gly Phe Asn Thr Phe Lys Asn Asn Val
65                  70                  75                  80

Phe Leu Asp Asp Asp Val Leu Gly Leu Lys Ala Val Phe Tyr Arg Ser
                85                  90                  95

Arg Ile Lys Asp Tyr Ile His Asn Val Tyr Gly Lys Trp Trp Asn Thr
            100                 105                 110

Gln Ala Gly Leu Pro Pro Ser Trp Val Thr Thr Thr Gly Leu Ser Tyr
        115                 120                 125

Thr Ile Gln His Arg Asn Tyr Gln Lys Arg Val Asn Lys Arg Gly Leu
    130                 135                 140

Glu Leu Glu Leu Asn Tyr Asp Ala Gly Arg Phe Phe Thr Asn Leu Ser
145                 150                 155                 160

Tyr Ala Tyr Gln Lys Thr Asn Gln Pro Thr Asn Tyr Ser Asp Ala Ser
                165                 170                 175

Glu Ser Pro Asn Asn Ala Ser Lys Gln Asp Gln Ile Lys Gln Gly Tyr
            180                 185                 190

Gly Leu Thr Lys Ile Ser Met Leu Pro Arg Asp Tyr Gly Arg Leu Glu
        195                 200                 205

Ile Gly Ser Arg Trp Phe Asp Arg Lys Leu Thr Ile Gly Ser Ala Val
    210                 215                 220

Arg Tyr Tyr Gly Lys Ser Lys Arg Ala Thr Thr Glu Glu Arg Tyr Ile
225                 230                 235                 240

Asp Gly Thr Lys Pro Gly Asn Thr Ala Asp Pro His Asn Ile Gly Lys
                245                 250                 255

Arg Val Ile Lys Glu Thr Glu Thr Ile Asp Lys Gln Pro Leu Val Val
            260                 265                 270

Asp Phe Tyr Val Ala Tyr Glu Pro Val Glu Asn Leu Val Ile Arg Ala
            275                 280                 285

Asp Ile Gln Asn Ala Phe Asp Lys Arg Tyr Ile Asp Pro Leu Asp Ala
        290                 295                 300

Ala Asn Asp Ala Ala Thr Gln Arg Tyr Phe Ser Thr Phe Glu Asn Leu
305                 310                 315                 320

Asn Ser Tyr Gly Asp Asp Ile Val Gln Cys Asp Ser Asn Gly Leu Cys
                325                 330                 335

Asn Gly Arg Tyr Gly Gly Lys Thr Asn Ser Ile Leu Asn Asn Tyr Ala
            340                 345                 350

Arg Gly Arg Thr Phe Val Leu Ser Val Ser Tyr Lys Phe
            355                 360                 365

<210> SEQ ID NO 53
<211> LENGTH: 924
<212> TYPE: PRT
<213> ORGANISM: Aggregatibacter aphrophilus NJ8700

<400> SEQUENCE: 53

Met Arg Lys Thr Ile Lys Leu Asn Leu Ile Thr Phe Cys Leu Leu Asn
1               5                   10                  15

Val Ile Asn Ile Thr Tyr Ala Glu Glu Gln Leu Asn Gln Ile Asp Val
            20                  25                  30

Val Glu Lys Ile Ile Ala Asn Glu Lys Lys Pro Phe Thr Glu Ala Lys
        35                  40                  45

Ala Lys Ser Thr Arg Glu His Val Phe Lys Glu Thr Gln Ser Ile Asp
    50                  55                  60

Asn Val Val Arg Ser Ile Pro Gly Ala Phe Thr Gln Gln Asp Lys Gly
65                  70                  75                  80

Ser Gly Val Leu Ser Leu Asn Ile Arg Gly Glu Thr Gly Phe Gly Arg
                85                  90                  95

Ala Asn Thr Met Val Asp Gly Ile Thr Gln Thr Phe Tyr Ser Thr Ser
            100                 105                 110

Met Asp Ser Gly Gln Ala Gly Asn Ser Gln Phe Gly Ala Ser Leu
        115                 120                 125

Asp Pro Asn Phe Ile Ala Gly Ile Asp Leu Thr Lys Gly Asn Phe Ser
    130                 135                 140

Gly Thr Asn Gly Val Asn Ser Leu Tyr Gly Ser Ala Asn Phe Arg Thr
145                 150                 155                 160

Leu Gly Val Asn Asp Val Ile Leu Gly Asp Lys Asn Leu Gly Phe Ile
                165                 170                 175

Ile Lys Gly Met Thr Gly Thr Asn Ala Thr Lys Ser Asn Tyr Met Ala
            180                 185                 190

Met Ala Ala Thr Arg Lys Trp Leu Asp Asn Gly Gly Tyr Val Gly Met
        195                 200                 205

Leu Tyr Gly Tyr Ser Arg Arg Glu Val Ser Gln Asp Tyr Lys Ile Gly
    210                 215                 220

Gly Gly Gly Lys Lys Ile Ala Asp Val Gly Asp Asp Phe Leu Gln Gln
225                 230                 235                 240

Gln Lys Asn Lys Gln Phe Thr Glu Ala Gly Phe Val Phe Asp Arg Ala
                245                 250                 255

```
Lys Gly Arg Trp Met Pro Asp Leu Asn Lys Asn Leu Trp Ala Cys Asn
                260                 265                 270

Ala Pro Val Pro Ser Gln Pro Glu Pro Tyr Asp Cys Lys Tyr Tyr Lys
                275                 280                 285

Asn Ala Glu Arg Lys Arg Ile Leu Glu Asp Pro Asp Asn Ser Pro Glu
            290                 295                 300

Leu Gln Lys Gln Ile Asp Glu Thr Asn Ala Ala Phe Glu Arg Asn Asn
305                 310                 315                 320

Glu Gln Tyr Arg Leu Ala Pro Leu Asp Pro Ser Ser Val Arg Gln Ser
                325                 330                 335

Ser His Ser His Leu Val Lys Leu Glu Tyr Gly Asp Asp Arg His Thr
            340                 345                 350

Leu Asn Leu Gln Leu Arg Ala Leu Asp Asn Ala Ile Gly Thr Arg Lys
                355                 360                 365

Ile Glu Asn Arg Asn Tyr Gln Leu Asn Tyr Asn Phe Asn Asn Asn Gly
370                 375                 380

Tyr Ile Asp Met Asn Leu Leu Leu Ala His Asn Val Gly Lys Ser Lys
385                 390                 395                 400

Tyr Pro Lys Gly Ser Arg Phe Thr Gly Trp Glu Val Leu Lys Tyr Leu
                405                 410                 415

Glu Thr Lys Asn Ala Ala Asp Ile Phe Asp Ile Ser Asn Ser Tyr Thr
            420                 425                 430

Phe Thr Leu Pro Lys Glu Val Asp Leu Lys Thr Thr Leu Gly Phe Asn
            435                 440                 445

Phe Phe Lys Asn Glu Tyr Ser Lys Asn Arg Phe Pro Glu Glu Leu Ser
450                 455                 460

Leu Phe Tyr Asp Gly Ser Ser Gln Arg Gly Gly Leu Tyr Asp Phe Leu
465                 470                 475                 480

Gly Arg Tyr Lys Gly Ser Lys Gly Leu Leu Pro Gln Lys Ser Ser Ile
                485                 490                 495

Leu His Pro Ser Gly Glu Gln Lys Phe His Thr Phe Tyr Leu Asp Thr
                500                 505                 510

Ser Leu Thr Arg Asp Ile Tyr Arg Leu Asp Tyr Ser Val Asn Phe Ile
            515                 520                 525

Lys Tyr Lys Phe Asn Gly Glu Tyr Ala Gly Tyr Asn Ser Pro Glu
            530                 535                 540

Asp Phe Glu Lys Ala Phe Gly Lys Asp Ser Gln Ile Tyr Lys Lys Tyr
545                 550                 555                 560

Cys Lys Pro Asn Gly Gly Cys Gln Ile Tyr Glu Pro Leu Glu Arg Lys
                565                 570                 575

Thr Gly His Lys Thr Ala Val Asn His Ser Ala Ile Phe Ser Ala His
            580                 585                 590

Leu His Asp Tyr Phe Met Pro Phe Met Gly Tyr Ala Arg Thr His Arg
                595                 600                 605

Met Pro Asn Ile Gln Glu Met Tyr Phe Ser Gln Val Ser Asp Ala Gly
            610                 615                 620

Val Asn Thr Asp Leu Lys Pro Glu Arg Ala Ser Thr Tyr Gln Leu Gly
625                 630                 635                 640

Phe Asn Thr Phe Lys Glu Gly Ile Trp Lys Asn Asp Asp Val Leu Gly
                645                 650                 655

Ile Lys Val Val Gly Tyr Arg Ser Tyr Ile Lys Asn Tyr Ile His Asn
                660                 665                 670
```

Val Trp Gly Glu Trp Trp Gln Gly Gly Ala Pro Thr Trp Ala Glu Ser
            675                 680                 685

Asn Gly Phe Gln Phe Thr Ile Ala His Arg Asn Tyr Ala Lys Thr Val
    690                 695                 700

Lys Lys Ser Gly Val Glu Leu Glu Leu Asn Tyr Asp Met Gly Arg Phe
705                 710                 715                 720

Phe Thr Asn Leu Ser Tyr Ala Tyr Gln Arg Thr Asn Gln Pro Thr Asn
                725                 730                 735

Tyr Ser Asp Ala Ser Pro Arg Pro Asn Ala Ser Lys Glu Asp Val
            740                 745                 750

Leu Lys Gln Gly Tyr Gly Leu Thr Arg Ile Ser Ala Leu Pro Arg Asp
            755                 760                 765

Tyr Gly Arg Leu Glu Leu Gly Ser Arg Trp Phe Asp Arg Lys Leu Thr
    770                 775                 780

Val Gly Gly Ala Val Arg Tyr Tyr Gly Glu Ser Lys Arg Ala Ser Ile
785                 790                 795                 800

Glu Glu Lys Tyr Ile Asp Gly Thr Lys Phe Lys Asn Ala Leu Arg
                805                 810                 815

Arg His His His Ala Ile Lys Glu Thr Glu Thr Ile Glu Lys Gln Pro
            820                 825                 830

Leu Ile Phe Asp Leu Tyr Val Ser Tyr Glu Pro Ile Glu Asn Leu Ile
            835                 840                 845

Leu Lys Thr Glu Val Gln Asn Leu Phe Asp Lys Lys Tyr Ile Asp Pro
    850                 855                 860

Leu Asp Ala Gly Asn Asp Ala Ala Thr Gln Arg Tyr Tyr Ser Ser Ile
865                 870                 875                 880

Ser Ser Ala Pro Ser Gln Pro Cys Ala Pro Gly Glu Leu Cys His Lys
                885                 890                 895

Asp Gly His Ser Gly Lys Thr Gln Ser Ile Leu Asn Asn Tyr Ala Arg
            900                 905                 910

Gly Arg Thr Ile Val Phe Ser Leu Ser Tyr Lys Phe
            915                 920

<210> SEQ ID NO 54
<211> LENGTH: 758
<212> TYPE: PRT
<213> ORGANISM: Campylobacter coli RM2228

<400> SEQUENCE: 54

Met Lys Lys Leu Ser Leu Phe Cys Ala Val Gly Leu Cys Phe Ala Asn
1               5                   10                  15

Phe Ala Phe Ser Glu Glu Leu Glu Phe Asp Ser Leu Glu Ile Ser Gly
                20                  25                  30

Ser Lys Ile Lys Asn Asp Glu Lys Pro Phe Val Thr Pro Gly Ala Thr
            35                  40                  45

Ser Thr Arg Asp Asn Leu Asn Ser Asn Thr Gln Ser Ile Asp Ser Ile
        50                  55                  60

Val Arg Ser Val Pro Gly Ala Tyr Thr Gln Val Asp Gln Ala Gln Gly
65                  70                  75                  80

Gly Val Ser Val Asn Ile Arg Gly Met Thr Gly Leu Gly Arg Val Asn
                85                  90                  95

Thr Gln Ile Asp Gly Val Thr Gln Thr Phe Gly Ser Ala Ser Asp
            100                 105                 110

Asp Ser Phe His Gly Gln Ile Gly Thr Ser Ser Phe Thr Ala Pro Ile
        115                 120                 125

```
Asp Lys Asn Phe Leu Val Ala Leu Asp Val Asn Arg Gly Thr Phe Ser
130                 135                 140

Gly Ala Asn Gly Ala Asn Ala Leu Met Gly Ser Ala Asn Phe Arg Thr
145                 150                 155                 160

Ile Gly Val Asp Asp Ile Val Gln Glu Gly Arg Val Phe Gly Phe Leu
                165                 170                 175

Gly Lys Tyr Ser Tyr Gly Ser Asn Ala Ile Gly Pro Asn Phe Met Gly
                180                 185                 190

Ala Ile Ala Gly Lys Thr Met Leu Glu Asn Asn Ala Asn Leu Gly Ile
                195                 200                 205

Leu Phe Ala Tyr Ser Gly Gln Asn Val Ser Gln Asn Tyr Lys Ile Gly
210                 215                 220

Gly Gly Gly Tyr Ile Gly Asp Gln Lys Pro Pro Phe Asp Thr Asp Asp
225                 230                 235                 240

Asp Gly Ile Pro Asp Asp Asn Leu Ala Ala Pro Ile Asn Pro Asn Asn
                245                 250                 255

Leu Tyr Asn Gln Pro Arg Ser Gln Leu Phe Lys Val Glu Tyr Lys Ser
                260                 265                 270

Asp Ile Ser Glu Ala Ile Leu Asn Tyr Arg Ala Tyr Lys Asn Asn Leu
                275                 280                 285

Ala Gly Arg Lys Ile Thr Asn Asp Thr Tyr Gln Ile Asp Tyr Arg Leu
290                 295                 300

Asn Pro Asp Ser Asn Leu Leu Asp Leu Lys Phe Leu Phe Ala Tyr Asn
305                 310                 315                 320

Asp Gly Lys Gln Lys Tyr Asn Gln Gly Ser Thr Trp Gly Tyr His Asp
                325                 330                 335

Met Ser Gly Val Lys Thr Lys Asn Arg Ala Val Thr Phe Asp Leu Ser
                340                 345                 350

Asn Thr Met Asn Lys Glu Phe Ser Gln Asp Ser Asn Leu Tyr Phe Thr
                355                 360                 365

Tyr Gly Val Asn Ile Leu Asn Asn His Tyr Ser Asn Asp Phe Pro Gln
370                 375                 380

Asp Arg Val Leu Leu Pro Tyr Ile Leu Thr Ser Phe Tyr Pro Lys Gly
385                 390                 395                 400

Lys Gln Asp Ile Lys Thr Leu Tyr Leu Asp Thr Ser Phe Thr Lys Gly
                405                 410                 415

Ile Phe Thr Leu Asn Ser Asn Ile Asn Trp Thr Asn Ala Gln Leu Ser
                420                 425                 430

Gly Tyr Lys Gly Ile Cys Ser Met Ala Asn Pro Tyr Cys Gln Pro Lys
                435                 440                 445

Asn Ala Thr Asn Leu Glu Lys Asp Tyr Asn Asn Phe Asn Tyr Ser Leu
450                 455                 460

Met Leu Ser Ala Asp Ile His Pro Leu Phe Asn Pro Phe Ile Ser Tyr
465                 470                 475                 480

Ser Lys Ser His Arg Ile Pro Asn Val Gln Glu Tyr Phe Phe Thr His
                485                 490                 495

Asp Ala Ser Phe Glu His Asn Met Asn Thr Phe Leu Lys Ala Glu Ser
                500                 505                 510

Ala Asp Thr Tyr Gln Ile Gly Phe Asn Ser Phe Thr His Glu Ile Leu
                515                 520                 525

Asn Asp Ser Asp Thr Leu Gly Phe Lys Met Leu Tyr Tyr Asp Thr Lys
530                 535                 540
```

-continued

```
Val Lys Asn Tyr Ile Tyr Asn Arg Arg Tyr Trp Gln Lys Ala Asp Asp
545                 550                 555                 560

Ala Ile Phe Leu Met Gln Leu Asn Asp Asp Glu Lys Ala Lys Phe His
            565                 570                 575

Gly Val Glu Leu Glu Phe Lys Tyr Asp Thr Gly Phe Phe Tyr Ser Ile
        580                 585                 590

Leu Ser Tyr Thr Tyr Gln Lys Ser Lys His Lys Phe Ser Asp Thr Glu
    595                 600                 605

Ser Leu Glu Phe Gly Gly Ala Gln Ser Gly Gln Ser Gln Phe Ala Gln
610                 615                 620

Leu Pro Glu His Tyr Ala Asn Leu Asp Met Gly Val Arg Leu Phe Glu
625                 630                 635                 640

Glu Lys Leu Thr Leu Gly Ala Leu Ala Lys Tyr Thr Gly Lys Ala Lys
            645                 650                 655

Arg Ile Val Pro Val Gly Ser Leu Asp Asp Pro Ser Asn Pro Asp
        660                 665                 670

Ala Met Ala Pro Leu Lys Thr Thr Asp Glu Leu Pro Lys Ile Pro Thr
    675                 680                 685

Ile Val Asp Leu Tyr Ala Asn Tyr Lys Ile Leu Lys Asn Phe Thr Ile
690                 695                 700

Lys Ala Glu Val Gln Asn Leu Phe Asp Lys Asn Tyr Met Asp Ala Leu
705                 710                 715                 720

Tyr Ser Tyr Asn Thr Gly Glu Asn Gln Asn Ala Gly Gly Leu Phe Asp
            725                 730                 735

Pro Ile Tyr Ile Tyr Asn Asn Ser Ala Arg Gly Arg Thr Phe Ile Val
        740                 745                 750

Ser Phe Glu Tyr Lys Tyr
    755
```

<210> SEQ ID NO 55
<211> LENGTH: 758
<212> TYPE: PRT
<213> ORGANISM: Campylobacter upsaliensis RM3195

<400> SEQUENCE: 55

```
Met Lys Lys Leu Ser Leu Phe Cys Val Met Gly Leu Tyr Phe Ala Asn
1               5                   10                  15

Phe Ala Phe Ser Glu Glu Leu Glu Phe Asp Ser Leu Glu Ile Ser Gly
            20                  25                  30

Ser Lys Ile Lys Asn Asp Glu Lys Pro Phe Val Thr Pro Gly Ala Thr
        35                  40                  45

Ser Thr Arg Asp Asn Leu Asn Ser Ser Thr Gln Ser Ile Asp Ser Ile
    50                  55                  60

Val Arg Ser Val Pro Gly Ala Tyr Thr Gln Val Asp Gln Ala Gln Gly
65                  70                  75                  80

Gly Val Ser Val Asn Ile Arg Gly Met Thr Gly Leu Gly Arg Val Asn
            85                  90                  95

Thr Gln Ile Asp Gly Val Thr Gln Thr Phe Phe Gly Ser Ala Ser Asp
        100                 105                 110

Asp Ser Phe His Gly Gln Ile Gly Thr Ser Ser Phe Thr Ala Pro Ile
    115                 120                 125

Asp Lys Asn Phe Leu Val Ala Leu Asp Val Asn Arg Gly Thr Phe Ser
130                 135                 140

Gly Ala Asn Gly Ala Asn Ala Leu Met Gly Ser Ala Asn Phe Arg Thr
145                 150                 155                 160
```

```
Ile Gly Val Asp Asp Ile Val Gln Glu Gly Arg Val Phe Gly Phe Leu
                165                 170                 175

Gly Lys Tyr Ser Tyr Gly Ser Asn Ala Ile Gly Pro Asn Phe Met Gly
            180                 185                 190

Ala Ile Ala Gly Lys Thr Met Leu Glu Asn Asn Ala Asn Leu Gly Ile
        195                 200                 205

Leu Phe Ala Tyr Ser Gly Gln Asn Val Ser Gln Asn Tyr Lys Ile Gly
    210                 215                 220

Gly Gly Gly Tyr Ile Gly Asp Gln Lys Pro Pro Phe Asp Thr Asp Asp
225                 230                 235                 240

Asp Gly Thr Pro Asp Asp Asn Leu Ala Ala Pro Ile Asn Pro Asn Asn
                245                 250                 255

Leu Tyr Asn Gln Pro Arg Ser Gln Leu Phe Lys Val Glu Tyr Lys Ser
            260                 265                 270

Asp Ile Ser Glu Ala Ile Leu Asn Tyr Arg Ala Tyr Lys Asn Asn Leu
        275                 280                 285

Ala Gly Arg Lys Ile Thr Asn Asp Thr Tyr Gln Ile Asp Tyr Arg Leu
    290                 295                 300

Asn Pro Asp Ser Asn Leu Leu Asp Leu Lys Phe Leu Phe Ala Tyr Asn
305                 310                 315                 320

Asp Gly Lys Gln Lys Tyr Asn Gln Asp Lys Thr Trp Gly Tyr His Asn
                325                 330                 335

Met Ser Gly Ile Lys Thr Lys Asn Arg Ala Val Thr Phe Asp Leu Ser
            340                 345                 350

Asn Thr Met Asn Lys Glu Phe Ser Gln Asp Ser Asn Leu Tyr Phe Thr
        355                 360                 365

Tyr Gly Val Asn Ile Leu Asn Asn His Tyr Ser Asn Asp Phe Pro Glu
    370                 375                 380

Asp Arg Val Leu Leu Pro Tyr Ile Leu Thr Ser Phe Tyr Pro Lys Gly
385                 390                 395                 400

Lys Gln Glu Ile Lys Thr Phe Tyr Leu Asp Thr Ser Phe Thr Lys Gly
                405                 410                 415

Ile Phe Thr Leu Asn Ser Asn Val Asn Trp Ile Asn Ala Gln Leu Ser
            420                 425                 430

Gly Tyr Lys Gly Val Cys Ser Met Val Asn Pro Tyr Cys Gln Pro Lys
        435                 440                 445

Asn Ala Thr Asn Leu Glu Lys Asp Tyr Asn Asn Phe Asn Tyr Ser Leu
    450                 455                 460

Met Leu Ser Ala Asp Ile His Pro Leu Phe Asn Pro Phe Ile Ser Tyr
465                 470                 475                 480

Ser Lys Ser His Arg Ile Pro Asn Val Gln Glu Tyr Phe Phe Thr His
                485                 490                 495

Asp Ala Ser Gly Glu His Asn Met Asn Thr Phe Leu Arg Ala Glu Ser
            500                 505                 510

Ala Asn Thr Tyr Gln Ile Gly Phe Asn Ser Phe Ala His Glu Ile Leu
        515                 520                 525

Asn Asn Asn Asp Thr Leu Gly Phe Lys Val Leu Tyr Tyr Asp Thr Lys
    530                 535                 540

Val Lys Asn Tyr Ile Tyr Asn Arg Arg Tyr Trp Leu Lys Ala Asp Lys
545                 550                 555                 560

Ala Ile Phe Ile Met Gln Leu Asn Asp Asp Glu Lys Ala Lys Phe His
                565                 570                 575
```

```
Gly Val Glu Leu Glu Phe Lys Tyr Asp Thr Gly Phe Phe Tyr Ser Ile
            580                 585                 590

Leu Ser Tyr Thr Tyr Gln Lys Ser Lys His Lys Phe Ser Asp Thr Glu
        595                 600                 605

Ser Leu Glu Thr Gly Gly Ala Gln Ser Gly Gln Ser Gln Phe Ala Gln
    610                 615                 620

Leu Pro Glu His Tyr Ala Asn Leu Asp Met Gly Val Arg Leu Phe Glu
625                 630                 635                 640

Glu Lys Leu Thr Leu Gly Ala Leu Ala Lys Tyr Thr Gly Lys Ala Lys
                645                 650                 655

Arg Ile Ala Pro Val Gly Ser Leu Glu Asp Asp Pro Ser Asn Pro Asp
            660                 665                 670

Ala Met Ala Pro Leu Lys Thr Thr Asp Lys Leu Pro Lys Ile Pro Thr
        675                 680                 685

Ile Val Asp Leu Tyr Ala Asn Tyr Lys Ile Leu Lys Asn Phe Thr Ile
    690                 695                 700

Lys Ala Glu Ile Gln Asn Leu Phe Asp Lys Asn Tyr Met Asp Ala Leu
705                 710                 715                 720

Tyr Thr Tyr Asn Thr Gly Asp Ser Gln Asn Val Gly Gly Leu Phe Asn
                725                 730                 735

Pro Ile Tyr Ile Tyr Asn Asn Ser Ala Arg Gly Arg Thr Phe Ile Val
            740                 745                 750

Ser Phe Glu Tyr Lys Tyr
        755

<210> SEQ ID NO 56
<211> LENGTH: 921
<212> TYPE: PRT
<213> ORGANISM: Haemophilus influenzae 3655

<400> SEQUENCE: 56

Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Glu Thr Leu Gly
            20                  25                  30

Gln Ile Asp Val Val Glu Lys Val Ile Ser Asn Asp Lys Lys Pro Phe
        35                  40                  45

Thr Glu Ala Lys Ala Lys Ser Thr Arg Glu Asn Val Phe Lys Glu Thr
    50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
        115                 120                 125

Gly Ala Ala Ile Asp Pro Asn Phe Ile Ala Gly Val Asp Val Asn Lys
    130                 135                 140

Ser Asn Phe Ser Gly Ala Ser Gly Ile Asn Ala Leu Ala Gly Ser Ala
145                 150                 155                 160

Asn Phe Arg Thr Leu Ser Val Asn Asp Val Ile Thr Asp Asp Lys Pro
                165                 170                 175

Phe Gly Ile Ile Leu Lys Gly Met Thr Gly Ser Asn Ala Thr Lys Ser
            180                 185                 190
```

```
Asn Phe Met Thr Thr Ala Ala Gly Arg Lys Trp Leu Asp Asn Gly
            195                 200                 205

Tyr Val Gly Val Val Tyr Gly Tyr Ser Gln Arg Glu Val Ser Gln Asp
210                 215                 220

Tyr Arg Ile Gly Gly Glu Arg Leu Ala Ser Leu Gly Gln Asp Val
225                 230                 235                 240

Leu Ala Lys Glu Lys Glu Lys Ile Phe Arg Asn Asp Gly Tyr Val Leu
                245                 250                 255

Asn Ser Ala Gly Gln Trp Ala Pro Asp Leu Ser Gln Asn Ser Trp Thr
                260                 265                 270

Cys Asn Ala Lys Lys Pro Tyr Leu Ala Asp Glu Arg Val Thr Glu Gly
                275                 280                 285

Phe Lys Pro Asp Cys Lys Phe Ile Ala Phe Pro Lys Ser Pro Thr Thr
                290                 295                 300

Ile Lys Arg Lys Lys Ile Leu Gln Asp Ile Asp Asp Gly Lys Pro Leu
305                 310                 315                 320

Gln Asp Ile Pro Glu Leu Gln Ala Asp Ile Lys Glu Thr Asp Asp Ser
                325                 330                 335

Phe Glu Arg Asn Lys Asp Gln Tyr Ser Val Ala Pro Ile Glu Pro Gly
                340                 345                 350

Ser Leu Gln Ser Arg Ser Arg Ser His Leu Leu Lys Phe Glu Tyr Gly
                355                 360                 365

Asp Asp His His Thr Leu Gly Ala Gln Ile Arg Thr Leu Asp Asn Lys
                370                 375                 380

Ile Gly Ser Arg Lys Ile Glu Asn Arg Asn Tyr Gln Ala Asn Tyr Asn
385                 390                 395                 400

Phe Asn Asn Asn Ser Tyr Leu Asp Leu Asn Leu Met Ala Ala His Asn
                405                 410                 415

Ile Gly Lys Thr Ile Tyr Pro Lys Gly Gly Phe Phe Ala Gly Trp Gln
                420                 425                 430

Val Ala Asp Lys Leu Ile Ala Lys Asn Val Ala Asn Ile Val Asp Ile
                435                 440                 445

Asn Asn Ser His Thr Phe Leu Leu Pro Lys Glu Ile Asp Leu Lys Thr
                450                 455                 460

Thr Leu Gly Phe Asn Tyr Phe Thr Asn Glu Tyr Ser Lys Asn Arg Phe
465                 470                 475                 480

Pro Glu Glu Leu Ser Leu Phe Tyr Val Asn Glu Ser His Asp Gln Gly
                485                 490                 495

Leu Tyr Ser Leu Ser Asn Lys Gly Arg Tyr Ser Gly Ser Lys Gly Leu
                500                 505                 510

Leu Pro Gln Arg Ser Val Ile Leu Gln Pro Ser Gly Lys Gln Lys Phe
                515                 520                 525

Lys Thr Val Tyr Phe Asp Thr Ala Leu Ser Lys Gly Ile Tyr His Leu
530                 535                 540

Asn Tyr Ser Val Asn Phe Thr His Tyr Ala Phe Asn Gly Glu Tyr Val
545                 550                 555                 560

Gly Tyr Lys Asn Thr Ala Asp Lys Ile Asn Glu Pro Ile Leu His Lys
                565                 570                 575

Ser Gly His Lys Lys Ala Phe Asn His Ser Ala Thr Leu Ser Ala Glu
                580                 585                 590

Leu Ser Asp Tyr Phe Met Pro Phe Phe Thr Tyr Ser Arg Thr His Arg
                595                 600                 605
```

```
Met Pro Asn Ile Gln Glu Met Phe Ser Gln Val Ser Asp Ala Gly
    610                 615                 620

Val Asn Thr Ala Leu Lys Pro Glu Gln Ser Asp Thr Tyr Gln Leu Gly
625                 630                 635                 640

Phe Asn Thr Tyr Lys Lys Gly Leu Phe Thr Gln Asp Val Leu Gly
                645                 650                 655

Val Lys Leu Val Gly Tyr Arg Ser Phe Ile Lys Asn Tyr Ile His Asn
                660                 665                 670

Val Tyr Gly Asp Trp Ser Arg Asp Gly Val Ile Pro Glu Trp Ala Lys
                675                 680                 685

Leu Asn Gly Phe Arg Leu Thr Ile Ala His Gln Asn Tyr Gln Pro Ile
                690                 695                 700

Val Lys Lys Ser Gly Ala Glu Leu Glu Leu Asn Tyr Asp Met Gly Arg
705                 710                 715                 720

Phe Phe Ala Asn Leu Ser Tyr Ala Tyr Gln Arg Thr Asn Gln Pro Thr
                725                 730                 735

Asn Tyr Ala Asp Ala Ser Pro Arg Pro Arg Asn Ala Ser Lys Glu Glu
                740                 745                 750

Ile Leu Lys Gln Gly Tyr Gly Leu Ser Arg Ile Thr Met Leu Pro Lys
                755                 760                 765

Asp Tyr Gly Arg Leu Glu Leu Gly Thr Arg Trp Phe Asp Gln Lys Leu
                770                 775                 780

Thr Leu Gly Ile Ala Ala Arg Tyr Tyr Gly Lys Ser Lys Arg Ala Thr
785                 790                 795                 800

Thr Gln Glu Glu Tyr Ile Asn Gly Ser Arg Tyr Glu Lys Asn Thr Thr
                805                 810                 815

Arg Asp Arg Ile Tyr Tyr Ala Ile Lys Lys Thr Glu Glu Ile Lys Lys
                820                 825                 830

Gln Pro Ile Ile Leu Asp Leu His Val Ser Tyr Glu Pro Ile Lys Asp
                835                 840                 845

Leu Ile Ile Lys Ala Glu Val Gln Asn Leu Leu Asp Lys Arg Tyr Val
    850                 855                 860

Asp Pro Leu Asp Ala Gly Asn Asp Ala Ala Ser Gln Arg Tyr Tyr Ser
865                 870                 875                 880

Ser Leu Asn Asp Ser Leu Ala Cys Lys Ile Asn Glu Ser Thr Cys Asn
                885                 890                 895

Asp Gly Ser Asp Lys Ser Val Leu Tyr Asn Phe Ala Arg Gly Arg Thr
                900                 905                 910

Tyr Ile Leu Ser Leu Asn Tyr Lys Phe
                915                 920

<210> SEQ ID NO 57
<211> LENGTH: 950
<212> TYPE: PRT
<213> ORGANISM: Haemophilus influenzae 6P18H1

<400> SEQUENCE: 57

Met Lys Lys Ala Ile Lys Leu Asn Leu Ile Thr Leu Ser Leu Ile Asn
1               5                   10                  15

Thr Ile Gly Ile Thr Ile Thr Gln Ala Gln Ala Glu Glu Thr Leu Gly
                20                  25                  30

Gln Ile Asp Val Val Glu Lys Val Ile Ser Asn Asp Lys Lys Pro Phe
                35                  40                  45

Thr Glu Ala Lys Ala Lys Ser Thr Arg Glu Asn Val Phe Lys Glu Thr
    50                  55                  60
```

```
Gln Thr Ile Asp Gln Val Ile Arg Ser Ile Pro Ala Phe Thr Gln
 65                  70                  75                  80

Gln Asp Lys Gly Ser Gly Val Val Ser Val Asn Ile Arg Gly Glu Asn
                 85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
            115                 120                 125

Gly Ala Ala Ile Asp Pro Asn Phe Ile Ala Gly Val Asp Val Asn Lys
130                 135                 140

Ser Asn Phe Ser Gly Ala Ser Gly Ile Asn Ala Leu Ala Gly Ser Ala
145                 150                 155                 160

Asn Phe Arg Thr Leu Ser Val Asn Asp Val Ile Thr Asp Asp Lys Pro
                165                 170                 175

Phe Gly Ile Ile Leu Lys Gly Met Thr Gly Ser Asn Ala Thr Lys Ser
            180                 185                 190

Asn Phe Met Thr Thr Ala Ala Gly Arg Lys Trp Leu Asp Asn Gly Gly
            195                 200                 205

Tyr Val Gly Val Val Tyr Gly Tyr Ser Gln Arg Glu Val Ser Gln Asp
210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Phe
                245                 250                 255

Thr Asn Gly Gln Trp Thr Pro Asp Leu Asn Lys Asn His Trp Ser Cys
            260                 265                 270

Asn Leu Glu Lys Pro Lys Tyr Ser Gly Ser Gln Asp Pro Ile Val Lys
            275                 280                 285

Thr Asn Glu Leu Thr Gly Glu Thr Gly Thr Ile Trp Thr Asp Ser Asn
290                 295                 300

Cys Ile Thr Asn Ile Glu Lys Thr Thr Asp Pro Ser Asp Pro Ser Thr
305                 310                 315                 320

Lys Thr Thr Tyr Lys Thr Asn Ile Tyr Lys Asn Asn Thr Arg Gln Asp
                325                 330                 335

Ile Leu Lys Lys Leu Lys Ala Gly Thr Lys Pro Glu Asn Ile Asp Glu
            340                 345                 350

Leu Gln Asn Gly Lys Asp Gly Ile Lys Glu Thr Asp Lys Ser Phe Glu
            355                 360                 365

Asp Asn Lys Asp Gln Tyr Ser Val Ala Pro Ile Glu Pro Gly Ser Leu
            370                 375                 380

Gln Ser Arg Ser Arg Ser His Leu Leu Lys Phe Glu Tyr Gly Asp Asp
385                 390                 395                 400

His His Thr Leu Gly Ala Gln Ile Arg Thr Leu Asp Asn Lys Ile Gly
                405                 410                 415

Ser Arg Lys Ile Glu Asn Arg Asn Tyr Gln Val Asn Tyr Asn Phe Asn
            420                 425                 430

Asn Asn Ser Tyr Leu Asp Leu Asn Leu Met Ala Ala His Asn Ile Gly
            435                 440                 445

Lys Thr Ile Tyr Pro Lys Gly Gly Phe Phe Ala Gly Trp Gln Val Ala
            450                 455                 460

Asp Lys Leu Ile Thr Lys Asn Val Ala Asn Ile Val Asp Ile Asn Asn
465                 470                 475                 480
```

-continued

```
Ser His Thr Phe Leu Leu Pro Lys Glu Ile Asp Leu Lys Thr Thr Leu
            485                 490                 495

Gly Phe Asn Tyr Phe Thr Asn Glu Tyr Ser Lys Asn Arg Phe Pro Glu
            500                 505                 510

Glu Leu Ser Leu Phe Tyr Asn Asp Ala Ser His Asp Gln Gly Leu Tyr
            515                 520                 525

Ser His Ser Lys Arg Gly Arg Tyr Ser Gly Thr Lys Ser Leu Leu Pro
530                 535                 540

Gln Arg Ser Val Ile Leu Gln Pro Ser Gly Lys Gln Lys Phe Lys Thr
545                 550                 555                 560

Val Tyr Phe Asp Thr Ala Leu Ser Lys Gly Ile Tyr His Leu Asn Tyr
                565                 570                 575

Ser Val Asn Phe Thr His Tyr Ala Phe Asn Gly Glu Tyr Val Gly Tyr
            580                 585                 590

Glu Asn Thr Thr Asn Lys Asp Asn Glu Pro Ile Leu His Lys Ser Gly
            595                 600                 605

His Lys Lys Ala Phe Asn His Ser Ala Thr Leu Ser Ala Glu Leu Ser
            610                 615                 620

Asp Tyr Phe Met Pro Phe Phe Thr Tyr Ser Arg Thr His Arg Met Pro
625                 630                 635                 640

Asn Ile Gln Glu Met Phe Phe Ser Gln Val Ser Asn Ala Gly Val Asn
                645                 650                 655

Thr Ala Leu Lys Pro Glu Gln Ser Asp Thr Tyr Gln Leu Gly Phe Asn
            660                 665                 670

Thr Tyr Lys Lys Gly Leu Phe Thr Gln Asp Asp Val Leu Gly Val Lys
            675                 680                 685

Leu Val Gly Tyr Arg Ser Phe Ile Lys Asn Tyr Ile His Asn Val Tyr
690                 695                 700

Gly Val Trp Trp Arg Asp Gly Val Pro Thr Trp Ala Asp Ser Asn Gly
705                 710                 715                 720

Phe Arg Phe Thr Ile Ala His Gln Asn Tyr Lys Pro Ile Val Lys Lys
                725                 730                 735

Ser Gly Ala Glu Leu Glu Ile Asn Tyr Asp Met Gly Arg Phe Phe Ala
            740                 745                 750

Asn Val Ser Tyr Ala Tyr Gln Arg Thr Asn Gln Pro Thr Asn Tyr Ala
            755                 760                 765

Asp Ala Ser Pro Arg Pro Asn Asn Ala Ser Gln Glu Asp Ile Leu Lys
770                 775                 780

Gln Gly Tyr Gly Leu Ser Arg Val Ser Met Leu Pro Lys Asp Tyr Gly
785                 790                 795                 800

Arg Leu Glu Leu Gly Thr Arg Trp Phe Asp Gln Lys Leu Thr Leu Gly
                805                 810                 815

Leu Ala Ala Arg Tyr Tyr Gly Lys Ser Lys Arg Ala Thr Ile Glu Glu
            820                 825                 830

Glu Tyr Ile Asn Gly Ser His Tyr Glu Gln Lys Thr Ser Gly Ser Arg
            835                 840                 845

Thr Tyr Tyr Ala Val Lys Lys Thr Glu Asp Ile Lys Lys Gln Pro Ile
850                 855                 860

Ile Leu Asp Leu His Val Ser Tyr Glu Pro Ile Lys Asp Leu Ile Ile
865                 870                 875                 880

Lys Ala Glu Val Gln Asn Leu Leu Asp Lys Arg Tyr Val Asp Pro Leu
                885                 890                 895

Asp Ala Gly Asn Asp Ala Ala Ser Gln Arg Tyr Tyr Ser Ser Leu Asn
```

```
                900                 905                 910
Asp Ser Ile Cys Asn Gln Lys Ala Asn Ser Cys Glu Gly Gly Gly Lys
            915                 920                 925

Asp Lys Thr Val Leu Tyr Asn Phe Ala Arg Gly Arg Thr Tyr Ile Leu
        930                 935                 940

Ser Leu Asn Tyr Lys Phe
945                 950

<210> SEQ ID NO 58
<211> LENGTH: 915
<212> TYPE: PRT
<213> ORGANISM: Haemophilus influenzae 7P49H1

<400> SEQUENCE: 58

Met Lys Lys Ala Ile Lys Leu Asn Leu Ile Thr Leu Ser Leu Ile Asn
1               5                   10                  15

Thr Ile Gly Met Thr Ile Thr Gln Ala Gln Ala Glu Glu Thr Leu Gly
                20                  25                  30

Gln Ile Asp Val Val Glu Lys Val Ile Ser Asn Asp Lys Lys Pro Phe
            35                  40                  45

Thr Glu Ala Lys Ala Lys Ser Thr Arg Glu Asn Val Phe Lys Glu Thr
        50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
        115                 120                 125

Gly Ala Ala Ile Asp Pro Asn Phe Ile Ala Gly Val Asp Val Asn Lys
    130                 135                 140

Ser Asn Phe Ser Gly Ala Ser Gly Ile Asn Ala Leu Ala Gly Ser Ala
145                 150                 155                 160

Asn Phe Arg Thr Leu Ser Val Asn Asp Val Ile Thr Asp Lys Lys Pro
                165                 170                 175

Phe Gly Ile Ile Leu Lys Gly Met Thr Gly Ser Asn Ala Thr Lys Ser
            180                 185                 190

Asn Phe Met Thr Thr Ala Ala Gly Arg Lys Trp Leu Asp Asn Gly Gly
        195                 200                 205

Tyr Val Gly Val Val Tyr Gly Tyr Ser Gln Arg Glu Val Ser Gln Asp
    210                 215                 220

Tyr Arg Ile Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Leu
                245                 250                 255

Asn Ser Ala Gly Gln Trp Thr Pro Asp Leu Ser Lys Asn His Trp Ser
            260                 265                 270

Cys Ser Lys Glu Lys Pro Ser Leu Ala Asp Ala Arg Lys Ile Gly Asp
        275                 280                 285

Tyr Thr Pro Lys Cys Gly Asp Phe Ala Pro Pro Arg Asp Pro Thr Thr
    290                 295                 300

Met Lys Arg Lys Lys Ile Leu Lys Asp Ile Asp Ala Lys Lys Pro Leu
305                 310                 315                 320
```

```
Gln Glu Ile Gln Glu Leu Gln Ala Asp Ile Asn Lys Thr Asp Lys Ser
                325                 330                 335

Phe Glu Asn Asn Lys Asp Gln Tyr Ser Val Ala Pro Ile Glu Pro Gly
            340                 345                 350

Ser Leu Gln Ser Arg Ser Arg Ser His Leu Leu Lys Phe Glu Tyr Gly
        355                 360                 365

Asp Asp His His Thr Leu Gly Ala Gln Ile Arg Thr Leu Asp Asn Lys
370                 375                 380

Ile Gly Ser Arg Lys Ile Glu Asn Arg Asn Tyr Gln Val Asn Tyr Asn
385                 390                 395                 400

Phe Asn Asn Asn Ser Tyr Leu Asp Leu Asn Leu Met Ala Ala His Asn
                405                 410                 415

Ile Gly Lys Thr Ile Tyr Pro Lys Gly Gly Phe Phe Ala Gly Trp Gln
            420                 425                 430

Val Ala Asp Lys Leu Ile Thr Lys Asn Val Ala Asn Ile Val Asp Ile
        435                 440                 445

Asn Asn Ser His Thr Phe Leu Leu Pro Lys Glu Ile Asp Leu Lys Thr
    450                 455                 460

Thr Leu Gly Phe Asn Tyr Phe Thr Asn Glu Tyr Ser Lys Asn Arg Phe
465                 470                 475                 480

Pro Glu Glu Leu Ser Leu Phe Tyr Asp Asp Pro Ser His Asp Arg Gly
                485                 490                 495

Asn Tyr Ser Asn Leu Gly Arg Leu Lys Gly Ala Arg Gly Leu Leu Pro
            500                 505                 510

Gln Arg Ser Val Ile Leu Gln Pro Ser Gly Lys Gln Lys Phe Lys Thr
        515                 520                 525

Val Tyr Phe Asp Thr Ala Leu Ser Lys Gly Ile Tyr His Leu Asn Tyr
    530                 535                 540

Ser Val Asn Phe Ile His Tyr Ala Phe Asn Gly Glu Tyr Val Gly Tyr
545                 550                 555                 560

Glu Asn Gly Ala Glu Pro Ile Leu His Lys Ser Gly His Lys Lys Ala
                565                 570                 575

Phe Asn His Ser Ala Thr Leu Ser Ala Glu Leu Ser Asp Tyr Phe Met
            580                 585                 590

Pro Phe Phe Thr Tyr Ser Arg Thr His Arg Met Pro Asn Ile Gln Glu
        595                 600                 605

Met Phe Phe Ser Gln Val Ser Asp Ala Gly Val Asn Thr Ala Leu Lys
    610                 615                 620

Pro Glu Gln Ser Asp Thr Tyr Gln Leu Gly Phe Asn Thr Tyr Lys Lys
625                 630                 635                 640

Gly Leu Phe Thr Gln Asp Asp Val Leu Gly Val Lys Leu Val Gly Tyr
                645                 650                 655

Arg Ser Phe Ile Lys Asn Tyr Ile His Asn Val Tyr Gly Val Trp Trp
            660                 665                 670

Arg Asp Gly Val Val Pro Thr Trp Ala Asn Ser Asn Gly Phe Arg Phe
        675                 680                 685

Thr Ile Ala His Gln Asn Tyr Gln Pro Ile Val Lys Lys Ser Gly Ala
    690                 695                 700

Glu Leu Glu Leu Asn Tyr Asp Met Gly Arg Phe Phe Ala Asn Val Ser
705                 710                 715                 720

Tyr Ala Tyr Gln Arg Thr Asn Gln Pro Thr Asn Tyr Ala Asp Ala Ser
                725                 730                 735

Pro Arg Pro Asn Asn Ala Ser Lys Glu Asp Ile Leu Lys Gln Gly Tyr
```

```
                     740                 745                 750
Gly Leu Ser Arg Val Ser Met Leu Pro Lys Asp Tyr Gly Arg Leu Glu
                755                 760                 765

Leu Gly Thr Arg Trp Phe Asp Gln Lys Leu Thr Leu Gly Met Ala Ala
            770                 775                 780

Arg Tyr Tyr Gly Lys Ser Lys Arg Ala Thr Ile Glu Glu Glu Tyr Ile
785                 790                 795                 800

Asn Gly Ser His Tyr Glu Gln Asn Thr Ser Gly Ser Arg Thr His Tyr
                805                 810                 815

Ala Val Lys Lys Thr Glu Glu Ile Glu Lys Gln Pro Ile Ile Leu Asp
                820                 825                 830

Leu His Val Ser Tyr Glu Pro Ile Lys Asp Leu Ile Ile Lys Ala Glu
                835                 840                 845

Val Gln Asn Leu Leu Asp Lys Arg Tyr Val Asp Pro Leu Asp Ala Gly
                850                 855                 860

Asn Asp Ala Ala Ser Gln Arg Tyr Tyr Ser Ser Leu Asn Asp Ser Ile
865                 870                 875                 880

Cys Ser Lys Gln Asn Asp Ile Cys Glu Gly Gly Lys Asp Lys Thr
                885                 890                 895

Val Leu Tyr Asn Phe Ala Arg Gly Arg Thr Tyr Ile Leu Ser Leu Asn
                900                 905                 910

Tyr Lys Phe
        915

<210> SEQ ID NO 59
<211> LENGTH: 915
<212> TYPE: PRT
<213> ORGANISM: Haemophilus influenzae 86-028NP

<400> SEQUENCE: 59

Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Glu Thr Leu Gly
                20                  25                  30

Gln Ile Asp Val Val Glu Lys Val Ile Ser Asn Asp Lys Lys Pro Phe
            35                  40                  45

Thr Glu Ala Lys Ala Lys Ser Thr Arg Glu Asn Val Phe Lys Glu Thr
        50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
        115                 120                 125

Gly Ala Ala Ile Asp Pro Asn Phe Ile Ala Gly Val Asp Val Asn Lys
    130                 135                 140

Ser Asn Phe Ser Gly Ala Ser Gly Ile Asn Ala Leu Ala Gly Ser Ala
145                 150                 155                 160

Asn Phe Arg Thr Leu Gly Val Asn Asp Val Ile Thr Asp Asp Lys Pro
                165                 170                 175

Phe Gly Ile Ile Leu Lys Gly Met Thr Gly Ser Asn Ala Thr Lys Ser
            180                 185                 190
```

```
Asn Phe Met Thr Met Ala Ala Gly Arg Lys Trp Leu Asp Asn Gly Gly
            195                 200                 205

Tyr Val Gly Val Val Tyr Gly Tyr Ser Gln Arg Glu Val Ser Gln Asp
    210                 215                 220

Tyr Arg Ile Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Leu
                245                 250                 255

Asn Asp Ala Gly Gln Trp Thr Pro Asp Leu Ser Lys Asn Ala Trp Ser
            260                 265                 270

Cys Asn Glu Asp Pro Pro Arg Leu Ala Glu Asn Ile Glu Asn Val Lys
        275                 280                 285

Cys Thr His Tyr Ser Phe Asp Pro Arg Lys Asn Asp Arg Lys Glu Ile
        290                 295                 300

Leu Lys Lys Leu Lys Ala Gly Thr Lys Pro Glu Asn Ile Asp Glu Leu
305                 310                 315                 320

Gln Asn Gly Lys Asp Gly Ile Lys Glu Thr Asp Lys Ser Phe Glu Arg
                325                 330                 335

Asn Lys Asp Gln Tyr Ser Val Ala Pro Ile Glu Pro Gly Ser Leu Gln
            340                 345                 350

Ser Arg Ser Arg Ser His Leu Leu Lys Phe Glu Tyr Gly Asp Asp His
        355                 360                 365

Gln Asn Leu Gly Ala Gln Ile Arg Thr Leu Asp Asn Lys Ile Gly Ser
            370                 375                 380

Arg Lys Ile Glu Asn Arg Asn Tyr Gln Val Asn Tyr Asn Phe Asn Asn
385                 390                 395                 400

Asn Asn Tyr Leu Asp Leu Asn Leu Met Ala Ala His Asn Ile Gly Lys
                405                 410                 415

Thr Ile Tyr Pro Lys Gly Gly Phe Phe Ala Gly Trp Arg Val Ala Asp
            420                 425                 430

Lys Leu Ile Thr Lys Asn Val Ala Asn Ile Val Asp Ile Asn Asn Ser
        435                 440                 445

His Thr Phe Leu Leu Pro Lys Glu Ile Asp Leu Lys Thr Thr Leu Gly
        450                 455                 460

Phe Asn Tyr Phe Thr Asn Glu Tyr Ser Lys Asn Arg Phe Pro Glu Glu
465                 470                 475                 480

Leu Ser Leu Phe Tyr Asn Asp Asp Ser His Asp Gln Gly Asn Tyr Ser
                485                 490                 495

Asn Leu Gly Arg Phe Arg Gly Asn Arg Asn Leu Leu Pro Gln Arg Ser
            500                 505                 510

Val Ile Leu Gln Pro Ser Gly Lys Gln Lys Phe Lys Thr Val Tyr Phe
        515                 520                 525

Asp Thr Ala Leu Ser Lys Gly Ile Tyr His Leu Asn Tyr Ser Val Asn
        530                 535                 540

Phe Thr His Tyr Ala Phe Asn Gly Glu Tyr Val Gly Tyr Glu Asn Thr
545                 550                 555                 560

Ala Asn Gln Ile Asn Glu Pro Ile Leu His Lys Ser Gly His Lys Lys
                565                 570                 575

Ala Phe Asn His Ser Ala Thr Leu Ser Ala Glu Leu Ser Asp Tyr Phe
            580                 585                 590

Met Pro Phe Phe Thr Tyr Ser Arg Thr His Arg Met Pro Asn Ile Gln
        595                 600                 605

Glu Met Phe Phe Ser Gln Val Ser Asn Ala Gly Val Asn Thr Ala Leu
```

```
                610               615               620
Lys Pro Glu Gln Ser Asp Thr Tyr Gln Leu Gly Phe Asn Thr Tyr Lys
625                 630                 635                 640

Lys Gly Leu Phe Thr Gln Asp Asp Val Leu Gly Ile Lys Leu Val Gly
                645                 650                 655

Tyr Arg Ser Phe Ile Lys Asn Tyr Ile His Asn Val Tyr Gly Val Trp
                660                 665                 670

Trp Arg Asp Gly Val Val Pro Thr Trp Ala Asp Ser Thr Gly Phe Arg
                675                 680                 685

Phe Thr Ile Ala His Gln Asn Tyr Gln Pro Ile Val Lys Lys Ser Gly
690                 695                 700

Ala Glu Leu Glu Leu Asn Tyr Asp Met Gly Arg Phe Phe Ala Asn Val
705                 710                 715                 720

Ser Tyr Ala Tyr Gln Arg Thr Asn Gln Pro Thr Asn Tyr Ala Asp Ala
                725                 730                 735

Ser Ser Arg Pro Asn Asn Ala Ser Lys Glu Asp Ile Leu Lys Gln Gly
                740                 745                 750

Tyr Gly Leu Ser Arg Val Ser Met Leu Pro Lys Asp Tyr Gly Arg Leu
                755                 760                 765

Glu Ile Gly Thr Arg Trp Phe Asp Gln Lys Leu Thr Leu Gly Met Ala
770                 775                 780

Ala Arg Tyr Tyr Gly Lys Ser Lys Arg Ala Thr Ile Glu Glu Glu Tyr
785                 790                 795                 800

Ile Asn Gly Ser His Phe Glu Leu Lys Thr Ser Gly Lys Arg Thr Tyr
                805                 810                 815

Tyr Val Val Lys Lys Thr Glu Glu Ile Lys Lys Gln Pro Ile Ile Leu
                820                 825                 830

Asp Leu His Val Ser Tyr Glu Pro Ile Lys Asp Leu Ile Ile Lys Ala
                835                 840                 845

Glu Val Gln Asn Leu Leu Asp Lys Arg Tyr Val Asp Pro Leu Asp Ala
850                 855                 860

Gly Asn Asp Ala Ala Ser Gln Arg Tyr Tyr Ser Ser Leu Asn Asp Ser
865                 870                 875                 880

Ile Cys Ser Lys Ser Gln Asp Cys Glu Asp Gly Lys Asp Lys Thr
                885                 890                 895

Val Leu Tyr Asn Phe Ala Arg Gly Arg Thr Tyr Ile Leu Ser Leu Asn
                900                 905                 910

Tyr Lys Phe
        915

<210> SEQ ID NO 60
<211> LENGTH: 910
<212> TYPE: PRT
<213> ORGANISM: Haemophilus influenzae NT127

<400> SEQUENCE: 60

Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Glu Thr Leu Gly
                20                  25                  30

Gln Ile Asp Val Val Glu Lys Val Ile Ser Asn Asp Lys Lys Pro Phe
                35                  40                  45

Thr Glu Ala Lys Ala Lys Ser Thr Arg Glu Asn Val Phe Lys Glu Thr
50                  55                  60
```

```
Gln Thr Ile Asp Gln Val Ile Arg Ser Ile Pro Gly Ala Phe Thr Gln
 65                  70                  75                  80

Gln Asp Lys Gly Ser Gly Val Val Ser Val Asn Ile Arg Gly Glu Asn
                 85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Ser Ser Gln Phe
        115                 120                 125

Gly Ala Ile Asp Pro Asn Phe Ile Ala Gly Val Asp Val Asn Lys
    130                 135                 140

Ser Asn Phe Ser Gly Ser Ser Gly Ile Asn Ala Leu Ala Gly Ser Ala
145                 150                 155                 160

Asn Phe Arg Thr Leu Gly Val Asn Asp Val Ile Thr Asp Asp Lys Pro
            165                 170                 175

Phe Gly Ile Ile Leu Lys Gly Met Thr Gly Ser Asn Ala Thr Lys Ser
            180                 185                 190

Asn Phe Met Thr Met Ala Ala Gly Arg Lys Trp Leu Asp Asn Gly Gly
        195                 200                 205

Tyr Val Gly Val Val Tyr Gly Tyr Ser Gln Arg Glu Val Ser Gln Asp
    210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Leu
                245                 250                 255

Asn Pro Glu Gly Gln Trp Ala Pro Asp Leu Ser Lys Asn His Trp Ser
            260                 265                 270

Cys Asn Lys Lys Asn Pro Glu Leu Val Asp Lys Arg Phe Ser Ser Phe
        275                 280                 285

Arg Cys Asn Ile Tyr Ser Asn Ser Asp Arg Lys Glu Ile Leu Lys Glu
            290                 295                 300

Leu Leu Glu Gln Asn Lys Asn Pro Lys Asp Ile Thr Lys Leu Gln Asn
305                 310                 315                 320

Gly Lys Asp Gly Ile Lys Glu Thr Asp Glu Ser Phe Glu Arg Asn Lys
                325                 330                 335

Asp Gln Tyr Ser Val Ala Pro Ile Glu Pro Gly Ser Leu Gln Ser Arg
            340                 345                 350

Ser Arg Ser His Leu Leu Lys Phe Glu Tyr Gly Asp Asp His Gln Asn
        355                 360                 365

Leu Gly Ala Gln Ile Arg Thr Leu Asp Asn Lys Ile Gly Ser Arg Lys
    370                 375                 380

Ile Glu Asn Arg Asn Tyr Gln Val Asn Tyr Asn Val Asn Asn Ser
385                 390                 395                 400

Tyr Leu Asp Leu Asn Leu Met Ala Ala His Asn Ile Gly Lys Thr Ile
                405                 410                 415

Tyr Pro Lys Gly Gly Phe Phe Ala Gly Trp Gln Val Ala Asp Lys Leu
            420                 425                 430

Ile Thr Lys Asn Val Ala Asn Ile Val Asp Ile Asn Asn Ser His Thr
        435                 440                 445

Phe Leu Leu Pro Lys Glu Ile Asp Leu Lys Thr Thr Leu Gly Phe Asn
    450                 455                 460

Tyr Phe Thr Asn Glu Tyr Ser Lys Asn Arg Phe Pro Glu Glu Leu Ser
465                 470                 475                 480

Leu Phe Tyr Lys Asp Asp Ser His Asp Arg Gly Asn Tyr Ser His Leu
```

```
                485                 490                 495
Gly Arg Leu Ser Gly Ala Gln Gly Leu Leu Pro Gln Arg Ser Val Ile
            500                 505                 510
Leu Gln Pro Ser Gly Lys Gln Lys Phe Lys Thr Val Tyr Phe Asp Thr
            515                 520                 525
Ala Leu Ser Lys Gly Ile Tyr His Leu Asn Tyr Ser Val Asn Phe Ile
            530                 535                 540
His Tyr Ala Phe Asn Gly Glu Tyr Val Gly Tyr Glu Thr Thr Ala Glu
545                 550                 555                 560
Pro Ile Leu His Lys Ser Gly His Lys Lys Ala Phe Asn His Ser Ala
                565                 570                 575
Thr Leu Ser Ala Glu Leu Ser Asp Tyr Phe Met Pro Phe Thr Tyr
            580                 585                 590
Ser Arg Thr His Arg Met Pro Asn Ile Gln Glu Met Phe Phe Ser Gln
            595                 600                 605
Val Ser Asp Ala Gly Val Asn Thr Ala Leu Lys Pro Glu Gln Ser Asp
            610                 615                 620
Thr Tyr Gln Leu Gly Phe Asn Thr Tyr Lys Lys Gly Leu Phe Thr Gln
625                 630                 635                 640
Asp Asp Val Leu Gly Ile Lys Leu Val Gly Tyr Arg Ser Phe Ile Lys
                645                 650                 655
Asn Tyr Ile His Asn Val Tyr Gly Val Trp Trp Arg Asp Gly Lys Val
            660                 665                 670
Pro Thr Trp Ala Asp Thr Asn Gly Phe Arg Phe Asn Ile Ala His Gln
            675                 680                 685
Asn Tyr Gln Pro Ile Val Lys Lys Ser Gly Ala Glu Leu Glu Leu Asn
            690                 695                 700
Tyr Asp Met Gly Arg Phe Phe Ala Asn Val Ser Tyr Ala Tyr Gln Arg
705                 710                 715                 720
Thr Asn Gln Pro Thr Asn Tyr Ala Asp Ala Ser Pro Arg Pro Asn Asn
                725                 730                 735
Ala Ser Lys Glu Asp Ile Leu Lys Gln Gly Tyr Gly Leu Ser Arg Val
            740                 745                 750
Ser Met Leu Pro Lys Asp Tyr Gly Arg Leu Glu Leu Gly Thr Arg Trp
            755                 760                 765
Phe Asp Lys Lys Leu Thr Leu Gly Met Ala Ala Arg Tyr Tyr Gly Lys
            770                 775                 780
Ser Lys Arg Ala Thr Ile Glu Glu Tyr Ile Asn Gly Ser His Phe
785                 790                 795                 800
Glu Lys Asn Thr Ala Arg Asn Arg Thr Tyr Tyr Ala Val Lys Lys Thr
                805                 810                 815
Glu Glu Ile Lys Lys Gln Pro Ile Ile Leu Asp Leu His Val Ser Tyr
            820                 825                 830
Glu Pro Ile Lys Asp Leu Ile Ile Lys Ala Glu Val Gln Asn Leu Leu
            835                 840                 845
Asp Lys Arg Tyr Val Asp Pro Leu Asp Ala Gly Asn Asp Ala Ala Ser
            850                 855                 860
Gln Arg Tyr Tyr Ser Ser Leu Asn Asp Ser Ile Cys Asn Lys Lys Ala
865                 870                 875                 880
Asp Ser Cys Glu Gly Glu Gly Lys Asp Lys Ser Val Leu Tyr Asn Phe
                885                 890                 895
Ala Arg Gly Arg Thr Tyr Ile Leu Ser Leu Asn Tyr Lys Phe
            900                 905                 910
```

<210> SEQ ID NO 61
<211> LENGTH: 921
<212> TYPE: PRT
<213> ORGANISM: Haemophilus influenzae PittAA

<400> SEQUENCE: 61

```
Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Glu Thr Leu Gly
            20                  25                  30

Gln Ile Asp Val Val Glu Lys Val Ile Ser Asn Asp Lys Lys Pro Phe
        35                  40                  45

Thr Glu Ala Lys Ala Lys Ser Thr Arg Glu Asn Val Phe Lys Glu Thr
    50                  55                  60

Gln Thr Ile Asp Gln Val Ile Arg Ser Ile Pro Gly Ala Phe Thr Gln
65                  70                  75                  80

Gln Asp Lys Gly Ser Gly Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Ser Ser Gln Phe
        115                 120                 125

Gly Ala Ala Ile Asp Pro Asn Phe Ile Ala Gly Val Asp Val Asn Lys
    130                 135                 140

Ser Asn Phe Ser Gly Ser Ser Gly Ile Asn Ala Leu Ala Gly Ser Ala
145                 150                 155                 160

Asn Phe Arg Thr Leu Gly Val Asn Asp Val Ile Thr Asp Asp Lys Pro
                165                 170                 175

Phe Gly Ile Ile Leu Lys Gly Met Thr Gly Ser Asn Ala Thr Lys Ser
            180                 185                 190

Asn Phe Met Thr Met Ala Ala Gly Arg Lys Trp Leu Asp Asn Gly Gly
        195                 200                 205

Tyr Val Gly Val Val Tyr Gly Tyr Ser Gln Arg Glu Val Ser Gln Asp
    210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Leu
                245                 250                 255

Asn Gln Ala Gly Gln Trp Ile Pro Asp Leu Asn Lys Asn His Trp Ser
            260                 265                 270

Cys Asn His Pro Thr Glu Pro Lys Leu Ala Asp Pro Arg Lys Ile Gly
        275                 280                 285

Asp Phe Thr Pro Glu Cys Lys Trp Tyr Asn Asn Ser Glu Arg Lys
    290                 295                 300

Glu Ile Leu Lys Gln Leu Ile Gln Glu Lys Lys Asp Pro Ser Glu Ile
305                 310                 315                 320

Glu Lys Leu Gln Lys Gly Asp Asp Gly Ile Glu Lys Thr Asp Lys Ser
                325                 330                 335

Phe Glu Asp Asn Lys Glu Gln Tyr Ser Val Ala Pro Ile Glu Pro Gly
            340                 345                 350

Ser Leu Gln Ser Arg Ser Arg Ser His Leu Leu Lys Phe Glu Tyr Ser
        355                 360                 365

Asp Asp His His Thr Leu Gly Ala Gln Ile Arg Thr Leu Asp Asn Lys
```

```
                370                 375                 380
Ile Gly Ser Arg Lys Ile Glu Asn Arg Asn Tyr Gln Val Asn Tyr Asn
385                 390                 395                 400

Phe Asn Asn Asn Ser Tyr Leu Asp Leu Asn Leu Met Ala Ala His Asn
                405                 410                 415

Ile Gly Lys Thr Ile Tyr Pro Lys Gly Gly Phe Phe Ala Gly Trp Arg
                420                 425                 430

Val Ala Asp Lys Leu Ile Thr Lys Asn Val Ala Asn Ile Val Asp Ile
                435                 440                 445

Asn Asn Ser His Thr Phe Leu Leu Pro Lys Glu Ile Asp Leu Lys Thr
                450                 455                 460

Thr Leu Gly Phe Asn Tyr Phe Thr Asn Glu Tyr Ser Lys Asn Arg Phe
465                 470                 475                 480

Pro Glu Glu Leu Ser Leu Phe Tyr Val Asn Glu Ser His Asp Gln Gly
                485                 490                 495

Leu Phe Ser Tyr Ser Gln Lys Gly Arg Tyr Ser Gly Thr Arg Gly Leu
                500                 505                 510

Leu Pro Gln Arg Ser Val Ile Leu Gln Pro Ser Gly Lys Gln Lys Phe
                515                 520                 525

Lys Thr Val Tyr Phe Asp Thr Ala Leu Ser Lys Gly Ile Tyr His Leu
530                 535                 540

Asn Tyr Ser Val Asn Phe Thr His Tyr Ala Phe Asn Gly Glu Tyr Val
545                 550                 555                 560

Gly Tyr Glu Asn Thr Glu Gly Lys Ile Asn Glu Pro Ile Leu His Lys
                565                 570                 575

Ser Gly His Lys Lys Ala Phe Asn His Ser Ala Thr Leu Ser Ala Glu
                580                 585                 590

Leu Ser Asp Tyr Phe Met Pro Phe Phe Thr Tyr Ser Arg Thr His Arg
                595                 600                 605

Met Pro Asn Ile Gln Glu Met Phe Phe Ser Gln Val Ser Asp Ala Gly
610                 615                 620

Val Asn Thr Ala Leu Lys Pro Glu Gln Ser Asp Thr Tyr Gln Leu Gly
625                 630                 635                 640

Phe Asn Thr Tyr Lys Lys Gly Leu Phe Thr Gln Asp Asp Val Leu Gly
                645                 650                 655

Ile Lys Leu Val Gly Tyr Arg Ser Phe Ile Lys Asn Tyr Ile His Asn
                660                 665                 670

Val Tyr Gly Asp Trp Ser Lys Asp Gly Val Thr Pro Ile Trp Ala Thr
                675                 680                 685

Ala Asn Gly Phe Arg Leu Thr Ile Ala His Gln Asn Tyr Gln Pro Ile
                690                 695                 700

Val Lys Lys Ser Gly Ala Glu Leu Glu Leu Asn Tyr Asp Met Gly Arg
705                 710                 715                 720

Phe Phe Ala Asn Phe Ser Tyr Ala Tyr Gln Arg Thr Asn Gln Pro Thr
                725                 730                 735

Asn Tyr Ala Asp Ala Ser Ser Arg Pro Asn Asn Ala Ser Lys Gly Asp
                740                 745                 750

Ile Leu Lys Gln Gly Tyr Gly Leu Ser Arg Ile Thr Met Leu Pro Lys
                755                 760                 765

Asp Tyr Gly Arg Leu Glu Leu Gly Thr Arg Trp Phe Asp Gln Lys Leu
                770                 775                 780

Thr Leu Gly Ile Ala Ala Arg Tyr Tyr Gly Lys Ser Lys Arg Ala Thr
785                 790                 795                 800
```

```
Thr Gln Glu Glu Tyr Ile Asn Gly Ser Arg Tyr Lys Asn Thr Thr
                805                 810                 815

Arg Asp Arg Ile Tyr Tyr Ala Ile Lys Lys Thr Glu Ile Lys Lys
                820                 825                 830

Gln Pro Ile Ile Leu Asp Leu His Val Ser Tyr Glu Pro Ile Lys Asp
                835                 840                 845

Leu Ile Ile Lys Ala Glu Val Gln Asn Leu Leu Asp Lys Arg Tyr Val
                850                 855                 860

Asp Pro Leu Asp Ala Gly Asn Asp Ala Ala Ser Gln Arg Tyr Tyr Ser
865                 870                 875                 880

Ser Leu Asn Asp Ser Leu Ala Cys Lys Ile Asn Glu Ser Thr Cys Asn
                885                 890                 895

Asp Gly Ser Asp Lys Thr Val Leu Tyr Asn Phe Ala Arg Gly Arg Thr
                900                 905                 910

Tyr Ile Leu Ser Leu Asn Tyr Lys Phe
                915                 920

<210> SEQ ID NO 62
<211> LENGTH: 915
<212> TYPE: PRT
<213> ORGANISM: Haemophilus influenzae PittHH

<400> SEQUENCE: 62

Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Glu Thr Leu Gly
                20                  25                  30

Gln Ile Asp Val Val Glu Lys Val Ile Ser Asn Asp Lys Lys Pro Phe
            35                  40                  45

Thr Glu Ala Lys Ala Lys Ser Thr Arg Glu Asn Val Phe Lys Glu Thr
        50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
                100                 105                 110

Tyr Ser Thr Ala Leu Asp Ser Gly Gln Ser Gly Gly Ser Ser Gln Phe
            115                 120                 125

Gly Ala Ala Ile Asp Pro Asn Phe Ile Ala Gly Val Asp Val Asn Lys
        130                 135                 140

Ser Asn Phe Ser Gly Ser Gly Ile Asn Ala Leu Ala Gly Ser Ala
145                 150                 155                 160

Asn Phe Arg Thr Leu Gly Val Asn Asp Val Ile Thr Asp Asp Lys Pro
                165                 170                 175

Phe Gly Ile Ile Leu Lys Gly Met Thr Gly Ser Asn Ala Thr Lys Ser
                180                 185                 190

Asn Phe Met Thr Met Ala Ala Gly Arg Lys Trp Leu Asp Asn Gly Gly
            195                 200                 205

Tyr Val Gly Val Val Tyr Gly Tyr Ser Gln Arg Glu Val Ser Gln Asp
        210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Ile Leu
```

-continued

```
                245                 250                 255
Asn Pro Glu Gly Gln Trp Ala Pro Asp Leu Asn Lys Pro His Trp Tyr
                260                 265                 270
Cys Asn Lys Pro Asp Tyr Gln Ser Thr Ser Asn Asn Glu Cys Arg
            275                 280                 285
Arg Gly Tyr Arg Leu Gly Ser Ala Ala Gln Asp Arg Gln Asp Ile Leu
            290                 295                 300
Lys Glu Leu Leu Thr Glu Asn Lys Lys Pro Glu Asn Ile Glu Lys Leu
305                 310                 315                 320
Gln Lys Gly Asn Asp Gly Ile Lys Glu Thr Asp Lys Ser Phe Glu Arg
                325                 330                 335
Asn Lys Asp Gln Tyr Ser Val Ala Pro Ile Glu Pro Gly Ser Leu Gln
                340                 345                 350
Ser Arg Ser Arg Ser His Leu Leu Lys Phe Glu Tyr Gly Asp Asp His
            355                 360                 365
Gln Asn Leu Gly Ala Gln Ile Arg Thr Leu Asp Asn Lys Ile Gly Ser
            370                 375                 380
Arg Lys Ile Glu Asn Arg Asn Tyr Gln Val Asn Tyr Asn Phe Asn Asn
385                 390                 395                 400
Asn Asn Tyr Leu Asp Leu Asn Leu Met Ala Ala His Asn Ile Gly Lys
                405                 410                 415
Thr Ile Tyr Pro Lys Gly Gly Phe Phe Ala Gly Trp Arg Val Ala Asp
                420                 425                 430
Lys Leu Ile Thr Lys Asn Val Ala Asn Ile Val Asp Ile Asn Asn Ser
            435                 440                 445
His Thr Phe Leu Leu Pro Lys Glu Ile Asp Leu Lys Thr Thr Leu Gly
            450                 455                 460
Phe Asn Tyr Phe Thr Asn Glu Tyr Ser Lys Asn Arg Phe Pro Glu Glu
465                 470                 475                 480
Leu Ser Leu Phe Tyr Asn Asp Asp Ser His Asp Gln Gly Thr Tyr Ser
                485                 490                 495
Asn Leu Gly Arg Phe Lys Gly Asp Arg Asn Leu Leu Pro Gln Arg Ser
                500                 505                 510
Val Ile Leu Gln Pro Ser Gly Lys Gln Lys Phe Lys Thr Val Tyr Phe
            515                 520                 525
Asp Thr Ala Leu Ser Lys Gly Ile Tyr His Leu Asn Tyr Ser Val Asn
            530                 535                 540
Phe Ile His Tyr Ala Phe Asn Gly Glu Tyr Val Gly Tyr Glu Asn Thr
545                 550                 555                 560
Thr Ser Gln Ile Asn Glu Pro Ile Leu His Thr Ser Gly His Lys Lys
                565                 570                 575
Ala Phe Asn His Ser Ala Thr Leu Ser Ala Glu Leu Ser Asp Tyr Phe
                580                 585                 590
Met Pro Phe Phe Thr Tyr Ser His Thr His Arg Met Pro Asn Ile Gln
            595                 600                 605
Glu Met Phe Phe Ser Gln Val Ser Asp Ala Gly Val Asn Thr Ala Leu
            610                 615                 620
Lys Pro Glu Gln Ser Asp Thr Tyr Gln Leu Gly Phe Asn Thr Tyr Lys
625                 630                 635                 640
Lys Gly Leu Phe Thr Gln Asp Val Leu Gly Ile Lys Leu Val Gly
                645                 650                 655
Tyr Arg Ser Phe Ile Lys Asn Tyr Ile His Asn Val Tyr Gly Val Trp
            660                 665                 670
```

```
Trp Arg Asn Gly Val Val Pro Thr Trp Ala Asn Ser Thr Arg Phe Arg
            675                 680                 685

Phe Thr Ile Ala His Gln Asn Tyr Gln Pro Ile Val Lys Lys Ser Gly
        690                 695                 700

Ala Glu Leu Glu Leu Asn Tyr Asp Met Gly Arg Phe Phe Ala Asn Val
705                 710                 715                 720

Ser Tyr Ala Tyr Gln Arg Thr Asn Gln Pro Thr Asn Tyr Ala Asp Ala
                725                 730                 735

Ser Pro Arg Pro Asn Asn Ala Ser Lys Glu Asp Ile Leu Lys Gln Gly
            740                 745                 750

Tyr Gly Leu Ser Arg Val Ser Met Leu Pro Lys Asp Tyr Gly Arg Leu
        755                 760                 765

Glu Leu Gly Thr Arg Trp Phe Asp Gln Lys Leu Thr Leu Gly Met Ala
    770                 775                 780

Ala Arg Tyr Tyr Gly Lys Ser Lys Arg Ala Thr Ile Glu Glu Glu Tyr
785                 790                 795                 800

Ile Asn Gly Ser Arg Tyr Glu Lys Tyr Thr Ala Gly Asp Arg Thr Tyr
                805                 810                 815

Tyr Ala Val Lys Lys Thr Glu Glu Ile Lys Lys Gln Pro Ile Ile Leu
            820                 825                 830

Asp Leu His Val Ser Tyr Glu Pro Ile Lys Asp Leu Ile Ile Lys Ala
        835                 840                 845

Glu Val Gln Asn Leu Leu Asp Lys Arg Tyr Val Asp Pro Leu Asp Ala
    850                 855                 860

Gly Asn Asp Ala Ala Ser Gln Arg Tyr Tyr Ser Leu Asn Asn Ser
865                 870                 875                 880

Ile Glu Cys Ala Gln Asp Ser Ser Ala Cys Gly Gly Ser Asp Lys Thr
                885                 890                 895

Val Leu Tyr Asn Phe Ala Arg Gly Arg Thr Tyr Ile Leu Ser Leu Asn
            900                 905                 910

Tyr Lys Phe
        915

<210> SEQ ID NO 63
<211> LENGTH: 915
<212> TYPE: PRT
<213> ORGANISM: Haemophilus influenzae PittII

<400> SEQUENCE: 63

Met Lys Lys Ala Ile Lys Leu Asn Leu Ile Thr Leu Gly Leu Ile Asn
1               5                   10                  15

Thr Ile Gly Ile Thr Ile Thr Gln Ala Gln Ala Glu Glu Thr Leu Gly
            20                  25                  30

Gln Ile Asp Val Val Glu Lys Val Ile Ser Asn Asp Lys Lys Pro Phe
        35                  40                  45

Thr Glu Ala Lys Ala Lys Ser Thr Arg Glu Asn Val Phe Lys Glu Thr
    50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
```

```
            115                 120                 125
Gly Ala Ala Ile Asp Pro Asn Phe Ile Ala Gly Val Asp Val Asn Lys
    130                 135                 140

Ser Asn Phe Ser Gly Ala Ser Gly Ile Asn Ala Leu Ala Gly Ser Ala
145                 150                 155                 160

Asn Phe Arg Thr Leu Ser Val Asn Asp Val Ile Thr Asp Lys Pro
                165                 170                 175

Phe Gly Ile Ile Leu Lys Gly Met Thr Gly Ser Asn Ala Thr Lys Ser
                180                 185                 190

Asn Phe Met Thr Thr Ala Ala Gly Arg Lys Trp Leu Asp Asn Gly Gly
            195                 200                 205

Tyr Val Gly Val Val Tyr Gly Tyr Ser Gln Arg Glu Val Ser Gln Asp
    210                 215                 220

Tyr Arg Ile Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Phe
                245                 250                 255

Thr Asn Gly Gln Trp Thr Pro Asp Leu Asn Lys Asn His Trp Ser Cys
            260                 265                 270

Asn Leu Pro Thr Pro Lys Leu Ala Asp Ser Thr Gln Leu Asn Gly Ile
        275                 280                 285

Asn Glu Thr Ser Ala Cys Arg Leu Tyr Tyr Lys Asn Ser Lys Arg Lys
        290                 295                 300

Glu Ile Leu Lys Glu Leu Glu Lys Lys Asp Pro Ser Lys Ile Thr
305                 310                 315                 320

Glu Leu Gln Lys Asp Ile Thr Glu Thr Asp Lys Ser Phe Glu Arg Asn
                325                 330                 335

Lys Asp Gln Tyr Ser Val Ala Pro Ile Glu Pro Gly Ser Leu Gln Ser
            340                 345                 350

Arg Ser Arg Ser His Leu Leu Lys Phe Glu Tyr Ser Asp Asp Arg His
        355                 360                 365

Thr Leu Gly Ala Gln Ile Arg Thr Leu Asp Asn Lys Ile Gly Ser Arg
    370                 375                 380

Lys Ile Glu Asn Arg Asn Tyr Gln Val Asn Tyr Asn Phe Asn Asn Asn
385                 390                 395                 400

Ser Tyr Leu Asp Leu Asn Leu Met Thr Ala His Asn Ile Gly Lys Thr
                405                 410                 415

Ile Tyr Pro Lys Gly Gly Phe Phe Ala Gly Trp Arg Val Ala Asp Lys
            420                 425                 430

Leu Ile Thr Lys Asn Val Ala Asn Ile Ile Asp Ile Asn Asn Ser His
        435                 440                 445

Thr Phe Leu Leu Pro Lys Glu Ile Asp Leu Lys Thr Thr Leu Gly Phe
        450                 455                 460

Asn Tyr Phe Thr Asn Glu Tyr Ser Lys Asn Arg Phe Pro Glu Glu Leu
465                 470                 475                 480

Ser Leu Phe Tyr Asn Asp Asp Ser His Asn Gln Gly Asn Tyr Ser Tyr
                485                 490                 495

Leu Gly Arg Phe Gln Gly Ser Lys Ser Gly Leu Pro Gln Arg Ser Val
            500                 505                 510

Ile Leu Gln Pro Ser Gly Lys Gln Lys Phe Lys Thr Val Tyr Phe Asp
        515                 520                 525

Thr Ala Leu Ser Lys Gly Ile Tyr His Leu Asn Tyr Ser Val Asn Phe
        530                 535                 540
```

Thr His Tyr Ala Phe Asn Gly Glu Tyr Val Gly Tyr Glu Asn Lys Pro
545                 550                 555                 560

Thr Gln Ile Asn Glu Pro Ile Leu His Lys Ser Gly His Lys Lys Ala
            565                 570                 575

Phe Asn His Ser Ala Thr Leu Ser Ala Glu Leu Ser Asp Tyr Phe Met
        580                 585                 590

Pro Phe Phe Thr Tyr Ser Arg Thr His Arg Met Pro Asn Ile Gln Glu
    595                 600                 605

Met Phe Phe Ser Gln Val Ser Asn Ala Gly Val Asn Thr Ala Leu Lys
610                 615                 620

Pro Glu Gln Ser Asp Thr Tyr Gln Leu Gly Phe Asn Thr Tyr Lys Lys
625                 630                 635                 640

Gly Leu Phe Thr Gln Asp Asp Val Leu Gly Ile Lys Leu Val Gly Tyr
            645                 650                 655

Arg Ser Phe Ile Lys Asn Tyr Ile His Asn Val Tyr Gly Val Trp Trp
        660                 665                 670

Arg Asp Gly Val Val Pro Thr Trp Ala Ser Ser Asn Gly Phe Arg Phe
    675                 680                 685

Thr Ile Ala His Gln Asn Tyr Gln Pro Ile Val Lys Lys Ser Gly Ala
690                 695                 700

Glu Leu Glu Leu Asn Tyr Asp Met Gly Arg Phe Phe Ala Asn Val Ser
705                 710                 715                 720

Tyr Ala Tyr Gln Arg Thr Asn Gln Pro Thr Asn Tyr Ala Asp Ala Ser
            725                 730                 735

Pro Arg Pro Asn Asn Ala Ser Lys Asp Ile Leu Lys Gln Gly Tyr
        740                 745                 750

Gly Leu Ser Arg Val Ser Met Leu Pro Lys Tyr Gly Arg Leu Glu
    755                 760                 765

Leu Gly Thr Arg Trp Phe Asp Gln Lys Leu Thr Leu Gly Met Ala Ala
770                 775                 780

Arg Tyr Tyr Gly Lys Ser Lys Arg Ala Thr Ile Glu Glu Tyr Ile
785                 790                 795                 800

Asn Gly Ser Arg Tyr Glu Asn Tyr Thr Val Gly Asp Arg Thr Tyr Tyr
            805                 810                 815

Ala Val Lys Lys Thr Glu Glu Ile Lys Lys Gln Pro Ile Ile Leu Asp
        820                 825                 830

Leu His Val Ser Tyr Glu Pro Ile Lys Asp Leu Ile Ile Lys Ala Glu
    835                 840                 845

Val Gln Asn Leu Leu Asp Lys Arg Tyr Val Asp Pro Leu Asp Ala Gly
850                 855                 860

Asn Asp Ala Ala Ser Gln Arg Tyr Tyr Ser Ser Leu Asn Asp Ser Ile
865                 870                 875                 880

Cys Ser Lys Gly Asn Thr Thr Cys Glu Asp Gly Gly Lys Asp Lys Thr
            885                 890                 895

Val Leu Tyr Asn Phe Ala Arg Gly Arg Thr Tyr Ile Leu Ser Leu Asn
        900                 905                 910

Tyr Lys Phe
        915

<210> SEQ ID NO 64
<211> LENGTH: 934
<212> TYPE: PRT
<213> ORGANISM: Haemophilus influenzae R2846

```
<400> SEQUENCE: 64

Met Lys Lys Ala Ile Lys Leu Asn Leu Ile Thr Leu Gly Leu Ile Asn
1               5                   10                  15

Thr Ile Gly Met Thr Ile Thr Gln Ala Leu Ala Glu Glu Thr Leu Gly
            20                  25                  30

Gln Ile Asp Val Val Glu Lys Val Ile Ser Asn Asp Lys Lys Pro Phe
        35                  40                  45

Thr Glu Ala Lys Ala Lys Ser Thr Arg Glu Asn Val Phe Lys Glu Thr
    50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
            100                 105                 110

Tyr Ser Thr Ala Leu Asp Ser Gly Gln Ser Gly Gly Ser Ser Gln Phe
        115                 120                 125

Gly Ala Ala Ile Asp Pro Asn Phe Ile Ala Gly Val Asp Val Asn Lys
130                 135                 140

Ser Asn Phe Ser Gly Ser Ser Gly Ile Asn Ala Leu Ala Gly Ser Ala
145                 150                 155                 160

Asn Phe Arg Thr Leu Gly Val Asn Asp Val Ile Thr Asp Asp Lys Pro
                165                 170                 175

Phe Gly Ile Ile Leu Lys Gly Met Thr Gly Ser Asn Ala Thr Lys Ser
            180                 185                 190

Asn Phe Met Thr Met Ala Ala Gly Arg Lys Trp Leu Asp Asn Gly Gly
        195                 200                 205

Tyr Val Gly Val Val Tyr Gly Tyr Ser Gln Arg Glu Val Ser Gln Asp
    210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Val Leu
                245                 250                 255

Asn Ser Ala Gly Gln Trp Ala Pro Asp Leu Asn Lys Asn His Trp Ser
            260                 265                 270

Cys Asn Asp Gln Thr Pro Lys Phe Asn Gly Ser Asn Glu Lys Thr Thr
        275                 280                 285

Ser Thr Asn Pro Leu Thr Gln Glu Thr Glu Thr Ile Trp Thr Glu Ser
290                 295                 300

Asn Cys Ile Thr His Ile Gln Lys Asn Asp Glu Pro Glu Ile Thr Gln
305                 310                 315                 320

Asn Ile Tyr Lys Asn Lys Asp Arg Glu Lys Ile Leu Glu Asp Leu Lys
                325                 330                 335

Lys Asp Pro Asn Pro Glu Asn Ile Pro Glu Leu Gln Ala Glu Ile Lys
            340                 345                 350

Lys Thr Asp Glu Ser Phe Glu Arg Asn Lys Asp Gln Tyr Ser Val Ala
        355                 360                 365

Pro Ile Glu Pro Gly Ser Leu Gln Ser Arg Ser Arg Ser His Leu Leu
370                 375                 380

Lys Phe Glu Tyr Gly Asp Asp His Gln Asn Leu Gly Ala Gln Ile Arg
385                 390                 395                 400

Thr Leu Asp Asn Lys Ile Gly Ser Arg Lys Ile Glu Asn Arg Asn Tyr
                405                 410                 415
```

```
Gln Val Asn Tyr Asn Phe Asn Asn Ser Tyr Leu Asp Leu Asn Leu
            420                 425                 430

Met Ala Ala His Asn Ile Gly Lys Thr Ile Tyr Pro Lys Gly Gly Phe
            435                 440                 445

Phe Ala Gly Trp Gln Val Ala Asp Lys Leu Ile Thr Lys Asn Val Ala
450                 455                 460

Asn Ile Val Asp Ile Asn Asn Ser His Thr Phe Leu Leu Pro Lys Glu
465                 470                 475                 480

Ile Asp Leu Lys Thr Thr Leu Gly Phe Asn Tyr Phe Thr Asn Glu Tyr
                485                 490                 495

Ser Lys Asn Arg Phe Pro Glu Glu Leu Ser Leu Phe Tyr Asn Asp Asp
            500                 505                 510

Ser His Asp Arg Gly Asn Tyr Ser Asn Leu Gly Arg Leu Lys Gly Ala
            515                 520                 525

Gln Gly Leu Leu Pro Gln Arg Ser Val Ile Leu Gln Pro Ser Gly Lys
    530                 535                 540

Gln Lys Phe Lys Thr Val Tyr Phe Asp Thr Ala Leu Ser Lys Gly Ile
545                 550                 555                 560

Tyr His Leu Asn Tyr Ser Val Asn Phe Thr His Tyr Ala Phe Asn Gly
                565                 570                 575

Glu Tyr Val Gly Tyr Glu Asn Thr Ala Glu Pro Ile Leu His Lys Ser
            580                 585                 590

Gly His Lys Lys Ala Phe Asn His Ser Ala Thr Leu Ser Ala Glu Leu
            595                 600                 605

Ser Asp Tyr Phe Met Pro Phe Phe Thr Tyr Ser Arg Thr His Arg Met
    610                 615                 620

Pro Asn Ile Gln Glu Met Phe Phe Ser Gln Val Ser Asp Ala Gly Val
625                 630                 635                 640

Asn Thr Ala Leu Lys Pro Glu Gln Ser Asp Thr Tyr Gln Leu Gly Phe
                645                 650                 655

Asn Thr Tyr Lys Lys Gly Leu Phe Thr Gln Asp Asp Val Leu Gly Ile
            660                 665                 670

Lys Leu Val Gly Tyr Arg Ser Phe Ile Lys Asn Tyr Ile His Asn Val
            675                 680                 685

Tyr Gly Val Trp Trp Arg Asn Gly Lys Val Pro Asp Trp Ala Ala Thr
    690                 695                 700

Asn Gly Phe Arg Phe Asn Ile Ala His Gln Asn Tyr Gln Pro Ile Val
705                 710                 715                 720

Lys Lys Ser Gly Ala Glu Leu Glu Leu Asn Tyr Asp Met Gly Arg Phe
                725                 730                 735

Phe Ala Asn Val Ser Tyr Ala Tyr Gln Arg Thr Asn Gln Pro Thr Asn
            740                 745                 750

Tyr Ala Asp Ala Ser Pro Arg Pro Asn Asn Ala Ser Lys Glu Asp Ile
            755                 760                 765

Leu Lys Gln Gly Tyr Gly Leu Ser Arg Val Ser Met Leu Pro Lys Asp
    770                 775                 780

Tyr Gly Arg Leu Glu Leu Gly Thr Arg Trp Phe Asp Lys Lys Leu Thr
785                 790                 795                 800

Leu Gly Met Ala Ala Arg Tyr Tyr Gly Lys Ser Lys Arg Ala Thr Ile
                805                 810                 815

Glu Glu Glu Tyr Ile Asn Gly Ser His Phe Glu Lys Asn Thr Ser Gly
            820                 825                 830
```

```
Ser Arg Thr Tyr Tyr Ala Val Lys Thr Glu Glu Ile Lys Lys Gln
            835                 840                 845

Pro Ile Ile Leu Asp Leu His Val Ser Tyr Glu Pro Ile Lys Asp Leu
850                 855                 860

Ile Ile Lys Ala Glu Val Gln Asn Leu Leu Asp Lys Arg Tyr Val Asp
865                 870                 875                 880

Pro Leu Asp Ala Gly Asn Asp Ala Ala Ser Gln Arg Tyr Tyr Ser Ser
                885                 890                 895

Leu Asn Asp Ser Ile Cys Lys Gly Asn Thr Cys Glu Asp Gly Gly Lys
            900                 905                 910

Asp Lys Thr Val Leu Tyr Asn Phe Ala Arg Gly Arg Thr Tyr Ile Leu
            915                 920                 925

Ser Leu Asn Tyr Lys Phe
    930

<210> SEQ ID NO 65
<211> LENGTH: 929
<212> TYPE: PRT
<213> ORGANISM: Haemophilus influenzae R2866

<400> SEQUENCE: 65

Met Thr Ile Thr Gln Ala Gln Ala Glu Glu Thr Leu Gly Gln Ile Asp
1               5                   10                  15

Val Val Glu Lys Val Ile Ser Asn Asp Lys Pro Phe Thr Glu Ala
                20                  25                  30

Lys Ala Lys Ser Thr Arg Glu Asn Val Phe Lys Glu Thr Gln Thr Ile
                35                  40                  45

Asp Gln Val Ile Arg Ser Ile Pro Gly Ala Phe Thr Gln Gln Asp Lys
50                  55                  60

Gly Ser Gly Val Val Ser Val Asn Ile Arg Gly Glu Asn Gly Leu Gly
65                  70                  75                  80

Arg Val Asn Thr Met Val Asp Gly Val Thr Gln Thr Phe Tyr Ser Thr
                85                  90                  95

Ala Leu Asp Ser Gly Gln Ser Gly Gly Ser Ser Gln Phe Gly Ala Ala
                100                 105                 110

Ile Asp Pro Asn Phe Ile Ala Gly Val Asp Val Asn Lys Ser Asn Phe
            115                 120                 125

Ser Gly Ala Ser Gly Ile Asn Ala Leu Ala Gly Ser Ala Asn Phe Arg
    130                 135                 140

Thr Leu Ser Val Asn Asp Val Ile Thr Asp Lys Pro Phe Gly Ile
145                 150                 155                 160

Ile Leu Lys Gly Met Thr Gly Ser Asn Ala Thr Lys Ser Asn Phe Met
                165                 170                 175

Thr Thr Ala Ala Gly Arg Lys Trp Leu Asp Asn Gly Tyr Val Gly
                180                 185                 190

Val Val Tyr Gly Tyr Ser Gln Arg Glu Val Ser Gln Asp Tyr Arg Ile
            195                 200                 205

Gly Gly Gly Glu Arg Leu Ala Ser Leu Gly Gln Asp Ile Leu Ala Lys
    210                 215                 220

Glu Lys Glu Ala Tyr Phe Arg Asn Ala Gly Tyr Ile Leu Asn Pro Ala
225                 230                 235                 240

Gly Gln Trp Ala Pro Asp Leu Ser Lys Asn His Trp Ser Cys Asn Ala
                245                 250                 255

Pro Asp Pro Lys Phe Asn Gly Ser Thr Lys Lys Thr Glu Ser Ser Asn
            260                 265                 270
```

```
Asp Leu Thr Gly Glu Arg Glu Thr Ile Trp Thr Asp Lys Asp Cys Val
        275                 280                 285

Phe His Arg Glu Lys Tyr Asn Ile Tyr Asp Val Pro Thr Lys Lys Glu
290                 295                 300

Glu Thr Lys Asp Lys Ile Tyr Glu Asp Pro Val Arg Lys Lys Ile Leu
305                 310                 315                 320

Glu Asp Ile Asn Lys Asn Thr Pro Leu Lys Asp Ile Pro Glu Leu Gln
                325                 330                 335

Lys Gly Ile Glu Lys Thr Asp Lys Ser Phe Glu Asp Asn Lys Glu Gln
                340                 345                 350

Tyr Ser Val Ala Pro Ile Glu Pro Gly Ser Leu Gln Ser Arg Ser Arg
        355                 360                 365

Ser His Leu Leu Lys Phe Glu Tyr Gly Asp Asp His His Thr Leu Gly
        370                 375                 380

Ala Gln Ile Arg Thr Leu Asp Asn Lys Ile Gly Ser Arg Lys Ile Glu
385                 390                 395                 400

Asn Arg Asn Tyr Gln Val Asn Tyr Asn Phe Asn Asn Ser Tyr Leu
                405                 410                 415

Asp Leu Asn Leu Met Ala Ala His Asn Ile Gly Lys Thr Ile Tyr Pro
                420                 425                 430

Lys Gly Gly Phe Phe Ala Gly Trp Arg Val Arg Asp Lys Leu Ile Thr
                435                 440                 445

Lys Asn Val Ala Asn Ile Val Asp Ile Asn Asn Ser His Thr Phe Leu
                450                 455                 460

Leu Pro Lys Glu Ile Asp Leu Lys Thr Thr Leu Gly Phe Asn Tyr Phe
465                 470                 475                 480

Thr Asn Glu Tyr Ser Lys Asn Arg Phe Pro Glu Glu Leu Ser Leu Phe
                485                 490                 495

Tyr Lys Glu Ala Ser Gly Asp Pro Gly Arg Tyr Thr Tyr Thr Gln Gly
                500                 505                 510

Thr Gly Gly Thr Gln Asn Leu Leu Pro Gln Arg Ser Val Ile Leu Gln
                515                 520                 525

Pro Ser Gly Lys Gln Lys Phe Lys Thr Val Tyr Phe Asp Thr Ala Leu
                530                 535                 540

Ser Lys Gly Ile Tyr His Leu Asn Tyr Asn Val Asn Phe Thr His Tyr
545                 550                 555                 560

Ala Phe Asn Gly Glu Tyr Val Gly Tyr Glu Asn Lys Pro Thr Gln Ile
                565                 570                 575

Asn Glu Pro Ile Leu His Lys Ser Gly His Lys Lys Ala Phe Asn His
                580                 585                 590

Ser Ala Thr Leu Ser Ala Glu Leu Ser Asp Tyr Phe Met Pro Phe Phe
        595                 600                 605

Thr Tyr Ser Arg Thr His Arg Met Pro Asn Ile Gln Glu Met Phe Phe
        610                 615                 620

Ser Gln Val Ser Asn Ala Gly Val Asn Thr Ala Leu Lys Pro Glu Gln
625                 630                 635                 640

Ser Asp Thr Tyr Gln Leu Gly Phe Asn Thr Tyr Lys Lys Gly Leu Phe
                645                 650                 655

Thr Gln Asp Asp Val Leu Gly Val Lys Leu Val Gly Tyr Arg Ser Phe
                660                 665                 670

Ile Lys Asn Tyr Ile His Asn Val Tyr Gly Glu Trp Trp Lys Asn Asp
                675                 680                 685
```

Val Pro Ile Trp Ala Asp Ser Asn Gly Phe Arg Phe Thr Ile Ala His
690                 695                 700

Gln Asn Tyr Lys Pro Ile Val Lys Ser Gly Val Glu Leu Glu Ile
705                 710                 715                 720

Asn Tyr Asp Met Gly Arg Phe Phe Ala Asn Val Ser Tyr Ala Tyr Gln
                725                 730                 735

Arg Thr Asn Gln Pro Thr Asn Tyr Ala Asp Ala Ser Pro Arg Ala Lys
                740                 745                 750

Asn Thr Ser Asn Lys Asp Ile Leu Lys Gln Gly Tyr Gly Leu Ser Arg
                755                 760                 765

Ile Thr Met Leu Pro Arg Asp Tyr Gly Arg Leu Glu Leu Gly Thr Arg
770                 775                 780

Trp Phe Asp Gln Lys Leu Thr Leu Gly Met Ala Ala Arg Tyr Tyr Gly
785                 790                 795                 800

Lys Ser Lys Arg Ala Ser Ile Lys Asp Glu Cys Val Lys Gly Val Pro
                805                 810                 815

Cys Lys Ile Gln Gly Thr Gly Glu Lys Ala Glu Val Val His Asn Ala
                820                 825                 830

Ile Lys Lys Thr Glu Asp Ile Lys Lys Gln Pro Ile Ile Leu Asp Leu
                835                 840                 845

His Val Ser Tyr Glu Pro Ile Lys Asp Leu Ile Ile Lys Ala Glu Val
                850                 855                 860

Gln Asn Leu Leu Asp Lys Arg Tyr Val Asp Pro Leu Asp Ala Gly Asn
865                 870                 875                 880

Asp Ala Ala Ser Gln Arg Tyr Tyr Ser Ser Leu Asn Asp Ser Ile Cys
                885                 890                 895

Ser Lys Asp Gly Thr Cys Glu Asp Gly Gly Lys Asp Lys Pro Val Leu
                900                 905                 910

Tyr Asn Phe Ala Arg Gly Arg Thr Tyr Ile Leu Ser Leu Asn Tyr Lys
                915                 920                 925

Phe

<210> SEQ ID NO 66
<211> LENGTH: 913
<212> TYPE: PRT
<213> ORGANISM: Haemophilus influenzae Rd KW20

<400> SEQUENCE: 66

Met Lys Lys Ala Ile Lys Leu Asn Leu Ile Thr Leu Gly Leu Ile Asn
1               5                   10                  15

Thr Ile Gly Met Thr Ile Thr Gln Ala Gln Ala Glu Thr Leu Gly
                20                  25                  30

Gln Ile Asp Val Val Glu Lys Val Ile Ser Asn Asp Lys Lys Pro Phe
                35                  40                  45

Thr Glu Ala Lys Ala Lys Ser Thr Arg Glu Asn Val Phe Lys Glu Thr
                50                  55                  60

Gln Thr Ile Asp Gln Val Ile Arg Ser Ile Pro Gly Ala Phe Thr Gln
65                  70                  75                  80

Gln Asp Lys Gly Ser Gly Val Val Ser Val Asn Ile Arg Gly Glu Asn
                85                  90                  95

Gly Leu Gly Arg Val Asn Thr Met Val Asp Gly Val Thr Gln Thr Phe
                100                 105                 110

Tyr Ser Thr Ala Leu Asp Ser Gly Gln Ser Gly Gly Ser Gln Phe
                115                 120                 125

```
Gly Ala Ala Ile Asp Pro Asn Phe Ile Ala Gly Val Asp Val Asn Lys
        130                 135                 140

Ser Asn Phe Ser Gly Ala Ser Gly Ile Asn Ala Leu Ala Gly Ser Ala
145                 150                 155                 160

Asn Phe Arg Thr Leu Gly Val Asn Asp Val Ile Thr Asp Asp Lys Pro
                165                 170                 175

Phe Gly Ile Ile Leu Lys Gly Met Thr Gly Ser Asn Ala Thr Lys Ser
                180                 185                 190

Asn Phe Met Thr Met Ala Ala Gly Arg Lys Trp Leu Asp Asn Gly Gly
            195                 200                 205

Tyr Val Gly Val Val Tyr Gly Tyr Ser Gln Arg Glu Val Ser Gln Asp
        210                 215                 220

Tyr Arg Ile Gly Gly Gly Glu Arg Leu Ala Ser Leu Gly Gln Asp Ile
225                 230                 235                 240

Leu Ala Lys Glu Lys Glu Ala Tyr Phe Arg Asn Ala Gly Tyr Ile Leu
                245                 250                 255

Asn Pro Glu Gly Gln Trp Thr Pro Asp Leu Ser Lys Lys His Trp Ser
                260                 265                 270

Cys Asn Lys Pro Asp Tyr Gln Lys Asn Gly Asp Cys Ser Tyr Tyr Arg
            275                 280                 285

Ile Gly Ser Ala Ala Lys Thr Arg Arg Glu Ile Leu Gln Glu Leu Leu
        290                 295                 300

Thr Asn Gly Lys Lys Pro Lys Asp Ile Glu Lys Leu Gln Lys Gly Asn
305                 310                 315                 320

Asp Gly Ile Glu Glu Thr Asp Lys Ser Phe Glu Arg Asn Lys Asp Gln
                325                 330                 335

Tyr Ser Val Ala Pro Ile Glu Pro Gly Ser Leu Gln Ser Arg Ser Arg
                340                 345                 350

Ser His Leu Leu Lys Phe Glu Tyr Gly Asp Asp His Gln Asn Leu Gly
            355                 360                 365

Ala Gln Leu Arg Thr Leu Asp Asn Lys Ile Gly Ser Arg Lys Ile Glu
        370                 375                 380

Asn Arg Asn Tyr Gln Val Asn Tyr Asn Phe Asn Asn Ser Tyr Leu
385                 390                 395                 400

Asp Leu Asn Leu Met Ala Ala His Asn Ile Gly Lys Thr Ile Tyr Pro
                405                 410                 415

Lys Gly Gly Phe Phe Ala Gly Trp Gln Val Ala Asp Lys Leu Ile Thr
                420                 425                 430

Lys Asn Val Ala Asn Ile Val Asp Ile Asn Asn Ser His Thr Phe Leu
            435                 440                 445

Leu Pro Lys Glu Ile Asp Leu Lys Thr Thr Leu Gly Phe Asn Tyr Phe
        450                 455                 460

Thr Asn Glu Tyr Ser Lys Asn Arg Phe Pro Glu Glu Leu Ser Leu Phe
465                 470                 475                 480

Tyr Asn Asp Ala Ser His Asp Gln Gly Leu Tyr Ser His Ser Lys Arg
                485                 490                 495

Gly Arg Tyr Ser Gly Thr Lys Ser Leu Leu Pro Gln Arg Ser Val Ile
                500                 505                 510

Leu Gln Pro Ser Gly Lys Gln Lys Phe Lys Thr Val Tyr Phe Asp Thr
            515                 520                 525

Ala Leu Ser Lys Gly Ile Tyr His Leu Asn Tyr Ser Val Asn Phe Thr
        530                 535                 540

His Tyr Ala Phe Asn Gly Glu Tyr Val Gly Tyr Glu Asn Thr Ala Gly
```

```
545                 550                 555                 560
Gln Gln Ile Asn Glu Pro Ile Leu His Lys Ser Gly His Lys Lys Ala
                565                 570                 575

Phe Asn His Ser Ala Thr Leu Ser Ala Glu Leu Ser Asp Tyr Phe Met
                580                 585                 590

Pro Phe Phe Thr Tyr Ser Arg Thr His Arg Met Pro Asn Ile Gln Glu
                595                 600                 605

Met Phe Phe Ser Gln Val Ser Asn Ala Gly Val Asn Thr Ala Leu Lys
                610                 615                 620

Pro Glu Gln Ser Asp Thr Tyr Gln Leu Gly Phe Asn Thr Tyr Lys Lys
625                 630                 635                 640

Gly Leu Phe Thr Gln Asp Val Leu Gly Val Lys Leu Val Gly Tyr
                645                 650                 655

Arg Ser Phe Ile Lys Asn Tyr Ile His Asn Val Tyr Gly Val Trp Trp
                660                 665                 670

Arg Asp Gly Met Pro Thr Trp Ala Glu Ser Asn Gly Phe Lys Tyr Thr
                675                 680                 685

Ile Ala His Gln Asn Tyr Lys Pro Ile Val Lys Lys Ser Gly Val Glu
                690                 695                 700

Leu Glu Ile Asn Tyr Asp Met Gly Arg Phe Phe Ala Asn Val Ser Tyr
705                 710                 715                 720

Ala Tyr Gln Arg Thr Asn Gln Pro Thr Asn Tyr Ala Asp Ala Ser Pro
                725                 730                 735

Arg Pro Asn Asn Ala Ser Gln Glu Asp Ile Leu Lys Gln Gly Tyr Gly
                740                 745                 750

Leu Ser Arg Val Ser Met Leu Pro Lys Asp Tyr Gly Arg Leu Glu Leu
                755                 760                 765

Gly Thr Arg Trp Phe Asp Gln Lys Leu Thr Leu Gly Leu Ala Ala Arg
                770                 775                 780

Tyr Tyr Gly Lys Ser Lys Arg Ala Thr Ile Glu Glu Tyr Ile Asn
785                 790                 795                 800

Gly Ser Arg Phe Lys Lys Asn Thr Leu Arg Arg Glu Asn Tyr Tyr Ala
                805                 810                 815

Val Lys Lys Thr Glu Asp Ile Lys Lys Gln Pro Ile Ile Leu Asp Leu
                820                 825                 830

His Val Ser Tyr Glu Pro Ile Lys Asp Leu Ile Ile Lys Ala Glu Val
                835                 840                 845

Gln Asn Leu Leu Asp Lys Arg Tyr Val Asp Pro Leu Asp Ala Gly Asn
850                 855                 860

Asp Ala Ala Ser Gln Arg Tyr Tyr Ser Ser Leu Asn Asn Ser Ile Glu
865                 870                 875                 880

Cys Ala Gln Asp Ser Ser Ala Cys Gly Gly Ser Asp Lys Thr Val Leu
                885                 890                 895

Tyr Asn Phe Ala Arg Gly Arg Thr Tyr Ile Leu Ser Leu Asn Tyr Lys
                900                 905                 910

Phe

<210> SEQ ID NO 67
<211> LENGTH: 913
<212> TYPE: PRT
<213> ORGANISM: Haemophilus influenzae RdAW

<400> SEQUENCE: 67

Met Lys Lys Ala Ile Lys Leu Asn Leu Ile Thr Leu Gly Leu Ile Asn
```

-continued

```
1               5                   10                  15
Thr Ile Gly Met Thr Ile Thr Gln Ala Gln Ala Glu Glu Thr Leu Gly
                20                  25                  30
Gln Ile Asp Val Val Glu Lys Val Ile Ser Asn Asp Lys Lys Pro Phe
                35                  40                  45
Thr Glu Ala Lys Ala Lys Ser Thr Arg Glu Asn Val Phe Lys Glu Thr
                50                  55                  60
Gln Thr Ile Asp Gln Val Ile Arg Ser Ile Pro Gly Ala Phe Thr Gln
65                  70                  75                  80
Gln Asp Lys Gly Ser Gly Val Val Ser Val Asn Ile Arg Gly Glu Asn
                85                  90                  95
Gly Leu Gly Arg Val Asn Thr Met Val Asp Gly Val Thr Gln Thr Phe
                100                 105                 110
Tyr Ser Thr Ala Leu Asp Ser Gly Gln Ser Gly Gly Ser Ser Gln Phe
                115                 120                 125
Gly Ala Ala Ile Asp Pro Asn Phe Ile Ala Gly Val Asp Val Asn Lys
                130                 135                 140
Ser Asn Phe Ser Gly Ala Ser Gly Ile Asn Ala Leu Ala Gly Ser Ala
145                 150                 155                 160
Asn Phe Arg Thr Leu Gly Val Asn Asp Val Ile Thr Asp Lys Pro
                165                 170                 175
Phe Gly Ile Ile Leu Lys Gly Met Thr Gly Ser Asn Ala Thr Lys Ser
                180                 185                 190
Asn Phe Met Thr Met Ala Ala Gly Arg Lys Trp Leu Asp Asn Gly Gly
                195                 200                 205
Tyr Val Gly Val Val Tyr Gly Tyr Ser Gln Arg Glu Val Ser Gln Asp
                210                 215                 220
Tyr Arg Ile Gly Gly Glu Arg Leu Ala Ser Leu Gly Gln Asp Ile
225                 230                 235                 240
Leu Ala Lys Glu Lys Glu Ala Tyr Phe Arg Asn Ala Gly Tyr Ile Leu
                245                 250                 255
Asn Pro Glu Gly Gln Trp Thr Pro Asp Leu Ser Lys Lys His Trp Ser
                260                 265                 270
Cys Asn Lys Pro Asp Tyr Gln Lys Asn Gly Asp Cys Ser Tyr Tyr Arg
                275                 280                 285
Ile Gly Ser Ala Ala Lys Thr Arg Arg Glu Ile Leu Gln Glu Leu Leu
                290                 295                 300
Thr Asn Gly Lys Lys Pro Lys Asp Ile Glu Lys Leu Gln Lys Gly Asn
305                 310                 315                 320
Asp Gly Ile Glu Glu Thr Asp Lys Ser Phe Glu Arg Asn Lys Asp Gln
                325                 330                 335
Tyr Ser Val Ala Pro Ile Glu Pro Gly Ser Leu Gln Ser Arg Ser Arg
                340                 345                 350
Ser His Leu Leu Lys Phe Glu Tyr Gly Asp Asp His Gln Asn Leu Gly
                355                 360                 365
Ala Gln Leu Arg Thr Leu Asp Asn Lys Ile Gly Ser Arg Lys Ile Glu
                370                 375                 380
Asn Arg Asn Tyr Gln Val Asn Tyr Asn Phe Asn Asn Ser Tyr Leu
385                 390                 395                 400
Asp Leu Asn Leu Met Ala Ala His Asn Ile Gly Lys Thr Ile Tyr Pro
                405                 410                 415
Lys Gly Gly Phe Phe Ala Gly Trp Gln Val Ala Asp Lys Leu Ile Thr
                420                 425                 430
```

```
Lys Asn Val Ala Asn Ile Val Asp Ile Asn Asn Ser His Thr Phe Leu
            435                 440                 445

Leu Pro Lys Glu Ile Asp Leu Lys Thr Thr Leu Gly Phe Asn Tyr Phe
    450                 455                 460

Thr Asn Glu Tyr Ser Lys Asn Arg Phe Pro Glu Glu Leu Ser Leu Phe
465                 470                 475                 480

Tyr Asn Asp Ala Ser His Asp Gln Gly Leu Tyr Ser His Ser Lys Arg
                485                 490                 495

Gly Arg Tyr Ser Gly Thr Lys Ser Leu Leu Pro Gln Arg Ser Val Ile
                500                 505                 510

Leu Gln Pro Ser Gly Lys Gln Lys Phe Lys Thr Val Tyr Phe Asp Thr
            515                 520                 525

Ala Leu Ser Lys Gly Ile Tyr His Leu Asn Tyr Ser Val Asn Phe Thr
        530                 535                 540

His Tyr Ala Phe Asn Gly Glu Tyr Val Gly Tyr Glu Asn Thr Ala Gly
545                 550                 555                 560

Gln Gln Ile Asn Glu Pro Ile Leu His Lys Ser Gly His Lys Lys Ala
                565                 570                 575

Phe Asn His Ser Ala Thr Leu Ser Ala Glu Leu Ser Asp Tyr Phe Met
            580                 585                 590

Pro Phe Phe Thr Tyr Ser Arg Thr His Arg Met Pro Asn Ile Gln Glu
        595                 600                 605

Met Phe Phe Ser Gln Val Ser Asn Ala Gly Val Asn Thr Ala Leu Lys
    610                 615                 620

Pro Glu Gln Ser Asp Thr Tyr Gln Leu Gly Phe Asn Thr Tyr Lys Lys
625                 630                 635                 640

Gly Leu Phe Thr Gln Asp Asp Val Leu Gly Val Lys Leu Val Gly Tyr
                645                 650                 655

Arg Ser Phe Ile Lys Asn Tyr Ile His Asn Val Tyr Gly Val Trp Trp
                660                 665                 670

Arg Asp Gly Met Pro Thr Trp Ala Glu Ser Asn Gly Phe Lys Tyr Thr
            675                 680                 685

Ile Ala His Gln Asn Tyr Lys Pro Ile Val Lys Ser Gly Val Glu
        690                 695                 700

Leu Glu Ile Asn Tyr Asp Met Gly Arg Phe Phe Ala Asn Val Ser Tyr
705                 710                 715                 720

Ala Tyr Gln Arg Thr Asn Gln Pro Thr Asn Tyr Ala Asp Ala Ser Pro
                725                 730                 735

Arg Pro Asn Asn Ala Ser Gln Glu Asp Ile Leu Lys Gln Gly Tyr Gly
            740                 745                 750

Leu Ser Arg Val Ser Met Leu Pro Lys Asp Tyr Gly Arg Leu Glu Leu
        755                 760                 765

Gly Thr Arg Trp Phe Asp Gln Lys Leu Thr Leu Gly Leu Ala Ala Arg
    770                 775                 780

Tyr Tyr Gly Lys Ser Lys Arg Ala Thr Ile Glu Glu Tyr Ile Asn
785                 790                 795                 800

Gly Ser Arg Phe Lys Lys Asn Thr Leu Arg Arg Glu Asn Tyr Ala
                805                 810                 815

Val Lys Lys Thr Glu Asp Ile Lys Lys Gln Pro Ile Ile Leu Asp Leu
            820                 825                 830

His Val Ser Tyr Glu Pro Ile Lys Asp Leu Ile Lys Ala Glu Val
        835                 840                 845
```

```
Gln Asn Leu Leu Asp Lys Arg Tyr Val Asp Pro Leu Asp Ala Gly Asn
    850                 855                 860

Asp Ala Ala Ser Gln Arg Tyr Tyr Ser Ser Leu Asn Asn Ser Ile Glu
865                 870                 875                 880

Cys Ala Gln Asp Ser Ser Ala Cys Gly Gly Ser Asp Lys Thr Val Leu
                885                 890                 895

Tyr Asn Phe Ala Arg Gly Arg Thr Tyr Ile Leu Ser Leu Asn Tyr Lys
                900                 905                 910

Phe

<210> SEQ ID NO 68
<211> LENGTH: 915
<212> TYPE: PRT
<213> ORGANISM: Haemophilus somnus 129PT

<400> SEQUENCE: 68

Met Ser Asn Lys Phe Lys Leu Thr Ala Val Ala Phe Ser Val Leu Ser
1               5                   10                  15

Thr Cys Val Tyr Ala Glu Glu Met Leu Asp Gln Ile Asn Val Glu Tyr
                20                  25                  30

Lys Leu Pro Pro Lys Gln Glu Val Phe Lys Lys Ala Gly Ala Thr Ser
            35                  40                  45

Val Arg Glu Asn Ile Ser Thr Ser Thr Gln Ser Ile Asp Asp Ile Ile
50                  55                  60

Arg Thr Val Pro Gly Ala Phe Thr Asn Leu Asp Lys Ser Ser Gly Ile
65                  70                  75                  80

Val Ser Val Asn Val Arg Gly Gln Thr Gly Phe Gly Arg Val Asn Thr
                85                  90                  95

Met Val Asp Gly Ile Ser Gln Thr Phe Phe Ala Thr Ser Gly Asp Asn
            100                 105                 110

Ser Glu Lys Ala Gly Gly Thr Ser Gln Phe Gly Ala Thr Ile Asp Pro
        115                 120                 125

Ala Phe Ile Thr Ser Val Asp Ile Gln Arg Gly Ser Phe Asp Gly Lys
130                 135                 140

Ala Gly Ala Asn Ala Leu Val Gly Ser Ala Asn Phe Arg Thr Ile Gly
145                 150                 155                 160

Val Asp Asp Val Ile Ser Glu Gly Arg Asn Val Gly Ala Leu Leu Asn
                165                 170                 175

Ala Gly Gly Gly Thr Asn Ala Thr Gly Pro Asn Tyr Met Gly Ala Val
            180                 185                 190

Ala Phe Arg Tyr Pro Phe Ser Asp Thr Arg Thr Leu Gly Phe Met Tyr
        195                 200                 205

Ala Tyr Ser Trp Arg Lys Ser Ser Gln Asp Phe Lys Val Gly Gly Gly
210                 215                 220

Arg Ser Ile Lys Asp Val Asp Ala Glu Val Gly Arg Ile Val Lys
225                 230                 235                 240

Glu Ala Cys Lys Gly Glu Phe Leu Cys Lys Glu Asp Glu Lys Arg Lys
                245                 250                 255

Leu Tyr Gly Leu Gln Pro Tyr Asp Pro Ser Lys Leu Leu His Tyr Pro
            260                 265                 270

Gln Ser His Leu Ala Lys Ile Glu Tyr Asn Asp Lys Tyr Asn Lys Ala
        275                 280                 285

Ile Leu Ser Tyr Arg Ser Leu Ser Thr Ala Leu Ser Gly Arg Asn Leu
290                 295                 300
```

```
Glu Asn Lys Asn Tyr Gln Leu Asn Tyr Gln Leu Lys Pro Lys Glu Asn
305                 310                 315                 320

Leu Gln Phe Glu Leu Ile Leu Ala Asp Asn Thr Ser Thr Gln Thr Tyr
            325                 330                 335

His Lys Gly Ser Val Phe Asn Gly Lys Met Leu Lys Asp Val Leu Glu
            340                 345                 350

Ser Lys Asn Ser Ala Lys Thr Thr Asp Ile Asn Met His Phe Ser Ile
            355                 360                 365

Pro Phe Thr Glu Lys Phe Ser Tyr Glu Ala Thr Leu Gly Ala Asn Ile
            370                 375                 380

Leu Lys Asn Lys Tyr Ser Lys Asn Arg His Pro Arg Glu Leu Gly Tyr
385                 390                 395                 400

Tyr Phe Asp Gly Gly Glu Pro Asn Ser Arg Asp Phe Cys Asp Tyr Val
            405                 410                 415

Gly Lys Tyr Lys Asn Ala Cys Ile Tyr His Gly Ile Arg Ser Asn Thr
            420                 425                 430

Phe Gln Pro Asp Gly Glu Gln Arg Phe Lys Thr Leu Tyr Phe Asp Gln
            435                 440                 445

Thr Phe Lys Tyr Asp Ile Tyr Thr Leu Lys Val Asn Ala Asn Arg Gln
            450                 455                 460

Ile Tyr Lys Tyr Ser Gly Ala Thr Phe Pro Arg Asp Pro Arg Asp Arg
465                 470                 475                 480

Val Thr Arg Tyr Phe Pro Ala Asp Pro Glu Gln Lys Thr Lys Asp Gly
                485                 490                 495

Tyr Thr Val Tyr Val Asn Gly Asn Ser Ser Ala Ile Val His Lys Tyr
            500                 505                 510

Gly Tyr Asp Gly Ala Ile Lys Phe Gly Cys Tyr His Tyr Glu Asn Asp
            515                 520                 525

Glu Glu Gln Trp Val Asp Val Tyr Asn Cys Pro Thr Phe Tyr Ser Val
            530                 535                 540

Gln Lys Gly Asn Ser Arg Ala His Asp Asn Tyr Ser Met Ser Phe Ser
545                 550                 555                 560

Ala Asp Phe His Pro Leu Phe Ser Pro Phe Val Ser Tyr Ala Lys Thr
            565                 570                 575

His Arg Val Pro Asn Ile Lys Glu Met Tyr Phe Ser Glu Phe Gly Thr
            580                 585                 590

Leu Ala Ile Arg Pro Asp Leu Lys Ser Glu Lys Ala Lys Thr Ile Gln
            595                 600                 605

Phe Gly Ile Asn Gly Tyr Lys Asn Gly Ile Phe Ser Asp Phe Asp Ala
            610                 615                 620

Leu Gly Phe Lys Val Leu Ala Tyr Gln Thr Lys Ile Arg Asp Tyr Ile
625                 630                 635                 640

Ile Asn Ile Lys Gln Glu Cys Ser Ser Asn Ser Trp Arg Gly Ala Asp
                645                 650                 655

Lys Ala Pro Thr Ile Tyr Asp Cys Val Gly His Leu Thr His Ile Asn
            660                 665                 670

Tyr Glu Gly Gly Lys Thr Ile Leu Lys Thr Glu Met Val Asp Ser Gly
            675                 680                 685

Ser Gly Phe Lys Val Pro Leu Asn Gln Leu Ile Pro Ala Asp Ser Ser
            690                 695                 700

Pro Ile Val Lys Ile Gln Gly Leu Glu Leu Glu Leu Asn Tyr Asp Ile
705                 710                 715                 720

Gly Trp Phe Tyr Ala Asn Leu Ser Tyr Ala Arg Gln Lys Thr Asn Gln
```

```
                    725                 730                 735
Pro Ser Ser Tyr Ser Asp Ser Ser Asn Ser Val Gly Asp Asp Ser Glu
                740                 745                 750
Thr Gly Gln Tyr Leu Gln Gly Phe Gly Leu Ser Lys Ile Ser Ser Leu
            755                 760                 765
Pro Lys Asp Tyr Gly Ser Leu Asp Leu Gly Thr Arg Leu Phe Asp Gly
        770                 775                 780
Lys Leu Thr Leu Gly Gly Thr Ala Lys Tyr Tyr Gly Lys Ser Lys Arg
785                 790                 795                 800
Ala Arg Leu Asp Lys Ala Asp Gly Asp Val Ile Leu Pro Gly Thr Phe
                805                 810                 815
Thr Ser Arg Lys Thr Gly Glu Thr Phe Leu Thr Tyr Val Arg Ile Ser
            820                 825                 830
Gly Thr Glu Glu Ile Lys Ala Gln Pro Ile Ile Phe Asp Phe Tyr Ala
        835                 840                 845
Ile Tyr Gln Pro Thr Glu Asn Leu Thr Ile Lys Gly Glu Ile Gln Asn
    850                 855                 860
Ala Phe Asp Lys Lys Tyr Ile Asn Pro Leu Asp Ala Asn Asn Asp Ser
865                 870                 875                 880
Ala Asn Gln Met Thr Tyr Ala Met Gly Val Gly Asp Gly Tyr Gln Lys
                885                 890                 895
Ala Leu Asn Asn Tyr Ser Lys Gly Arg Thr Phe Val Leu Asn Val Asn
            900                 905                 910
Tyr Lys Phe
        915

<210> SEQ ID NO 69
<211> LENGTH: 917
<212> TYPE: PRT
<213> ORGANISM: Haemophilus somnus 2336

<400> SEQUENCE: 69

Met Met Thr Asn Lys Phe Lys Leu Thr Ala Val Ala Phe Ser Val Leu
1               5                   10                  15
Ser Thr Cys Val Tyr Ala Glu Glu Met Leu Asp Gln Ile Asn Val Glu
                20                  25                  30
Tyr Lys Leu Pro Pro Lys Gln Glu Val Phe Lys Lys Ala Gly Ala Thr
            35                  40                  45
Ser Val Arg Glu Asn Ile Ser Thr Ser Thr Gln Ser Ile Asp Asp Ile
        50                  55                  60
Ile Arg Thr Val Pro Gly Ala Phe Thr Asn Leu Asp Lys Ser Ser Gly
65                  70                  75                  80
Thr Val Ser Val Asn Val Arg Gly Gln Thr Gly Phe Gly Arg Val Asn
                85                  90                  95
Thr Met Val Asp Gly Ile Ser Gln Thr Phe Phe Ala Thr Ser Gly Asp
                100                 105                 110
Asn Ser Glu Lys Ala Gly Gly Thr Ser Gln Phe Gly Ala Thr Ile Asp
            115                 120                 125
Pro Ala Phe Ile Thr Ser Val Asp Ile Gln Arg Gly Ser Phe Asp Gly
        130                 135                 140
Lys Ala Gly Ala Asn Ala Leu Val Gly Ser Ala Asn Phe Arg Thr Ile
145                 150                 155                 160
Gly Val Asp Asp Val Ile Ser Glu Gly Arg Asn Val Gly Ala Leu Leu
                165                 170                 175
```

```
Asn Val Gly Gly Gly Thr Asn Ala Thr Gly Pro Asn Tyr Met Gly Ala
            180                 185                 190

Val Ala Phe Arg Tyr Pro Phe Ser Asp Thr Arg Thr Leu Gly Phe Met
            195                 200                 205

Tyr Ala Tyr Ser Trp Arg Lys Ser Ser Gln Asp Phe Lys Val Gly Gly
        210                 215                 220

Gly Arg Ser Ile Lys Asp Val Asp Ala Glu Glu Val Gly Arg Ile Val
225                 230                 235                 240

Glu Glu Ala Cys Lys Gly Glu Ala Phe Cys Asp Arg Asn Glu Lys Arg
                245                 250                 255

Lys Leu Tyr Gly Leu Gln Pro Tyr Asp Pro Ser Lys Leu Leu His Tyr
            260                 265                 270

Pro Gln Ser His Leu Ala Lys Ile Glu Tyr Asn Asp Lys Tyr Asn Lys
            275                 280                 285

Ala Ile Leu Ser Tyr Arg Ser Leu Ser Thr Ala Leu Ser Gly Arg Asn
            290                 295                 300

Leu Glu Asn Lys Asn Tyr Gln Leu Asn Tyr Gln Leu Lys Pro Lys Glu
305                 310                 315                 320

Asn Leu Gln Phe Glu Leu Ile Leu Ala Asp Asn Thr Ser Thr Gln Thr
                325                 330                 335

Tyr His Lys Gly Ser Val Phe Asn Gly Lys Met Leu Lys Asp Val Leu
            340                 345                 350

Glu Ser Lys Asn Ser Ala Lys Thr Thr Asp Ile Asn Met His Phe Ser
            355                 360                 365

Ile Pro Phe Thr Glu Lys Phe Ser Tyr Glu Ala Thr Leu Gly Ala Asn
370                 375                 380

Ile Leu Lys Asn Lys Tyr Ser Lys Asn Arg His Pro Arg Glu Leu Gly
385                 390                 395                 400

Tyr Tyr Phe Asp Gly Glu Pro Asn Ser Leu Asp Ala Cys Asp Glu
                405                 410                 415

Val Gly Lys Tyr Lys Asn Ala Cys Lys Tyr His Gly Ile Arg Ser Asn
            420                 425                 430

Thr Phe Gln Pro Asp Gly Glu Gln Arg Phe Lys Thr Leu Tyr Phe Asp
            435                 440                 445

Gln Thr Phe Lys Tyr Asp Ile Tyr Thr Leu Lys Val Asn Ala Asn Arg
        450                 455                 460

Gln Ile Tyr Lys Tyr Glu Gly Arg Ile Phe Pro Leu Asp Pro Lys Asp
465                 470                 475                 480

Arg Phe Ser Ser Arg Thr Trp His Asp Ser His Lys Lys Met Lys Asn
                485                 490                 495

Gly Lys Pro Ile Trp Val Asn Ser Asn Ser Ser Glu Ile Val Ala Lys
            500                 505                 510

Tyr Gly Val Glu Glu Ala Glu Lys Leu Gly Cys Tyr Thr Gly Pro Asn
            515                 520                 525

Asp Asp Asp Thr Thr Trp Asp Val Tyr Asn Cys Pro Ser Phe Tyr Ser
530                 535                 540

Val His Lys Gly Asp Ser Arg Ser His Asp Asn Tyr Ser Met Ser Phe
545                 550                 555                 560

Ser Ala Asp Phe His Pro Leu Phe Ser Pro Phe Val Ser Tyr Ala Lys
                565                 570                 575

Thr His Arg Val Pro Asn Ile Lys Glu Met Tyr Phe Ser Glu Phe Gly
            580                 585                 590

Thr Leu Ala Ile Arg Pro Asp Leu Lys Ser Glu Lys Ala Lys Thr Ile
```

```
                595                 600                 605

Gln Phe Gly Ile Asn Gly Tyr Lys Asn Gly Ile Phe Ser Asp Phe Asp
    610                 615                 620

Ala Leu Gly Phe Lys Ile Leu Ala Tyr Gln Thr Lys Ile Arg Asp Tyr
625                 630                 635                 640

Ile Ile Asn Ile Lys Gln Glu Cys Ser Ser Asn Ala Trp Arg Gly Ser
                645                 650                 655

Asn Lys Ala Pro Thr Ile Tyr Asp Cys Val Glu His Leu Thr His Ile
            660                 665                 670

Asn Tyr Glu Gly Gly Lys Thr Ile Leu Lys Thr Asp Leu Val Asp Thr
        675                 680                 685

Gly Asp Gly Lys Thr Lys Val Pro Ser Asn Gln Leu Ile Pro Ala Asp
690                 695                 700

Ser Ser Pro Ile Val Lys Ile Gln Gly Leu Glu Leu Glu Leu Asn Tyr
705                 710                 715                 720

Asp Ile Gly Trp Phe Tyr Ala Asn Leu Ser Tyr Ala Arg Gln Lys Thr
                725                 730                 735

Asn Gln Pro Ser Ser Phe Ser Asp Ser Ser Tyr Asn Val Ser Asp Asp
            740                 745                 750

Ser Glu Thr Gly Gln Tyr Leu Gln Gly Phe Gly Leu Ser Lys Ile Ser
        755                 760                 765

Ser Leu Pro Lys Asp Tyr Gly Ser Leu Asp Leu Gly Thr Arg Leu Phe
770                 775                 780

Asp Gly Lys Leu Thr Leu Gly Thr Ala Lys Tyr Tyr Gly Lys Ser
785                 790                 795                 800

Lys Arg Ala Arg Leu Asp Lys Ala Asp Gly Asp Val Ile Leu Pro Gly
                805                 810                 815

Thr Phe Thr Ser Arg Lys Thr Gly Glu Thr Phe Leu Thr Tyr Val Arg
            820                 825                 830

Ile Ser Gly Thr Glu Glu Ile Lys Ala Gln Pro Ile Ile Phe Asp Phe
        835                 840                 845

Tyr Ala Ile Tyr Gln Pro Thr Glu Asn Leu Thr Ile Lys Gly Glu Ile
850                 855                 860

Gln Asn Ala Phe Asp Lys Lys Tyr Ile Asn Pro Leu Asp Ala Asn Asn
865                 870                 875                 880

Asp Ser Ala Asn Gln Met Thr Tyr Ala Met Gly Val Gly Asp Gly Tyr
                885                 890                 895

Gln Lys Ala Leu Asn Asn Tyr Ser Lys Gly Arg Thr Phe Val Leu Asn
            900                 905                 910

Val Asn Tyr Lys Phe
        915

<210> SEQ ID NO 70
<211> LENGTH: 902
<212> TYPE: PRT
<213> ORGANISM: Moraxella catarrhalis

<400> SEQUENCE: 70

Met Met Ile Thr Gly Asn Thr Met Asn Gln Ile Phe His Leu Met Thr
1               5                   10                  15

Gln Thr Lys His Thr Asn His Thr Lys Lys Val Leu Lys Leu Ser Met
            20                  25                  30

Leu Ser Leu Cys Leu Leu His Ile Thr Gln Thr Ala Met Ala Glu Asp
        35                  40                  45
```

-continued

```
Thr Leu Lys Asp Val Pro Lys Ala Thr Asp Phe Ser Val Ile Leu Asp
     50                  55                  60

Glu Val Val Thr Ala Thr Asn Gly Thr Lys Lys Ser Gln Lys Pro
 65              70                  75                  80

Phe Thr Lys Ala Ser Ala Thr Ser Val Arg Glu Asn Val Phe Asn Ala
                 85                  90                  95

Ser Glu Asn Ile Asp Ala Ile Val Arg Ser Val Pro Gly Ala Phe Thr
                100                 105                 110

Gln Gln Asp Lys Ser Ser Gly Leu Val Ser Leu Asn Val Arg Gly Asp
                115                 120                 125

Ser Gly Phe Gly Arg Ala Asn Ser Met Val Asp Gly Val Thr Gln Thr
     130                 135                 140

Phe Tyr Ser Thr Ser Thr Asp Ala Gly Arg Gly Gly Thr Ser Gln
 145                 150                 155                 160

Phe Gly Ala Val Ile Asp Gln Asn Phe Ile Ala Gly Val Glu Leu Asn
                 165                 170                 175

Lys Gly Ser Phe Asn Gly Lys Gly Gly Leu Asn Thr Leu Thr Gly Ser
                 180                 185                 190

Ala Asn Phe Arg Thr Leu Asn Ala Asp Asp Val Ile Lys Asp Lys
     195                 200                 205

Asn Phe Gly Phe Ile Ala Lys Gly Leu Thr Gly Lys Asn Ala Thr Asp
     210                 215                 220

Lys Asn Phe Met Leu Ala Ala Gly Gly Arg Gly Trp Leu Asp Asn Gly
 225                 230                 235                 240

Ser Ile Ser Ala Leu Tyr Ala Tyr Ser His Lys Asp Ile Ser Gln Asn
                 245                 250                 255

Tyr Lys Val Gly Gly Gly Gly Thr His Ile Gly Asn Val Gly Asp Asp
                 260                 265                 270

Leu Leu Leu Ser Lys Gln Lys Gln Val Phe Ala Lys Glu His Ala Leu
         275                 280                 285

Thr Tyr Asn Glu Ala Ser Arg Ser Trp Gln Lys Asp Leu Thr Lys Leu
     290                 295                 300

Asp Lys Glu Thr Gly Lys Pro Leu Trp Asp Arg Lys Tyr Gln Phe Gly
 305                 310                 315                 320

Gly Lys Cys Tyr Gly Leu Gly Cys Ile Asp Thr Lys Glu Lys Phe Asp
                 325                 330                 335

Glu Tyr Val Ala Asp Lys Gln Gln Trp Gln Lys His Gly Ala Lys
                 340                 345                 350

Glu Tyr Ser Ile Thr Pro Ile Asp Ile Thr Ala Leu Asn Gln Thr Ser
     355                 360                 365

Lys Ser His Leu Ala Lys Ile Arg Tyr Asn Asn Asp Thr Ser Asp Val
 370                 375                 380

Gly Leu Gln Leu Arg Lys Met Asp Thr Thr Ile Gly Ser Arg Arg Ile
 385                 390                 395                 400

Ser Asn Asp Asn Tyr Gln Leu Asp Ala Ala Tyr Asn Pro Asn Glu Ile
                 405                 410                 415

Ile Asp Leu Lys Val Leu Ala Ala His Asn Val Gly Val Gln Lys Tyr
                 420                 425                 430

Pro Lys Gly Ser Thr Phe Thr Gly Trp Lys Leu Asp Lys Asp Phe Glu
     435                 440                 445

Thr Lys Asn Thr Ala Asn Leu Phe Asp Leu Asn Asn Thr His Thr Phe
 450                 455                 460

Asn Leu Pro Lys Gln Met Asp Leu Thr Thr Thr Val Gly Leu Asn Ile
```

-continued

```
            465                 470                 475                 480
Leu His Asn Glu Tyr Ser Lys Asn Arg Phe Pro Asp Glu Leu Gly Leu
                    485                 490                 495

Phe Tyr Thr Asn Asp Leu Leu Cys Gly Gly Tyr Asp Ala Cys Gly
            500                 505                 510

Gly Arg Phe Gln Gly Thr Ser Thr Leu Pro Lys Lys Ser Val Ile
            515                 520                 525

Val Gln Pro Ser Gly Lys Gln Arg Phe His Ser Ile Tyr Leu Asp Thr
    530                 535                 540

Ser Leu Gln Lys Asp Lys Tyr Gln Leu Asp Tyr Ser Val Asn Ala Ser
545                 550                 555                 560

Gln Tyr Arg Phe Ser Gly Glu His Ala Ser Tyr Tyr Ser Ser Gln Lys
                565                 570                 575

Glu Phe Gln Asp Lys Phe Gly Glu Asp Ser Gln Ile Tyr Lys Gln His
            580                 585                 590

Cys Ser Pro Ser Cys Asp Val Tyr Glu Pro Leu Val Thr Thr Ser Gly
            595                 600                 605

Lys Lys His Ala Ile Asn His Ser Val Thr Leu Ser Ala Lys Tyr Asp
    610                 615                 620

Thr Gly Phe Met Pro Phe Val Ser Phe Ala Arg Thr His Arg Met Pro
625                 630                 635                 640

Asn Ile Gln Glu Met Phe Phe Ser Gln Ile Gly Asp Val Gly Val Asn
                645                 650                 655

Thr Ala Leu Lys Pro Glu Gln Ala Asn Thr Tyr Gln Leu Gly Phe Asn
            660                 665                 670

Val Phe Lys Arg Asn Leu Leu Thr Asp Asn Asp Thr Leu Gly Leu Lys
            675                 680                 685

Val Val Gly Tyr Gln Ser Arg Ile Asn Asn Tyr Ile His Asn Val Tyr
    690                 695                 700

Gly Lys Trp Tyr Asp Thr Lys Asn Pro Pro Ser Trp Val Thr Ser Gly
705                 710                 715                 720

Ala Leu Lys Gly Asp Thr Ile Gln His Arg Asn Trp Gln Met Pro Val
                725                 730                 735

His Lys Gln Gly Leu Glu Leu Glu Ile Asn Tyr Asp Ala Gly Arg Tyr
            740                 745                 750

Phe Thr Asn Leu Ser Tyr Ala Arg Gln Lys Thr Asp Gln Pro Thr Asn
            755                 760                 765

Tyr Ser Asp Ala Ser Glu Ser Pro Arg Asn Ser Ser Lys Glu Asp Gln
    770                 775                 780

Leu Thr Gln Gly Tyr Gly Leu Ser Lys Val Ser Met Leu Pro Lys Asp
785                 790                 795                 800

Tyr Gly Arg Phe Glu Leu Gly Val Arg Gly Phe Asp Asp Lys Leu Thr
                805                 810                 815

Ile Gly Ser Ala Val Arg Tyr Gly Gln Ser Pro Arg Ala Thr Ile
            820                 825                 830

Glu Pro Arg Tyr Ile Asp Gly Thr His Gly Gly Asn Thr Ser His Ser
            835                 840                 845

Asp Asp Lys Gly Ala His Val Ile Lys Gln Ile Glu Met Leu Lys Arg
    850                 855                 860

Gln Pro Leu Val His Asp Phe Tyr Val Ala Tyr Glu Pro Ile Lys Asp
865                 870                 875                 880

Leu Val Met Arg Leu Asp Val Gln Asn Ala Phe Asp Lys Leu Tyr Ile
                885                 890                 895
```

Asp Pro Leu Asp Ala Asn
            900

<210> SEQ ID NO 71
<211> LENGTH: 860
<212> TYPE: PRT
<213> ORGANISM: Pasteurella dagmatis ATCC 43325

<400> SEQUENCE: 71

Met Asn Lys Ser Arg Lys Gly Leu Ser Tyr Ile Leu Pro Leu Ile Ile
1               5                   10                  15

Pro Phe Cys Ala Tyr Ala Glu Thr Thr Glu Leu Asp Val Ile Ser Val
            20                  25                  30

Glu Thr Glu Ala Phe Lys Glu Lys Asp Lys Val Phe Leu Lys Gln Ser
        35                  40                  45

Ala Ser Ser Thr Arg Thr Asn Phe Glu Thr Ser Thr Gln Ser Leu Asp
    50                  55                  60

Thr Val Leu Arg Ser Val Pro Gly Ala Phe Thr Gln Ile Asp Lys Ser
65                  70                  75                  80

Ser Gly Thr Val Ser Val Asn Val Arg Gly Gly Thr Gly Phe Gly Arg
                85                  90                  95

Val Asn Ser Met Ile Asp Gly Val Ser Gln Thr Phe Tyr Ala Ser Ser
            100                 105                 110

Ala Asp Gly Gly Ser Arg Ser Ser Thr Ser Gln Phe Gly Asn Leu
        115                 120                 125

Ile Asp Pro Gly Phe Leu Asn Ser Val Asp Ile Asp Arg Gly Ser Phe
    130                 135                 140

Glu Gly Ser Ser Gly Ala Asn Thr Leu Leu Gly Ser Ala Asn Phe Lys
145                 150                 155                 160

Thr Ile Gly Val Lys Asp Leu Val Thr Glu Gly Arg Gln Ile Gly Phe
                165                 170                 175

Met Gly Lys Tyr Leu Trp Gly Ser Asn Ala Thr Lys Pro Gln Ile Leu
            180                 185                 190

Gly Ala Val Ala Phe Lys Arg Asp Phe Glu Lys Glu Arg Trp Ile Gly
        195                 200                 205

Leu Leu Tyr Gly Phe Ser Glu Arg His Leu Ser Gln Asp Tyr Arg Ile
    210                 215                 220

Gly Gly Gly Arg Lys Val Thr Glu Ser Ser Ile Asp Leu Thr Gly Leu
225                 230                 235                 240

Asp Glu Asp Asp Ile Glu Gln Thr Asp Thr Ser Pro Phe Asp Ala Ala
                245                 250                 255

His Val Arg Gln Arg Pro Ile Ser His Leu Ala Lys Leu Glu Tyr Gly
            260                 265                 270

Asp His Tyr Gln Gln Ser Thr Leu Ser Tyr Arg Gln Tyr Gln Thr Gly
        275                 280                 285

Val Gly Gly Arg Ser Ile Gln Asn Asn Tyr Gln Val Asn Tyr Asn
    290                 295                 300

Phe Thr Leu Pro Asp Ser Ser Trp Leu Asp Phe Asn Phe Leu Ala Ala
305                 310                 315                 320

Arg Asn Glu Ser Ser Gln Lys Tyr Ala Lys Gly Ala Met Ile Ile Gly
                325                 330                 335

Lys Pro Leu Leu Glu Pro Leu Thr Val Asn Asn Lys Ala Asp Thr Ile
            340                 345                 350

Asp Ile Asn Asn Thr Phe Arg Phe Glu Leu Pro Phe Glu Thr Ala Leu

-continued

```
                355                 360                 365
Lys Thr Arg Ile Gly Leu Thr Thr Leu Lys Ser Arg Tyr Phe Lys Asn
370                 375                 380

Arg Asp Pro Ser Glu Glu Leu Asn Ile Asn Leu Glu Asp Glu Asp Lys
385                 390                 395                 400

Pro Tyr Asp Phe Asp Cys Phe Gly Leu Gly Cys Val Arg Lys Ser Leu
                405                 410                 415

Gly Lys Ala Thr Phe Gln Pro Asn Gly Lys Gln Asn Ile Ile Thr Phe
                420                 425                 430

Tyr Ile Asp Asn Asn Leu Ser Trp Lys Ile Leu Ser Phe Asp Tyr Asn
                435                 440                 445

Val Asn Leu Ser Arg Tyr Ser Leu Lys Gly Glu Arg Leu Lys Tyr Leu
450                 455                 460

Pro Gln Tyr Ile Ser Asp Thr Ser Ala Glu Ile Asn Val Leu Ser Arg
465                 470                 475                 480

Lys Ile Ala Arg Glu Lys Asn Pro Glu Val Arg Lys Gln Leu Gln Thr
                485                 490                 495

Gln Ile Gln Glu Leu Glu Ser Lys Leu Ala Tyr Ile Lys Gln His Asn
                500                 505                 510

Cys Val Arg Thr Tyr Asp Glu Asp Leu Asp Glu Tyr Leu Glu Glu Cys
                515                 520                 525

Arg Glu Val His Phe Thr Leu Pro Asp Ser Ser Ala Gly Lys Met Tyr
530                 535                 540

Asn Tyr Ser Ala Thr Leu Ser Ala Asn Ile His Asp Leu Phe Thr Pro
545                 550                 555                 560

Phe Ile Ser Tyr Ser Lys Ser His Arg Ala Pro Asn Ile Arg Glu Val
                565                 570                 575

Phe Phe Ser Ser Val Ser Asp Tyr Gly Val Asn Thr Asn Leu Arg Pro
                580                 585                 590

Glu Lys Ala Lys Val Ile Gln Phe Gly Ile Asn Gly Tyr Gln Glu Lys
                595                 600                 605

Val Phe Thr Asp Asn Asp Lys Leu Gly Tyr Lys Val Val Tyr Tyr Asn
                610                 615                 620

Thr His Val Lys Asp Phe Ile Tyr Asn Ser Asp Asn Arg Gln Pro Leu
625                 630                 635                 640

Val Ala Gly Lys Leu Arg Tyr Leu Asn Asp Thr Asn Ile Leu His Lys
                645                 650                 655

Asn Tyr Gln Gln Arg Val Lys Met Thr Gly Ile Glu Thr Glu Leu Ser
                660                 665                 670

Tyr Asp Leu Gly Asn Ile Tyr Phe Asn Leu Ala Tyr Ala Arg Gln Lys
                675                 680                 685

Asn Asn Gln Pro Val Ser Phe Thr Asp Gly Ser Ala Arg Gly Lys Gly
                690                 695                 700

Ala Ser Glu Thr Glu Arg Leu Leu Gln Gly Phe Gly Ala Ser Lys Ile
705                 710                 715                 720

Ser Ile Leu Pro Lys Asp Tyr Gly Ser Leu Glu Ile Gly Thr Arg Phe
                725                 730                 735

Leu Asp Gly Lys Leu Asn Phe Ser Gly Thr Ala Lys Tyr Tyr Gly Ser
                740                 745                 750

Ser Lys Arg Val Leu Ser Lys Pro Leu Thr Ile Lys Ser Gly Asp Ala
                755                 760                 765

Arg Asp Thr Val Lys Glu Arg Ile Arg Val Thr Glu Glu Ile Pro Lys
770                 775                 780
```

Gln Pro Ile Ile Val Asp Leu Gln Val Ser Tyr Glu Pro Leu Lys Asn
785                 790                 795                 800

Leu Val Leu Lys Ala Glu Val Gln Asn Val Phe Asp Lys Arg Tyr Val
            805                 810                 815

Asn Pro Leu Asp Ser Asn Asn Asp Ala Ala Ser Gln Ser Val Phe Asn
        820                 825                 830

Leu Asp Leu Ser Asp Gln Thr Ile Asn Val Leu Asn Asn Phe Ala Arg
    835                 840                 845

Gly Arg Thr Tyr Val Phe Thr Val Ser Tyr Lys Tyr
850                 855                 860

<210> SEQ ID NO 72
<211> LENGTH: 23
<212> TYPE: DNA
<213> ORGANISM: Escherichia coli
<220> FEATURE:
<221> NAME/KEY: misc_feature
<222> LOCATION: (12)..(12)
<223> OTHER INFORMATION: n is a, c, g, or t

<400> SEQUENCE: 72
gaaatgttat antataacat ttc                                           23

<210> SEQ ID NO 73
<211> LENGTH: 23
<212> TYPE: DNA
<213> ORGANISM: Neisseria meningitidis

<400> SEQUENCE: 73
gtaatgttat ataataacaa act                                           23

<210> SEQ ID NO 74
<211> LENGTH: 23
<212> TYPE: DNA
<213> ORGANISM: Neisseria meningitidis

<400> SEQUENCE: 74
caaacgttat acagtatcat atc                                           23

<210> SEQ ID NO 75
<211> LENGTH: 30
<212> TYPE: DNA
<213> ORGANISM: Artificial Sequence
<220> FEATURE:
<223> OTHER INFORMATION: primer sequence

<400> SEQUENCE: 75
gatcatatgc atgaaactga gcaatcggtg                                    30

<210> SEQ ID NO 76
<211> LENGTH: 33
<212> TYPE: DNA
<213> ORGANISM: Artificial Sequence
<220> FEATURE:
<223> OTHER INFORMATION: primer sequence

<400> SEQUENCE: 76
gatggatcct taaatcttca cgttcacgcc gcc                                33

<210> SEQ ID NO 77
<211> LENGTH: 26
<212> TYPE: DNA
<213> ORGANISM: Artificial Sequence
<220> FEATURE:
<223> OTHER INFORMATION: primer sequence

<400> SEQUENCE: 77
tgacgcgtct cgacgctgag gtctgc                                26

<210> SEQ ID NO 78
<211> LENGTH: 28
<212> TYPE: DNA
<213> ORGANISM: Artificial Sequence
<220> FEATURE:
<223> OTHER INFORMATION: primer sequence

<400> SEQUENCE: 78
tgtgtacagt cgacttcaga cggccacg                              28

<210> SEQ ID NO 79
<211> LENGTH: 31
<212> TYPE: DNA
<213> ORGANISM: Artificial Sequence
<220> FEATURE:
<223> OTHER INFORMATION: primer sequence

<400> SEQUENCE: 79
gcatcatatg gcacaaacta cactcaaacc c                          31

<210> SEQ ID NO 80
<211> LENGTH: 32
<212> TYPE: DNA
<213> ORGANISM: Artificial Sequence
<220> FEATURE:
<223> OTHER INFORMATION: primer sequence

<400> SEQUENCE: 80
atgacgtctt aaaacttcac gttcacgccg cc                         32

<210> SEQ ID NO 81
<211> LENGTH: 20
<212> TYPE: DNA
<213> ORGANISM: Artificial Sequence
<220> FEATURE:
<223> OTHER INFORMATION: primer sequence

<400> SEQUENCE: 81
gtacgatgat tgtgccgacc                                       20

<210> SEQ ID NO 82
<211> LENGTH: 40
<212> TYPE: DNA
<213> ORGANISM: Artificial Sequence
<220> FEATURE:
<223> OTHER INFORMATION: primer sequence

<400> SEQUENCE: 82
actttaaact ccgtcgacgc aagtcgactg cggggggttaa                40

<210> SEQ ID NO 83
<211> LENGTH: 40
<212> TYPE: DNA
<213> ORGANISM: Artificial Sequence
<220> FEATURE:
<223> OTHER INFORMATION: primer sequence

<400> SEQUENCE: 83 ttaaccccccg cagtcgactt gcgtcgacgg agtttaaagt                40

<210> SEQ ID NO 84
<211> LENGTH: 21
<212> TYPE: DNA
<213> ORGANISM: Artificial Sequence
<220> FEATURE:
<223> OTHER INFORMATION: primer sequence

<400> SEQUENCE: 84
gccatactgt tgcggatttg a                                             21

<210> SEQ ID NO 85
<211> LENGTH: 20
<212> TYPE: DNA
<213> ORGANISM: Artificial Sequence
<220> FEATURE:
<223> OTHER INFORMATION: primer sequence

<400> SEQUENCE: 85
ttcgccgatg gcggaataca                                               20

<210> SEQ ID NO 86
<211> LENGTH: 40
<212> TYPE: DNA
<213> ORGANISM: Artificial Sequence
<220> FEATURE:
<223> OTHER INFORMATION: primer sequence

<400> SEQUENCE: 86
ctttcagcgc aaagtcgact ccgtcgacgc gtgcctgttc                         40

<210> SEQ ID NO 87
<211> LENGTH: 40
<212> TYPE: DNA
<213> ORGANISM: Artificial Sequence
<220> FEATURE:
<223> OTHER INFORMATION: primer sequence

<400> SEQUENCE: 87
gaacaggcac gcgtcgacgg agtcgacttt gcgctgaaag                         40

<210> SEQ ID NO 88
<211> LENGTH: 20
<212> TYPE: DNA
<213> ORGANISM: Artificial Sequence
<220> FEATURE:
<223> OTHER INFORMATION: primer sequence

<400> SEQUENCE: 88
tcctattgcg caataccccc                                               20

<210> SEQ ID NO 89
<211> LENGTH: 67
<212> TYPE: PRT
<213> ORGANISM: Neisseria meningitidis

<400> SEQUENCE: 89

Arg Asp Gln Tyr Gly Leu Pro Ala His Ser His Glu Tyr Asp Asp Cys
1               5                   10                  15

His Ala Asp Ile Ile Trp Gln Lys Ser Leu Ile Asn Lys Arg Tyr Leu
            20                  25                  30

Gln Leu Tyr Pro His Leu Leu Thr Glu Glu Asp Ile Asp Tyr Asp Asn
        35                  40                  45

Pro Gly Leu Ser Cys Gly Phe His Asp Asp Asn Ala His Ala His
    50                  55                  60

Thr His Ser
65

<210> SEQ ID NO 90
<211> LENGTH: 758
<212> TYPE: PRT
<213> ORGANISM: Neisseria meningitidis MC58

<400> SEQUENCE: 90

```
Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285

Gln Leu Tyr Pro His Leu Leu Thr Glu Glu Asp Ile Asp Tyr Asp Asn
    290                 295                 300

Pro Gly Leu Ser Cys Gly Phe His Asp Asp Asn Ala His Ala His
305                 310                 315                 320

Thr His Ser Gly Arg Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
            340                 345                 350

Val His Leu Asn Arg Asn Asp Tyr Arg His Asp Glu Lys Ala Gly Asp
```

```
            355                 360                 365
Ala Val Glu Asn Phe Phe Asn Asn Gln Thr Gln Asn Ala Arg Ile Glu
370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                    405                 410                 415

Lys Gln Pro Met Leu Leu Asp Asn Lys Val Gln His Tyr Ser Phe Phe
                420                 425                 430

Gly Val Glu Gln Ala Asn Trp Asp Asn Phe Thr Leu Glu Gly Gly Val
            435                 440                 445

Arg Val Glu Lys Gln Lys Ala Ser Ile Gln Tyr Asp Lys Ala Leu Ile
        450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
                500                 505                 510

Ser Thr Gln Glu Leu Tyr Ala His Gly Lys His Val Ala Thr Asn Thr
            515                 520                 525

Phe Glu Val Gly Asn Lys His Leu Asn Lys Arg Ser Asn Asn Ile
530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Ser Glu Met Lys Leu
                580                 585                 590

Val Arg Tyr Asn Gln Ser Gly Ala Asp Phe Tyr Gly Ala Glu Gly Glu
            595                 600                 605

Ile Tyr Phe Lys Pro Thr Pro Arg Tyr Arg Ile Gly Val Ser Gly Asp
        610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Phe His Leu Lys Ala Ser Leu
                660                 665                 670

Thr Asp Arg Ile Asp Ala Asn Leu Asp Tyr Tyr Arg Val Phe Ala Gln
            675                 680                 685

Asn Lys Leu Ala Arg Tyr Glu Thr Arg Thr Pro Gly His His Met Leu
        690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
                740                 745                 750

Gly Val Asn Val Lys Phe
            755

<210> SEQ ID NO 91
```

```
<211> LENGTH: 758
<212> TYPE: PRT
<213> ORGANISM: Neisseria meningitidis O53322

<400> SEQUENCE: 91

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Gly
            20                  25                  30

Leu Glu Thr Val Thr Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
        195                 200                 205

Tyr Arg Lys Ser Gly Asp Tyr Ala Val Pro Arg Tyr Arg Asn Leu Lys
    210                 215                 220

Arg Leu Pro Asp Ser His Ala Asp Ser Lys Thr Gly Ser Ile Gly Leu
225                 230                 235                 240

Ser Trp Val Gly Glu Lys Gly Phe Ile Gly Ala Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
        275                 280                 285

Gln Leu Tyr Pro His Leu Leu Thr Glu Glu Asp Val Asp Tyr Asp Asn
    290                 295                 300

Pro Gly Leu Ser Cys Gly Phe His Asp Asp Asn Ala His Ala His
305                 310                 315                 320

Thr His Asn Gly Lys Pro Trp Ile Asp Leu Arg Asn Lys Arg Tyr Glu
                325                 330                 335

Leu Arg Ala Glu Trp Lys Gln Pro Leu Pro Gly Phe Glu Ala Leu Arg
            340                 345                 350

Val His Leu Asn Arg Asn Asp Tyr His His Asp Glu Lys Ala Gly Asp
        355                 360                 365

Ala Val Glu Asn Phe Phe Asn Asn Lys Thr Gln Asn Ala Arg Ile Glu
    370                 375                 380

Leu Arg His Gln Pro Ile Gly Arg Leu Lys Gly Ser Trp Gly Val Gln
```

```
            385                 390                 395                 400
Tyr Leu Gln Gln Lys Ser Ser Ala Leu Ser Ala Ile Ser Glu Ala Val
                    405                 410                 415
Lys Gln Pro Met Leu Leu Asp Asn Lys Val Gln His Tyr Ser Phe Phe
                420                 425                 430
Gly Val Glu Gln Ala Glu Trp Asp Asn Phe Thr Leu Glu Gly Gly Val
            435                 440                 445
Arg Val Glu Lys Gln Lys Ala Ser Ile Gln Tyr Asp Lys Ala Leu Ile
        450                 455                 460
Asp Arg Glu Asn Tyr Tyr Lys Gln Pro Leu Pro Asp Leu Gly Ala His
465                 470                 475                 480
Arg Gln Thr Ala Arg Ser Phe Ala Leu Ser Gly Asn Trp Tyr Phe Thr
                485                 490                 495
Pro Gln His Lys Leu Ser Leu Thr Ala Ser His Gln Glu Arg Leu Pro
                500                 505                 510
Ser Thr Gln Glu Leu Tyr Ala His Gly Lys His Val Ala Thr Asn Thr
            515                 520                 525
Phe Glu Val Gly Asn Lys His Leu Asn Lys Glu Arg Ser Asn Asn Ile
        530                 535                 540
Glu Leu Ala Leu Gly Tyr Glu Gly Asp Arg Trp Gln Tyr Asn Leu Ala
545                 550                 555                 560
Leu Tyr Arg Asn Arg Phe Gly Asn Tyr Ile Tyr Ala Gln Thr Leu Asn
                565                 570                 575
Asp Gly Arg Gly Pro Lys Ser Ile Glu Asp Ser Glu Met Lys Leu
                580                 585                 590
Val Arg Tyr Asn Gln Ser Gly Ala Asp Phe Tyr Gly Ala Glu Gly Glu
            595                 600                 605
Ile Tyr Phe Lys Pro Thr Pro Arg Tyr Arg Ile Gly Val Ser Gly Asp
        610                 615                 620
Tyr Val Arg Gly Arg Leu Lys Asn Leu Pro Ser Leu Pro Gly Arg Glu
625                 630                 635                 640
Asp Ala Tyr Gly Asn Arg Pro Phe Ile Ala Gln Asp Gln Asn Ala
                645                 650                 655
Pro Arg Val Pro Ala Ala Arg Leu Gly Val His Leu Lys Ala Ser Leu
                660                 665                 670
Thr Asp Arg Ile Asp Ala Asn Leu Asp Tyr Tyr Arg Val Phe Ala Gln
            675                 680                 685
Asn Lys Leu Ala Arg Tyr Glu Thr Arg Thr Pro Gly His His Met Leu
        690                 695                 700
Asn Leu Gly Ala Asn Tyr Arg Arg Asn Thr Arg Tyr Gly Glu Trp Asn
705                 710                 715                 720
Trp Tyr Val Lys Ala Asp Asn Leu Leu Asn Gln Ser Val Tyr Ala His
                725                 730                 735
Ser Ser Phe Leu Ser Asp Thr Pro Gln Met Gly Arg Ser Phe Thr Gly
                740                 745                 750
Gly Val Asn Val Lys Phe
        755

<210> SEQ ID NO 92
<211> LENGTH: 758
<212> TYPE: PRT
<213> ORGANISM: Neisseria meningitidis Z2491

<400> SEQUENCE: 92
```

```
Met Ala Gln Thr Thr Leu Lys Pro Ile Val Leu Ser Ile Leu Leu Ile
1               5                   10                  15

Asn Thr Pro Leu Leu Ser Gln Ala His Gly Thr Glu Gln Ser Val Gly
            20                  25                  30

Leu Glu Thr Val Ser Val Val Gly Lys Ser Arg Pro Arg Ala Thr Ser
        35                  40                  45

Gly Leu Leu His Thr Ser Thr Ala Ser Asp Lys Ile Ile Ser Gly Asp
    50                  55                  60

Thr Leu Arg Gln Lys Ala Val Asn Leu Gly Asp Ala Leu Asp Gly Val
65                  70                  75                  80

Pro Gly Ile His Ala Ser Gln Tyr Gly Gly Ala Ser Ala Pro Val
                85                  90                  95

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
        115                 120                 125

Asp Ser Ala Leu Ser Gln Gln Val Glu Ile Leu Arg Gly Pro Val Thr
    130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
            165                 170                 175

Gly Leu Arg Leu Ser Ser Gly Asn Leu Glu Lys Leu Thr Ser Gly Gly
        180                 185                 190

Ile Asn Ile Gly Leu Gly Lys Asn Phe Val Leu His Thr Glu Gly Leu
    195                 200                 205

Tyr Arg Lys Ser Gly Asp Tyr Ala Val Pro Arg Tyr Arg Asn Leu Lys
210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Ala Ala Tyr Ser Asp Arg
            245                 250                 255

Arg Asp Gln Tyr Gly Leu Pro Ala His Ser His Glu Tyr Asp Asp Cys
        260                 265                 270

His Ala Asp Ile Ile Trp Gln Lys Ser Leu Ile Asn Lys Arg Tyr Leu
    275                 280                 285

Gln Leu Tyr Pro His Leu Leu Thr Glu Glu Asp Ile Asp Tyr Asp Asn
290                 295                 300

Pro Gly Leu Ser Cys Gly Phe His Asp Asp Asp Ala His Ala His
305                 310                 315                 320

Ala His Asn Gly Lys Pro Trp Ile Asp Leu Arg Asn Lys Arg Tyr Glu
            325                 330                 335

Leu Arg Ala Glu Trp Lys Gln Pro Phe Pro Gly Phe Glu Ala Leu Arg
        340                 345                 350

Val His Leu Asn Arg Asn Asp Tyr Arg His Asp Glu Lys Ala Gly Asp
    355                 360                 365

Ala Val Glu Asn Phe Phe Asn Asn Gln Thr Gln Asn Ala Arg Ile Glu
370                 375                 380

Leu Arg His Gln Pro Ile Gly Arg Leu Lys Gly Ser Trp Gly Val Gln
385                 390                 395                 400

Tyr Leu Gly Gln Lys Ser Ser Ala Leu Ser Ala Thr Ser Glu Ala Val
            405                 410                 415

Lys Gln Pro Met Leu Leu Asp Asn Lys Val Gln His Tyr Ser Phe Phe
```

```
                420                 425                 430
Gly Val Glu Gln Ala Asn Trp Asp Asn Phe Thr Leu Glu Gly Gly Val
            435                 440                 445

Arg Val Glu Lys Gln Lys Ala Ser Ile Arg Tyr Asp Lys Ala Leu Ile
        450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Arg Ser Asn Asn Ile
            530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Ser Glu Met Lys Leu
            580                 585                 590

Val Arg Tyr Asn Gln Ser Gly Ala Asp Phe Tyr Gly Ala Glu Gly Glu
        595                 600                 605

Ile Tyr Phe Lys Pro Thr Pro Arg Tyr Arg Ile Gly Val Ser Gly Asp
            610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Leu Ile Ala Gln Ala Asp Gln Asn Ala
                645                 650                 655

Pro Arg Val Pro Ala Ala Arg Leu Gly Val His Leu Lys Ala Ser Leu
            660                 665                 670

Thr Asp Arg Ile Asp Ala Asn Leu Asp Tyr Tyr Arg Val Phe Ala Gln
        675                 680                 685

Asn Lys Leu Ala Arg Tyr Glu Thr Arg Thr Pro Gly His His Met Leu
            690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
            740                 745                 750

Gly Val Asn Val Lys Phe
        755

<210> SEQ ID NO 93
<211> LENGTH: 758
<212> TYPE: PRT
<213> ORGANISM: Neisseria meningitidis FAM18

<400> SEQUENCE: 93

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
            20                  25                  30
```

```
Leu Glu Thr Val Ser Val Val Gly Lys Ser Arg Pro Arg Ala Thr Ser
         35                  40                  45

Gly Leu Leu His Thr Ser Thr Ala Ser Asp Lys Ile Leu Ser Gly Asp
 50                  55                  60

Thr Leu Arg Gln Lys Ala Val Asn Leu Gly Asp Ala Leu Asp Gly Val
 65                  70                  75                  80

Pro Gly Ile His Ala Ser Gln Tyr Gly Gly Ala Ser Ala Pro Val
                 85                  90                  95

Ile Arg Gly Gln Thr Gly Arg Arg Ile Lys Val Leu Asn His His Gly
                100                 105                 110

Glu Thr Gly Asp Met Ala Asp Phe Ser Pro Asp His Ala Ile Met Val
        115                 120                 125

Asp Thr Ala Leu Ser Gln Gln Val Glu Ile Leu Arg Gly Pro Val Thr
130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
                180                 185                 190

Ile Asn Ile Gly Leu Gly Lys Asn Phe Val Leu His Thr Glu Gly Leu
                195                 200                 205

Tyr Arg Lys Ser Gly Asp Tyr Ala Val Pro Arg Tyr Arg Asn Leu Lys
                210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
                245                 250                 255

Arg Asp Gln Tyr Gly Leu Pro Ala His Ser His Glu Tyr Asp Asp Cys
                260                 265                 270

His Ala Asp Ile Ile Trp Gln Lys Ser Leu Ile Asn Lys Arg Tyr Leu
                275                 280                 285

Gln Leu Tyr Pro His Leu Leu Thr Glu Glu Asp Ile Asp Tyr Asp Asn
                290                 295                 300

Pro Gly Leu Ser Cys Gly Phe His Asp Asp Asp Ala His Ala His
305                 310                 315                 320

Thr His Ser Gly Arg Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
                340                 345                 350

Val His Leu Asn Arg Asn Asp Tyr Arg His Asp Glu Lys Ala Gly Asp
                355                 360                 365

Ala Val Glu Asn Phe Phe Asn Asn Gln Thr Gln Asn Ala Arg Ile Glu
                370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                405                 410                 415

Lys Gln Pro Met Leu Leu Asp Asn Lys Val Gln His Tyr Ser Phe Phe
                420                 425                 430

Gly Val Glu Gln Ala Asn Trp Asp Asn Phe Thr Leu Glu Gly Gly Val
                435                 440                 445

Arg Val Glu Lys Gln Lys Ala Ser Ile Arg Tyr Asp Lys Ala Leu Ile
```

```
            450                 455                 460
Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Asp Ser Glu Met Lys Leu
            580                 585                 590

Val Arg Tyr Asn Gln Ser Gly Ala Asp Phe Tyr Gly Ala Glu Gly Glu
        595                 600                 605

Ile Tyr Phe Lys Pro Thr Pro Arg Tyr Arg Ile Gly Val Ser Gly Asp
    610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Val His Leu Lys Ala Ser Leu
            660                 665                 670

Thr Asp Arg Ile Asp Ala Asn Leu Asp Tyr Tyr Arg Val Phe Ala Gln
        675                 680                 685

Asn Lys Leu Ala Arg Tyr Glu Thr Arg Thr Pro Gly His His Met Leu
    690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
            740                 745                 750

Gly Val Asn Val Lys Phe
        755

<210> SEQ ID NO 94
<211> LENGTH: 758
<212> TYPE: PRT
<213> ORGANISM: Neisseria meningitidis alpha14

<400> SEQUENCE: 94

Met Ala Gln Thr Thr Leu Lys Pro Ile Val Leu Ser Ile Leu Leu Ile
1               5                   10                  15

Asn Thr Pro Leu Leu Ala Gln Ala His Glu Thr Glu Gln Ser Val Asp
                20                  25                  30

Leu Glu Thr Val Ser Val Val Gly Lys Ser Arg Pro Arg Ala Thr Ser
            35                  40                  45

Gly Leu Leu His Thr Ser Thr Ala Ser Asp Lys Ile Ile Ser Gly Asp
        50                  55                  60
```

```
Thr Leu Arg Gln Lys Ala Val Asn Leu Gly Asp Ala Leu Asp Gly Val
 65                  70                  75                  80

Pro Gly Ile His Ala Ser Gln Tyr Gly Gly Ala Ser Ala Pro Val
             85                  90                  95

Ile Arg Gly Gln Thr Gly Arg Arg Ile Lys Val Leu Asn His His Gly
             100                 105                 110

Glu Thr Gly Asp Met Ala Asp Phe Ser Pro Asp His Ala Ile Met Val
             115                 120                 125

Asp Thr Ala Leu Ser Gln Gln Val Glu Ile Leu Arg Gly Pro Val Thr
             130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
             165                 170                 175

Gly Leu Arg Leu Ser Ser Gly Asn Leu Glu Lys Leu Thr Ser Gly Gly
             180                 185                 190

Ile Asn Ile Gly Leu Gly Lys Asn Phe Val Leu His Thr Glu Gly Leu
             195                 200                 205

Tyr Arg Lys Ser Gly Asp Tyr Ala Val Pro Arg Tyr Arg Asn Leu Lys
             210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Val Ala Tyr Ser Asp Arg
             245                 250                 255

Arg Asp Gln Tyr Gly Leu Pro Ala His Ser His Glu Tyr Asp Asp Cys
             260                 265                 270

His Ala Asp Ile Ile Trp Gln Lys Ser Leu Ile Asn Lys Arg Tyr Leu
             275                 280                 285

Gln Leu Tyr Pro His Leu Leu Thr Glu Glu Asp Val Asp Tyr Asp Asn
             290                 295                 300

Pro Gly Leu Ser Cys Gly Phe His Asp Asp Asp Ala His Ala His
305                 310                 315                 320

Ala His Asn Gly Lys Pro Trp Ile Asp Leu Arg Asn Lys Arg Tyr Glu
             325                 330                 335

Leu Arg Ala Glu Trp Lys Gln Pro Phe Pro Gly Phe Glu Ala Leu Arg
             340                 345                 350

Val His Leu Asn Arg Asn Asp Tyr Arg His Asp Glu Lys Ala Gly Asp
             355                 360                 365

Ala Val Glu Asn Phe Phe Asn Asn Gln Thr Gln Asn Ala Arg Ile Glu
             370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Thr Ser Glu Ala Val
             405                 410                 415

Lys Gln Pro Met Leu Leu Asp Asn Lys Val Gln His Tyr Ser Phe Phe
             420                 425                 430

Gly Val Glu Gln Ala Asn Trp Asp Asn Phe Thr Leu Glu Gly Gly Val
             435                 440                 445

Arg Val Glu Lys Gln Lys Ala Ser Ile Arg Tyr Asp Lys Ala Leu Ile
             450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
```

```
                    485                 490                 495
Pro Gln His Lys Leu Ser Leu Thr Ala Ser His Gln Glu Arg Leu Pro
                500                 505                 510
Ser Thr Gln Glu Leu Tyr Ala His Gly Lys His Val Ala Thr Asn Thr
            515                 520                 525
Phe Glu Val Gly Asn Lys His Leu Asn Lys Glu Arg Ser Asn Asn Ile
        530                 535                 540
Glu Leu Ala Leu Gly Tyr Glu Gly Asp Arg Trp Gln Tyr Asn Leu Ala
545                 550                 555                 560
Leu Tyr Arg Asn Arg Phe Gly Asn Tyr Ile Tyr Ala Gln Thr Leu Asn
                565                 570                 575
Asp Gly Arg Gly Pro Lys Ser Ile Glu Asp Ser Glu Met Lys Leu
            580                 585                 590
Val Arg Tyr Asn Gln Ser Gly Ala Asp Phe Tyr Gly Ala Glu Gly Glu
        595                 600                 605
Ile Tyr Phe Lys Pro Thr Pro Arg Tyr Arg Ile Gly Val Ser Gly Asp
        610                 615                 620
Tyr Val Arg Gly Arg Leu Lys Asn Leu Pro Ser Leu Pro Gly Arg Glu
625                 630                 635                 640
Asp Ala Tyr Gly Asn Arg Pro Phe Ile Ala Gln Asp Gln Asn Ala
            645                 650                 655
Pro Arg Val Pro Ala Ala Arg Leu Gly Val His Leu Lys Ala Ser Leu
        660                 665                 670
Thr Asp Arg Ile Asp Ala Asn Leu Asp Tyr Tyr Arg Val Phe Ala Gln
            675                 680                 685
Asn Lys Leu Ala Arg Tyr Glu Thr Arg Thr Pro Gly His His Met Leu
        690                 695                 700
Asn Leu Gly Ala Asn Tyr Arg Arg Asn Thr Arg Tyr Gly Glu Trp Asn
705                 710                 715                 720
Trp Tyr Val Lys Ala Asp Asn Leu Leu Asn Gln Ser Val Tyr Ala His
                725                 730                 735
Ser Ser Phe Leu Ser Asp Thr Pro Gln Met Gly Arg Ser Phe Thr Gly
            740                 745                 750
Gly Val Asn Val Lys Phe
        755

<210> SEQ ID NO 95
<211> LENGTH: 758
<212> TYPE: PRT
<213> ORGANISM: Neisseria meningitidis alpha153

<400> SEQUENCE: 95

Met Ala Gln Thr Thr Leu Lys Pro Ile Val Leu Ser Ile Leu Leu Ile
1               5                   10                  15
Asn Thr Pro Leu Leu Ala Gln Ala His Glu Thr Asp Arg Ser Val Asp
            20                  25                  30
Leu Glu Thr Val Ser Val Val Gly Lys Ser Arg Pro Arg Ala Thr Ser
        35                  40                  45
Gly Leu Leu His Thr Ser Thr Ala Ser Asp Lys Ile Ile Ser Gly Asp
    50                  55                  60
Thr Leu Arg Gln Lys Ala Val Asn Leu Gly Asp Ala Leu Asp Gly Val
65                  70                  75                  80
Pro Gly Ile His Ala Ser Gln Tyr Gly Gly Gly Ala Ser Ala Pro Val
                85                  90                  95
```

Ile Arg Gly Gln Thr Gly Arg Arg Ile Lys Val Leu Asn His His Gly
            100                 105                 110

Glu Thr Gly Asp Met Ala Asp Phe Ser Pro Asp His Ala Ile Met Val
            115                 120                 125

Asp Thr Ala Leu Ser Gln Gln Val Glu Ile Leu Arg Gly Pro Val Thr
130                 135                 140

Leu Leu Tyr Ser Ser Gly Asn Val Ala Gly Leu Val Asp Val Ala Asp
145                 150                 155                 160

Gly Lys Ile Pro Glu Lys Met Pro Glu Asn Gly Val Ser Gly Glu Leu
                165                 170                 175

Gly Leu Arg Leu Ser Ser Gly Asn Leu Glu Lys Leu Thr Ser Gly Gly
            180                 185                 190

Ile Asn Ile Gly Leu Gly Lys Asn Phe Val Leu His Thr Glu Gly Leu
            195                 200                 205

Tyr Arg Lys Ser Gly Asp Tyr Ala Val Pro Arg Tyr Arg Asn Leu Lys
            210                 215                 220

Arg Leu Pro Asp Ser His Ala Asp Ser Gln Thr Gly Ser Ile Gly Leu
225                 230                 235                 240

Ser Trp Val Gly Glu Lys Gly Phe Ile Gly Ala Ala Tyr Ser Asp Arg
                245                 250                 255

Arg Asp Gln Tyr Gly Leu Pro Ala His Ser His Glu Tyr Asp Asp Cys
            260                 265                 270

His Ala Asp Ile Ile Trp Gln Lys Ser Leu Ile Asn Lys Arg Tyr Leu
            275                 280                 285

Gln Leu Tyr Pro His Leu Leu Thr Glu Glu Asp Ile Asp Tyr Asp Asn
290                 295                 300

Pro Gly Leu Ser Cys Gly Phe His Asp Asp Asp Ala His Ala His
305                 310                 315                 320

Ala His Asn Gly Lys Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
            340                 345                 350

Val His Leu Asn Arg Asn Asp Tyr Arg His Asp Glu Lys Ala Gly Asp
            355                 360                 365

Ala Val Glu Asn Phe Phe Asn Asn Gln Thr Gln Asn Ala Arg Ile Glu
370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Thr Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
            435                 440                 445

Arg Val Glu Lys Gln Lys Ala Ser Ile Arg Tyr Asp Lys Ala Leu Ile
450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr

```
                515                 520                 525
Phe Glu Val Gly Asn Lys His Leu Asn Lys Glu Arg Ser Asn Asn Ile
    530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Ser Glu Met Lys Leu
            580                 585                 590

Val Arg Tyr Asn Gln Ser Gly Ala Asp Phe Tyr Gly Ala Glu Gly Glu
                595                 600                 605

Ile Tyr Phe Lys Pro Thr Pro Arg Tyr Arg Ile Gly Val Ser Gly Asp
    610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Val His Leu Lys Ala Ser Leu
                660                 665                 670

Thr Asp Arg Ile Asp Ala Asn Leu Asp Tyr Tyr Arg Val Phe Ala Gln
                675                 680                 685

Asn Lys Leu Ala Arg Tyr Glu Thr Arg Thr Pro Gly His His Met Leu
    690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
                725                 730                 735

Ser Ser Phe Leu Ser Asp Thr Pro Gln Met Gly Arg Ser Phe Thr Gly
                740                 745                 750

Gly Val Asn Val Lys Phe
            755

<210> SEQ ID NO 96
<211> LENGTH: 728
<212> TYPE: PRT
<213> ORGANISM: Neisseria meningitidis alpha 275

<400> SEQUENCE: 96

Val Asp Leu Glu Thr Val Ser Val Val Gly Lys Ser Arg Pro Arg Ala
1               5                   10                  15

Thr Ser Gly Leu Leu His Thr Ser Thr Ala Ser Asp Lys Ile Ile Ser
                20                  25                  30

Gly Asp Thr Leu Arg Gln Lys Ala Val Asn Leu Gly Asp Ala Leu Asp
            35                  40                  45

Gly Val Pro Gly Ile His Ala Ser Gln Tyr Gly Gly Ala Ser Ala
        50                  55                  60

Pro Val Ile Arg Gly Gln Thr Gly Arg Arg Ile Lys Val Leu Asn His
65                  70                  75                  80

His Gly Glu Thr Gly Asp Met Ala Asp Phe Ser Pro Asp His Ala Ile
                85                  90                  95

Met Val Asp Ser Ala Leu Ser Gln Gln Val Glu Ile Leu Arg Gly Pro
                100                 105                 110

Val Thr Leu Leu Tyr Ser Ser Gly Asn Val Ala Gly Leu Val Asp Val
            115                 120                 125
```

Ala Asp Gly Lys Ile Pro Glu Lys Met Pro Glu Asn Gly Val Ser Gly
    130                 135                 140

Glu Leu Gly Leu Arg Leu Ser Ser Gly Asn Leu Glu Lys Leu Thr Ser
145                 150                 155                 160

Gly Gly Ile Asn Ile Gly Leu Gly Lys Asn Phe Val Leu His Thr Glu
                165                 170                 175

Gly Leu Tyr Arg Lys Ser Gly Asp Tyr Ala Val Pro Arg Tyr Arg Asn
            180                 185                 190

Leu Lys Arg Leu Pro Asp Ser His Ala Asp Ser Gln Thr Gly Ser Ile
        195                 200                 205

Gly Leu Ser Trp Val Gly Glu Lys Gly Phe Ile Gly Ala Ala Tyr Ser
    210                 215                 220

Asp Arg Arg Asp Gln Tyr Gly Leu Pro Ala His Ser His Glu Tyr Asp
225                 230                 235                 240

Asp Cys His Ala Asp Ile Ile Trp Gln Lys Ser Leu Ile Asn Lys Arg
                245                 250                 255

Tyr Leu Gln Leu Tyr Pro His Leu Leu Thr Glu Glu Asp Ile Asp Tyr
            260                 265                 270

Asp Asn Pro Gly Leu Ser Cys Gly Phe His Asp Asp Asp Ala His
        275                 280                 285

Ala His Ala His Asn Gly Lys Pro Trp Ile Asp Leu Arg Asn Lys Arg
    290                 295                 300

Tyr Glu Leu Arg Ala Glu Trp Lys Gln Pro Phe Pro Gly Phe Glu Ala
305                 310                 315                 320

Leu Arg Val His Leu Asn Arg Asn Asp Tyr His His Asp Glu Lys Ala
                325                 330                 335

Gly Asp Ala Val Glu Asn Phe Phe Asn Asn Gln Thr Gln Asn Ala Arg
            340                 345                 350

Ile Glu Leu Arg His Gln Pro Ile Gly Arg Leu Lys Gly Ser Trp Gly
        355                 360                 365

Val Gln Tyr Leu Gly Gln Lys Ser Ser Ala Leu Ser Ala Thr Ser Glu
    370                 375                 380

Ala Val Lys Gln Pro Met Leu Leu Asp Asn Lys Val Gln His Tyr Ser
385                 390                 395                 400

Phe Phe Gly Val Glu Gln Ala Asn Trp Asp Asn Phe Thr Leu Glu Gly
                405                 410                 415

Gly Val Arg Val Glu Lys Gln Lys Ala Ser Ile Arg Tyr Asp Lys Ala
            420                 425                 430

Leu Ile Asp Arg Glu Asn Tyr Tyr Asn His Pro Leu Pro Asp Leu Gly
        435                 440                 445

Ala His Arg Gln Thr Ala Arg Ser Phe Ala Leu Ser Gly Asn Trp Tyr
    450                 455                 460

Phe Thr Pro Gln His Lys Leu Ser Leu Thr Ala Ser His Gln Glu Arg
465                 470                 475                 480

Leu Pro Ser Thr Gln Glu Leu Tyr Ala His Gly Lys His Val Ala Thr
                485                 490                 495

Asn Thr Phe Glu Val Gly Asn Lys His Leu Asn Lys Glu Arg Ser Asn
            500                 505                 510

Asn Ile Glu Leu Ala Leu Gly Tyr Glu Gly Asp Arg Trp Gln Tyr Asn
        515                 520                 525

Leu Ala Leu Tyr Arg Asn Arg Phe Gly Asn Tyr Ile Tyr Ala Gln Thr
    530                 535                 540

Leu Asn Asp Gly Arg Gly Pro Lys Ser Ile Glu Asp Asp Ser Glu Met

```
            545                 550                 555                 560
Lys Leu Val Arg Tyr Asn Gln Ser Gly Ala Asp Phe Tyr Gly Ala Glu
                565                 570                 575
Gly Glu Ile Tyr Phe Lys Pro Thr Pro Arg Tyr Arg Ile Gly Val Ser
                580                 585                 590
Gly Asp Tyr Val Arg Gly Arg Leu Lys Asn Leu Pro Ser Leu Pro Gly
                595                 600                 605
Arg Glu Asp Ala Tyr Gly Asn Arg Pro Phe Ile Ala Gln Asp Gln
                610                 615                 620
Asn Ala Pro Arg Val Pro Ala Ala Arg Leu Gly Val His Leu Lys Ala
625                 630                 635                 640
Ser Leu Thr Asp Arg Ile Asp Ala Asn Leu Asp Tyr Tyr Arg Val Phe
                645                 650                 655
Ala Gln Asn Lys Leu Ala Arg Tyr Glu Thr Arg Thr Pro Gly His His
                660                 665                 670
Met Leu Asn Leu Gly Ala Asn Tyr Arg Arg Asn Thr Arg Tyr Gly Glu
                675                 680                 685
Trp Asn Trp Tyr Val Lys Ala Asp Asn Leu Leu Asn Gln Ser Val Tyr
                690                 695                 700
Ala His Ser Ser Phe Leu Ser Asp Thr Pro Gln Met Gly Arg Ser Phe
705                 710                 715                 720
Thr Gly Gly Val Asn Val Lys Phe
                725

<210> SEQ ID NO 97
<211> LENGTH: 803
<212> TYPE: PRT
<213> ORGANISM: Acinetobacter baumannii

<400> SEQUENCE: 97

Met Leu Asn Lys Ser Lys Leu Phe Leu Ala Leu Ile Thr Leu Gly Ala
1               5                   10                  15

Ser Lys Ile Leu Leu Ala Ala Glu Gly Pro Val Thr Thr Leu Asn Thr
                20                  25                  30

Ile Val Leu Thr Ala Gln Ser Asp Glu Leu Gly Ser Glu Leu Leu Gly
                35                  40                  45

Lys Ser Leu Asn Val Ser Asn Gln Phe Ile Asp Thr Ser Lys Leu Lys
                50                  55                  60

Gln Arg Ser Thr Thr Leu Gly Asp Ala Leu Gly Thr Glu Leu Gly Ile
65              70                  75                  80

His Ser Asn Gln Tyr Gly Gly Gly Ala Ser Ala Pro Ile Ile Arg Gly
                85                  90                  95

Gln Glu Gly Lys Arg Ile Lys Val Leu Gln Asn Asn Ala Asp Val Leu
                100                 105                 110

Asp Met Ser Asn Met Ser Pro Asp His Ala Val Thr Val Glu Pro Ser
                115                 120                 125

Leu Ala Lys Ser Ile Glu Ile Ile Arg Gly Ala Ser Thr Leu Leu Tyr
                130                 135                 140

Ser Ser Asn Ser Ala Ala Gly Val Val Asn Val Ile Asp Tyr Lys Ile
145                 150                 155                 160

Pro Thr Gln Met Pro Gln Asp Gly Leu Glu Gly Asn Thr Thr Leu Arg
                165                 170                 175

Phe Asn Thr Gly Ser Asn Glu Lys Leu Thr Thr Ala Gly Val Thr Val
                180                 185                 190
```

-continued

```
Gly Leu Ser Pro Arg Val Ala Leu Arg Ala Glu Gly Leu Tyr Arg Asn
            195                 200                 205

Ala Gly Asn Tyr Lys Thr Pro His Tyr Gln Ser Ser Tyr Asn Ser
    210                 215                 220

Leu Glu Asp Leu Glu Asn Gln Asn Ile Val Tyr Lys Asn Leu Lys Tyr
225                 230                 235                 240

Leu Pro Glu Ser Trp Ala Glu Ser Arg Leu Gly Thr Leu Gly Leu Ser
                245                 250                 255

Trp Ile Asp Asp Asn Thr Tyr Leu Gly Val Ser Tyr Thr His Arg His
                260                 265                 270

Asp Glu Tyr Gly Leu Pro Ala His Ser His Leu Tyr Glu Gly Cys Gly
            275                 280                 285

Ala Ser Ala Ile Ser Ile Asn Thr Arg Ile Ser Gly Leu Lys Asn Tyr
    290                 295                 300

Leu Leu Tyr Tyr Pro Gln Leu Met Glu Glu Gln Asp Ile Asn Tyr Val
305                 310                 315                 320

Asn Pro Arg Pro Asp Cys His Gln His Asn His Ile His Glu Thr Thr
                325                 330                 335

Phe Ser His Asn Ala Pro Tyr Ile Asp Leu Asn Thr Arg Arg Tyr Asp
            340                 345                 350

Met Arg Gly Glu Phe Thr Gln Pro Phe Thr Gly Ile Asp Lys Ile Arg
    355                 360                 365

Thr Ser Leu Ser Tyr Ile Asp Tyr Phe His Asn Glu Leu Glu Gly Asp
370                 375                 380

Lys Ile Thr Asn Phe Phe Lys Asn Thr Gly Lys Val Gly Arg Ile Glu
385                 390                 395                 400

Leu Ser His Gln Pro Leu Gly Glu Leu Thr Gly Ile Leu Gly Leu Gln
                405                 410                 415

Tyr Leu Glu Gln Asp Asn Ser Ala Leu Ser Pro Val His Ser Gln Glu
            420                 425                 430

Gly His Thr Thr Tyr Leu Asp Thr Gln Gln Leu Leu Asn Arg Asn Val
    435                 440                 445

Thr Lys Asn Phe Ser Val Phe Gly Leu Glu Lys Tyr Asn Trp Asn Asp
450                 455                 460

Phe Thr Phe Glu Leu Gly Ala Arg Ile Glu Lys Gln Lys Val Ser Met
465                 470                 475                 480

Asp Tyr Asp Ile Glu Lys Ile Lys Asp Ser Met Lys Pro Trp Pro Asn
                485                 490                 495

Lys Tyr Asn Ser Pro Tyr Val Glu Lys Asn Asn Lys Ile Arg Ala Gln
            500                 505                 510

Asn Leu Lys Ser Ile Leu Glu Ala Val Gln Pro Asn Lys Glu Thr Ala
    515                 520                 525

Phe Ser Tyr Ala Gly Thr Val His Trp Arg Phe Ala Pro Asn Tyr Ile
530                 535                 540

Leu Ser Leu Thr Gly Thr His Gln Glu Arg Leu Pro Asn Ala Gln Glu
545                 550                 555                 560

Met Tyr Thr His Gly Met His Leu Ala Thr Asn Ser Phe Glu Ile Gly
                565                 570                 575

Asn Arg Phe Leu Arg Lys Glu Lys Ser Asn Asn Leu Glu Ile Ser Leu
            580                 585                 590

Ala Tyr Lys Asp Asp Leu Leu Asp Tyr Gln Ile Ser Thr Tyr Tyr Tyr
    595                 600                 605

Asp Phe Asp Asn Tyr Ile Tyr Leu Gln Thr Leu Asn Glu Val Leu Gly
```

```
                610                615                620
Thr Thr Lys Val Arg Asp Gln His Thr Leu Arg Ile Asn His Tyr Ser
625                630                635                640

Gln Ser Ala Ala Asn Phe Tyr Gly Leu Glu Gly Asn Ile Gly Tyr Gln
                     645                650                655

Phe Asn Ser Val Tyr His Gly Ser Leu Phe Gly Asp Tyr Val Lys Gly
                660                665                670

Arg Leu Thr Asn Leu Pro Asp Ala Val Ile Ala Tyr Asp Ile Trp Asn
            675                680                685

Arg Glu Pro Thr Leu Ala Pro Gln Lys Asp Arg Tyr Thr Pro Arg Leu
        690                695                700

Pro Pro Ala Arg Leu Gly Thr Arg Leu Lys Ala Asp Phe Asp Glu Ser
705                710                715                720

Leu Lys Gly Glu Ile Glu Tyr Tyr Arg Val Phe Lys Gln Asp Asn Ile
                    725                730                735

Ser Lys Phe Glu Gln Val Thr Ser Gly Tyr Asn Met Leu Asn Met Thr
                740                745                750

Leu Ala Tyr Lys Asn Lys Leu Ser His Thr Glu Tyr Asp Leu Phe Phe
            755                760                765

Lys Ala Asn Asn Leu Leu Asp Gln Lys Val Tyr Ala His Glu Thr Phe
770                775                780

Leu Pro Tyr Ile Pro Gln Ile Gly Arg Asn Phe Ser Leu Gly Leu Asn
785                790                795                800

Leu Asn Phe

<210> SEQ ID NO 98
<211> LENGTH: 790
<212> TYPE: PRT
<213> ORGANISM: Actinobacillus pleuropneumoniae

<400> SEQUENCE: 98

Met Phe Asn Lys Lys Leu Leu Ala Val Leu Ile Ser Ala Gln Phe Ser
1               5                   10                  15

Pro Leu Val Trp Ala Asn Asn Asn Asp Val Ala Val Leu Asp Glu Val
                20                  25                  30

Ser Val Val Gly Ser Thr Pro Ser Ile Ser Gln Gly Ser Glu Val Thr
            35                  40                  45

Leu Leu Lys Val Ser Asp Lys Ile Ile Ala Gly Lys Glu Phe Lys Lys
        50                  55                  60

Arg Ser Ala Thr Leu Gly Asn Ala Leu Ala Ala Glu Leu Gly Val His
65                  70                  75                  80

Ser Asn Pro Phe Gly Gly Ala Ser Lys Pro Ile Ile Arg Gly Gln
                85                  90                  95

Glu Gly Ala Arg Ile Arg Ile Leu Gln Asn Gly Ser Asp Val Ile Asp
                100                 105                 110

Met Ser Asn Leu Ser Pro Asp His Ala Val Val Ala Asp Ser Leu Leu
            115                 120                 125

Ala Lys Gln Val Glu Ile Leu Arg Gly Ser Ser Thr Leu Leu Tyr Ala
        130                 135                 140

Ser Ser Ser Pro Ala Gly Ile Val Asn Val Val Asp Lys Arg Ile Pro
145                 150                 155                 160

Thr Glu Ile Pro Glu Lys Gly Tyr Glu Val Glu Leu Asn Ser Arg Phe
                165                 170                 175

Asp Thr Ala Ala Lys Glu Lys Val Gly Ala Leu Gly Ala Thr Phe Gly
```

```
            180                 185                 190
Ile Gly Lys His Ile Ala Val Arg Ala Glu Gly Leu Thr Arg His Ser
            195                 200                 205
Asp Asn Tyr Arg Val Pro Gly Ile Asn Leu Gly Glu Arg Leu Asn Tyr
            210                 215                 220
Val Pro Asp Thr Tyr Asn Lys Ser Lys Val Gly Thr Leu Gly Leu Ser
225                 230                 235                 240
Phe Val Gly Glu Gln Gly Tyr Ile Gly Ala Ser Tyr Ser Lys Arg Arg
                245                 250                 255
Asp Asn Tyr Gly Leu Pro Gly His Asn His Lys Phe Asp Phe Cys Ile
            260                 265                 270
Gly His Ile Tyr Gly Asn Lys Gln Gly Lys Tyr Ala Tyr Thr Tyr Leu
            275                 280                 285
Tyr Pro His Leu Ile Gly Glu Glu Asn Ile Gly Ser Asn Pro His Phe
            290                 295                 300
His Cys Gly Thr Asp His Ala Glu Asp Gly Thr His Ser His Asp Asn
305                 310                 315                 320
Pro Phe Gly His Asp His Asp His Thr His Pro Gly Pro Trp Val Asp
                325                 330                 335
Leu Glu Ser Lys Arg Phe Asp Val Lys Ala Glu Leu Arg Gln Pro Phe
                340                 345                 350
Lys Gly Ile Asp Lys Ile Lys Val Ser Tyr Ala Asp Ala Asp Tyr Tyr
            355                 360                 365
His Asp Glu Lys Asp Ala Gly Val Leu Ala Thr Arg Tyr His Lys Gln
            370                 375                 380
Leu Lys Lys Asp Gln Asp Tyr Gly Lys Pro Val Asn Ile Phe Lys Asn
385                 390                 395                 400
Arg Gly Lys Asn Ala Arg Leu Glu Ile Tyr His Ala Pro Leu Gly Gly
                405                 410                 415
Leu Thr Gly Val Trp Gly Val Gln Tyr Gln Thr Gln Lys Ser Ser Met
            420                 425                 430
His Ala Pro Lys Asp Arg Glu Val Lys Phe Pro Leu Val Glu Asn Thr
            435                 440                 445
Asn Lys Gln Met Ser Leu Phe Gly Ile Glu Gln Tyr Met Trp Asp Asn
            450                 455                 460
Phe Ala Leu Glu Phe Ala Gly Arg Val Glu Lys Gln Lys Ile Glu Ile
465                 470                 475                 480
Glu Tyr Asp Arg Asn Glu Ile Lys Arg Leu Gln Asp His Tyr Arg Ile
                485                 490                 495
Ser Gly Gly Lys Gln Val Glu Pro Asp Leu Ser Pro Tyr Asn Gln Asn
            500                 505                 510
Ala Tyr Ala Tyr Ser Ser Thr Leu Asn Trp Phe Phe His Pro Asp Tyr
            515                 520                 525
Gln Leu Ser Phe Thr Ala Ser His Asn Glu Arg Phe Pro Thr Pro Met
            530                 535                 540
Glu Leu Tyr Tyr His Gly Gln His Ile Ala Thr Asn Ser Phe Glu Tyr
545                 550                 555                 560
Gly Asn Lys Asp Leu Lys Lys Glu Gln Ser Asn Asn Val Glu Leu Gly
                565                 570                 575
Leu Gly Tyr Gln Thr Glu Arg Val Gly Tyr Lys Val Asn Val Tyr Tyr
            580                 585                 590
Asn His Phe Lys Asn Tyr Ile Tyr Asn Glu Asn Leu Phe Arg Glu Asn
            595                 600                 605
```

```
Gln Leu Phe Met Arg Arg Tyr Asn Gln Ala Lys Ala Arg Phe Tyr Gly
    610                 615                 620

Ile Glu Ala Glu Ala Ser Tyr Arg Phe Asn Asp Lys Tyr Gln Ala Thr
625                 630                 635                 640

Ile Phe Gly Asp Met Val Arg Gly Trp Leu Thr Asn Leu Pro Pro Leu
                645                 650                 655

Thr Val Asn Ser Asp Tyr Ser Val Phe Lys Asp Tyr Leu Pro Lys Asp
                660                 665                 670

Ala Lys Pro Gly Glu Asp Tyr Leu Ile Tyr Arg Ala Asp Gln Asn Thr
            675                 680                 685

Pro Arg Thr Pro Pro Val Arg Leu Gly Phe Arg Phe Asn Ala Glu Phe
        690                 695                 700

Thr Pro Asn Trp Ser Gly Asp Leu Glu Leu Ile Arg Thr Phe Thr Gln
705                 710                 715                 720

Arg Arg Thr Ser Gln Leu Glu Tyr Ile Thr Glu Gly Asn Thr Met Leu
                725                 730                 735

Asn Ile Gly Val Ala Tyr Ser Asn Lys Trp Lys Asp Leu Asp Tyr Lys
                740                 745                 750

Ile Ser Leu Asn Gly Thr Asn Leu Leu Asn Gln Pro Val Tyr Ile His
            755                 760                 765

Thr Ser Tyr His Gln Phe Val Pro Gln Thr Gly Arg Asn Phe Ile Leu
        770                 775                 780

Val Val Asn Val Lys Phe
785                 790

<210> SEQ ID NO 99
<211> LENGTH: 809
<212> TYPE: PRT
<213> ORGANISM: Haemophilus parasuis

<400> SEQUENCE: 99

Met Ile Asn Asn Arg Thr Thr Glu Gln Gln Asn Asn Arg Thr Thr Ala
1               5                   10                  15

Phe Ser Leu Ala Phe Ser Leu Leu Cys Cys Leu Gly Ile Asn Ala
                20                  25                  30

Glu Gln Leu Glu Leu Asp Glu Ile Ser Val Met Gly Lys Val Pro Glu
            35                  40                  45

Gly Asn Ser Ile Ser Phe Leu Lys Val Ser Asp Ala Ile Ile Asp Gly
        50                  55                  60

Glu Lys Phe Lys Asn Arg Ser Ala Thr Leu Gly Asn Ala Leu Ser Ser
65                  70                  75                  80

Glu Leu Gly Val His Ser Thr Pro Phe Gly Gly Ala Ser Ala Pro
                85                  90                  95

Ile Ile Arg Gly Gln Glu Gly Val Arg Val Lys Ile Leu Gln Asn Asn
            100                 105                 110

Ala Asp Val Val Asp Met Ser Asn Ile Ser Pro Asp His Ala Ile Thr
        115                 120                 125

Ala Asp Thr Leu Leu Ala Asn Gln Val Glu Ile Leu Arg Gly Ala Ser
    130                 135                 140

Thr Leu Leu Tyr Ala Ser Ser Pro Ala Gly Ile Val Asn Ile Val
145                 150                 155                 160

Asp Gln Arg Ile Pro Asn Lys Met Pro Lys Lys Gly Tyr Glu Val Thr
                165                 170                 175

Leu Ser Ser Arg Phe Asp Thr Ala Ser Lys Glu Lys Val Tyr Ala Leu
```

```
                180                 185                 190
Gly Thr Thr Ile Gly Ile Gly Lys His Leu Ala Leu Arg Leu Glu Gly
            195                 200                 205
Leu Asp Arg Gln Ser Gln Asn Tyr Lys Val Pro Gln Ile Lys Leu Gly
        210                 215                 220
Glu Thr Leu Asn Tyr Val Pro Asp Thr Tyr His Gln Ser Lys Val Gly
225                 230                 235                 240
Thr Ile Gly Leu Ser Phe Ile Gly Glu Lys Gly Tyr Leu Gly Ala Ser
                245                 250                 255
Tyr Asn Gln Arg Lys Asp Arg Tyr Gly Leu Pro Gly His Asn His Lys
            260                 265                 270
Phe Asp Thr Cys Ile Ala His Ile Tyr Asp Met Arg Leu Gln Gly Lys
        275                 280                 285
His Ser Tyr Thr Asn Leu Tyr Pro His Leu Met Ser Asp Glu Met Val
        290                 295                 300
Thr Glu Asn Pro His Phe His Cys Gly Thr Asp Tyr Asp Leu Asp Pro
305                 310                 315                 320
Ser His Ser His Asp His Pro Tyr Gly His Asp His Asp His Thr His
                325                 330                 335
Ile Gly Pro Trp Val Asp Leu His Ser Lys Arg Ile Asp Ile Lys Gly
                340                 345                 350
Glu Ile Lys Gln Pro Leu Pro Met Leu Asp Lys Ile Gln Leu Ser Tyr
            355                 360                 365
Ala Gln Thr Asp Tyr Tyr His Asp Glu Lys Asp Ala Gly Lys Ser Gly
        370                 375                 380
Asp Thr Ile Asn Pro Asn Arg Val Asp Lys Ser Lys Asp Phe Gly Lys
385                 390                 395                 400
Pro Val Asn Ile Phe Lys Asn Gln Gly Lys Asn Ala Arg Leu Glu Phe
                405                 410                 415
Phe His Thr Pro Ile Gly Gly Leu Thr Gly Met Phe Gly Val Gln Tyr
                420                 425                 430
Gln Thr Leu Gln Ser Ser Ala Asn Thr Pro Asn Asn Arg Glu Val Gln
            435                 440                 445
Trp Pro Leu Val Asp Asn Arg Asn Lys Gln Ile Ser Leu Phe Ala Leu
        450                 455                 460
Glu Gln Tyr Ala Trp Asp Asn Phe Ala Ile Glu Leu Gly Leu Arg Thr
465                 470                 475                 480
Glu Lys Gln Asn Ile His Ile Asp Tyr Asp Leu Ala Lys Ile Gln Lys
                485                 490                 495
Gln Gln Lys Phe Asn Glu Arg Thr Tyr Gly Lys Gln Val Asp Pro Asp
            500                 505                 510
Leu Ser Asp Tyr Asp Glu Lys Ala Ile Ser Tyr Thr Gly Ala Phe Asn
        515                 520                 525
Trp Phe Phe His Pro Asp Tyr Gln Leu Ser Phe Thr Ala Ser His Asn
        530                 535                 540
Glu Arg Leu Pro Thr Pro Met Glu Leu Tyr Tyr His Gly Gln His Leu
545                 550                 555                 560
Ala Thr Asn Ser Phe Glu Tyr Gly Asn Lys Asp Leu Lys Lys Glu Ile
                565                 570                 575
Ser Asn Asn Phe Glu Leu Gly Leu Gly Tyr His Thr Glu Lys Leu Asp
            580                 585                 590
Tyr Lys Leu Ser Thr Tyr Tyr Asn Asn Phe Asp Asn Tyr Ile Tyr Asn
        595                 600                 605
```

```
Glu Thr Leu Tyr Arg Ser Asn Asn Leu Phe Met Arg Arg Tyr Asn Gln
    610                 615                 620

Ala Lys Ala Thr Phe Tyr Gly Leu Glu Gly Ile Ile Asn Tyr Arg Phe
625                 630                 635                 640

Thr Pro Asp Tyr Gln Phe Ser Val Phe Gly Asp Met Val Lys Gly Lys
                    645                 650                 655

Leu Lys Gln Leu Pro Asp Ile Lys Gly Leu Asn Asp Val Tyr Gly Glu
                660                 665                 670

Pro Ile Leu Asn Pro Asp Tyr Asp Pro Glu Tyr Asp Glu Pro Glu Asp
            675                 680                 685

Gln Tyr Tyr Arg Pro Tyr Leu Gly Lys Glu Met Ile Lys Gln Ala Asp
        690                 695                 700

Arg Val Ser Pro Arg Leu Pro Pro Ile Arg Leu Gly Ala Arg Phe Asn
705                 710                 715                 720

Ala Gln Leu Thr Glu Asn Leu Ser Gly Ser Val Glu Trp Met Lys Val
                725                 730                 735

Phe Thr Gln Asn Lys Val Ser Lys Leu Glu Ser Ser Thr Lys Gly Tyr
                740                 745                 750

Gln Leu Leu Asn Ala Ser Leu Asn Tyr Arg Arg Gln Ile Lys Gly Val
                755                 760                 765

Glu Tyr Thr Val Ser Leu Thr Gly Asn Asn Leu Leu Asn Gln Ala Val
770                 775                 780

Tyr Ile His Asn Ser Tyr His Pro Tyr Val Pro Gln Met Gly Arg Asn
785                 790                 795                 800

Phe Ile Leu Gly Leu Asp Leu Ser Phe
                805

<210> SEQ ID NO 100
<211> LENGTH: 693
<212> TYPE: PRT
<213> ORGANISM: Bordetella pertussis

<400> SEQUENCE: 100

Met Arg Phe Glu Arg His Pro Leu Ser Ala Ala Leu Ala Leu Ala Leu
1               5                   10                  15

Ala Trp Gln Gly Ala His Ala Gln Ala Ser Ala Asp Gly Thr Ser Glu
            20                  25                  30

Ala Ala Thr Leu Ala Pro Ile Thr Val Ser Ala Ser Pro Leu Ala Gly
        35                  40                  45

Asp Leu Asp Ser Met Thr Ala Pro Ala Ala Val Leu Glu Gly Asp Gln
    50                  55                  60

Leu Leu Leu Arg Arg Gln Gly Thr Leu Gly Thr Leu Asp Gly Leu
65                  70                  75                  80

Pro Gly Val His Ala Asp Thr Phe Gly Gly Ala Ser Arg Pro Val
                85                  90                  95

Ile Arg Gly Gln Thr Ala Pro Arg Val Lys Val Leu Ser Asp Gly Ser
                100                 105                 110

Glu Leu Met Asp Ala Ser Ala Ile Ser Pro Asp His Ala Val Thr Thr
            115                 120                 125

Glu Pro Leu Leu Ala Asp Lys Ile Glu Val Leu Arg Gly Pro Ala Thr
        130                 135                 140

Leu Leu Tyr Gly Gly Gly Ala Ile Gly Gly Val Val Asn Val Leu Asp
145                 150                 155                 160

Arg Lys Ile Pro Thr Ala Val Pro Gln Gln Gly Ile Glu Ala Glu Ala
```

```
                    165                 170                 175
Glu Leu Arg Gly Ala Thr Gly Thr Lys Glu Arg Ala Gly Ala Ile Gly
                180                 185                 190
Ile Thr Ala Gly Ser Gly Asn Phe Ala Val Arg Val Glu Gly Leu Lys
                195                 200                 205
Arg Arg Ser Ser Asp Tyr Arg Val Pro Asp Trp Pro Asp Gly Lys Leu
            210                 215                 220
Ala Gly Ser Tyr Ser Glu Ser Gly Gln Gly Thr Val Gly Met Ser Trp
225                 230                 235                 240
Ile Thr Pro Arg Gly Tyr Val Gly Val Ala Phe Thr His Leu Glu Ser
                245                 250                 255
Lys Tyr Gly Leu Pro Gly His Asn His Glu Tyr Gly Cys His Pro
                260                 265                 270
His Gly Ser His Leu His Cys Gly Gly His Asp His Gly His Gly
            275                 280                 285
His Asp Glu His Glu Glu Gly Glu Ala Glu His Asp His Gly His Glu
            290                 295                 300
His Gly Ala Gly Asp Val Pro Tyr Val Lys Leu Arg Ser Asn Arg Thr
305                 310                 315                 320
Asp Leu Arg Ala Glu Tyr Thr Asp Pro Phe Ala Gly Phe Glu Lys Ile
                325                 330                 335
Arg Phe Arg Gly Gly Leu Thr Tyr Arg His Asp Glu Ile Glu Gly
            340                 345                 350
Gly Gln Leu Gly Thr Arg Phe Gln Asn Arg Gly Tyr Asp Ala Arg Leu
            355                 360                 365
Glu Leu Thr His Arg Pro Leu Tyr Gly Trp His Gly Val Val Gly Val
            370                 375                 380
Gln Thr Ser Tyr Ser Asp Phe Arg Ala Thr Gly Glu Glu Ala Phe Leu
385                 390                 395                 400
Pro Arg Ser Lys Thr Arg Ala His Gly Leu Phe Leu Leu Glu Glu Tyr
                405                 410                 415
Arg Trp Ala Asp Trp Arg Phe Glu Leu Gly Ala Arg Gln Asp Trp Gln
                420                 425                 430
Arg Val Ser Pro Gln Ser Gly Ala Pro Ala Ser Arg Thr Ala Gly Thr
            435                 440                 445
Ser Leu Ser Ala Ala Ala Ile Trp Asp Phe Ala Pro Gln Tyr Ser Leu
450                 455                 460
Ala Leu Ser Val Ser Arg Ser Gln Arg Leu Pro Ser Ala Gln Glu Leu
465                 470                 475                 480
Tyr Ala Asp Gly Val His Leu Ala Thr Asn Thr Tyr Glu Ile Gly Asp
                485                 490                 495
Pro Gly Leu Asp Arg Glu Thr Ser Arg Asn Val Asp Leu Thr Leu Arg
                500                 505                 510
Lys His Ser Gly Asp Thr Thr Phe Ser Val Ser Ala Phe His Asn Arg
                515                 520                 525
Val Lys Asn Tyr Ile Tyr Ala Asn Thr Leu Asp Arg Tyr Glu Asp Phe
            530                 535                 540
Arg Leu Ile Glu Tyr Thr Gln Arg Asp Ala Glu Phe Thr Gly Val Glu
545                 550                 555                 560
Gly Glu Val Arg His Arg Phe Gly Lys Val Phe Ser Ala Ala Val Phe
                565                 570                 575
Gly Asp Tyr Val Arg Gly Arg Leu Thr Gly Gly Gly Asn Leu Pro
            580                 585                 590
```

```
Arg Ile Pro Ala Ala Arg Leu Gly Val Arg Ala Asp Ala Gln Trp Gln
            595                 600                 605
Asn Trp Ala Gly Gly Val Glu Tyr Phe His Val Tyr Arg Gln Asp Asp
        610                 615                 620
Ile Ala Ala Tyr Glu Ser Ser Thr Pro Gly Tyr Asp Met Val Asn Ala
625                 630                 635                 640
Thr Ile Arg Tyr Arg Gly Lys Leu Asp Arg Thr Ala Tyr Glu Ile Tyr
                645                 650                 655
Leu Arg Gly Asn Asn Leu Leu Asn Lys Leu Ala Phe Asn His Ala Ser
            660                 665                 670
Phe Ile Ser Thr Val Ala Pro Leu Pro Gly Arg Ser Val Leu Leu Gly
        675                 680                 685
Val Arg Leu Thr Tyr
    690

<210> SEQ ID NO 101
<211> LENGTH: 818
<212> TYPE: PRT
<213> ORGANISM: Moraxella catarrhalis

<400> SEQUENCE: 101

Met Lys Val Thr Met Ile Lys Lys Pro Leu Ala Cys Ala Ile Leu Ala
1               5                   10                  15
Thr Phe Ser Met Pro Met Leu Ala Glu Ala Asn Leu Lys Asp Lys Pro
            20                  25                  30
Thr Val Ile Leu Asp Gly Val Ser Ile Thr Ser Leu Ala Asp Gln Asn
        35                  40                  45
Thr Glu Phe Gly Val Asn His Ser Lys Thr Val Ser Gly Ile Thr Val
    50                  55                  60
Ser Lys Glu Gln Leu Gln Gln Arg Ala Thr Thr Leu Gly Asp Ala Leu
65                  70                  75                  80
Ala Gly Glu Leu Gly Val His Ser Asn His Phe Gly Gly Gly Ala Ser
                85                  90                  95
Ala Pro Ile Ile Arg Gly Gln Glu Gly Lys Arg Leu Lys Ile Leu Gln
            100                 105                 110
Asn Gly Ser Glu Val Val Asp Met Ser Gly Leu Ser Pro Asp His Ala
        115                 120                 125
Ile Ala Val Asp Thr Thr Leu Ala Lys Gln Val Glu Ile Val Arg Gly
    130                 135                 140
Ser Gly Ala Leu Leu Tyr Ala Ser Gly Asn Ser Ala Gly Val Val Asn
145                 150                 155                 160
Val Val Asp Asp Lys Ile Pro Ser Lys Leu Pro Ser Lys Leu Gln Gly
                165                 170                 175
Asp Val Thr Val Arg Leu Ser Ser Ala Asn Arg Glu Lys Leu Ile Thr
            180                 185                 190
Ala Ser Ala Glu Ala Pro Leu Gly Glu His Val Ala Val Arg Val Ala
        195                 200                 205
Gly Leu Ser Lys Gln Ala Ala Asp Tyr Lys Thr Pro Arg Phe Asp Arg
    210                 215                 220
His Val Phe Asn Lys Lys His Glu Asp Asp Thr Gln Pro Glu Phe
225                 230                 235                 240
Ile Tyr Lys Asp Thr Leu Lys His Leu Pro Asp Ser His Ala Lys Ser
                245                 250                 255
Asn Ala Gly Thr Leu Gly Val Ser Trp Val Gly Asn Gln Gly Phe Leu
```

```
             260                 265                 270
Gly Ala Ser Val Ser Leu Arg Arg Asp Lys Tyr Gly Leu Pro Asn His
            275                 280                 285

Ser His Glu Tyr Glu Glu Cys Ser Val His Gly Ile Ser Gln Ser Ala
            290                 295                 300

Leu Gln Tyr Lys Pro Tyr Leu Arg Leu Tyr Pro Phe Leu Met Glu Asn
305                 310                 315                 320

Asp Asp Leu Glu Phe Asp Asn Ala Gly Leu Glu Cys His Thr His Asp
                325                 330                 335

Asp His Asp His Glu His Asp His Ala His Asp His Glu His Asp His
            340                 345                 350

Glu His Asp His Gly Lys Pro Trp Ile Asp Leu Lys Met Lys Arg Tyr
            355                 360                 365

Asp Val Gln Gly Gln Ile Asn Ala Pro Phe Ala Gly Ile Asp Lys Ile
            370                 375                 380

Arg Ala Ser Met Gly Lys Val Asp Tyr His His Asp Glu Ile Asp Gly
385                 390                 395                 400

Gly Glu Lys Thr Ser Phe Phe Asp Asn Gln Ala Asn Val Trp Arg Leu
                405                 410                 415

Glu Ala Ser His Thr Pro Ile His Thr Pro Met Gly Lys Phe Ser Gly
            420                 425                 430

Val Phe Gly Val Gly Tyr Leu Thr Ser Lys Asn Ser Gly Leu Val Pro
            435                 440                 445

Pro Arg Tyr Glu Asp Gly Asn Lys Gln Asp Thr Gln Asn Ile Leu His
            450                 455                 460

Asn Asn Lys Thr Lys Thr Gly Ser Val Phe Trp Phe Glu Glu Tyr Lys
465                 470                 475                 480

Pro Asn Asp Lys Leu Thr Val Asp Ala Ala Arg Ile Glu Lys Gln
                485                 490                 495

Thr Ile Thr Met Asp Tyr Asp Lys Asp Ala Ile Tyr Gln Ser Leu Asn
                500                 505                 510

Leu Gly Leu Ala Thr Ala His Glu Pro Asp Ile Arg Phe Lys Arg Leu
            515                 520                 525

Leu Asp Ser Gly Thr Leu Asn Pro Lys Lys Gln Thr Ala Arg Ser Tyr
            530                 535                 540

Ala Val Gly Thr His Leu Gln Leu Thr Pro Lys His Lys Leu Ser Leu
545                 550                 555                 560

Asn Leu Ser His Gln Glu Arg Leu Pro Asn Ala Gln Glu Leu Tyr Ala
                565                 570                 575

His Gly Met His Leu Ala Thr Asn Ser Phe Glu Ile Gly Asn Arg Phe
            580                 585                 590

Leu Asn Lys Glu Lys Ser Asn Asn Ile Asp Leu Gly Leu Thr Phe Gln
            595                 600                 605

Gly Asp Lys Trp Asp Tyr Arg Leu Gly Gly Tyr His Tyr Asp Phe Asp
            610                 615                 620

Asn Tyr Val Phe Leu Gln Thr Leu Ser Gln Tyr Lys Gln Gly Leu Arg
625                 630                 635                 640

Gly Met Arg His Asp Lys Asp Leu Lys Thr Ala Arg Tyr Glu Gln Ala
                645                 650                 655

Ala Ala Lys Phe Tyr Gly Phe Asp Val Asn Ile Gly Tyr Gln Ile Asn
                660                 665                 670

Asp Val Tyr His Val Ala Leu Phe Gly Asp Tyr Ile Arg Gly Lys Leu
            675                 680                 685
```

```
Thr Asn Leu Pro Asp Lys Lys Gly Arg Thr Asp Ala Tyr Gly Asn Arg
            690                 695                 700

Pro Leu Ile Lys Gln Pro Asp Ser His Thr Pro Arg Leu Pro Pro Lys
705                 710                 715                 720

Arg Leu Gly Met Lys Leu Thr Ala Asn Val Asn Ala Asn Trp Ser Gly
                725                 730                 735

Phe Leu Glu Tyr Arg His Thr Phe Lys Gln Asp Lys Leu Ala Asn Phe
            740                 745                 750

Glu Arg Pro Thr Pro Ala His Asn Leu Val Asn Leu Gly Leu Asn Tyr
        755                 760                 765

Gln His Lys Pro Ser His Gln Ala Gly Ser Val Gln Val Phe Phe Asn
        770                 775                 780

Ala Asn Asn Leu Leu Asn Asp Lys Val Phe Ala His Glu Thr Phe Phe
785                 790                 795                 800

Pro Asp Met Pro Gln Met Gly Arg Asn Phe Met Leu Gly Ala Asn Phe
                805                 810                 815

Lys Phe

<210> SEQ ID NO 102
<211> LENGTH: 766
<212> TYPE: PRT
<213> ORGANISM: Mannheimia haemolytica

<400> SEQUENCE: 102

Met Leu Lys Lys Asn Tyr Leu Thr Val Ser Ile Leu Leu Ala Ile Ser
1               5                   10                  15

Gly Val Gly Tyr Ala Asn Glu Ile Ser Leu Glu Thr Ile Thr Val Asp
            20                  25                  30

Gly Asn Thr Pro Ser Thr Lys Gly Lys Leu Leu Gly Gly Glu Leu Asn
        35                  40                  45

Ser Asn Glu Ser Val Val Asp Glu Lys Asn Leu Lys Gln Gly Ser Ile
    50                  55                  60

Thr Leu Gly Asn Ala Leu Ser Gly Glu Leu Gly Ile His Ser Ser Gln
65                  70                  75                  80

Phe Gly Gly Gly Ala Ser Thr Pro Ile Ile Arg Gly Gln Glu Ser Lys
                85                  90                  95

Arg Ala Lys Ile Leu Gln Asn Asn Gly Glu Asn Leu Asp Met Ser Gly
            100                 105                 110

Met Ser Pro Asp His Ala Val Thr Val Asp Ala Leu Leu Ala Lys Arg
        115                 120                 125

Ile Glu Ile Leu Arg Gly Pro Thr Thr Leu Leu Tyr Ser Ala Gly Asn
    130                 135                 140

Thr Ala Gly Val Ile Asn Val Val Asp Asn Lys Ile Pro Thr Ala Ile
145                 150                 155                 160

Pro Glu Lys Gly Tyr Glu Gly Gln Phe Gly Val Arg Phe Gly Ser Ala
                165                 170                 175

Ser Lys Glu Arg Leu Thr Tyr Ala Gly Ser Thr Phe Ala Leu Gly Asn
            180                 185                 190

His Leu Ala Leu Arg Val Gln Gly Met Tyr Asn Lys Ala Ser Glu Tyr
        195                 200                 205

Tyr Ala Pro His Phe Thr Ile Glu Gly Lys Pro Tyr His Arg Val Pro
    210                 215                 220

Asp Ser Asp Val Gln Ser Gln Thr Gly Thr Val Ser Leu Ser Trp Ile
225                 230                 235                 240
```

```
Gly Glu Arg Gly His Leu Gly Ile Ala Tyr Thr Asp Arg Asp Lys
            245                 250                 255

Tyr Gly Leu Ile Gly His Thr His Lys Tyr Asp His Tyr Thr Ile Ser
            260                 265                 270

Ile Ile Arg Gln Ala Val Met Phe Ala Lys Gly Tyr Leu Arg Phe Tyr
            275                 280                 285

Pro His Leu Ala Glu Glu Gly Asp Ile Asp Tyr Asn Asn Pro Gly Ile
            290                 295                 300

Arg Leu Leu His Thr His Ile Pro Gly Gly Ser His Tyr Gly Gln Asp
305                 310                 315                 320

Thr His Glu His Gly Lys Pro Trp Ile Asp Met His Ser Lys Arg Tyr
            325                 330                 335

Asp Ile Asp Gly Ser Leu Gln Asn Pro Leu Pro Gly Phe Glu Glu Ala
            340                 345                 350

Lys Ile Ser Ala Asn Tyr Val Asp Tyr His Asp Glu Lys Asp Gly
            355                 360                 365

Lys Arg Val Glu Asn Tyr Phe Lys Asn Lys Gly Lys Asn Leu Arg Phe
370                 375                 380

Glu Leu Val His Lys Glu Trp Lys Gly Leu Lys Gly Ala Ile Gly Val
385                 390                 395                 400

Gln Tyr Thr Asn Gln Ser Thr Ser Ala Leu Ala Leu Glu Ala Ser Arg
            405                 410                 415

Ala Ala Lys Val Phe Asn Lys Gln Pro Leu Leu Asn Asn Pro Lys Thr
            420                 425                 430

Lys Leu Trp Ser Leu Phe Ala Ile Glu Arg Leu Asn Leu Gly Asp Phe
            435                 440                 445

Thr Phe Glu Leu Ser Gly Arg Ala Glu Arg Gln Lys Ile Ala Met Asp
            450                 455                 460

Tyr Asp Val Lys Leu Ile Asp Arg Trp Leu Gly Phe Asn Thr Pro Met
465                 470                 475                 480

Pro Asn Leu Asp Pro His Lys Asp Lys Gly Tyr Ser Tyr Ser Phe Ala
            485                 490                 495

Thr His Trp Tyr Phe Ala Pro Asn His Lys Leu Thr Leu Asn Ala Ala
            500                 505                 510

His Gln Glu Arg Leu Pro Asn Ala Gln Glu Leu Tyr Ala His Gly Lys
            515                 520                 525

His Ile Ala Leu Asn Ala Phe Glu Ala Gly Asn Lys Asn Leu Lys Lys
            530                 535                 540

Glu Arg Ser Asn Gln Ile Glu Leu Ser Leu Ala Tyr Val Gly Asp Lys
545                 550                 555                 560

Trp Asp Tyr Lys Leu Asn Leu Tyr His Thr Arg Tyr Gly Asn Tyr Ile
            565                 570                 575

Tyr Pro Leu Thr Leu Asn Asp Asn Arg Gly Pro Lys Ser Phe Thr Asp
            580                 585                 590

Glu Tyr Asn Leu Lys Val Asn Arg Tyr Tyr Gln Gly Glu Ala Arg Phe
            595                 600                 605

Ser Gly Ala Glu Gly Glu Ile Gly Tyr Leu Phe Thr Pro Asn Tyr Arg
            610                 615                 620

Leu Ala Val Phe Gly Asp Tyr Val Arg Gly Lys Leu Val Asn Leu Pro
625                 630                 635                 640

Asn Ile Ala Met Ser Tyr Asn Ile Trp Thr Gly Glu Val Asp Lys Trp
            645                 650                 655
```

-continued

```
Ala Ser Gln Pro Asp Ile Ser Ala Pro Arg Ile Pro Pro Leu Arg Leu
            660                 665                 670

Gly Ala Arg Phe Asn Ala Asp Phe Asn Leu Asn Trp Ser Gly Met Leu
        675                 680                 685

Glu Tyr Tyr Arg Val Phe Ala Gln Lys Lys Val Ser Lys Tyr Glu Gln
    690                 695                 700

Val Thr Pro Gly His His Gln Val Asn Leu Gly Val Thr Tyr Ser Asn
705                 710                 715                 720

His Phe Asn Gln Thr Glu Tyr Gln Val Phe Leu Lys Val Asp Asn Leu
                725                 730                 735

Leu Asn Gln Lys Met Tyr Gln His Ala Ser Tyr Leu Pro His Ile Pro
            740                 745                 750

Gln Met Gly Arg Asn Ala Met Leu Gly Met Asn Ile Ser Phe
            755                 760                 765

<210> SEQ ID NO 103
<211> LENGTH: 797
<212> TYPE: PRT
<213> ORGANISM: Pasteurella multocida

<400> SEQUENCE: 103

Met Arg Lys Ile Ser Tyr Leu Ser Leu Cys Val Ile Ser Ala Leu Tyr
1               5                   10                  15

Ser Gln Leu Ala Val Ala Gln Ser Pro Leu Lys Asn Thr Ser Glu His
            20                  25                  30

Ile Glu Leu Glu Pro Ile Phe Val Asn Thr Leu Ile Glu Ser Arg Glu
        35                  40                  45

Gly Ala Pro Leu Gly Gly Arg Leu Met Ala Ser Glu Lys Ile Ile Pro
    50                  55                  60

Ala Tyr Ser Leu Lys Gln Arg Gly Ser Asn Leu Gly Asp Ala Leu Ser
65                  70                  75                  80

Ser Glu Leu Gly Ile His Ala Ser Gln Phe Gly Gly Gly Ala Ser Ala
                85                  90                  95

Pro Val Ile Arg Gly Gln Glu Gly Lys Arg Ile Lys Val Leu Ser Ser
            100                 105                 110

Gly Asn Glu Thr Leu Asp Met Ser Ala Met Ser Pro Asp His Ala Val
        115                 120                 125

Ala Val Asp Ser Leu Leu Ala Lys Lys Val Glu Ile Leu Arg Gly Ala
    130                 135                 140

Asn Thr Leu Leu Tyr Ser Ser Gly Asn Ala Ala Gly Val Val Asn Val
145                 150                 155                 160

Val Asp Asn Lys Ile Pro Thr Ala Glu Val Val Gly Val Glu Gly Glu
                165                 170                 175

Val Gly Leu Arg Thr Gly Ser Ala Asp Asn Glu Arg Leu Val Asn Val
            180                 185                 190

Ala Leu Asp Val Gly Leu Ser Lys His Phe Ala Leu His Leu Glu Gly
        195                 200                 205

Leu His Lys Lys Ala Gly Asp Tyr Arg Thr Pro Ser Tyr Gln Tyr Gln
    210                 215                 220

Gly Ser Thr His His Lys Leu Ala Asn Ser Phe Val Asp Asn Arg Ser
225                 230                 235                 240

Gly Ser Val Gly Leu Ser Trp Val Gly Asp Lys Gly Tyr Leu Gly Val
                245                 250                 255

Ala Tyr Ser Gln Arg Lys Asp Lys Tyr Gly Leu Pro Ala His Ser His
            260                 265                 270
```

```
Leu Tyr Asp Glu Tyr Tyr Met His Val Leu Ser Asp Ala His Trp
        275                 280                 285

Arg Lys Pro Tyr Leu Lys His Tyr Pro Phe Leu Met Glu Glu Thr Asp
        290                 295                 300

Ile Asp Tyr Asn Asn Pro Gly Ile Asp Cys Ile Lys Lys Glu Trp His
305                 310                 315                 320

Ser His Gly His Leu Cys Asn His Gly His Ala His Gly Asn Gly
                325                 330                 335

Gln His Ser His Asp His His Ala His Ala Asp Pro His Ile Ala Leu
                340                 345                 350

Asn Thr Gln Arg Trp Asp Leu Arg Gly Glu Trp Lys Asn Pro Val Lys
        355                 360                 365

Gly Leu Asp Lys Val Arg Phe Ser Ile Ala Lys Val Gly Tyr Arg His
        370                 375                 380

Asp Glu Lys Ser Gly Ala Ile Ser Asp Asn Ser Phe Lys Asn Lys Gly
385                 390                 395                 400

Tyr Ser Ala Arg Val Glu Phe Leu His Gln Pro Ile Ala Gly Val Ser
                405                 410                 415

Gly Leu Ile Gly Leu Ser His Val Tyr Gln Asp Ser Tyr Ala Leu Asp
        420                 425                 430

Asn His Thr Leu Glu Tyr Arg Lys Gln Asn Leu Leu Ser Asp His Thr
        435                 440                 445

Thr Ala Gln Gln Ser Leu Phe Leu Met Glu His Val Glu Leu Gly Lys
450                 455                 460

Trp Gln Phe Asp Ile Gly Gly Arg Val Glu Lys Gln Arg Ile Ala Met
465                 470                 475                 480

Lys Tyr His Phe Asn Val Pro Lys Asp Glu Gln Pro Glu Glu Leu
                485                 490                 495

Thr Arg Pro His Lys Ser Lys Ala Tyr Ser Tyr Ala Leu Ser Ala Asn
                500                 505                 510

Tyr Gln Leu Asn Glu Gln His Gln Phe Asn Met Ile Val Ser His Gln
        515                 520                 525

Glu Arg Leu Pro Asn Ala Gln Glu Leu Tyr Ala His Gly Lys His Leu
        530                 535                 540

Ala Thr Asn Ser Phe Glu Ala Gly Asn Lys Asn Leu Thr Lys Glu Arg
545                 550                 555                 560

Ser Asn Asn Val Glu Leu Gly Trp Gly Tyr Thr Gly Glu Lys Leu Gly
                565                 570                 575

Ile Lys Leu Ser Gly Tyr Tyr Gln Gln Phe Ser Asn Tyr Ile Tyr Ala
                580                 585                 590

Ala Ile Leu Asn Asn Lys Thr Ser Cys Pro Trp Arg Pro Asn Ser Arg
        595                 600                 605

Cys Leu Arg Ser Leu Ser Asp Asp Tyr Pro Leu Arg Leu Tyr Arg Tyr
        610                 615                 620

Asn Gln Ala Lys Ala Lys Ile Tyr Gly Leu Glu Ala Glu Val Ser Tyr
625                 630                 635                 640

Gln Ile Ser Ser Thr His Ser Val Ser Ile Phe Gly Asp Tyr Val Arg
                645                 650                 655

Gly Lys Leu Lys Asp Leu Pro Ser Leu Pro Ile Gly Tyr Lys Tyr Ile
                660                 665                 670

Tyr Asn Glu Asn Tyr Asp Met Val Gly Val Gln Pro Thr Gly Trp Glu
        675                 680                 685
```

```
Lys Gln Pro Asp Gly Asn Ala Pro Arg Met Ser Pro Met Arg Leu Gly
    690                 695                 700
Ile Lys Trp Asn Ala Tyr Phe Asp Asn Gly Ile Ser Phe Asn Thr Gln
705                 710                 715                 720
Leu Tyr Arg Val Phe Ala Gln Asn Lys Val Ala Arg Leu Glu Thr Pro
                725                 730                 735
Thr Lys Gly His Thr Met Leu Asn Leu Gly Met Ser Tyr Asp Gly Lys
            740                 745                 750
Met Gly Asn Asn Glu Tyr Thr Leu Phe Ala Asn Val Asn Val Leu
        755                 760                 765
Asn Ser Arg Val Tyr Asn His Thr Ser Phe Leu Ser Tyr Ile Pro Gln
    770                 775                 780
Ser Gly Leu Gly Leu Asn Val Gly Met Asn Phe Lys Phe
785                 790                 795

<210> SEQ ID NO 104
<211> LENGTH: 758
<212> TYPE: PRT
<213> ORGANISM: Neisseria meningitidis

<400> SEQUENCE: 104

Met Ala Gln Thr Thr Leu Lys Pro Ile Val Leu Ser Ile Leu Leu Ile
1               5                   10                  15
Asn Thr Pro Leu Leu Ala Gln Ala His Glu Thr Glu Gln Ser Val Asp
                20                  25                  30
Leu Glu Thr Val Ser Val Val Gly Lys Ser Arg Pro Arg Ala Thr Ser
            35                  40                  45
Gly Leu Leu His Thr Ser Thr Ala Ser Asp Lys Ile Ile Ser Gly Asp
        50                  55                  60
Thr Leu Arg Gln Lys Ala Val Asn Leu Gly Asp Ala Leu Asp Gly Val
65                  70                  75                  80
Pro Gly Ile His Ala Ser Gln Tyr Gly Gly Gly Ala Ser Ala Pro Val
                85                  90                  95
Ile Arg Gly Gln Thr Gly Arg Arg Ile Lys Val Leu Asn His His Gly
                100                 105                 110
Glu Thr Gly Asp Met Ala Asp Phe Ser Pro Asp His Ala Ile Met Val
            115                 120                 125
Asp Thr Ala Leu Ser Gln Gln Val Glu Ile Leu Arg Gly Pro Val Thr
        130                 135                 140
Leu Leu Tyr Ser Ser Gly Asn Val Ala Gly Leu Val Asp Val Ala Asp
145                 150                 155                 160
Gly Lys Ile Pro Glu Lys Met Pro Glu Asn Gly Val Ser Gly Glu Leu
                165                 170                 175
Gly Leu Arg Leu Ser Ser Gly Asn Glu Lys Leu Thr Ser Gly Gly
                180                 185                 190
Ile Asn Ile Gly Leu Gly Lys Asn Phe Val Leu His Thr Glu Gly Leu
            195                 200                 205
Tyr Arg Lys Ser Gly Asp Tyr Ala Val Pro Arg Tyr Arg Asn Leu Lys
        210                 215                 220
Arg Leu Pro Asp Ser His Ala Asp Ser Gln Thr Gly Ser Ile Gly Leu
225                 230                 235                 240
Ser Trp Val Gly Glu Lys Gly Phe Ile Gly Val Ala Tyr Ser Asp Arg
                245                 250                 255
Arg Asp Gln Tyr Gly Leu Pro Ala His Ser His Glu Tyr Asp Asp Cys
                260                 265                 270
```

```
His Ala Asp Ile Ile Trp Gln Lys Ser Leu Ile Asn Lys Arg Tyr Leu
            275                 280                 285

Gln Leu Tyr Pro His Leu Leu Thr Glu Glu Asp Ile Asp Tyr Asp Asn
        290                 295                 300

Pro Gly Leu Ser Cys Gly Phe His Asp Asp Asn Ala His Ala His
305                 310                 315                 320

Thr His Ser Gly Arg Pro Trp Ile Asp Leu Arg Asn Lys Arg Tyr Glu
                325                 330                 335

Leu Arg Ala Glu Trp Lys Gln Pro Phe Pro Gly Phe Glu Ala Leu Arg
                340                 345                 350

Val His Leu Asn Arg Asn Asp Tyr Arg His Asp Glu Lys Ala Gly Asp
            355                 360                 365

Ala Val Glu Asn Phe Phe Asn Asn Gln Thr Gln Asn Ala Arg Ile Glu
        370                 375                 380

Leu Arg His Gln Pro Ile Gly Arg Leu Lys Gly Ser Trp Gly Val Gln
385                 390                 395                 400

Tyr Leu Gln Gln Lys Ser Ser Ala Leu Ser Ala Ile Ser Glu Ala Val
                405                 410                 415

Lys Gln Pro Met Leu Leu Asp Asn Lys Val Gln His Tyr Ser Phe Phe
            420                 425                 430

Gly Val Glu Gln Ala Asn Trp Asp Asn Phe Thr Leu Glu Gly Gly Val
        435                 440                 445

Arg Val Glu Lys Gln Lys Ala Ser Ile Gln Tyr Asp Lys Ala Leu Ile
450                 455                 460

Asp Arg Glu Asn Tyr Tyr Asn His Pro Leu Pro Asp Leu Gly Ala His
465                 470                 475                 480

Arg Gln Thr Ala Arg Ser Phe Ala Leu Ser Gly Asn Trp Tyr Phe Thr
                485                 490                 495

Pro Gln His Lys Leu Ser Leu Thr Ala Ser His Gln Glu Arg Leu Pro
            500                 505                 510

Ser Thr Gln Glu Leu Tyr Ala His Gly Lys His Val Ala Thr Asn Thr
        515                 520                 525

Phe Glu Val Gly Asn Lys His Leu Asn Lys Glu Arg Ser Asn Asn Ile
530                 535                 540

Glu Leu Ala Leu Gly Tyr Glu Gly Asp Arg Trp Gln Tyr Asn Leu Ala
545                 550                 555                 560

Leu Tyr Arg Asn Arg Phe Gly Asn Tyr Ile Tyr Ala Gln Thr Leu Asn
                565                 570                 575

Asp Gly Arg Gly Pro Lys Ser Ile Glu Asp Asp Ser Glu Met Lys Leu
            580                 585                 590

Val Arg Tyr Asn Gln Ser Gly Ala Asp Phe Tyr Gly Ala Glu Gly Glu
        595                 600                 605

Ile Tyr Phe Lys Pro Thr Pro Arg Tyr Arg Ile Gly Val Ser Gly Asp
610                 615                 620

Tyr Val Arg Gly Arg Leu Lys Asn Leu Pro Ser Leu Pro Gly Arg Glu
625                 630                 635                 640

Asp Ala Tyr Gly Asn Arg Pro Phe Ile Ala Gln Asp Gln Asn Ala
                645                 650                 655

Pro Arg Val Pro Ala Ala Arg Leu Gly Phe His Leu Lys Ala Ser Leu
            660                 665                 670

Thr Asp Arg Ile Asp Ala Asn Leu Asp Tyr Tyr Arg Val Phe Ala Gln
        675                 680                 685
```

```
Asn Lys Leu Ala Arg Tyr Glu Thr Arg Thr Pro Gly His His Met Leu
    690                 695                 700

Asn Leu Gly Ala Asn Tyr Arg Arg Asn Thr Arg Tyr Gly Glu Trp Asn
705                 710                 715                 720

Trp Tyr Val Lys Ala Asp Asn Leu Leu Asn Gln Ser Val Tyr Ala His
            725                 730                 735

Ser Ser Phe Leu Ser Asp Thr Pro Gln Met Gly Arg Ser Phe Thr Gly
            740                 745                 750

Gly Val Asn Val Lys Phe
        755

<210> SEQ ID NO 105
<211> LENGTH: 14
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Ser or Ala or Val
<220> FEATURE:
<221> NAME/KEY: MISC_FEATURE
<222> LOCATION: (3)..(3)
<223> OTHER INFORMATION: Xaa = Ser or Ala or Val or Gly
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = Val or Ile or Met
<220> FEATURE:
<221> NAME/KEY: MISC_FEATURE
<222> LOCATION: (7)..(7)
<223> OTHER INFORMATION: Xaa = Val or Ile
<220> FEATURE:
<221> NAME/KEY: MISC_FEATURE
<222> LOCATION: (10)..(10)
<223> OTHER INFORMATION: Xaa = Gln or Met or Leu
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = Gly or Ser or Ala
<220> FEATURE:
<221> NAME/KEY: MISC_FEATURE
<222> LOCATION: (13)..(13)
<223> OTHER INFORMATION: Xaa = any amino acid

<400> SEQUENCE: 105

Gly Xaa Xaa Xaa Pro Xaa Xaa Arg Gly Xaa Xaa Xaa Xaa Arg
1               5                   10

<210> SEQ ID NO 106
<211> LENGTH: 11
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Val or Ala or Met
<220> FEATURE:
<221> NAME/KEY: MISC_FEATURE
<222> LOCATION: (3)..(3)
<223> OTHER INFORMATION: Xaa = Ser or Ala
```

```
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (6)..(6)
<223> OTHER INFORMATION: Xaa = Ser or Gly
<220> FEATURE:
<221> NAME/KEY: MISC_FEATURE
<222> LOCATION: (7)..(7)
<223> OTHER INFORMATION: Xaa = Pro or Ala
<220> FEATURE:
<221> NAME/KEY: MISC_FEATURE
<222> LOCATION: (10)..(10)
<223> OTHER INFORMATION: Xaa = Thr or Ala or Asn
<220> FEATURE:
<221> NAME/KEY: MISC_FEATURE
<222> LOCATION: (11)..(11)
<223> OTHER INFORMATION: Xaa = Val or Ile

<400> SEQUENCE: 106

Asp Xaa Xaa Xaa Xaa Xaa Xaa Asp His Xaa Xaa
1               5                   10

<210> SEQ ID NO 107
<211> LENGTH: 11
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Leu or Val or Ala or Ile
<220> FEATURE:
<221> NAME/KEY: MISC_FEATURE
<222> LOCATION: (3)..(3)
<223> OTHER INFORMATION: Xaa = Val or Ile
<220> FEATURE:
<221> NAME/KEY: MISC_FEATURE
<222> LOCATION: (4)..(4)
<223> OTHER INFORMATION: Xaa = Asn or Asp
<220> FEATURE:
<221> NAME/KEY: MISC_FEATURE
<222> LOCATION: (5)..(5)
<223> OTHER INFORMATION: Xaa = Val or Ile or Leu
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = any amino acid
<220> FEATURE:
<221> NAME/KEY: MISC_FEATURE
<222> LOCATION: (9)..(9)
<223> OTHER INFORMATION: Xaa = Lys or Arg
<220> FEATURE:
<221> NAME/KEY: MISC_FEATURE
<222> LOCATION: (10)..(10)
<223> OTHER INFORMATION: Xaa = Ile or Leu or Val

<400> SEQUENCE: 107

Gly Xaa Xaa Xaa Xaa Xaa Asp Xaa Xaa Xaa Pro
1               5                   10

<210> SEQ ID NO 108
<211> LENGTH: 16
<212> TYPE: PRT
<213> ORGANISM: Artificial Sequence
<220> FEATURE:
<223> OTHER INFORMATION: conserved motif
<220> FEATURE:
```

```
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = Gly or Ser or Ala
<220> FEATURE:
<221> NAME/KEY: MISC_FEATURE
<222> LOCATION: (4)..(4)
<223> OTHER INFORMATION: Xaa = Tyr or Phe or Trp or Val
<220> FEATURE:
<221> NAME/KEY: MISC_FEATURE
<222> LOCATION: (5)..(5)
<223> OTHER INFORMATION: Xaa = Gly or Ser or Thr or Asn
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Gln or Arg or Leu
<220> FEATURE:
<221> NAME/KEY: MISC_FEATURE
<222> LOCATION: (8)..(10)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = Leu or Ile or Val
<220> FEATURE:
<221> NAME/KEY: MISC_FEATURE
<222> LOCATION: (14)..(14)
<223> OTHER INFORMATION: Xaa = Leu or Ile or Pro
<220> FEATURE:
<221> NAME/KEY: MISC_FEATURE
<222> LOCATION: (15)..(15)
<223> OTHER INFORMATION: Xaa = Gly or Ala
<220> FEATURE:
<221> NAME/KEY: MISC_FEATURE
<222> LOCATION: (16)..(16)
<223> OTHER INFORMATION: Xaa = His or Asp

<400> SEQUENCE: 108

Gly Xaa Xaa Xaa Xaa Xaa Xaa Xaa Xaa Xaa Tyr Gly Xaa Xaa Xaa Xaa
1               5                   10                  15

<210> SEQ ID NO 109
<211> LENGTH: 30
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = Asp or Glu
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Arg or Lys or Gln or Asp
<220> FEATURE:
<221> NAME/KEY: MISC_FEATURE
<222> LOCATION: (6)..(6)
<223> OTHER INFORMATION: Xaa = Gly or Thr or Ser or Ala
<220> FEATURE:
<221> NAME/KEY: MISC_FEATURE
<222> LOCATION: (7)..(7)
```

<223> OTHER INFORMATION: Xaa = Glu or Gln or Ser or Asp
<220> FEATURE:
<221> NAME/KEY: MISC_FEATURE
<222> LOCATION: (8)..(10)
<223> OTHER INFORMATION: Xaa = any amino acid
<220> FEATURE:
<221> NAME/KEY: MISC_FEATURE
<222> LOCATION: (12)..(14)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = Ile or Phe or Val or Leu
<220> FEATURE:
<221> NAME/KEY: MISC_FEATURE
<222> LOCATION: (16)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = Arg or Ala or Lys or Gln
<220> FEATURE:
<221> NAME/KEY: MISC_FEATURE
<222> LOCATION: (20)..(24)
<223> OTHER INFORMATION: Xaa = any amino acid
<220> FEATURE:
<221> NAME/KEY: MISC_FEATURE
<222> LOCATION: (25)..(25)
<223> OTHER INFORMATION: Xaa = Asp or Asn or Arg or Gly
<220> FEATURE:
<221> NAME/KEY: MISC_FEATURE
<222> LOCATION: (27)..(27)
<223> OTHER INFORMATION: Xaa = any amino acid
<220> FEATURE:
<221> NAME/KEY: MISC_FEATURE
<222> LOCATION: (29)..(29)
<223> OTHER INFORMATION: Xaa = any amino acid

<400> SEQUENCE: 109

Arg Xaa Xaa Xaa Xaa Xaa Xaa Xaa Xaa Pro Xaa Xaa Xaa Xaa Xaa
1               5                   10                  15

Xaa Xaa Xaa Xaa Xaa Xaa Xaa Xaa Xaa Tyr Xaa His Xaa Glu
            20                  25                  30

<210> SEQ ID NO 110
<211> LENGTH: 35
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Ala or Pro or Val or Thr
<220> FEATURE:
<221> NAME/KEY: MISC_FEATURE
<222> LOCATION: (6)..(6)
<223> OTHER INFORMATION: Xaa = Gln or Glu or Met
<220> FEATURE:
<221> NAME/KEY: MISC_FEATURE
<222> LOCATION: (8)..(8)
<223> OTHER INFORMATION: Xaa = Leu or Met
<220> FEATURE:
<221> NAME/KEY: MISC_FEATURE
<222> LOCATION: (9)..(9)
<223> OTHER INFORMATION: Xaa = Tyr or Phe
<220> FEATURE:
<221> NAME/KEY: MISC_FEATURE

```
<222> LOCATION: (10)..(10)
<223> OTHER INFORMATION: Xaa = Ala or Ser or Tyr or Thr
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (13)..(13)
<223> OTHER INFORMATION: Xaa = any amino acid
<220> FEATURE:
<221> NAME/KEY: MISC_FEATURE
<222> LOCATION: (15)..(15)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = Thr or Leu or Ser
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = Thr or Ser or Ala
<220> FEATURE:
<221> NAME/KEY: MISC_FEATURE
<222> LOCATION: (20)..(20)
<223> OTHER INFORMATION: Xaa = Phe or Tyr or Ile or Val
<220> FEATURE:
<221> NAME/KEY: MISC_FEATURE
<222> LOCATION: (21)..(21)
<223> OTHER INFORMATION: Xaa = Glu or Gln
<220> FEATURE:
<221> NAME/KEY: MISC_FEATURE
<222> LOCATION: (22)..(22)
<223> OTHER INFORMATION: Xaa = any amino acid
<220> FEATURE:
<221> NAME/KEY: MISC_FEATURE
<222> LOCATION: (23)..(23)
<223> OTHER INFORMATION: (optional) Xaa = any amino acid
<220> FEATURE:
<221> NAME/KEY: MISC_FEATURE
<222> LOCATION: (24)..(24)
<223> OTHER INFORMATION: (optional) Xaa = any amino acid
<220> FEATURE:
<221> NAME/KEY: MISC_FEATURE
<222> LOCATION: (25)..(25)
<223> OTHER INFORMATION: (optional) Xaa = any amino acid
<220> FEATURE:
<221> NAME/KEY: MISC_FEATURE
<222> LOCATION: (26)..(26)
<223> OTHER INFORMATION: (optional) Xaa = any amino acid
<220> FEATURE:
<221> NAME/KEY: MISC_FEATURE
<222> LOCATION: (27)..(27)
<223> OTHER INFORMATION: (optional) Xaa = any amino acid
<220> FEATURE:
<221> NAME/KEY: MISC_FEATURE
<222> LOCATION: (28)..(28)
<223> OTHER INFORMATION: (optional) Xaa = any amino acid
<220> FEATURE:
<221> NAME/KEY: MISC_FEATURE
<222> LOCATION: (29)..(29)
<223> OTHER INFORMATION: (optional) Xaa = any amino acid
<220> FEATURE:
<221> NAME/KEY: MISC_FEATURE
<222> LOCATION: (30)..(30)
<223> OTHER INFORMATION: (optional) Xaa = any amino acid
<220> FEATURE:
<221> NAME/KEY: MISC_FEATURE
<222> LOCATION: (32)..(32)
<223> OTHER INFORMATION: Xaa = Asp or Asn or Gln
<220> FEATURE:
<221> NAME/KEY: MISC_FEATURE
<222> LOCATION: (33)..(34)
<223> OTHER INFORMATION: Xaa = any amino acid
```

<400> SEQUENCE: 110

Arg Xaa Pro Xaa Xaa Xaa Glu Xaa Xaa Xaa Xaa Gly Xaa His Xaa Ala
1               5                   10                  15

Xaa Xaa Xaa Xaa Xaa Xaa Xaa Xaa Xaa Xaa Xaa Xaa Xaa Gly Xaa
            20                  25                  30

Xaa Xaa Leu
        35

<210> SEQ ID NO 111
<211> LENGTH: 34
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = Gln or Gly
<220> FEATURE:
<221> NAME/KEY: MISC_FEATURE
<222> LOCATION: (4)..(5)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = Phe or Tyr or Leu or Ile
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = Glu or Asp
<220> FEATURE:
<221> NAME/KEY: MISC_FEATURE
<222> LOCATION: (13)..(13)
<223> OTHER INFORMATION: Xaa = Gly or Ala or Val
<220> FEATURE:
<221> NAME/KEY: MISC_FEATURE
<222> LOCATION: (14)..(16)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = Tyr or Phe or His or Gln
<220> FEATURE:
<221> NAME/KEY: MISC_FEATURE
<222> LOCATION: (18)..(25)
<223> OTHER INFORMATION: Xaa = any amino acid
<220> FEATURE:
<221> NAME/KEY: MISC_FEATURE
<222> LOCATION: (26)..(26)
<223> OTHER INFORMATION: Xaa = Gly or Ser or Ala or Thr
<220> FEATURE:
<221> NAME/KEY: MISC_FEATURE
<222> LOCATION: (27)..(27)
<223> OTHER INFORMATION: Xaa = any amino acid
<220> FEATURE:
<221> NAME/KEY: MISC_FEATURE
<222> LOCATION: (28)..(28)
<223> OTHER INFORMATION: Xaa = Phe or Ser
<220> FEATURE:

```
<221> NAME/KEY: MISC_FEATURE
<222> LOCATION: (31)..(31)
<223> OTHER INFORMATION: Xaa = any amino acid
<220> FEATURE:
<221> NAME/KEY: MISC_FEATURE
<222> LOCATION: (32)..(32)
<223> OTHER INFORMATION: Xaa = Val or Ile
<220> FEATURE:
<221> NAME/KEY: MISC_FEATURE
<222> LOCATION: (33)..(33)
<223> OTHER INFORMATION: Xaa = Arg or Lys or Asn
<220> FEATURE:
<221> NAME/KEY: MISC_FEATURE
<222> LOCATION: (34)..(34)
<223> OTHER INFORMATION: Xaa = Ala or Gly

<400> SEQUENCE: 111

Tyr Xaa Xaa Xaa Xaa Ala Xaa Xaa Xaa Gly Xaa Xaa Xaa Xaa Xaa Xaa
1               5                   10                  15

Xaa Xaa Xaa Xaa Xaa Xaa Xaa Xaa Xaa Xaa Xaa Gly Asp Xaa Xaa
            20                  25                  30

Xaa Xaa

<210> SEQ ID NO 112
<211> LENGTH: 9
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (1)..(1)
<223> OTHER INFORMATION: Xaa = Pro or Ala
<220> FEATURE:
<221> NAME/KEY: MISC_FEATURE
<222> LOCATION: (3)..(3)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Pro or Ser or Ala
<220> FEATURE:
<221> NAME/KEY: MISC_FEATURE
<222> LOCATION: (5)..(5)
<223> OTHER INFORMATION: Xaa = Ala or Pro or Gly
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = Leu or Val or Ala
<220> FEATURE:
<221> NAME/KEY: MISC_FEATURE
<222> LOCATION: (9)..(9)
<223> OTHER INFORMATION: Xaa = Ser or Gly

<400> SEQUENCE: 112

Xaa Arg Xaa Xaa Xaa Xaa Arg Xaa Xaa
1               5

<210> SEQ ID NO 113
<211> LENGTH: 41
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Ser or Thr
<220> FEATURE:
```

```
<221> NAME/KEY: MISC_FEATURE
<222> LOCATION: (3)..(3)
<223> OTHER INFORMATION: Xaa = Val or Ile
<220> FEATURE:
<221> NAME/KEY: MISC_FEATURE
<222> LOCATION: (7)..(7)
<223> OTHER INFORMATION: Xaa = Phe or Tyr
<220> FEATURE:
<221> NAME/KEY: MISC_FEATURE
<222> LOCATION: (9)..(9)
<223> OTHER INFORMATION: Xaa = Gln or Asn
<220> FEATURE:
<221> NAME/KEY: MISC_FEATURE
<222> LOCATION: (10)..(10)
<223> OTHER INFORMATION: Xaa = Gln or Val or Leu or Ile
<220> FEATURE:
<221> NAME/KEY: MISC_FEATURE
<222> LOCATION: (12)..(12)
<223> OTHER INFORMATION: Xaa = Lys or Gln
<220> FEATURE:
<221> NAME/KEY: MISC_FEATURE
<222> LOCATION: (13)..(13)
<223> OTHER INFORMATION: Xaa = Gly or Ala or Ser
<220> FEATURE:
<221> NAME/KEY: MISC_FEATURE
<222> LOCATION: (14)..(14)
<223> OTHER INFORMATION: Xaa = Ser or Gln
<220> FEATURE:
<221> NAME/KEY: MISC_FEATURE
<222> LOCATION: (16)..(16)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = Val or Leu
<220> FEATURE:
<221> NAME/KEY: MISC_FEATURE
<222> LOCATION: (19)..(19)
<223> OTHER INFORMATION: Xaa = Val or Leu
<220> FEATURE:
<221> NAME/KEY: MISC_FEATURE
<222> LOCATION: (21)..(21)
<223> OTHER INFORMATION: Xaa = Val or Ile
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (25)..(25)
<223> OTHER INFORMATION: Xaa = Ser or Asn or Thr
<220> FEATURE:
<221> NAME/KEY: MISC_FEATURE
<222> LOCATION: (27)..(27)
<223> OTHER INFORMATION: Xaa = Phe or Leu
<220> FEATURE:
<221> NAME/KEY: MISC_FEATURE
<222> LOCATION: (30)..(30)
<223> OTHER INFORMATION: Xaa = Val or Ala
<220> FEATURE:
<221> NAME/KEY: MISC_FEATURE
<222> LOCATION: (32)..(32)
<223> OTHER INFORMATION: Xaa = Ser or Thr
<220> FEATURE:
<221> NAME/KEY: MISC_FEATURE
<222> LOCATION: (33)..(33)
<223> OTHER INFORMATION: Xaa = Met or Gln
<220> FEATURE:
<221> NAME/KEY: MISC_FEATURE
<222> LOCATION: (34)..(34)
<223> OTHER INFORMATION: Xaa = Val or Ile
<220> FEATURE:
<221> NAME/KEY: MISC_FEATURE
<222> LOCATION: (37)..(37)
<223> OTHER INFORMATION: Xaa = Val or Ile
<220> FEATURE:
<221> NAME/KEY: MISC_FEATURE
<222> LOCATION: (38)..(38)
<223> OTHER INFORMATION: Xaa = Ser or Thr
```

-continued

<400> SEQUENCE: 113

Arg Xaa Xaa Pro Gly Ala Xaa Thr Xaa Xaa Asp Xaa Xaa Xaa Gly Xaa
1               5                   10                  15

Xaa Ser Xaa Asn Xaa Arg Gly Xaa Xaa Gly Xaa Gly Arg Xaa Asn Xaa
            20                  25                  30

Xaa Xaa Asp Gly Xaa Xaa Gln Thr Phe
        35                  40

<210> SEQ ID NO 114
<211> LENGTH: 23
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Ser or Asn or Asp or Glu
<220> FEATURE:
<221> NAME/KEY: MISC_FEATURE
<222> LOCATION: (4)..(4)
<223> OTHER INFORMATION: Xaa = Ser or Thr or Ala or Lys
<220> FEATURE:
<221> NAME/KEY: MISC_FEATURE
<222> LOCATION: (5)..(5)
<223> OTHER INFORMATION: Xaa = Ala or Gly or Ser or Asn
<220> FEATURE:
<221> NAME/KEY: MISC_FEATURE
<222> LOCATION: (7)..(7)
<223> OTHER INFORMATION: Xaa = Ile or Leu or Val or Ala
<220> FEATURE:
<221> NAME/KEY: MISC_FEATURE
<222> LOCATION: (9)..(9)
<223> OTHER INFORMATION: Xaa = Ser or Thr or Ala
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (16)..(16)
<223> OTHER INFORMATION: Xaa = Leu or Phe
<220> FEATURE:
<221> NAME/KEY: MISC_FEATURE
<222> LOCATION: (17)..(17)
<223> OTHER INFORMATION: Xaa = Arg or Lys
<220> FEATURE:
<221> NAME/KEY: MISC_FEATURE
<222> LOCATION: (19)..(19)
<223> OTHER INFORMATION: Xaa = Leu or Ile
<220> FEATURE:
<221> NAME/KEY: MISC_FEATURE
<222> LOCATION: (20)..(20)
<223> OTHER INFORMATION: Xaa = Gly or Asn or Ser
<220> FEATURE:
<221> NAME/KEY: MISC_FEATURE
<222> LOCATION: (21)..(21)
<223> OTHER INFORMATION: Xaa = Val or Ala
<220> FEATURE:
<221> NAME/KEY: MISC_FEATURE
<222> LOCATION: (22)..(22)
<223> OTHER INFORMATION: Xaa = Asp or Asn

<400> SEQUENCE: 114

Phe Xaa Gly Xaa Xaa Gly Xaa Asn Xaa Leu Xaa Gly Ser Ala Asn Xaa
1               5                   10                  15

Xaa Thr Xaa Xaa Xaa Xaa Asp
            20

<210> SEQ ID NO 115
<211> LENGTH: 14

```
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (3)..(3)
<223> OTHER INFORMATION: Xaa = Arg or Lys or Gln
<220> FEATURE:
<221> NAME/KEY: MISC_FEATURE
<222> LOCATION: (4)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Val or Ile or Ser or Leu
<220> FEATURE:
<221> NAME/KEY: MISC_FEATURE
<222> LOCATION: (6)..(6)
<223> OTHER INFORMATION: Xaa = Ser or Ala
<220> FEATURE:
<221> NAME/KEY: MISC_FEATURE
<222> LOCATION: (8)..(8)
<223> OTHER INFORMATION: Xaa = Asn or Asp
<220> FEATURE:
<221> NAME/KEY: MISC_FEATURE
<222> LOCATION: (9)..(9)
<223> OTHER INFORMATION: Xaa = Tyr or Phe
<220> FEATURE:
<221> NAME/KEY: MISC_FEATURE
<222> LOCATION: (10)..(10)
<223> OTHER INFORMATION: Xaa = Arg or Lys
<220> FEATURE:
<221> NAME/KEY: MISC_FEATURE
<222> LOCATION: (11)..(11)
<223> OTHER INFORMATION: Xaa = Val or Ile

<400> SEQUENCE: 115

Ser Xaa Xaa Xaa Xaa Xaa Gln Xaa Xaa Xaa Xaa Gly Gly Gly
1               5                   10

<210> SEQ ID NO 116
<211> LENGTH: 35
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = Phe or Ala or Leu or Val
<220> FEATURE:
<221> NAME/KEY: MISC_FEATURE
<222> LOCATION: (4)..(4)
<223> OTHER INFORMATION: Xaa = Leu or Ile or Phe or Val
<220> FEATURE:
<221> NAME/KEY: MISC_FEATURE
<222> LOCATION: (5)..(5)
<223> OTHER INFORMATION: Xaa = Glu or Arg
<220> FEATURE:
<221> NAME/KEY: MISC_FEATURE
<222> LOCATION: (7)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = Gly or Asn or Asp or Ser
<220> FEATURE:
<221> NAME/KEY: MISC_FEATURE
<222> LOCATION: (9)..(9)
<223> OTHER INFORMATION: Xaa = Val or Asp or Lys or His
<220> FEATURE:
<221> NAME/KEY: MISC_FEATURE
```

```
<222> LOCATION: (10)..(13)
<223> OTHER INFORMATION: Xaa = any amino acid
<220> FEATURE:
<221> NAME/KEY: MISC_FEATURE
<222> LOCATION: (14)..(14)
<223> OTHER INFORMATION: Xaa = Thr or Gly or Asn or Ile
<220> FEATURE:
<221> NAME/KEY: MISC_FEATURE
<222> LOCATION: (15)..(15)
<223> OTHER INFORMATION: Xaa = Ala or Leu
<220> FEATURE:
<221> NAME/KEY: MISC_FEATURE
<222> LOCATION: (16)..(16)
<223> OTHER INFORMATION: Xaa = Gln or Asn or Ser
<220> FEATURE:
<221> NAME/KEY: MISC_FEATURE
<222> LOCATION: (17)..(17)
<223> OTHER INFORMATION: Xaa = Phe or Leu or Ile or Tyr
<220> FEATURE:
<221> NAME/KEY: MISC_FEATURE
<222> LOCATION: (19)..(19)
<223> OTHER INFORMATION: Xaa = any amino acid
<220> FEATURE:
<221> NAME/KEY: MISC_FEATURE
<222> LOCATION: (20)..(20)
<223> OTHER INFORMATION: Xaa = Leu or Met or Tyr
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (22)..(22)
<223> OTHER INFORMATION: Xaa = Thr or Asn
<220> FEATURE:
<221> NAME/KEY: MISC_FEATURE
<222> LOCATION: (23)..(23)
<223> OTHER INFORMATION: Xaa = any amino acid
<220> FEATURE:
<221> NAME/KEY: MISC_FEATURE
<222> LOCATION: (24)..(24)
<223> OTHER INFORMATION: Xaa = Ile or Leu or Val
<220> FEATURE:
<221> NAME/KEY: MISC_FEATURE
<222> LOCATION: (25)..(25)
<223> OTHER INFORMATION: Xaa = Gly or Ala or Ser
<220> FEATURE:
<221> NAME/KEY: MISC_FEATURE
<222> LOCATION: (26)..(26)
<223> OTHER INFORMATION: Xaa = Ser or Thr or Gly
<220> FEATURE:
<221> NAME/KEY: MISC_FEATURE
<222> LOCATION: (28)..(28)
<223> OTHER INFORMATION: Xaa = Lys or Arg or Asn or Ser
<220> FEATURE:
<221> NAME/KEY: MISC_FEATURE
<222> LOCATION: (29)..(29)
<223> OTHER INFORMATION: Xaa = Ile or Leu
<220> FEATURE:
<221> NAME/KEY: MISC_FEATURE
<222> LOCATION: (30)..(30)
<223> OTHER INFORMATION: Xaa = any amino acid
<220> FEATURE:
<221> NAME/KEY: MISC_FEATURE
<222> LOCATION: (32)..(32)
<223> OTHER INFORMATION: Xaa = Arg or Asp or Lys or Asn
<220> FEATURE:
<221> NAME/KEY: MISC_FEATURE
<222> LOCATION: (33)..(33)
<223> OTHER INFORMATION: Xaa = Asn or Thr

<400> SEQUENCE: 116

Leu Xaa Lys Xaa Xaa Tyr Xaa Xaa Xaa Xaa Xaa Xaa Xaa Xaa Xaa
1               5                  10                  15

Xaa Arg Xaa Xaa Xaa Xaa Xaa Xaa Xaa Xaa Arg Xaa Xaa Xaa Asn Xaa
            20                  25                  30
```

Xaa Tyr Gln
        35

<210> SEQ ID NO 117
<211> LENGTH: 13
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = any amino acid
<220> FEATURE:
<221> NAME/KEY: MISC_FEATURE
<222> LOCATION: (4)..(4)
<223> OTHER INFORMATION: Xaa = Ser or Lys or Glu
<220> FEATURE:
<221> NAME/KEY: MISC_FEATURE
<222> LOCATION: (6)..(6)
<223> OTHER INFORMATION: Xaa = any amino acid
<220> FEATURE:
<221> NAME/KEY: MISC_FEATURE
<222> LOCATION: (7)..(7)
<223> OTHER INFORMATION: Xaa = Phe or Ile
<220> FEATURE:
<221> NAME/KEY: MISC_FEATURE
<222> LOCATION: (8)..(8)
<223> OTHER INFORMATION: Xaa = Asn or His or Lys or Ile
<220> FEATURE:
<221> NAME/KEY: MISC_FEATURE
<222> LOCATION: (9)..(9)
<223> OTHER INFORMATION: Xaa = Thr or Ser
<220> FEATURE:
<221> NAME/KEY: MISC_FEATURE
<222> LOCATION: (10)..(10)
<223> OTHER INFORMATION: Xaa = Phe or Ile or Val or Leu
<220> FEATURE:
<221> NAME/KEY: MISC_FEATURE
<222> LOCATION: (12)..(12)
<223> OTHER INFORMATION: Xaa = Phe or Leu or Ile

<400> SEQUENCE: 117

Pro Xaa Gly Xaa Gln Xaa Xaa Xaa Xaa Xaa Tyr Xaa Asp
1               5                   10

<210> SEQ ID NO 118
<211> LENGTH: 35
<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (2)..(2)
<223> OTHER INFORMATION: Xaa = His or Tyr
<220> FEATURE:
<221> NAME/KEY: MISC_FEATURE
<222> LOCATION: (4)..(4)
<223> OTHER INFORMATION: Xaa = Val or Ala or Leu or Met
<220> FEATURE:
<221> NAME/KEY: MISC_FEATURE
<222> LOCATION: (5)..(5)
<223> OTHER INFORMATION: Xaa = Ser or Thr or Ile or Met
<220> FEATURE:
<221> NAME/KEY: MISC_FEATURE
<222> LOCATION: (6)..(6)
<223> OTHER INFORMATION: Xaa = Ile or Leu or Phe
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = Phe or Tyr or Leu or Ile

```
<220> FEATURE:
<221> NAME/KEY: MISC_FEATURE
<222> LOCATION: (11)..(11)
<223> OTHER INFORMATION: Xaa = Gly or Asp or Ser or His
<220> FEATURE:
<221> NAME/KEY: MISC_FEATURE
<222> LOCATION: (12)..(12)
<223> OTHER INFORMATION: Xaa = Asp or Thr or Pro
<220> FEATURE:
<221> NAME/KEY: MISC_FEATURE
<222> LOCATION: (13)..(13)
<223> OTHER INFORMATION: Xaa = Tyr or Gly or Leu
<220> FEATURE:
<221> NAME/KEY: MISC_FEATURE
<222> LOCATION: (15)..(15)
<223> OTHER INFORMATION: Xaa = Met or Asn or Ser or Thr
<220> FEATURE:
<221> NAME/KEY: MISC_FEATURE
<222> LOCATION: (18)..(18)
<223> OTHER INFORMATION: Xaa = any amino acid
<220> FEATURE:
<221> NAME/KEY: MISC_FEATURE
<222> LOCATION: (19)..(19)
<223> OTHER INFORMATION: Xaa = Ser or Thr or Gly
<220> FEATURE:
<221> NAME/KEY: MISC_FEATURE
<222> LOCATION: (20)..(20)
<223> OTHER INFORMATION: Xaa = Tyr or Phe
<220> FEATURE:
<221> NAME/KEY: MISC_FEATURE
<222> LOCATION: (21)..(21)
<223> OTHER INFORMATION: Xaa = Ser or Ala
<220> FEATURE:
<221> NAME/KEY: MISC_FEATURE
<222> LOCATION: (22)..(22)
<223> OTHER INFORMATION: Xaa = Arg or His or Lys
<220> FEATURE:
<221> NAME/KEY: MISC_FEATURE
<222> LOCATION: (23)..(23)
<223> OTHER INFORMATION: Xaa = Thr or Ser
<220> FEATURE:
<221> NAME/KEY: MISC_FEATURE
<222> LOCATION: (26)..(26)
<223> OTHER INFORMATION: Xaa = Met or Ile or Val or Ala
<220> FEATURE:
<221> NAME/KEY: MISC_FEATURE
<222> LOCATION: (29)..(29)
<223> OTHER INFORMATION: Xaa = Ile or Val
<220> FEATURE:
<221> NAME/KEY: MISC_FEATURE
<222> LOCATION: (30)..(30)
<223> OTHER INFORMATION: Xaa = Gln or Lys or Arg
<220> FEATURE:
<221> NAME/KEY: MISC_FEATURE
<222> LOCATION: (32)..(32)
<223> OTHER INFORMATION: Xaa = Met or Tyr or Val
<220> FEATURE:
<221> NAME/KEY: MISC_FEATURE
<222> LOCATION: (33)..(33)
<223> OTHER INFORMATION: Xaa = Tyr or Phe
<220> FEATURE:
<221> NAME/KEY: MISC_FEATURE
<222> LOCATION: (35)..(35)
<223> OTHER INFORMATION: Xaa = Ser or Thr

<400> SEQUENCE: 118

Asn Xaa Ser Xaa Xaa Xaa Ser Ala Xaa Xaa Xaa Xaa Xaa Phe Xaa Pro
1               5                   10                  15

Phe Xaa Xaa Xaa Xaa Xaa Xaa His Arg Xaa Pro Asn Xaa Xaa Glu Xaa
            20                  25                  30

Xaa Phe Xaa
        35

<210> SEQ ID NO 119
<211> LENGTH: 15
```

```
-continued

<212> TYPE: PRT
<213> ORGANISM: Artificial Sequence
<220> FEATURE:
<223> OTHER INFORMATION: conserved motif
<220> FEATURE:
<221> NAME/KEY: MISC_FEATURE
<222> LOCATION: (1)..(1)
<223> OTHER INFORMATION: Xaa = Glu or Asp
<220> FEATURE:
<221> NAME/KEY: MISC_FEATURE
<222> LOCATION: (2)..(2)
<223> OTHER INFORMATION: Xaa = Val or Ile
<220> FEATURE:
<221> NAME/KEY: MISC_FEATURE
<222> LOCATION: (3)..(3)
<223> OTHER INFORMATION: Xaa = Lys or Gln
<220> FEATURE:
<221> NAME/KEY: MISC_FEATURE
<222> LOCATION: (5)..(5)
<223> OTHER INFORMATION: Xaa = Leu or Ala or Val
<220> FEATURE:
<221> NAME/KEY: MISC_FEATURE
<222> LOCATION: (6)..(6)
<223> OTHER INFORMATION: Xaa = Phe or Leu
<220> FEATURE:
<221> NAME/KEY: MISC_FEATURE
<222> LOCATION: (8)..(8)
<223> OTHER INFORMATION: Xaa = Arg or Lys
<220> FEATURE:
<221> NAME/KEY: MISC_FEATURE
<222> LOCATION: (9)..(9)
<223> OTHER INFORMATION: Xaa = Arg or Leu or Lys or Asn
<220> FEATURE:
<221> NAME/KEY: MISC_FEATURE
<222> LOCATION: (11)..(11)
<223> OTHER INFORMATION: Xaa = Ile or Val or Met
<220> FEATURE:
<221> NAME/KEY: MISC_FEATURE
<222> LOCATION: (12)..(12)
<223> OTHER INFORMATION: Xaa = Asp or Asn
<220> FEATURE:
<221> NAME/KEY: MISC_FEATURE
<222> LOCATION: (13)..(13)
<223> OTHER INFORMATION: Xaa = Pro or Ala
<220> FEATURE:
<221> NAME/KEY: MISC_FEATURE
<222> LOCATION: (15)..(15)
<223> OTHER INFORMATION: Xaa = Asp or Tyr

<400> SEQUENCE: 119

Xaa Xaa Xaa Asn Xaa Xaa Asp Xaa Xaa Tyr Xaa Xaa Xaa Leu Xaa
1               5                   10                  15
```